United States Patent
Chu et al.

(10) Patent No.: US 11,084,832 B2
(45) Date of Patent: Aug. 10, 2021

(54) BRIDGED TRICYCLIC CARBAMOYLPYRIDONE COMPOUNDS AND THEIR PHARMACEUTICAL USE

(71) Applicant: Gilead Sciences, Inc., Foster City, CA (US)

(72) Inventors: Hang Chu, San Mateo, CA (US); Ana Z. Gonzalez Buenrostro, San Mateo, CA (US); Hongyan Guo, San Mateo, CA (US); Xiaochun Han, San Jose, CA (US); Lan Jiang, Foster City, CA (US); Jiayao Li, Foster City, CA (US); Michael L. Mitchell, Castro Valley, CA (US); Hyung-Jung Pyun, Fremont, CA (US); Scott D. Schroeder, Union City, CA (US); Gregg M. Schwarzwalder, Redwood City, CA (US); Nathan D. Shapiro, Belmont, CA (US); Devleena M. Shivakumar, Menlo Park, CA (US); Qiaoyin Wu, Foster City, CA (US); Hong Yang, Fremont, CA (US); Jennifer R. Zhang, Union City, CA (US)
m

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 16/825,142

(22) Filed: Mar. 20, 2020

(65) Prior Publication Data
US 2020/0317689 A1    Oct. 8, 2020

Related U.S. Application Data

(60) Provisional application No. 62/948,697, filed on Dec. 16, 2019, provisional application No. 62/822,703, filed on Mar. 22, 2019.

(51) Int. Cl.
*C07D 498/18* (2006.01)
*C07D 471/18* (2006.01)
*A61P 31/18* (2006.01)

(52) U.S. Cl.
CPC ............ *C07D 498/18* (2013.01); *A61P 31/18* (2018.01); *C07D 471/18* (2013.01)

(58) Field of Classification Search
CPC ........................... C07D 471/18; C07D 498/18
See application file for complete search history.

(56) References Cited

U.S. PATENT DOCUMENTS

| | | | |
|---|---|---|---|
| 9,522,912 B2 | 12/2016 | Bacon et al. | |
| 2013/0171214 A1 | 7/2013 | Mundhra et al. | |
| 2019/0284208 A1 | 9/2019 | Johns et al. | |
| 2019/0315769 A1 | 10/2019 | Graham et al. | |
| 2019/0322666 A1 | 10/2019 | Yu et al. | |

FOREIGN PATENT DOCUMENTS

| | | |
|---|---|---|
| JP | 2006342115 A | 12/2006 |
| WO | WO-2006088173 A1 | 8/2006 |
| WO | WO-2006116764 A1 | 11/2006 |
| WO | WO-2007019098 A2 | 2/2007 |
| WO | WO-2007049675 A1 | 5/2007 |
| WO | WO-2007050510 A2 | 5/2007 |
| WO | WO-2007148780 A1 | 12/2007 |
| WO | WO-2008010964 A1 | 1/2008 |
| WO | WO-2008048538 A1 | 4/2008 |
| WO | WO-2009088729 A1 | 7/2009 |
| WO | WO-2009154870 A1 | 12/2009 |
| WO | WO-2010000030 A1 | 1/2010 |
| WO | WO-2010011812 A1 | 1/2010 |
| WO | WO-2010011814 A1 | 1/2010 |
| WO | WO-2010011815 A1 | 1/2010 |
| WO | WO-2010011816 A1 | 1/2010 |
| WO | WO-2010011818 A1 | 1/2010 |
| WO | WO-2010011819 A1 | 1/2010 |
| WO | WO-2010042391 A3 | 4/2010 |
| WO | WO-2010068253 A1 | 6/2010 |
| WO | WO-2010088167 A1 | 8/2010 |
| WO | WO-2010147068 A1 | 12/2010 |
| WO | WO-2011011483 A1 | 1/2011 |

(Continued)

OTHER PUBLICATIONS (2020) "Product Monograph Including Patient Medication Information" VIIV Healthcare ULC, 51 pages.

(Continued)

*Primary Examiner* — Susanna Moore

(57) ABSTRACT

Compounds for use in treating or preventing human immunodeficiency virus (HIV) infection are disclosed. The compounds have the following formula (I):

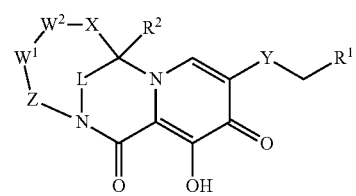

including stereoisomers and pharmaceutically acceptable salts thereof, wherein $R^1$, $R^2$, L, $W^1$, $W^2$, X, Y, and Z are as defined herein. Methods associated with the preparation and use of such compounds, as well as pharmaceutical compositions comprising such compounds, are also disclosed.

47 Claims, No Drawings

(56) References Cited

FOREIGN PATENT DOCUMENTS

| | | |
|---|---|---|
| WO | WO-2011025683 A1 | 3/2011 |
| WO | WO-2011045330 A1 | 4/2011 |
| WO | WO-2011094150 A1 | 8/2011 |
| WO | WO-2011105590 A1 | 9/2011 |
| WO | WO-2011121105 A1 | 10/2011 |
| WO | WO-2011129095 A1 | 10/2011 |
| WO | WO-2012018065 A1 | 2/2012 |
| WO | WO-2012058173 A1 | 5/2012 |
| WO | WO-2013054862 A1 | 4/2013 |
| WO | WO-2014004279 A1 | 1/2014 |
| WO | WO-2014008636 A1 | 1/2014 |
| WO | WO-2014014933 A1 | 1/2014 |
| WO | WO-2014028384 A1 | 2/2014 |
| WO | WO-2014072188 A1 | 5/2014 |
| WO | WO-2014099586 A1 | 6/2014 |
| WO | WO-2014100323 A1 | 6/2014 |
| WO | WO-2014183532 A1 | 11/2014 |
| WO | WO-2014200880 A1 | 12/2014 |
| WO | WO-2015006731 A1 | 1/2015 |
| WO | WO-2015006733 A1 | 1/2015 |
| WO | WO-2015039348 A1 | 3/2015 |
| WO | WO-2015048363 A1 | 4/2015 |
| WO | WO-2015089847 A1 | 6/2015 |
| WO | WO-2016027879 A1 | 2/2016 |
| WO | WO-2016033009 A1 | 3/2016 |
| WO | WO-2016090545 A1 | 6/2016 |
| WO | WO-2016094198 A1 | 6/2016 |
| WO | WO-2016106237 A1 | 6/2016 |
| WO | WO-2016154527 A1 | 9/2016 |
| WO | WO-2016161382 A1 | 10/2016 |
| WO | WO-2016187788 A1 | 12/2016 |
| WO | WO-2017087256 A1 | 5/2017 |
| WO | WO-2017087257 A1 | 5/2017 |
| WO | WO-2017106071 A1 | 6/2017 |
| WO | WO-2017113288 A1 | 7/2017 |
| WO | WO-2017223280 A2 | 12/2017 |
| WO | WO-2018102485 A1 | 6/2018 |
| WO | WO-2018102634 A1 | 6/2018 |
| WO | WO-2018109786 A1 | 6/2018 |
| WO | WO-2018140368 A1 | 8/2018 |
| WO | WO-2019160783 A1 | 8/2019 |
| WO | WO-2019209667 A1 | 10/2019 |
| WO | WO-2019223408 A1 | 11/2019 |
| WO | WO-2019230857 A1 | 12/2019 |
| WO | WO-2019230858 A1 | 12/2019 |
| WO | WO-2019236396 A1 | 12/2019 |
| WO | WO-2019244066 A2 | 12/2019 |
| WO | WO-2020086555 A1 | 4/2020 |
| WO | WO-2020112931 A1 | 6/2020 |
| WO | WO-2020221294 A1 | 11/2020 |
| WO | WO-2020246910 A1 | 12/2020 |

OTHER PUBLICATIONS

Bowers, G. et al. (2016) "Disposition and metabolism of cabotegravir: a comparison of biotransformation and excretion between different species and routes of administration in humans" Xenobiotica, 46(2):147-162.
Brooks, K. et al. (2019) "Integrase Inhibitors: After 10 Years of Experience, Is the Best Yet to Come?" Pharmacotherapy, 1-23.
Burns, J. et al. (2020) "No overall change in the rate of weight gain after switching to an integrase-inhibitor in virologically suppressed adults with HIV" AIDS, 34:109-114.
Castellino, S. et al. (2013) "Metabolism, Excretion, and Mass Balance of the HIV-1 Integrase Inhibitor Dolutegravir in Humans" 57(8):3536-3546.
Cook, N. et al. (2019) "Structural basis of second-generation HIV Integrase inhibitor action and viral resistance" Science, 1-9.
Flexner, C. (2020) "Novel Approaches to HIV Treatment and Prevention using Long Acting Drug Delivery" Johns Hopkins University, Division of Clinical Pharmacology, 45 pages.
Gallant, J. et al. (2017) "Antiviral Activity, Safety, and Pharmacokinetics of Bictegravir as 10-Day Monotherapy in HIV-1-Infected Adults" J Acquir Immune Defic Syndr, 75(1):61-66.
Groseclose, M. et al. (2019) "Intramuscular and subcutaneous drug depot characterization of a long-acting abotegravir nanoformulation by MALDI IMS" International Journal of Mass Spectometry, 437:92-98.
Hill, L. et al. (2018) "Profile of bictegravir/emtricitabine/tenofovir alafenamide fixed dose combination and its potential in the treatment of HIV-1 infection: evidence to date" HIV/AIDS—Research and Palliative Care, 10:203-213.
Hughes, D. (2019) "Review of Synthetic Routes and Final Forms of Integrase Inhibitors Dolutegravir, Cabotegravir, and Bictegravir" Organic Process Research & Development, 23:716-729.
Intl. Search Report and Written Opinion dated May 27, 2020 for Intl. Appl. No. PCT/US2020/023819.
Jiskoot, W. (2020) "Long-actinginjectables& implantables: immunogenicityconcerns" Third Long-Acting Injectables & Implantables Conference, 32 pages.
Johns, B. et al. (2013) "Carbamoyl Pyridone HIV?1 Integrase Inhibitors 3. A Diastereomeric Approach to Chiral Nonracemic Tricyclic Ring Systems and the Discovery of Dolutegravir (S/GSK1349572) and (S/GSK1265744)" J. Med. Chem., 56:5901-5916.
Kandel, C. et al. (2015) "Dolutegravir—a review of the pharmacology, efficacy, and safety in the treatment of HIV" Drug Design, Development and Therapy, 9:3547-3555.
Lalezari, J. et al. (2009) "Potent Antiviral Activity of S/GSK1349572, A Next Generation Integrase Inhibitor (INI), in INI-Naive HIV-1-Infected Patients: ING111521 Protocol" IAS 2009, 5th Conference on HIV Pathogenesis, Abstract TUAB105, 15 pages.
Landovitz, R. et al. (2018) "Safety, tolerability, and pharmacokinetics of long-acting injectable cabotegravir in low-risk HIV-uninfected individuals: HPTN 077, a phase 2a randomized controlled trial" PLoS Med, 15(11):1-22.
Le Hingrat, Q. et al. (2018) "A New Mechanism of Resistance of Human Immunodeficiency Virus Type 2 to Integrase Inhibitors: A 5-Amino-Acid Insertion in the Integrase C-Terminal Domain" Clinical Infectious Diseases, 1-11.
Liu, S. et al. (2019) "Mechanistic Assessment of Extrahepatic Contributions to Glucuronidation of Integrase Strand Transfer Inhibitors" Drug Metabolism and Disposition, 47(5) 535-544.
Mcmillan, J. et al. (2019) "Pharmacokinetic testing of a first generation cabotegravir prodrug in rhesus macaques" AIDS, 33(3):585-588.
Muller, R. et al. (2011) "State of the art of nanocrystals—Special features, production, nanotoxicology aspects and intracellular delivery" European Journal of Pharmaceuticals and Biopharmaceutics, 78:1-9.
Office Action dated Jan. 27, 2021 for Taiwan Appl. No. 109109428.
Orkin, C. et al. (2020) "Long-Acting Cabotegravir + Rilpivirine for HIV Treatment: Flair Week 96 Results" Conference on Retroviruses and Opportunistic Infections, Poster 0482, 1 page.
Passos, D. et al. (2020) "Structural basis for strand transfer inhibitor binding to HIV intasomes" Science, 1-9.
Passos, D. et al. (2020) Supplementary Materials for "Structural basis for strand transfer inhibitor binding to HIV intasomes" Science, Supplementary Text, 38 pages.
Raheem, I. et al. (2015) "Discovery of 2?Pyridinone Aminals: A Prodrug Strategy to Advance a Second Generation of HIV?1 Integrase Strand Transfer Inhibitors" J. Med. Chem., 58:8154-8165.
Scarsi, K. et al. (2020) "HIV-1 Integrase Inhibitors: A Comparative Review of Efficacy and Safety" Drugs, 80(16):1649-1676.
Shaik, J. et al. (2019) "A Phase 1 Study to Evaluate the Pharmacokinetics and Safety of Cabotegravir in Patients With Hepatic Impairment and Healthy Matched Controls" Clinical Pharmacology in Drug Development, 00(0):1-10.
Spreen, W. et al. (2013) "Pharmacokinetics, Safety, and Monotherapy Antiviral Activity of GSK1265744, an HIV Integrase Strand Transfer Inhibitor" HIV Clinical Trials, 14(5):192-203.
Spreen, W. et al. (2014) "GSK1265744 Pharmacokinetics in Plasma and Tissue After Single-Dose Long-Acting Injectable Administration in Healthy Subjects" J Acquir Immune Defic Syndr, 67(5):481-486.

(56) References Cited

OTHER PUBLICATIONS

Trezza, C. et al. (2015) "Formulation and pharmacology of long-acting cabotegravir" Current Opinion—HIV and AIDS, 10(4):239-245.

Walji, A. et al. (2015) "Discovery of MK-8970: An Acetal Carbonate Prodrug of Raltegravir with Enhanced Colonic Absorption" ChemMedChem, 10:245-252.

Weller, S. et al. (2014) "Pharmacokinetics of dolutegravir in HIV-seronegative subjects with severe renal impairment" Eur J Clin Pharmacol 70:29-35.

Yoshinaga, T. et al. (2015) "Antiviral Characteristics of GSK1265744, an HIV Integrase Inhibitor Dosed Orally or by Long-Acting Injection" 59(1):397-406.

Yoshinaga, T. et al. (2018) "Novel secondary mutations C56S and G149A confer resistance to HIV-1 integrase strand transfer inhibitors" Antiviral Research, 152:1-9.

Zhang, W. et al. (2018) "Accumulation of Multiple Mutations In Vivo Confers Cross-Resistance to New and Existing Integrase Inhibitors" The Journal of Infectious Diseases, 218:1773-1776.

BRIDGED TRICYCLIC CARBAMOYLPYRIDONE COMPOUNDS AND THEIR PHARMACEUTICAL USE

CROSS REFERENCE

This application claims priority to U.S. Provisional Application No. 62/822,703, filed Mar. 22, 2019, and U.S. Provisional Application No. 62/948,697, filed Dec. 16, 2019, both of which applications are incorporated herein in their entireties for all purposes.

BACKGROUND

Field

Compounds, compositions, and methods that may be used for treating or preventing human immunodeficiency virus (HIV) infection are disclosed. In particular, novel bridged tricyclic carbamoylpyridone compounds and methods for their preparation and use as therapeutic or prophylactic agents are disclosed.

Description of Related Art

Human immunodeficiency virus infection and related diseases are a major public health problem worldwide. Human immunodeficiency virus encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains may limit their usefulness (Palella, et al. *N. Engl. J Med.* (1998) 338:853-860; Richman, D. D. *Nature* (2001) 410:995-1001). Accordingly, there is a need for new agents that inhibit the replication of HIV.

A goal of antiretroviral therapy is to achieve viral suppression in the HIV infected patient. Current treatment guidelines published by the United States Department of Health and Human Services provide that achievement of viral suppression requires the use of combination therapies, i.e., several drugs from at least two or more drug classes (Panel on Antiretroviral Guidelines for Adults and Adolescents. Guidelines for the Use of Antiretroviral Agents in Adults and Adolescents Living with HIV. Department of Health and Human Services. Available at http://www.aidsinfo.nih.gov/ContentFiles/AdultandAdolescentGL.pdf. Accessed Feb. 12, 2019). In addition, decisions regarding the treatment of HIV infected patients are complicated when the patient requires treatment for other medical conditions (Id. at F-8). Because the standard of care requires the use of multiple different drugs to suppress HIV, as well as to treat other conditions the patient may be experiencing, the potential for drug interaction is a criterion for selection of a drug regimen. As such, there is a need for antiretroviral therapies having a decreased potential for drug interactions.

In addition, the HIV virus is known to mutate in infected subjects (Tang, et al. *Drugs* (2012) 72 (9) e1-e25). Because of the proclivity of the HIV virus to mutate, there is a need for anti-HIV drugs to be effective against a range of known HIV variants (Hurt, et al. *HIV/AIDS CID* (2014) 58, 423-431).

For certain patients, for example, those with difficult or limited access to health care, adherence to daily oral treatment or prophylactic regimens can be challenging. Drugs that offer favorable pharmaceutical properties (for example, improved potency, long-acting pharmacokinetics, low solubility, low clearance, and/or other properties) are amenable to less frequent administration and provide for better patient compliance. Such improvements can, in turn, optimize drug exposure and limit the emergence of drug resistance.

SUMMARY

The present disclosure is directed to novel compounds having antiviral activity and pharmaceutically acceptable salts thereof. In some embodiments, the compounds may be used to treat HIV infections, to inhibit the activity of HIV integrase and/or to reduce HIV replication. In some embodiments, compounds disclosed herein may be effective against a range of known drug-resistant HIV mutants. In some embodiments, compounds disclosed herein may have a decreased propensity to cause drug-drug interactions when co-administered with other drugs. In some embodiments, compounds disclosed herein may be administered with less than daily frequency, for example, at weekly, monthly, or longer intervals.

In one embodiment, compounds having the following formula (I) or pharmaceutically acceptable salts thereof are provided:

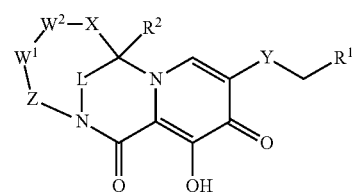

wherein
$R^1$ is H or $C_{6-10}$aryl, wherein $C_{6-10}$aryl is optionally substituted with one to four $R^{41}$, wherein each $R^{41}$ is independently halo, $C_{1-6}$alkyl, $C_{1-4}$haloalkyl, cyano, —O—$C_{1-4}$alkyl, or $C_{1-4}$alkyl-O—$C_{1-4}$alkyl;
$R^2$ is H, $C_{1-6}$alkyl, or $C_{1-4}$haloalkyl;
L is —$CR^{3a}R^{3b}$—, —C(O)—, —$SO_2$—, —$CH_2$—$CH_2$—, or —N($R^a$)—;
$W^1$ is a bond or —$CR^{4a}R^{4b}$—;
$W^2$ is —$CR^{5a}R^{5b}$—, —$CR^{5a}R^{5b}CR^{5c}R^{5d}$—, —$CR^{6a}$=$CR^{6b}$—, —N($R^7$)—, —O—, —S(O)$_{11}$—, —C(O)—, —C(O)O—, —C(O)NH—, —$CR^{5a}R^{5b}$—N($R^7$)—, —$CR^{5a}R^{5b}$—O—, —$CR^{5a}R^{5b}$—S(O)$_n$—, —$CR^{5a}R^{5b}$—C(O)—, —$CR^{5a}R^{5b}$—C(O)O—, —$CR^{5a}R^{5b}$—OC(O)—, —$CR^{5a}R^{5b}$—C(O)NH—, or —$CR^{5a}R^{5b}$—NHC(O)—;
X is a bond or —$CR^{8a}R^{8b}$—;
Y is —C(O)NH— or Q, wherein Q is

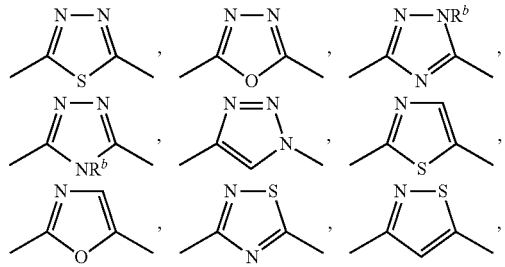

-continued

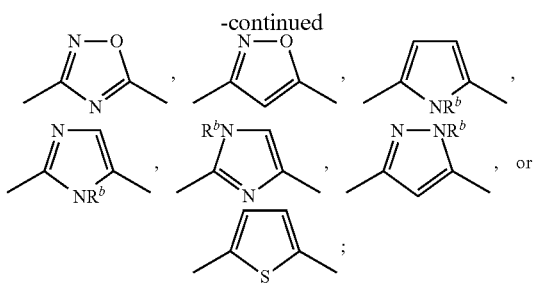

Z is —CR$^{9a}$R$^{9b}$—, —CR$^{9a}$R$^{9b}$CR$^{9c}$R$^{9d}$—, or —CR$^{10a}$=CR$^{10b}$—;

R$^{3a}$ and R$^{3b}$ are independently H, C$_{1-6}$alkyl, C$_{1-4}$haloalkyl, or —O—C$_{1-4}$alkyl; or optionally:

R$^{3a}$ and R$^{3b}$ together with the carbon atom to which they are attached form a 3- to 7-membered saturated or partially unsaturated spiro ring containing 0 to 2 heteroatoms selected from N, O, and S, wherein the spiro ring is optionally substituted with one to three R$^{A2}$, wherein each R$^{A2}$ is independently halo, C$_{1-4}$ alkyl or C$_{1-4}$haloalkyl;

R$^{4a}$ and R$^{4b}$ are independently H, C$_{1-6}$alkyl, C$_{1-4}$haloalkyl, or halo;

R$^{5a}$, R$^{5b}$, R$^{5c}$, and R$^{5d}$ are independently H, C$_{1-6}$alkyl, C$_{1-4}$haloalkyl, halo, hydroxyl, cyano, —O—C$_{1-4}$alkyl, or C$_{1-4}$alkylene-O—C$_{1-4}$alkyl; or optionally:

R$^{5a}$ and R$^{5b}$ or R$^{5c}$ and R$^{5d}$ together with the carbon atom to which they are attached form a 3- to 7-membered saturated or partially unsaturated spiro ring containing 0 to 2 heteroatoms selected from N, O, and S, wherein the spiro ring is optionally substituted with one to three R$^{A3}$, wherein each R$^{A3}$ is independently halo, C$_{1-4}$alkyl or C$_{1-4}$haloalkyl; or R$^{5a}$ and R$^{5c}$ or R$^{5b}$ and R$^{5d}$ together with the carbon atoms to which each is attached form a 3- to 7-membered saturated or partially unsaturated fused ring containing 0 heteroatoms or 1 heteroatom selected from N, O, and S, wherein the fused ring is optionally substituted with one to three R$^{A3}$, wherein each R$^{A3}$ is independently halo, C$_{1-4}$alkyl or C$_{1-4}$haloalkyl;

each R$^{6a}$ and R$^{1b}$ is independently H, halo, C$_{1-4}$haloalkyl, or C$_{1-6}$alkyl; optionally:

R$^{6a}$ and R$^{6b}$ together with the carbon atoms to which each is attached form a 5- to 10-membered partially unsaturated fused ring containing 0 heteroatoms or 1 heteroatom selected from N, O, and S, or a 5- to 10-membered fused aromatic ring, or a 5- to 10-membered fused heteroaromatic ring containing 1 to 2 heteroatoms selected from N, O and S, wherein the partially unsaturated fused ring, fused aromatic ring, or fused heteroaromatic ring is optionally substituted with one to four R$^{A4}$, wherein each R$^{A4}$ is independently halo or C$_{1-4}$alkyl;

R$^{7}$ is H, C$_{1-6}$alkyl, C$_{1-4}$haloalkyl, C(O)R$^{c}$, or SO$_{2}$R$^{c}$;

R$^{8a}$ and R$^{8b}$ are each independently H, hydroxyl, —O—C$_{1-4}$alkyl, C$_{1-4}$alkylene-O—C$_{1-4}$alkyl, C$_{1-6}$alkyl, C$_{1-4}$haloalkyl, cyano, or halo; or optionally:

R$^{8a}$ and R$^{8b}$ together with the carbon atom to which they are attached form a 3- to 7-membered saturated or partially unsaturated spiro ring containing 0 to 2 heteroatoms selected from N, O and S, wherein the spiro ring is optionally substituted with one to four R$^{A5}$, wherein each R$^{A5}$ is independently halo, C$_{1-4}$alkyl or C$_{1-4}$haloalkyl; or optionally:

R$^{8a}$ is H, hydroxyl, —O—C$_{1-4}$alkyl, C$_{1-4}$alkylene-O—C$_{1-4}$alkyl, C$_{1-6}$alkyl, C$_{1-4}$haloalkyl, cyano, or halo; and R$^{8b}$ and one of R$^{5a}$, R$^{5b}$, R$^{5c}$, R$^{5d}$, and R$^{7}$ together with the atoms to which each is attached form a 3- to 7-membered saturated or partially unsaturated fused ring containing 0 to 2 heteroatoms selected from N, O and S, wherein the fused ring is optionally substituted with one to four R$^{A5}$, wherein each R$^{A5}$ is independently halo or C$_{1-4}$alkyl; or R$^{8b}$ and R$^{2}$ together with the carbon atoms to which each is attached form a 3- to 7-membered saturated or partially unsaturated fused ring containing 0 to 2 heteroatoms selected from N, O and S, wherein the fused ring is optionally substituted with one to four R$^{A5}$, wherein each R$^{A5}$ is independently halo or C$_{1-4}$alkyl;

R$^{9a}$, R$^{9b}$, R$^{9c}$, and R$^{9d}$ are each independently H, C$_{1-6}$alkyl, C$_{1-4}$haloalkyl, or halo; or optionally:

R$^{9a}$ and R$^{9b}$ or R$^{9c}$ and R$^{9d}$ together with the carbon atom to which they are attached form a 3- to 7-membered saturated or partially unsaturated spiro ring containing 0 to 2 heteroatoms selected from N, O, and S, wherein the spiro ring is optionally substituted with one to three R$^{A6}$, wherein each R$^{A6}$ is independently halo, C$_{1-4}$alkyl or C$_{1-4}$haloalkyl; or R$^{9a}$ and R$^{9c}$ or R$^{9b}$ and R$^{9d}$ together with the carbon atoms to which each is attached form a 3- to 7-membered saturated or partially unsaturated fused ring containing 0 heteroatoms or 1 heteroatom selected from N, O, and S, wherein the fused ring is optionally substituted with one to three R$^{A6}$, wherein each R$^{A6}$ is independently halo, C$_{1-4}$alkyl, or C$_{1-4}$haloalkyl; or one of R$^{9a}$, R$^{9b}$, R$^{9c}$, and R$^{9d}$ and one of R$^{4a}$, R$^{4b}$, R$^{5a}$, R$^{5b}$, and R$^{7}$ together with the atoms to which each is attached form a 3- to 7-membered saturated or partially unsaturated fused ring containing 0 to 2 heteroatoms selected from N, O and S, wherein the fused ring is optionally substituted with one to four R$^{A6}$, wherein each R$^{A6}$ is independently halo or C$_{1-4}$alkyl;

R$^{10a}$ and R$^{10b}$ are independently H, halo, C$_{1-4}$haloalkyl, or C$_{1-6}$alkyl; or optionally:

R$^{10a}$ and R$^{10b}$ together with the carbon atoms to which each is attached form a 5- to 10-membered partially unsaturated fused ring containing 0 heteroatoms or 1 heteroatom selected from N, O, and S, or a 5- to 10-membered fused aromatic ring, or a 5- to 10-membered fused heteroaromatic ring containing 1 to 2 heteroatoms selected from N, O and S, wherein the partially unsaturated fused ring, fused aromatic ring, or fused heteroaromatic ring is optionally substituted with one to four R$^{A7}$, wherein each R$^{A7}$ is independently halo or C$_{1-4}$alkyl;

R$^{a}$ is independently H, C$_{1-4}$alkyl, C$_{1-6}$haloalkyl, C(O)R$^{c}$, or SO$_{2}$R$^{c}$;

R$^{b}$ is H or C$_{1-4}$alkyl;

R$^{c}$ is C$_{1-4}$alkyl or —O—C$_{1-4}$alkyl; and each n is 0, 1, or 2.

In one aspect, a pharmaceutical composition is provided comprising a therapeutically effective amount of a compound of formula I or a pharmaceutically acceptable salt thereof, and a pharmaceutically acceptable excipient.

In another embodiment, a kit or an article of manufacture comprising a compound of formula I or a pharmaceutically acceptable salt thereof, and instructions for use.

In another embodiment, a method of treating an HIV infection in a human having or at risk of having the infection, by administering to the human a therapeutically effective amount of a compound of formula I or a pharmaceutically acceptable salt thereof, or a pharmaceutical composition of a compound of formula I or a pharmaceutically acceptable salt thereof, is provided.

In another embodiment, use of a compound of formula I or a pharmaceutically acceptable salt thereof, or a pharmaceutical composition of a compound of formula I or a pharmaceutically acceptable salt thereof, for treating an HIV infection in a human having or at risk of having the infection is provided.

In another embodiment, a compound of formula I or a pharmaceutically acceptable salt thereof, or a pharmaceutical composition of a compound of formula I or a pharmaceutically acceptable salt thereof, for use in medical therapy is provided.

In another embodiment, a compound of formula I or a pharmaceutically acceptable salt thereof, or a pharmaceutical composition of a compound of formula I or a pharmaceutically acceptable salt thereof, for use in treating an HIV infection is provided.

In another embodiment, use of a compound of formula I or a pharmaceutically acceptable salt thereof in the manufacture of a medicament for treating an HIV infection in a human having or at risk of having the infection is provided.

In another embodiment, a method of using a compound of formula I in therapy is provided. In particular, a method of treating the proliferation of the HIV virus, treating AIDS, or delaying the onset of AIDS or ARC symptoms in a mammal (e.g., a human), comprising administering to the mammal a compound of formula I or a pharmaceutically acceptable salt thereof, and a pharmaceutically acceptable excipient, is provided.

In another embodiment, a composition comprising a compound of formula I or a pharmaceutically acceptable salt thereof, and a pharmaceutically acceptable excipient, for use in a method of treating the proliferation of the HIV virus, treating AIDS, or delaying the onset of AIDS or ARC symptoms in a mammal (e.g., a human) is provided.

In another embodiment, a kit or an article of manufacture comprising a composition effective to treat or prevent an HIV infection; and packaging material comprising a label which indicates that the composition can be used to treat or prevent infection by HIV, is provided. Exemplary compositions comprise a compound of formula I as disclosed herein or a pharmaceutically acceptable salt thereof.

In still another embodiment, a method of inhibiting the replication of HIV is provided. The method comprises exposing the virus to an effective amount of a compound of formula I or a salt thereof, under conditions where replication of HIV is inhibited.

In another embodiment, the use of a compound of formula I to inhibit the activity of the HIV integrase enzyme is provided.

In another embodiment, the use of a compound of formula I or a pharmaceutically acceptable salt thereof to inhibit the activity of the HIV integrase enzyme is provided.

In another embodiment, the use of a compound of formula I or a salt thereof, to inhibit the replication of HIV is provided.

In another embodiment, the use of a compound of formula I or a pharmaceutically acceptable salt thereof, as a research tool is provided.

Other embodiments, objects, features, and advantages may be set forth in the detailed description of the embodiments that follows, and in part may be apparent from the description, or may be learned by practice, of the claimed embodiments. These objects and advantages may be realized and attained by the processes and compositions particularly pointed out in the description and claims thereof. The foregoing Summary has been made with the understanding that it is to be considered as a brief and general synopsis of some of the embodiments disclosed herein, is provided for the benefit and convenience of the reader, and is not intended to limit in any manner the scope, or range of equivalents, to which the appended claims are lawfully entitled.

DETAILED DESCRIPTION

In the following description, certain specific details are set forth in order to provide a thorough understanding of various embodiments disclosed herein. However, one skilled in the art will understand that the embodiments disclosed herein may be practiced without these details. The description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

Definitions

Unless the context requires otherwise, throughout the present disclosure and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment disclosed herein. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —NH$_2$ radical.

"Hydroxy" or "hydroxyl" refers to the —OH radical.

"Oxo" refers to the =O substituent.

A prefix such as "C$_{u-v}$" or (C$_u$-C$_v$) indicates that the following group has from u to v carbon atoms. For example, "C$_{1-6}$alkyl" indicates that the alkyl group has from 1 to 6 carbon atoms.

"Alkyl" refers to a straight or branched chain hydrocarbon radical consisting of carbon and hydrogen atoms, which is saturated, having from one to twelve carbon atoms (C$_{1-12}$ alkyl), in certain embodiments one to eight carbon atoms (C$_{1-8}$alkyl) or one to six carbon atoms (C$_{1-6}$alkyl), or one to four carbon atoms (C$_{1-4}$alkyl), and which is attached to the rest of the molecule by a single bond, e.g., methyl, ethyl, n-propyl, 1-methylethyl (iso-propyl), n-butyl, 1-methylpropyl (sec-butyl), 2-methylpropyl (iso-butyl), 1,1-dimethylethyl (t-butyl), n-pentyl, hexyl, 3-methylhexyl, 2-methylhexyl, and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 12 carbon atoms, 1 to 10 carbon atoms, 1 to 6 carbon atoms, or 1 to 4 atoms. Typical alkylene radicals include, but are not limited to, methylene (—CH$_2$—), 1,1 ethyl (—CH(CH$_3$)—), 1,2-ethyl (—CH$_2$CH$_2$—), 1,1-propyl (—CH(CH$_2$CH$_3$)—), 1,2-propyl (—CH$_2$CH(CH$_3$)—), 1,3-propyl (—CH$_2$CH$_2$CH$_2$—), 1,4-butyl (—CH$_2$CH$_2$CH$_2$CH$_2$—), and the like.

"Aryl" or "aromatic ring" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), 6 to 10 carbon ring atoms (i.e., $C_{6-10}$ aryl), or 5 to 10 carbon ring atoms (i.e., $C_{5-10}$ aryl). Examples of aryl groups include, but are not limited to, phenyl, naphthyl, fluorenyl, and anthryl.

"Cyano" or "carbonitrile" refers to the group —CN.

"Carbocyclic ring" refers to a non-aromatic hydrocarbon ring consisting of carbon and hydrogen atoms, having from three to fifteen carbon atoms, in certain embodiments having from three to ten carbon atoms or from three to seven carbon atoms, and which is saturated or partially unsaturated and attached to the rest of the molecule by a single bond. Carbocyclic rings include, for example, cyclopropane, cyclobutane, cyclopentane, cyclopentene, cyclohexane, cyclohexene, 1,3-cyclohexadiene, 1,4-cyclohexadiene, cycloheptane, cycloheptene, and cyclooctane.

"Fused" refers to a carbocyclic, heterocyclic, aromatic, or heteroaromatic ring structure described herein which is connected to an existing ring structure in the compounds disclosed herein via two adjacent atoms that are shared by the fused ring structure and the existing ring structure. For example, the bicyclic compounds depicted below incorporate fused cyclopropane (i.e., a cyclopropane ring fused to a cyclohexane ring), a fused pyrrolidine (i.e., a pyrrolidine ring fused to a benzene ring), and fused thiophene (i.e., a thiene ring fused to a furan ring), respectively:

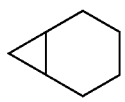 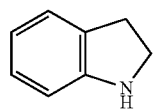 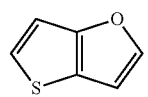

"Spiro" or "spirocyclic" refers to a carbocyclic or heterocyclic ring structure described herein which is connected to an existing ring structure in the compounds disclosed herein via a single atom that is shared by the spiro ring structure and the existing ring structure. For example, the bicyclic compounds below incorporate spiro cyclopropane (i.e., a cyclopropane ring that is spirocyclic to a cyclohexane ring), spiro 1,3-dithiolane (i.e., a 1,3-dithiolane ring that is spirocyclic to a cycloheptane ring), and spiro cyclopentene (i.e., a cyclopentene ring that is spirocyclic to a cyclohexene ring), respectively:

"Halo" or "halogen" refers to bromo, chloro, fluoro or iodo.

"Haloalkyl" refers to an alkyl group, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heteroaromatic ring" refers to an aromatic group having a single ring, multiple rings, or multiple fused rings, with one or more ring heteroatoms (for example, 1 to 3 ring heteroatoms, 1 to 2 ring heteroatoms, or 1 ring heteroatom) independently selected from nitrogen, oxygen, and sulfur. As used herein, heteroaryl includes 5 to 20 ring atoms (5 to 20 membered heteroaromatic ring), 5 to 12 ring atoms (5 to 12 membered heteroaromatic ring), 5 to 10 ring atoms (5 to 10 membered heteroaromatic ring) or 5 to 6 ring atoms (5 to 6 membered heteroaromatic ring). Examples of heteroaryl groups include pyrimidinyl, purinyl, pyridyl, pyridazinyl, benzothiazolyl, and pyrazolyl.

"Heterocyclyl" or "heterocyclic ring" refers to a non-aromatic radical or ring having from three to fifteen atoms wherein from one to six atoms are heteroatoms selected from the group consisting of nitrogen, oxygen and sulfur and attached to the rest of the molecule by a single bond. In certain embodiments, "heterocyclyl" has from three to ten atoms, wherein from one to four atoms are heteroatoms selected from the group consisting of nitrogen, oxygen and sulfur, or from three to seven atoms, wherein from one to two atoms are heteroatoms selected from the group consisting of nitrogen, oxygen and sulfur. The nitrogen, carbon or sulfur atoms in the heterocyclyl may be optionally oxidized; the nitrogen atom may be optionally quaternized. As used herein, "heterocyclyl" or "heterocyclic ring" refers to rings that are saturated unless otherwise indicated, e.g., in some embodiments "heterocyclyl" or "heterocyclic ring" refers to rings that are saturated or partially saturated where specified. Examples of such heterocyclyl include, but are not limited to, dioxolanyl, imidazolidinyl, isothiazolidinyl, isoxazolidinyl, morpholinyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuranyl, trithianyl, tetrahydropyranyl, thiomorpholinyl, thiamorpholinyl, 1-oxo-thiomorpholinyl, and 1,1-dioxo-thiomorpholinyl.

The embodiments disclosed herein are also meant to encompass all pharmaceutically acceptable compounds of formula I being isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. In certain embodiments, these radiolabeled compounds are useful to help determine or measure the effectiveness of the compounds, by characterizing, for example, the site or mode of action, or binding affinity to pharmacologically important site of action. Certain isotopically-labeled compounds of formula I, II, IIIa, IIIb, IV, Va, Vb, VI, VIIa, VIIb, VIII, IX, IXa, IXb, X, Xa, Xb, XI, XIa, or XIb, for example, those incorporating a radioactive isotope, are useful in drug and/or substrate tissue distribution studies. The radioactive isotopes tritium, i.e., $^3H$, and carbon-14, i.e., $^{14}C$, are particularly useful for this purpose in view of their ease of incorporation and ready means of detection.

In certain embodiments, substitution with heavier isotopes such as deuterium, i.e., $^2H$, may afford certain therapeutic advantages resulting from greater metabolic stability. For example, in vivo half-life may increase or dosage requirements may be reduced. Thus, heavier isotopes may be preferred in some circumstances.

Substitution with positron emitting isotopes, such as $^{11}C$, $^{18}F$, $^{15}O$, and $^{13}N$, can be useful in Positron Emission Topography (PET) studies for examining substrate receptor occupancy. Isotopically-labeled compounds of formula I can be prepared by techniques known to those skilled in the art or by processes analogous to those described in the Examples as set out below using an appropriate isotopically-labeled reagent in place of the non-labeled reagent previously employed.

The methods, compositions, kits and articles of manufacture provided herein use or include compounds (e.g., a compound of formula I, II, IIIa, IIIb, IV, Va, Vb, VI, VIIa, VIIb, VIII, IX, IXa, IXb, X, Xa, Xb, XI, XIa, or XIb) or pharmaceutically acceptable salts thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds increase resistance to metabolism, and thus are useful for increasing the half-life of compounds or pharmaceutically acceptable salts thereof, when administered to a mammal. See, e.g., Foster, "Deuterium Isotope Effects in Studies of Drug Metabolism", *Trends Pharmacol. Sci.*, 5(12):524-527 (1984). Such compounds can be synthesized by means known in the art, for example by employing starting materials in which one or more hydrogen atoms have been replaced by deuterium.

The embodiments disclosed herein are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the embodiments disclosed herein include compounds produced by a process comprising administering a compound according to the embodiments disclosed herein to a mammal for a period of time sufficient to yield a metabolic product thereof. Such products are typically identified by administering a radiolabeled compound according to the embodiments disclosed herein in a detectable dose to an animal, such as rat, mouse, guinea pig, monkey, or to human, allowing sufficient time for metabolism to occur, and isolating its conversion products from the urine, blood or other biological samples.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event or circumstances may or may not occur, and that the description includes instances where said event or circumstance occurs and instances in which it does not. For example, "optionally substituted heterocyclyl" means that the heterocyclyl radical may or may not be substituted and that the description includes both substituted heterocyclyl radicals and heterocyclyl radicals having no substitution.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or other pharmacologically inactive substance that is formulated in combination with a pharmacologically active ingredient of a pharmaceutical composition and is compatible with the other ingredients of the formulation and suitable for use in humans or domestic animals without undue toxicity, irritation, allergic response, and the like.

Examples of "pharmaceutically acceptable salts" of the compounds disclosed herein include salts derived from an appropriate base, such as an alkali metal (for example, sodium), an alkaline earth metal (for example, magnesium), ammonium and $NX_4^+$ (wherein X is $C_{1-4}$alkyl). Pharmaceutically acceptable salts of a nitrogen atom or an amino group include, for example, salts of organic carboxylic acids such as acetic, trifluoroacetic, adipic, ascorbic, aspartic, butyric, camphoric, cinnamic, citric, digluconic, glutamic, glycolic, glycerophosphoric, formic, hexanoic, benzoic, lactic, fumaric, tartaric, maleic, hydroxymaleic, malonic, malic, mandelic, isethionic, lactobionic, nicotinic, oxalic, pamoic, pectinic, phenylacetic, 3-phenylpropionic, pivalic, propionic, pyruvic, salicylic, stearic, sulfanilic, tartaric, undecanoic, and succinic acids; organic sulfonic acids, such as methanesulfonic, ethanesulfonic, camphorsulfonic, mesitylenesulfonic, benzenesulfonic, p-toluenesulfonic acids, naphthalenesulfonic, and 2-naphthalenesulfonic; and inorganic acids, such as hydrochloric, hydrobromic, sulfuric, phosphoric, nitric, and sulfamic acids. Pharmaceutically acceptable salts of a compound of a hydroxy group include the anion of said compound in combination with a suitable cation such as $Na^+$ and $NX_4^+$ (wherein X is independently selected from H or a $C_{1-4}$alkyl group).

For therapeutic use, salts of active ingredients of the compounds disclosed herein will typically be pharmaceutically acceptable, i.e., they will be salts derived from a physiologically acceptable acid or base. However, salts of acids or bases which are not pharmaceutically acceptable may also find use, for example, in the preparation or purification of a compound of formula I or another compound of the embodiments disclosed herein. All salts, whether or not derived from a physiologically acceptable acid or base, are within the scope of the embodiments disclosed herein.

Metal salts typically are prepared by reacting the metal hydroxide with a compound according to the embodiments disclosed herein. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines. Finally, it is to be understood that the compositions herein comprise compounds disclosed herein in their un-ionized, as well as zwitterionic form.

A "pharmaceutical composition" refers to a formulation of a compound of the embodiments disclosed herein and a medium generally accepted in the art for the delivery of the biologically active compound to mammals, e.g., humans. Such a medium includes all pharmaceutically acceptable excipients.

"Effective amount" or "therapeutically effective amount" refers to an amount of a compound according to the embodiments disclosed herein, which when administered to a patient in need thereof, is sufficient to effect treatment of disease-states, conditions, or disorders disclosed herein. Such an amount would be sufficient to elicit the biological or medical response of a tissue system, or patient that is sought by a researcher or clinician. The amount of a compound according to the embodiments disclosed herein which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination, or coincidentally, with the compounds of the embodiments disclosed herein, and the age, body weight, general health, sex and diet of the patient. Such a therapeutically effective amount can be determined by one of ordinary skill in the art having regard to their own knowledge, the state of the art, and this disclosure.

The terms "treating" and "treatment" as used herein are intended to mean the administration of a compound or composition according to the present embodiments disclosed herein to alleviate or eliminate one or more symptoms of HIV infection and/or to reduce viral load in a patient. In certain embodiments, the terms "treating" and "treatment" also encompass the administration of a compound or composition according to the present embodiments disclosed herein post-exposure of the individual to the virus but before the appearance of symptoms of the disease, and/or prior to the detection of the virus in the blood, to prevent the appearance of symptoms of the disease and/or to prevent the virus from reaching detectable levels in the blood, and the administration of a compound or composition according to the present embodiments disclosed herein to prevent perinatal transmission of HIV from mother to baby, by administration to the mother before giving birth and to the child within the first days of life. The terms "treating" and "treatment" also encompass the administration of a compound or composition according to the present embodiments disclosed herein before the exposure of the individual to the virus (also called pre-exposure prophylaxis or PrEP), to prevent HIV infection from taking hold if the individual is exposed to the virus and/or to keep the virus from establishing a permanent infection and/or to prevent the appearance of symptoms of the disease and/or to prevent the virus from reaching detectable levels in the blood. The terms "treating" and "treatment" also encompass the administration of a compound or composition according to the present embodiments disclosed herein both before and after the exposure of the individual to the virus.

As used herein, the terms "preventing" and "prevention" refer to the administration of a compound, composition, or pharmaceutically salt according to the present disclosure pre- or post-exposure of the human to the virus but before the appearance of symptoms of the disease, and/or prior to the detection of the virus in the blood. The terms also refer to prevention of the appearance of symptoms of the disease and/or to prevent the virus from reaching detectible levels in the blood. The terms include both pre-exposure prophylaxis (PrEP), as well as post-exposure prophylaxis (PEP) and event driven or "on demand" prophylaxis. The terms also refer to prevention of perinatal transmission of HIV from mother to baby, by administration to the mother before giving birth and to the child within the first days of life. The terms also refer to prevention of transmission of HIV through blood transfusion.

The term "antiviral agent" as used herein is intended to mean an agent (compound or biological) that is effective to inhibit the formation and/or replication of a virus in a human being, including but not limited to agents that interfere with either host or viral mechanisms necessary for the formation and/or replication of a virus in a human being.

The term "inhibitor of HIV replication" as used herein is intended to mean an agent capable of reducing or eliminating the ability of HIV to replicate in a host cell, whether in vitro, ex vivo or in vivo.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic, scalemic, and optically pure forms. Optically active (+) and (−), (R)- and (S)-, or (D)- and (L)-isomers may be prepared using chiral synthons or chiral reagents, or resolved using methods such as chromatography and fractional crystallization. Techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another. In any of the embodiments disclosed herein, compounds disclosed herein may be in the form of a stereoisomer thereof.

"Partially unsaturated" refers to a cyclic group which contains at least one double bond but is not aromatic.

Compounds

Provided herein are compounds that function as anti-HIV agents, pharmaceutical compositions comprising such compounds optionally in combination with one or more (e.g., two, three, or four) additional therapeutic agents, and methods of using such compounds and compositions. All compound embodiments described herein include any pharmaceutically acceptable salt, stereoisomer, or mixture of stereoisomers thereof.

In one embodiment, a compound of the following formula (I) is provided:

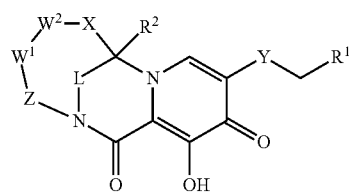

I or a pharmaceutically acceptable salt thereof, wherein
R$^1$ is H or C$_{6-10}$aryl, wherein C$_{6-10}$aryl is optionally substituted with one to four R$^{41}$, wherein each R$^{41}$ is independently halo, C$_{1-6}$alkyl, C$_{1-4}$haloalkyl, cyano, —O—C$_{1-4}$alkyl, or C$_{1-4}$alkyl-O—C$_{1-4}$alkyl;
R$^2$ is H, C$_{1-6}$alkyl, or C$_{1-4}$haloalkyl;
L is —CR$^{3a}$R$^{3b}$—, —C(O)—, —SO$_2$—, —CH$_2$—CH$_2$—, or —N(R$^a$)—;
W$^1$ is a bond or —CR$^{4a}$R$^{4b}$—;
W$^2$ is —CR$^{5a}$R$^{5b}$, —CR$^{5a}$R$^{5b}$CR$^{5c}$R$^{5d}$—, —CR$^{6a}$=CR$^{6b}$—, —N(R$^7$)—, —O—, —S(O)$_{11}$—, —C(O)—, —C(O)O—, —C(O)NH—, —CR$^{5a}$R$^{5b}$—N(R$^7$)—, —CR$^{5a}$R$^{5b}$—O—, —CR$^{5a}$R$^{5b}$—S(O)$_n$—, —CR$^{5a}$R$^{5b}$—C(O)—, —CR$^{5a}$R$^{5b}$—C(O)O—, —CR$^{5a}$R$^{5b}$—OC(O)—, —CR$^{5a}$R$^{5b}$—C(O)NH—, or —CR$^{5a}$R$^{5b}$—NHC(O)—;
X is a bond or —CR$^{8a}$R$^{8b}$—;
Y is —C(O)NH— or Q, wherein Q is

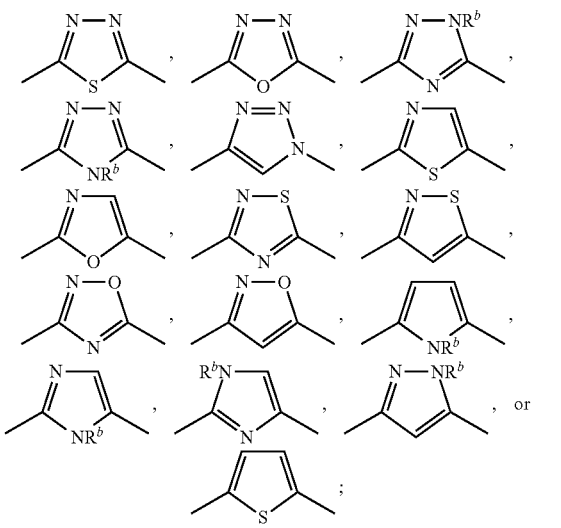

Z is —CR$^{9a}$R$^{9b}$—, —CR$^{9a}$R$^{9b}$—CR$^{9c}$R$^{9d}$—, or —CR$^{10a}$=CR$^{10b}$—;
R$^{3a}$ and R$^{3b}$ are independently H, C$_{1-6}$alkyl, C$_{1-4}$haloalkyl, or —O—C$_{1-4}$alkyl; or optionally:
R$^{3a}$ and R$^{3b}$ together with the carbon atom to which they are attached form a 3- to 7-membered saturated or partially unsaturated spiro ring containing 0 to 2 heteroatoms selected from N, O, and S, wherein the spiro ring is optionally substituted with one to three R$^{42}$, wherein each R$^{42}$ is independently halo, C$_{1-4}$alkyl or C$_{1-4}$haloalkyl;
R$^{4a}$ and R$^{4b}$ are independently H, C$_{1-6}$alkyl, C$_{1-4}$haloalkyl, or halo;
R$^{5a}$, R$^{5b}$, R$^{5c}$, and R$^{5d}$ are independently H, C$_{1-6}$alkyl, C$_{1-4}$haloalkyl, halo, hydroxyl, cyano, —O—C$_{1-4}$alkyl, or C$_{1-4}$alkylene-O—C$_{1-4}$alkyl; or optionally:
R$^{5a}$ and R$^{5b}$ or R$^{5c}$ and R$^{5d}$ together with the carbon atom to which they are attached form a 3- to 7-membered saturated or partially unsaturated spiro ring containing 0 to 2 heteroatoms selected from N, O, and S, wherein the spiro ring is optionally substituted with one to three R$^{43}$, wherein each R$^{43}$ is independently halo, C$_{1-4}$alkyl or C$_{1-4}$haloalkyl; or
R$^{5a}$ and R$^{5c}$ or R$^{5b}$ and R$^{5d}$ together with the carbon atoms to which each is attached form a 3- to 7-membered saturated or partially unsaturated fused ring containing 0 heteroatoms or 1 heteroatom selected from N, O, and S, wherein the fused ring is optionally substituted with one to three R$^{43}$, wherein each R$^{43}$ is independently halo, C$_{1-4}$alkyl or C$_{1-4}$haloalkyl;
each R$^{6a}$ and R$^{6b}$ is independently H, halo, C$_{1-4}$haloalkyl, or C$_{1-6}$alkyl; optionally:
R$^{6a}$ and R$^{6b}$ together with the carbon atoms to which each is attached form a 5- to 10-membered partially unsaturated fused ring containing 0 heteroatoms or 1 heteroatom selected from N, O, and S, or a 5- to 10-membered fused aromatic ring, or a 5- to 10-membered fused heteroaromatic ring containing 1 to 2 heteroatoms selected from N, O and S, wherein the partially unsaturated fused ring, fused aromatic ring, or fused heteroaromatic ring is optionally substituted with one to four R$^{44}$, wherein each R$^{44}$ is independently halo or C$_{1-4}$alkyl;
R$^7$ is H, C$_{1-6}$alkyl, C$_{1-4}$haloalkyl, C(O)R$^c$, or SO$_2$R$^c$;
R$^{8a}$ and R$^{8b}$ are each independently H, hydroxyl, —O—C$_{1-4}$alkyl, C$_{1-4}$alkylene-O—C$_{1-4}$alkyl, C$_{1-6}$alkyl, C$_{1-4}$haloalkyl, cyano, or halo; or optionally:
R$^{8a}$ and R$^{8b}$ together with the carbon atom to which they are attached form a 3- to 7-membered saturated or partially unsaturated spiro ring containing 0 to 2 heteroatoms selected from N, O, and S, wherein the spiro ring is optionally substituted with one to four R$^{45}$, wherein each R$^{45}$ is independently halo, C$_{1-4}$alkyl or C$_{1-4}$haloalkyl; or optionally:
R$^{8a}$ is H, hydroxyl, —O—C$_{1-4}$alkyl, C$_{1-4}$alkylene-O—C$_{1-4}$alkyl, C$_{1-6}$alkyl, C$_{1-4}$haloalkyl, cyano, or halo; and
R$^{8b}$ and one of R$^{5a}$, R$^{5b}$, R$^{5c}$, R$^{5d}$, and R$^7$ together with the atoms to which each is attached form a 3- to 7-membered saturated or partially unsaturated fused ring containing 0 to 2 heteroatoms selected from N, O and S, wherein the fused ring is optionally substituted with one to four R$^{45}$, wherein each R$^{45}$ is independently halo or C$_{1-4}$alkyl; or
R$^{8b}$ and R$^2$ together with the carbon atoms to which each is attached form a 3- to 7-membered saturated or partially unsaturated fused ring containing 0 to 2 heteroatoms selected from N, O and S, wherein the fused ring is optionally substituted with one to four R$^{45}$, wherein each R$^{45}$ is independently halo or C$_{1-4}$alkyl;
R$^{9a}$, R$^{9b}$, R$^{9c}$, and R$^{9d}$ are each independently H, C$_{1-6}$alkyl, C$_{1-4}$haloalkyl, or halo; or optionally:
R$^{9a}$ and R$^{9b}$ or R$^{9c}$ and R$^{9d}$ together with the carbon atom to which they are attached form a 3- to 7-membered saturated or partially unsaturated spiro ring containing 0 to 2 heteroatoms selected from N, O, and S, wherein the spiro ring is optionally substituted with one to three R$^{46}$, wherein each R$^{46}$ is independently halo, C$_{1-4}$alkyl or C$_{1-4}$haloalkyl; or
R$^{9a}$ and R$^{9c}$ or R$^{9b}$ and R$^{9d}$ together with the carbon atoms to which each is attached form a 3- to 7-membered saturated or partially unsaturated fused ring containing 0 heteroatoms or 1 heteroatom selected from N, O, and S, wherein the fused ring is optionally substituted with one to three R$^{46}$, wherein each R$^{46}$ is independently halo, C$_{1-4}$alkyl, or C$_{1-4}$haloalkyl; or
one of R$^{9a}$, R$^{9b}$, R$^{9c}$, and R$^{9d}$ and one of R$^{4a}$, R$^{4b}$, R$^{5a}$, R$^{5b}$, and R$^7$ together with the atoms to which each is attached form a 3- to 7-membered saturated or partially unsaturated fused ring containing 0 to 2 heteroatoms selected from N, O and S, wherein the fused ring is optionally substituted with one to four $R^{A6}$, wherein each $R^{A6}$ is independently halo or $C_{1-4}$alkyl;

$R^{10a}$ and $R^{10b}$ are independently H, halo, $C_{1-4}$haloalkyl, or $C_{1-6}$alkyl; or optionally:

$R^{10a}$ and $R^{10b}$ together with the carbon atoms to which each is attached form a 5- to 10-membered partially unsaturated fused ring containing 0 heteroatoms or 1 heteroatom selected from N, O, and S, or a 5- to 10-membered fused aromatic ring, or a 5- to 10-membered fused heteroaromatic ring containing 1 to 2 heteroatoms selected from N, O and S, wherein the partially unsaturated fused ring, fused aromatic ring, or fused heteroaromatic ring is optionally substituted with one to four $R^{A7}$, wherein each $R^{A7}$ is independently halo or $C_{1-4}$alkyl;

$R^a$ is independently H, $C_{1-6}$alkyl, $C_{1-6}$haloalkyl, C(O)$R^c$, or SO$_2R^c$;

$R^b$ is H or $C_{1-4}$alkyl;

$R^c$ is $C_{1-4}$alkyl or —O—$C_{1-4}$alkyl; and each n is 0, 1, or 2.

In some embodiments of the compound of formula I, or a pharmaceutically acceptable salt thereof, $R^2$ is H, $C_{1-4}$alkyl, or $C_{1-4}$haloalkyl. In some embodiments, $R^2$ is H or $C_{1-4}$ alkyl. In some embodiments, $R^2$ is H. In some embodiments, $R^2$ is $C_{1-4}$alkyl. In some embodiments, $R^2$ is methyl. In some embodiments, $R^2$ is H or methyl. In some embodiments, $R^2$ is $C_{1-4}$haloalkyl.

In some embodiments, $R^2$ is selected from the group consisting of H, —CH$_3$, —CH$_2$CH$_3$, and —CH$_2$F, or $R^2$ and $R^{8b}$ together with the carbon to which they are attached form a 3-membered fused carbocyclic ring. In some embodiments, $R^2$ is selected from the group consisting of H, —CH$_3$, —CH$_2$CH$_3$, and —CH$_2$F. In some embodiments, $R^2$ and $R^{8b}$ together with the carbon to which they are attached form a 3-membered fused carbocyclic ring.

In some embodiments of the compound of formula I, or a pharmaceutically acceptable salt thereof, Y is —C(O)NH—. In some embodiments, Y is Q. In some embodiments, Y is

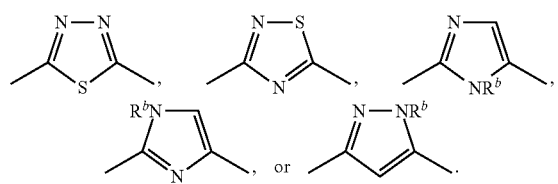

In some embodiments, the compound of formula I is a compound of formula (II):

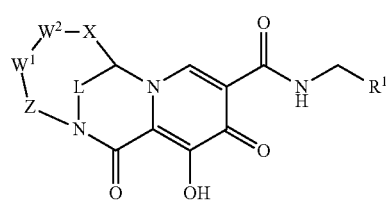

or a pharmaceutically acceptable salt thereof, wherein $R^1$, L, $W^1$, $W^2$, X, and Z are as defined in formula I.

In some embodiments of the compound of formula I or II, or a pharmaceutically acceptable salt thereof, $R^1$ is H. In some embodiments, $R^1$ is $C_{6-10}$aryl. In some embodiments, $R^1$ is phenyl, optionally substituted with one to four $R^{A1}$, wherein each $R^{A1}$ is independently halo, $C_{1-4}$alkyl, $C_{1-4}$haloalkyl, cyano, —O—$C_{1-4}$alkyl, or $C_{1-4}$alkyl-O—$C_{1-4}$alkyl. In some embodiments, $R^1$ is phenyl substituted with one, two, three, or four $R^{A1}$. In some embodiments, $R^1$ is phenyl substituted with one, two, three, or four $R^{A1}$. In some embodiments, $R^1$ is phenyl substituted with one, two, three, or four $R^{A1}$, wherein each $R^{A1}$ is independently halo, $C_{1-4}$alkyl, $C_{1-4}$ haloalkyl, or —O—$C_{1-4}$alkyl. In some embodiments, $R^1$ is phenyl substituted with one, two, three, or four $R^{A1}$, wherein each $R^{A1}$ is independently halo, $C_{1-4}$alkyl, or $C_{1-4}$haloalkyl. In some embodiments, $R^1$ is phenyl substituted with one, two, three, or four $R^{A1}$, wherein each $R^{A1}$ is independently halo or —O—$C_{1-4}$alkyl. In some embodiments, $R^1$ is phenyl substituted with one, two, three, or four halogens. In some embodiments, $R^1$ is phenyl substituted with one, two, or three halogens. In some embodiments, $R^1$ is phenyl substituted with two or three halogens. In some embodiments, $R^1$ is phenyl substituted with two or three halogens selected from chloro and fluoro. In some embodiments, $R^1$ is

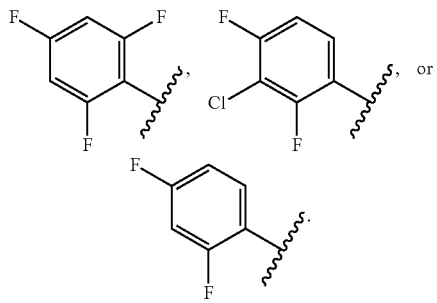

In some embodiments, of the compound of I or II, $R^1$ is selected from the group consisting of

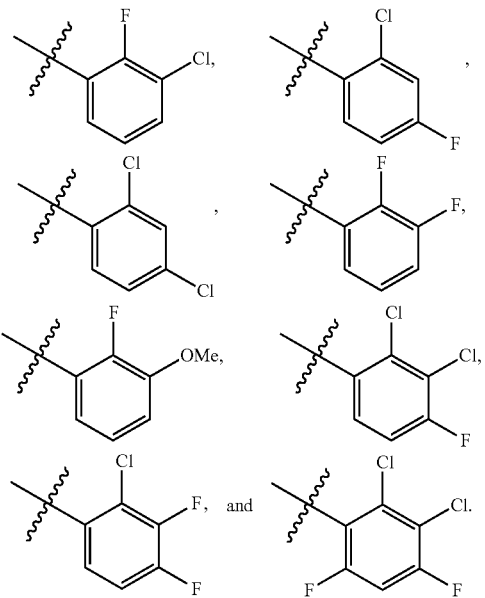

In some embodiments, of the compound of formula I or II, $R^1$ is selected from the group consisting of

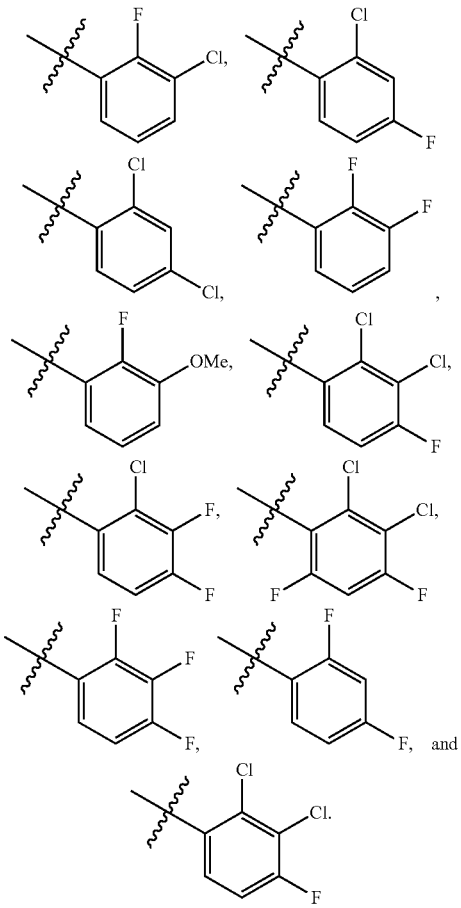

In some embodiments, $R^1$ is selected from the group consisting of

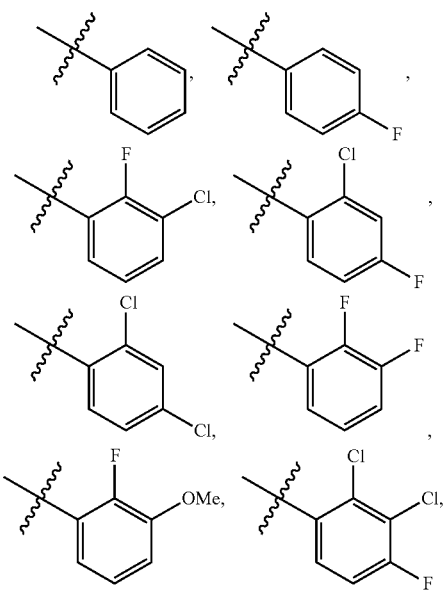

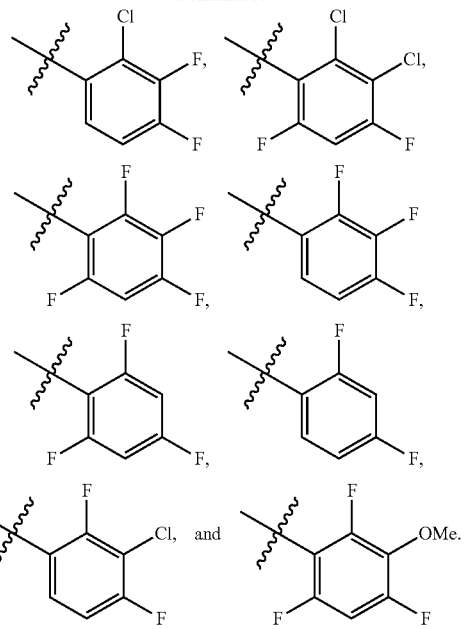

In some embodiments of the compound of formula I or II, or a pharmaceutically acceptable salt thereof, L is —$CR^{3a}R^{3b}$—, wherein $R^{3a}$ and $R^{3b}$ are independently H, $C_{1-4}$alkyl, $C_{1-6}$ haloalkyl, $C(O)R^c$, or $SO_2R^c$. In some embodiments, L is —$CR^{3a}R^{3b}$—, wherein $R^{3a}$ and $R^{3b}$ are independently H or $C_{1-4}$alkyl. In some embodiments, L is —$CH_2$—. In some embodiments, L is —$CH(CH_3)$—. In some embodiments, L is —C(O)—. In some embodiments, L is or —$CH_2$—$CH_2$—. In some embodiments, L is —$CH_2$—, —$CH(CH_3)$—, —C(O)—, or —$CH_2$—$CH_2$—. In some embodiments, L is —$N(R^a)$—.

In some embodiments, the compound of formula I or II is a compound of formula:

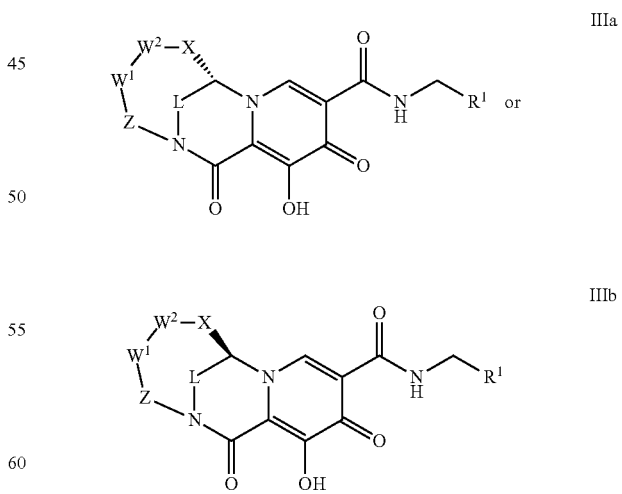

or a pharmaceutically acceptable salt thereof, wherein $R^1$, L, $W^1$, $W^2$, X, and Z are as defined in formula I.

In some embodiments, the compound of formula I or II is a compound of formula (IV):

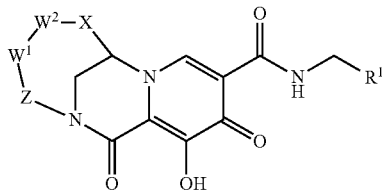

IV or a pharmaceutically acceptable salt thereof, wherein $R^1$, $W^1$, $W^2$, X, and Z are as defined in formula I.

In some embodiments, the compound of formula I, II, or IV is a compound of formula:

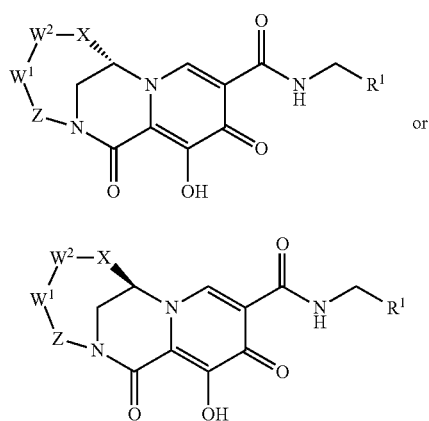

Va

Vb or a pharmaceutically acceptable salt thereof, wherein $R^1$, $W^1$, $W^2$, X, and Z are as defined in formula I.

In some embodiments, the compound of formula I or II is a compound of formula (VI):

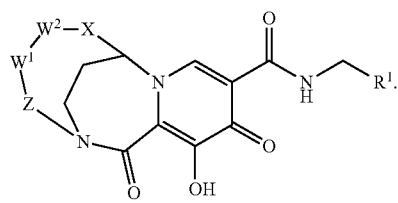

VI

In some embodiments, the compound of formula I, II, or VI is a compound of formula:

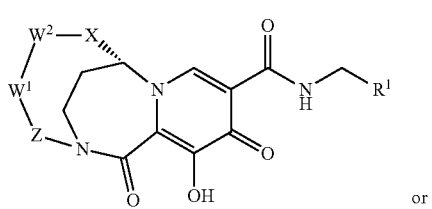

VIIa

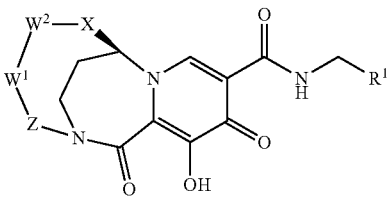

VIIb or a pharmaceutically acceptable salt thereof, wherein $R^1$, $W^1$, $W^2$, X, and Z are as defined in formula I.

In some embodiments of the compound of formula I, II, IIIa, IIIb, IV, Va, Vb, VI, VIIa, or VIIb, or a pharmaceutically acceptable salt thereof, $W^1$ is a bond. In some embodiments, $W^1$ is $-CR^{4a}R^{4b}-$. In some embodiments, $W^1$ is $-CR^{4a}R^{4b}-$, wherein $R^{4a}$ and $R^{4b}$ are independently H or halo. In some embodiments, $W^1$ is $-CH_2-$. In some embodiments, $W^1$ is $-CF_2-$. In some embodiments, $W^1$ is $-CH(F)-$. In some embodiments, $W^1$ is a bond, $-CH_2-$, $-CF_2-$ or $-CH(F)-$. In some embodiments, $W^1$ is a bond or $-CH_2-$.

In some embodiments of the compound of formula I, II, IIIa, IIIb, IV, Va, Vb, VI, VIIa, or VIIb, or a pharmaceutically acceptable salt thereof, W is a bond or $-CR^{4a}R^{4b}-$, wherein each $R^{4a}$ and $R^{4b}$ is independently H, halo, or $C_{1-6}$ alkyl. In some embodiment, $W^1$ is bond or $-CR^{4a}R^{4b}-$, wherein each $R^{4a}$ and $R^{4b}$ is independently H, halo, or $-CH_3$. In some embodiment, $W^1$ is bond, $-CH_2-$, $-CH(F)-$, $-CF_2$, $-CH(CH_3)-$ or $-CF(CH_3)-$.

In some embodiments of the compound of formula I, II, IIIa, IIIb, IV, Va, Vb, VI, VIIa, or VIIb, or a pharmaceutically acceptable salt thereof, $W^2$ is $-CR^{5a}R^{5b}-$, $-CR^{5a}R^{5b}-CR^{5c}R^{5d}-$, $-CR^{6a}=CR^{6b}-$, $-N(R^7)-$, $-O-$, $-CR^{5a}R^{5b}-N(R^7)-$, or $-CR^{5a}R^{5b}-O-$, wherein $R^{5a}$, $R^{5b}$, $R^{5c}$, $R^{5d}$, $R^{6a}$, $R^{6b}$, and $R^7$ are as defined for formula I. In some embodiments, $W^2$ is $-CR^{5a}R^{5b}-$. In some embodiments, $W^2$ is $-CR^{5a}R^{5b}-$, wherein $R^{5a}$ and $R^{5b}$ are independently H, $C_{1-4}$alkyl, $C_{1-4}$ haloalkyl, halo, hydroxyl, cyano, $-O-C_{1-4}$alkyl, or $C_{1-4}$alkylene-O-$C_{1-4}$alkyl. In some embodiments, $W^2$ is $-CR^{5a}R^{5b}-$, wherein $R^{5a}$ and $R^{5b}$ are independently H, $C_{1-4}$alkyl, $C_{1-4}$ haloalkyl, halo, or hydroxyl. In some embodiments, $W^2$ is $-CR^{5a}R^{5b}-$, wherein $R^{5a}$ and $R^{5b}$ are independently H or halo. In some embodiments, $W^2$ is $-CH_2-$. In some embodiments, $W^2$ is $-CF_2-$. In some embodiments, $W^2$ is $-CH(F)-$. In some embodiments, $W^2$ is $-CR^{5a}R^{5b}-CR^{5c}R^{5}$. In some embodiments, $W^2$ is $-CR^{5a}R^{5b}-CR^{5c}R^{5d}-$, wherein $R^{5a}$, $R^{5b}$, $R^{5c}$, and $R^{5d}$ are independently H, $C_{1-4}$alkyl, $C_{1-4}$haloalkyl, halo, hydroxyl, cyano, $-O-C_{1-4}$alkyl, or $C_{1-4}$alkylene-O-$C_{1-4}$alkyl. In some embodiments, $W^2$ is $-CR^{5a}R^{5b}-CR^{5c}R^{5d}-$, wherein $R^{5a}$, $R^{5b}$, $R^{5c}$, and $R^{5d}$ are independently H, $C_{1-4}$alkyl, $C_{1-4}$haloalkyl, halo, hydroxyl. In some embodiments, $W^2$ is $-CR^{5a}R^{5b}-CR^{5c}R^{5d}-$, wherein $R^{5a}$, $R^{5b}$, $R^{5c}$, and $R^{5d}$ are independently H or halo. In some embodiments, $W^2$ is $-CH_2CH_2-$. In some embodiments, $W^2$ is $-CR^{5a}R^{5b}-CR^{5c}R^{5d}-$, wherein $R^{5a}$ and $R^{5c}$ are independently H or halo and $R^{5b}$ and $R^{5d}$ together with the carbon atoms to which each is attached form a 3- to 7-membered saturated or partially unsaturated fused carbocyclic ring, optionally substituted with one to three $R^{43}$, wherein each $R^{43}$ is independently halo, $C_{1-4}$alkyl or $C_{1-4}$haloalkyl. In some embodiments, $W^2$ is $-CR^{5a}R^{5b}-CR^{5c}R^{5d}-$, wherein $R^{5a}$ and $R^{5c}$ are independently H or halo and $R^{5b}$ and $R^{5d}$ together with the carbon atoms to which each is attached form a 3- to 5-membered saturated fused carbocyclic ring. In some embodiments, W² is —CHR⁵ᵇ—CHR⁵ᵈ—, wherein R⁵' and R⁵ᵈ together with the carbon atoms to which each is attached form a 3-, 4-, or 5-membered saturated fused carbocyclic ring. In some embodiments, W² is

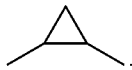

In some embodiments, W² is —CR⁶ᵃ═CR⁶—. In some embodiments, W² is —CR⁶ᵃ═CR⁶ᵇ—, wherein R⁶ᵃ and R⁶ᵇ are independently H, halo, C₁₋₄haloalkyl, or C₁₋₄alkyl. In some embodiments, W² is —CR⁶ᵃ═CR⁶ᵇ—, wherein R⁶ᵃ and R⁶ᵇ are independently H or halo. In some embodiments, W² is —CH═CH—. In some embodiments, W² is —CR⁶ᵃ═CR⁶ᵇ—, wherein R⁶ᵃ and R⁶ᵇ together with the carbon atoms to which each is attached form a 5- to 10-membered partially unsaturated fused ring containing 0 heteroatoms or 1 heteroatom selected from N, O, and S, or a 5- to 10-membered fused aromatic ring, or a 5- to 10-membered fused heteroaromatic ring containing 1 to 2 heteroatoms selected from N, O and S, wherein the partially unsaturated fused ring, fused aromatic ring, or fused heteroaromatic ring is optionally substituted with one to four R⁴⁴, wherein each R⁴⁴ is independently halo or C₁₋₄alkyl. In some embodiments, W² is —CR⁶ᵃ═CR⁶ᵇ—, wherein R⁶ᵃ and R⁶ᵇ together with the carbon atoms to which each is attached form a 5- to 10-membered partially unsaturated fused ring containing 0 heteroatoms or 1 heteroatom selected from N, O, and S, optionally substituted with one to four R⁴⁴, wherein each R⁴⁴ is independently halo or C₁₋₄alkyl. In some embodiments, W² is —CR⁶ᵃ═CR⁶ᵇ—, wherein R⁶ᵃ and R⁶ᵇ together with the carbon atoms to which each is attached form a 5- to 10-membered fused aromatic ring, optionally substituted with one to four R⁴⁴, wherein each R⁴⁴ is independently halo or C₁₋₄alkyl. In some embodiments, W² is —CR⁶ᵃ═CR⁶ᵇ—, wherein R⁶ᵃ and R⁶ᵇ together with the carbon atoms to which each is attached form a 5- to 10-membered fused heteroaromatic ring containing 1 to 2 heteroatoms selected from N, O and S, optionally substituted with one to four R⁴⁴, wherein each R⁴⁴ is independently halo or C₁₋₄alkyl. In some embodiments, W² is —CR⁶ᵃ═CR⁶ᵇ—, wherein R⁶ᵃ and R⁶ᵇ together with the atoms to which each is attached form a fused 1,2-phenylene ring, optionally substituted with one to four R⁴⁴, wherein each R⁴⁴ is independently halo or C₁₋₄alkyl. In some embodiments, W² is

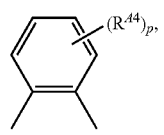

wherein p is 0, 1, 2, 3, or 4. In some embodiments, W² is

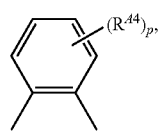

wherein each R⁴⁴ is independently halo. In some embodiments, W² is

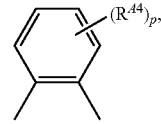

wherein each R⁴⁴ is independently halo and p is 0, 1, 2, or 3. In some embodiments, W² is

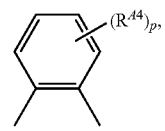

wherein each R⁴⁴ is independently halo and p is 0, 1, or 2. In some embodiments, W² is

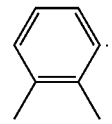

In some embodiments, W² is

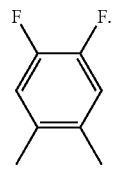

In some embodiments, W² is —N(R⁷)—. In some embodiments, W² is —N(R⁷)—, wherein R⁷ is H, C₁₋₄alkyl, C₁₋₄haloalkyl, C(O)Rᶜ, or SO₂Rᶜ. In some embodiments, W² is —N(R⁷)—, wherein R⁷ is H, C₁₋₄ alkyl, C(O)Rᶜ, or SO₂Rᶜ. In some embodiments, W² is —NH—. In some embodiments, W² is —N(CH₃)—. In some embodiments, W² is —N(CH(CH₃)₂)—. In some embodiments, W² is —N(C(O)Rᶜ)—. In some embodiments, W² is —N(C(O)CH₃)—. In some embodiments, W² is —N(SO₂Rᶜ)—. In some embodiments, W² is —N(SO₂CH₃)—. In some embodiments, W² is —O—. In some embodiments, W² is —CR⁵ᵃR⁵ᵇ—N(R⁷)—. In some embodiments, W² is —CH₂—N(R⁷)—. In some embodiments, W² is -CR⁵ᵃR⁵ᵇ—O—. In some embodiments, W² is or —CH₂—O—. In some embodiments, W² is —CH₂—, —CH₂CH₂—, —CH═CH—,

—NH—, —N(CH₃)—, —N(CH(CH₃)₂)—, —N(C(O)CH₃)—, —N(SO₂CH₃)—, —O—, or —CH₂—O—.

In some embodiments of the compound of formula I, II, IIIa, IIIb, IV, Va, or Vb, the compound has a formula (X):

Formula (X)

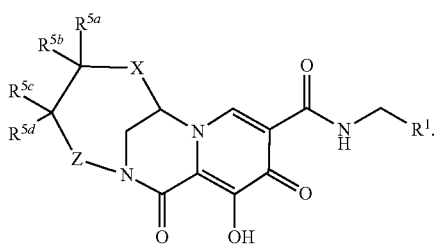

In some embodiments of the compound of formula I, II, IIIa, IIIb, IV, Va, or Vb, the compound has a formula (Xa):

Formula (Xa)

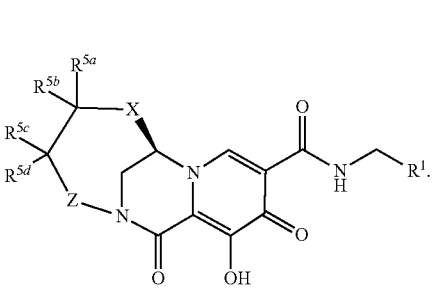

In some embodiments of the compound of formula I, II, IIIa, IIIb, IV, Va, or Vb, the compound has a formula (Xb):

Formula (Xb)

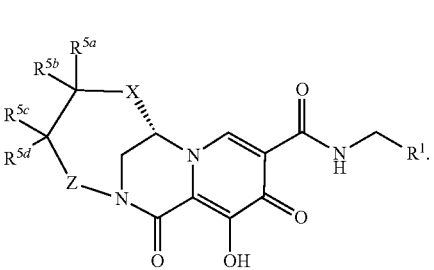

In some embodiments of the compound of formula I, II, IIIa, IIIb, IV, Va, or Vb, the compound has a formula (XI):

formula (XI)

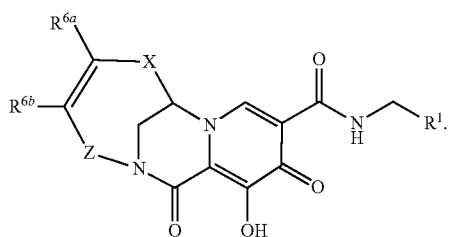

In some embodiments of the compound of formula I, II, IIIa, IIIb, IV, Va, Vb or X, the compound has a formula (XIa):

formula (XIa)

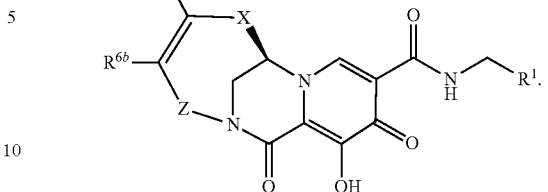

In some embodiments, the compound of formula I, II, IIIa, IIIb, IV, Va, Vb or X has a formula (XIb):

formula (XIb)

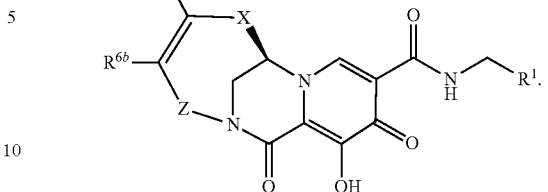

In some embodiments, of the compounds of Formula X, Xa, Xb, XI, XIa, or XIb, or the pharmaceutically acceptable salt thereof, X is bond or —$CR^{8a}R^{8b}$—; wherein $R^{8a}$ and $R^{8b}$ are each independently H, hydroxyl, —O—$C_{1-4}$alkyl, $C_{1-4}$alkylene-O—$C_{1-4}$alkyl, $C_{1-6}$alkyl, $C_{1-4}$ haloalkyl, cyano, or halo. In some embodiments, X is bond. In some embodiments, X is —$CR^{8a}R^{8b}$—; wherein $R^{8a}$ and $R^{8b}$ are each independently H, hydroxyl, —O—$C_{1-4}$alkyl, $C_{1-4}$alkylene-O—$C_{1-4}$alkyl, $C_{1-6}$alkyl, $C_{1-4}$haloalkyl, cyano, or halo. In some embodiments, X is —$CR^{8a}R^{8b}$—; wherein $R^{8a}$ and $R^{8b}$ are each independently H, $C_{1-6}$alkyl, $C_{1-4}$haloalkyl, or halo. In some embodiments, $R^{8a}$ and $R^{8b}$ are each independently H, —$CH_3$, —$CHF_2$, —$CH_2F$, or halo.

In some embodiments, for the compound of Formula X, Xa, Xb, XI, XIa, or XIb, or the pharmaceutically acceptable salt thereof, Z is —$CR^{9a}R^{9b}$— or —$CR^{9a}R^{9b}CR^{9c}R^{9d}$—; wherein $R^{9a}$, $R^{9b}$, $R^{9c}$, and $R^{9d}$ are each independently H, $C_{1-6}$alkyl, or $C_{1-4}$haloalkyl. In some embodiments, Z is —$CR^{9a}R^{9b}$—. In some embodiment, Z is —$CR^{9a}R^{9b}CR^{9c}R^{9d}$—. In some embodiments, $R^{9a}$, $R^{9b}$, $R^{9c}$, and $R^{9d}$ are each independently H, —$CH_3$, —$CHF_2$, or —$CH_2F$.

In some embodiments for the compounds of formula XI, XIa, or XIb, or the pharmaceutically acceptable salt thereof, each $R^{6a}$ and $R^{6b}$ is independently H, halo, $C_{1-4}$ haloalkyl, or $C_{1-6}$alkyl.

In some embodiments for the compounds of formula X, Xa, or Xb, or the pharmaceutically acceptable salt thereof, each $R^{5a}$, $R^{5b}$, $R^{5c}$, and $R^{5d}$ is independently H, halo, $C_{1-4}$haloalkyl, or $C_{1-6}$alkyl.

In some embodiments of the compound of formula I, II, IIIa, IIIb, IV, Va, Vb, VI, VIIa, VIIb, X, Xa, Xb, XI, XIa, or XIb, or a pharmaceutically acceptable salt thereof, X is a bond. In some embodiments, X is —$CR^{8a}R^{8b}$—. In some embodiments, X is —$CR^{8a}R^{8b}$—, wherein $R^{8a}$ and $R^{8b}$ are independently H, hydroxyl, $C_{1-4}$alkyl, or halo. In some embodiments, X is —$CR^{8a}R^{8b}$—, wherein $R^{8a}$ is H, fluoro, or hydroxyl and $R^{8b}$ is H or fluoro. In some embodiments, X is —CH$_2$—. In some embodiments, X is —CF$_2$—. In some embodiments, X is —CH(F)—. In some embodiments, X is —CH(OH)—. In some embodiments, X is —CH(CH$_3$)—. In some embodiments, X is —CF(CH$_3$)—. In some embodiments, X is —CH$_2$—, —CF$_2$—, —CH(F)—, —CH(OH)—, —CH(CH$_3$) or —CF(CH$_3$)—. In some embodiments, X is —CR$^{8a}$R$^{8b}$—, wherein R$^{8a}$ and R$^{8b}$ together with the carbon to which they are attached form a 3-, 4-, or 5-membered saturated spiro ring containing 0 to 2 heteroatoms selected from N, O, and S, wherein the spiro ring is optionally substituted with one to four R$^{45}$, wherein each R$^{45}$ is independently halo, C$_{1-4}$alkyl or C$_{1-4}$haloalkyl. In some embodiments, X is —CR$^{8a}$R$^{8b}$—, wherein R$^{8a}$ and R$^{8b}$ together with the carbon to which they are attached form a 3- to 5-membered saturated spiro ring containing 0 heteroatoms, wherein the spiro ring is optionally substituted with one to four R$^{45}$, wherein each R$^{45}$ is independently halo, C$_{1-4}$alkyl or C$_{1-4}$haloalkyl. In some embodiments, X is —CR$^{8a}$R$^{8b}$—, wherein R$^{8a}$ and R$^{8b}$ together with the carbon to which they are attached form an spiro cyclopropane ring.

In some embodiments of the compounds of formula I, II, IIIa, IIIb, IV, Va, Vb, VI, VIIa, VIIb, X, Xa, Xb, XI, XIa, or XIb, or a pharmaceutically acceptable salt thereof, X is a bond or —CR$^{8a}$R$^{8b}$—, wherein R$^{8a}$ and R$^{8b}$ are independently H, hydroxyl, —O—C$_{1-4}$alkyl, C$_{1-4}$alkyl, C$_{1-4}$haloalkyl, or halo, or wherein R$^{8a}$ and R$^{8b}$ together with the carbon to which they are attached form a 3 to 5-membered saturated spiro ring containing 0 to 2 heteroatoms selected from N, O, and S, wherein the spiro ring is optionally substituted with one to four R$^{45}$, wherein each R$^{45}$ is independently halo, C$_{1-4}$alkyl or C$_{1-4}$haloalkyl.

In some embodiments of the compounds of formula I, II, IIIa, IIIb, IV, Va, Vb, VI, VIIa, VIIb, X, Xa, Xb, XI, XIa, or XIb, or a pharmaceutically acceptable salt thereof, X is a bond or —CR$^{8a}$R$^{8b}$—, wherein R$^{8a}$ and R$^{8b}$ are independently H, hydroxyl, —O—C$_{1-4}$alkyl, C$_{1-4}$alkyl, C$_{1-4}$haloalkyl, or halo, or wherein R$^{8a}$ and R$^{8b}$ together with the carbon to which they are attached form a 3 to 5-membered saturated spiro heterocyclic ring containing 1 or 2 heteroatoms selected from N, O, and S, wherein the spiro ring is optionally substituted with one to four R$^{45}$, wherein each R$^{45}$ is independently halo, C$_{1-4}$alkyl or C$_{1-4}$haloalkyl. In some embodiments, X is a bond or —CR$^{8a}$R$^{8b}$—, wherein R$^{8a}$ and R$^{8b}$ are independently H, hydroxyl, —O—C$_{1-4}$alkyl, C$_{1-4}$alkyl, C$_{1-4}$haloalkyl, or halo, or wherein R$^{8a}$ and R$^{8b}$ together with the carbon to which they are attached form a 3 to 5-membered saturated spiro heterocyclic ring containing 1 or 2 heteroatoms selected from N, O, and S.

In some embodiments of the compounds of formula I, II, IIIa, IIIb, IV, Va, Vb, VI, VIIa, VIIb, X, Xa, Xb, XI, XIa, or XIb, or a pharmaceutically acceptable salt thereof, X is a bond or —CR$^{8a}$R$^{8b}$—, wherein R$^{8a}$ and R$^{8b}$ are independently H, hydroxyl, —O—C$_{1-4}$alkyl, C$_{1-4}$alkyl, C$_{1-4}$haloalkyl, or halo, or wherein R$^{8a}$ and R$^{8b}$ together with the carbon to which they are attached form a 3-5 membered saturated spiro carbocyclic ring, wherein the a 3-5 membered saturated spiro carbocyclic ring is optionally substituted with one to four R$^{45}$, wherein each R$^{45}$ is independently halo, C$_{1-4}$alkyl or C$_{1-4}$haloalkyl. In some embodiments, X is a bond or —CR$^{8a}$R$^{8b}$—, wherein R$^{8a}$ and R$^{8b}$ are independently H, hydroxyl, —O—C$_{1-4}$alkyl, C$_{1-4}$alkyl, C$_{1-4}$ haloalkyl, or halo, or wherein R$^{8a}$ and R$^{8b}$ together with the carbon to which they are attached form a 3-5 membered saturated spiro carbocyclic ring.

In some embodiments of the compounds of formula I, II, IIIa, IIIb, IV, Va, Vb, VI, VIIa, VIIb, X, Xa, Xb, XI, XIa, or XIb, or a pharmaceutically acceptable salt thereof, X is a bond or —CR$^{8a}$R$^{8b}$—, wherein R$^{8a}$ and R$^{8b}$ are independently H, hydroxyl, —O—C$_{1-4}$alkyl, C$_{1-4}$alkyl, C$_{1-4}$haloalkyl, or halo, or wherein R$^{8a}$ and R$^{8b}$ together with the carbon to which they are attached form a 3-membered saturated spiro carbocyclic ring, wherein the 3 membered saturated spiro carbocyclic ring is optionally substituted with one to four R$^{45}$, wherein each R$^{45}$ is independently halo, C$_{1-4}$alkyl or C$_{1-4}$haloalkyl. In some embodiments, X is a bond or —CR$^{8a}$R$^{8b}$—, wherein R$^{8a}$ and R$^{8b}$ are independently H, hydroxyl, —O—C$_{1-4}$alkyl, C$_{1-4}$alkyl, C$_{1-4}$haloalkyl, or halo, or wherein R$^{8a}$ and R$^{8b}$ together with the carbon to which they are attached form a 3-membered saturated spiro carbocyclic ring.

In some embodiments of the compounds of formula I, II, IIIa, IIIb, IV, Va, Vb, VI, VIIa, VIIb, X, Xa, Xb, XI, XIa, or XIb, or a pharmaceutically acceptable salt thereof, X is a bond, —CH$_2$—, —CF$_2$—, —CH(F)—, —CH(Cl)—, —CH(OH)—, —C(CH$_2$F)(OH)—, —C(CH$_3$)(OH)—, —CH(OCH$_3$)—, —C(CH$_2$CH$_3$)(OCH$_3$)—, —C(CH$_2$CH$_3$)(OH)—, —CH(CH$_3$)—, —CH(CH$_2$CH$_3$)—, —CF(CH$_3$)—, —CF(CH$_2$CH$_3$)—, or —CR$^{8a}$R$^{8b}$—, wherein R$^{8a}$ and R$^{8b}$ together with the carbon to which they are attached form a 3-membered saturated spiro carbocyclic ring. In some embodiments, X is a bond, —CH$_2$—, —CF$_2$—, —CH(F)—, —CH(Cl)—, —CH(OH)—, —C(CH$_2$F)(OH)—, —C(CH$_3$)(OH)—, —CH(OCH$_3$)—, —C(CH$_2$CH$_3$)(OCH$_3$)—, —C(CH$_2$CH$_3$)(OH)—, —CH(CH$_3$)—, —CH(CH$_2$CH$_3$)—, —CF(CH$_3$)—, or —CF(CH$_2$CH$_3$)—.

In some embodiments, X is a bond, —CH$_2$—, —CF$_2$—, —CH(F)—, —CH(Cl)—, —CH(OH)—, —C(CH$_2$F)(OH)—, —C(CH$_3$)(OH)—, —CH(OCH$_3$)—, —C(CH$_2$CH$_3$)(OCH$_3$)—, —C(CH$_2$CH$_3$)(OH)—, —CH(CH$_3$)—, —CH(CH$_2$CH$_3$)—, —CF(CH$_3$)—, —CF(CH$_2$CH$_3$)—, —C(CH$_2$F)(H)—, or —CR$^{8a}$R$^{8b}$—, wherein R$^{8a}$ and R$^{8b}$ together with the carbon to which they are attached form a 3-membered saturated spiro carbocyclic ring. In some embodiments, X is a bond, —CH$_2$—, —CF$_2$—, —CH(F)—, —CH(Cl)—, —CH(OH)—, —C(CH$_2$F)(OH)—, —C(CH$_3$)(OH)—, —CH(OCH$_3$)—, —C(CH$_2$CH$_3$)(OCH$_3$)—, —C(CH$_2$CH$_3$)(OH)—, —CH(CH$_3$)—, —CH(CH$_2$CH$_3$)—, —CF(CH$_3$)—, —C(CH$_2$F)(H)—, or —CF(CH$_2$CH$_3$)—.

In some embodiments of the compounds of formula I, II, IIIa, IIIb, IV, Va, Vb, VI, VIIa, VIIb, X, Xa, Xb, XI, XIa, or XIb, or a pharmaceutically acceptable salt thereof, X is —CR$^{8a}$R$^{8b}$—, wherein R$^{8a}$ and R$^{8b}$ together with the carbon to which they are attached form a 3 to 5-membered saturated spiro ring containing 0 to 2 heteroatoms selected from N, O, and S, wherein the spiro ring is optionally substituted with one to four R$^{45}$, wherein each R$^{45}$ is independently halo, C$_{1-4}$alkyl or C$_{1-4}$haloalky. In some embodiments, X is —CR$^{8a}$R$^{8b}$—, wherein R$^{8a}$ and R$^{8b}$ together with the carbon to which they are attached form a 3-5 membered saturated spiro carbocyclic ring, wherein the a 3-5 membered saturated spiro carbocyclic ring optionally substituted with one to four R$^{45}$, wherein each R$^{45}$ is independently halo, C$_{1-4}$alkyl or C$_{1-4}$ haloalkyl. In some embodiments. X is —CR$^{8a}$R$^{8b}$—, wherein R$^{8a}$ and R$^{8b}$ together with the carbon to which they are attached form a 3-membered spiro carbocyclic ring. In some embodiments, X is —CR$^{8a}$R$^{8b}$—, wherein R$^{8a}$ and R$^{8b}$ together with the carbon to which they are attached form a 3 to 5-membered saturated spiro heterocyclic ring containing 1 or 2 heteroatoms selected from N, O, and S, wherein the a 3 to 5-membered saturated spiro heterocyclic ring optionally substituted with one to four R$^{45}$, wherein each R$^{45}$ is independently halo, C$_{1-4}$alkyl or C$_{1-4}$haloalkyl. In some embodiments. X is —CR$^{8a}$R$^{8b}$—, wherein $R^{8a}$ and $R^{8b}$ together with the carbon to which they are attached form a 3 to 5-membered saturated spiro heterocyclic ring containing 1 or 2 heteroatoms selected from N, O, and S.

In some embodiments, the compound of formula I or II is a compound of formula (VIII):

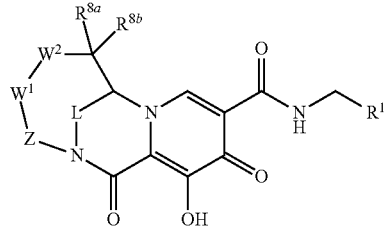

VIII or a pharmaceutically acceptable salt thereof, wherein $R^1$, L, $W^1$, $W^2$, and Z are as defined in formula I.

In some embodiments of the compound of formula I, II, IIIa, IIIb, IV, Va, Vb, VI, VIIa, VIIb, VIII, X, Xa, Xb, XI, XIa, or XIb, or a pharmaceutically acceptable salt thereof, Z is —$CR^{9a}R^{9b}$—. In some embodiments, Z is —$CR^{9a}R^{9b}$—, wherein $R^{9a}$ and $R^{9b}$ are independently H, $C_{1-4}$alkyl, $C_{1-4}$haloalkyl, or halo. In some embodiments, Z is —$CR^{9a}R^{9b}$—, wherein $R^{9a}$ and $R^{9b}$ are independently H or $C_{1-4}$alkyl. In some embodiments, Z is —$CH_2$—. In some embodiments, Z is —$CH(CH_3)$—. In some embodiments, Z is —$CR^{9a}R^{9b}$—$CR^{9c}R^{9d}$—. In some embodiments, Z is —$CR^{9a}R^{9b}$—$CR^{9c}R^{9d}$—, wherein $R^{9a}$, $R^{9b}$, $R^{9c}$, and $R^{9d}$ are independently H, $C_{1-4}$alkyl, $C_{1-4}$haloalkyl, or halo. In some embodiments, Z is —$CH_2$—$CH_2$—. In some embodiments, Z is —$CR^{10a}$=$CR^{10b}$—. In some embodiments, Z is —$CR^{10a}$=$CR^{10b}$—, wherein $R^{10a}$ and $R^{10b}$. In some embodiments, Z is —$CR^{10a}$=$CR^{10b}$—, wherein $R^{10a}$ and $R^{10b}$ together with the carbon atoms to which each is attached form a 5- to 10-membered partially unsaturated fused ring containing 0 heteroatoms or 1 heteroatom selected from N, O, and S, or a 5- to 10-membered fused aromatic ring, or a 5- to 10-membered fused heteroaromatic ring containing 1 to 2 heteroatoms selected from N, O and S, wherein the partially unsaturated fused ring, fused aromatic ring, or fused heteroaromatic ring is optionally substituted with one to four $R^{47}$, wherein each $R^{47}$ is independently halo or $C_{1-4}$alkyl. In some embodiments, Z is —$CR^{10a}$=$CR^{10b}$—, wherein $R^{10a}$ and $R^c$ together with the carbon atoms to which each is attached form a 5- to 10-membered partially unsaturated fused ring containing 0 heteroatoms or 1 heteroatom selected from N, O, and S, optionally substituted with one to four $R^{47}$, wherein each $R^{47}$ is independently halo or $C_{1-4}$alkyl. In some embodiments, Z is —$CR^{10a}$=$CR^{10b}$—, wherein $R^{10a}$ and $R^{10b}$ together with the carbon atoms to which each is attached form a 5- to 10-membered fused aromatic ring, optionally substituted with one to four $R^{47}$, wherein each $R^{47}$ is independently halo or $C_{1-4}$alkyl. In some embodiments, Z is —$CR^{10a}$=$CR^{10b}$—, wherein $R^{10a}$ and $R^{10b}$ together with the carbon atoms to which each is attached form a 5- to 10-membered fused heteroaromatic ring containing 1 to 2 heteroatoms selected from N, O and S, optionally substituted with one to four $R^{47}$, wherein each $R^{47}$ is independently halo or $C_{1-4}$alkyl. In some embodiments, Z is —$CR^{10a}$=$CR^{10b}$—, wherein $R^{10a}$ and $R^{10b}$ together with the atoms to which each is attached form a fused 1,2-phenylene ring, optionally substituted with one to four $R^{47}$, wherein each $R^{47}$ is independently halo or $C_{1-4}$alkyl. In some embodiments, Z is

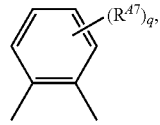

wherein q is 0, 1, 2, 3, or 4. In some embodiments, Z is

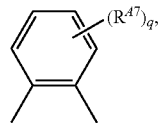

wherein each $R^{44}$ is independently halo. In some embodiments, Z is

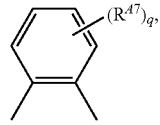

wherein each $R^{44}$ is independently halo and q is 0, 1, 2, or 3. In some embodiments, Z is

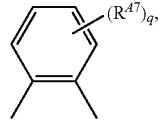

wherein each $R^{44}$ is independently halo and q is 0, 1, or 2. In some embodiments, Z is

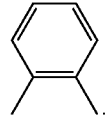

In some embodiments, Z is

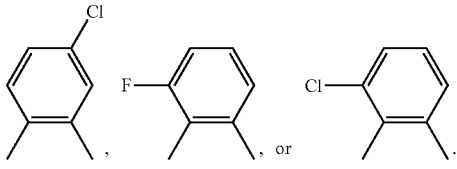

In some embodiments, Z is

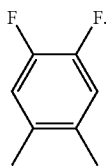

In some embodiments, Z is —CH$_2$—, —CH(CH$_3$)—, —CH$_2$—CH$_2$—,

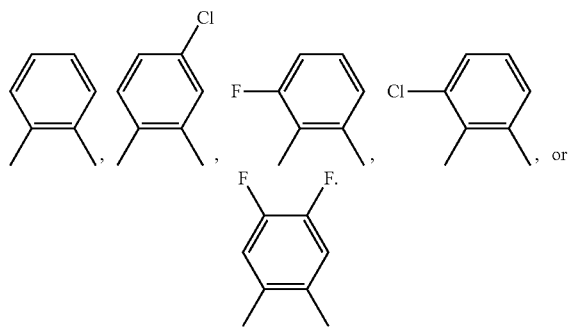

, or

In some embodiments of the compound of formula I, II, IIIa, IIIb, or VIII, or a pharmaceutically acceptable salt thereof, L is —CR$^{3a}$R$^{3b}$— and R$^{3a}$ and R$^{3b}$ are independently H, C$_{1-4}$alkyl, C$_{1-4}$haloalkyl, or —O—C$_{1-4}$alkyl. In some embodiments, R$^{3a}$ and R$^{3b}$ are independently H or C$_{1-4}$alkyl. In some embodiments, R$^{3a}$ and R$^{3b}$ are H. In some embodiments, R$^{3a}$ and R$^{3b}$ are C$_{1-4}$alkyl. In some embodiments, R$^{3a}$ is H and R$^{3b}$ is C$_{1-4}$alkyl. In some embodiments, R$^{3a}$ is H and R$^{3b}$ is methyl. In some embodiments, R$^{3a}$ and R$^{3b}$ together with the carbon atom to which they are attached form a 3- to 7-membered saturated or partially unsaturated spiro ring containing 0 to 2 heteroatoms selected from N, O, and S, wherein the spiro ring is optionally substituted with one to three R$^{A2}$, wherein each R$^{A2}$ is independently halo, C$_{1-4}$alkyl or C$_{1-4}$ haloalkyl. In some embodiments, R$^{3a}$ and R$^{3b}$ together with the carbon atom to which they are attached form a 3-, 4-, or 5-membered saturated or partially unsaturated spiro ring containing 0 to 2 heteroatoms selected from N, O, and S, wherein the spiro ring is optionally substituted with one to three R$^{A2}$, wherein each R$^{A2}$ is independently halo, C$_{1-4}$alkyl or C$_{1-4}$haloalkyl. In some embodiments, R$^{3a}$ and R$^{3b}$ together with the carbon atom to which they are attached form a 3- or 4-membered saturated spiro ring containing 0 heteroatoms or 1 heteroatom selected from N, O, and S, wherein the spiro ring is optionally substituted with one to three R$^{A2}$, wherein each R$^{A2}$ is independently halo, C$_{1-4}$alkyl or C$_{1-4}$haloalkyl. In some embodiments, R$^{3a}$ and R$^{3b}$ together with the carbon atom to which they are attached form a 3-membered saturated spiro ring containing 0 heteroatoms or 1 heteroatom selected from N, O, and S, wherein the spiro ring is optionally substituted with one to three R$^{A2}$, wherein each R$^{A2}$ is independently halo, C$_{1-4}$alkyl or C$_{1-4}$ haloalkyl. In some embodiments, R$^{3a}$ and R$^{3b}$ together with the carbon atom to which they are attached form a spiro cyclopropane ring.

In some embodiments of the compound of formula I, II, IIIa, IIIb, IV, Va, Vb, VI, VIIa, VIIb, or VIII, or a pharmaceutically acceptable salt thereof, W$^1$ is —CR$^{4a}$R$^{4b}$— and R$^{4a}$ and R$^{4b}$ are independently H, C$_{1-4}$alkyl, C$_{1-4}$haloalkyl, or halo. In some embodiments, R$^{4a}$ and R$^{4b}$ are independently H or halo. In some embodiments, R$^{4a}$ and R$^{4b}$ are H. In some embodiments, R$^{4a}$ and R$^{4b}$ are halo. In some embodiments, R$^{4a}$ and R$^{4b}$ are fluoro. In some embodiments, R$^{4a}$ is H and R$^{4b}$ is halo. In some embodiments, R$^{4a}$ is H and R$^{4b}$ is fluoro.

In some embodiments of the compound of formula I, II, IIIa, IIIb, IV, Va, Vb, VI, VIIa, VIIb, VIII, X, Xa, Xb, XI, XIa, or XIb, or a pharmaceutically acceptable salt thereof, W$^2$ is —CR$^{5a}$R$^{5b}$— and R$^{5a}$ and R$^{5b}$ are independently H, C$_{1-4}$alkyl, C$_{1-4}$haloalkyl, halo, hydroxyl, cyano, —O—C$_{1-4}$ alkyl, or C$_{1-4}$alkylene-O—C$_{1-4}$alkyl. In some embodiments, R$^{5a}$ and R$^{5b}$ are independently H, C$_{1-4}$alkyl, C$_{1-4}$haloalkyl, halo, or hydroxyl. In some embodiments, R$^{5a}$ and R$^{5b}$ are independently H or halo. In some embodiments, R$^{5a}$ and R$^{5b}$ are H. In some embodiment, R$^{5a}$ and R$^{5b}$ are halo. In some embodiments, R$^{5a}$ and R$^{5b}$ are fluoro. In some embodiments, R$^{5a}$ is H and R$^{5b}$ is halo. In some embodiments, R$^{5a}$ is H and R$^{5b}$ is fluoro. In some embodiments, R$^{5a}$ and R$^{5b}$ together with the carbon atom to which they are attached form a 3- to 7-membered saturated or partially unsaturated spiro ring containing 0 to 2 heteroatoms selected from N, O, and S, wherein the spiro ring is optionally substituted with one to three R$^{A3}$, wherein each R$^{A3}$ is independently halo, C$_{1-4}$alkyl or C$_{1-4}$haloalkyl. In some embodiments, R$^{5a}$ and R$^{5b}$ together with the carbon atom to which they are attached form a 3-, 4-, or 5-membered saturated or partially unsaturated spiro ring containing 0 to 2 heteroatoms selected from N, O, and S, wherein the spiro ring is optionally substituted with one to three R$^{A3}$, wherein each R$^{A3}$ is independently halo, C$_{1-4}$alkyl or C$_{1-4}$haloalkyl. In some embodiments, R$^{5a}$ and R$^{5b}$ together with the carbon atom to which they are attached form a 3- or 4-membered saturated spiro ring containing 0 heteroatoms or 1 heteroatom selected from N, O, and S, wherein the spiro ring is optionally substituted with one to three R$^{A3}$, wherein each R$^{A3}$ is independently halo, C$_{1-4}$alkyl or C$_{1-4}$ haloalkyl. In some embodiments, R$^{5a}$ and R$^{5b}$ together with the carbon atom to which they are attached form a 3-membered saturated spiro ring containing 0 heteroatoms or 1 heteroatom selected from N, O, and S, wherein the spiro ring is optionally substituted with one to three R$^{A3}$, wherein each R$^{A3}$ is independently halo, C$_{1-4}$alkyl or C$_{1-4}$haloalkyl. In some embodiments, R$^{5a}$ and R$^{5b}$ together with the carbon atom to which they are attached form a spiro cyclopropane ring.

In some embodiments of the compound of formula I, II, IIIa, IIIb, IV, Va, Vb, VI, VIIa, VIIb, VIII, X, Xa, Xb, XI, XIa, or XIb, or a pharmaceutically acceptable salt thereof, W$^2$ is —CR$^{5a}$R$^{5b}$CR$^{5c}$R$^{5d}$— and R$^{5a}$, R$^{5b}$, R$^{5c}$, and R$^{5d}$ are independently H, C$_{1-4}$alkyl, C$_{1-4}$haloalkyl, halo, hydroxyl, cyano, —O—C$_{1-4}$alkyl, or C$_{1-4}$alkylene-O—C$_{1-4}$alkyl. In some embodiments, R$^{5a}$, R$^{5b}$, R$^{5c}$, and R$^{5d}$ are independently H, C$_{1-4}$alkyl, C$_{1-4}$haloalkyl, halo, or hydroxyl. In some embodiments, R$^{5a}$, R$^{5b}$, R$^{5c}$, and R$^{5d}$ are independently H or halo. In some embodiments, R$^{5a}$, R$^{5b}$, R$^{5c}$, and R$^{5d}$ are H. In some embodiments, R$^{5a}$ and R$^{5c}$ are independently H or halo and R$^{5b}$ and R$^{5d}$ together with the carbon atoms to which each is attached form a 3- to 7-membered saturated or partially unsaturated fused carbocyclic ring, optionally substituted with one to three R$^{A3}$, wherein each R$^{A3}$ is independently halo, C$_{1-4}$alkyl or C$_{1-4}$haloalkyl. In some embodiments, R$^{5a}$ and R$^{5c}$ are independently H or halo and R$^{5b}$ and R$^{5d}$ together with the carbon atoms to which each is attached form a 3-, 4-, or 5-membered saturated fused carbocyclic ring. In some embodiments, R$^{5a}$ and R$^{5c}$ are H and R$^{5b}$ and R$^{5d}$ together with the carbon atoms to which each is attached form a 3-, 4-, or 5-membered saturated fused carbocyclic ring. In some embodiments, $R^{5a}$ and $R^{5c}$ are H and $R^{5b}$ and $R^{5d}$ together with the carbon atoms to which each is attached form a fused cyclopropane ring.

In some embodiments of the compound of formula I, II, IIIa, IIIb, IV, Va, Vb, VI, VIIa, VIIb, VIII, X, Xa, Xb, XI, XIa, or XIb, or a pharmaceutically acceptable salt thereof, $W^2$ is —$CR^{6a}$=$CR^{6b}$— and $R^{6a}$ and $R^{6b}$ are independently H, halo, $C_{1-4}$haloalkyl, or $C_{1-4}$alkyl. In some embodiments, $R^{6a}$ and $R^{6b}$ are independently H or halo. In some embodiments, $R^{6a}$ and $R^{6b}$ are H. In some embodiments, $R^{6a}$ and $R^{6b}$ together with the atoms to which each is attached form a 5- to 10-membered fused aromatic ring, optionally substituted with one to four $R^{44}$, wherein each $R^{44}$ is independently halo or $C_{1-4}$alkyl. In some embodiments, $R^{6a}$ and $R^{6b}$ together with the atoms to which each is attached form a fused 1,2-phenylene ring, optionally substituted with one to four $R^{44}$, wherein each $R^{44}$ is independently halo or $C_{1-4}$alkyl. In some embodiments, $R^{6a}$ and $R^{6b}$ together with the atoms to which each is attached form

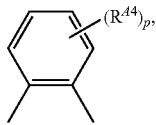

wherein p is 0, 1, 2, 3, or 4. In some embodiments, $R^{6a}$ and $R^{6b}$ together with the atoms to which each is attached form

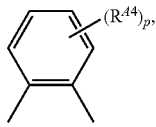

wherein each $R^{44}$ is independently halo. In some embodiments, $R^{6a}$ and $R^{6b}$ together with the atoms to which each is attached form

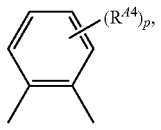

wherein each $R^{44}$ is independently halo and p is 0, 1, 2, or 3. In some embodiments, $R^{6a}$ and $R^{6b}$ together with the atoms to which each is attached form

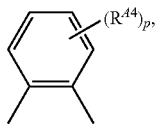

wherein each $R^{44}$ is independently halo and p is 0, 1, or 2. In some embodiments, $R^{6a}$ and $R^{6b}$ together with the atoms to which each is attached form

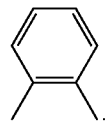

In some embodiments, $R^{6a}$ and $R^{6b}$ together with the atoms to which each is attached form

In some embodiments of the compound of formula I, II, IIIa, IIIb, IV, Va, Vb, VI, VIIa, VIIb, VIII, X, Xa, Xb, XI, XIa, or XIb, or a pharmaceutically acceptable salt thereof, $W^2$ is —$N(R^7)$— and $R^7$ is H, $C_{1-4}$alkyl, $C_{1-4}$haloalkyl, $C(O)R^c$, or $SO_2R$. In some embodiments, $R^7$ is H, $C_{1-4}$alkyl, $C(O)R^c$, or $SO_2R^c$. In some embodiments, $R^7$ is H. In some embodiments, $R^7$ is $C_{1-4}$ alkyl. In some embodiments, $R^7$ is methyl or 1-methylethyl. In some embodiments, $R^7$ is $C(O)R^c$. In some embodiments, $R^7$ is —$C(O)$—$C_{1-4}$alkyl. In some embodiments, $R^7$ is —$C(O)CH_3$. In some embodiments, $R^7$ is $SO_2R^c$. In some embodiments, $R^7$ is —$SO_2$—$C_{1-4}$alkyl. In some embodiments, $R^7$ is —$SO_2CH_3$.

In some embodiments of the compound of formula I, II, IIIa, IIIb, IV, Va, Vb, VI, VIIa, VIIb, VIII, X, Xa, Xb, XI, XIa, or XIb, or a pharmaceutically acceptable salt thereof, $W^2$ is selected from the group consisting of —$CR^{5a}R^{5b}$, —$CR^{5a}R^{5b}CR^{5c}R^{5d}$—, —$CR^{6a}$=$CR^{6b}$—, —$N(R^7)$—, —O—, —$S(O)_n$—, —C(O)—, —$CR^{5a}R^{5b}$—C(O)—, and —$CR^{5a}R^{5b}$—O—; wherein each $R^{5a}$, $R^{5b}$, $R^{5c}$, and $R^{5d}$ are independently H, $C_{1-4}$alkyl, $C_{1-4}$haloalkyl, halo, hydroxyl, cyano, —O—$C_{1-4}$alkyl, or $C_{1-4}$ alkylene-O—$C_{1-4}$alkyl; or $R^{5a}$ and $R^{5b}$, $R^{5c}$ and $R^{5d}$, $R^{5a}$ and $R^{5c}$, or $R^{5b}$ and $R^{5d}$ together with the carbon atoms to which each is attached form a 3 to 7 membered saturated or partially unsaturated carbocyclic ring, optionally substituted with one to three $R^{43}$, wherein each $R^{43}$ is independently halo, $C_{1-4}$alkyl or $C_{1-4}$haloalkyl; each $R^{6a}$ and $R^{6b}$ are independently H, halo, $C_{1-4}$ haloalkyl, or $C_{1-4}$alkyl; or $R^{6a}$ and $R^{6b}$ together with the atoms to which each is attached form (i) a 5 to 10 membered fused aromatic ring or (ii) a 5 to 10 membered fused heteroaromatic ring containing 1 to 2 heteroatoms selected from N, O and S, wherein the 5-10 membered fused aromatic ring or the 5-10-membered fused heteroaromatic ring is optionally substituted with one to four $R^{44}$, wherein each $R^{44}$ is independently halo or $C_{1-4}$alkyl; $R^7$ is H, $C_{1-4}$alkyl, $C_{1-4}$ haloalkyl, $C(O)R^c$, or $SO_2R^c$; $R^c$ is a $C_{1-4}$alkyl; and n is 0, 1, or 2.

In some embodiments of the compound of formula I, II, IIIa, IIIb, IV, Va, Vb, VI, VIIa, VIIb, VIII, X, Xa, Xb, XI, XIa, or XIb, or a pharmaceutically acceptable salt thereof, $W^2$ is selected from the group consisting of —$CR^{5a}R^{5b}$, —$CR^{5a}R^{5b}CR^{5c}R^{5d}$—, —$CR^{6a}$=$CR^{6b}$—, —$N(R^7)$—, —O—, —$S(O)_n$—, —C(O)—, —$CR^{5a}R^{5b}$—C(O)—, and —$CR^{5a}R^{5b}$—O—; wherein each $R^{5a}$, $R^{5b}$, $R^{5c}$, and $R^{5d}$ are independently H, $C_{1-4}$alkyl, $C_{1-4}$haloalkyl, halo, hydroxyl, cyano, —O—$C_{1-4}$alkyl, or $C_{1-4}$ alkylene-O—$C_{1-4}$alkyl; or $R^{5a}$ and $R^{5b}$, $R^{5c}$ and $R^{5d}$, $R^{5a}$ and $R^{5c}$, or $R^{5b}$ and $R^{5d}$ together with the carbon atoms to which each is attached form a 3 membered carbocyclic ring, optionally substituted with one to three $R^{43}$, wherein each $R^{43}$ is independently halo, $C_{1-4}$alkyl or $C_{1-4}$ haloalkyl; each $R^{6a}$ and $R^{6b}$ are independently H, halo, $C_{1-4}$haloalkyl, or $C_{1-4}$alkyl; or $R^{6a}$ and $R^{6b}$ together with the atoms to which each is attached form (i) a fused phenyl ring or (ii) a 5-6 membered fused heteroaromatic ring containing 1 to 2 heteroatoms selected from N, O and S, wherein the fused phenyl ring or the 5-6 membered fused heteroaromatic ring is optionally substituted with one to four $R^{44}$, wherein each $R^{44}$ is independently halo or $C_{1-4}$alkyl; $R^7$ is H, $C_{1-4}$alkyl, $C_{1-4}$haloalkyl, C(O)$R^c$, or SO$_2R^c$; Rc is a $C_{1-4}$alkyl; and n is 0, 1, or 2.

In some embodiments of the compound of formula I, II, IIIa, IIIb, IV, Va, Vb, VI, VIIa, VIIb, VIII, X, Xa, Xb, XI, XIa, or XIb, or a pharmaceutically acceptable salt thereof, $W^2$ is selected from the group consisting of —$CR^{5a}R^{5a}$—, —$CR^{5a}R^{5b}CR^{5c}R^{5d}$—, —$CR^{6a}$=$CR^{6b}$—, —N($R^7$)—, —O—, —S(O)$_n$—, —C(O)—, —$CR^{5a}R^{5b}$—C(O)—, and —$CR^{5a}R^{5b}$—O—; wherein each $R^{5a}$, $R^{5b}$, $R^{5c}$, and $R^{5d}$ are independently H, $C_{1-4}$alkyl, halo, hydroxyl, or —O—$C_{1-4}$alkyl; or $R^{5a}$ and R, $R^1$ and $R^{5d}$, $R^{5a}$ and $R^{5c}$, or $R^{5b}$ and $R^{5d}$ together with the carbon atoms to which each is attached form a 3-membered carbocyclic ring; each $R^{6a}$ and $R^{6b}$ are independently H, halo, or $C_{1-4}$alkyl; or $R^{6a}$ and $R^{6b}$ together with the atoms to which each is attached form (i) a fused phenyl ring or (ii) a 5-6 membered fused heteroaromatic ring containing 1 to 2 heteroatoms selected from N and O, wherein the fused phenyl ring or the 5-6 membered fused heteroaromatic ring is optionally substituted with one or two $R^{44}$, wherein each $R^{44}$ is independently halo or $C_{1-4}$alkyl; $R^7$ is H, $C_{1-4}$alkyl, $C_{1-4}$haloalkyl, C(O)$R^c$, or SO$_2R^c$; $R^c$ is a $C_{1-4}$alkyl; and n is 0 or 1.

In some embodiments, $W^2$ is selected from the group consisting of —$CR^{5a}R^{5b}$—, —$CR^{5a}R^{5b}CR^{5c}R^{5d}$—, —$CR^{6a}$=$CR^{6b}$—, —N($R^7$)—, —O—, —S(O)$_n$—, —C(O)—, —$CR^{5a}R^{5b}$—C(O)—, and —$CR^{5a}R^{5b}$—O—; wherein each $R^{5a}$, $R^{5b}$, $R^{5c}$, and $R^{5d}$ are independently H, —CH$_3$, halo, hydroxyl, or —OCH$_3$; or $R^{5a}$ and $R^{5b}$, $R^{5c}$ and $R^{5d}$, $R^{5a}$ and $R^{5c}$, or $R^{5b}$ and $R^{5d}$ together with the carbon atoms to which each is attached form a 3-membered carbocyclic ring; each $R^{6a}$ and $R^{6b}$ are independently H, halo, or CH$_3$; or $R^{6a}$ and $R^{6b}$ together with the atoms to which each is attached form (i) a fused phenyl ring or (ii) a 5 membered fused heteroaromatic ring containing 1 to 2 heteroatoms selected from N and O, wherein the fused phenyl ring or the 5-6 membered fused heteroaromatic ring is optionally substituted with one or two $R^{44}$, wherein each $R^{44}$ is independently halo or CH$_3$; $R^7$ is H, —CH$_3$, —CH(CH$_3$)$_2$, —CF$_3$, —C(O)$R^c$, or —SO$_2R^c$; $R^c$ is —CH$_3$; and n is 0 or 1.

In some embodiments, $W^2$ is selected from the group consisting of —$CR^{5a}R^{5b}$—, —$CR^{5a}R^{5b}CR^{5c}R^{5d}$—, —$CR^{6a}$=$CR^{6b}$—, —N($R^7$)—, —O—, —S(O)$_n$—, —C(O)—, —$CR^{5a}R^{5b}$—C(O)—, and —$CR^{5a}R^{5b}$—O—; wherein each $R^{5a}$, $R^{5b}$, $R^{5c}$, and $R^{5d}$ are independently H, —CH$_3$, halo, hydroxyl, or —OCH$_3$; each $R^{6a}$ and $R^{6b}$ are independently H, halo, or —CH$_3$; $R^7$ is H, —CH$_3$, —CH(CH$_3$)$_2$, —CF$_3$, —C(O)$R^c$, or —SO$_2R^c$; $R^c$ is —CH$_3$; and n is 0 or 1.

In some embodiments of the compound of formula I, II, IIIa, IIIb, IV, Va, Vb, VI, VIIa, VIIb, VIII, X, Xa, Xb, XI, XIa, or XIb, or a pharmaceutically acceptable salt thereof, X is —$CR^{8a}R^{8b}$— and $R^{8a}$ and $R^{8b}$ are independently H, hydroxyl, —O—$C_{1-4}$alkyl, $C_{1-4}$alkylene-O—$C_{1-4}$alkyl, $C_{1-4}$alkyl, $C_{1-4}$haloalkyl, cyano, or halo. In some embodiments, $R^{8a}$ and $R^{8b}$ are independently H, hydroxyl, $C_{1-4}$alkyl, or halo. In some embodiments, $R^{8a}$ is H, fluoro, or hydroxyl and $R^{8b}$ is H or fluoro. In some embodiments, $R^{8a}$ and $R^{5b}$ are H. In some embodiments, $R^{8a}$ and $R^{8b}$ are fluoro.

In some embodiments, $R^{8a}$ is H and $R^{8b}$ is halo. In some embodiments, $R^{8a}$ is H and $R^{8b}$ is fluoro. In some embodiments, $R^{8a}$ is H and $R^{8b}$ is hydroxyl. In some embodiments, $R^{8a}$ is H and $R^{8b}$ is $C_{1-4}$alkyl. In some embodiments, $R^{8a}$ is H and $R^b$ is methyl. In some embodiments, $R^{8a}$ is halo and $R^{8b}$ is $C_{1-4}$alkyl. In some embodiments, $R^{8a}$ is fluoro and $R^{8b}$ is methyl. In some embodiments, $R^{8a}$ and $R^{8b}$ together with the carbon to which they are attached form a 3-, 4-, or 5-membered saturated spiro ring containing 0 to 2 heteroatoms selected from N, O, and S, wherein the spiro ring is optionally substituted with one to four $R^{45}$, wherein each $R^{45}$ is independently halo, $C_{1-4}$alkyl or $C_{1-4}$haloalkyl. In some embodiments, $R^{8a}$ and $R^{8b}$ together with the carbon to which they are attached form a 3-, 4-, or 5-membered saturated spiro ring containing 0 heteroatoms, wherein the spiro ring is optionally substituted with one to four $R^{45}$, wherein each $R^{45}$ is independently halo, $C_{1-4}$alkyl or $C_{1-4}$haloalkyl. In some embodiments, $R^{8a}$ and $R^{8b}$ together with the carbon to which they are attached form an spiro cyclopropane ring.

In some embodiments of the compound of formula I, II, IIIa, IIIb, IV, Va, Vb, VI, VIIa, VIIb, VIII, X, Xa, Xb, XI, XIa, or XIb, or a pharmaceutically acceptable salt thereof, Z is —$CR^{9a}R^{9b}$— and $R^{9a}$ and $R^{9b}$ are independently H, $C_{1-4}$alkyl, $C_{1-4}$haloalkyl, or halo. In some embodiments, $R^{9a}$ and $R^{9b}$ are independently H or $C_{1-4}$alkyl. In some embodiments, $R^{9a}$ and $R^{9b}$ are H. In some embodiments, $R^{9a}$ and $R^{9b}$ are $C_{1-4}$alkyl. In some embodiments, $R^{9a}$ is H and $R^{9b}$ is $C_{1-4}$alkyl. In some embodiments, $R^{9a}$ is H and $R^{9b}$ is methyl.

In some embodiments of the compound of formula I, II, IIIa, IIIb, IV, Va, Vb, VI, VIIa, VIIb, VIII, X, Xa, Xb, XI, XIa, or XIb, or a pharmaceutically acceptable salt thereof, Z is —$CR^{9a}R^{9b}$—$CR^{9c}R^{9d}$— and $R^{9a}$, $R^{9b}$, $R^{9c}$, and $R^{9d}$ are independently H, $C_{1-4}$alkyl, $C_{1-4}$haloalkyl, or halo. In some embodiments, $R^{9a}$, $R^{9b}$, $R^{9c}$, and $R^{9d}$ are independently H or $C_{1-4}$alkyl. In some embodiments, $R^{9a}$, $R^{9b}$, $R^{9c}$, and $R^{9d}$ are H.

In some embodiments of the compound of formula I, II, IIIa, IIIb, IV, Va, Vb, VI, VIIa, VIIb, VIII, X, Xa, Xb, XI, XIa, or XIb, or a pharmaceutically acceptable salt thereof, Z is —$CR^{10a}$=$CR^{10b}$— and $R^{10a}$ and $R^{10b}$ are independently H, halo, $C_{1-4}$haloalkyl, or $C_{1-4}$alkyl. In some embodiments, $R^{10a}$ and $R^{10b}$ together with the atoms to which each is attached form a 5- to 10-membered fused aromatic ring or heteroaromatic ring containing 1 to 2 heteroatoms selected from N, O and S, wherein the aromatic or heteroaromatic ring is optionally substituted with one to four $R^{47}$, wherein each $R^{47}$ is independently halo or $C_{1-4}$alkyl. In some embodiments, $R^{10a}$ and $R^{10b}$ together with the atoms to which each is attached form a 5- to 10-membered fused aromatic ring, optionally substituted with one to four $R^{47}$, wherein each $R^{47}$ is independently halo or $C_{1-4}$ alkyl. In some embodiments, $R^{10a}$ and $R^{10b}$ together with the atoms to which each is attached form a fused 1,2-phenylene ring, optionally substituted with one to four $R^{47}$, wherein each $R^{47}$ is independently halo or $C_{1-4}$alkyl. In some embodiments, $R^{10a}$ and $R^{10b}$ together with the atoms to which each is attached form

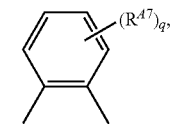

wherein q is 0, 1, 2, 3, or 4. In some embodiments, $R^{10a}$ and $R^{10b}$ together with the atoms to which each is attached form

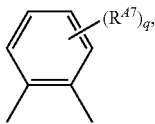

wherein each $R^{44}$ is independently halo. In some embodiments, $R^{10a}$ and $R^{10b}$ together with the atoms to which each is attached form

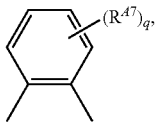

wherein each $R^{44}$ is independently halo and q is 0, 1, 2, or 3. In some embodiments, $R^{10a}$ and $R^{10b}$ together with the atoms to which each is attached form

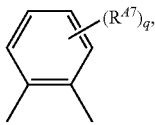

Wherein each $R^{44}$ is independently halo and q is 0, 1, or 2. In some embodiments, $R^{10a}$ and $R^{10b}$ together with the atoms to which each is attached form

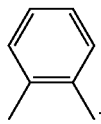

In some embodiments, $R^{10a}$ and $R^{10b}$ together with the atoms to which each is attached form

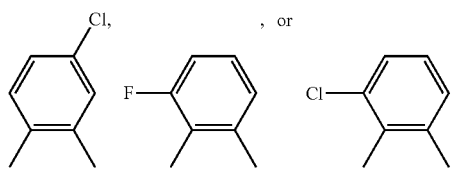

In some embodiments, $R^{10a}$ and $R^{10b}$ together with the atoms to which each is attached form

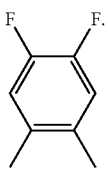

In some embodiments of the compound of formula I, II, IIIa, IIIb, IV, Va, Vb, VI, VIIa, VIIb, VIII, X, Xa, Xb, XI, XIa, or XIb, or a pharmaceutically acceptable salt thereof, Z is —$CR^{9a}R^{9b}$—, —$CR^{9a}R^{9b}CR^{9c}R^{9d}$—, or —$CR^{10a}$=$CR^{10b}$—; wherein $R^{9a}$, $R^{9b}$, $R^{9c}$, and $R^{9d}$ are each independently H, $C_{1-6}$alkyl, $C_{1-4}$haloalkyl, or halo; or $R^{9a}$ and $R^{9b}$ or $R^{9c}$ and $R^{9d}$ together with the carbon atom to which they are attached form a 3 to 7 membered saturated or partially unsaturated ring containing 0 to 2 heteroatoms selected from N, O, and S, wherein the spiro ring is optionally substituted with one to three $R^{46}$, wherein each $R^{46}$ is independently halo, $C_{1-4}$alkyl or $C_{1-4}$haloalkyl; $R^{10a}$ and $R^{10b}$ are independently H, halo, $C_{1-4}$haloalkyl, or $C_{1-6}$alkyl; or $R^{10a}$ and $R^{10b}$ together with the carbon atoms to which each is attached form (i) a 5-10 membered partially unsaturated fused ring containing 0 heteroatoms or 1 heteroatom selected from N, O, and S, (ii) a 5-10 membered fused aromatic ring, or (iii) a 5-10 membered fused heteroaromatic ring containing 1 to 2 heteroatoms selected from N, O and S, wherein the 5 to 10 membered partially unsaturated fused ring, 5-10 membered fused aromatic ring, or 5-10 membered fused heteroaromatic ring is optionally substituted with one to four $R^{47}$, wherein each $R^{47}$ is independently halo or $C_{1-4}$alkyl.

In some embodiments of the compound of formula I, II, IIIa, IIIb, IV, Va, Vb, VI, VIIa, VIIb, or VIII, or a pharmaceutically acceptable salt thereof, Z is —$CR^{9a}R^{9b}$—, —$CR^{9a}R^{9b}CR^{9c}R^{9d}$—, or —$CR^{10a}$=$CR^{10b}$—; wherein $R^{9a}$, $R^{9b}$, $R^{9c}$, and $R^{9d}$ are each independently H, $CH_3$, $CH_2CH_3$, $CHF_2$, or halo; or $R^{9a}$ and $R^{9b}$ or $R^{9c}$ and $R^{9d}$ together with the carbon atom to which they are attached form a 3-membered carbocyclic ring; $R^{10a}$ and $R^{10b}$ are independently H, halo, or $CH_3$; or $R^{10a}$ and $R^{10b}$ together with the carbon atoms to which each is attached form (i) a fused phenyl ring or (ii) a 5-6 membered fused heteroaromatic ring containing 1 to 2 heteroatoms selected from N, O and S, wherein the fused phenyl ring or the fused heteroaromatic ring is optionally substituted with one to two $R^{47}$, wherein each $R^{47}$ is independently halo or $CH_3$.

In some embodiments of the compound of formula I, II, IIIa, IIIb, IV, Va, Vb, VI, VIIa, VIIb, or VIII, or a pharmaceutically acceptable salt thereof, wherein $R^1$ is phenyl substituted with one, two, three, or four $R^{41}$, wherein each $R^{41}$ is independently halo or —O—$C_{1-4}$alkyl; X is a bond or $CR^{8a}R^{8b}$—, wherein $R^{8a}$ and $R^{8b}$ are independently H, hydroxyl, —O—$C_{1-4}$ alkyl, $C_{1-4}$alkyl, $C_{1-4}$haloalkyl, or halo, or $R^{8a}$ and $R^{8b}$ together with the carbon to which they are attached form a 3-membered saturated spiro carbocyclic ring;

$W^1$ is a bond or —$CR^{4a}R^{4b}$—; wherein $R^{4a}$ and $R^{4b}$ are independently H, $C_{1-6}$alkyl, or halo;

$W^2$ is selected from the group consisting of —$CR^{5a}R^{5b}$, —$CR^{5a}R^{5b}CR^{5c}R^{5d}$—, —$CR^{6a}$=$CR^{6b}$—, —N($R^7$)—, —O—, —S(O)$_n$—, —C(O)—, —$CR^{5a}R^{5b}$—C(O)—, and —$CR^{5a}R^{5b}$—O—; wherein each $R^{5a}$, $R^{5b}$, $R^{5c}$, and $R^{5d}$ are independently H, $C_{1-4}$alkyl, halo, hydroxyl, or —O—$C_{1-4}$alkyl; each $R^{6a}$ and $R^{6b}$ are independently H, halo, or $C_{1-4}$alkyl; $R^7$ is H, $C_{1-4}$alkyl, $C_{1-4}$haloalkyl, C(O)R, or $SO_2R^c$; $R^c$ is $C_{1-4}$alkyl; and n is 0 or 1; and Z is —$CR^{9a}R^{9b}$—, —$CR^{9a}R^{9b}CR^{9c}R^{9d}$—, or —$CR^{10a}$=$CR^{10b}$—; wherein $R^{9a}$, $R^{9b}$, $R^{9c}$, and $R^{9d}$ are each independently H, $C_{1-6}$alkyl, $C_{1-4}$haloalkyl, or halo; or $R^{9a}$ and $R^{9b}$ or $R^{9c}$ and $R^{9d}$ together with the carbon atom to which they are attached form a 3-membered carbocyclic ring; and $R^{10a}$ and $R^{10b}$ are independently H, halo, $C_{1-4}$haloalkyl, or $C_{1-6}$alkyl.

In some embodiments of the compound of formula I, II, IIIa, IIIb, IV, Va, Vb, VI, VIIa, VIIb, or VIII, or a pharmaceutically acceptable salt thereof, $R^1$ is phenyl substituted with one, two, three, or four $R^{41}$, wherein each $R^{41}$ is independently halo or $-O-C_{1-4}$alkyl;

X is a bond or $CR^{8a}R^{8b}-$, wherein $R^{8a}$ and $R^{8b}$ are independently H, hydroxyl, $-O-C_{1-4}$ alkyl, $C_{1-4}$alkyl, $C_{1-4}$haloalkyl, or halo;

$W^1$ is a bond or $-CR^{4a}R^{4b}-$; wherein $R^{4a}$ and $R^{4b}$ are independently H, $C_{1-6}$alkyl, or halo;

$W^2$ is $-CR^{5a}R^{5b}$; wherein each $R^{5a}$ and $R^{5b}$ are independently H, $C_{1-4}$alkyl, halo, hydroxyl, or $-O-C_{1-4}$alkyl; and Z is $-CR^{9a}R^{9b}-$; wherein $R^{9a}$ and $R^{9b}$ are each independently H, $C_{1-6}$alkyl, $C_{1-4}$ haloalkyl, or halo.

In some embodiments of the compound of formula I, II, IIIa, IIIb, IV, Va, Vb, VI, VIIa, VIIb, VIII, X, Xa, Xb, XI, XIa, or XIb, or a pharmaceutically acceptable salt thereof, $R^a$ is independently H, $C_{1-4}$alkyl, $C_{1-6}$haloalkyl, $C(O)R^c$, or $SO_2R^c$.

In some embodiments of the compound of formula I, II, IIIa, IIIb, IV, Va, Vb, VI, VIIa, VIIb, VIII, X, Xa, Xb, XI, XIa, or XIb, or a pharmaceutically acceptable salt thereof, $R^b$ is H. In some embodiments, $R^b$ is $C_{1-4}$alkyl. In some embodiments, $R^b$ is methyl.

In some embodiments of the compound of formula I, II, IIIa, IIIb, IV, Va, Vb, VI, VIIa, VIIb, VIII, X, Xa, Xb, XI, XIa, or XIb, or a pharmaceutically acceptable salt thereof, $R^c$ is $C_{1-4}$alkyl. In some embodiments, $R^c$ is methyl. In some embodiments, $R^c$ is $-O-C_{1-4}$alkyl.

In some embodiments of the compound of formula I, II, IIIa, IIIb, IV, Va, Vb, VI, VIIa, VIIb, or VIII, X, Xa, Xb, XI, XIa, or XIb, or a pharmaceutically acceptable salt thereof, n is 0. In some embodiments, n is 1. In some embodiments, n is 2.

In some embodiments, the compound of formula I, II, IIIa, IIIb, IV, Va, Vb, VI, VIIa, VIIb, or VIII, is a compound of formula (IX).

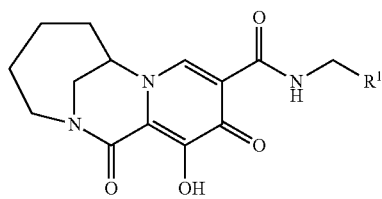

IX or a pharmaceutically acceptable salt thereof, wherein $R^1$ is H or $C_{6-10}$aryl, wherein $C_{6-10}$aryl is optionally substituted with one to four $R^{41}$, wherein each $R^{41}$ is independently halo, $C_{1-6}$alkyl, $C_{1-4}$haloalkyl, cyano, $-O-C_{1-4}$alkyl, or $C_{1-4}$alkyl-$O-C_{1-4}$alkyl.

In some embodiments, the compound of formula I, II, IIIa, IIIb, IV, Va, Vb, VI, VIIa, VIIb, VIII, or IX is a compound of formula (IXa):

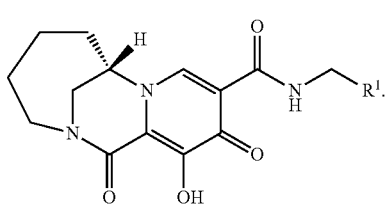

IXa

In some embodiments, the compound of formula I, II, IIIa, IIIb, IV, Va, Vb, VI, VIIa, VIIb, VIII, or IX is a compound of formula (IXb):

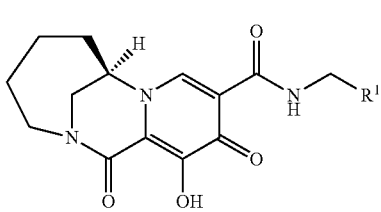

IXb or a pharmaceutically acceptable salt thereof, wherein $R^1$ is H or $C_{6-10}$aryl, wherein $C_{6-10}$aryl is optionally substituted with one to four $R^{41}$, wherein each $R^{41}$ is independently halo, $C_{1-6}$alkyl, $C_{1-4}$haloalkyl, cyano, $-O-C_{1-4}$alkyl, or $C_{1-4}$alkyl-$O-C_{1-4}$alkyl.

In some embodiments of the compound of formula I, II, IIIa, IIIb, IV, Va, Vb, VI, VIIa, VIIb, VIII, IX, IXa, IXb, X, Xa, or Xb, XI, XIa, or XIb, or a pharmaceutically acceptable salt thereof, $R^1$ is H. In some embodiments, $R^1$ is $C_{6-10}$aryl. In some embodiments, $R^1$ is phenyl, optionally substituted with one to four $R^{41}$, wherein each $R^{41}$ is independently halo, $C_{1-4}$alkyl, $C_{1-4}$haloalkyl, cyano, $-O-C_{1-4}$alkyl, or $C_{1-4}$alkyl-$O-C_{1-4}$alkyl. In some embodiments, $R^1$ is phenyl substituted with one, two, three, or four $R^{41}$. In some embodiments, $R^1$ is phenyl substituted with one, two, three, or four $R^{41}$. In some embodiments, $R^1$ is phenyl substituted with one, two, three, or four $R^{41}$, wherein each $R^{41}$ is independently halo, $C_{1-4}$alkyl, $C_{1-4}$ haloalkyl, or $-O-C_{1-4}$ alkyl. In some embodiments, $R^1$ is phenyl substituted with one, two, three, or four $R^{41}$, wherein each $R^{41}$ is independently halo, $C_{1-4}$alkyl, or $C_{1-4}$haloalkyl. In some embodiments, $R^1$ is phenyl substituted with one, two, three, or four $R^{41}$, wherein each $R^{41}$ is independently halo or $-O-C_{1-4}$ alkyl. In some embodiments, $R^1$ is phenyl substituted with one, two, three, or four halogens. In some embodiments, $R^1$ is phenyl substituted with one, two, or three halogens. In some embodiments, $R^1$ is phenyl substituted with two or three halogens. In some embodiments, $R^1$ is phenyl substituted with two or three halogens selected from chloro and fluoro. In some embodiments, $R^1$ is

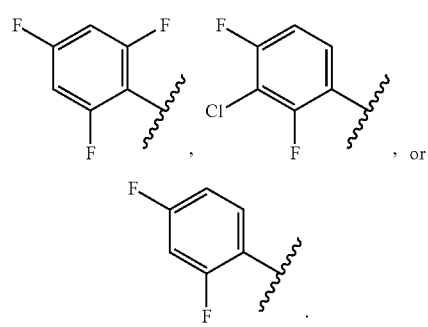

, or

In some embodiments, of the compound of formula I, II, IIIa, IIIb, IV, Va, Vb, VI, VIIa, VIIb, VIII, IX, IXa, IXb, X, Xa, Xb, XI, XIa, or XIb, $R^1$ is selected from the group consisting of

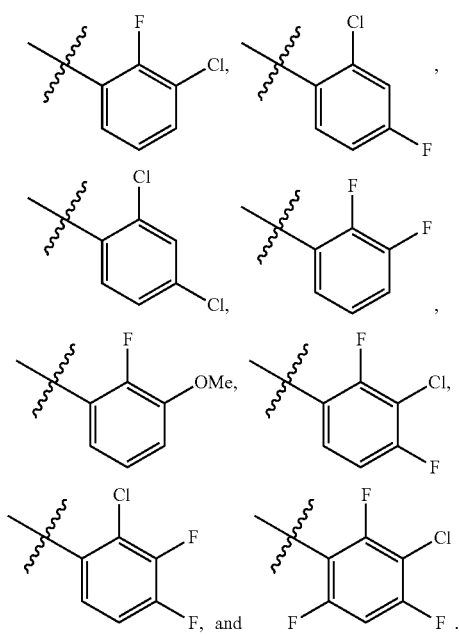
In some embodiments, of the compound of formula I or II, R¹ is selected from the group consisting of
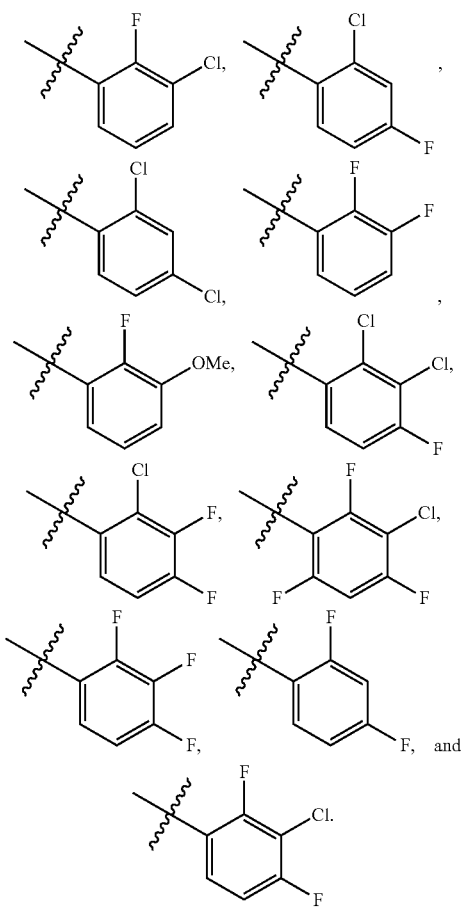
In some embodiments, the compounds have the formula:
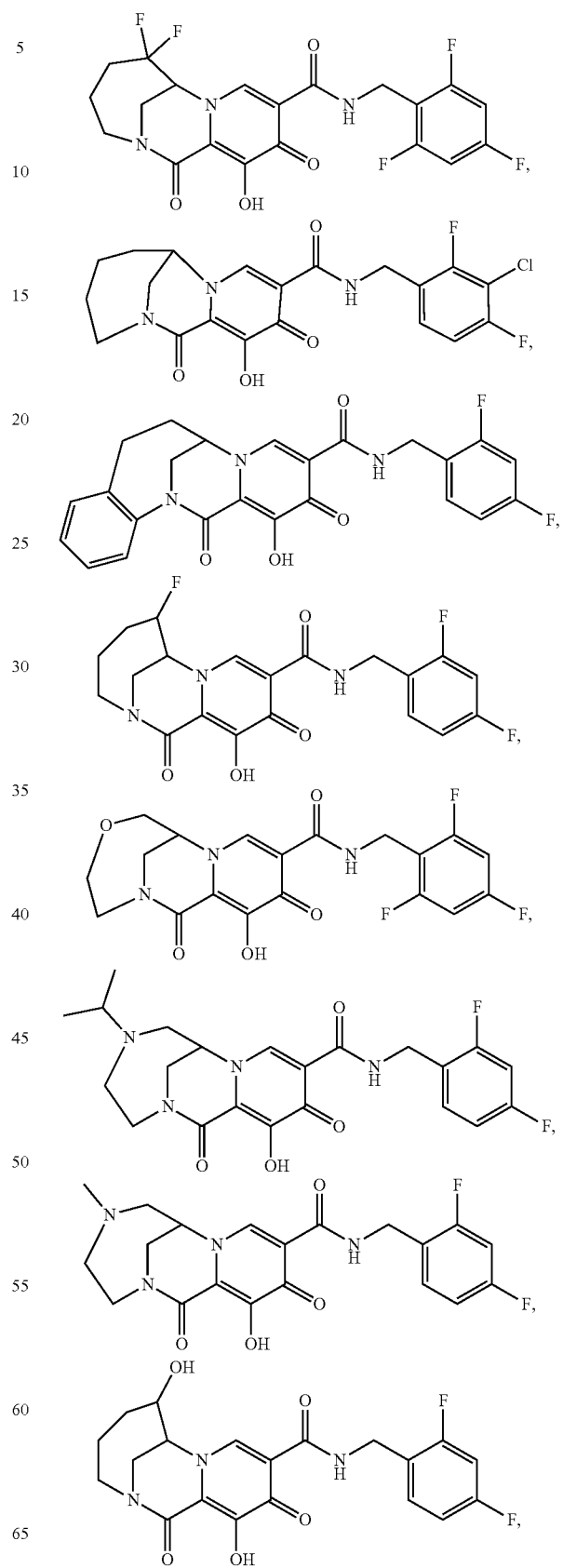

41
-continued
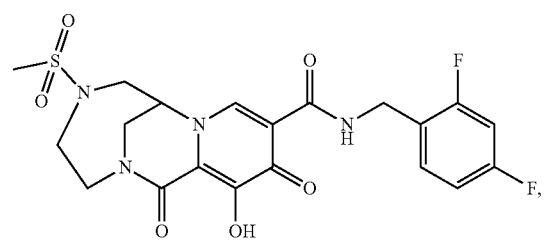
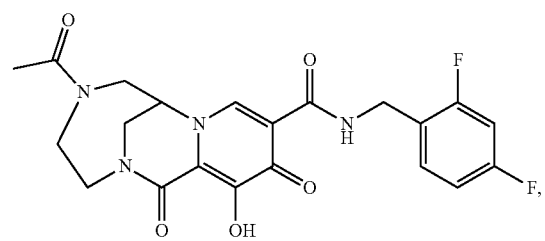
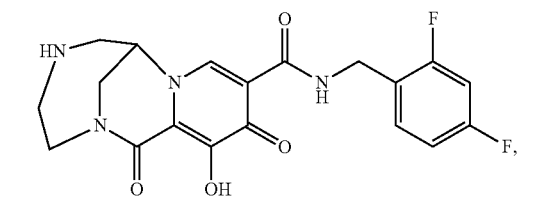
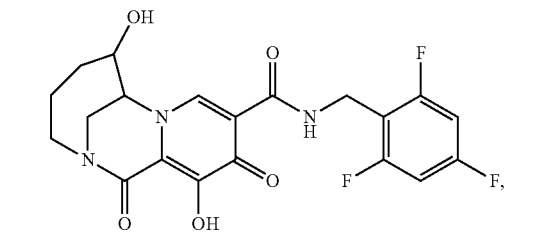
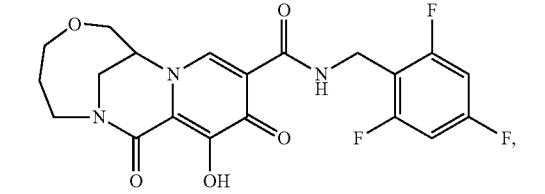
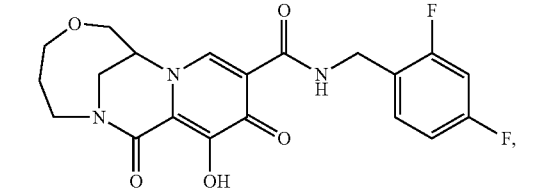
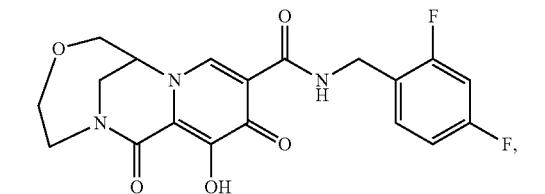
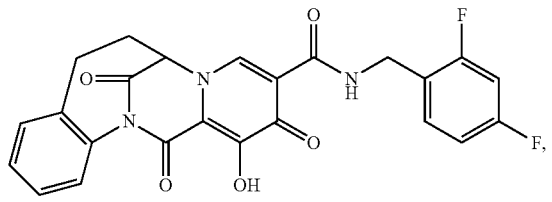
42
-continued
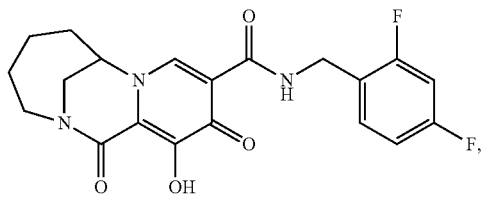
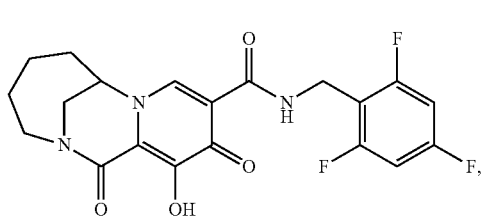
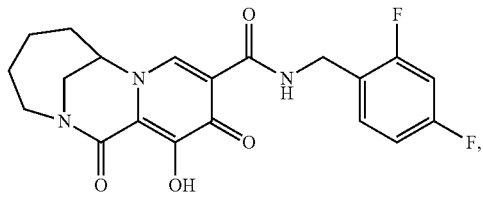
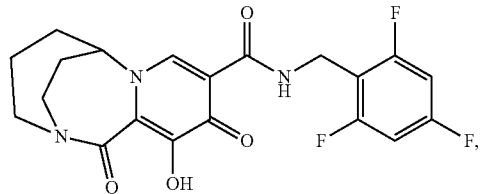
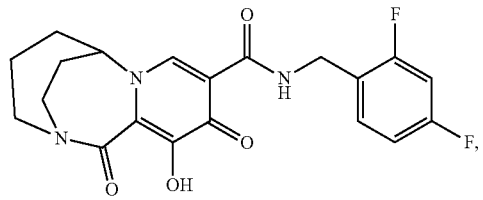
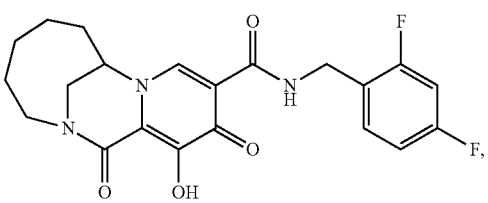
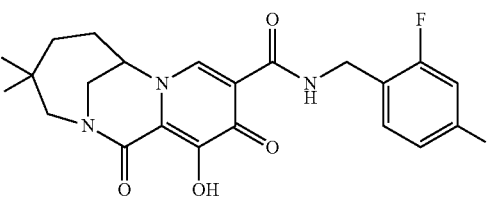
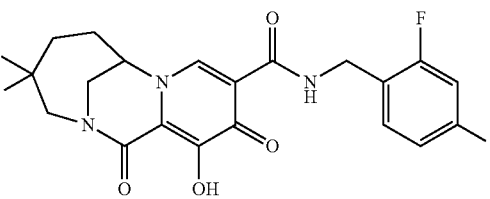

-continued
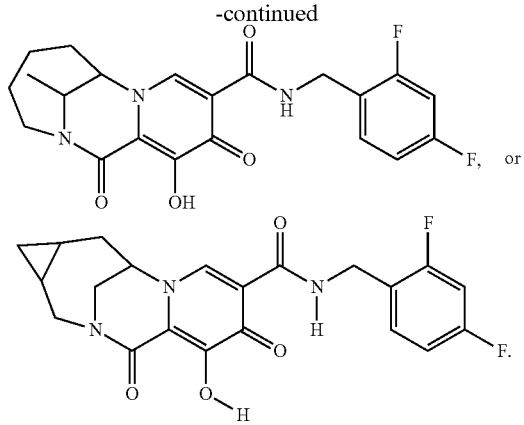
or
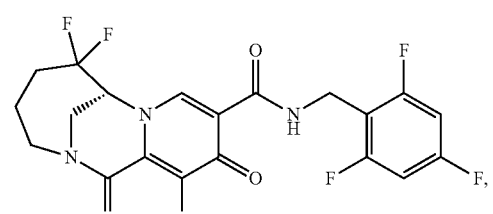
In some embodiments, the compounds have the formula:
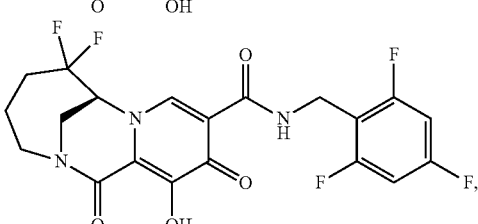
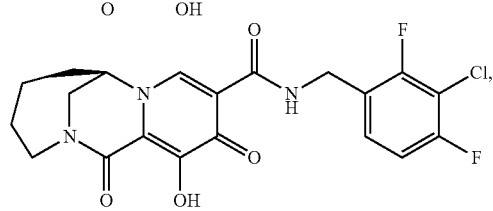
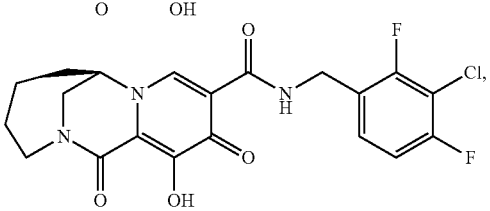
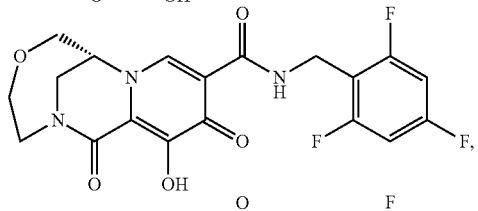
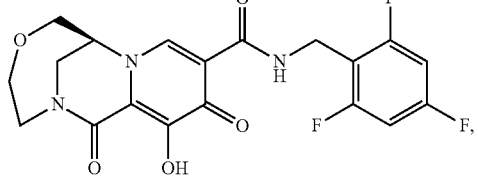
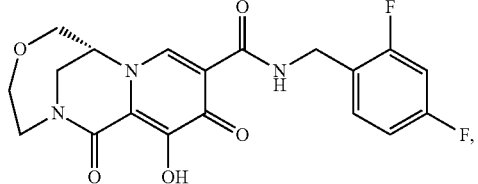
-continued
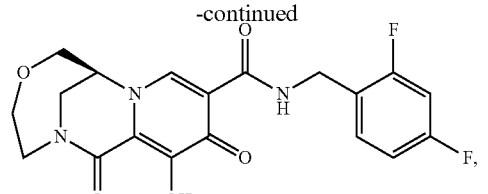
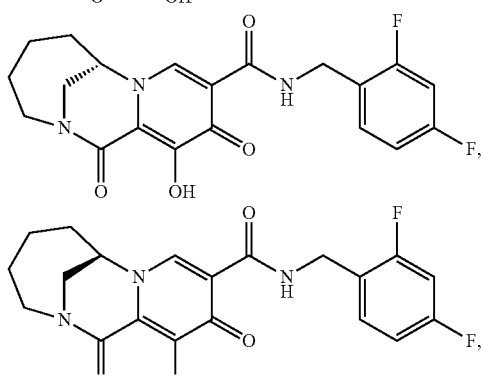
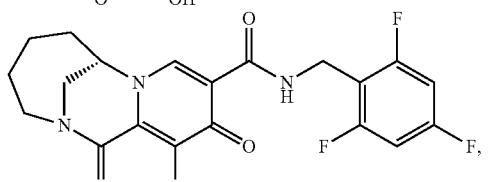
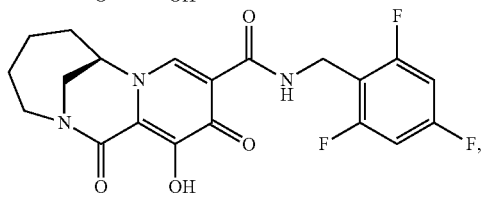
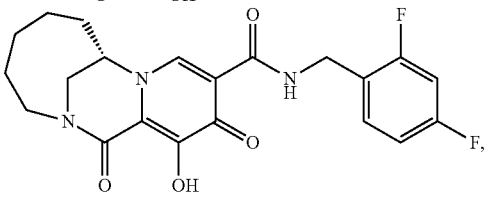
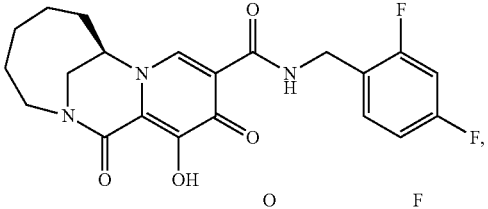
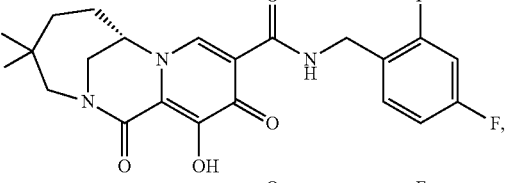
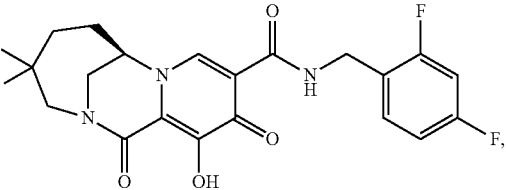

-continued
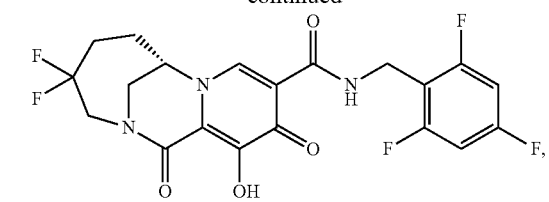
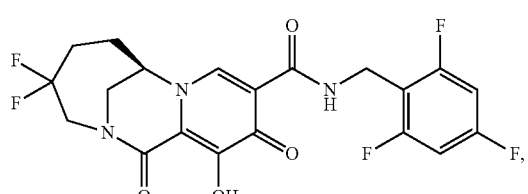
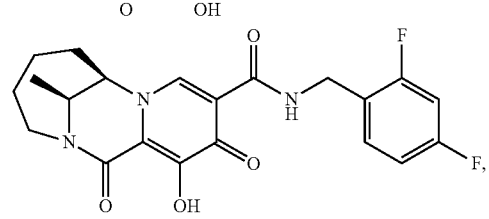
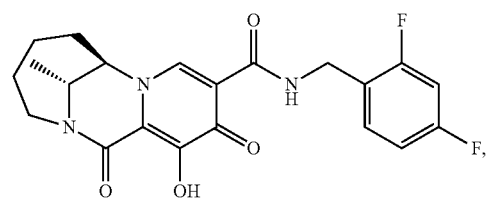
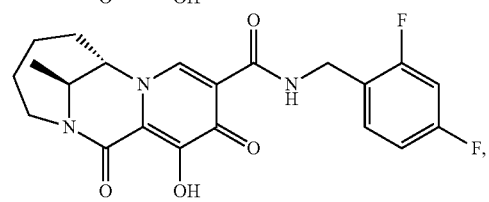
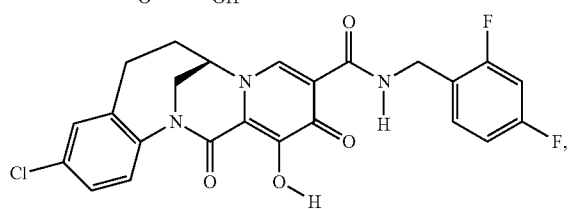
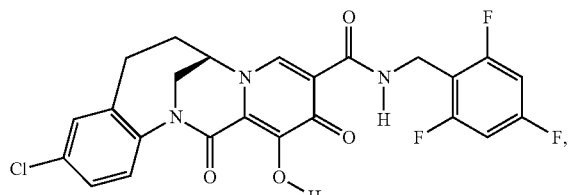
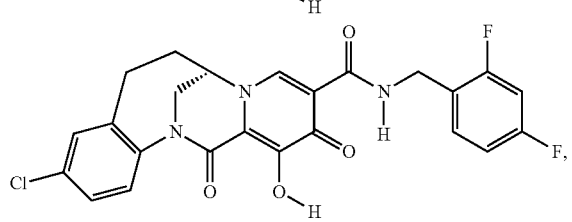
-continued
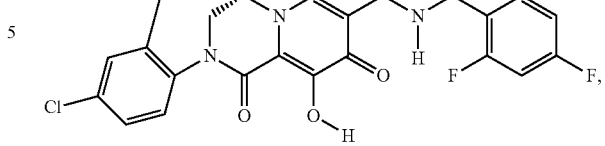
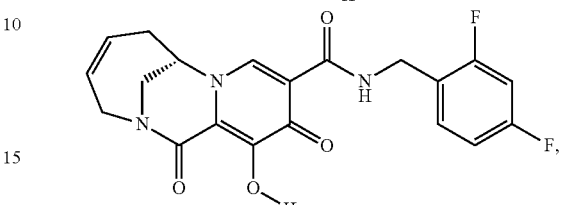
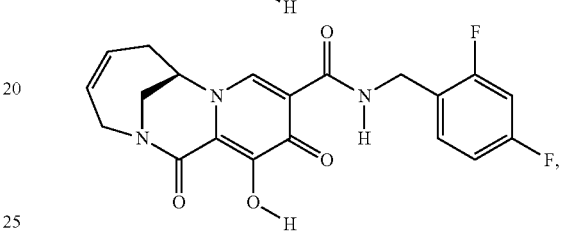
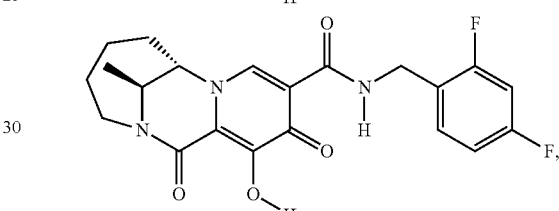
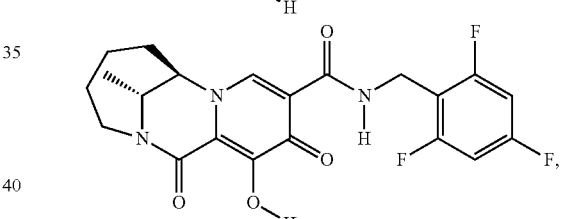
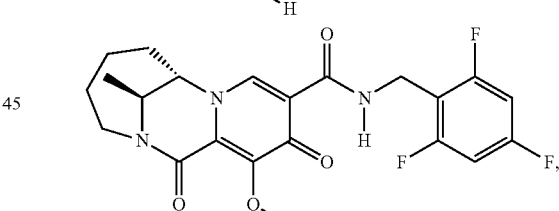
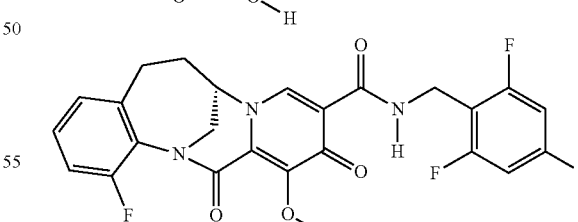
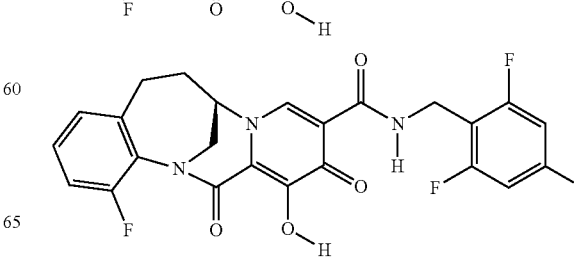

-continued
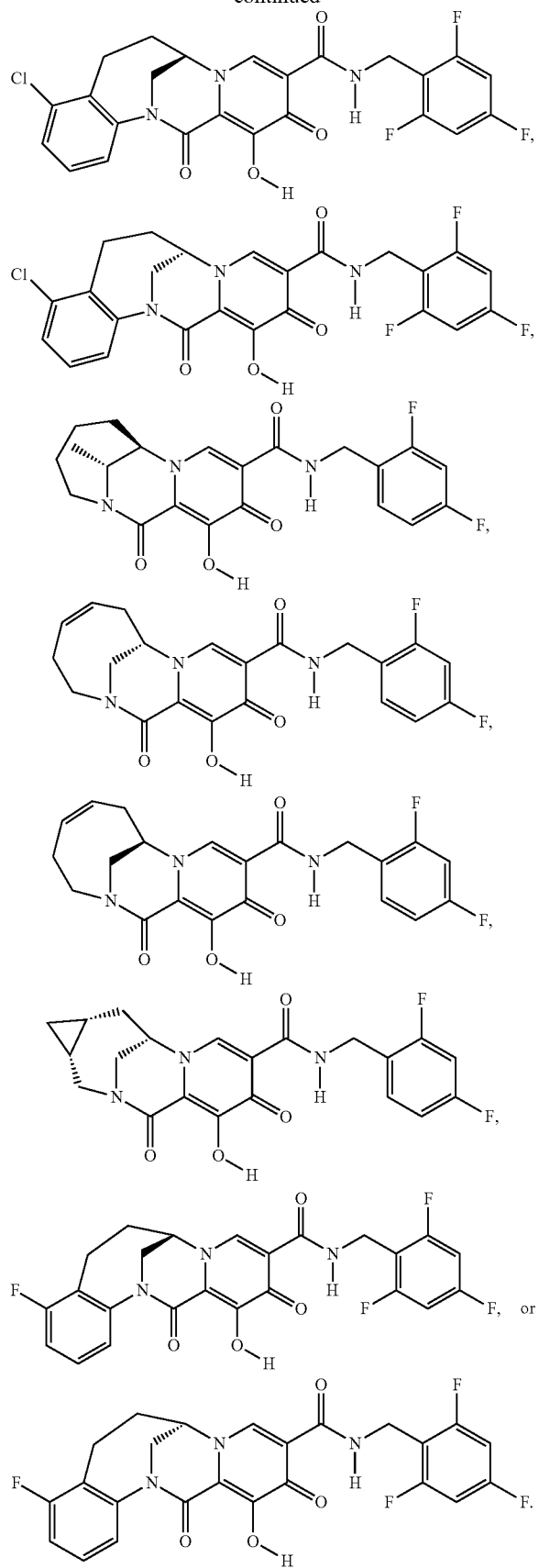
In some embodiment, the compound of formula I, II, IIIa, IIIb, IV, Va, Vb, VI, VIIa, VIIb, VIII, IX, IXa, IXb, X, Xa, Xb, XI, XIa, or XIb, is selected from the group consisting of:
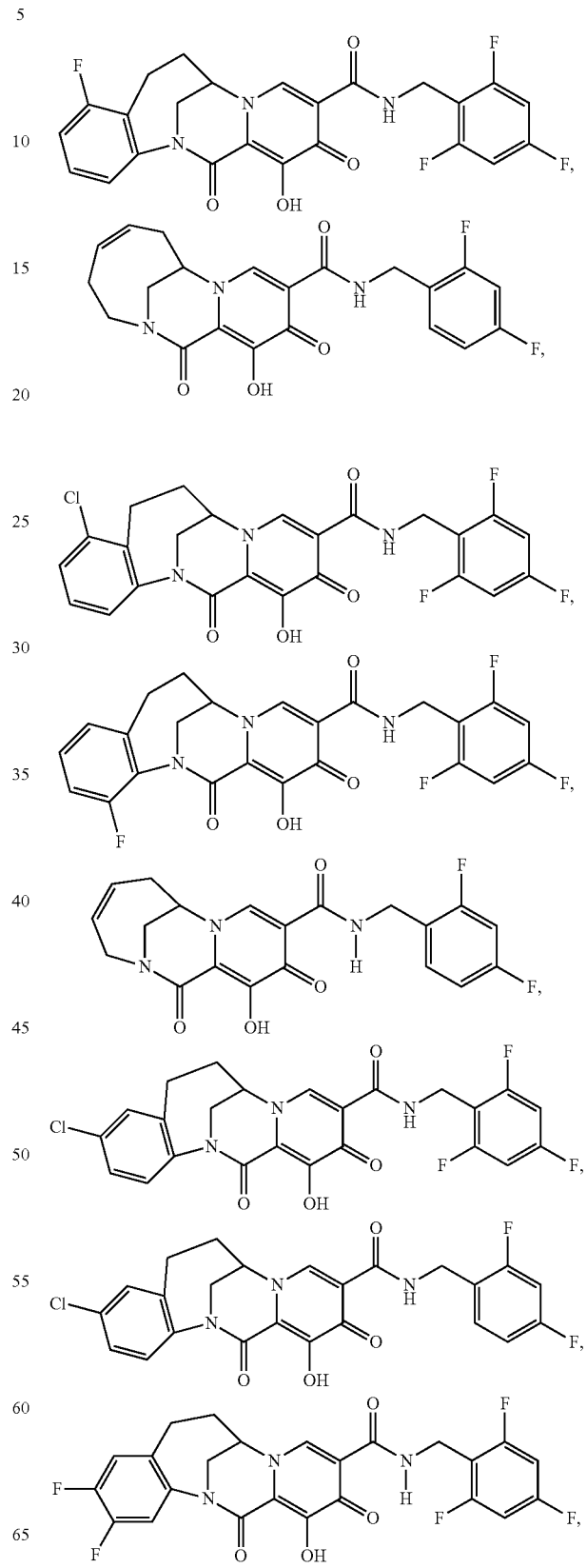

-continued
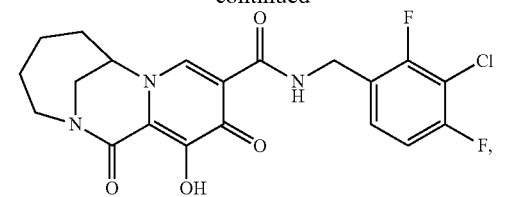
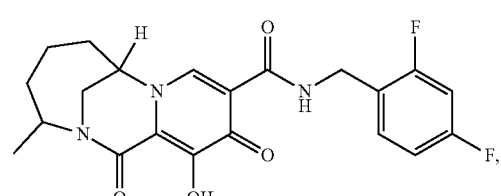
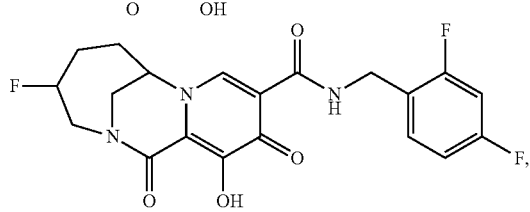
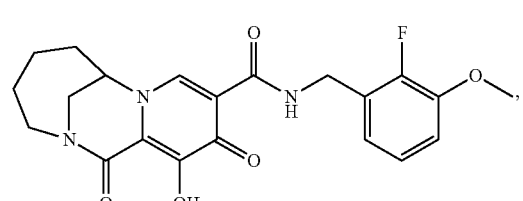
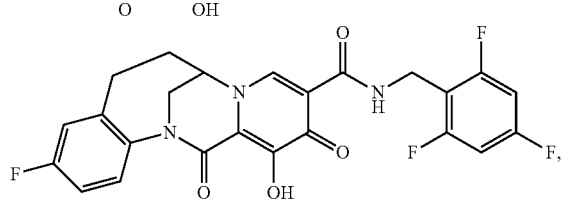
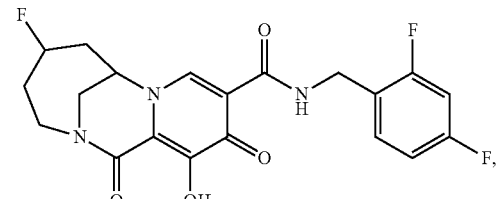
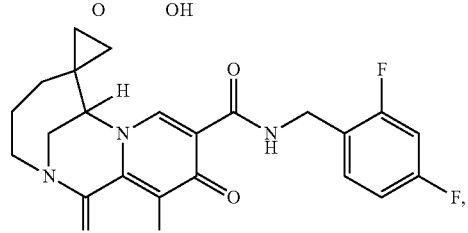
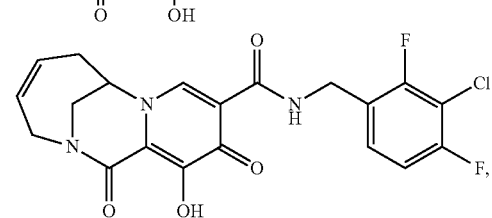
-continued
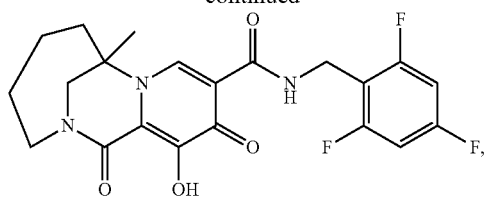
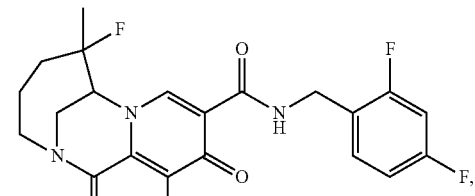
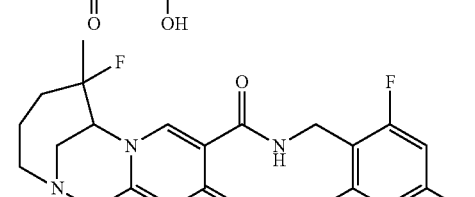
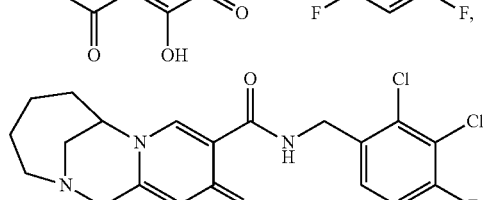
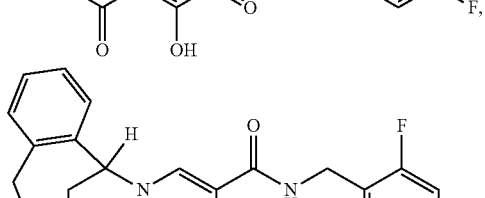
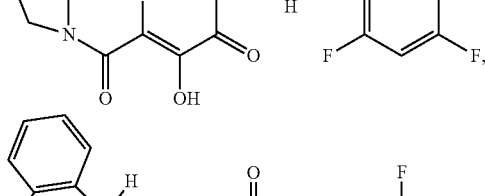
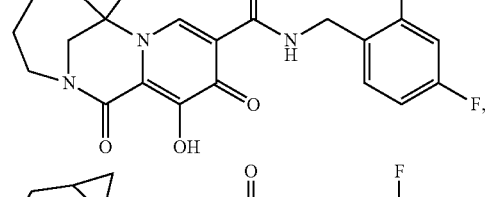
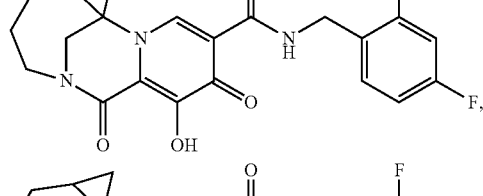
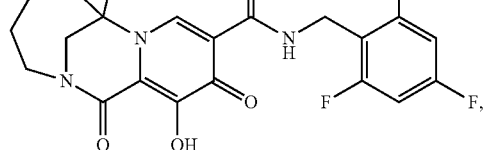

51
-continued
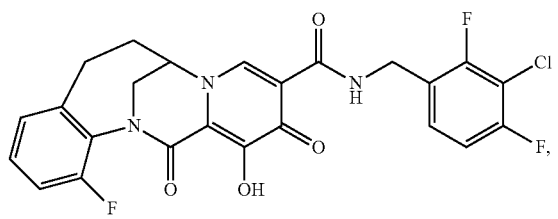
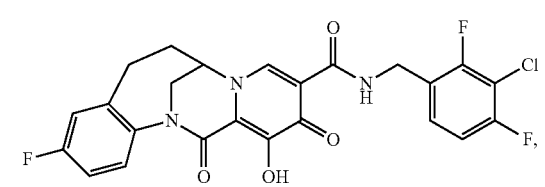
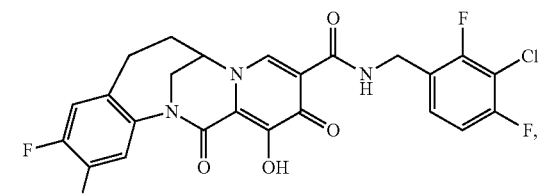
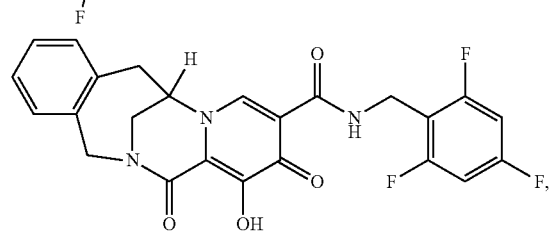
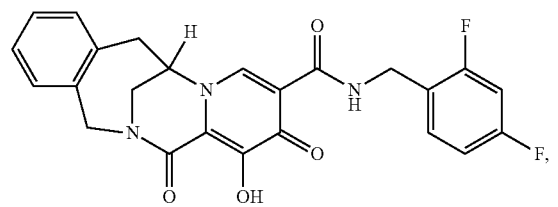
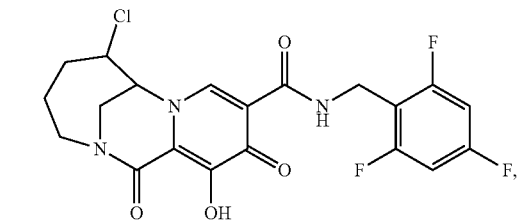
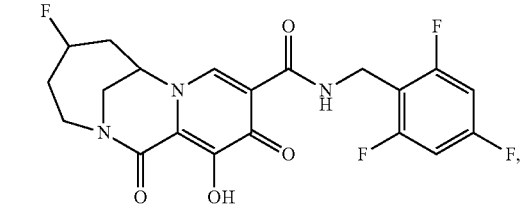
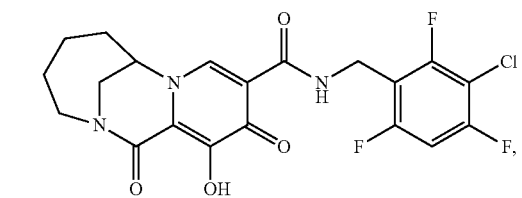
52
-continued
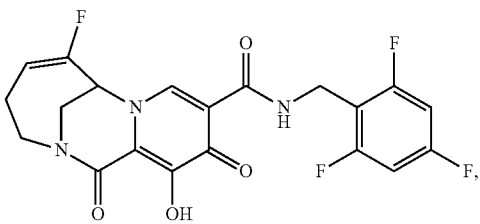
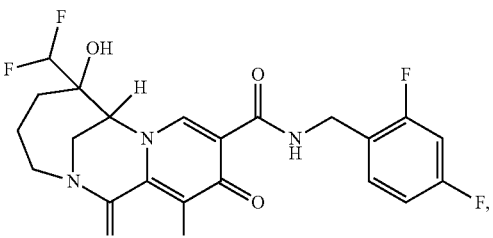
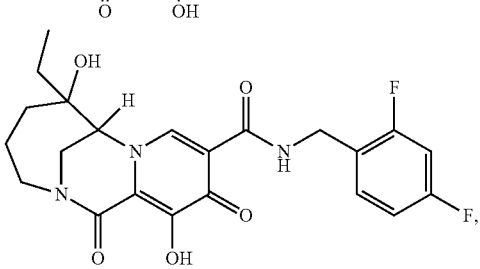
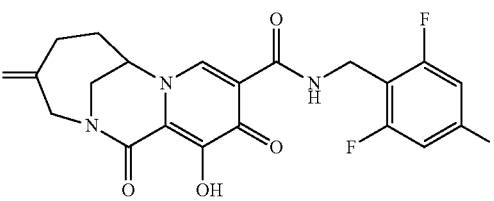
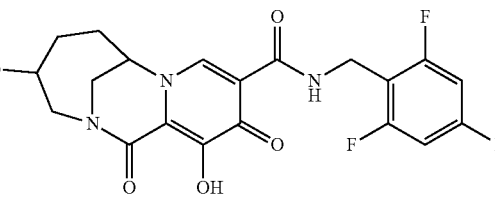
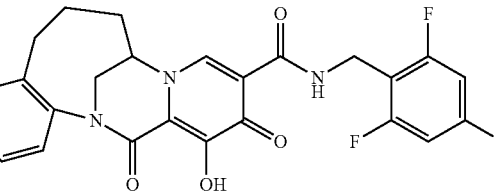
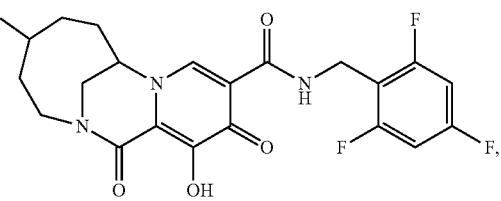
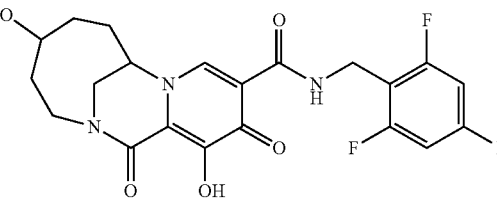

53
-continued
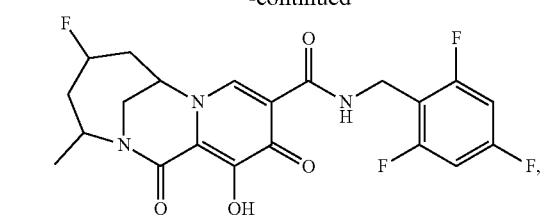
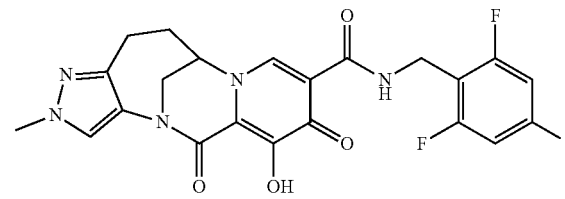
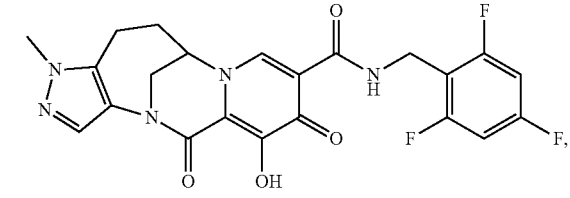
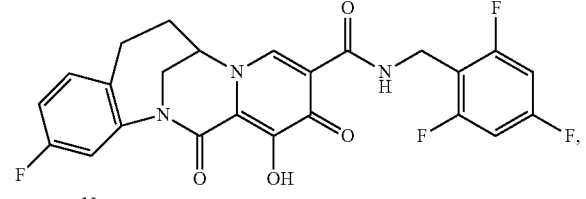
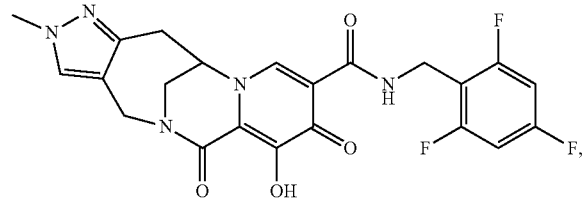
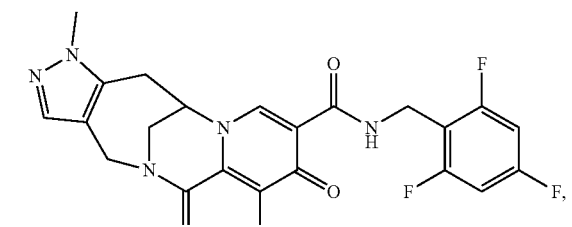
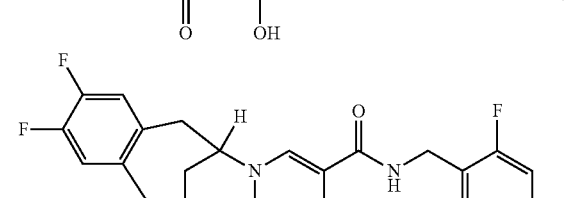
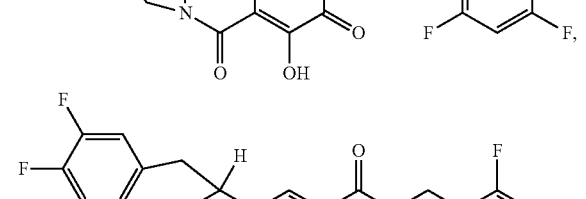
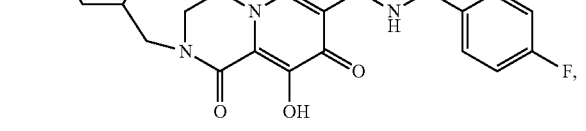
54
-continued
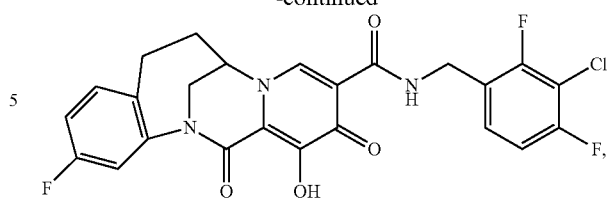
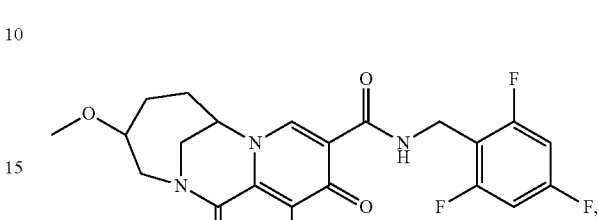
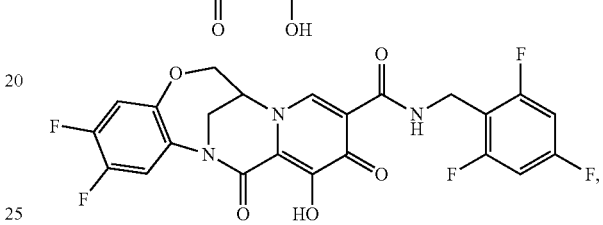
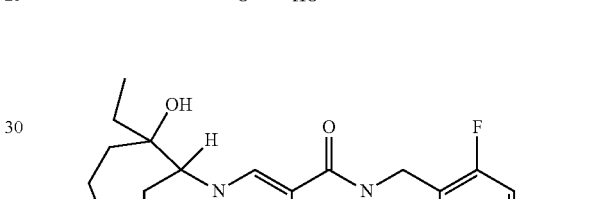
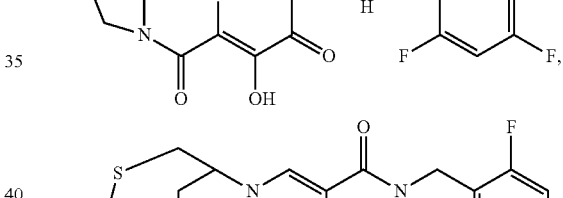
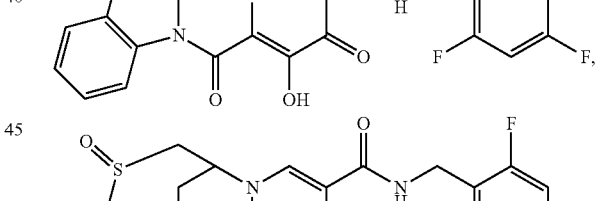
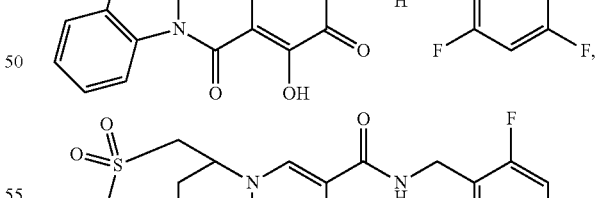
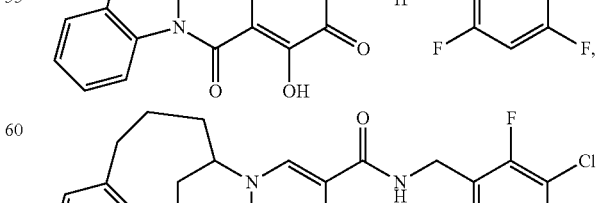
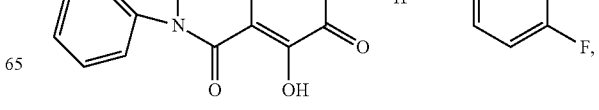

55
-continued
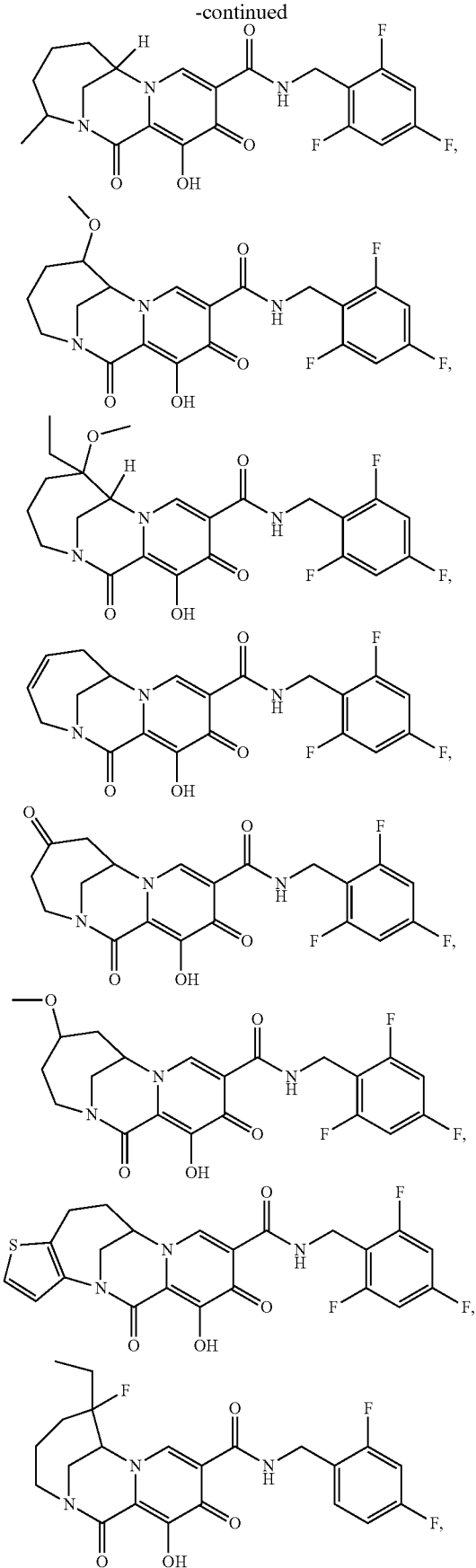
56
-continued
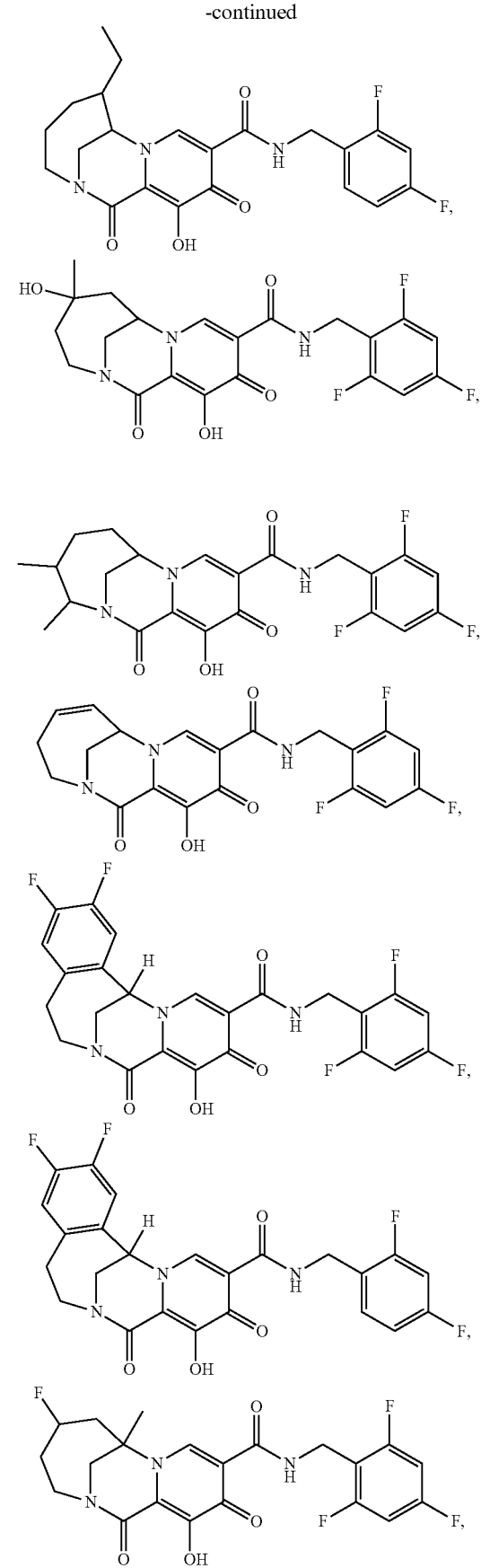

57
-continued
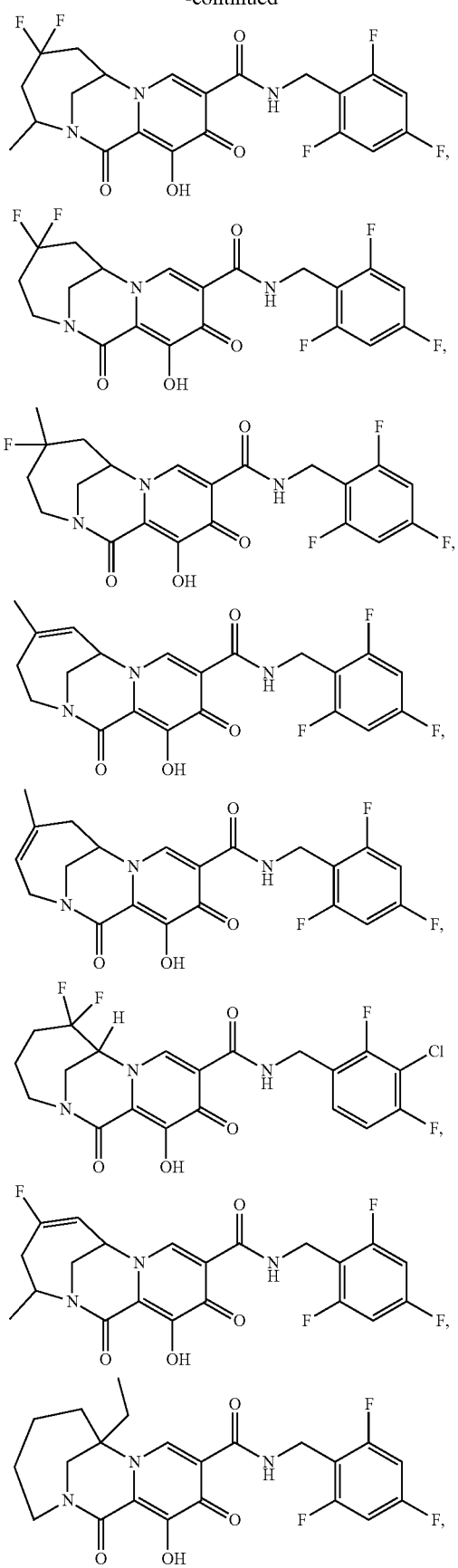
58
-continued
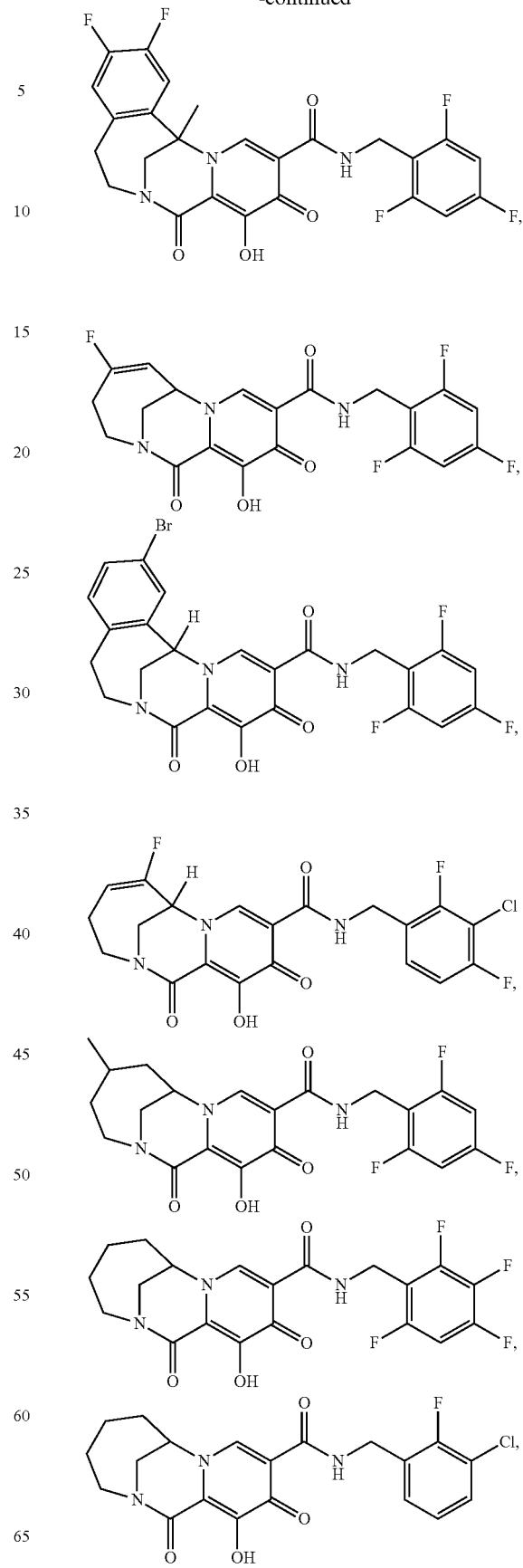

59
-continued
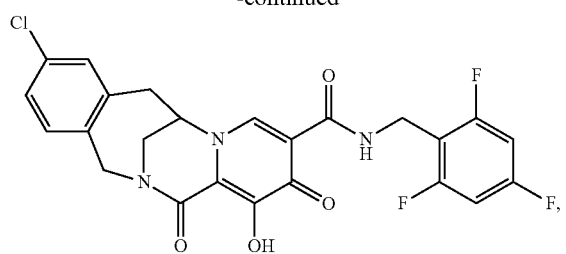
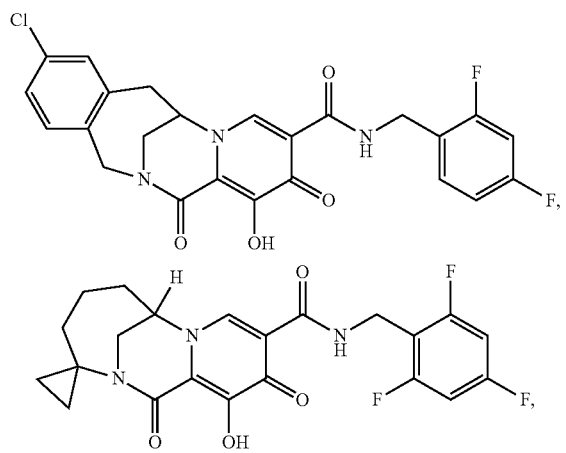
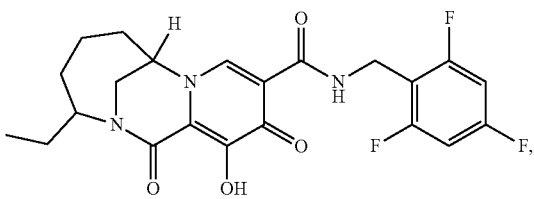
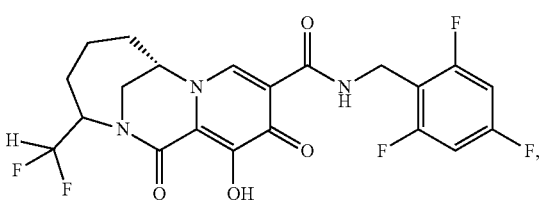
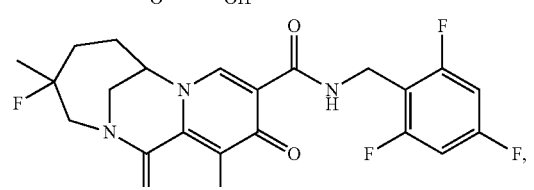
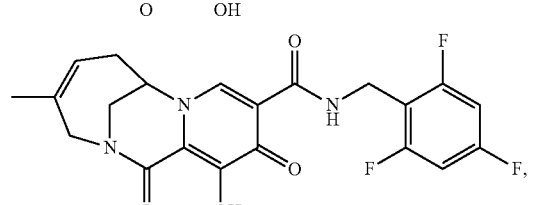
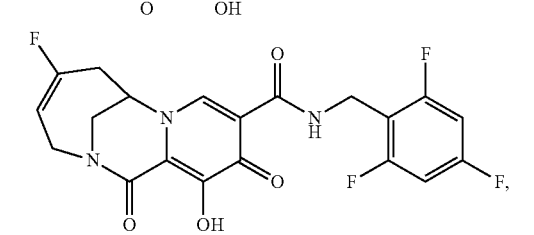
60
-continued
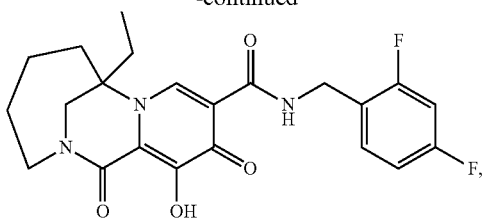
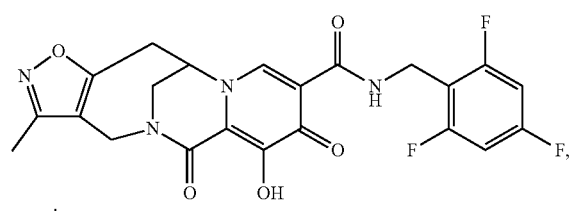
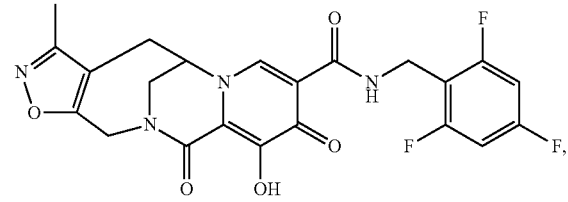
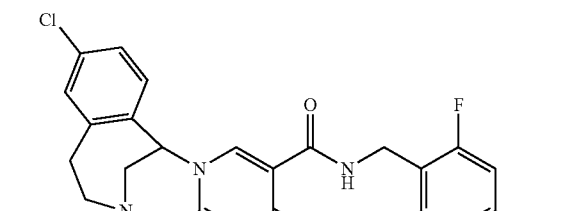
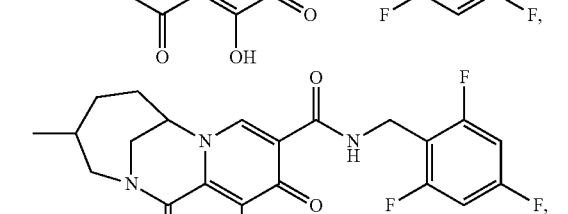
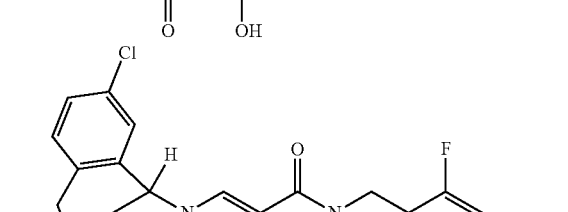
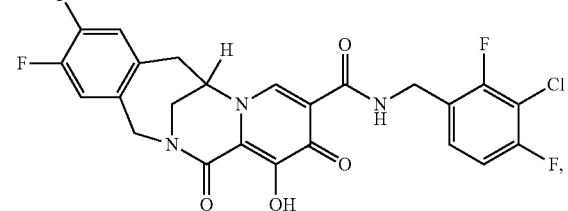

61
-continued
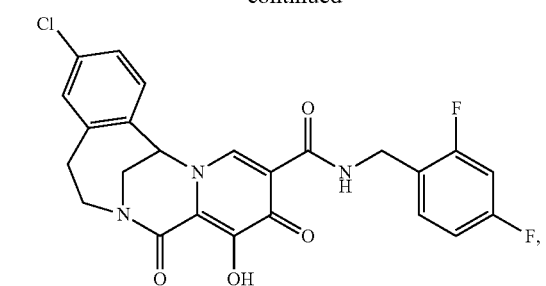
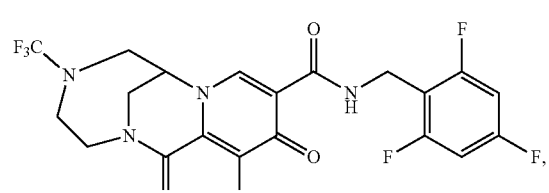
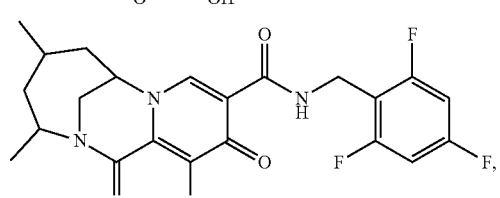
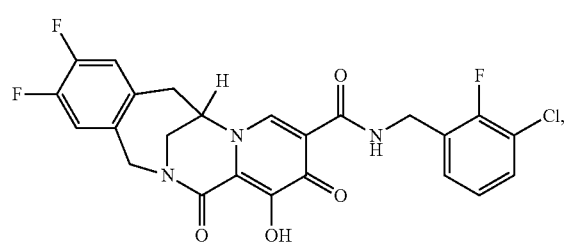
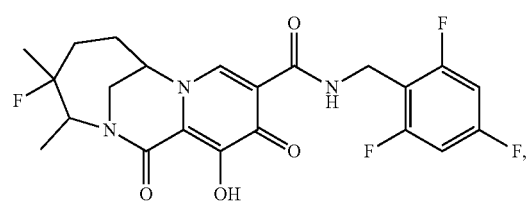
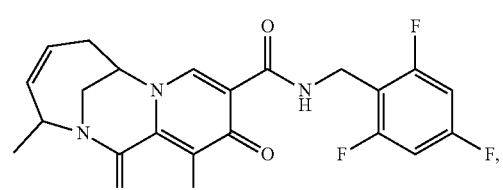
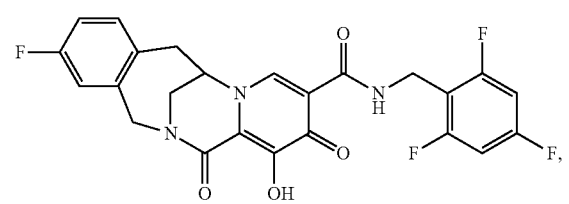
62
-continued
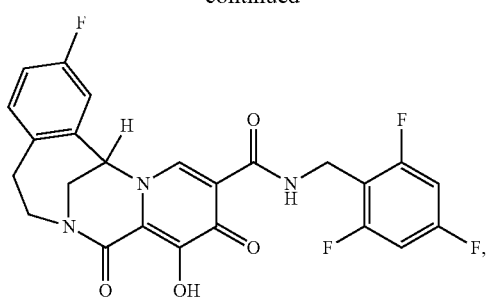
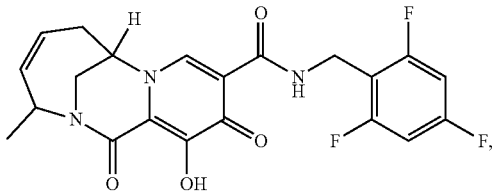
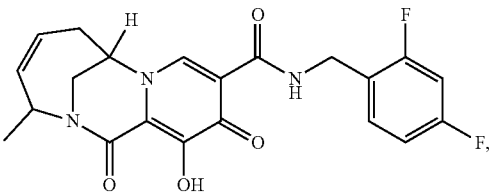
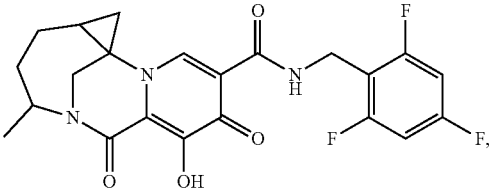
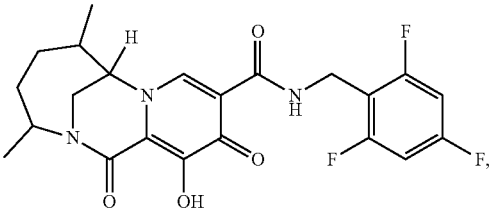
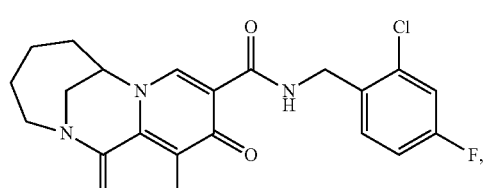
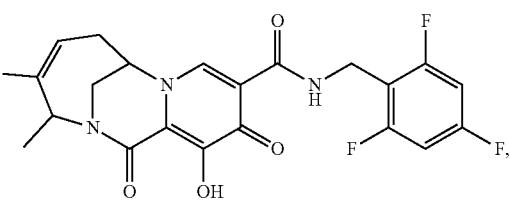

63
-continued
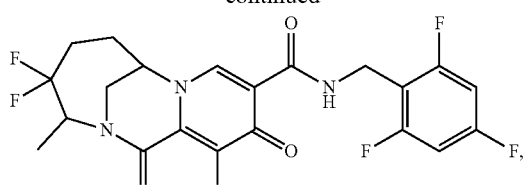
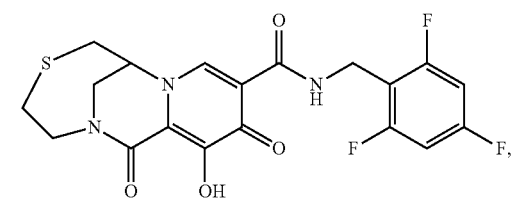
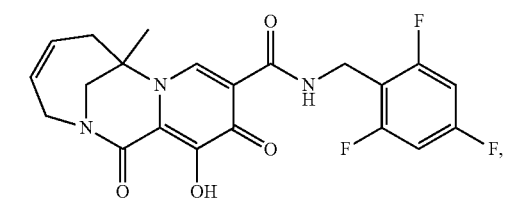
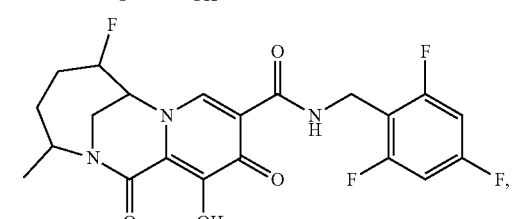
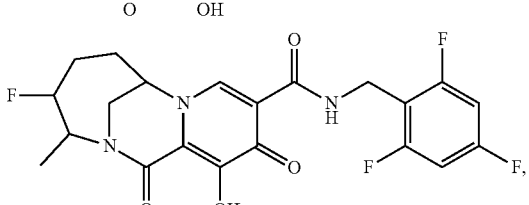
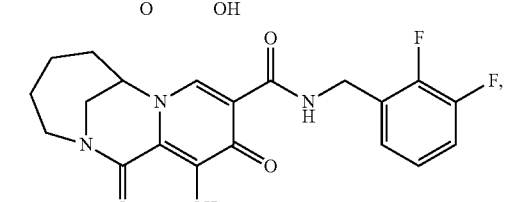
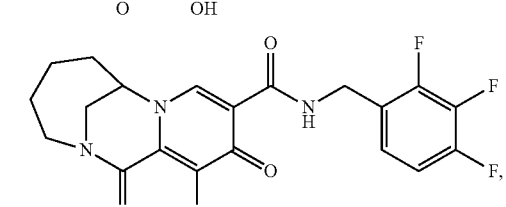
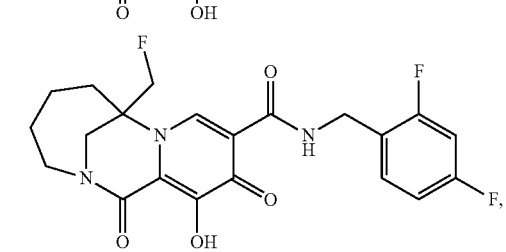
64
-continued
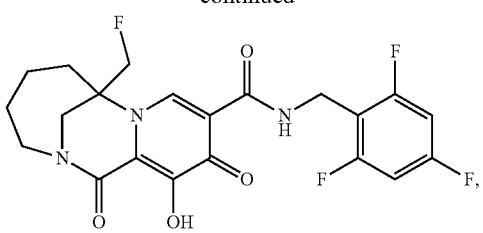
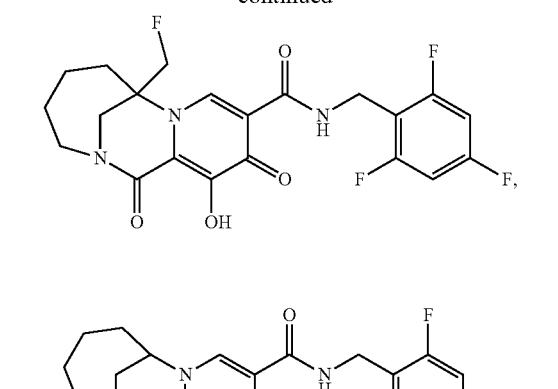
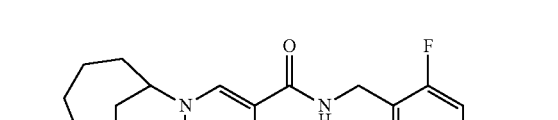 and
or a pharmaceutically acceptable salt thereof.
In some embodiment, the compound of formula I, II, IIIa, IIIb, IV, Va, Vb, VI, VIIa, VIIb, VIII, IX, IXa, or IXb, X, Xa, Xb, XI, XIa, or XIb, is selected from the group consisting of:
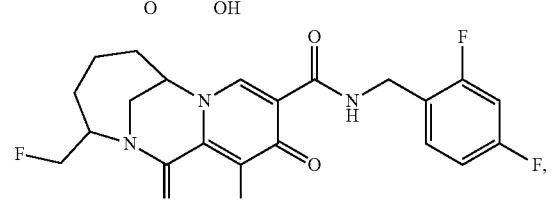
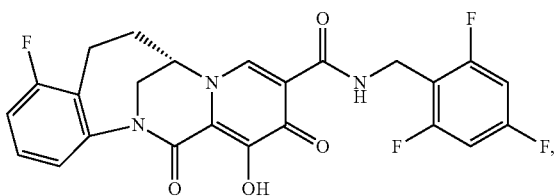
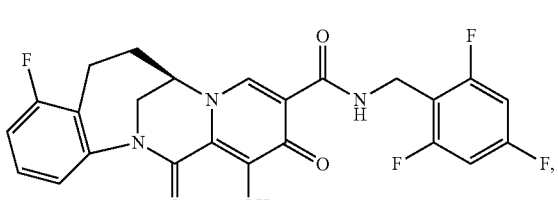
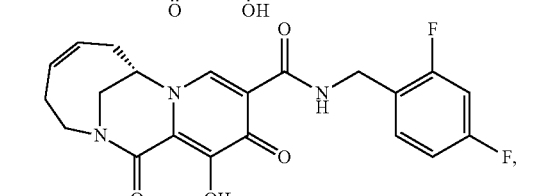
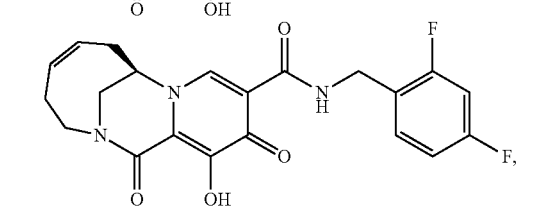

65
-continued
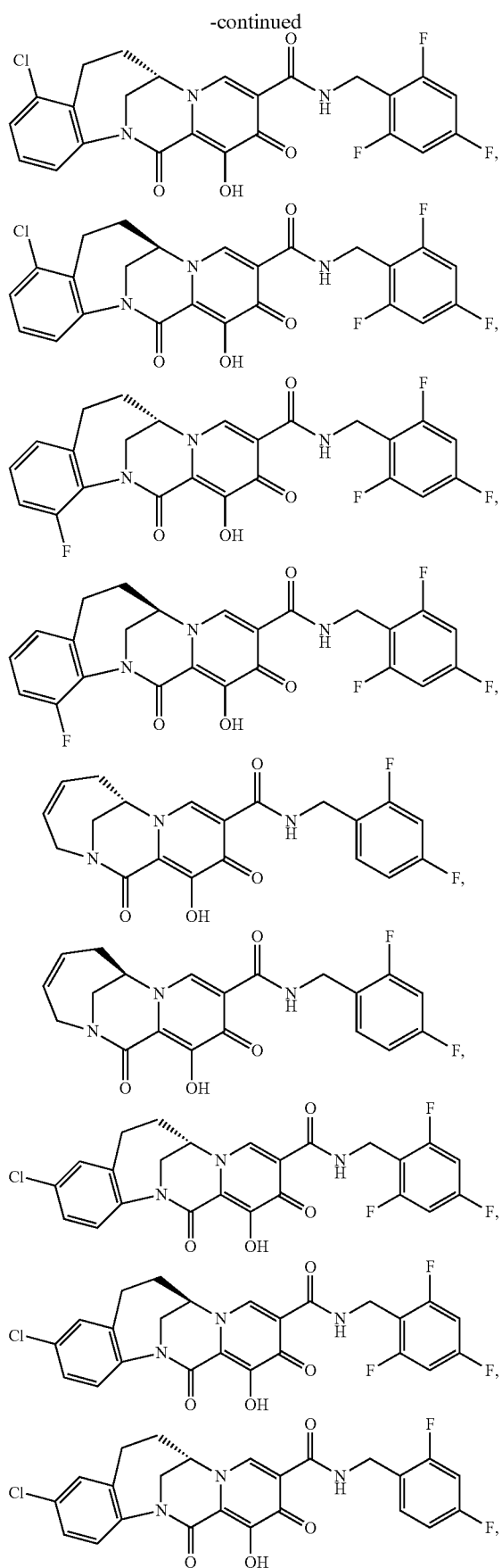
66
-continued
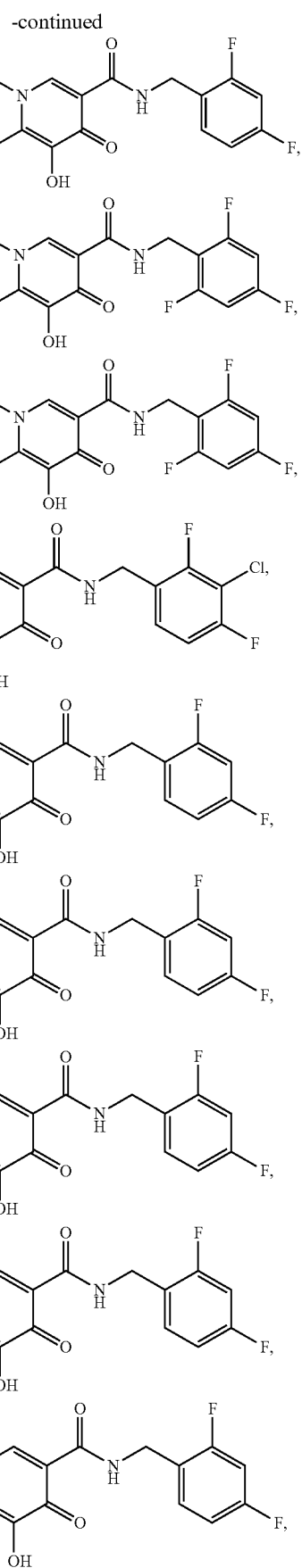

67
-continued
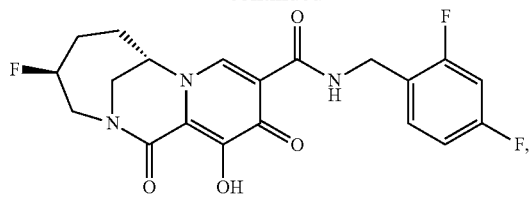
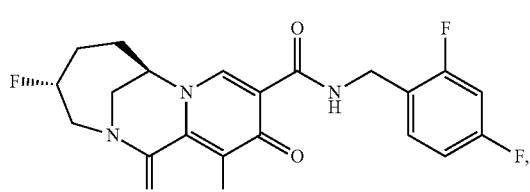
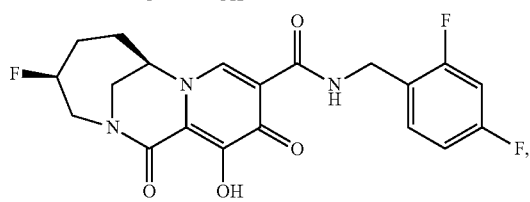
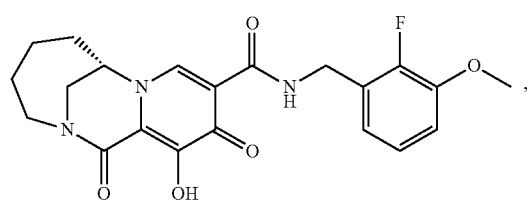
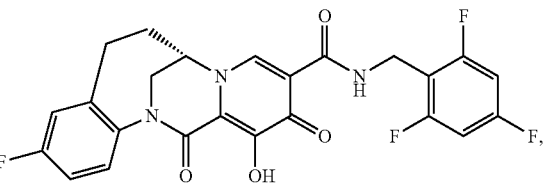
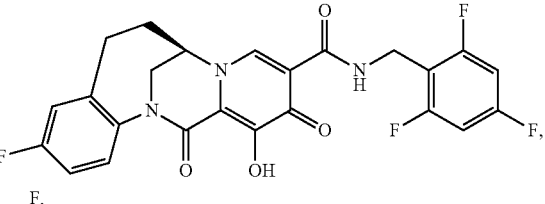
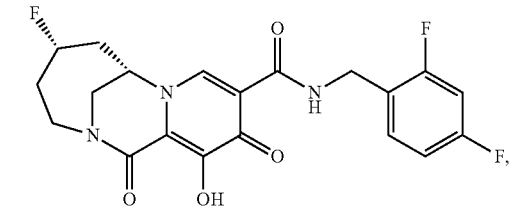
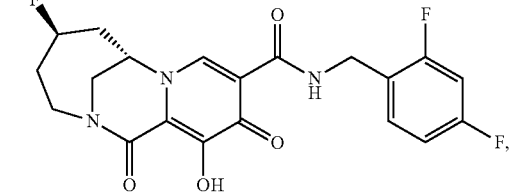
68
-continued
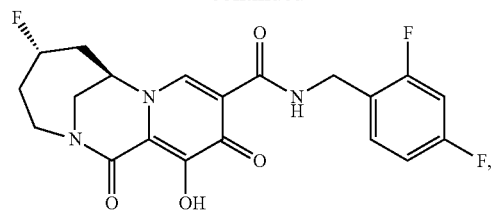
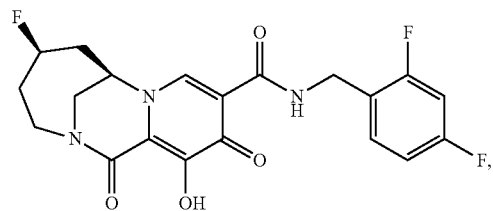
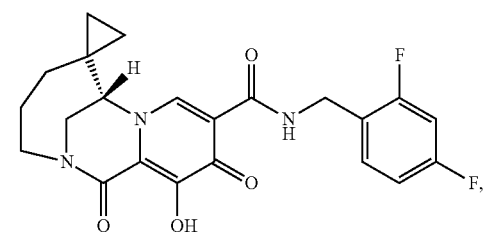
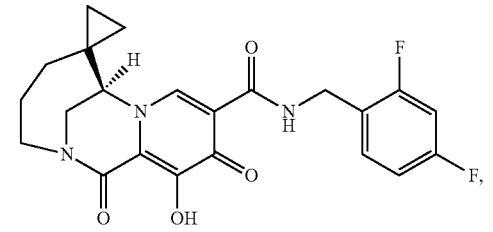
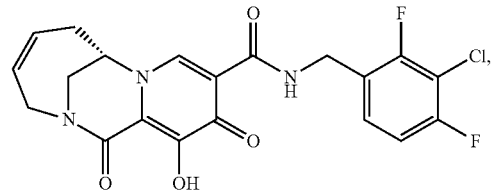
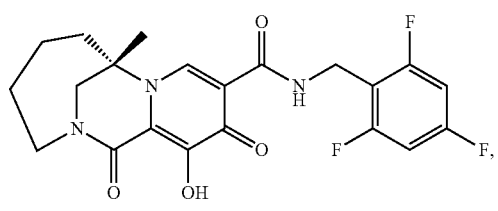
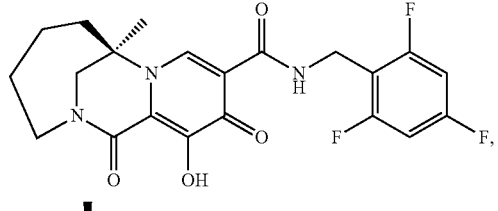
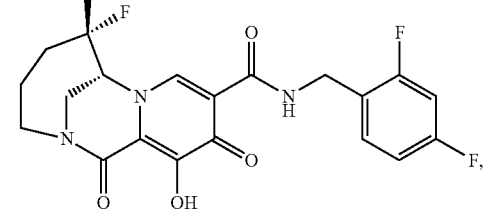

US 11,084,832 B2
69
-continued
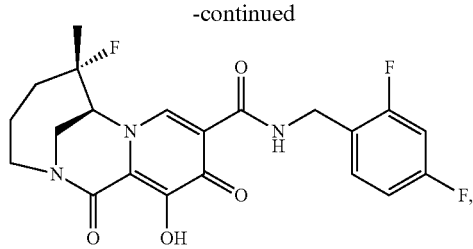
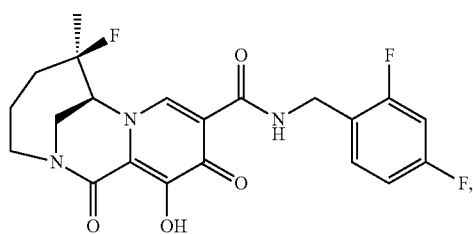
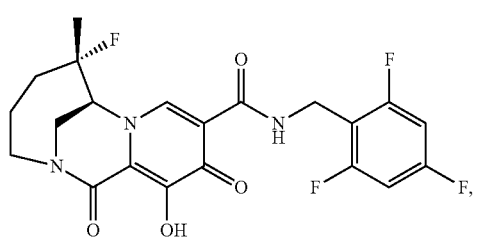
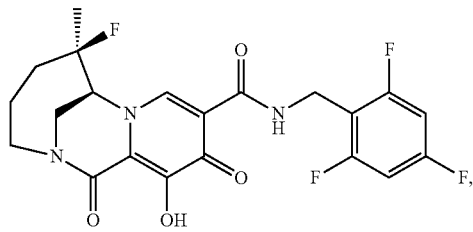
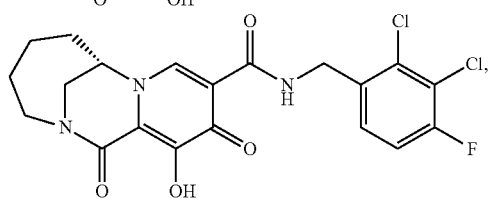
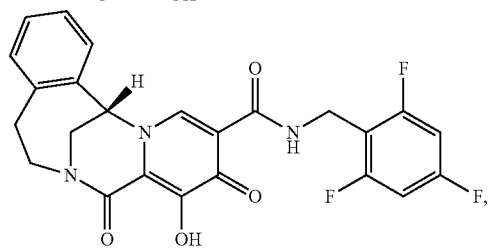
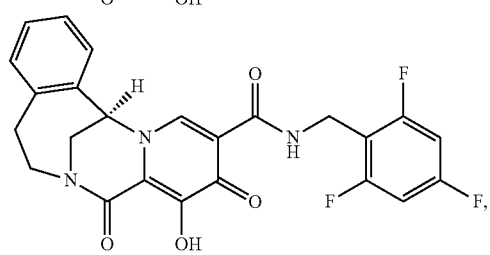
70
-continued
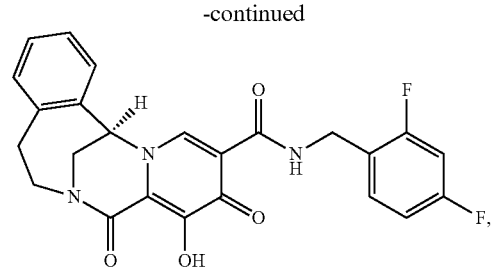
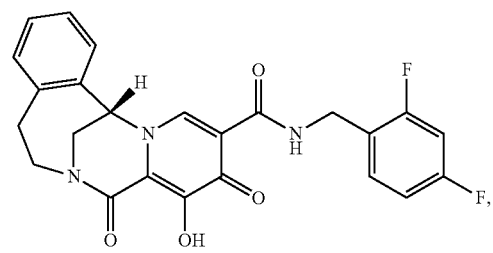
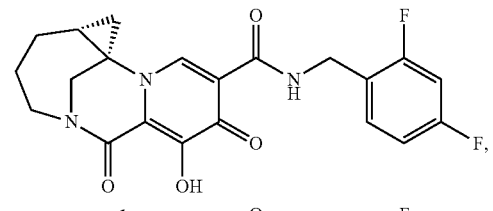
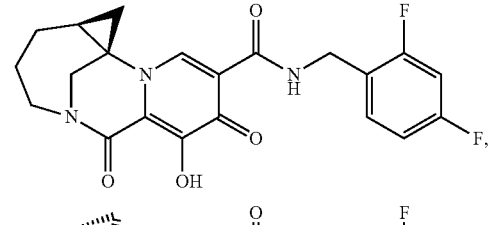
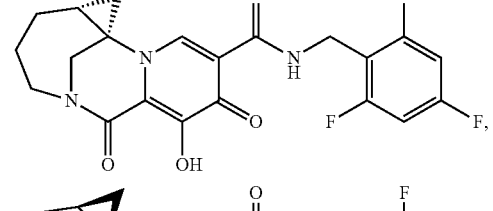
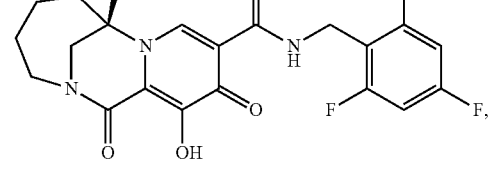
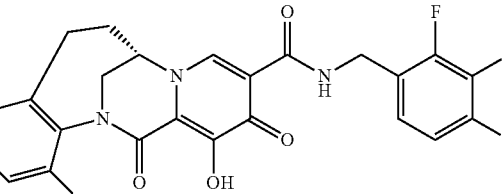
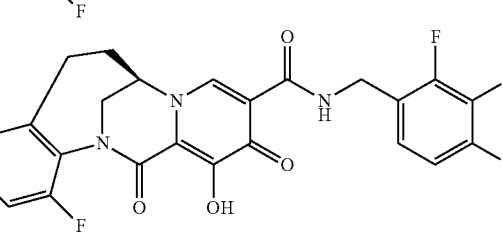

-continued
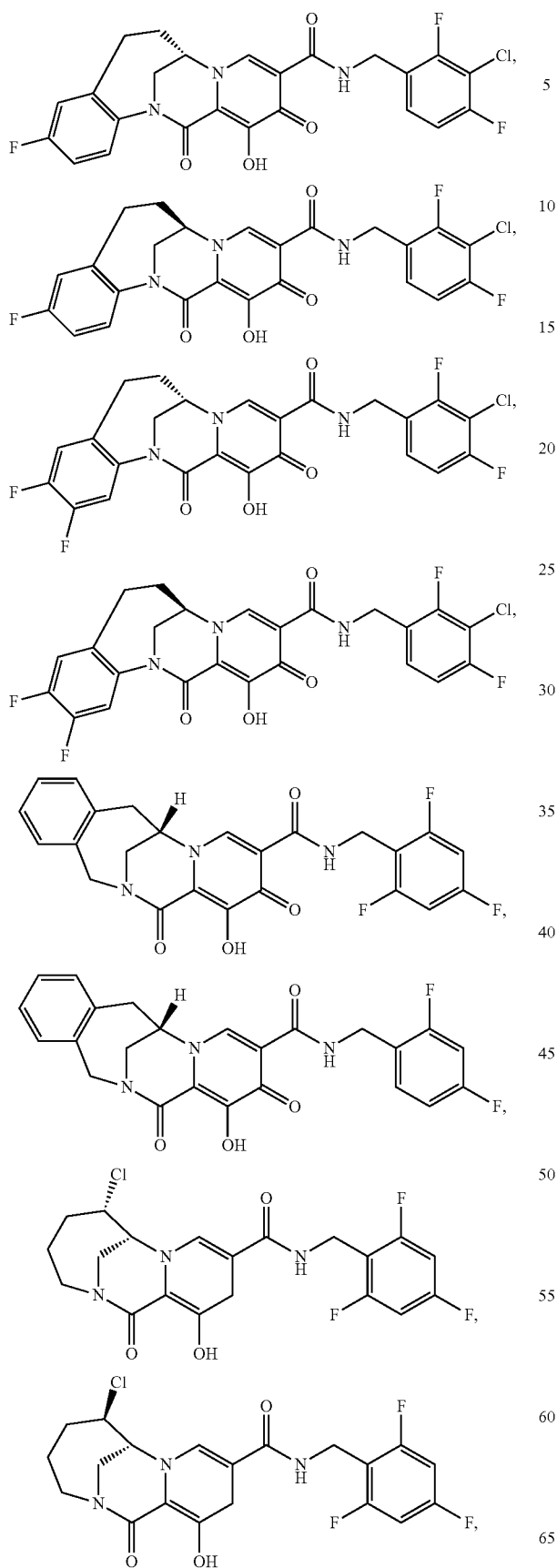
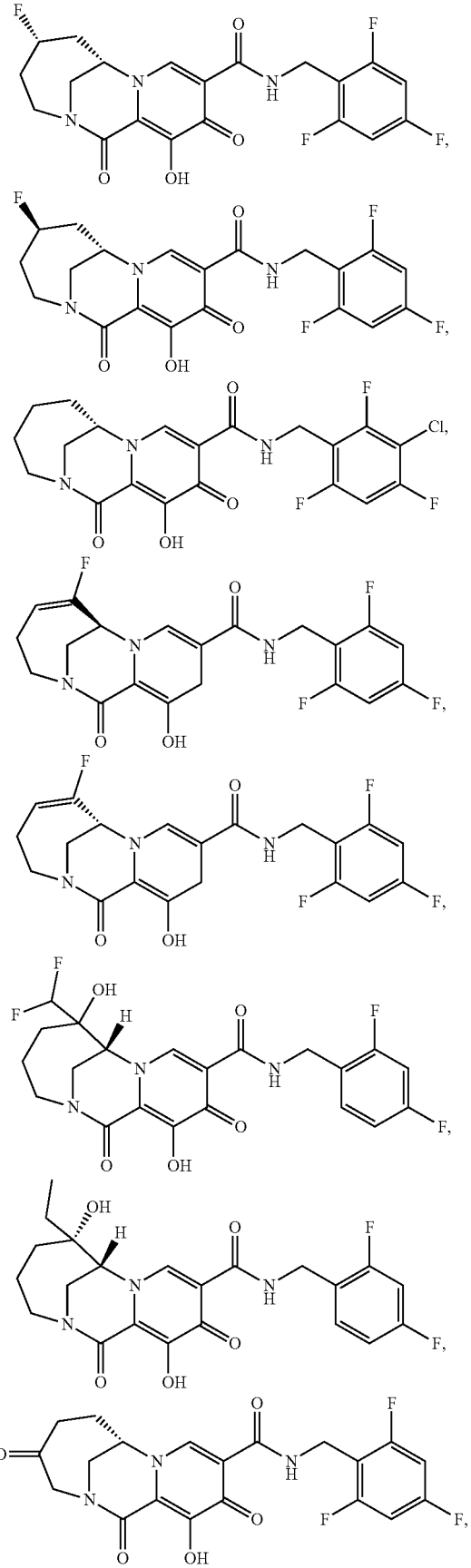

73
-continued
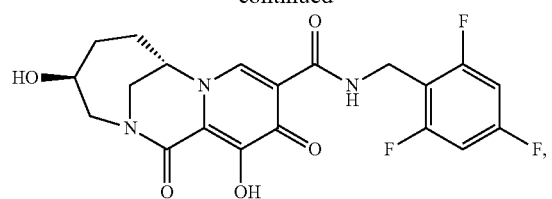
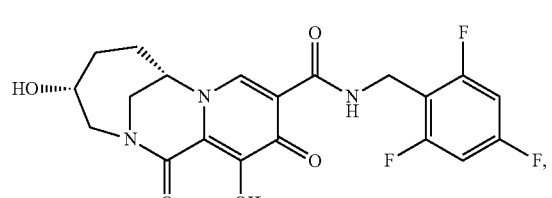
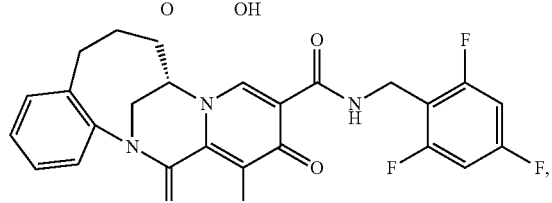
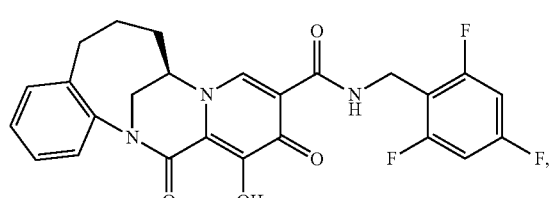
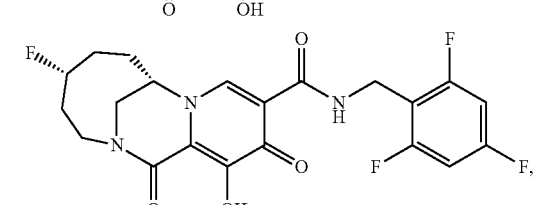
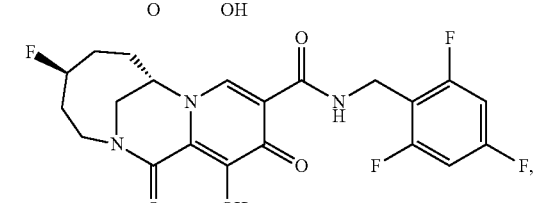
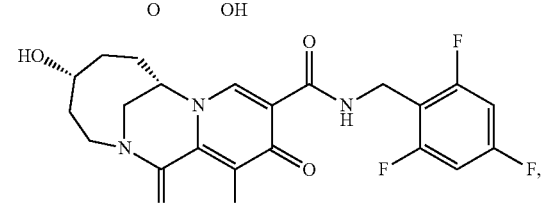
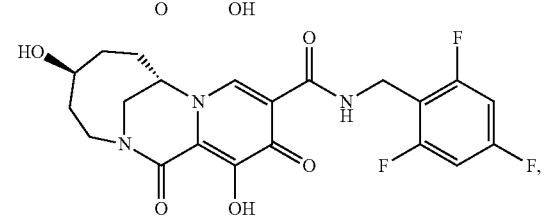
74
-continued
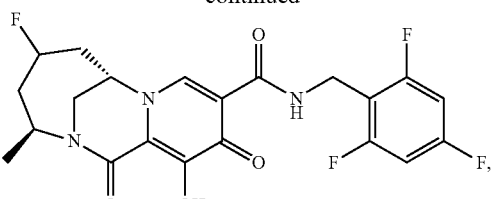
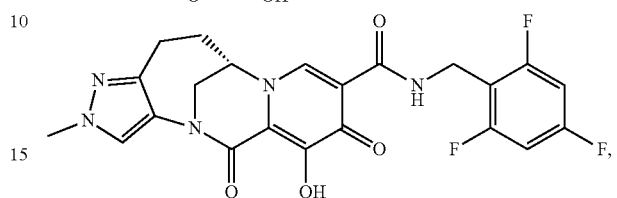
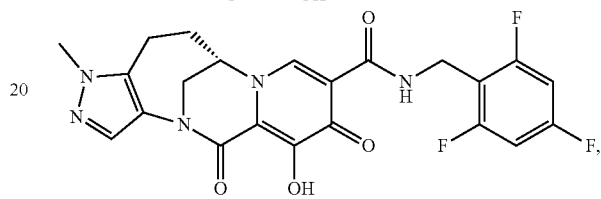
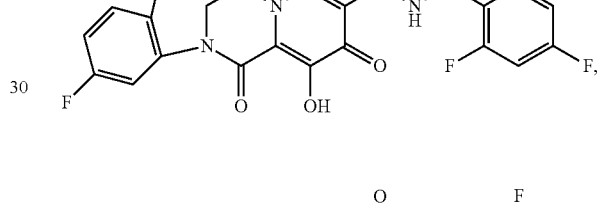
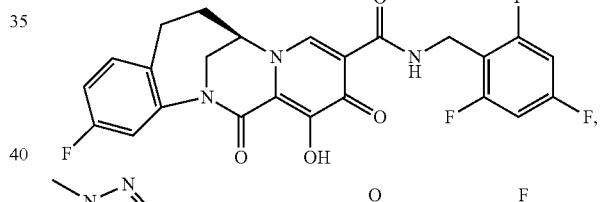
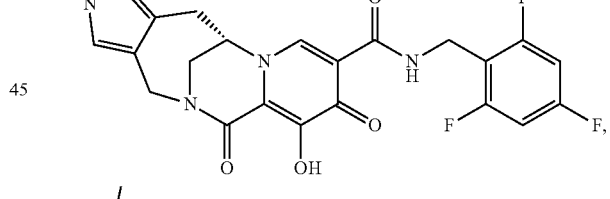
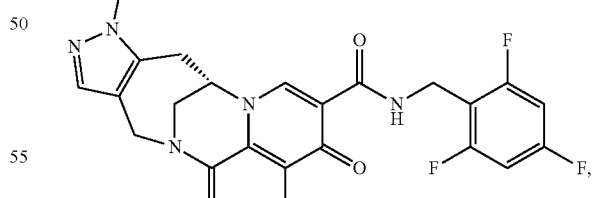
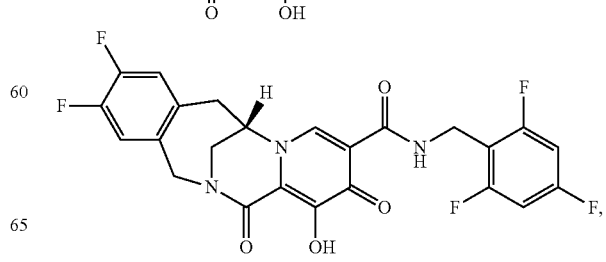

75
-continued
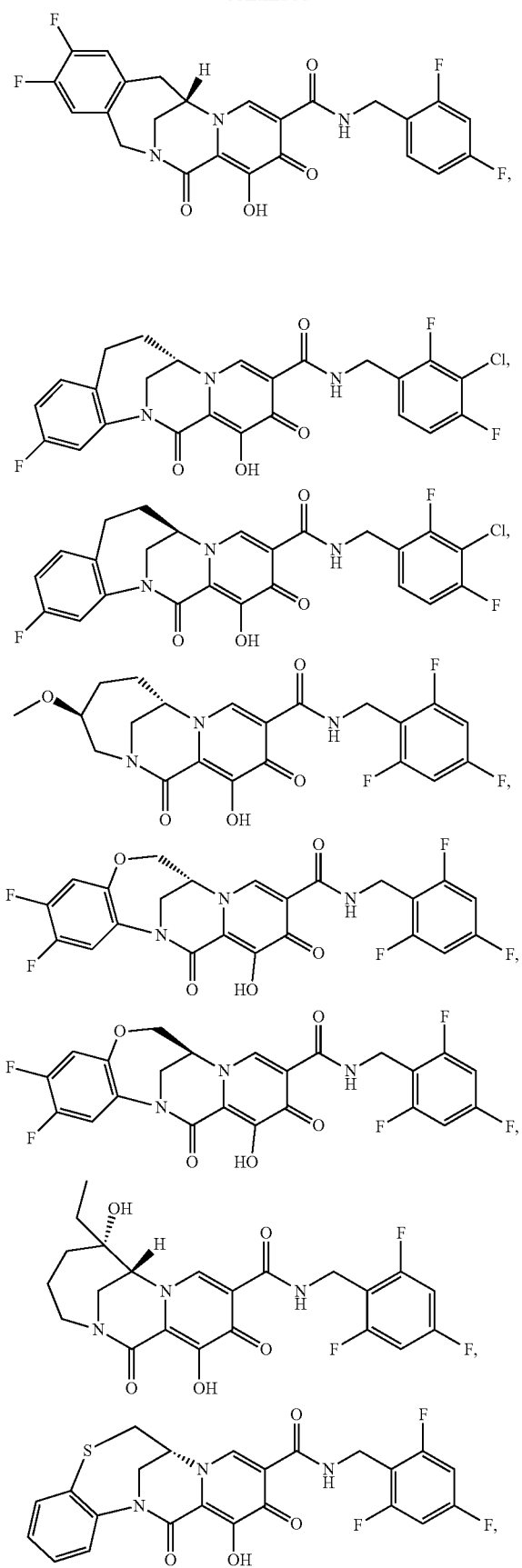
76
-continued
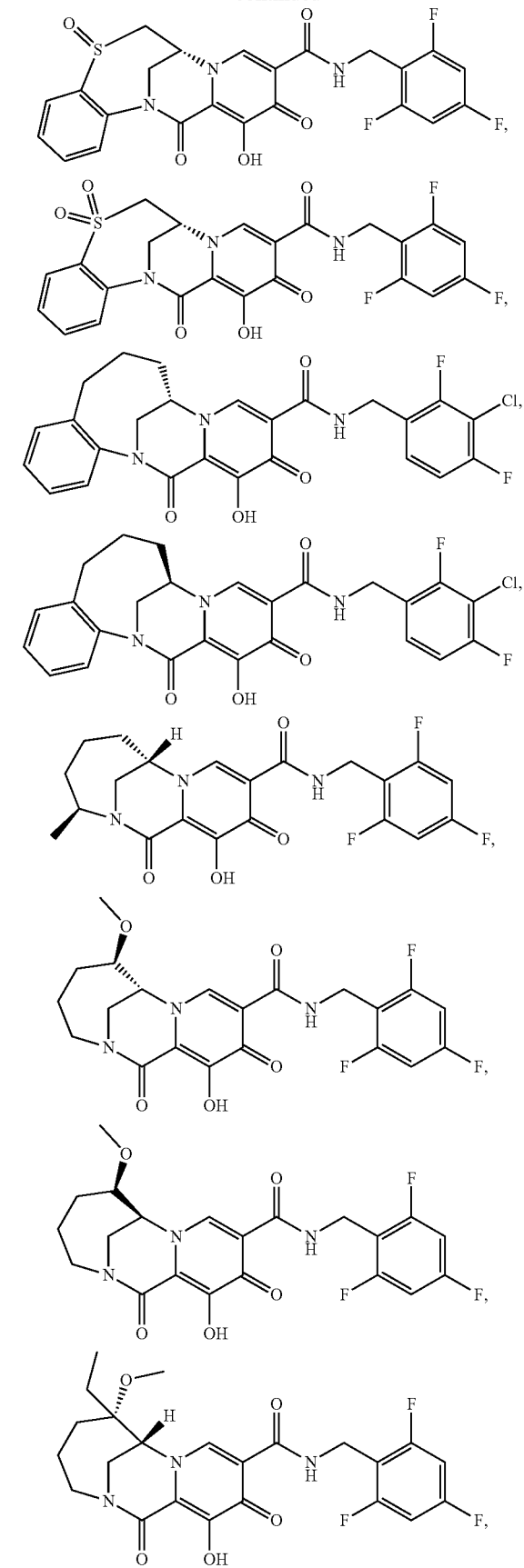

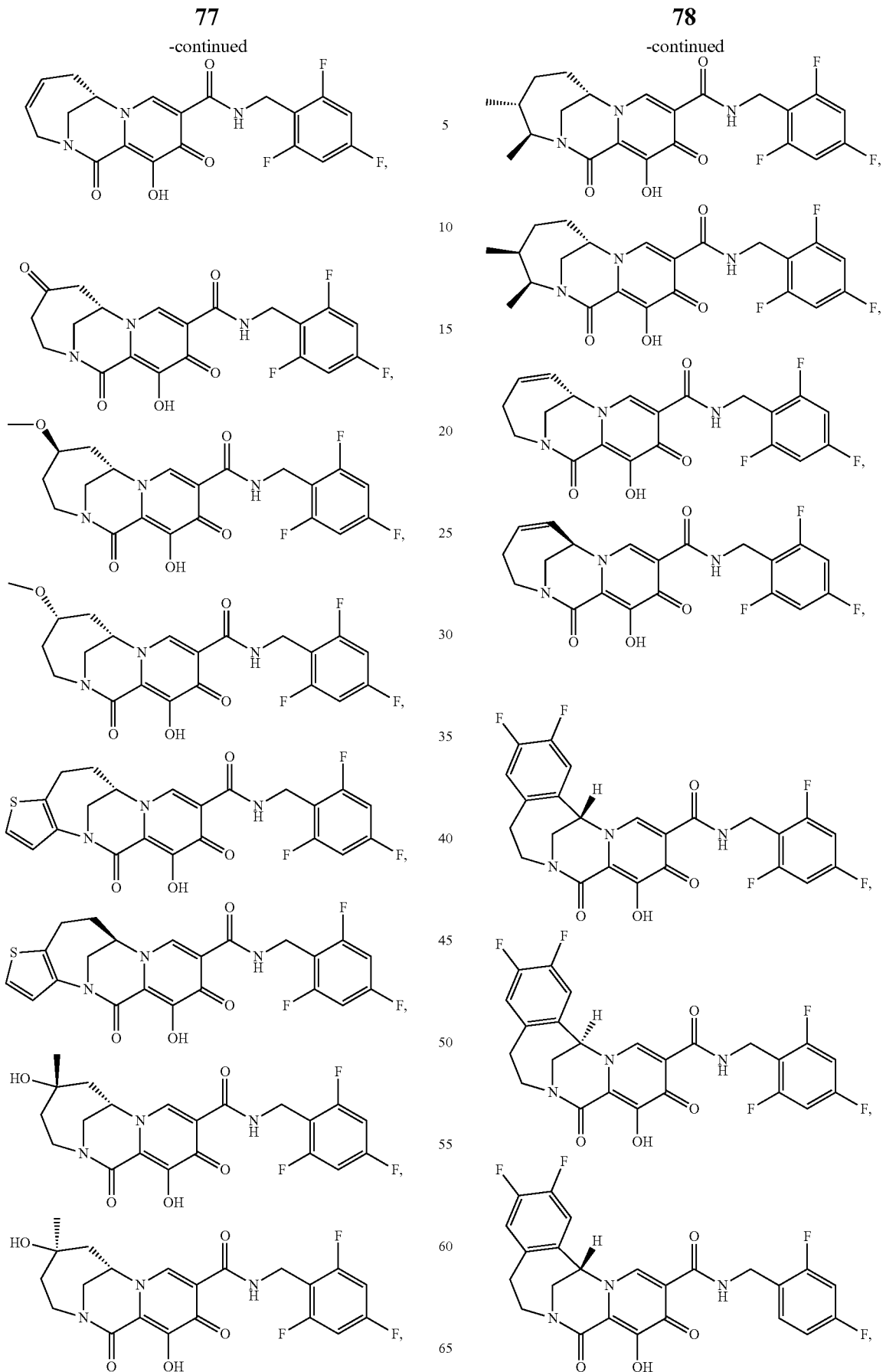

79
-continued
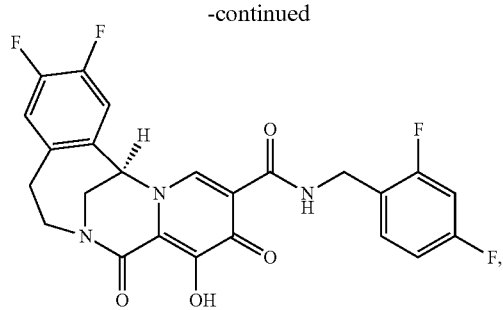
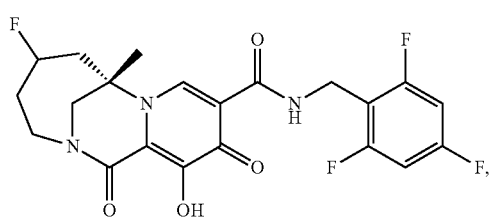
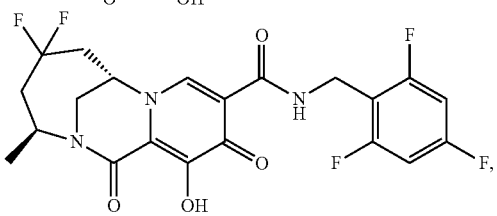
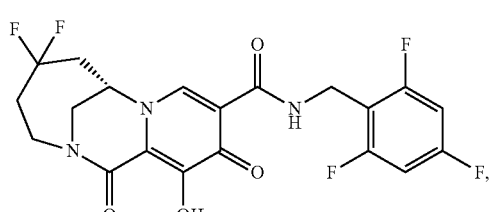
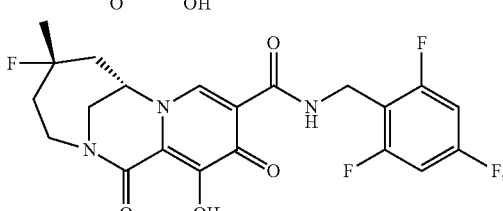
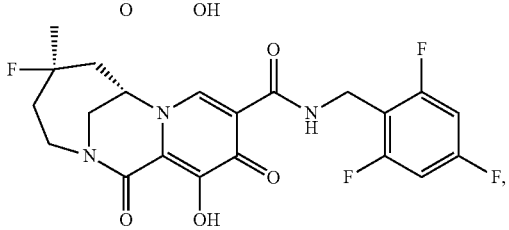
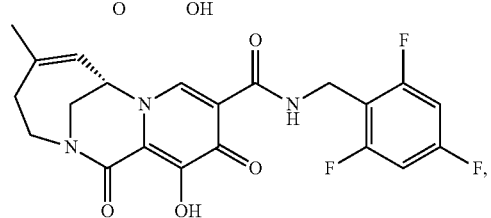
80
-continued
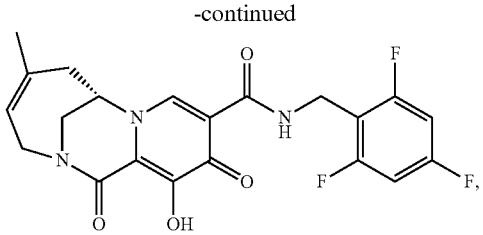
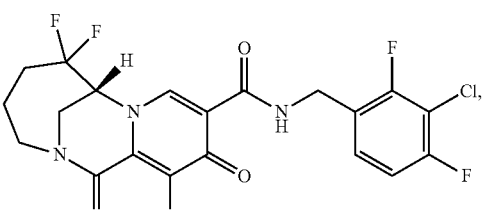
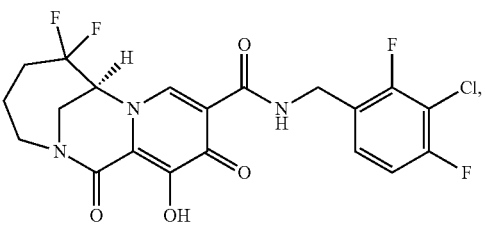
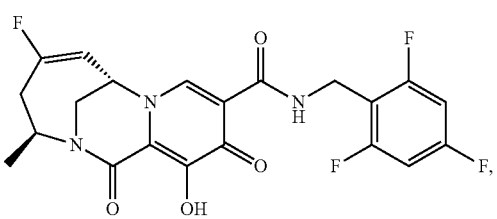
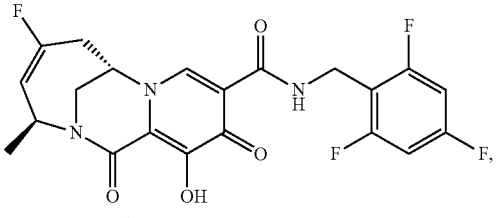
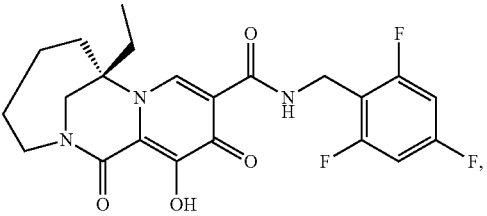
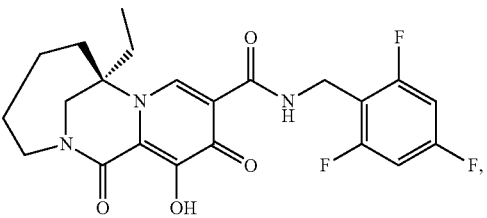

81
-continued
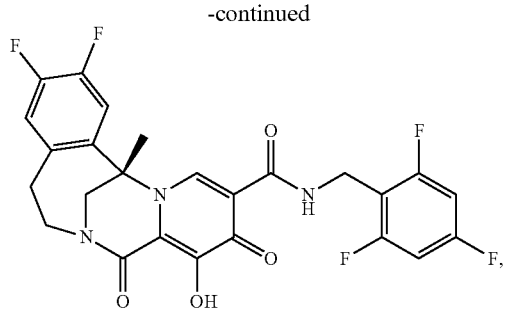
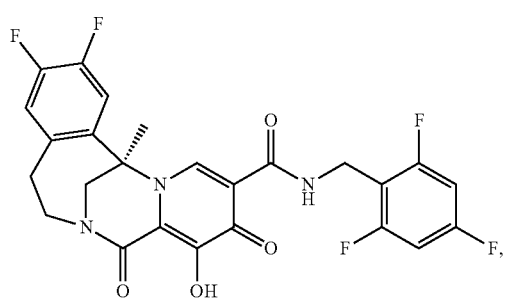
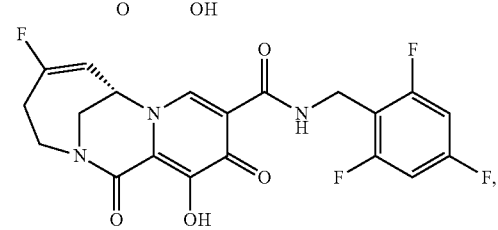
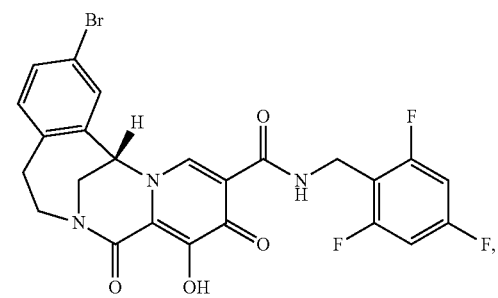
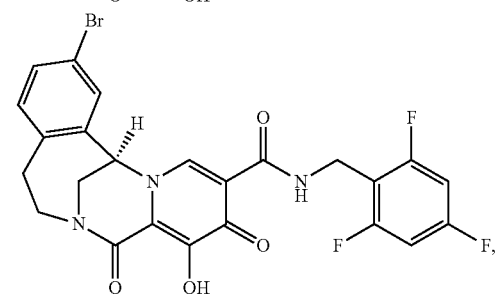
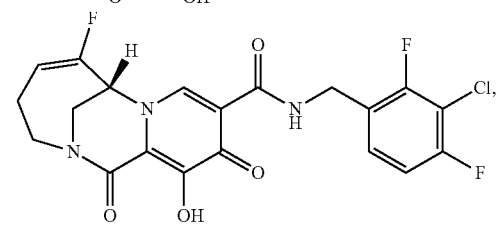
82
-continued
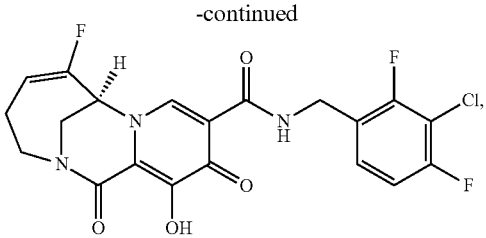
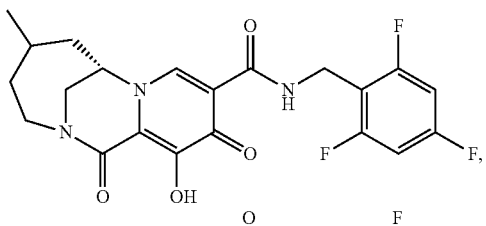
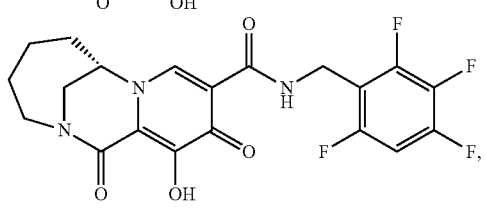
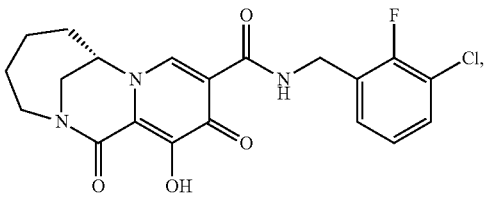
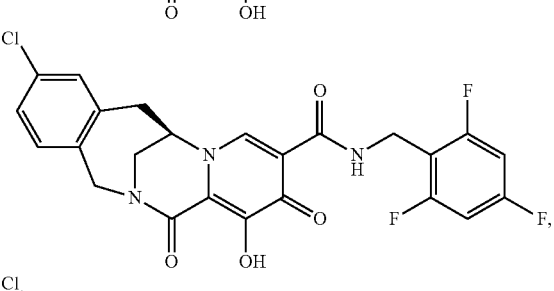
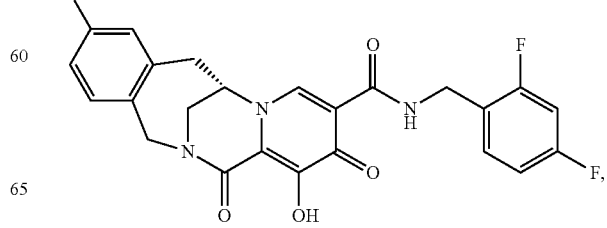

83
-continued
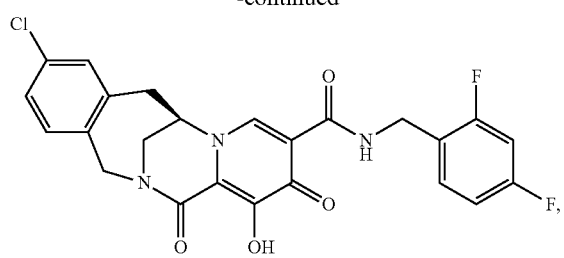
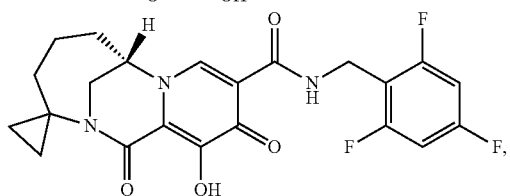
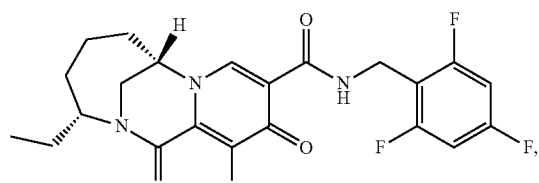
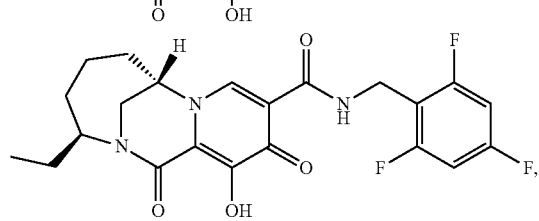
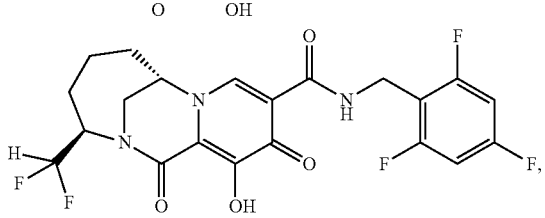
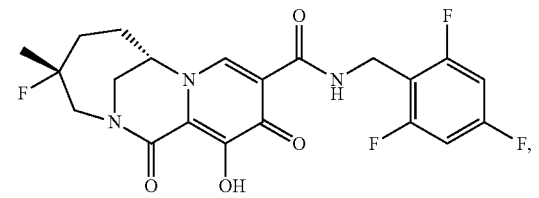
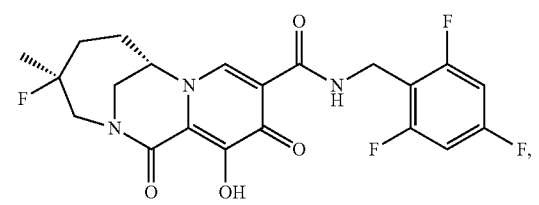
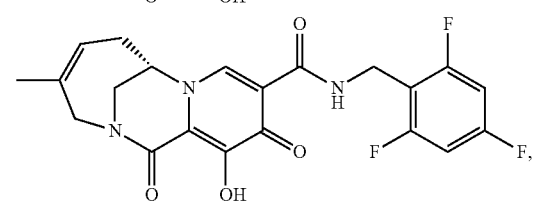
84
-continued
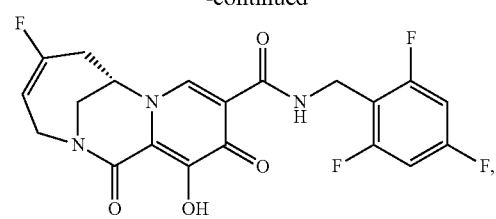
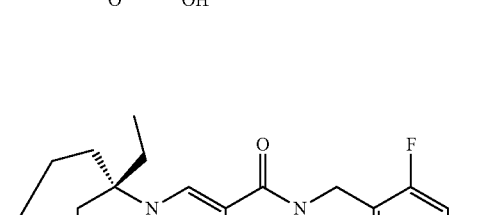
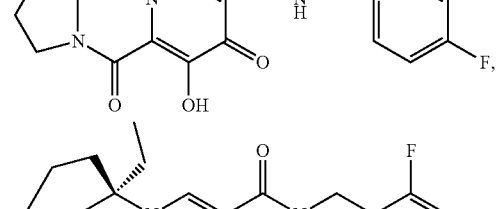
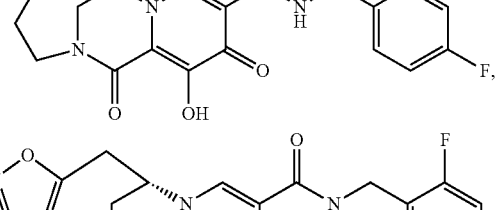
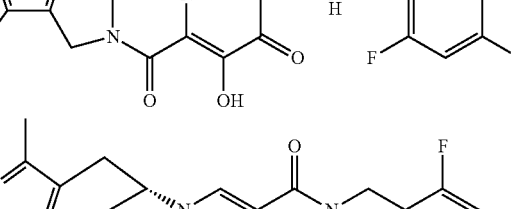
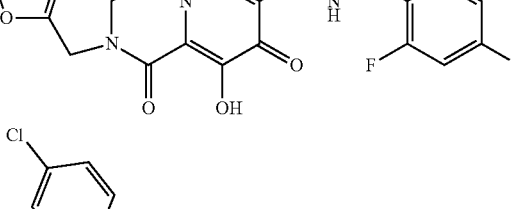
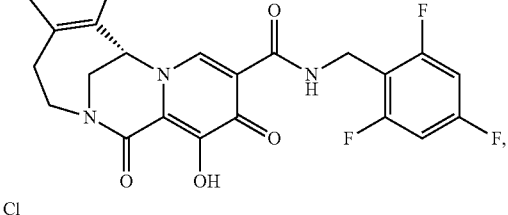
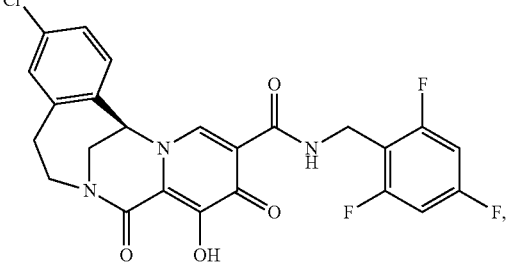

85
-continued
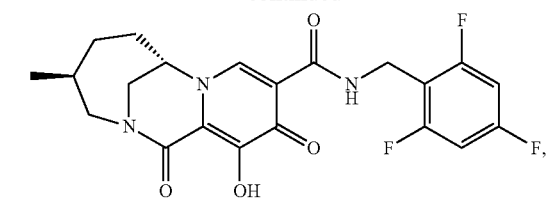
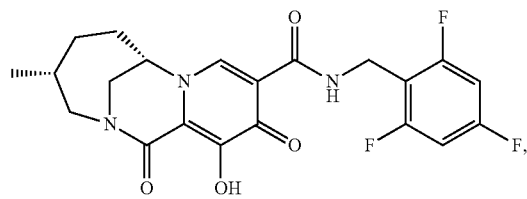
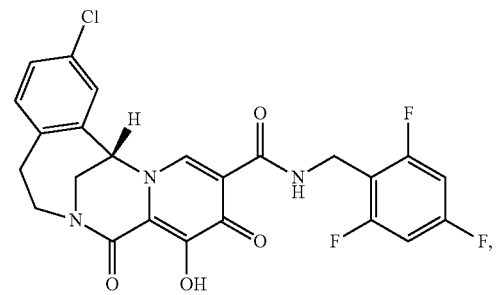
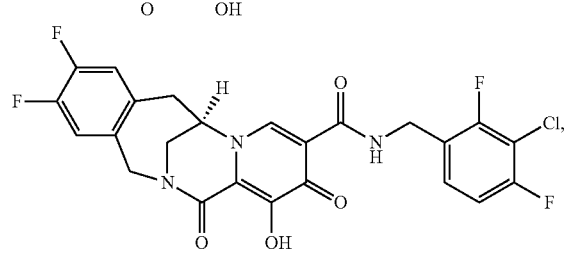
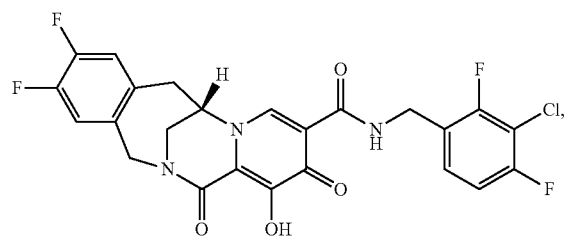
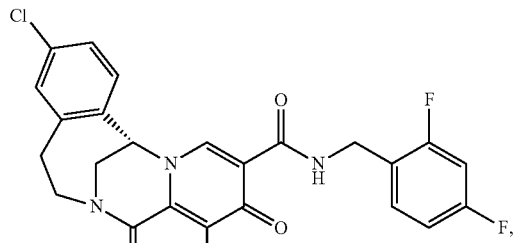
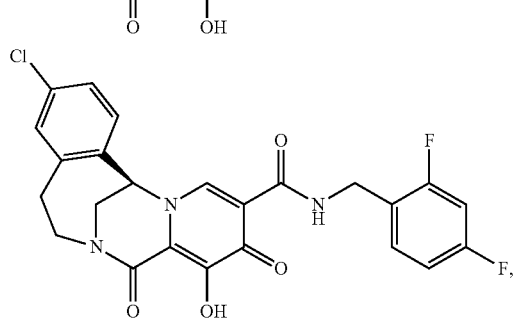
86
-continued
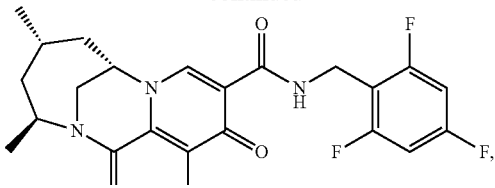
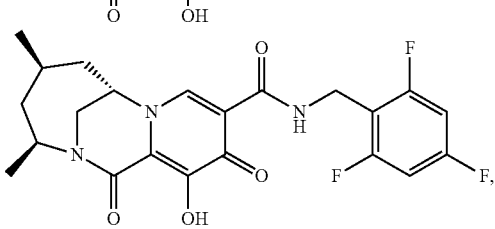
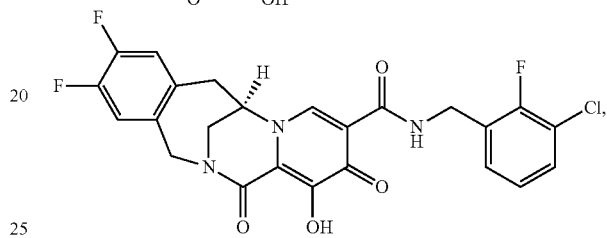
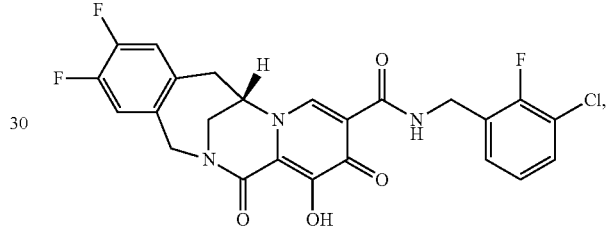
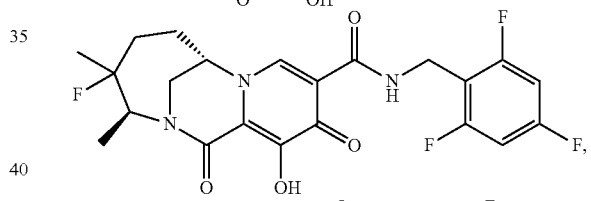
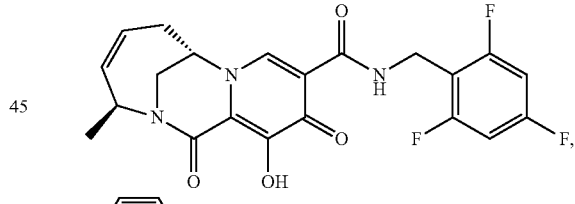
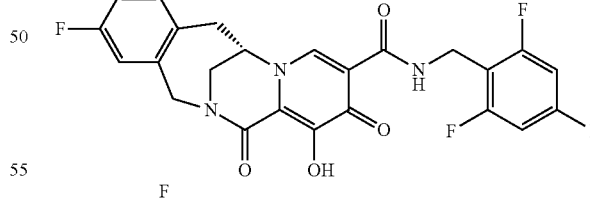
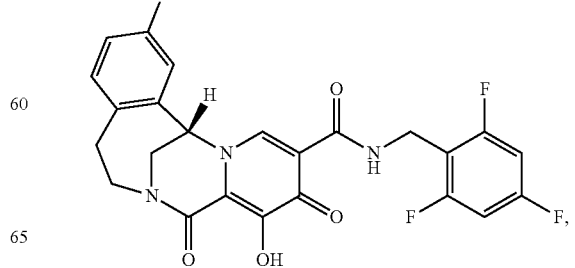

87
-continued
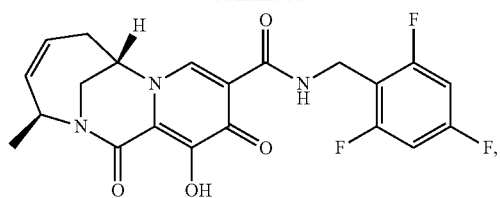
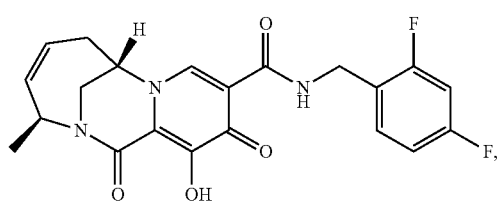
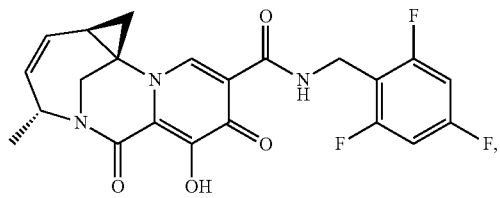
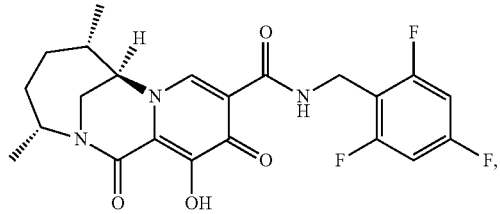
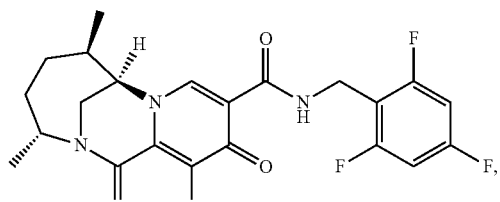
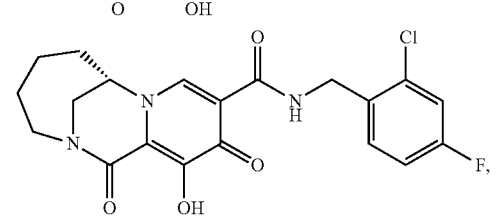
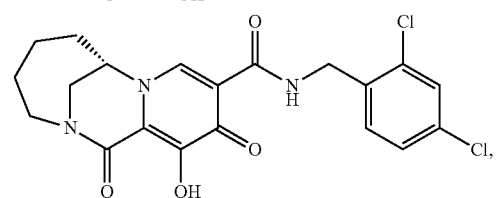
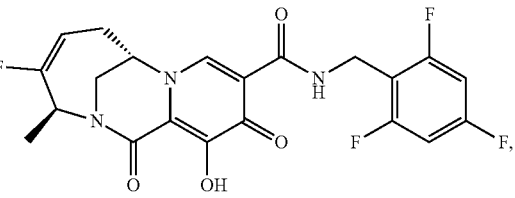
88
-continued
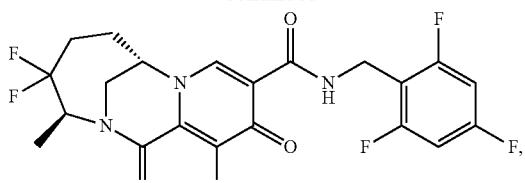
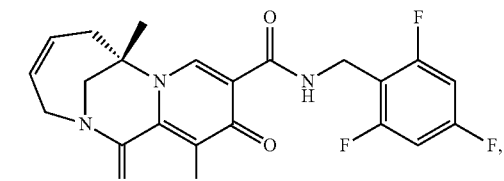
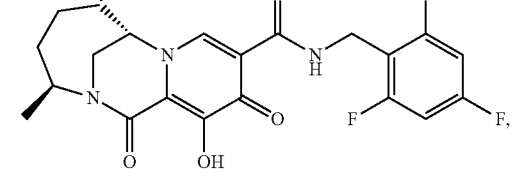
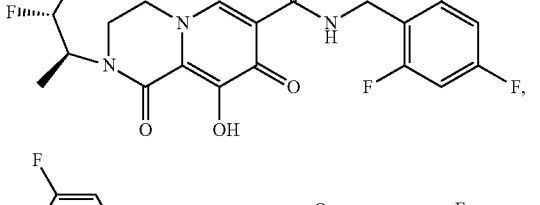
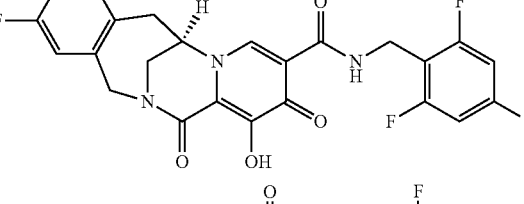
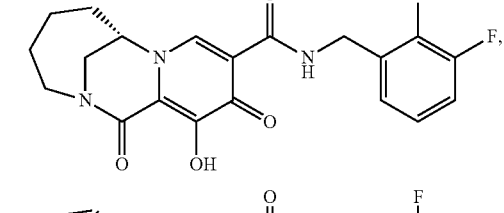
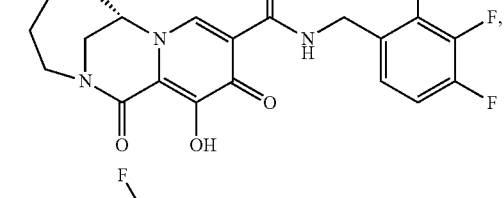
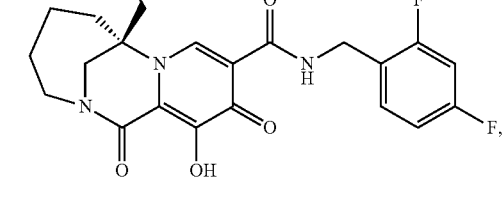

-continued

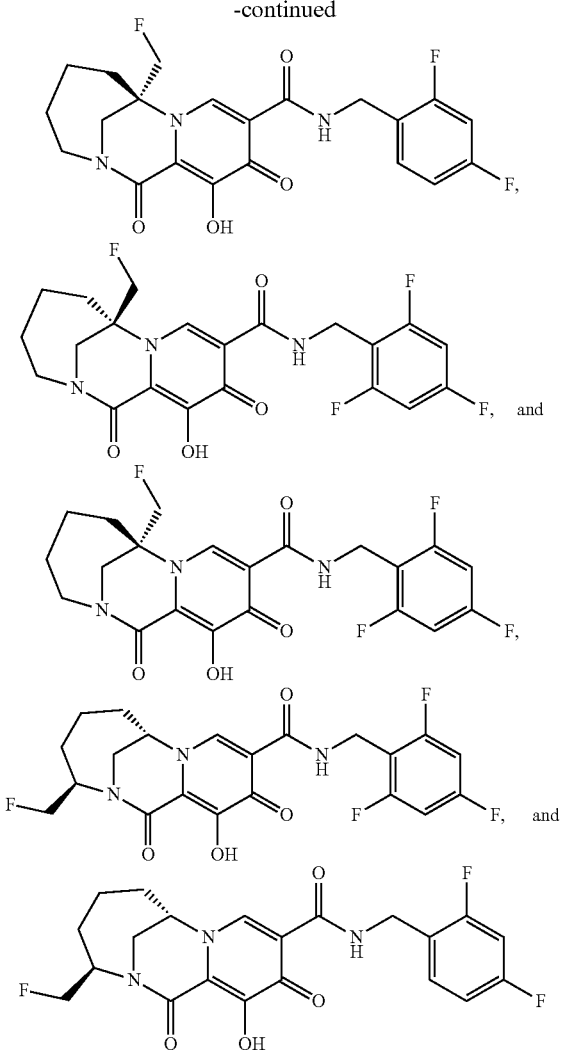

or a pharmaceutically acceptable salt thereof.

The compounds of formula I, II, IIIa, IIIb, IV, Va, Vb, VI, VIIa, VIIb, VIII, IX, IXa, IXb, X, Xa, Xb, XI, XIa, or XIb, may be described with reference to rings A, B, and C, as depicted below for formula I:

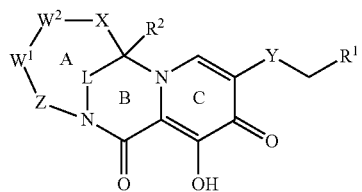

where A denotes a bridged ring relative to ring B, B denotes a bridged ring relative to ring A and a fused ring relative to ring C, and C denotes a fused ring relative to ring B. As noted above, the compounds may have one or more additional fused or spirocyclic rings.

When any variable is a non-symmetrical group, both orientations of the group are intended to be covered, unless specified otherwise. For example, when $W^2$ is $-CR^{5a}R^{5b}-N(R^7)-$, both orientations of $-CR^{5a}R^{5b}-N(R^7)-$ are included (i.e., both $Z-W^1-CR^{5a}R^{5b}-N(R^7)-X$ and $Z-W^1-N(R^7)-CR^{5a}R^{5b}-X$ are included), and when Z is

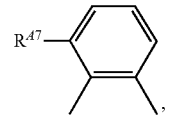

both orientations of

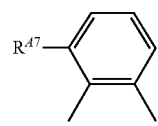

are included (i.e., both

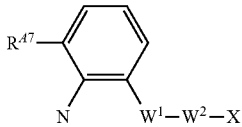 and 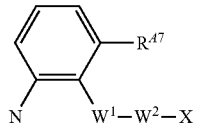

are included).

It is understood that any embodiment of the compounds of any one of formulas I, II, IIIa, IIIb, IV, Va, Vb, VI, VIIa, VIIb, VIII, IX, IXa, IXb, X, Xa, Xb, XI, XIa, or XIb, as set forth above, and any specific group or substituent set forth herein (e.g., $R^1$, $R^2$, L, $W^1$, $W^2$, X, Y, Z, and substituents thereof) in the compounds of formulas I, II, IIIa, IIIb, IV, Va, Vb, VI, VIIa, VIIb, VIII, IX, IXa, IXb, X, Xa, Xb, XI, XIa, or XIb, as set forth above, may be independently combined with other embodiments and/or substituents of compounds of any one of formulas I, II, IIIa, IIIb, IV, Va, Vb, VI, VIIa, VIIb, VIII, IX, IXa, IXb, X, Xa, Xb, XI, XIa, or XIb, to form embodiments not specifically set forth above. In addition, in the event that a list of substituents are not listed for any particular $R^1$, $R^2$, L, $W^1$, $W^2$, X, Y, and Z group in a particular embodiment and/or claim, it is understood that each individual substituent may be deleted from the particular embodiment and/or claim and that the remaining list of substituents will be considered to be within the scope of the embodiments disclosed herein.

Pharmaceutical Compositions

In another embodiment, pharmaceutical compositions comprising a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, and a pharmaceutically acceptable excipient are provided.

In some embodiments, the pharmaceutical compositions further comprise one, two, three, or four additional therapeutic agents. In certain embodiments, the additional therapeutic agent or agents are anti-HIV agents. In particular embodiments, the additional therapeutic agent or agents are HIV protease inhibitors, HIV non-nucleoside or non-nucleotide inhibitors of reverse transcriptase, HIV nucleoside or nucleotide inhibitors of reverse transcriptase, HIV capsid inhibitors, gp41 inhibitors, CXCR4 inhibitors, gp120 inhibitors, CCR5 inhibitors, latency reversing agents, capsid polymerization inhibitors, HIV bNAbs, TLR7 agonists, pharmacokinetic enhancers, other drugs for treating HIV, or combinations thereof. In one embodiment, the additional therapeutic agent or agents are abacavir, tenofovir alafenamide, tenofovir disoproxil, N—((S)-1-(3-(4-chloro-3-(methylsulfonamido)-1-(2,2,2-trifluoroethyl)-H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide, or a pharmaceutically acceptable salt thereof.

Kits and Articles of Manufacture

In some embodiments, the present disclosure relates to a kit comprising a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof. In one embodiment, the kit may comprise one, two, three, or four additional therapeutic agents as described hereinbefore. The kit may further comprise instructions for use, e.g., for use in inhibiting an HIV integrase, such as for use in treating an HIV infection or AIDS, or as a research tool. The instructions for use are generally written instructions, although electronic storage media (e.g., magnetic diskette or optical disk) containing instructions are also acceptable.

In some embodiments, the present disclosure also relates to a pharmaceutical kit comprising one or more containers comprising a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof. Optionally associated with such container(s) can be a notice in the form prescribed by a governmental agency regulating the manufacture, use or sale of pharmaceuticals, which notice reflects approval by the agency for the manufacture, use or sale for human administration. Each component (if there is more than one component) can be packaged in separate containers or some components can be combined in one container where cross-reactivity and shelf life permit. The kits may be in unit dosage forms, bulk packages (e.g., multi-dose packages) or sub-unit doses. Kits may also include multiple unit doses of the compounds and instructions for use and be packaged in quantities sufficient for storage and use in pharmacies (e.g., hospital pharmacies and compounding pharmacies).

In some embodiments, disclosed herein are articles of manufacture comprising a unit dosage of a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, in suitable packaging for use in the methods described herein. Suitable packaging is known in the art and includes, for example, vials, vessels, ampules, bottles, jars, flexible packaging and the like. An article of manufacture may further be sterilized and/or sealed.

Methods of Treatment

In one embodiment, methods of treating an HIV (e.g., HIV-1 and/or HIV-2) infection in a human having or at risk of having the infection comprising administering to the human a therapeutically effective amount of a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, or a pharmaceutical composition of a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, are provided.

In some embodiments, the methods further comprise administering to the human a therapeutically effective amount of one, two, three, or four additional therapeutic agents. In certain embodiments, the additional therapeutic agent or agents are anti-HIV agents. In particular embodiments, the additional therapeutic agent or agents are HIV protease inhibitors, HIV non-nucleoside or non-nucleotide inhibitors of reverse transcriptase, HIV nucleoside or nucleotide inhibitors of reverse transcriptase, HIV capsid inhibitors, gp41 inhibitors, CXCR4 inhibitors, gp120 inhibitors, CCR5 inhibitors, latency reversing agents, capsid polymerization inhibitors, HIV bNAbs (broadly neutralizing HIV antibodies), TLR7 agonists, pharmacokinetic enhancers, other drugs for treating HIV, or combinations thereof. In one embodiment, the additional therapeutic agent or agents are abacavir, tenofovir alafenamide, tenofovir disoproxil, N—((S)-1-(3-(4-chloro-3-(methylsulfonamido)-1-(2,2,2-trifluoroethyl)-H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide, or a pharmaceutically acceptable salt thereof.

In another embodiment, a use of a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, or a pharmaceutical composition of a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, for treating an HIV (e.g., HIV-1 and/or HIV-2) infection in a human having or at risk of having the infection is provided.

In another embodiment, a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, or a pharmaceutical composition of a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, for use in medical therapy is provided.

In another embodiment, a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, or a pharmaceutical composition of a compound of formula I, II, IIIa, IIIb, IV, Va, Vb, VI, VIIa, VIIb, VIII, IX, IXa, IXb, X, Xa, Xb, XI, XIa, or XIb, or pharmaceutically acceptable salt thereof, for use in treating an HIV infection is provided.

In another embodiment, a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, or a pharmaceutical composition of a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof for use in a method of treating an HIV infection in a human having or at risk of having the infection, is provided.

In another embodiment, a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, or a pharmaceutical composition of a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof for use in a method of treating an HIV infection in a human having or at risk of having the infection, is provided wherein said method further comprises administering to the human one, two, three, or four additional therapeutic agents.

In another embodiment, a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, or a pharmaceutical composition of a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof for use in a method of treating an HIV infection in a human having or at risk of having the infection, is provided wherein said method further comprises administering to the human one, two, three, or four additional therapeutic agents selected from the group consisting of HIV protease inhibitors, HIV non-nucleoside or non-nucleotide inhibitors of reverse transcriptase, HIV nucleoside or nucleotide inhibitors of reverse transcriptase, HIV capsid inhibitors, gp41 inhibitors, CXCR4 inhibitors, gp120 inhibitors, CCR5 inhibitors, latency reversing agents, capsid polymerization inhibitors, HIV bNAbs, TLR7 agonists, pharmacokinetic enhancers, other drugs for treating HIV, or combinations thereof. In one embodiment, the one, two, three, or four additional therapeutic agents are selected from HIV protease inhibitors, HIV non-nucleoside inhibitors of reverse transcriptase, HIV nucleoside or nucleotide inhibitors of reverse transcriptase, latency reversing agents, HIV capsid inhibitors, HIV bNAbs, TLR7 agonists, and combinations thereof.

In another embodiment, a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, or a pharmaceutical composition of a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof for use in a method of treating an HIV infection in a human having or at risk of having the infection, is provided wherein said method further comprises administering to the human a therapeutically effective amount of tenofovir disoproxil and emtricitabine.

In another embodiment, a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, or a pharmaceutical composition of a compound of formula I, II, IIIa, IIIb, IV, Va, Vb, V, VIIa, VIIb, VIII, IX, IXa, IXb, X, Xa, Xb, XI, XIa, or XIb, or a pharmaceutically acceptable salt thereof for use in a method of treating an HIV infection in a human having or at risk of having the infection, is provided wherein said method further comprises administering to the human a therapeutically effective amount of tenofovir alafenamide and emtricitabine.

In another embodiment, a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, or a pharmaceutical composition of a compound of formula I, II, IIIa, IIIb, IV, Va, Vb, V, VIIa, VIIb, VIII, IX, IXa, IXb, X, Xa, Xb, XI, XIa, or XIb, or a pharmaceutically acceptable salt thereof for use in a method of treating an HIV infection in a human having or at risk of having the infection, is provided wherein said method further comprises administering to the human a therapeutically effective amount of tenofovir disoproxil.

In another embodiment, a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, or a pharmaceutical composition of a compound of formula I, II, IIIa, IIIb, IV, Va, Vb, V, VIIa, VIIb, VIII, IX, IXa, IXb, X, Xa, Xb, XI, XIa, or XIb, or a pharmaceutically acceptable salt thereof for use in a method of treating an HIV infection in a human having or at risk of having the infection, is provided wherein said method further comprises administering to the human a therapeutically effective amount of tenofovir alafenamide.

In another embodiment, a method of using a compound of formula I, II, IIIa, IIIb, IV, Va, Vb, VI, VIIa, VIIb, VIII, IX, IXa, IXb, X, Xa, Xb, XI, XIa, or XIb, in therapy is provided. In particular, a method of treating the proliferation of the HIV virus, treating AIDS, or delaying the onset of AIDS or ARC symptoms in a mammal (e.g., a human) is provided, comprising administering to the mammal a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, and a pharmaceutically acceptable excipient.

In another embodiment, a composition comprising a compound of formula I, II, IIIa, IIIb, IV, Va, Vb, VI, VIIa, VIIb, VIII, IX, IXa, IXb, X, Xa, Xb, XI, XIa, or XIb, or pharmaceutically acceptable salt thereof, and a pharmaceutically acceptable excipient, for use in a method of treating the proliferation of the HIV virus, treating AIDS, or delaying the onset of AIDS or ARC symptoms in a mammal (e.g., a human) is provided.

In one embodiment, a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, or a pharmaceutical composition of a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, is provided for use in preventing HIV infection.

For example, in one embodiment, a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, or a pharmaceutical composition of a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, is provided for use in pre-exposure prophylaxis (PrEP), i.e., before the exposure of the individual to the HIV virus to prevent HIV infection from taking hold if the individual is exposed to the virus and/or to keep the virus from establishing a permanent infection and/or to prevent the appearance of symptoms of the disease and/or to prevent the virus from reaching detectable levels in the blood.

In another embodiment, the use of a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, for the manufacture of a medicament for treating an HIV infection in a human being having or at risk of having the infection is disclosed.

In another embodiment, the use of a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, as a research tool is disclosed.

In another embodiment, an article of manufacture comprising a composition effective to treat an HIV infection; and packaging material comprising a label which indicates that the composition can be used to treat infection by HIV is disclosed. Exemplary compositions comprise a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof.

In still another embodiment, a method of inhibiting the replication of HIV is disclosed. The method comprises exposing the virus to an effective amount of the compound of formula I, II, IIIa, IIIb, IV, Va, Vb, VI, VIIa, VIIb, VIII, IX, IXa, IXb, X, Xa, Xb, XI, XIa, or XIb, or a salt thereof, under conditions where replication of HIV is inhibited.

In another embodiment, the use of a compound of formula I, II, IIIa, IIIb, IV, Va, Vb, VI, VIIa, VIIb, VIII, IX, IXa, IXb, X, Xa, Xb, XI, XIa, or XIb, to inhibit the activity of the HIV integrase enzyme is disclosed.

In another embodiment, the use of a compound of formula I, II, IIIa, IIIb, IV, Va, Vb, VI, VIIa, VIIb, VIII, IX, IXa, IXb, X, Xa, Xb, XI, XIa, or XIb, or a salt thereof, to inhibit the replication of HIV is disclosed.

Administration

For the purposes of administration, in certain embodiments, the compounds described herein are administered as a raw chemical or are formulated as pharmaceutical compositions. Pharmaceutical compositions within the scope of the embodiments disclosed herein comprise a compound of formula I, II, IIIa, IIIb, IV, Va, Vb, VI, VIIa, VIIb, VIII, IX, IXa, IXb, X, Xa, Xb, XI, XIa, or XIb, and a pharmaceutically acceptable excipient. The compound of formula I, II, IIIa, IIIb, IV, Va, Vb, VI, VIIa, VIIb, VIII, IX, IXa, IXb, X, Xa, Xb, XI, XIa, or XIb, is present in the composition in an amount which is effective to treat a particular disease or condition of interest. The activity of compounds of formula I, II, IIIa, IIIb, IV, Va, Vb, VI, VIIa, VIIb, VIII, IX, IXa, IXb, X, Xa, Xb, XI, XIa, or XIb, can be determined as described in the Examples below.

Administration of the compounds of the embodiments disclosed herein, or their pharmaceutically acceptable salts, in pure form or in an appropriate pharmaceutical composition, can be carried out via any of the accepted modes of administration of agents for serving similar utilities. The pharmaceutical compositions of the embodiments disclosed herein can be prepared by combining a compound of the embodiments disclosed herein with an appropriate pharmaceutically acceptable excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, injectable, sublingual, buccal, rectal, vaginal, and intranasal. Pharmaceutical compositions of the embodiments disclosed herein are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the embodiments disclosed herein in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of a compound of the embodiments disclosed herein, or a pharmaceutically acceptable salt thereof, for treating a disease or condition of interest in accordance with the teachings of this disclosure.

In one embodiment, the pharmaceutical composition is an oral dosage unit. In one embodiment, the pharmaceutical composition is a solid oral dosage unit. In one embodiment, the pharmaceutical composition is a tablet.

In one embodiment, the pharmaceutical composition is a parenteral dosage unit. In one embodiment, the pharmaceutical composition is a subcutaneous, intramuscular, intravenous, intradermal, intrathecal, or epidural dosage unit. In one embodiment, the pharmaceutical composition is a subcutaneous, intramuscular, or intravenous dosage unit. In one embodiment, the pharmaceutical composition is injectable.

The pharmaceutical compositions disclosed herein may be prepared by methodology well known in the pharmaceutical art. For example, a pharmaceutical composition intended to be administered by injection can be prepared by combining a compound of the embodiments disclosed herein with sterile, distilled water so as to form a solution. A surfactant may be added to facilitate the formation of a homogeneous solution or suspension. Surfactants are compounds that non-covalently interact with the compound of the embodiments disclosed herein so as to facilitate dissolution or homogeneous suspension of the compound in the aqueous delivery system.

The compounds of the embodiments disclosed herein, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Combination Therapy

In certain embodiments, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one, two, three, or four additional therapeutic agents. In one embodiment, a method for treating an HIV infection in a human having or at risk of having the infection is provided, comprising administering to the human a therapeutically effective amount of a compound disclosed herein, or a pharmaceutically acceptable salt thereof, in combination with a therapeutically effective amount of one, two, three, or four additional therapeutic agents.

In one embodiment, pharmaceutical compositions comprising a compound disclosed herein, or a pharmaceutically acceptable salt thereof, in combination with one, two, three, or four additional therapeutic agents, and a pharmaceutically acceptable carrier, diluent, or excipient are provided.

In certain embodiments, the present disclosure provides a method for treating an HIV infection, comprising administering to a patient in need thereof a therapeutically effective amount of a compound disclosed herein, or a pharmaceutically acceptable salt thereof, in combination with a therapeutically effective amount of one, two, three, or four additional therapeutic agents which are suitable for treating an HIV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of HIV Combination Therapy

In certain embodiments, a compound disclosed herein is administered with one, two, three, or four additional therapeutic agents. Co-administration of a compound disclosed herein with one, two, three, or four additional therapeutic agents generally refers to simultaneous or sequential administration of a compound disclosed herein and one, two, three, or four additional therapeutic agents, such that therapeutically effective amounts of the compound disclosed herein and the one, two, three, or four additional therapeutic agents are both present in the body of the patient. When administered sequentially, the combination may be administered in two or more administrations.

Co-administration includes administration of unit dosages of the compounds disclosed herein before or after administration of unit dosages of one, two, three, or four additional therapeutic agents. For example, the compound disclosed herein may be administered within seconds, minutes, or hours of the administration of the one, two, three, or four additional therapeutic agents. In some embodiments, a unit dose of a compound disclosed herein is administered first, followed within seconds or minutes by administration of a unit dose of one, two, three, or four additional therapeutic agents. Alternatively, a unit dose of one, two, three, or four additional therapeutic agents is administered first, followed by administration of a unit dose of a compound disclosed herein within seconds or minutes. In other embodiments, a unit dose of a compound disclosed herein is administered first, followed, after a period of hours (e.g., 1-12 hours), by administration of a unit dose of one, two, three, or four additional therapeutic agents. In yet other embodiments, a unit dose of one, two, three, or four additional therapeutic agents is administered first, followed, after a period of hours (e.g., 1-12 hours), by administration of a unit dose of a compound disclosed herein.

In certain embodiments, a compound disclosed herein is combined with one, two, three, or four additional therapeutic agents in a unitary dosage form for simultaneous administration to a patient, for example as a solid dosage form for oral administration.

In certain embodiments, a kit comprising a compound disclosed herein (e.g., a compound of formula I, II, IIIa, IIIb, IV, Va, Vb, VI, VIIa, VIIb, VIII, IX, IXa, IXb, X, Xa, Xb, XI, XIa, or XIb), or a pharmaceutically acceptable salt thereof, in combination with one or more (e.g., one, two, three, or four) additional therapeutic agents is provided.

In certain embodiments, a compound of formula I, II, IIIa, IIIb, IV, Va, Vb, VI, VIIa, VIIb, VIII, IX, IXa, IXb, X, Xa, Xb, XI, XIa, or XIb, is formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing.

HIV Combination Therapy

In the above embodiments, the additional therapeutic agent or agents may be an anti-HIV agent, selected from HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T cell receptors, TCR-T, autologous T cell therapies), latency reversing agents, compounds that target the HIV capsid, capsid polymerization inhibitors, HIV bNAbs, immune-based therapies, phosphatidylinositol 3-kinase (PI3K) inhibitors, HIV antibodies, broadly neutralizing HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV viral infectivity factor inhibitors, TAT protein inhibitors, HIV Nef modulators, Hck tyrosine kinase modulators, mixed lineage kinase-3 (MLK-3) inhibitors, HIV splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent or agents are selected from combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

HIV Combination Drugs

Examples of combination drugs include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); SYMTUZA® (darunavir, tenofovir alafenamide, emtricitabine, and cobicistat); BIKTARVY® (bictegravir, tenofovir alafenamide, and emtricitabine); bictegravir, tenofovir disoproxil and emtricitabine; bictegravir, tenofovir alafenamide and lamivudine; bictegravir, tenofovir disoproxil and lamivudine; bictegravir, abacavir and lamivudine; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); JULUCA® (dolutegravir, ripilvirine); TRIZIVR® (abacavir sulfate, zidovudine, and lamivudine; ABC+AZT+3TC); dolutegravir and lamivudine; dolutegravir and abacavir; cabotegravir and lamivudine; cabotegravir and abacavir; cabotegravir and rilpivirine; atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine; lamivudine+abacavir+zidovudine; lamivudine+abacavir; lamivudine+tenofovir disoproxil fumarate; lamivudine+zidovudine+nevirapine; lopinavir+ritonavir; lopinavir+ritonavir+abacavir+lamivudine; lopinavir+ritonavir+zidovudine+lamivudine; tenofovir+lamivudine; and tenofovir disoproxil fumarate+emtricitabine+rilpivirine hydrochloride.

Other HIV Drugs

Examples of other drugs for treating HIV include acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCR5RZ, MazF gene therapy, BlockAide, ABX-464, AG-1105, APH-0812, BIT-225, CYT-107, HGTV-43, HPH-116, HS-10234, IMO-3100, IND-02, MK-1376, MK-2048, MK-4250, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, MK-8122, TMB-607, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, ACC-007, AIC-292, KM-023, PC-1005, and elsulfavirine (VM-1500).

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, rovafovir etalafenamide (GS-9131), GS-9148, MK-8504, MK-8591, MK-858, VM-2500 and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169, VM-3500 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include ceniciviroc, CCR5 inhibitors, gp41 inhibitors, CD4 attachment inhibitors, gp120 inhibitors, and CXCR4 inhibitors.

Examples of CCR5 inhibitors include aplaviroc, vicriviroc, maraviroc, cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, and vMIP (Haimipu).

Examples of gp41 inhibitors include albuvirtide, enfuvirtide, BMS-986197, enfuvirtide biobetter, enfuvirtide biosimilar, HIV fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs.

Examples of gp120 inhibitors include Radha-108 (receptol) 3B3-PE38, BanLec, bentonite-based nanomedicine, fostemsavir tromethamine, IQP-0831, and BMS-663068.

Examples of CXCR4 inhibitors include plerixafor, ALT-1188, N15 peptide, and vMIP (Haimipu).

HIV Maturation Inhibitors

Examples of HIV maturation inhibitors include BMS-955176, GSK-3640254 and GSK-2838232.

Latency Reversing Agents

Examples of latency reversing agents include histone deacetylase (HDAC) inhibitors, proteasome inhibitors such as velcade, protein kinase C (PKC) activators, Smyd2 inhibitors, BET-bromodomain 4 (BRD4) inhibitors, ionomycin, PMA, SAHA (suberanilohydroxamic acid, or suberoyl, anilide, and hydroxamic acid), IL-15 modulating antibodies, JQ1, disulfiram, amphotericin B, and ubiquitin inhibitors such as largazole analogs, APH-0812, GSK-343, and toll-like receptor modulators.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include capsid polymerization inhibitors or capsid disrupting compounds, HIV nucleocapsid p7 (NCp7) inhibitors such as azodicarbonamide, HIV p24 capsid protein inhibitors, GS-6207, AVI-621, AVI-101, AVI-201, AVI-301, and AVI-CAN1-15 series.

Immune-Based Therapies

Examples of immune-based therapies include toll-like receptors modulators such as TLR1, TLR2, TLR3, TLR4, TLR5, TLR6, TLR7, TLR8, TLR9, TLR10, TLR11, TLR12, and TLR13; programmed cell death protein 1 (Pd-1) modulators; programmed death-ligand 1 (PDL-1) modulators; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; polymer polyethyleneimine (PEI); gepon; IL-12; WF-10; VGV-1; MOR-22; BMS-936559; CYT-107, interleukin-15/Fc fusion protein, AM-0015, ALT-803, NIZ-985, NKTR-255, normferon, peginterferon alfa-2a, peginterferon alfa-2b, recombinant interleukin-15, RPI-MN, STING modulators, RIG-I modulators, NOD2 modulators, SB-9200, and IR-103.

Examples of TLR agonists include vesatolimod (GS-9620), lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, and telratolimod.

Phosphatidylinositol 3-kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

alpha-4/beta-7 Antagonists

Examples of Integrin alpha-4/beta-7 antagonists include PTG-100, TRK-170, abrilumab, etrolizumab, carotegrast methyl, and vedolizumab.

HIV Antibodies, Bispecific Antibodies, and "Antibody-Like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bispecific antibodies, trispecific antibodies, multivalent antibodies, bNAbs (broadly neutralizing HIV antibodies), BMS-936559, TMB-360, and those targeting HIV gp120 or gp41, antibody-recruiting Molecules targeting HIV, anti-CD63 monoclonal antibodies, CD3 bispecific antibodies, CD16 bispecific antibodies, anti-GB virus C antibodies, anti-GP120/CD4, CCR5 bispecific antibodies, anti-Nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, and MB-66.

Examples of those targeting HIV in such a manner include bavituximab, UB-421, C2F5, 2G12, C4E10, C2F5+C2G12+C4E10, 8ANC195, 3BNC117, 3BNC117-LS, 3BNC60, 10-1074, 10-1074-LS, GS-9722, DH411-2, PGT145, PGT121, PGT-151, PGT-133, MDX010 (ipilimumab), DH511, N6, N6LS, N49P6, N49P7, N49P9, N49P11, VRC01 VRC-01-LS, PGDM1400, A32, 7B2, 10E8, 10E8VLS, 3810109, 10E8v4, CAP256-VRC26.25, DRVIA7, SAR-441236, VRC-07-523, VRC07-523LS, VRC-HIVMAB080-00-AB, VRC-HIVMAB060-00-AB, P2G12, and VRC07. Examples of HIV bispecific antibodies include MGD014, and TMB-bispecific.

Example of in vivo delivered bNAbs such as AAV8-VRC07; mRNA encoding anti-HIV antibody VRC01.

Pharmacokinetic Enhancers

Examples of pharmacokinetic enhancers include cobicistat and ritonavir.

Additional Therapeutic Agents

Examples of additional therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences), WO 2013/091096 (Boehringer Ingelheim), WO 2018/145021 (Gilead Sciences), and WO2017/106346 (Gilead Sciences), each of which is herein incorporated by reference in its entirety.

HIV Vaccines

Examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/AIDSVAX B/E (gp120) (RV144), monomeric gp120 HIV subtype C vaccine, Remune, ITV-1, Contre Vir, Ad5-ENVA-48, DCVax-001 (CDX-2401), Vacc-4x, Vacc-C5, VAC-3S, multiclade DNA recombinant adenovirus-5 (rAd5), rAd5 gag-pol env A/B/C vaccine, Pennvax-G, Pennvax-G/MVA-CMDR, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), gp140[delta]V2.TV1+MF-59, rVSVIN HIV gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV, Ad-4 (Ad4-env Clade C+Ad4-mGag), Paxvax, EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, Ad26.Mod.HIV+MVA mosaic vaccine+gp140, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine, DNA.HTI and MVA.HTI, VRC-HIVDNA016-00-VP+VRC-HIVADV014-00-VP, INO-6145, JNJ-9220, gp145 C.6980; eOD-GT8 60mer based vaccine, PD-201401, env (A, B, C, A/E)/gag (C) DNA Vaccine, gp120 (A,B,C,A/E) protein vaccine, PDPHV-201401, Ad4-EnvCN54, EnvSeq-1 Envs HIV vaccine (GLA-SE adjuvanted), HIV p24gag pri, me-boost plasmid DNA vaccine, arenavirus vector-based immunotherapies (Vaxwave, TheraT), MVA-BN HIV vaccine regimen, UBI HIV gp120, mRNA based prophylactic vaccines, and TBL-1203HI, HIV Combination Therapy In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

It will be appreciated by one of skill in the art that the additional therapeutic agents listed above may be included in more than one of the classes listed above. The particular classes are not intended to limit the functionality of those compounds listed in those classes.

In a specific embodiment, a compound disclosed herein, or a pharmaceutically acceptable salt thereof, is combined with an HIV nucleoside or nucleotide inhibitor of reverse transcriptase. In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase. In a specific embodiment, a compound disclosed herein, or a pharmaceutically acceptable salt thereof, is combined with an HIV nucleoside or nucleotide inhibitor of reverse transcriptase and an HIV capsid inhibitor or an HIV capsid polymerization inhibitor. In a specific embodiment, a compound disclosed herein, or a pharmaceutically acceptable salt thereof, is combined with an HIV capsid inhibitor or an HIV capsid polymerization inhibitor. In a specific embodiment, a compound disclosed herein, or a pharmaceutically acceptable salt thereof, is combined with one, two, three or four HIV bNAbs. In a specific embodiment, a compound disclosed herein, or a pharmaceutically acceptable salt thereof, is combined with one, two, three or four HIV bNAbs and a HIV capsid inhibitor or an HIV capsid polymerization inhibitor. In a specific embodiment, a compound disclosed herein, or a pharmaceutically acceptable salt thereof, is combined with one, two, three or four HIV bNAbs, an HIV capsid inhibitor or an HIV capsid polymerization inhibitor, and an HIV nucleoside or nucleotide inhibitor of reverse transcriptase.

A compound as disclosed herein (e.g., any compound of formula I) may be combined with one, two, three, or four additional therapeutic agents in any dosage amount of the compound of formula I (e.g., from 1 mg to 500 mg of compound).

In one embodiment, kits comprising a compound disclosed herein, or a pharmaceutically acceptable salt thereof, in combination with one or more (e.g., one, two, three, one or two, or one to three) additional therapeutic agents are provided.

In one embodiment, the additional therapeutic agent or agents of the kit is an anti-HIV agent, selected from HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T cell receptors, TCR-T, autologous T cell therapies), compounds that target the HIV capsid, latency reversing agents, capsid polymerization inhibitors, HIV bNAbs, immune-based therapies, phosphatidylinositol 3-kinase (PI3K) inhibitors, HIV antibodies, broadly neutralizing HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV viral infectivity factor inhibitors, TAT protein inhibitors, HIV Nef modulators, Hck tyrosine kinase modulators, mixed lineage kinase-3 (MLK-3) inhibitors, HIV splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent or agents of the kit are selected from combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In a specific embodiment, the kit includes a compound disclosed herein, or a pharmaceutically acceptable salt thereof, and an HIV nucleoside or nucleotide inhibitor of reverse transcriptase. In a specific embodiment, the kit includes a compound disclosed herein, or a pharmaceutically acceptable salt thereof, and an HIV nucleoside or nucleotide inhibitor of reverse transcriptase and an HIV non-nucleoside inhibitor of reverse transcriptase. In another specific embodiment, the kit includes a compound disclosed herein, or a pharmaceutically acceptable salt thereof, and an HIV nucleoside or nucleotide inhibitor of reverse transcriptase, and an HIV protease inhibiting compound. In an additional embodiment, the kit includes a compound disclosed herein, or a pharmaceutically acceptable salt thereof, an HIV nucleoside or nucleotide inhibitor of reverse transcriptase, an HIV non-nucleoside inhibitor of reverse transcriptase, and a pharmacokinetic enhancer. In certain embodiments, the kit includes a compound disclosed herein, or a pharmaceutically acceptable salt thereof, at least one HIV nucleoside inhibitor of reverse transcriptase, an integrase inhibitor, and a pharmacokinetic enhancer. In another embodiment, the kit includes a compound disclosed herein, or a pharmaceutically acceptable salt thereof, and two HIV nucleoside or nucleotide inhibitors of reverse transcriptase. In a specific embodiment, the kit includes a compound disclosed herein, or a pharmaceutically acceptable salt thereof, an HIV nucleoside or nucleotide inhibitor of reverse transcriptase and an HIV capsid inhibitor or an HIV capsid polymerization inhibitor. In a specific embodiment, the kit includes a compound disclosed herein, or a pharmaceutically acceptable salt thereof, and an HIV capsid inhibitor or an HIV capsid polymerization inhibitor. In a specific embodiment, the kit includes a compound disclosed herein, or a pharmaceutically acceptable salt thereof, and one, two, three or four HIV bNAbs. In a specific embodiment, the kit includes a compound disclosed herein, or a pharmaceutically acceptable salt thereof, one, two, three or four HIV bNAbs and a HIV capsid inhibitor or an HIV capsid polymerization inhibitor. In a specific embodiment, the kit includes a compound disclosed herein, or a pharmaceutically acceptable salt thereof, one, two, three or four HIV bNAbs, an HIV capsid inhibitor or an HIV capsid polymerization inhibitor, and an HIV nucleoside or nucleotide inhibitor of reverse transcriptase.

Birth Control (Contraceptive) Combination Therapy

Therapeutic agents used for birth control (contraceptive) include cyproterone acetate, desogestrel, dienogest, drospirenone, estradiol valerate, ethinyl estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segesterone acetate, ulipristal acetate, and any combinations thereof.

Gene Therapy and Cell Therapy

Gene therapy and cell therapy includes the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; and genetic approaches to modify cellular activity to further alter endogenous immune responsiveness against the infection.

Examples of dendritic cell therapy include AGS-004.

Example of CCR5 gene editing drugs such as SB-728T

Example of CCR5 gene inhibitors such as Cal-1

C34-CCR5/C34-CXCR4 expressing CD4-positive T cells

AGT-103-transduced autologous T cell therapy

AAV-eCD4-Ig gene therapy

Gene Editors

The genome editing system is selected from the group consisting of: a CRISPR/Cas9 system, a zinc finger nuclease system, a TALEN system, a homing endonucleases system, and a meganuclease system.

Examples of HIV targeting CRISPR/Cas9 systems include EBT-101.

CAR-T Cell Therapy

A population of immune effector cells engineered to express a chimeric antigen receptor (CAR), wherein the CAR comprises an HIV antigen-binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T cell or an NK cell. In some embodiments, the T cell is a CD4+ T cell, a CD8+ T cell, or a combination thereof. Cells can be autologous or allogeneic.

Examples of HIV CAR-T include VC-CAR-T, anti-CD4 CART cell therapy, autologous hematopoietic stem cells genetically engineered to express a CD4 CAR and the C46 peptide.

TCR-T Cell Therapy

TCR-T cells are engineered to target HIV derived peptides present on the surface of virus-infected cells.

HIV Long-Acting Therapy

Examples of drugs that are being developed as long-acting regimens include cabotegravir, rilpivirine, any integrase LA, VM-1500 LAI, maraviroc (LAI), tenofovir implant, MK-8591 implant, doravirine, raltegravir, and long-acting dolutegravir.

In certain embodiments, when a compound disclosed herein is combined with one, two, three, or four additional therapeutic agents as described above, the components of the composition are administered as a simultaneous or sequential regimen. When administered sequentially, the combination may be administered in two or more administrations.

Routes of Administration

The compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, (also referred to herein as the active ingredient) can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that a suitable route may vary with, for example, the condition of the recipient. n certain embodiments, the compounds disclosed can be dosed parenterally. In certain embodiments, the compounds disclosed can be dosed intravenous, subcutaneous, or intramuscular. In certain embodiments, the compounds disclosed are orally bioavailable and can be dosed orally.

In some embodiments, the compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, is administered with a syringe suitable for administration of the compound. In some embodiments, the syringe is disposable. In some embodiments, the syringe is reusable. In some embodiments, the syringe is pre-filled with the compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof.

In some embodiments, the compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, is administered with an auto-injector comprising a syringe. In some embodiments, the syringe is disposable. In some embodiments, the syringe is reusable. In some embodiments, the syringe is pre-filled with the compound formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof.

Dosing Regimen

In some embodiments, the compound, such as a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, is administered to a subject in accordance with an effective dosing regimen for a desired period of time or duration, such as at least about once a day, at least about once a week, at least about once a month, at least about once every 2 months, at least about once every 3 months, at least about once every 4 months, at least about once every 6 months, or at least about once every 12 months or longer. In some embodiments, the compound is administered on a daily or intermittent schedule. In some embodiments, the compound is administered on a weekly schedule. In some embodiments, the compound is administered on a monthly schedule. In some embodiments, the compound is administered every two months. In some embodiments, the compound is administered every three months. In some embodiments, the compound is administered every four months. In some embodiments, the compound is administered every five months. In some embodiments, the compound is administered every 6 months.

In some embodiments, the compound, such as a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, is subcutaneously or intramuscularly administered to a subject at least about once a month. In some embodiments, the compound (e.g., a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof), is subcutaneously or intramuscularly administered to a subject at least about once every 2 months or at least about once every 3 months, or at least about once every 4 months, or at least about once every 6 months. In some embodiments, the compound (e.g., a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof), is subcutaneously administered to a subject at least about once a month. In some embodiments, the compound (e.g., a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof), is subcutaneously administered to a subject at least about once every 2 months. In some embodiments, the compound (e.g., a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof), is subcutaneously administered to a subject at least about once every 3 months.

In some embodiments, the dosage or dosing frequency of a compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, is adjusted over the course of the treatment, based on the judgment of the administering physician.

In some embodiments, a compound as disclosed herein (e.g., a compound of formula I, II, IIIa, IIIb, IV, Va, Vb, VI, VIIa, VIIb, VIII, IX, IXa, IXb, X, Xa, Xb XI, XIa, or XIb) or a pharmaceutically acceptable salt thereof, may be administered in a dosage amount that is effective. For example, the dosage amount can be from 1 mg to 1000 mg of compound.

In some embodiments, the methods disclosed herein comprise event-driven administration of the compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, to the subject.

As used herein, the terms "event-driven" and "event-driven administration" refer to administration of the compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, (1) prior to an event (e.g., 2 hours, 1 day, 2 days, 5 day, or 7 or more days prior to the event) that would expose the individual to HIV (or that would otherwise increase the individual's risk of acquiring HIV); and/or (2) during an event (or more than one recurring event) that would expose the individual to HIV (or that would otherwise increase the individual's risk of acquiring HIV); and/or (3) after an event (or after the final event in a series of recurring events) that would expose the individual to HIV (or that would otherwise increase the individual's risk of acquiring HIV). In some embodiments, the event driven administration is performed pre-exposure of the subject to the HIV. In some embodiments, the event driven administration is performed post-exposure of the subject to the HIV. In some embodiments, the event driven administration is performed pre-exposure of the subject to the HIV and post-exposure of the subject to the HIV.

In some embodiments, the compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, is administered before exposure of the subject to the HIV.

An example of event driven dosing regimen includes administration of the compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, within 24 to 2 hours prior to HIV exposure (e.g., first sexual activity with sex partner known to be HIV positive, including sexual intercourse), followed by administration of the compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt, every 24 hours during the period of exposure (e.g., sexual activity with sex partner known to be HIV positive), followed by a further administration of the compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, after the last exposure (e.g., sexual activity with sex partner known to be HIV positive), and one last administration of the compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, 24 hours later.

A further example of an event driven dosing regimen includes administration of the compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, within 24 hours before HIV exposure (e.g., sexual activity with sex partner known to be HIV positive), then daily administration during the period of exposure (e.g., sexual activity with sex partner known to be HIV positive, including the last sexual intercourse), followed by a last administration approximately 24 hours later after the last exposure (which may be an increased dose, such as a double dose).

In certain embodiments, e.g., when administered as PrEP, the compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, is administered daily. In certain embodiments, e.g., when administered as event-driven PrEP, the compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, is administered 1 hour to 10 days, 1 hour to 7 days, 1 hour to 5 days, 1 to 72 hours, 1 to 48 hours, 1 to 24 hours, or 12 to 12 hours prior to an event that would increase the individual's risk of acquiring HIV (e.g., prior to sex or other exposure to the HIV virus). In some embodiments, the compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, is administered within 10 days, 7 days, 5 days, 72 hours, 60 hours, 48 hours, 24 hours, 12 hours, 9 hours, 6 hours, 4 hours, 3 hours, 2 hours, or 1 hour prior to an event that would increase the individual's risk of acquiring HIV (e.g., prior to sex or other exposure to the HIV virus). In certain embodiments, when the compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, is administered prior to an event (e.g., administered prior to the event) that would increase the individual's risk of acquiring HIV, it is administered daily prior to the event (e.g., sexual activity). In certain embodiments, when the compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, is administered prior to an event that would increase the individual's risk of acquiring HIV, it is administered one to three times prior to the event.

In some embodiments, e.g., when administered as part of a an event-driven PrEP regimen, the compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, is administered during the time of HIV-exposure. In certain embodiments wherein the compound of formula I, II, IIIa, IIIb, IV, Va, Vb, V, VIIa, VIIb, VIII, IX, IXa, IXb, X, Xa, Xb, XI, XIa, or XIb, is administered before exposure, the compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, is administered daily (e.g., as a single dose) during the time of HIV-exposure (e.g., during the time period of sexual activity with sex partner known to be HIV positive). In some embodiments, the compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, is administered daily (e.g., for 1 to 7 days) after final exposure to the HIV (e.g., after a period of sexual activity with sex partner known to be HIV positive). In some embodiments, the administration is continued for 1 or 2 days after final exposure to HIV.

Additional examples of PrEP and/or PEP can be found, for example, at the clinical trial summary titled "On Demand Antiretroviral Pre-exposure Prophylaxis for HIV Infection in Men Who Have Sex With Men" (Clinical Trial #NCT01473472); the clinical trial summary titled "Prevention of HIV in Ile-de-France" (Clinical Trials #NCT03113123), and at Molina, et al. *N. Engl. J. Med.* 2015, 353:2237-2246, the disclosure of each of which is incorporated herein by reference in its entirety.

In some embodiments, methods for reducing the risk of acquiring HIV (e.g., HIV-1 and/or HIV-2) comprise administration of the compound of formula I, II, IIIa, IIIb, IV, Va, Vb, VI, VIIa, VIIb, VIII, IX, IXa, IXb, X, Xa, Xb, XI, XIa, or XIb, or a pharmaceutically acceptable salt thereof, in combination with safer sex practices. In certain embodiments, methods for reducing the risk of acquiring HIV (e.g., HIV-1 and/or HIV-2) comprise administration to an individual at risk of acquiring HIV. Examples of individuals at high risk for acquiring HIV include, without limitation, an individual who is at risk of sexual transmission of HIV.

In some embodiments, the reduction in risk of acquiring HIV is at least about 40%, 50%, 60%, 70%, 80%, 90%, or 95%. In some embodiments, the reduction in risk of acquiring HIV is at least about 75%. In some embodiments, the reduction in risk of acquiring HIV is about 80%, 85%, or 90%.

Formulation

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. In certain embodiments the suspension is a microsuspension. In certain embodiments the suspension is a nanosuspension.

In some embodiments, formulations suitable for parenteral administration (e.g., intramuscular (IM) and subcutaneous (SC) administration) will include one or more excipients. Excipients should be compatible with the other ingredients of the formulation and physiologically innocuous to the recipient thereof. Examples of suitable excipients are well known to the person skilled in the art of parenteral formulation and may be found, e.g., in Handbook of Pharmaceutical Excipients (eds. Rowe, Sheskey & Quinn), 6th edition 2009.

In certain embodiments, the active ingredient (e.g., a compound of formula I, II, IIIa, IIIb, IV, Va, Vb, V, VIIa, VIIb, VIII, IX, IXa, IXb, X, Xa, Xb XI, XIa, or XIb) is present as a free acid.

In certain embodiments the pharmaceutical composition disclosed herein is a parenteral formulation. In certain embodiments, the formulation is administered subcutaneously to a subject in need thereof. In certain embodiments, the formulation is administered intramuscularly to a subject in need thereof.

The amount of active ingredient that may be combined with the inactive ingredients to produce a dosage form may vary depending upon the intended treatment subject and the particular mode of administration. For example, in some embodiments, a dosage form for oral administration to humans may contain approximately 1 to 1000 mg of active material formulated with an appropriate and convenient amount of carrier material (e.g., inactive ingredient or excipient material). In certain embodiments, the carrier material varies from about 5 to about 95% of the total compositions (weight:weight).

It should be understood that in addition to the ingredients particularly mentioned above the compositions of these embodiments may include other agents conventional in the art having regard to the type of composition in question, for example those suitable for oral administration may include flavoring agents.

Abbreviations

The abbreviations as used herein have respective meanings as follows:
ACN acetonitrile
aq. aqueous
AXI anion exchange isocratic
AZ-H amylose tris(3-chloro-4-methylphenylcarbamate)
AZT azidothymidine or zidovudine
atm atmospheres
Bn benzyl
bNAbs broadly neutralizing HIV antibodies
Boc or BOC tert-butoxycarbonyl
$Boc_2O$ di-tert-butyl dicarbonate
Cbz benzyloxycarbonyl
CbzCl or Cbz-Cl benzyl chloroformate
Cp cyclopentadienyl
$CC_{50}$ 50% cytotoxic concentration
CCM cell culture medium
$Cp_2TiMe_2$ dimethyltitanocene or bis(cyclopentadienyl)dimethyltitanium or Petasis reagent
DBU 1,8-diazabicyclo[5.4.0]undec-7-ene
DCE dichloroethane
DCM dichloromethane
dd doublet of doublets
ddd doublet of doublet of doublets
dddd doublet of doublet of doublet of doublets
ddq doublet of doublet of quartets
ddt doublet of doublet of triplets
DIPEA N,N-diisopropylethylamine
DMF dimethylformamide
DMP Dess Martin periodinane
DMSO dimethylsulfoxide
dpm dipivaloylmethanato or 2,2,6,6-tetramethyl-3,5-heptanedionato
dq doublet of quartets
dt doublet of triplets
dtd doublet of triplet of doublets
$EC_{50}$ half maximal effective concentration
Et ethyl
$Et_2O$ diethyl ether
$Et_3N$ triethylamine
EtOAc ethyl acetate
EtOH ethanol
FBS fetal bovine serum (culture medium)
Gen Generation
Grubbs Gen 1 Grubbs Catalyst™ $1^{st}$ Generation
h hour(s)
HATU 2-(7-aza-1H-benzotriazole-1-yl)-1,1,3,3-tetramethyluronium hexafluorophosphate
HPLC high pressure liquid chromatography
HS human serum
Hz hertz
IA amylose tris(3,5-dimethylphenylcarbamate)
IB cellulose tris(3,5-dimethylphenylcarbamate)
IPA isopropyl alcohol
LA long-acting
LCMS or LC-MS liquid chromatography-mass spectrometry
m multiplet
M Molar
Me methyl
MeCN acetonitrile
MeI methyl iodide
MeLi methyllithium
MeMgBr methylmagnesium bromide
MeOH methanol
$Me_2S$ dimethyl sulfide
$Me_3SiCHN_2$ (trimethylsilyl)diazomethane
MHz megahertz
min. minute(s)
mmol millimole
μM micromolar
μmol micromole
mL milliliter
$Mn(dpm)_3$ tris(dipivaloylmethanato)manganese
MS mass spectroscopy
MT-4 or MT4 metallothionein 4 human T cell line
m/z Mass to charge
N Normal
NMR nuclear magnetic resonance
OAc acetate
OD-H cellulose tris(3,5-dimethylphenylcarbamate)
p pentet
PA protein adjusted
Ph phenyl
PhCHO benzaldehyde
$PhSiH_3$ phenylsilane
ppm parts per million
prep. Preparative
q quartet
qd quartet of doublets
rac racemic
rel relative (stereochemistry or configuration)
RLuc *Renilla* luciferase or *Renilla*-luciferin 2-monooxygenase
RP reverse phase
RPMI Roswell Park Memorial Institute (culture medium)
RT or R.T. room temperature
s singlet
SFC supercritical fluid chromatography
SGC solvating gas chromatography
STAB sodium triacetoxyborohydride
t triplet
td triplet of doublets
tdd triplet of doublet of doublets
TFA trifluoroacetic acid
THF tetrahydrofuran
$Ti(OEt)_4$ titanium(IV) ethoxide
TMS trimethylsilyl
TLR toll-like receptor
tt triplet of triplets
UV ultraviolet
wt weight The following examples are provided for purposes of illustration, not limitation.

EXAMPLES

Example 1: Preparation of (S)— and (R)—N-(2,4-difluorobenzyl)-13-hydroxy-1,12-dioxo-1,4,5,7,8,12-hexahydro-3H-2,8-methanopyrido[1,2-d][1,4,7]oxadiazecine-11-carboxamide (1-1, 1-2)

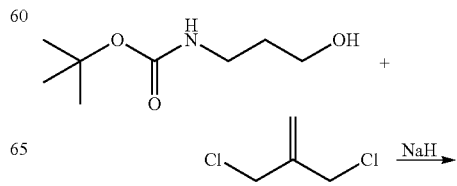

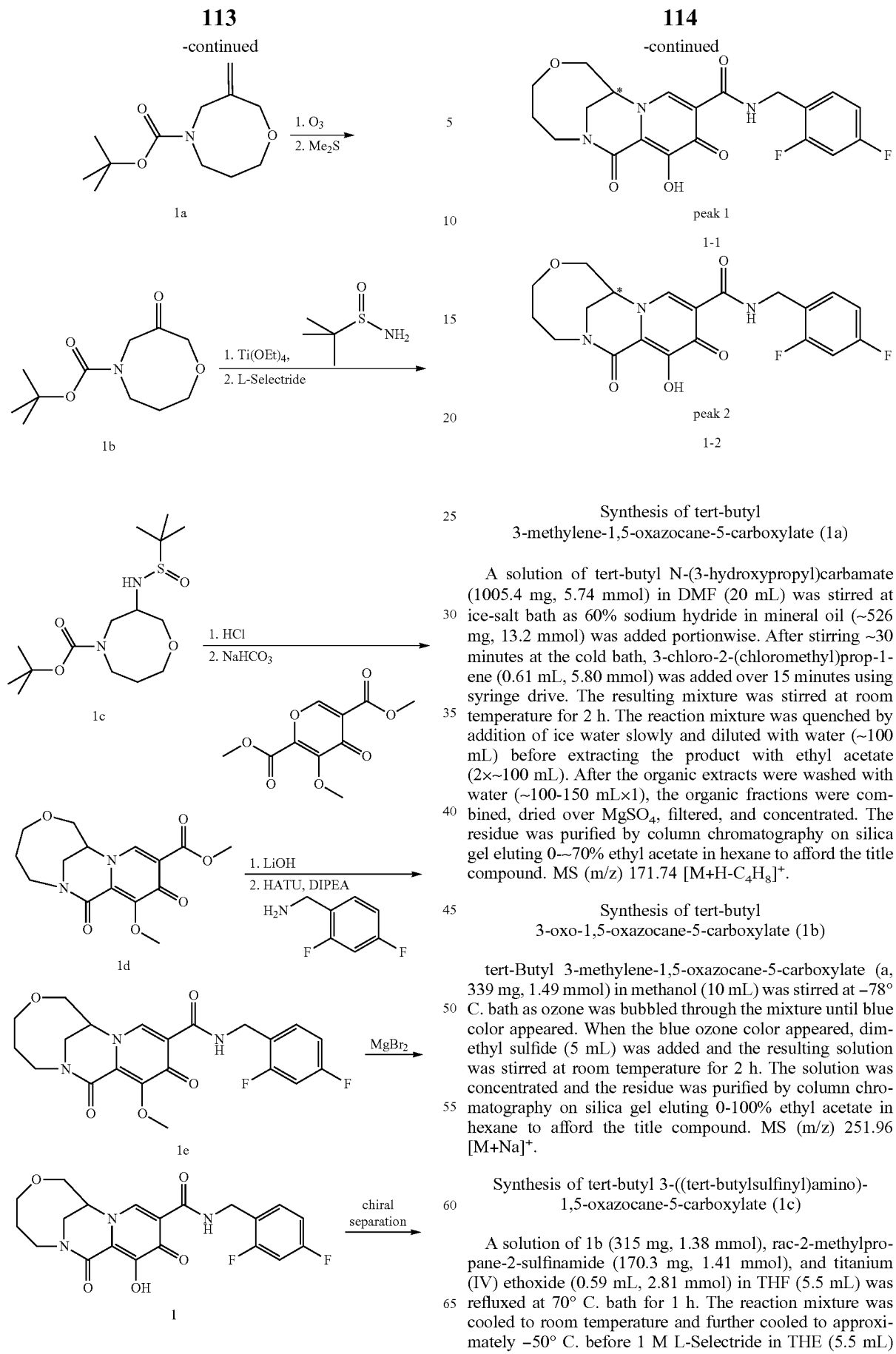

Synthesis of tert-butyl 3-methylene-1,5-oxazocane-5-carboxylate (1a)

A solution of tert-butyl N-(3-hydroxypropyl)carbamate (1005.4 mg, 5.74 mmol) in DMF (20 mL) was stirred at ice-salt bath as 60% sodium hydride in mineral oil (~526 mg, 13.2 mmol) was added portionwise. After stirring ~30 minutes at the cold bath, 3-chloro-2-(chloromethyl)prop-1-ene (0.61 mL, 5.80 mmol) was added over 15 minutes using syringe drive. The resulting mixture was stirred at room temperature for 2 h. The reaction mixture was quenched by addition of ice water slowly and diluted with water (~100 mL) before extracting the product with ethyl acetate (2×~100 mL). After the organic extracts were washed with water (~100-150 mL×1), the organic fractions were combined, dried over MgSO$_4$, filtered, and concentrated. The residue was purified by column chromatography on silica gel eluting 0-~70% ethyl acetate in hexane to afford the title compound. MS (m/z) 171.74 [M+H-C$_4$H$_8$]$^+$.

Synthesis of tert-butyl 3-oxo-1,5-oxazocane-5-carboxylate (1b)

tert-Butyl 3-methylene-1,5-oxazocane-5-carboxylate (a, 339 mg, 1.49 mmol) in methanol (10 mL) was stirred at −78° C. bath as ozone was bubbled through the mixture until blue color appeared. When the blue ozone color appeared, dimethyl sulfide (5 mL) was added and the resulting solution was stirred at room temperature for 2 h. The solution was concentrated and the residue was purified by column chromatography on silica gel eluting 0-100% ethyl acetate in hexane to afford the title compound. MS (m/z) 251.96 [M+Na]$^+$.

Synthesis of tert-butyl 3-((tert-butylsulfinyl)amino)-1,5-oxazocane-5-carboxylate (1c)

A solution of 1b (315 mg, 1.38 mmol), rac-2-methylpropane-2-sulfinamide (170.3 mg, 1.41 mmol), and titanium (IV) ethoxide (0.59 mL, 2.81 mmol) in THF (5.5 mL) was refluxed at 70° C. bath for 1 h. The reaction mixture was cooled to room temperature and further cooled to approximately −50° C. before 1 M L-Selectride in THF (5.5 mL)

was added. After 30 min, the reaction mixture was slowly warmed to room temperature over 2 h. The reaction mixture was cooled to 0° C. again and methanol added until there was no gas evolution. Brine was added to the solution with vigorous stirring, the resulting mixture was filtered through Celite®, and the solids were washed with ethyl acetate. After the filtrate was extracted with ethyl acetate (×3), the combined organic fractions were washed with brine (×1), combined, dried over $MgSO_4$, filtered, and concentrated. The residue was purified by column chromatography on silica gel eluting 50-100% ethyl acetate in hexane, followed by 0-20% methanol in ethyl acetate to afford the title compound. MS (m/z) 334.94 $[M+H]^+$.

Synthesis of methyl 13-methoxy-1,12-dioxo-1,4,5,7,8,12-hexahydro-3H-2,8-methanopyrido[1,2-d][1,4,7]oxadiazecine-11-carboxylate (1d)

A solution of 1c (274 mg, 0.82 mmol) in dichloromethane (2 mL) was stirred at room temperature as 4 N HCl in dioxane (4 mL) was added. After 1 h, the resulting suspension was concentrated and dried overnight. To the flask containing the residue were added dimethyl 3-methoxy-4-oxo-4H-pyran-2,5-dicarboxylate (242.5 mg, 1.00 mmol) and sodium bicarbonate (278.4 mg, 3.31 mmol) in water (1 mL) and methanol (3 mL) and the resulting mixture was stirred at room temperature for 24 h and at 40° C. bath.

The reaction mixture was cooled to room temperature, concentrated, and the residue was dissolved in aqueous DMF, filtered, and purified by preparative HPLC (column, Gemini 10μ C18 110A, AXI/; 250×21.2 mm) eluting 10-60% acetonitrile (0.1% TFA) in water (0.1% TFA) over 20 minutes. Combined fractions were freeze-dried to afford the title compound. MS (m/z) 323.16 $[M+H]^+$.

Synthesis of N-(2,4-difluorobenzyl)-13-methoxy-1,12-dioxo-1,4,5,7,8,12-hexahydro-3H-2,8-methanopyrido[1,2-d][1,4,7]oxadiazecine-11-carboxamide (1e)

To a solution of methyl 13-methoxy-1,12-dioxo-1,4,5,7,8,12-hexahydro-3H-2,8-methanopyrido[1,2-d][1,4,7]oxadiazecine-11-carboxylate (1d, 30.8 mg, 95.6 μmol) in methanol (0.5 mL) was added 1 N lithium hydroxide (0.2 mL) at room temperature and stirred at room temperature for 1 h. After the reaction mixture was acidified with 1 N HCl (~0.2 mL), the resulting solution was concentrated to dryness and co-evaporated with toluene (×3). To the previous residue were added (2,4-difluorophenyl)methanamine (26.1 mg, 182 μmol), 1-[bis(dimethylamino)methylene]-1H-1,2,3-triazolo[4,5-b]pyridinium 3-oxid hexafluorophosphate (HATU, 62.2 mg, 163.5 μmol), and DMF (1 mL) and stirred at room temperature as N,N-diisopropylethylamine (0.1 mL, 574.1 μmol). After 1 h, the reaction mixture was dissolved in ethyl acetate and washed with saturated ammonium chloride solution (×2), saturated sodium bicarbonate solution (×2) and brine (×1). After the aq. fractions were extracted with ethyl acetate (×1), the two organic fractions were combined, dried over $MgSO_4$, filtered, and concentrated. The residue was dissolved in DMF, filtered, and purified by preparative HPLC (column, Gemini 10μ C18 110A, AXI/; 250×21.2 mm) eluting 10-60% acetonitrile (0.1% TFA) in water (0.1% TFA) over 20 minutes. Combined fractions were freeze-dried to afford the title compound. MS (m/z) 434.22 $[M+H]^+$.

Synthesis of (rac), (S)— and (R)—N-(2,4-difluorobenzyl)-13-hydroxy-1,12-dioxo-1,4,5,7,8,12-hexahydro-3H-2,8-methanopyrido[1,2-d][1,4,7]oxadiazecine-11-carboxamide (1, 1-1, 1-2)

To a solution of N-(2,4-difluorobenzyl)-13-methoxy-1,12-dioxo-1,4,5,7,8,12-hexahydro-3H-2,8-methanopyrido[1,2-d][1,4,7]oxadiazecine-11-carboxamide (1e, 13.7 mg, 31.6 mol) in acetonitrile (1 mL) was added magnesium bromide (16.2 mg, 88.5 μmol) at room temperature and the resulting mixture was stirred at 50° C. bath. After 1 h, the reaction mixture was concentrated and the residue was triturated with 2 N HCl (~0.5 mL) and water (~1.5 mL) at 0° C. After sonication, the suspension was diluted with DMF (3 mL) to make it a solution, before filtration. The filtered solution was purified by preparative HPLC (column, Gemini 10μ C18 110A, AXI/; 250×21.2 mm) eluting 10-60% acetonitrile (0.1% TFA) in water (0.1% TFA) over 20 minutes. Combined fractions were freeze-dried to afford the title compound. MS (m/z) 420.23 $[M+H]^+$. $^1$H NMR (400 MHz, Acetonitrile-$d_3$) δ 10.31 (s, 1H), 8.40 (s, 1H), 7.40 (td, J=8.8, 6.4 Hz, 1H), 6.93 (ddq, J=10.8, 5.8, 2.8 Hz, 2H), 4.57 (d, J=5.2 Hz, 2H), 4.43-4.26 (m, 2H), 4.07 (d, J=33.0 Hz, 4H), 3.95 (dd, J=14.9, 1.7 Hz, 1H), 3.75 (s, 1H), 3.13 (ddd, J=13.9, 7.5, 4.6 Hz, 1H), 2.06-1.96 (m, 1H), 1.86 (s, 1H). $^{19}$F NMR (376 MHz, Acetonitrile-$d_3$) δ −114.07 (p, J=7.6 Hz), −116.55 (q, J=8.7 Hz).

N-(2,4-Difluorobenzyl)-13-hydroxy-1,12-dioxo-1,4,5,7,8,12-hexahydro-3H-2,8-methanopyrido[1,2-d][1,4,7]oxadiazecine-11-carboxamide (1, 15 mg) was separated into its individual enantiomers by preparative SFC chromatography on an AZ-H column using ethanol-TFA co-solvent to provide 1-1 and 1-2.

Example 2: Preparation of 13-hydroxy-1,12-dioxo-N-(2,4,6-trifluorobenzyl)-1,4,5,7,8,12-hexahydro-3H-2,8-methanopyrido[1,2-d][1,4,7]oxadiazecine-11-carboxamide (2)

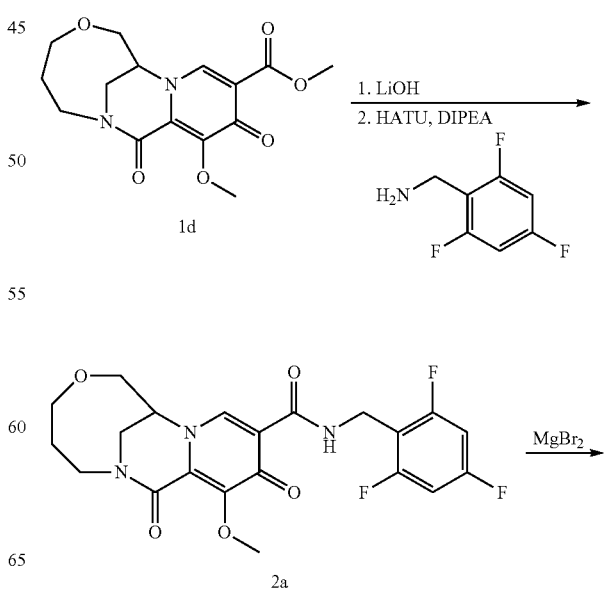

-continued

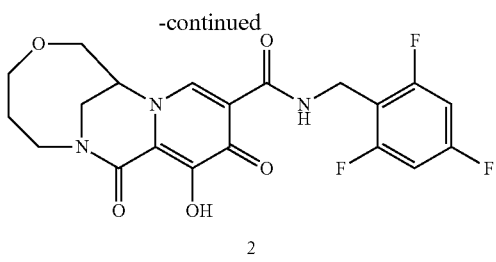

2

Synthesis of 13-methoxy-1,12-dioxo-N-(2,4,6-trifluorobenzyl)-1,4,5,7,8,12-hexahydro-3H-2,8-methanopyrido[1,2-d][1,4,7]oxadiazecine-11-carboxamide (2a)

To a solution of methyl 13-methoxy-1,12-dioxo-1,4,5,7,8,12-hexahydro-3H-2,8-methanopyrido[1,2-d][1,4,7]oxadiazecine-11-carboxylate (1d, 32.7 mg, 101.5 μmol) in methanol (0.5 mL) was added 1 N lithium hydroxide (0.2 mL) at room temperature and stirred at room temperature for 1 h. After the reaction mixture was acidified with 1 N HCl (~0.2 mL), the resulting solution was concentrated to dryness and co-evaporated with toluene (×3). To the previous residue were added (2,4,6-trifluorophenyl)methanamine (30.8 mg, 191.15 μmol), 1-[bis(dimethylamino)methylene]-1H-1,2,3-triazolo[4,5-b]pyridinium 3-oxid hexafluorophosphate (HATU, 57.9 mg, 152.2 μmol), and DMF (1 mL) and stirred at room temperature as N,N-diisopropylethylamine (0.1 mL, 574.1 μmol). After 1 h, the reaction mixture was dissolved in ethyl acetate and washed with saturated ammonium chloride solution (×2), saturated sodium bicarbonate solution (×2) and brine (×1). After the aq. fractions were extracted with ethyl acetate (×1), the two organic fractions were combined, dried over MgSO$_4$, filtered, and concentrated. The residue was dissolved in DMF, filtered, and purified by preparative HPLC, twice (column, Gemini 10μ C18 110A, AXI/; 250×21.2 mm) eluting 10-60% acetonitrile (0.1% TFA) in water (0.1% TFA) over 20 minutes. Combined fractions were freeze-dried to afford the title compound. MS (m/z) 452.23 [M+H]$^+$.

Synthesis of 13-hydroxy-1,12-dioxo-N-(2,4,6-trifluorobenzyl)-1,4,5,7,8,12-hexahydro-3H-2,8-methanopyrido[1,2-d][1,4,7]oxadiazecine-11-carboxamide (2)

To a solution of 13-methoxy-1,12-dioxo-N-(2,4,6-trifluorobenzyl)-1,4,5,7,8,12-hexahydro-3H-2,8-methanopyrido[1,2-d][1,4,7]oxadiazecine-11-carboxamide (2a, 9.3 mg, 20.6 mol) in acetonitrile (1 mL) was added magnesium bromide (16.2 mg, 88.0 μmol) at room temperature and the resulting mixture was stirred at 50° C. bath. After 30 min, the reaction mixture was cooled and concentrated, and the residue was dissolved in DMF (0.5 mL) and 2 N HCl (0.1 mL). After filtering the solution, the filtrate was purified by preparative HPLC (column, Gemini 10μ C18 110A, AXI/; 250×21.2 mm) eluting 10-60% acetonitrile (0.1% TFA) in water (0.1% TFA) over 20 minutes. Combined fractions were freeze-dried to afford the title compound. MS (m/z) 420.23 [M+H]$^+$. $^1$H NMR (400 MHz, Acetonitrile-d$_3$) δ 10.31 (s, 1H), 8.40 (s, 1H), 7.40 (td, J=8.8, 6.4 Hz, 1H), 6.93 (ddq, J=10.8, 5.8, 2.8 Hz, 2H), 4.57 (d, J=5.2 Hz, 2H), 4.43-4.26 (m, 2H), 4.07 (d, J=33.0 Hz, 4H), 3.95 (dd, J=14.9, 1.7 Hz, 1H), 3.75 (s, 1H), 3.13 (ddd, J=13.9, 7.5, 4.6 Hz, 1H), 2.06-1.96 (m, 1H), 1.86 (s, 1H). $^{19}$F NMR (376 MHz, Acetonitrile-d$_3$) δ −114.07 (p, J=7.6 Hz), −116.55 (q, J=8.7 Hz).

Example 3: Preparation of (R)- and (S)-(7R)-4,4-difluoro-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (3-1, 3-2)

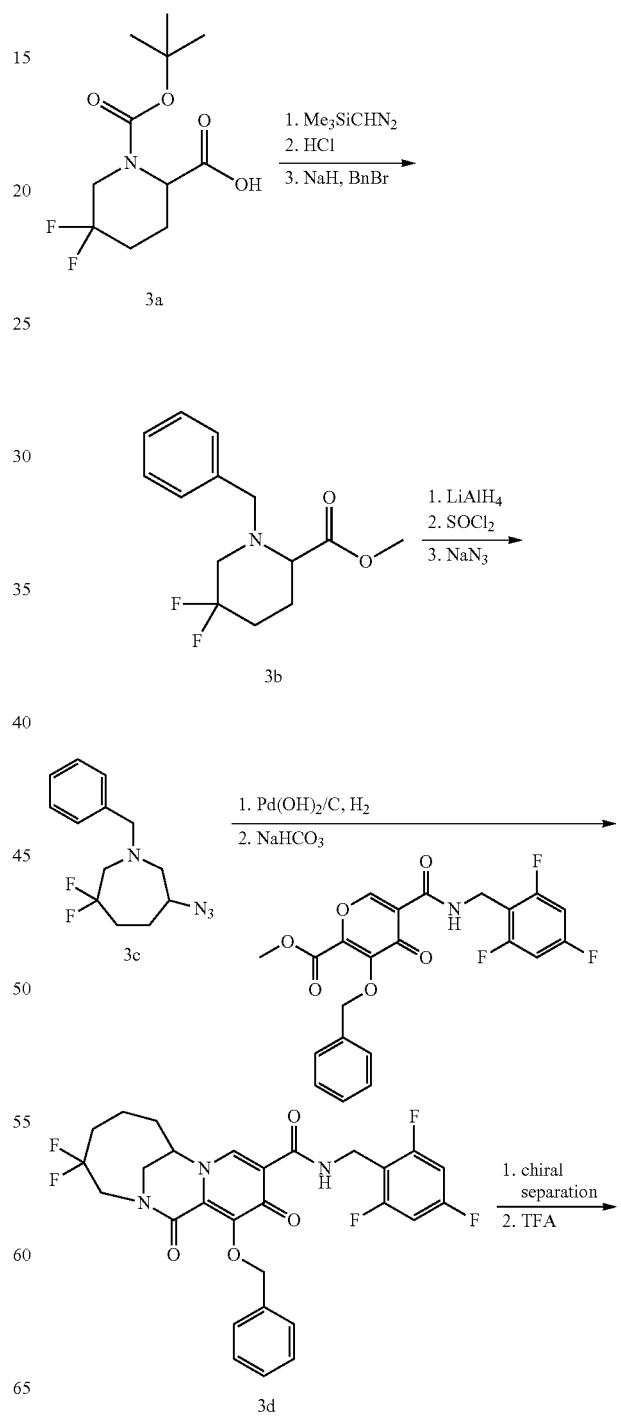

-continued

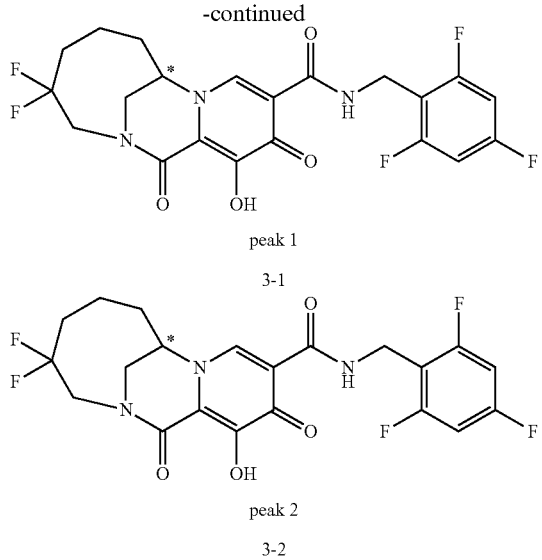

peak 1

3-1 peak 2

3-2

Synthesis of
1-benzyl-5,5-difluoropiperidine-2-carboxylate (3b)

A solution of 1-tert-butoxycarbonyl-5,5-difluoro-piperidine-2-carboxylic acid (3a, 1.999 g, 7.54 mmol) was dissolved in methanol at 0° C., and 2 M (trimethylsilyl) diazomethane in diethyl ether (10 mL) was added until yellow color persisted. After 15 min, dilute acetic acid was added to the reaction mixture until the yellow color disappeared, and the mixture was concentrated. The resulting residue was purified by column chromatography on silica gel eluting 0-30% ethyl acetate in hexane to afford 1-(tert-butyl) 2-methyl 5,5-difluoropiperidine-1,2-dicarboxylate.

A solution of 1-(tert-butyl) 2-methyl 5,5-difluoropiperidine-1,2-dicarboxylate (1.94 g, 6.93 mmol) was dissolved in dichloromethane (15 mL) and 4 N HCl in dioxane (15 mL) and stirred at room temperature. After 3 h, the solution was concentrated and the residue was dissolved in saturated sodium bicarbonate solution and the product was extracted with ethyl acetate (×2). The organic extracts were washed with brine (×1), dried over $MgSO_4$, filtered, and concentrated. The residue was purified by column chromatography on silica gel eluting 0-100% ethyl acetate in hexane to afford methyl 5,5-difluoropiperidine-2-carboxylate.

A solution of methyl 5,5-difluoropiperidine-2-carboxylate (962 mg, 5.37 mmol) in DMF (15 mL) was stirred at 0° C. as 60% sodium hydride in mineral oil (305 mg, 7.63 mmol) was added portion wise. After 30 minutes at 0° C., benzyl bromide (0.96 mL, 8.1 mmol) was added. After the reaction mixture was stirred at 0° C. for 1 h and room temperature for 1 h, additional 60% sodium hydride in mineral oil (150 mg, 3.75 mmol) and benzyl bromide (0.5 mL, 4.20 mmol) were added at room temperature and stirred at room temperature for 2.5 h. The reaction mixture was quenched with 2 N HCl (~4 mL) at 0° C. and diluted with saturated sodium bicarbonate solution (~100 mL) before the product was extracted with ethyl acetate (~100 mL×2). The organic extracts were washed with water (150 mL×1), combined, dried over $MgSO_4$, filtered, concentrated, and purified by column chromatography on silica gel eluting 0-100% ethyl acetate in hexane to afford the title compound. MS (m/z) 270.10 $[M+H]^+$.

Synthesis of 6-azido-1-benzyl-3,3-difluoroazepane (3c)

A solution of methyl 1-benzyl-5,5-difluoro-piperidine-2-carboxylate (1011 mg, 3.76 mmol) in THF (10 mL) was stirred at 0° C. as 1 M $LiAlH_4$ (5 mL, 5 mmol) was added. After 30 minutes at 0° C., the reaction mixture was vigorously stirred at 0° C. and quenched by dropwise addition of water (0.19 mL), 15% NaOH (0.19 mL), and water (0.57 mL), sequentially, and diluted with ethyl ether (15 mL). After the resulting suspension was vigorously stirred for 30 minutes at 0° C., the mixture was filtered through Celite® and the filtrate was treated with $MgSO_4$ and filtered again. The filtrate was concentrated to afford (1-benzyl-5,5-difluoropiperidin-2-yl)methanol. MS (m/z) 242.10 $[M+H]^+$.

(1-Benzyl-5,5-difluoro-2-piperidyl)methanol (606.6 mg, 2.51 mmol) was dissolved in toluene (10 mL) and thionyl chloride (3 mL, 41.1 mmol) was added. The resulting mixture was stirred at 60° C. After 1.25 h, the reaction mixture was concentrated and the residue was dissolved in saturated sodium bicarbonate solution (~20 mL) and ethyl acetate (~25 mL). After two fractions were separated, the aqueous fraction was extracted with ethyl acetate (~25 mL×1). The organic fractions were washed with brine (~20 mL×1), combined, dried over $MgSO_4$, filtered, and concentrated to afford unpurified 1-benzyl-2-(chloromethyl)-5,5-difluoropiperidine. MS (m/z) 260.10 $[M+H]^+$.

The unpurified chloride and sodium azide (187 mg, 2.88 mmol) in DMSO (4 mL) was stirred at 90° C. bath for 4 h and cooled at room temperature. The reaction mixture was diluted with water (~50 mL) and saturated sodium bicarbonate solution (~5 mL) and the product was extracted with ethyl acetate (~30 mL×3). The extracts were washed with water (~50 mL×1), combined, dried ($Na_2SO_4$), and concentrated. The residue was purified using column chromatography on silica gel eluting 0-10% ethyl acetate in hexane to afford the title compound. MS (m/z) 267.06 $[M+H]^+$.

Synthesis of 12-(benzyloxy)-4,4-difluoro-1,11-dioxo-N-(2,4,6-trifluorobenzyl)-1,4,5,6,7,11-hexahydro-3H-2,7-methanopyrido[1,2-a][1,4]diazonine-10-carboxamide (3d)

A suspension of 6-azido-1-benzyl-3,3-difluoro-azepane (323 mg, 1.21 mmol) and 20% palladium hydroxide on carbon (49 mg) in methanol (10 mL) and concentrated HCl (0.5 mL) was stirred under $H_2$ atmosphere for 3 h. The reaction mixture was filtered through Celite® and washed with methanol. The filtrate and washes were combined and concentrated completely to obtain unpurified 6,6-difluoroazepan-3-amine dihydrochloride.

Unpurified 6,6-difluoroazepan-3-amine dihydrochloride (119.9 mg, 0.54 mmol), methyl 3-(benzyloxy)-4-oxo-5-((2,4,6-trifluorobenzyl)carbamoyl)-4H-pyran-2-carboxylate (280.8 mg, 0.63 mmol), and sodium bicarbonate (238.7 mg, 2.84 mmol) were dissolved in methanol (5 mL) and water (1 mL) and the resulting solution was stirred at 55° C. bath for 20 h. The reaction mixture was concentrated and the residue was dissolved in ethyl acetate and water. After two fractions were separated, the aqueous fraction was extracted with ethyl acetate (×1), and the two organic fractions were washed with water (×1), combined, dried over $MgSO_4$, filtered, and concentrated. The residue was purified by column chromatography on silica gel eluting 0-5% methanol in dichloromethane to afford partially purified product.

The partially purified product was dissolved in DMF, filtered, and purified by preparative HPLC (column, Gemini 10µ C18 110A, AXI; 250×21.2 mm) eluting 30-90% acetonitrile (0.1% TFA) in water (0.1% TFA) over 20 min, and the collected fraction was freeze-dried to afford the title compound. MS (m/z) 548.14 [M+H]⁺.

Synthesis of (R)- and (S)-(7R)-4,4-difluoro-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (3-1, 3-2)

12-(Benzyloxy)-4,4-difluoro-1,11-dioxo-N-(2,4,6-trifluorobenzyl)-1,4,5,6,7,11-hexahydro-3H-2,7-methanopyrido[1,2-a][1,4]diazonine-10-carboxamide (3d, 140.7 mg) was separated into enantiomers by preparative SFC chromatography on an IA column using methanol co-solvent to provide 47.4 mg of 3d-1 and 46.9 mg of 3d-2. The separated enantiomers were dissolved in toluene (0.5 mL) and trifluoroacetic acid (3 mL) and stirred at room temperature for 30 minutes. The individual reactions were concentrated and the residue was purified using column chromatography on silica gel eluting 0-14% methanol in dichloromethane to provide the respective title compounds. MS (m/z) 458.16 [M+H]⁺. ¹H NMR (400 MHz, Acetonitrile-d₃) δ 12.34 (s, 1H), 10.38 (s, 1H), 8.27 (s, 1H), 7.02-6.66 (m, 2H), 5.45 (s, 2H), 4.70 (ddt, J=14.4, 11.6, 2.8 Hz, 1H), 4.59 (d, J=5.8 Hz, 1H), 4.37 (dd, J=13.5, 4.2 Hz, 1H), 4.04 (dd, J=13.6, 8.2 Hz, 1H), 3.89 (ddt, J=11.8, 7.8, 3.7 Hz, 1H), 3.19 (ddd, J=31.8, 14.2, 1.9 Hz, 1H), 2.42-2.22 (m, 1H), 2.22-2.06 (m, 1H), 2.06-1.98 (m, 1H), 1.80-1.62 (m, 1H).

Example 4: Preparation of (R)- and (S)-(7R)—N-(2,4-difluorobenzyl)-4,4-difluoro-12-hydroxy-1,11-dioxo-1,4,5,6,7,11-hexahydro-3H-2,7-methanopyrido[1,2-a][1,4]diazonine-10-carboxamide (4-1, 4-2)

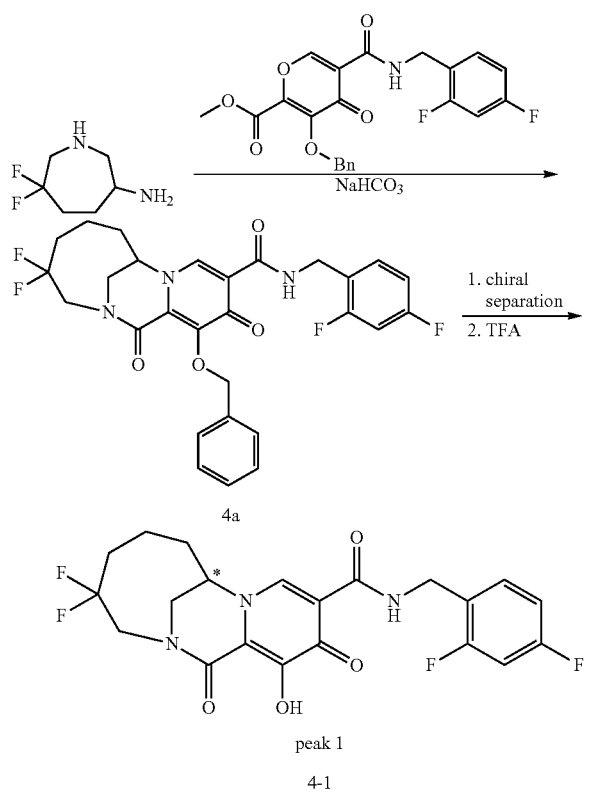

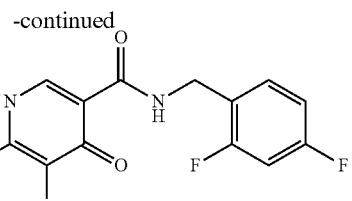

peak 2

4-2

Synthesis of 12-(benzyloxy)-N-(2,4-difluorobenzyl)-4,4-difluoro-1,11-dioxo-1,4,5,6,7,11-hexahydro-3H-2,7-methanopyrido[1,2-a][1,4]diazonine-10-carboxamide (4a)

Unpurified 6,6-difluoroazepan-3-amine dihydrochloride (116.7 mg, 0.52 mmol), methyl 3-(benzyloxy)-4-oxo-5-((2,4,6-trifluorobenzyl)carbamoyl)-4H-pyran-2-carboxylate (273.2 mg, 0.64 mmol), and sodium bicarbonate (225.7 mg, 2.69 mmol) were dissolved in methanol (5 mL) and water (1 mL) and the resulting solution was stirred at 55° C. bath for 20 h. The reaction mixture was concentrated and the residue was dissolved in ethyl acetate and water. After the two fractions were separated, the aqueous fraction was extracted with ethyl acetate (×1), and the two organic fractions were washed with water (×1), combined, dried over MgSO₄, filtered, and concentrated. The residue was purified by column chromatography on silica gel eluting 0-5% methanol in dichloromethane to afford partially purified product.

The partially purified product was dissolved in DMF, filtered, and purified by preparative HPLC (column, Gemini 10µ C18 110A, AXI; 250×21.2 mm) eluting 30-90% acetonitrile (0.1% TFA) in water (0.1% TFA) over 20 min, and the collected fraction was freeze-dried to afford the title compound. MS (m/z) 530.12 [M+H]⁺.

Synthesis of (R)- and (S)-(7R)—N-(2,4-difluorobenzyl)-4,4-difluoro-12-hydroxy-1,11-dioxo-1,4,5,6,7,11-hexahydro-3H-2,7-methanopyrido[1,2-a][1,4]diazonine-10-carboxamide (4-1, 4-2)

12-(Benzyloxy)-N-(2,4-difluorobenzyl)-4,4-difluoro-1,11-dioxo-1,4,5,6,7,11-hexahydro-3H-2,7-methanopyrido[1,2-a][1,4]diazonine-10-carboxamide (4a, 133 mg) was separated into its individual enantiomers by preparative SFC chromatography on an IA column using methanol co-solvent to provide 4a-1 and 4a-2. The separated enantiomers were dissolved in toluene (0.5 mL) and trifluoroacetic acid (3 mL) and stirred at room temperature for 30 minutes. The individual reactions were concentrated and the residue was purified using column chromatography on silica gel eluting 0-14% methanol in dichloromethane to provide the title compounds. MS (m/z) 440.19 [M+H]⁺. ¹H NMR (400 MHz, Acetonitrile-d₃) δ 12.36 (s, 1H), 10.40 (s, 1H), 8.28 (s, 1H), 7.47-7.31 (m, 1H), 6.94 (ddq, J=11.0, 5.2, 2.8 Hz, 2H), 4.71 (tt, J=11.7, 2.8 Hz, 1H), 4.57 (d, J=6.0 Hz, 2H), 4.38 (dd, J=13.5, 4.2 Hz, 1H), 4.06 (dd, J=13.6, 8.1 Hz, 1H), 3.90 (td, J=8.2, 4.2 Hz, 1H), 3.20 (ddd, J=31.8, 14.2, 1.9 Hz, 1H), 2.38-2.22 (m, 1H), 2.19-2.08 (m, 1H), 2.07-1.98 (m, 1H), 1.80-1.63 (m, 1H).

Example 5: Preparation of (R)- and (S)—N-(2,4-difluorobenzyl)-13-hydroxy-1,12-dioxo-1,3,4,5,6,7,8,12-octahydro-2,8-methanopyrido[1,2-a][1,4]diazecine-11-carboxamide (5-1, 5-2)

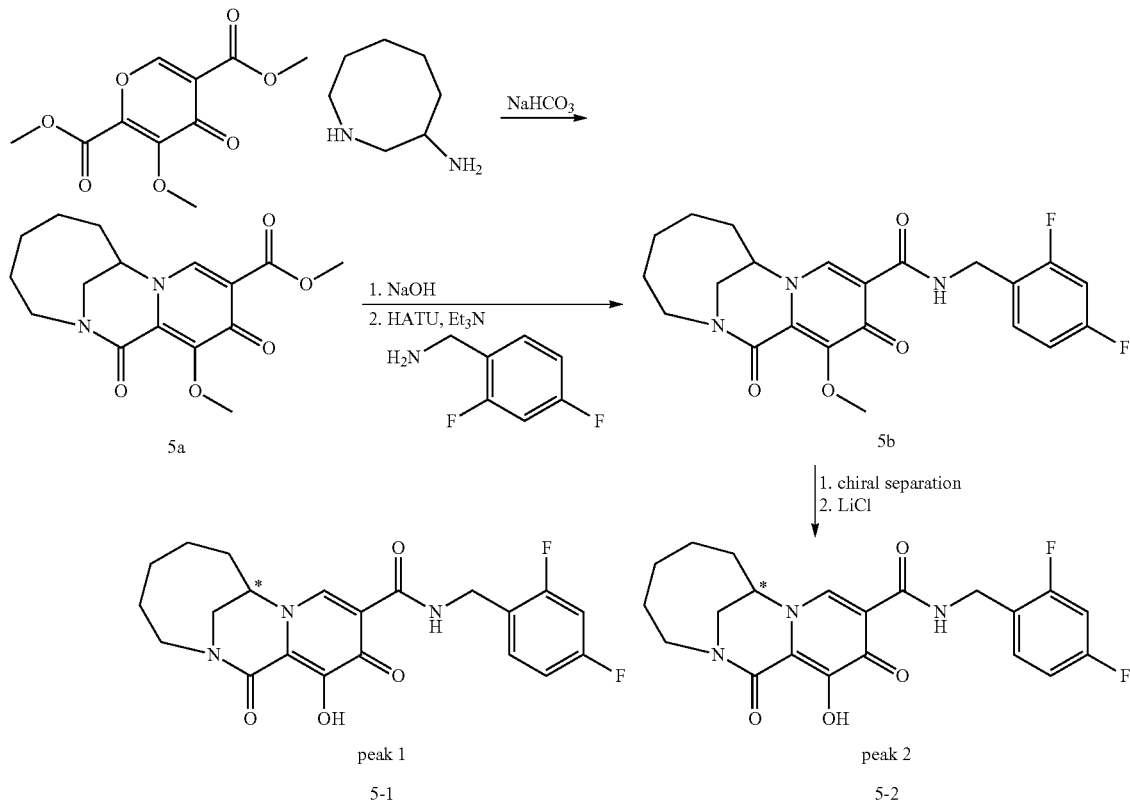

Synthesis of methyl 13-methoxy-1,12-dioxo-1,3,4,5,6,7,8,12-octahydro-2,8-methanopyrido[1,2-a][1,4]diazecine-11-carboxylate (5a)

A vial was charged with azocan-3-amine (0.13 g, 1.0 mmol), sodium bicarbonate (66 mg, 0.79 mmol), methanol (3 mL), and water (0.3 mL). Dimethyl 3-methoxy-4-oxo-4H-pyran-2,5-dicarboxylate (100 mg, 0.41 mmol) was added and the mixture was stirred at 30° C. After 2 h, the mixture was concentrated to dryness and purified by flash column chromatography (hexanes/EtOAc/MeOH) to provide the title compound. MS (m/z) 321.1 [M+H]$^+$. $^1$H NMR (400 MHz, Acetonitrile-d3) δ 8.07 (s, 1H), 4.43 (ddd, J=13.6, 8.8, 4.4 Hz, 1H), 4.18 (ddt, J=7.9, 5.3, 2.2 Hz, 1H), 4.05 (s, 3H), 3.94 (dd, J=14.4, 2.7 Hz, 1H), 3.85 (s, 3H), 3.65 (dd, J=14.5, 2.1 Hz, 1H), 2.86 (ddd, J=14.0, 6.2, 4.2 Hz, 1H), 2.16 (ddd, J=15.1, 8.7, 5.4 Hz, 1H), 2.00-1.56 (m, 6H), 1.57-1.45 (m, 1H).

Synthesis of N-(2,4-difluorobenzyl)-13-methoxy-1,12-dioxo-1,3,4,5,6,7,8,12-octahydro-2,8-methanopyrido[1,2-a][1,4]diazecine-11-carboxamide (5b)

Methyl 13-methoxy-1,12-dioxo-1,3,4,5,6,7,8,12-octahydro-2,8-methanopyrido[1,2-a][1,4]diazecine-11-carboxylate (80 mg, 0.25 mmol) was dissolved in methanol (3 mL), and 1M NaOH (0.75 mL, 0.75 mmol) was added. After 25 minutes, the reaction was quenched via the addition of 2M HCl and concentrated to dryness. The residue was dissolved in DCM (2 mL) with (2,4-difluorophenyl)methanamine (54 mg, 0.37 mmol) and triethylamine (0.10 mL, 0.75 mmol). HATU (114 mg, 0.30 mmol) was added and the mixture was stirred at room temperature. After 15 minutes, the reaction was concentrated to dryness, purified by preparatory HPLC (MeCN/water with 0.1% TFA), and lyophilized to provide the title compound. MS (m/z) 432.2 [M+H]$^+$.

Synthesis of (8R)— and (8S)—N-(2,4-difluorobenzyl)-13-hydroxy-1,12-dioxo-1,3,4,5,6,7,8,12-octahydro-2,8-methanopyrido[1,2-a][1,4]diazecine-11-carboxamide (5-1, 5-2)

N-(2,4-Difluorobenzyl)-13-methoxy-1,12-dioxo-1,3,4,5,6,7,8,12-octahydro-2,8-methanopyrido[1,2-a][1,4]diazecine-11-carboxamide (43 mg) was separated into its individual enantiomers by preparative SFC chromatography on an IB column using MeOH co-solvent to provide 5c-1 and 5c-2. The separated enantiomers were dissolved in DMF (0.5 mL) with lithium chloride (84 mg, 2.0 mmol) and stirred at 100° C. for 1 h. The individual reactions were cooled to room temperature, diluted with aqueous TFA, purified by preparatory HPLC (MeCN/water with 0.1% TFA), and lyophilized to provide the title compounds. MS (m/z) 418.2 [M+H]$^+$. $^1$H NMR (400 MHz, Acetonitrile-d3) δ 10.47 (s, 1H), 8.37 (s, 1H), 7.43 (td, J=9.3, 8.8, 6.5 Hz, 1H), 7.10-6.83 (m, 2H), 4.60 (d, J=5.8 Hz, 2H), 4.48 (tt, J=6.1, 2.5 Hz, 1H), 4.25 (ddd, J=13.6, 8.3, 5.2 Hz, 1H), 3.91 (dd, J=14.5, 2.8 Hz, 1H), 3.80 (dd, J=14.5, 2.1 Hz, 1H), 3.03 (ddd, J=13.8, 6.0, 4.8 Hz, 1H), 2.30-2.17 (m, 1H), 1.94-1.70 (m, 3H), 1.62-1.47 (m, 4H).

Example 6: Preparation of (7R,13R)—N-(2,4-difluorobenzyl)-12-hydroxy-13-methyl-1,11-dioxo-1,4,5,6,7,11-hexahydro-3H-2,7-methanopyrido[1,2-a][1,4]diazonine-10-carboxamide (7)

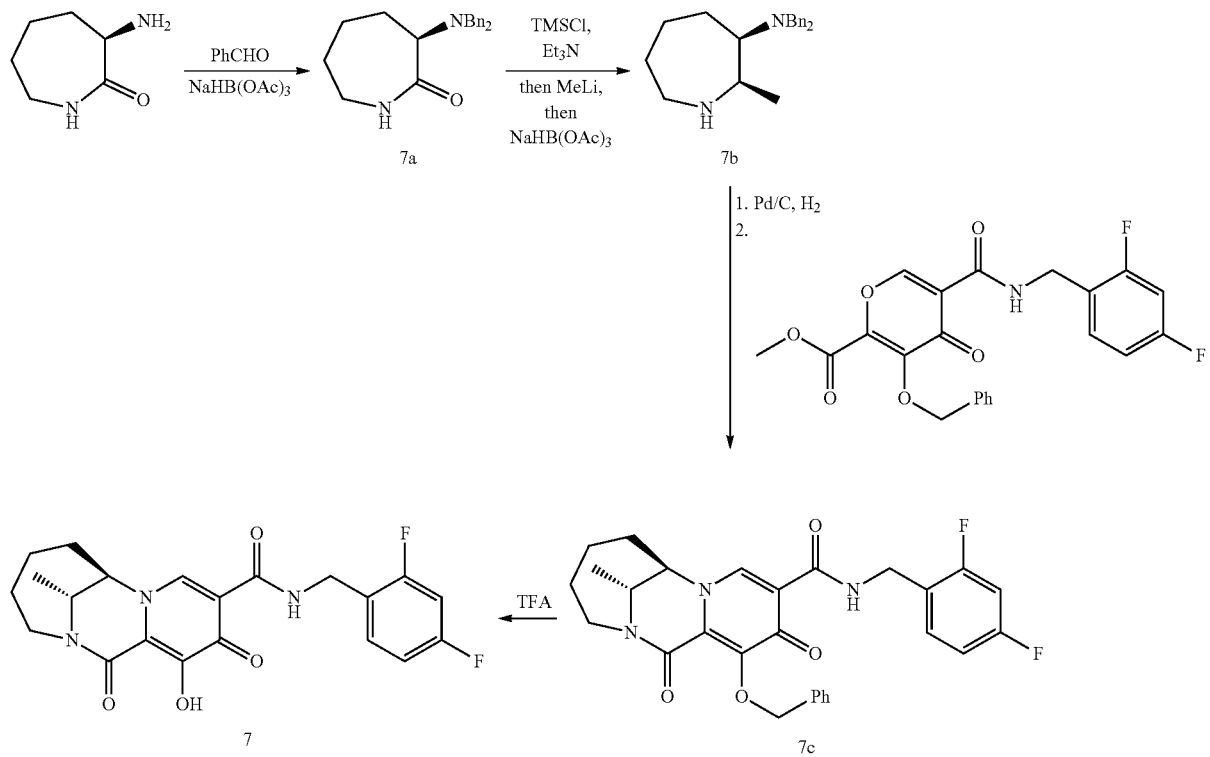

Synthesis of (R)-3-(dibenzylamino)azepan-2-one (7a)

(3R)-3-Aminoazepan-2-one (1.51 g, 11.8 mmol) was combined with benzaldehyde (3.61 mL, 35 mmol) and molecular sieves (4 g) in 1,2-DCE at 15° C. Sodium triacetoxyborohydride (7.49 g, 35.3 mmol) was added. After stirring for 90 minutes, the mixture was quenched with aqueous sodium bicarbonate and filtered. The organic layer was separated, dried over $Na_2SO_4$, filtered, concentrated, and purified by flash column chromatography (hexanes/EtOAc) to provide the title compound. MS (m/z) 309.4 $[M+H]^+$. $^1H$ NMR (400 MHz, Chloroform-d) δ 7.41 (d, J=7.2 Hz, 4H), 7.37-7.30 (m, 4H), 7.27-7.19 (m, 2H), 5.64 (s, 1H), 4.09 (d, J=14.4 Hz, 2H), 3.91 (d, J=14.4 Hz, 2H), 3.44 (d, J=10.1 Hz, 1H), 3.12 (dt, J=14.0, 6.7 Hz, 1H), 2.92 (ddd, J=15.3, 10.8, 5.4 Hz, 1H), 2.01 (d, J=11.4 Hz, 2H), 1.96-1.65 (m, 2H), 1.53-1.32 (m, 2H).

Synthesis of (2R,3R)—N,N-dibenzyl-2-methylazepan-3-amine (7b)

(3R)-3-(Dibenzylamino)azepan-2-one (7a, 637 mg, 2.07 mmol) was suspended in toluene (20 mL) with triethylamine (0.57 mL, 4.1 mmol) at 0° C. Chlorotrimethylsilane (0.29 mL, 2.3 mmol) in toluene (3 mL) was added dropwise. After 5 minutes, the mixture was warmed to 50° C. and stirred for 3 h. The slurry was cooled to 5° C. and the precipitate was removed by filtration, rinsing forward with 1:1 hexanes: ether. The supernatant was concentrated to dryness and placed under high vacuum overnight. The residue was dissolved in ether (30 mL), cooled to −78° C. and 1.6 M MeLi (2.84 mL) was added slowly. The reaction was allowed to warm to room temperature and an additional 1.6M MeLi (1 mL) was added. After 3 h the reaction was cooled to 5° C., quenched with aqueous ammonium chloride, and diluted with aqueous sodium bicarbonate and ethyl acetate. The organic layer was removed, dried over $Na_2SO_4$, filtered, and concentrated. The unpurified mixture was dissolved in DCM (50 mL) with 5 g 3 Å molecular sieves at 5° C. After stirring for 5 minutes, sodium triacetoxyborohydride (0.88 g, 4.1 mmol) was added and the reaction was stirred overnight, warming slowly to room temperature. The reaction was quenched with aqueous sodium bicarbonate and filtered. The organic layer was separated, dried over $Na_2SO_4$, filtered, concentrated, and purified by flash column chromatography (hexanes/EtOAc) to provide the title compound. MS (m/z) 309.2 $[M+H]^+$. $^1H$ NMR (400 MHz, Chloroform-d) δ 7.48 (d, J=7.2 Hz, 4H), 7.33 (dd, J=8.3, 6.8 Hz, 4H), 7.24 (t, J=7.2 Hz, 2H), 4.15 (d, J=14.3 Hz, 2H), 3.53 (d, J=14.3 Hz, 2H), 3.19-3.01 (m, 1H), 2.96-2.79 (m, 1H), 2.69 (dt, J=10.4, 6.1 Hz, 1H), 2.45 (td, J=12.3, 3.1 Hz, 1H), 2.13-2.00 (m, 1H), 1.94-1.68 (m, 3H), 1.58-1.38 (m, 1H), 1.28 (d, J=6.9 Hz, 3H), 1.26-1.11 (m, 1H).

Synthesis of (7R,13R)-12-(benzyloxy)-N-(2,4-difluorobenzyl)-13-methyl-1,11-dioxo-1,4,5,6,7,11-hexahydro-3H-2,7-methanopyrido[1,2-a][1,4]diazonine-10-carboxamide (7c)

(2R,3R)—N,N-Dibenzyl-2-methyl-azepan-3-amine (7b, 90 mg, 290 μmol) was combined with Pd/C (10 wt %, wet, E101 NE/W, 155 mg) in ethanol (20 mL) and stirred under an atmosphere of hydrogen gas for 120 h. The mixture was degassed with argon, filtered through Celite®, and 2M HCl (2 mL) was added. The solution was concentrated to dryness to provide (2R,3R)-2-methylazepan-3-amine as its hydrochloride salt. MS (m/z) 129.2 [M+H]+.

(2R,3R)-2-Methylazepan-3-amine dihydrochloride (58 mg, 0.29 mmol) was dissolved in methanol (3 mL) and water (0.5 mL) with sodium bicarbonate (151 mg, 1.79 mmol). Methyl 3-(benzyloxy)-5-((2,4-difluorobenzyl)carbamoyl)-4-oxo-4H-pyran-2-carboxylate (110 mg, 0.26 mmol) was added, and the mixture was stirred at 65° C. for 4 h. The mixture was cooled to room temperature, concentrated, dissolved in DCM, filtered, concentrated, purified by preparatory HPLC (MeCN/water with 0.1% TFA), and lyophilized to provide the title compound. MS (m/z) 508.6 [M+H]+.

Synthesis of (1R,14R)—N-[(2,4-difluorophenyl)methyl]-6-hydroxy-14-methyl-5,8-dioxo-2,9-diazatricyclo[7.4.1.02,7]tetradeca-3,6-diene-4-carboxamide (7)

(7R,13R)-12-(Benzyloxy)-N-(2,4-difluorobenzyl)-13-methyl-1,11-dioxo-1,4,5,6,7,11-hexahydro-3H-2,7-methanopyrido[1,2-a][1,4]diazonine-10-carboxamide (66 mg, 0.13 mmol) was dissolved in toluene (1 mL) with TFA (2 mL). After 135 minutes, the reaction was concentrated to dryness, purified by preparatory HPLC (MeCN/water with 0.1% TFA), and lyophilized to provide the title compound. Chiral HPLC analysis revealed it to be a mixture of enantiomers. MS (m/z) 418.4 [M+H]+. 1H NMR (400 MHz, Acetonitrile-d3) δ 10.43 (s, 1H), 8.43 (s, 1H), 7.44 (td, J=9.3, 8.8, 6.5 Hz, 1H), 7.21-6.78 (m, 2H), 4.60 (d, J=5.9 Hz, 2H), 4.44 (dt, J=5.2, 2.2 Hz, 1H), 4.26 (ddd, J=13.3, 8.9, 7.5 Hz, 1H), 3.86 (qd, J=6.9, 1.7 Hz, 1H), 3.21 (ddd, J=13.3, 7.4, 2.9 Hz, 1H), 2.13-1.99 (m, 1H), 1.89-1.60 (m, 1H), 1.28 (d, J=15.2 Hz, 1H), 1.22 (d, J=6.9 Hz, 3H).

Example 7: Preparation of (7S,13S)-12-hydroxy-13-methyl-1,11-dioxo-N-(2,4,6-trifluorobenzyl)-1,4,5,6,7,11-hexahydro-3H-2,7-methanopyrido[1,2-a][1,4]diazonine-10-carboxamide (8)

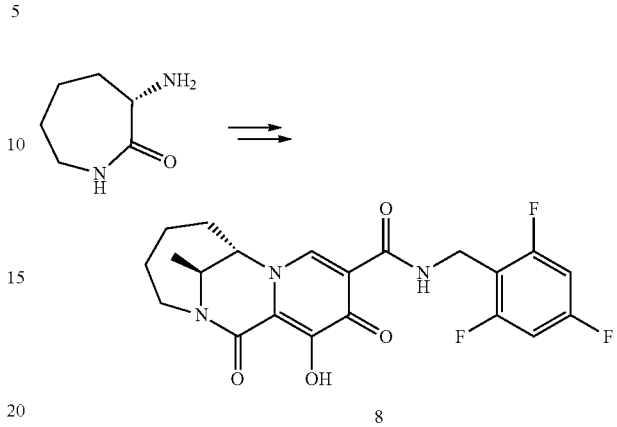

(7S,13S)-12-hydroxy-13-methyl-1,11-dioxo-N-(2,4,6-trifluorobenzyl)-1,4,5,6,7,11-hexahydro-3H-2,7-methanopyrido[1,2-a][1,4]diazonine-10-carboxamide (8) was prepared analogous to (7R,13R)—N-(2,4-difluorobenzyl)-12-hydroxy-13-methyl-1,11-dioxo-1,4,5,6,7,11-hexahydro-3H-2,7-methanopyrido[1,2-a][1,4]diazonine-10-carboxamide (7), beginning with (S)-3-aminoazepan-2-one and utilizing methyl 3-(benzyloxy)-4-oxo-5-((2,4,6-trifluorobenzyl)carbamoyl)-4H-pyran-2-carboxylate in place of methyl 3-(benzyloxy)-5-((2,4-difluorobenzyl)carbamoyl)-4-oxo-4H-pyran-2-carboxylate. HPLC analysis indicated a mixture of enantiomers. MS (m/z) 436.2 [M+H]+. 1H NMR (400 MHz, Acetonitrile-d3) δ 10.40 (s, 1H), 8.43 (s, 1H), 6.98-6.79 (m, 2H), 4.62 (d, J=5.5 Hz, 2H), 4.52-4.37 (m, 1H), 4.24 (ddd, J=13.3, 8.9, 7.5 Hz, 1H), 3.86 (qd, J=6.9, 1.7 Hz, 1H), 3.20 (ddd, J=13.4, 7.4, 2.9 Hz, 1H), 2.06-2.00 (m, 1H), 1.88-1.66 (m, 2H), 1.34-1.13 (m, 4H).

Example 8: Preparation of (7R,13S)—N-(2,4-difluorobenzyl)-12-hydroxy-13-methyl-1,11-dioxo-1,4,5,6,7,11-hexahydro-3H-2,7-methanopyrido[1,2-a][1,4]diazonine-10-carboxamide (9)

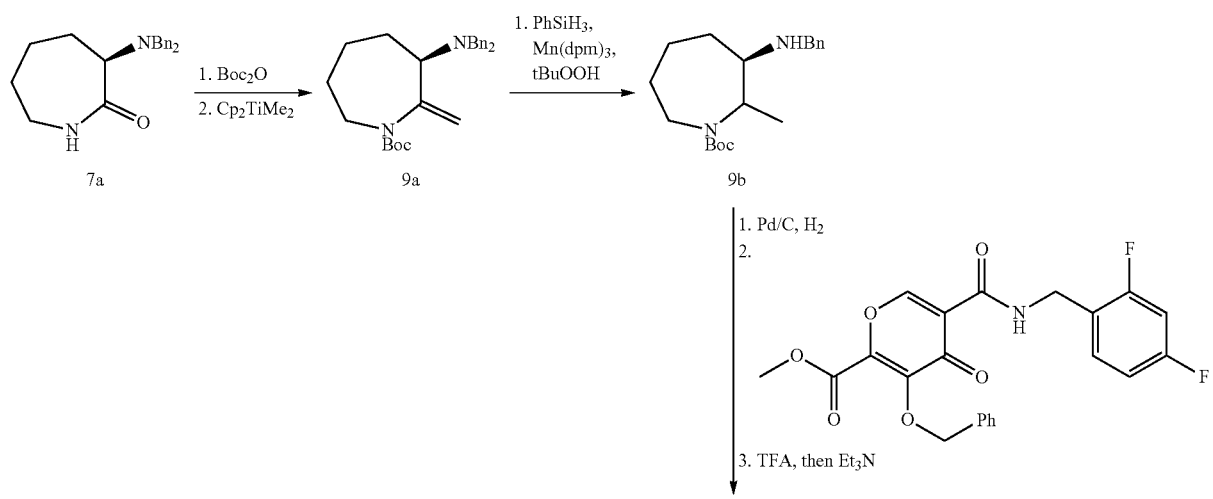

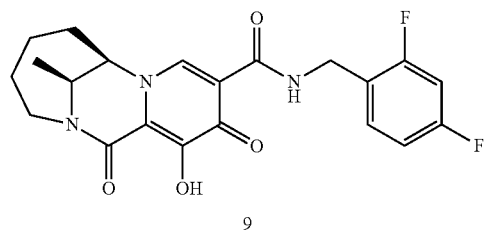

9

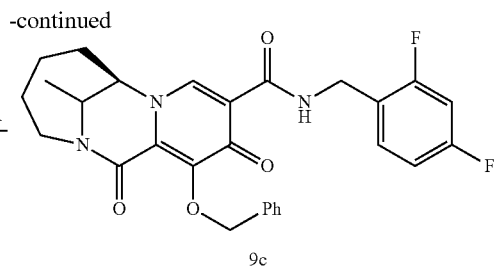

9c

Synthesis of tert-butyl (R)-3-(dibenzylamino)-2-methyleneazepane-1-carboxylate (9a)

(3R)-3-(Dibenzylamino)azepan-2-one (7a, 735 mg, 2.38 mmol) was combined in 1,2-DCE with triethylamine (0.66 mL, 4.77 mmol), 4-(dimethylamino)pyridine (87 mg, 0.71 mmol), and $Boc_2O$ (780 mg, 3.6 mmol). The mixture was stirred for 3 days at 35° C. Additional 4-(dimethylamino)pyridine (291 mg, 2.38 mmol) and $Boc_2O$ (630 mg, 2.9 mmol) were added, and the mixture was stirred at 60° C. for 4.5 h. The mixture was cooled to 45° C. and more $Boc_2O$ (1040 mg, 4.77 mmol) was added. The reaction was stirred overnight, cooled to room temperature and quenched with aqueous ammonium chloride solution. The organic layer was separated, dried over $Na_2SO_4$, filtered, concentrated, and purified by flash column chromatography (hexanes/EtOAc) to provide tert-butyl (R)-3-(dibenzylamino)-2-oxoazepane-1-carboxylate. MS (m/z) 409.5 $[M+H]^+$. $^1H$ NMR (400 MHz, Chloroform-d) δ 7.37 (d, J=7.2 Hz, 4H), 7.30 (t, J=7.4 Hz, 4H), 7.22 (t, J=7.2 Hz, 2H), 4.12-4.07 (m, 1H), 4.05 (d, J=14.5 Hz, 2H), 3.87 (d, J=14.3 Hz, 2H), 3.63-3.47 (m, 1H), 2.83 (dd, J=15.4, 10.4 Hz, 1H), 2.03-1.68 (m, 3H), 1.55 (d, J=0.8 Hz, 9H), 1.53-1.38 (m, 2H).

tert-Butyl (3R)-3-(dibenzylamino)-2-oxo-azepane-1-carboxylate (463 mg, 1.13 mmol) was placed in a round-bottom flask under argon and a solution of dimethyl titanocene (5% in toluene/THF, 16 mL) was added. The mixture was stirred at 80° C. for 75 minutes, cooled to 15° C., and quenched with aqueous sodium bicarbonate solution. The organic layer was separated, dried over $Na_2SO_4$, filtered, concentrated, and purified by flash column chromatography (hexanes/EtOAc) to provide the title compound. MS (m/z) 407.5 $[M+H]^+$. $^1H$ NMR (400 MHz, Chloroform-d) δ 7.41 (d, J=7.2 Hz, 4H), 7.37-7.29 (m, 4H), 7.27-7.19 (m, 2H), 5.82 (d, J=2.0 Hz, 1H), 5.17 (s, 1H), 3.97 (d, J=14.0 Hz, 2H), 3.79 (dt, J=14.1, 4.4 Hz, 1H), 3.47 (d, J=14.0 Hz, 2H), 3.35 (dt, J=9.9, 2.4 Hz, 1H), 2.85 (s, 1H), 1.95 (q, J=16.1, 12.0 Hz, 2H), 1.69-1.58 (m, 1H), 1.55-1.47 (m, 1H), 1.38 (s, 9H), 1.25-1.16 (m, 1H).

Synthesis of tert-butyl (3R)-3-(benzylamino)-2-methyl-azepane-1-carboxylate (9b)

tert-Butyl (3R)-3-(dibenzylamino)-2-methylene-azepane-1-carboxylate (9a, 256 mg, 0.63 mmol) was combined in isopropanol (3 mL) with tert-butyl hydroperoxide (5-6M in decane, 214 μl) and phenylsilane (78 μl, 0.63 mmol) under argon. Tris(dipivaloylmethanato)manganese (34 mg, 0.056 mmol) was added and the reaction was stirred at room temperature. After 1 h, additional Tris(dipivaloylmethanato) manganese (11 mg, 0.019 mmol) was added and stirring was continued. After an additional 30 minutes, the reaction was concentrated, and purified by flash column chromatography (hexanes/EtOAc) to provide the title compound as a mixture of diastereomers. MS (m/z) 319.3 $[M+H]^+$.

Synthesis of (7R)-12-(benzyloxy)-N-(2,4-difluorobenzyl)-13-methyl-1,11-dioxo-1,4,5,6,7,11-hexahydro-3H-2,7-methanopyrido[1,2-a][1,4]diazonine-10-carboxamide (9c)

tert-Butyl (3R)-3-(benzylamino)-2-methyl-azepane-1-carboxylate (138 mg, 433 μmol) was combined with Pd/C (10 wt %, wet, E101 NE/W, 138 mg) in ethanol (10 mL) under an atmosphere of hydrogen gas and stirred vigorously overnight. The reaction was filtered through Celite® and concentrated to dryness to provide unpurified tert-butyl (3R)-3-amino-2-methyl-azepane-1-carboxylate. MS (m/z) 229.0 $[M+H]^+$. This material was dissolved in methanol (5 mL) and water (0.5 mL), and sodium bicarbonate (146 mg, 1.73 mmol) was added, followed by methyl 3-benzyloxy-5-[(2,4-difluorophenyl)methylcarbamoyl]-4-oxo-pyran-2-carboxylate (186 mg, 0.43 mmol). The mixture was stirred at 45° C. for 5 minutes, warmed to 65° C., and stirred for 40 minutes. The reaction was cooled to room temperature, concentrated to dryness, dissolved in DCM, dried over $Na_2SO_4$, filtered, and concentrated. The residue was dissolved in toluene (4 mL), and TFA (2 mL) was added. The reaction was concentrated to dryness, dissolved in methanol (5 mL), and triethylamine (2 mL) was added. The mixture was warmed to 60° C. and stirred overnight. The reaction was concentrated to dryness, purified by preparatory HPLC (MeCN/water with 0.1% TFA), and lyophilized to provide the title compound as a mixture of diastereomers with the major isomer being (7R,13S)-12-(benzyloxy)-N-(2,4-difluorobenzyl)-13-methyl-1,11-dioxo-1,4,5,6,7,11-hexahydro-3H-2,7-methanopyrido[1,2-a][1,4]diazonine-10-carboxamide. MS (m/z) 508.4 $[M+H]^+$.

Synthesis of (7R,13S)—N-(2,4-difluorobenzyl)-12-hydroxy-13-methyl-1,11-dioxo-1,4,5,6,7,11-hexahydro-3H-2,7-methanopyrido[1,2-a][1,4]diazonine-10-carboxamide (9)

(1R)-6-Benzyloxy-N-[(2,4-difluorophenyl)methyl]-14-methyl-5,8-dioxo-2,9-diazatricyclo[7.4.1.02,7]tetradeca-3,6-diene-4-carboxamide (99 mg, 0.20 mmol) was dissolved in 4 mL toluene and 2 mL TFA, and stirred at 30° C. After 1 h, the reaction was concentrated, purified by preparatory HPLC (MeCN/water with 0.1% TFA), and lyophilized to provide the title compound. MS (m/z) 418.3 $[M+H]^+$. $^1H$ NMR (400 MHz, Acetonitrile-d3) δ 10.42 (s, 1H), 8.38 (s, 1H), 7.51-7.35 (m, 1H), 7.09-6.91 (m, 2H), 4.60 (d, J=5.8 Hz, 2H), 4.44 (d, J=4.4 Hz, 1H), 4.37 (dt, J=14.3, 9.4 Hz, 1H), 4.24-4.14 (m, 1H), 2.23-2.05 (m, 2H), 2.04-1.98 (m, 1H), 1.78-1.62 (m, 2H), 1.50 (d, J=7.4 Hz, 3H), 1.19-1.02 (m, 1H).

Example 9: Preparation of (7S- and 7R-)-6,6-difluoro-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (10-1, 10-2)
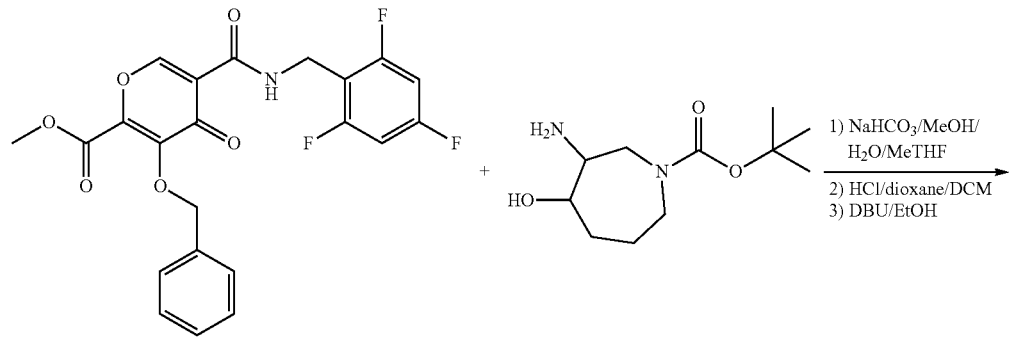
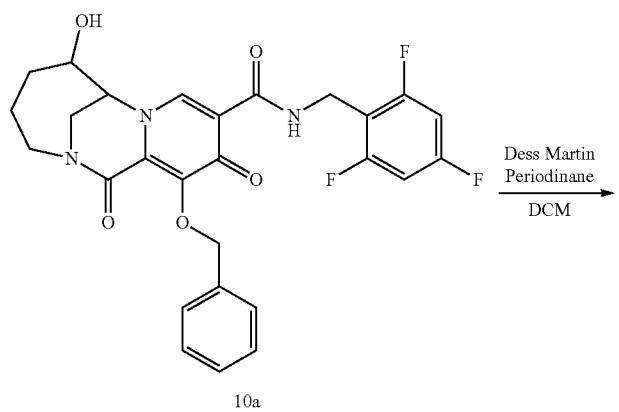
10a
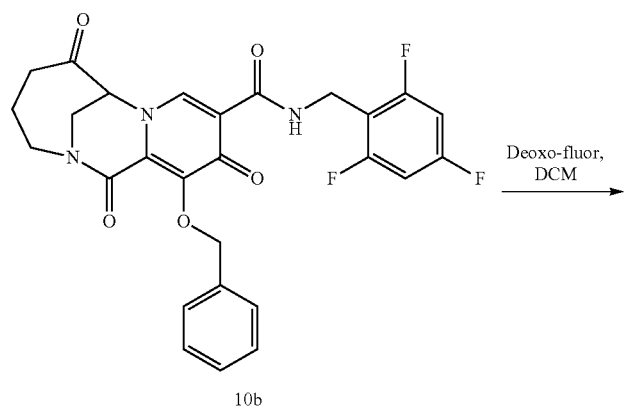
10b -continued

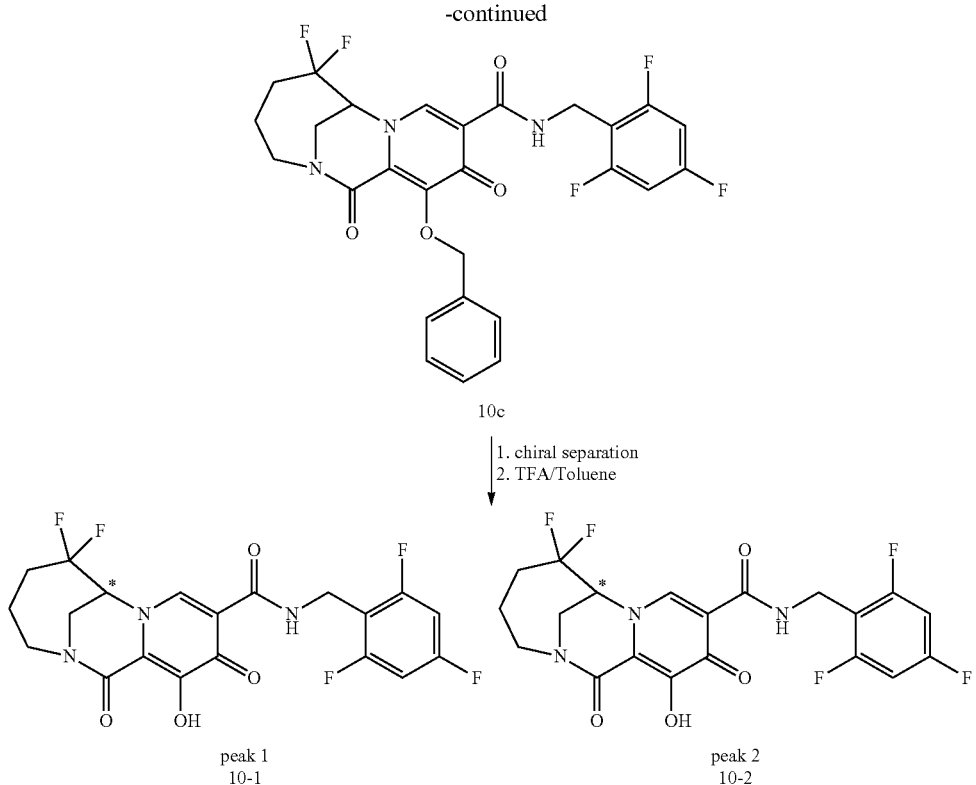

1. chiral separation
2. TFA/Toluene peak 1
10-1 peak 2
10-2

Synthesis of 12-(benzyloxy)-6-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (10a)

A vial was charged with methyl 3-(benzyloxy)-4-oxo-5-((2,4,6-trifluorobenzyl)carbamoyl)-4H-pyran-2-carboxylate (350 mg, 0.78 mmol), tert-butyl 3-amino-4-hydroxyazepane-1-carboxylate (180 mg, 0.78 mmol) and sodium bicarbonate (131 mg, 1.56 mmol). Methanol (3.5 mL), water (3.5 mL) and 2-methyl tetrahydrofuran (2 mL) were added. The reaction mixture was stirred at room temperature overnight and partitioned between 1 N HCl and ethyl acetate. The organic layer was separated and concentrated to dryness. The residue was dissolved in 1 mL of DCM and 3 mL of 4N HCl in dioxane, and the solution was stirred at room temperature for 2 h to remove the Boc protecting group and concentrated to dryness. To the residue was added 10 mL of ethanol and DBU (0.47 mL, 3.12 mmol). The reaction mixture was heated to 120° C. for 30 minutes in microwave. After cooling to room temperature, the reaction mixture was partitioned between 1 N HCl and ethyl acetate. The organic layer was separated and concentrated to dryness to afford the title compound. MS (m/z) 528.17 [M+H]$^+$.

Synthesis of 12-(benzyloxy)-1,6,11-trioxo-N-(2,4,6-trifluorobenzyl)-1,4,5,6,7,11-hexahydro-3H-2,7-methanopyrido[1,2-a][1,4]diazonine-10-carboxamide (10b)

To a solution of 12-(benzyloxy)-6-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (10a) (320 mg, 0.61 mmol) in dry DCM (15 mL) was added Dess Martin periodinane and the mixture was stirred for 20 minutes at room temperature. DCM was added and the organic phase was washed twice with 10% sodium thiosulphate solution, twice with 0.5 N NaOH and with brine. The organic phase was dried and evaporated. The residue was purified by silica gel chromatography eluting with methanol in DCM to afford the title compound. MS (m/z) 526.28 [M+H]$^+$.

Synthesis of 12-(benzyloxy)-6,6-difluoro-1,11-dioxo-N-(2,4,6-trifluorobenzyl)-1,4,5,6,7,11-hexahydro-3H-2,7-methanopyrido[1,2-a][1,4]diazonine-10-carboxamide (10c)

To a solution of 12-(benzyloxy)-1,6,11-trioxo-N-(2,4,6-trifluorobenzyl)-1,4,5,6,7,11-hexahydro-3H-2,7-methanopyrido[1,2-a][1,4]diazonine-10-carboxamide (10b) (200 mg. 0.38 mmol) in DCM (5 mL) cooled at −78° C. under argon was added Deoxo-Fluor® (1.1 mmol, 0.42 mL, 50% in toluene) under argon. The resulting mixture was stirred at −78° C. and allowed to gradually warm to room temperature overnight. The mixture was cooled at −78° C. and Deoxo-Fluor® (0.76 mmol, 0.28 mL, 50% in toluene) was added under argon. The reaction mixture was stirred at room temperature for 1 day and diluted with DCM. The mixture was cooled in an ice/water bath and quenched by dropwise addition of saturated aqueous sodium bicarbonate. The resulting mixture was stirred for 1 h, more saturated aqueous sodium bicarbonate was added, stirring continued for 10 minutes until bubbling ceased. The organic layer was separated, dried over Na$_2$SO$_4$ and filtered. The filtrate was concentrated to dryness. The residue was purified via silica gel chromatography eluting with EtOAc/hexane and purified by preparatory HPLC (MeCN/water with 0.1% TFA), and lyophilized to afford the title compound. MS (m/z) 548.25 [M+H]+.

Synthesis of (7S- and 7R-)-6,6-difluoro-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (10-1, 10-2)

12-(Benzyloxy)-6,6-difluoro-1,11-dioxo-N-(2,4,6-trifluorobenzyl)-1,4,5,6,7,11-hexahydro-3H-2,7-methanopyrido[1,2-a][1,4]diazonine-10-carboxamide (10c, 40 mg) was separated into its individual enantiomers by preparative SFC chromatography on an IA column using MeOH co-solvent to provide 10c-1 and 10c-2. The separated enantiomers were dissolved in 0.5 mL toluene and 1 mL TFA and stirred at room temperature for 1 h. The reaction mixture was concentrated and purified by RP-HPLC eluting with ACN/water (0.1% TFA) to provide the title compounds. Peak 1: MS (m/z) 458.12 [M+H]+. 1H NMR (400 MHz, DMSO-d6) δ 10.63 (s, 1H), 10.26 (t, J=5.8 Hz, 1H), 8.48 (s, 1H), 7.22 (t, J=8.7 Hz, 2H), 5.26-5.17 (m, 1H), 4.58 (d, J=5.8 Hz, 2H), 4.20 (dt, J=13.3, 8.7 Hz, 1H), 4.07-3.97 (m, 1H), 3.87 (dd, J=15.5, 1.9 Hz, 1H), 3.18 (dd, J=13.3, 6.7 Hz, 1H), 2.21 (s, 1H), 2.05-1.83 (m, 2H), 1.60 (dt, J=34.9, 14.0 Hz, 1H). Peak 2: MS (m/z) 458.13 [M+H]+. 1H NMR (400 MHz, DMSO-d6) δ 10.63 (s, 1H), 10.27 (t, J=5.8 Hz, 1H), 8.48 (s, 1H), 7.22 (t, J=8.7 Hz, 2H), 5.21 (d, J=8.0 Hz, 1H), 4.58 (d, J=5.8 Hz, 2H), 4.32-4.15 (m, 1H), 4.10-3.94 (m, 1H), 3.87 (dd, J=15.5, 2.0 Hz, 1H), 3.18 (dd, J=13.4, 6.6 Hz, 1H), 2.22 (s, 1H), 1.92 (d, J=8.1 Hz, 2H), 1.71-1.43 (m, 1H).

Example 10: Preparation of 6,12-dihydroxy-1,11-dioxo-N-(2,4,6-trifluorobenzyl)-1,4,5,6,7,11-hexahydro-3H-2,7-methanopyrido[1,2-a][1,4]diazonine-10-carboxamide (11)

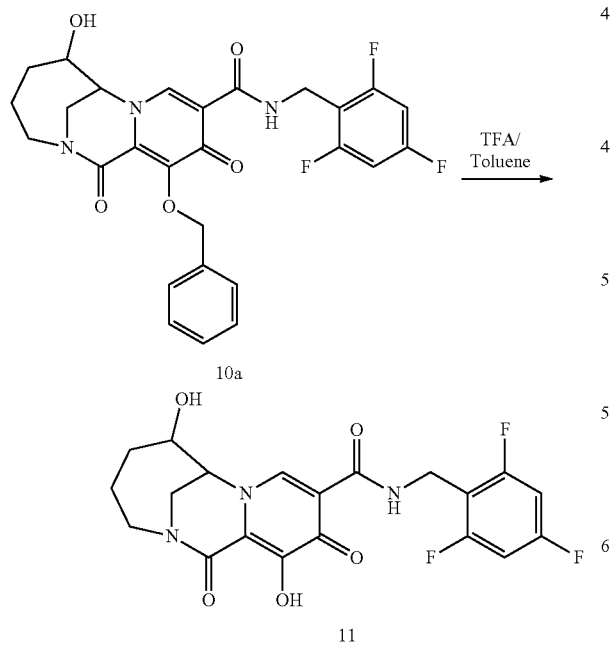

12-(Benzyloxy)-6-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (10a)(20 mg) was dissolved in 0.3 mL toluene and 0.6 mL of TFA and stirred at room temperature for 30 minutes. The reaction mixture was concentrated to dryness and the residue was purified by RP-HPLC eluting with ACN/water (0.1% TFA) to provide the title compound. MS (m/z) 438.18 [M+H]+. H NMR (400 MHz, DMSO-d6) δ 10.74 (s, 1H), 10.44 (t, J=5.8 Hz, 1H), 8.28 (s, 1H), 7.28-7.15 (m, 2H), 4.57 (d, J=5.6 Hz, 3H), 4.13 (dt, J=13.2, 9.2 Hz, 1H), 3.91-3.78 (m, 2H), 3.62 (dd, J=15.0, 1.6 Hz, 1H), 3.12 (dt, J=13.1, 4.5 Hz, 1H), 1.84 (d, J=6.8 Hz, 2H), 1.66 (d, J=14.5 Hz, 1H), 1.02 (td, J=14.4, 13.5, 5.8 Hz, 1H).

Example 11: Preparation of N-(2,4-difluorobenzyl)-6,12-dihydroxy-1,11-dioxo-1,4,5,6,7,11-hexahydro-3H-2,7-methanopyrido[1,2-a][1,4]diazonine-10-carboxamide (12)

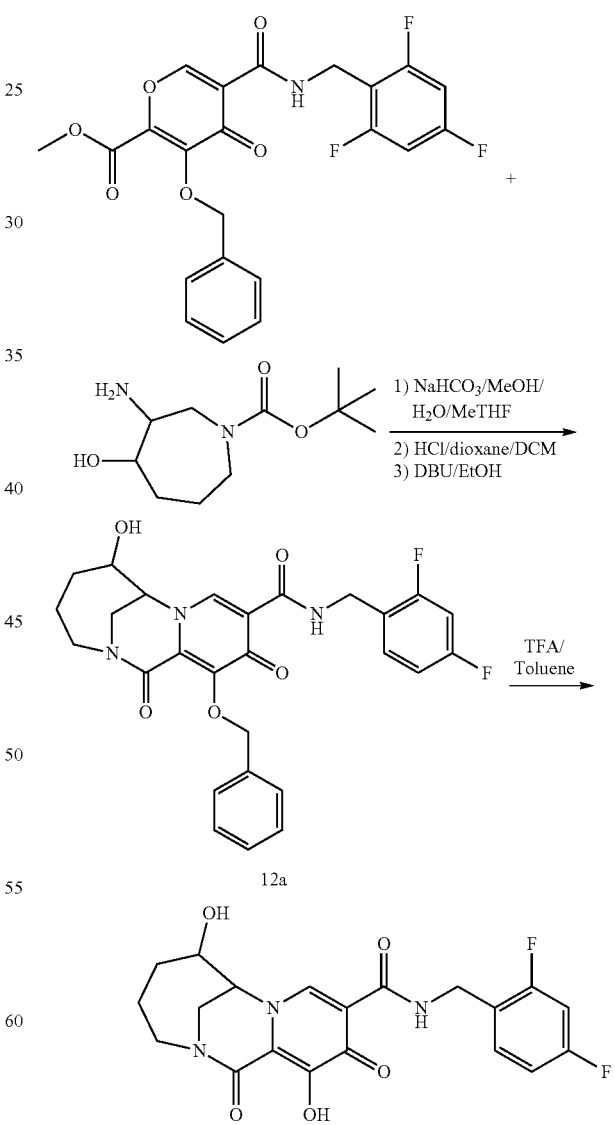

Synthesis of 12-(benzyloxy)-N-(2,4-difluorobenzyl)-6-hydroxy-1,11-dioxo-1,4,5,6,7,11-hexahydro-3H-2,7-methanopyrido[1,2-a][1,4]diazonine-10-carboxamide (12a)

12-(Benzyloxy)-N-(2,4-difluorobenzyl)-6-hydroxy-1,11-dioxo-1,4,5,6,7,11-hexahydro-3H-2,7-methanopyrido[1,2-a][1,4]diazonine-10-carboxamide (12a) was prepared similarly to compound 10a using methyl 3-(benzyloxy)-5-((2,4-difluorobenzyl)carbamoyl)-4-oxo-4H-pyran-2-carboxylate. MS (m/z) 510.23 [M+H]$^+$.

Synthesis of N-(2,4-difluorobenzyl)-6,12-dihydroxy-1,11-dioxo-1,4,5,6,7,11-hexahydro-3H-2,7-methanopyrido[1,2-a][1,4]diazonine-10-carboxamide (12)

The title compound was prepared similarly to compound 11 using compound 12a. MS (m/z) 420.15 [M+H]$^+$. $^1$H NMR (400 MHz, DMSO-d6) δ 10.77 (s, 1H), 10.43 (t, J=5.9 Hz, 1H), 8.31 (s, 1H), 7.41 (td, J=8.7, 6.6 Hz, 1H), 7.25 (ddd, J=10.6, 9.3, 2.6 Hz, 1H), 7.12-7.02 (m, 1H), 5.37 (s, 1H), 4.61-4.52 (m, 3H), 4.20-4.08 (m, 1H), 3.86 (td, J=14.0, 13.0, 4.4 Hz, 2H), 3.68-3.59 (m, 1H), 3.17-3.09 (m, 1H), 1.85 (d, J=7.4 Hz, 2H), 1.68 (d, J=14.9 Hz, 1H), 1.04 (s, 1H).

Example 12: Preparation of N-(2,4-difluorobenzyl)-6-fluoro-12-hydroxy-1,11-dioxo-1,4,5,6,7,11-hexahydro-3H-2,7-methanopyrido[1,2-a][1,4]diazonine-10-carboxamide (13)

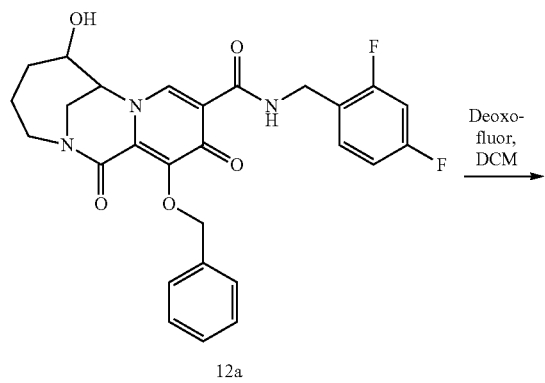

12a

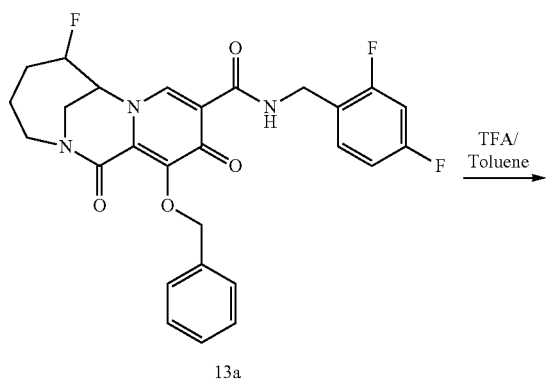

13a

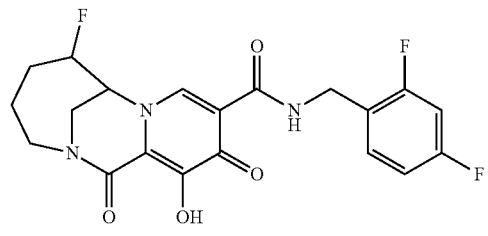

13

Synthesis of 12-(benzyloxy)-N-(2,4-difluorobenzyl)-6-fluoro-1,11-dioxo-1,4,5,6,7,11-hexahydro-3H-2,7-methanopyrido[1,2-a][1,4]diazonine-10-carboxamide (13a)

To a solution of 12-(benzyloxy)-N-(2,4-difluorobenzyl)-6-hydroxy-1,11-dioxo-1,4,5,6,7,11-hexahydro-3H-2,7-methanopyrido[1,2-a][1,4]diazonine-10-carboxamide (12a, 47 mg. 0.092 mmol) in DCM (3 mL) cooled at −78° C. under argon was added Deoxo-Fluor® (0.14 mmol, 0.05 mL, 50% in toluene) under argon. The resulting mixture was stirred at −78° C. and allowed to gradually warm to room temperature overnight. The mixture was cooled at −78° C., and Deoxo-Fluor® (0.14 mmol, 0.05 mL, 50% in toluene) was added under argon. The reaction mixture was stirred at room temperature for 2 h and diluted with DCM. The mixture was cooled in an ice/water bath and the reaction was quenched by dropwise addition of saturated aqueous sodium bicarbonate. The resulting mixture was stirred for 1 h and more saturated aqueous sodium bicarbonate was added, and stirring continued for 10 minutes until bubbling ceased. The organic layer was separated, dried over Na$_2$SO$_4$ and filtered. The filtrate was concentrated to dryness to afford the title compound. MS (m/z) 512.22 [M+H]$^+$.

Synthesis of N-(2,4-difluorobenzyl)-6-fluoro-12-hydroxy-1,11-dioxo-1,4,5,6,7,11-hexahydro-3H-2,7-methanopyrido[1,2-a][1,4]diazonine-10-carboxamide (13)

The title compound was prepared similarly to compound 11 using 13a. MS (m/z) 422.18 [M+H]$^+$. $^1$H NMR (400 MHz, DMSO-d6) δ 10.61 (s, 1H), 10.33 (t, J=5.9 Hz, 1H), 8.60 (s, 1H), 7.41 (td, J=8.7, 6.6 Hz, 1H), 7.25 (td, J=9.6, 2.6 Hz, 1H), 7.07 (td, J=8.7, 2.5 Hz, 1H), 5.10-5.03 (m, 1H), 4.98-4.89 (m, 1H), 4.56 (d, J=6.0 Hz, 2H), 4.13 (dt, J=13.2, 7.9 Hz, 1H), 3.90 (d, J=15.0 Hz, 1H), 3.83 (dd, J=15.1, 2.0 Hz, 1H), 3.13 (ddd, J=13.2, 7.1, 2.9 Hz, 1H), 2.18-2.05 (m, 1H), 2.04 (s, 1H), 1.82-1.64 (m, 1H), 1.53-1.20 (m, 1H).

Example 13: Preparation of (6S,7R)—N-(2,4-difluorobenzyl)-6,12-dihydroxy-6-methyl-1,11-dioxo-1,4,5,6,7,11-hexahydro-3H-2,7-methanopyrido[1,2-a][1,4]diazonine-10-carboxamide and (6R,7S)—N-(2,4-difluorobenzyl)-6,12-dihydroxy-6-methyl-1,11-dioxo-1,4,5,6,7,11-hexahydro-3H-2,7-methanopyrido[1,2-a][1,4]diazonine-10-carboxamide (14-1, 14-2)
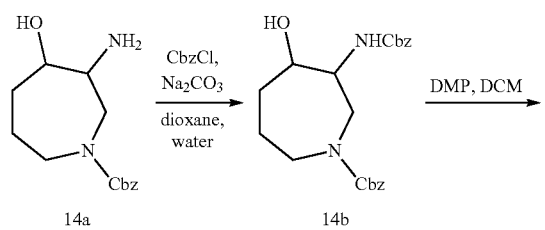
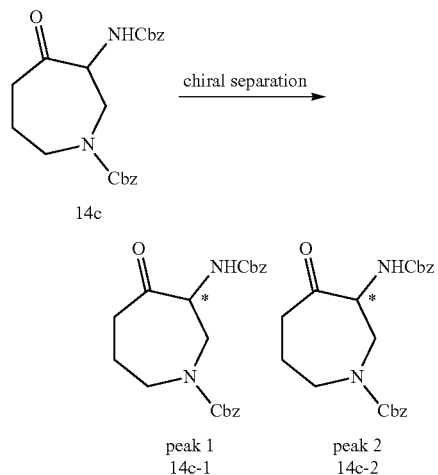
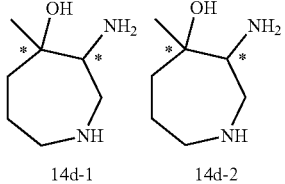
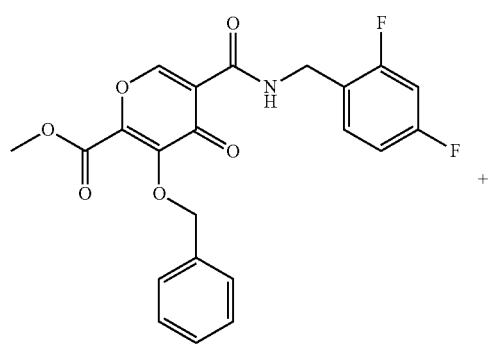
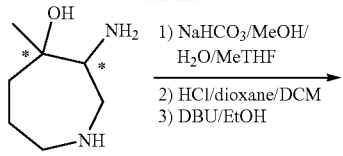
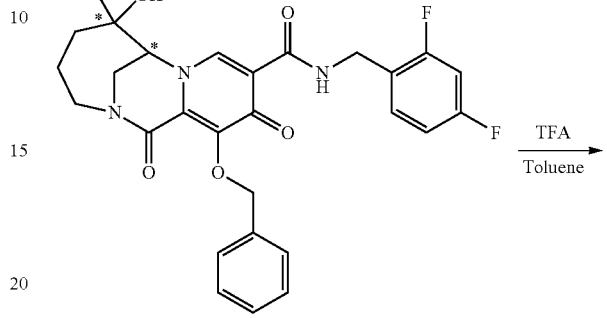
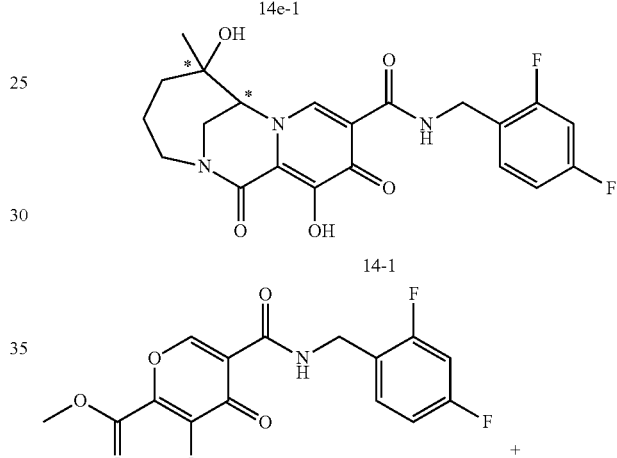
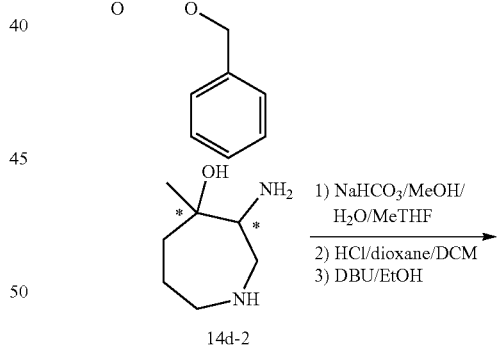
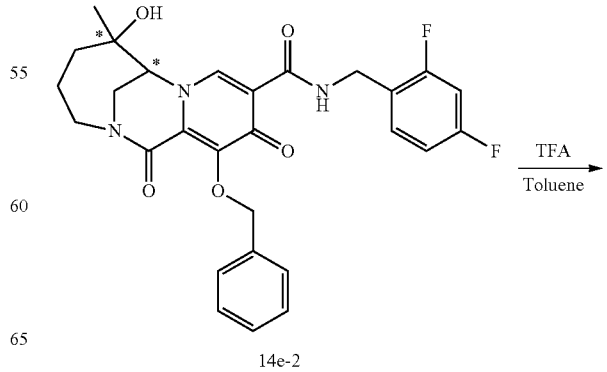

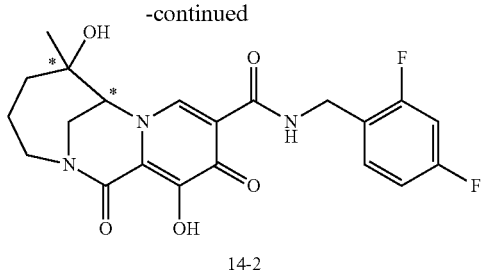

14-2

Synthesis of benzyl 3-(((benzyloxy)carbonyl)amino)-4-hydroxyazepane-1-carboxylate (14b)

To a solution of benzyl 3-amino-4-hydroxyazepane-1-carboxylate (1.1 g, 4.16 mmol) and Na$_2$CO$_3$ (310 mg, 4.99 mmol) in dioxane (7 mL) and water (7 mL) was added Cbz-Cl (0.7 mL, 4.99 mmol) at 0° C. The reaction mixture was warmed to room temperature and stirred for 3 h. Ethyl acetate was added. The organic layer was separated, washed with brine, dried (sodium sulfate), filtered and concentrated under reduced pressure. The residue was purified by silica gel chromatography eluting with hexane/ethyl acetate to give the title compound. MS (m/z) 399.26 [M+H]$^+$.

Synthesis of benzyl (S), and (R)-3-(((benzyloxy)carbonyl)amino)-4-oxoazepane-1-carboxylate (14c-1 and 14c-2)

To a solution of benzyl 3-(((benzyloxy)carbonyl)amino)-4-hydroxyazepane-1-carboxylate (14b) (760 mg, 1.9 mmol) in 5 mL of DCM was added Dess Martin periodinane (1.2 g, 2.8 mmol). The reaction mixture was stirred for 30 minutes at room temperature. DCM was added and the organic phase was washed twice with 10% sodium thiosulphate solution, twice with 0.5 M NaOH and with brine. The organic phase was dried and evaporated. The residue was purified by SGC eluting with EtOAc/hexane to afford benzyl 3-(((benzyloxy)carbonyl)amino)-4-hydroxyazepane-1-carboxylate (14c). MS (m/z) 397.53 [M+H]+. Compound 14c was separated into individual enantiomers by preparative SFC chromatography on an IA column using MeOH co-solvent to provide 14c-1 and 14c-2.

Synthesis of benzyl ((3S,4R), and (3R,4S)-4-hydroxy-4-methylazepan-3-yl)carbamate (14d-1, 14d-2)

To a flask was added methyl Grignard (1.02 mL, 3.05 mmol, [3 M in Et$_2$O]) at 0° C. A solution of 14c-1 or 14c-2 (302 mg, 0.76 mmol) in 1 mL TH was added slowly while stirring. The reaction was allowed to warm to room temperature and stirred overnight. The reaction was quenched with NH$_4$Cl and extracted into ethyl acetate, washed with brine, dried with MgSO$_4$, filtered, and solvent was removed under vacuum to afford benzyl ((3S,4R)-4-hydroxy-4-methylazepan-3-yl)carbamate or benzyl ((3R,4S)-4-hydroxy-4-methylazepan-3-yl)carbamate. MS (m/z) 413.50 [M+H]$^+$.

The residue was dissolved in absolute ethanol and was sparged under an argon atmosphere. Palladium hydroxide (101 mg, 20% Pd weight) was added and the mixture was sparged under a hydrogen atmosphere (1 atm, balloon). The mixture was stirred vigorously for a weekend and sparged under an argon atmosphere. It was filtered through a pad of Celite®. The Celite® was washed with absolute ethanol and the filtrate was concentrated in vacuo to afford the title compounds. MS (m/z) 145.16 [M+H]$^+$.

Synthesis of (6S,7R), and (6R,7S)—N-(2,4-difluorobenzyl)-6,12-dihydroxy-6-methyl-1,11-dioxo-1,4,5,6,7,11-hexahydro-3H-2,7-methanopyrido[1,2-a][1,4]diazonine-10-carboxamide (14-1, 14-2)

The title compounds were prepared similarly to compound 12 using compounds 14d-1 and 14d-2. MS (m/z) 434.15 [M+H]$^+$. $^1$H NMR (400 MHz, DMSO-d6) δ 10.80 (s, 1H), 10.46 (t, J=6.0 Hz, 1H), 8.34 (s, 1H), 7.41 (td, J=8.7, 6.6 Hz, 1H), 7.25 (ddd, J=11.7, 9.4, 2.6 Hz, 1H), 7.08 (td, J=8.6, 2.7 Hz, 1H), 4.99 (s, 1H), 4.56 (d, J=5.9 Hz, 2H), 4.30 (s, 1H), 4.15 (dt, J=13.0, 8.8 Hz, 1H), 3.85 (dd, J=15.2, 3.0 Hz, 1H), 3.68 (dd, J=15.2, 1.7 Hz, 1H), 3.10 (dt, J=13.0, 4.8 Hz, 1H), 1.81 (d, J=7.2 Hz, 2H), 1.47 (d, J=15.4 Hz, 1H), 1.35 (s, 3H), 1.23 (dt, J=14.4, 6.5 Hz, 1H).

Example 14: Preparation of (6R,7S)-, and (6S,7R)-6-fluoro-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (15-1, 15-2)

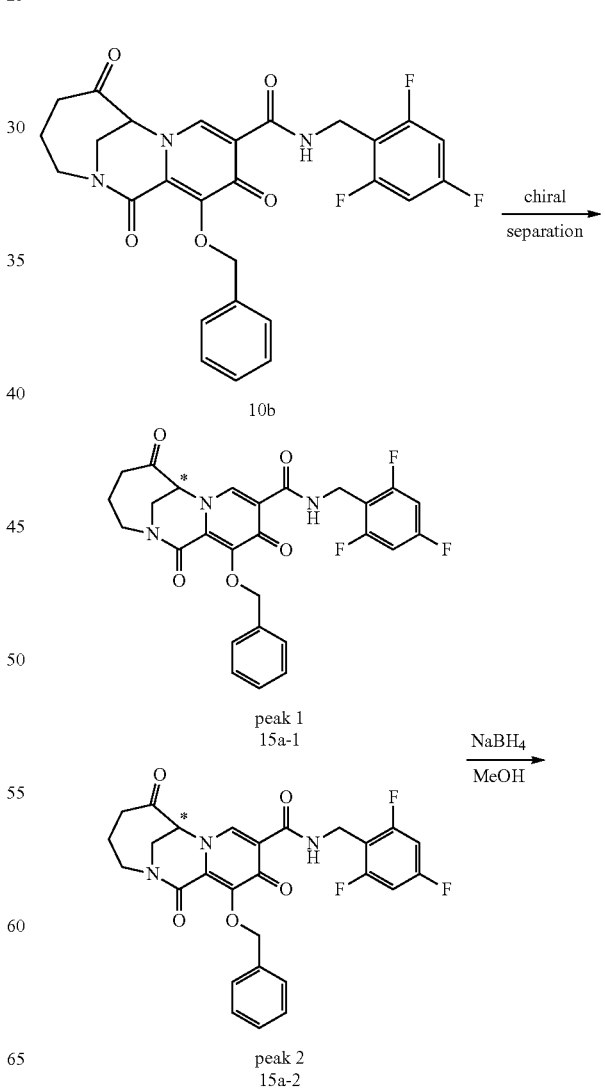

-continued

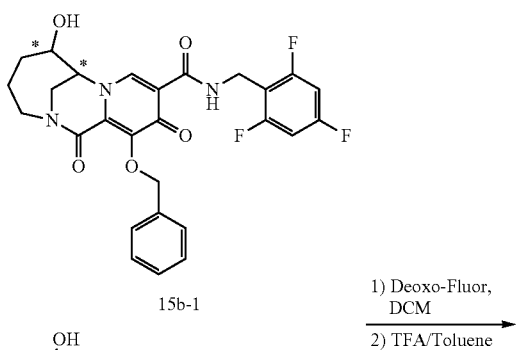

15b-1

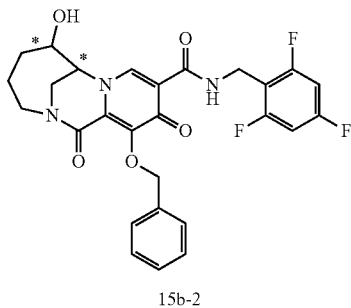

15b-2

1) Deoxo-Fluor, DCM
2) TFA/Toluene

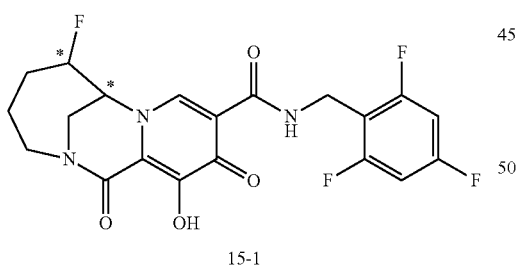

15-1

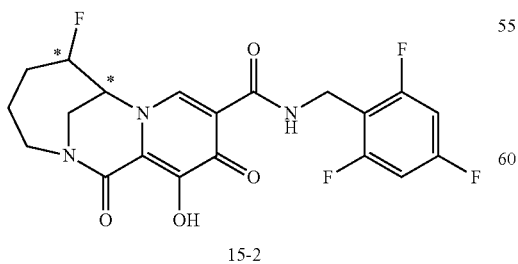

15-2

Synthesis of (7S)-, and (7R)-12-(benzyloxy)-1,6,11-trioxo-N-(2,4,6-trifluorobenzyl)-1,4,5,6,7,11-hexahydro-3H-2,7-methanopyrido[1,2-a][1,4]diazonine-10-carboxamide (15a-1, 15a-2)

12-(Benzyloxy)-1,6,11-trioxo-N-(2,4,6-trifluorobenzyl)-1,4,5,6,7,11-hexahydro-3H-2,7-methanopyrido[1,2-a][1,4]diazonine-10-carboxamide (10b) (350 mg) was separated into its individual enantiomers by preparative SFC chromatography on an IA column using MeOH co-solvent to provide 15a-1 and 15a-2. MS (m/z) 526.00 [M+H]+.

Synthesis of (6S,7S)-, and (6R,7R)-12-(benzyloxy)-6-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (15b-1, 15b-2)

To a solution of 15a-1 or 15a-2 (150 mg, 0.285 mmol) in 7 mL of methanol was added NaBH$_4$ (21.6 mg, 0.57 mmol) at 0° C. The reaction was stirred for 30 minutes at room temperature. The reaction was quenched with 1 N HCl and extracted with DCM. The organic phase was dried over MgSO$_4$ and concentrated to dryness to afford the title compounds. MS (m/z) 528.26 [M+H]+.

Synthesis of (6R,7S)-, and (6S,7R)-6-fluoro-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (15-1, 15-2)

The title compounds were prepared similar to compound 13, using compounds 15b-1 and 15b-2. 15-1: MS (m/z) 440.22 [M+H]+. $^1$H NMR (400 MHz, DMSO-d6) δ 10.59 (s, 1H), 10.35 (t, J=5.8 Hz, 1H), 8.58 (s, 1H), 7.28-7.15 (m, 2H), 5.12-4.78 (m, 2H), 4.65-4.50 (m, 2H), 4.18-4.06 (m, 1H), 3.89-3.80 (m, 2H), 3.12 (ddd, J=13.2, 7.2, 2.9 Hz, 1H), 2.19-1.95 (m, 2H), 1.79-1.70 (m, 1H), 1.56-1.21 (m, 1H). 15-2: MS (m/z) 440.20 [M+H]$^+$. $^1$H NMR (400 MHz, DMSO-d6) δ 10.57 (s, 1H), 10.35 (t, J=5.8 Hz, 1H), 8.58 (s, 1H), 7.28-7.15 (m, 2H), 5.12-4.81 (m, 2H), 4.65-4.50 (m, 2H), 4.12 (dt, J=13.3, 8.1 Hz, 1H), 3.89 (d, J=15.0 Hz, 1H), 3.86-3.77 (m, 1H), 3.12 (ddd, J=13.1, 7.0, 2.9 Hz, 1H), 2.22-1.95 (m, 2H), 1.79-1.70 (m, 1H), 1.50-1.28 (m, 1H).

Example 15: Preparation of (7S)-, and (7R)—N-(2,4-difluorobenzyl)-6,6-difluoro-12-hydroxy-1,11-dioxo-1,4,5,6,7,11-hexahydro-3H-2,7-methanopyrido[1,2-a][1,4]diazonine-10-carboxamide (16-1, 16-2)

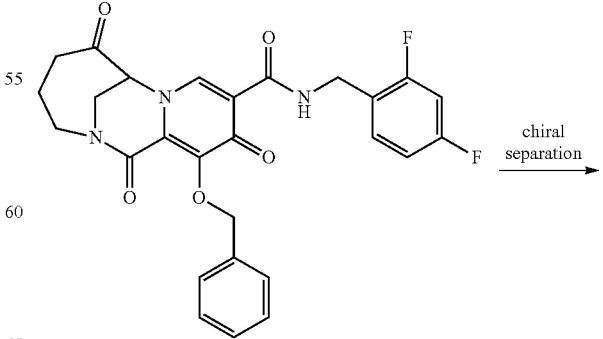

16a chiral separation

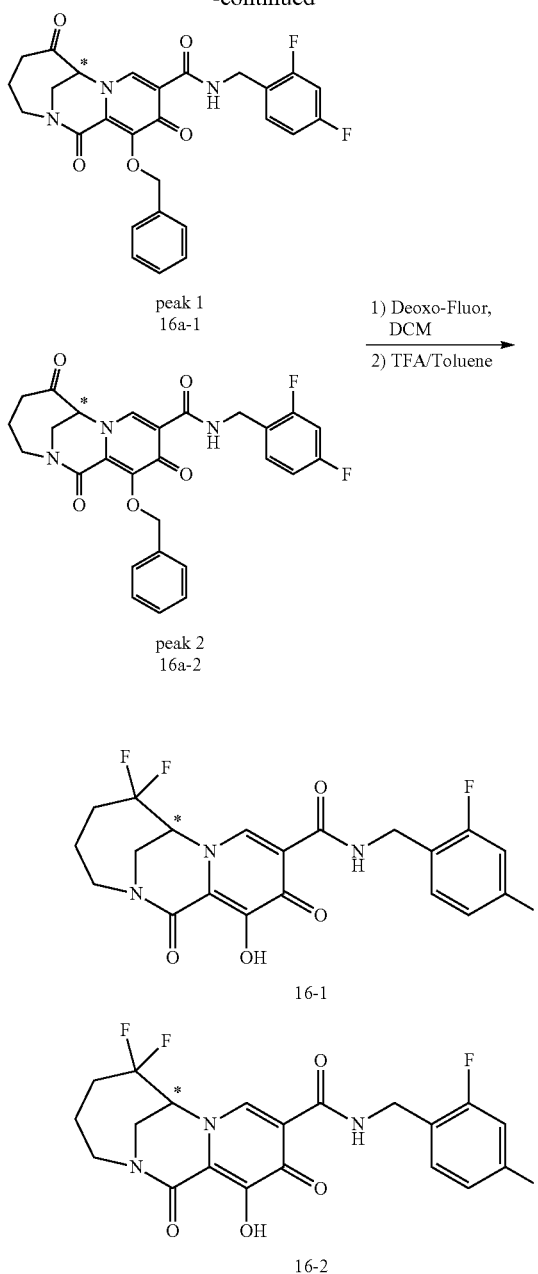

Synthesis of (7S)-, and (7R)-12-(benzyloxy)-N-(2,4-difluorobenzyl)-1,6,11-trioxo-1,4,5,6,7,11-hexahydro-3H-2,7-methanopyrido[1,2-a][1,4]diazonine-10-carboxamide (16a-1, 16a-2)

12-(Benzyloxy)-N-(2,4-difluorobenzyl)-1,6,11-trioxo-1,4,5,6,7,11-hexahydro-3H-2,7-methanopyrido[1,2-a][1,4]diazonine-10-carboxamide (16a) was prepared similarly to compound 10b using methyl 3-(benzyloxy)-5-((2,4-difluorobenzyl)carbamoyl)-4-oxo-4H-pyran-2-carboxylate (16a). MS (m/z) 508.15[M+H]+. Compound 16a was separated into its individual enantiomers by preparative SFC chromatography on an OD-H column using IPA-NH3 co-solvent to provide 16a-1 and 16a-2.

Synthesis of (7S)-, and (7R)—N-(2,4-difluorobenzyl)-6,6-difluoro-12-hydroxy-1,11-dioxo-1,4,5,6,7,11-hexahydro-3H-2,7-methanopyrido[1,2-a][1,4]diazonine-10-carboxamide (16-1, 16-2)

The title compounds were prepared similarly to compounds 10-1 and 10-2 using 16a-1 and 16a-2. 16-1: MS (m/z) 440.20 [M+H]+. $^1$H NMR (400 MHz, DMSO-d6) δ 10.64 (s, 1H), 10.24 (t, J=6.0 Hz, 1H), 8.50 (s, 1H), 7.42 (td, J=8.6, 6.6 Hz, 1H), 7.26 (ddd, J=10.5, 9.4, 2.6 Hz, 1H), 7.07 (td, J=8.5, 7.6, 4.2 Hz, 1H), 5.24 (s, 1H), 4.56 (d, J=5.8 Hz, 2H), 4.27-4.15 (m, 1H), 4.04 (d, J=16.5 Hz, 1H), 3.92-3.83 (m, 1H), 3.19 (dd, J=13.2, 6.8 Hz, 1H), 2.22 (s, 1H), 1.96 (d, J=21.8 Hz, 2H), 1.71-1.54 (m, 1H). 16-2: MS (m/z) 440.27 [M+H]+. $^1$H NMR (400 MHz, DMSO-d6) δ 10.64 (s, 1H), 10.24 (t, J=5.9 Hz, 1H), 8.50 (s, 1H), 7.42 (td, J=8.7, 6.6 Hz, 1H), 7.31-7.20 (m, 1H), 7.07 (td, J=8.4, 2.7 Hz, 1H), 5.24 (s, 1H), 4.56 (d, J=5.9 Hz, 2H), 4.21 (q, J=10.2, 9.7 Hz, 1H), 4.04 (d, J=15.8 Hz, 1H), 3.88 (dd, J=15.4, 2.0 Hz, 1H), 3.18 (dd, J=13.1, 6.7 Hz, 1H), 2.22 (s, 1H), 1.97 (d, J=22.4 Hz, 2H), 1.62 (dd, J=35.1, 14.3 Hz, 1H).

Example 16: Preparation of N-(2,4-difluorobenzyl)-6-fluoro-12-hydroxy-6-methyl-1,11-dioxo-1,4,5,6,7,11-hexahydro-3H-2,7-methanopyrido[1,2-a][1,4]diazonine-10-carboxamide (17-1a) and N-(2,4-difluorobenzyl)-12-hydroxy-6-methyl-1,11-dioxo-1,4,5,6,7,11-hexahydro-3H-2,7-methanopyrido[1,2-a][1,4]diazonine-10-carboxamide (17-1b, 17-2b)

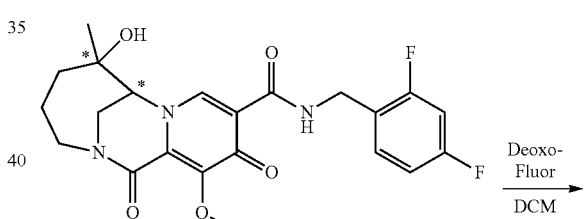

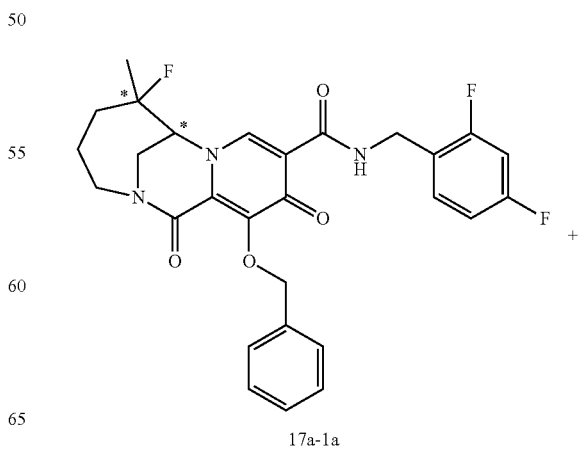

147
-continued

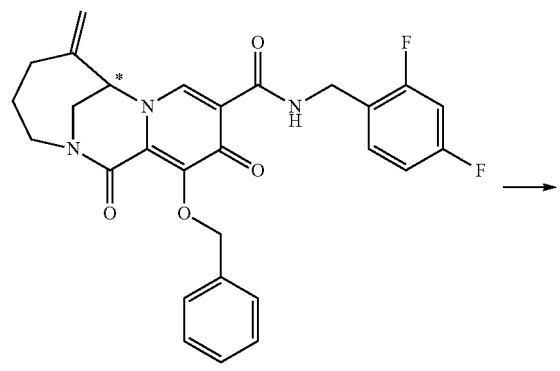

17a-1b

148
-continued

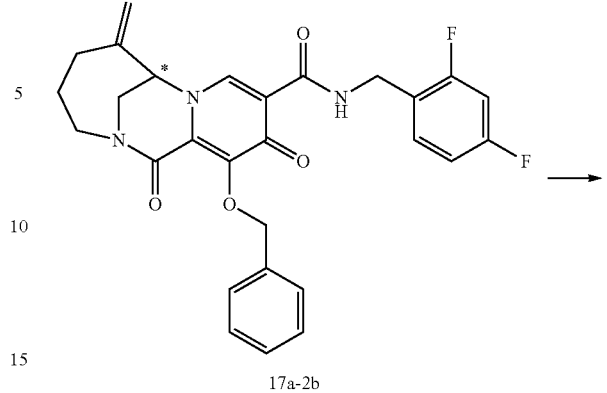

17a-2b

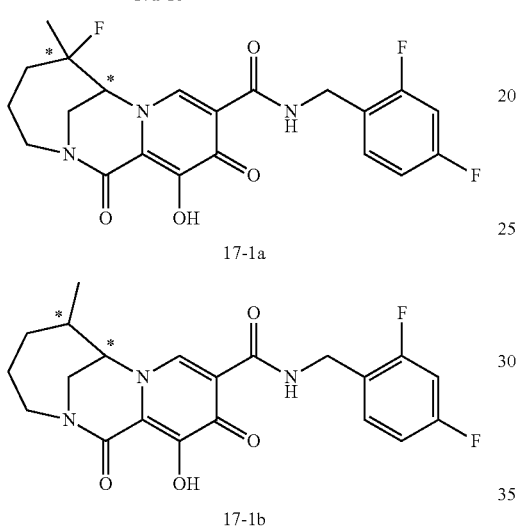

17-1a 17-1b 14e-2

17a-2a

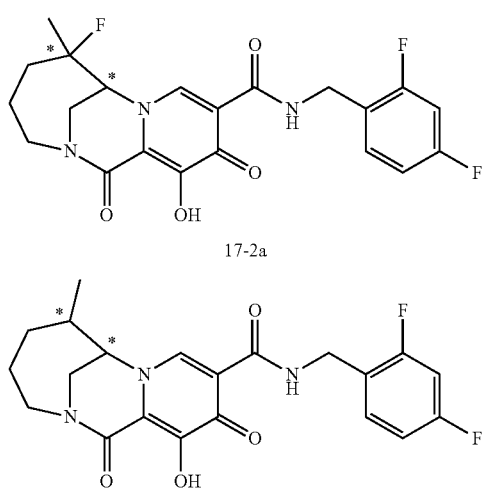

17-2a 17-2b

Synthesis of 12-(benzyloxy)-N-(2,4-difluorobenzyl)-6-fluoro-6-methyl-1,11-dioxo-1,4,5,6,7,11-hexahydro-3H-2,7-methanopyrido[1,2-a][1,4]diazonine-10-carboxamide (17a-1a, 17a-2a) and 12-(benzyloxy)-N-(2,4-difluorobenzyl)-6-methylene-1,11-dioxo-1,4,5,6,7,11-hexahydro-3H-2,7-methanopyrido[1,2-a][1,4]diazonine-10-carboxamide (17a-1b, 17a-2b1)

The title compounds were prepared similarly to compound 13a using compounds 14e-1 and 14e-2. MS (m/z) 526.16 [M+H]+. Side products (17a-b, 17a-2b) were generated. MS (m/z) 506.13[M+H]+.

Synthesis of N-(2,4-difluorobenzyl)-6-fluoro-12-hydroxy-6-methyl-1,11-dioxo-1,4,5,6,7,11-hexahydro-3H-2,7-methanopyrido[1,2-a][1,4]diazonine-10-carboxamide (17-1a) and N-(2,4-difluorobenzyl)-12-hydroxy-6-methyl-1,11-dioxo-1,4,5,6,7,11-hexahydro-3H-2,7-methanopyrido[1,2-a][1,4]diazonine-10-carboxamide (17-1b, 17-2b)

The mixture of products (17a-1a and 17a-1b, 40 mg, –0.07 mmol) or (17a-2a and 17a-2b) from previous steps was dissolved in absolute ethanol (10 mL) and the solution sparged under an argon atmosphere. Palladium hydroxide (20%, 11 mg) was added and the mixture was sparged under a hydrogen atmosphere (1 atm, balloon). The mixture was stirred vigorously for 2 h, sparged under an argon atmosphere, and filtered through a pad of Celite®. The Celite® was washed with absolute ethanol and the filtrate was concentrated in vacuo. The residue was purified by preparatory HPLC (MeCN/water with 0.1% TFA), and lyophilized to afford the title compounds. For 17-1a: MS (m/z) 436.25 [M+H]⁺. ¹H NMR (400 MHz, DMSO-d6) δ 10.82 (s, 1H), 10.33 (t, J=6.0 Hz, 1H), 8.65 (s, 1H), 7.42 (td, J=8.7, 6.6 Hz, 1H), 7.26 (ddd, J=10.6, 9.3, 2.6 Hz, 1H), 7.08 (td, J=8.6, 2.7 Hz, 1H), 4.81 (d, J=11.5 Hz, 1H), 4.63-4.48 (m, 2H), 4.16 (q, J=11.1 Hz, 1H), 3.92 (dd, J=15.0, 2.5 Hz, 1H), 3.80 (d, J=16.1 Hz, 1H), 3.16 (dd, J=13.0, 7.8 Hz, 1H), 2.17-2.06 (m, 1H), 1.92 (dt, J=13.7, 6.4 Hz, 1H), 1.73 (dt, J=19.6, 9.6 Hz, 1H), 1.49-1.16 (m, 4H). For 17-1b: MS (m/z) 418.28 [M+H]+. ¹H NMR (400 MHz, DMSO-d6) δ 10.90 (s, 1H), 10.42 (t, J=5.9 Hz, 1H), 8.63 (d, J=18.6 Hz, 0H), 8.43 (s, 1H), 7.42 (td, J=8.7, 6.6 Hz, 1H), 7.26 (ddd, J=10.6, 9.3, 2.6 Hz, 1H), 7.13-7.03 (m, 1H), 4.69 (s, 1H), 4.63-4.48 (m, 2H), 4.22-4.09 (m, 1H), 3.94 (dd, J=14.6, 2.8 Hz, 1H), 3.71 (dd, J=14.4, 1.7 Hz, 1H), 3.14 (dd, J=12.9, 6.7 Hz, 1H), 2.11-1.99 (m, 1H), 1.91 (t, J=7.8 Hz, 2H), 1.55 (m, 1H), 1.50 (m, 1H), 0.85 (d, J=6.9 Hz, 3H). For 17-2b: MS (m/z) 418.24 [M+H]⁺. ¹H NMR (400 MHz, DMSO-d6) δ 10.90 (s, 1H), 10.42 (t, J=6.0 Hz, 1H), 8.43 (s, 1H), 7.48-7.37 (m, 1H), 7.31-7.21 (m, 1H), 7.08 (t, J=9.7 Hz, 1H), 4.69 (s, 1H), 4.56 (d, J=5.1 Hz, 2H), 4.22-4.11 (m, 1H), 3.98-3.89 (m, 1H), 3.70 (d, J=14.6 Hz, 1H), 3.14 (dd, J=12.9, 6.3 Hz, 1H), 2.01 (m, 1H), 1.92 (m, 2H), 1.55 (m, 1H), 1.50 (m, 1H), 0.85 (d, J=6.9 Hz, 3H).

Example 17: Preparation of 12-hydroxy-7-methyl-1,11-dioxo-N-(2,4,6-trifluorobenzyl)-1,4,5,6,7,11-hexahydro-3H-2,7-methanopyrido[1,2-a][1,4]diazonine-10-carboxamide (18)

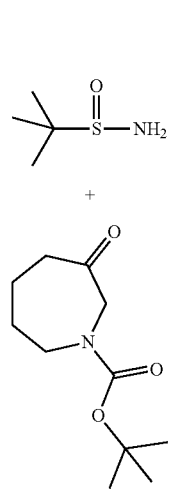

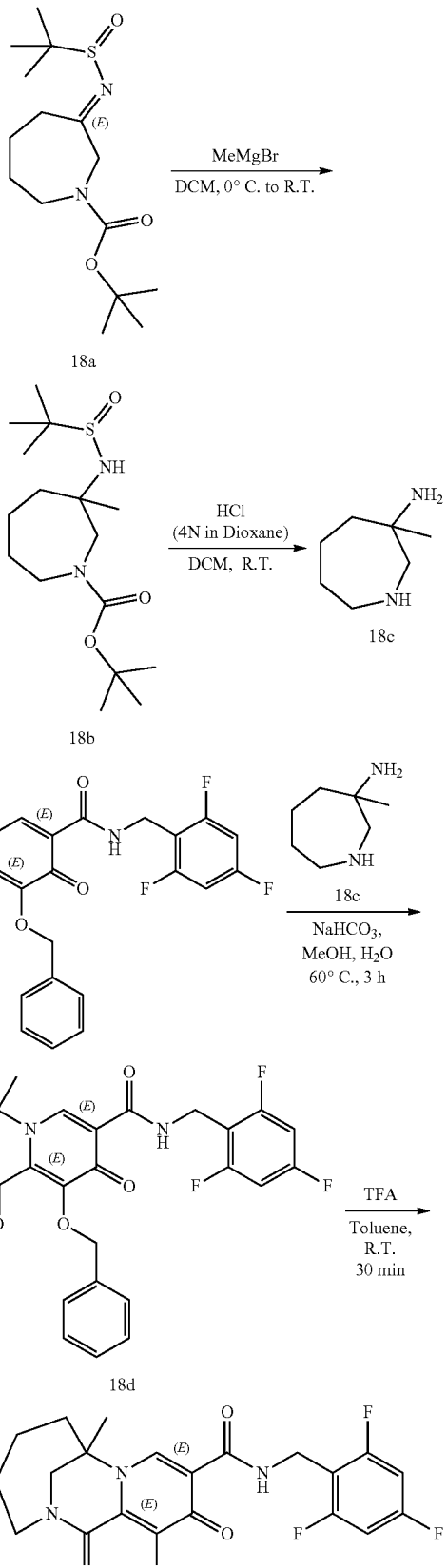

Synthesis of tert-butyl (E)-3-((tert-butylsulfinyl)imino)azepane-1-carboxylate (18a)

To a solution of tert-butyl 3-oxoazepane-1-carboxylate (0.52 g, 2.44 mmol) and 2-methylpropane-2-sulfinamide (0.35 g, 2.93 mmol) in THF (10 mL) was added titanium (IV) ethoxide (1.03 mL, 4.91 mmol) at room temperature. The resulting solution was stirred at room temperature overnight.

The reaction mixture was diluted with ethyl acetate (10 mL), and quenched with aq. NaHCO$_3$ (~5 mL). Celite® was added to the mixture and the solid was filtered off, the filter cake was washed with ethyl acetate (10 mL×2). The combined washes were concentrated in vacuo. The residue was purified by CombiFlash® using EtOAc/Hexanes to afford the title compound. MS (m/z) 317.2 [M+H]$^+$

Synthesis of tert-butyl 3-((tert-butylsulfinyl)amino)-3-methylazepane-1-carboxylate (18b)

At 0° C., to tert-butyl (E)-3-((tert-butylsulfinyl)imino) azepane-1-carboxylate (0.15 g, 0.47 mmol) in DCM was added 3M MeMgBr (0.95 mL) dropwise. The reaction mixture was warmed to room temperature and stirred at room temperature overnight.

The reaction mixture was diluted with ethyl acetate and washed with saturated NH$_4$Cl and brine. The mixture was dried with MgSO$_4$, and the solvent was removed under vacuum. The residue was purified by Silica Gel Column with ethyl acetate/hexane to afford the title compound. MS (m/z) 333.2 [M+H]$^+$

Synthesis of 3-methylazepan-3-amine (18c)

At room temperature, 4M HCl (0.07 mL) in dioxane was added to solution of tert-butyl 3-(tert-butylsulfinylamino)-3-methyl-azepane-1-carboxylate (18b, 0.03 g, 0.1 mmol) in DCM (2 mL). After 2 h, solvent was removed under vacuum, and the unpurified material was used directly in the next step. MS (m/z) 129.2 [M+H]$^+$

Synthesis of 12-(benzyloxy)-7-methyl-1,11-dioxo-N-(2,4,6-trifluorobenzyl)-1,4,5,6,7,11-hexahydro-3H-2,7-methanopyrido[1,2-a][1,4]diazonine-10-carboxamide (18d)

To a mixture of 3-methylazepan-3-amine (18c, 0.013 g, 0.1 mmol) and sodium bicarbonate (45.07 mg, 0.54 mmol) in MeOH (2 mL) and water (2 mL) was added methyl 3-benzyloxy-4-oxo-5-[(2,4,6-trifluorophenyl)methylcarbamoyl]pyran-2-carboxylate (30 mg, 0.07 mmol) at room temperature. The mixture was stirred at 60° C. for 3 h. The reaction mixture was diluted with ethyl acetate and washed with water and brine, and dried with MgSO$_4$. Solvent was removed under vacuum and the residue was purified to afford the title compound. MS (m/z) 526.2 [M+H]$^+$

Synthesis of 12-hydroxy-7-methyl-1,11-dioxo-N-(2,4,6-trifluorobenzyl)-1,4,5,6,7,11-hexahydro-3H-2,7-methanopyrido[1,2-a][1,4]diazonine-10-carboxamide (18)

12-(Benzyloxy)-7-methyl-1,11-dioxo-N-(2,4,6-trifluorobenzyl)-1,4,5,6,7,11-hexahydro-3H-2,7-methanopyrido[1,2-a][1,4]diazonine-10-carboxamide (0.03 g, 0.06 mmol) was dissolved in toluene (2 mL) and TFA (2 mL) was added. The reaction mixture was stirred at room temperature for 1 h. Solvent was removed under vacuum and the residue was purified by HPLC to afford the title compound. MS (m/z) 436.1 [M+H]$^+$. 1H NMR (400 MHz, Chloroform-d) δ 10.46 (s, 1H), 8.57 (s, 1H), 6.74-6.62 (m, 2H), 4.69 (m, 1H), 4.47 (m, 1H), 4.30-4.14 (m, 1H), 3.65-3.77 (m, 3H), 3.40 (m, 1H), 3.09 (m, 1H), 2.15-1.7 (m, 7H)

Example 18: Preparation of (7S)-12-hydroxy-1,11-dioxo-N-(2,4,6-trifluorobenzyl)-1,3,4,6,7,11-hexahydro-2,7-methanopyrido[1,2-d][1,4,7]oxadiazonine-10-carboxamide (19)

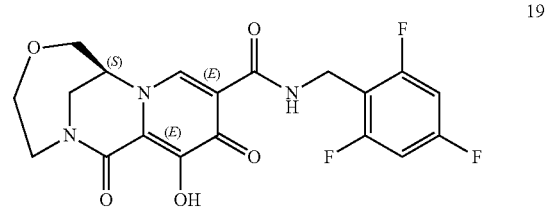

(7S)-12-Hydroxy-1,11-dioxo-N-(2,4,6-trifluorobenzyl)-1,3,4,6,7,11-hexahydro-2,7-methanopyrido[1,2-d][1,4,7] oxadiazonine-10-carboxamide (19) was prepared similarly to 12-hydroxy-7-methyl-1,11-dioxo-N-(2,4,6-trifluorobenzyl)-1,4,5,6,7,11-hexahydro-3H-2,7-methanopyrido[1,2-a][1,4]diazonine-10-carboxamide (18) using (S)-1,4-oxazepan-6-amine to replace 3-methylazepan-3-amine. 1H NMR (400 MHz, DMSO-d6) δ 10.41 (t, J=5.8 Hz, 1H), 8.51 (s, 1H), 7.35-6.97 (m, 2H), 4.71 (s, 1H), 4.57 (d, J=5.7 Hz, 2H), 4.28 (ddd, J=13.1, 9.4, 7.3 Hz, 1H), 4.11 (d, J=13.9 Hz, 1H), 4.07-3.78 (m, 6H). MS (m/z) 514.2 [M+H]$^+$

Example 19: Preparation of (7R)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (20)

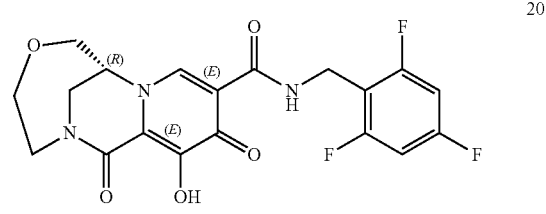

(7R)-12-Hydroxy-1,11-dioxo-N-(2,4,6-trifluorobenzyl)-1,3,4,6,7,11-hexahydro-2,7-methanopyrido[1,2-d][1,4,7] oxadiazonine-10-carboxamide (20) was prepared similarly to 12-hydroxy-7-methyl-1,11-dioxo-N-(2,4,6-trifluorobenzyl)-1,4,5,6,7,11-hexahydro-3H-2,7-methanopyrido[1,2-a][1,4]diazonine-10-carboxamide (18) using (R)-1,4-oxazepan-6-amine to replace 3-methylazepan-3-amine. $^1$H NMR (400 MHz, DMSO-d6) δ 10.41 (s, 1H), 8.51 (s, 1H), 7.22 (dd, J=9.2, 8.0 Hz, 2H), 4.71 (d, J=3.1 Hz, 1H), 4.57 (d, J=5.7 Hz, 2H), 4.27 (ddd, J=12.9, 9.1, 7.1 Hz, 1H), 4.16-3.62 (m, 6H). MS (m/z) 514.2 [M+H]$^+$

Example 20: Preparation of N-(2,4-difluorobenzyl)-11-hydroxy-1,10-dioxo-1,3,4,5,6,10-hexahydro-2,6-ethanopyrido[1,2-a][1,4]diazocine-9-carboxamide (23)

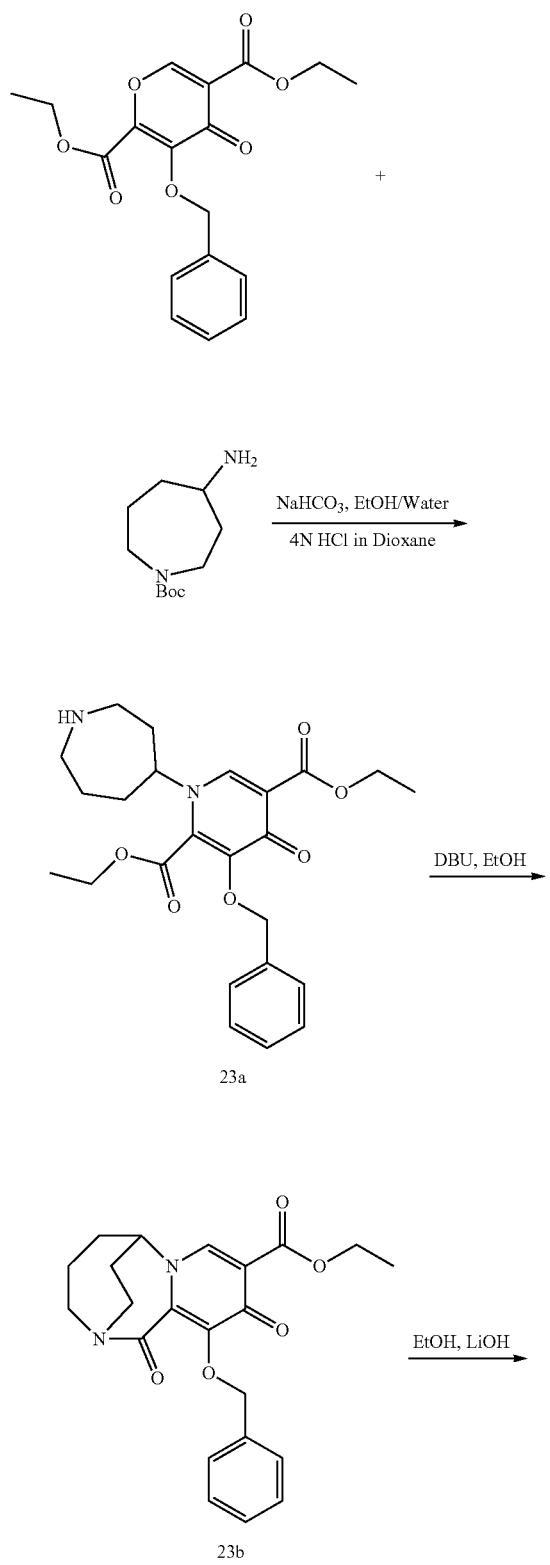

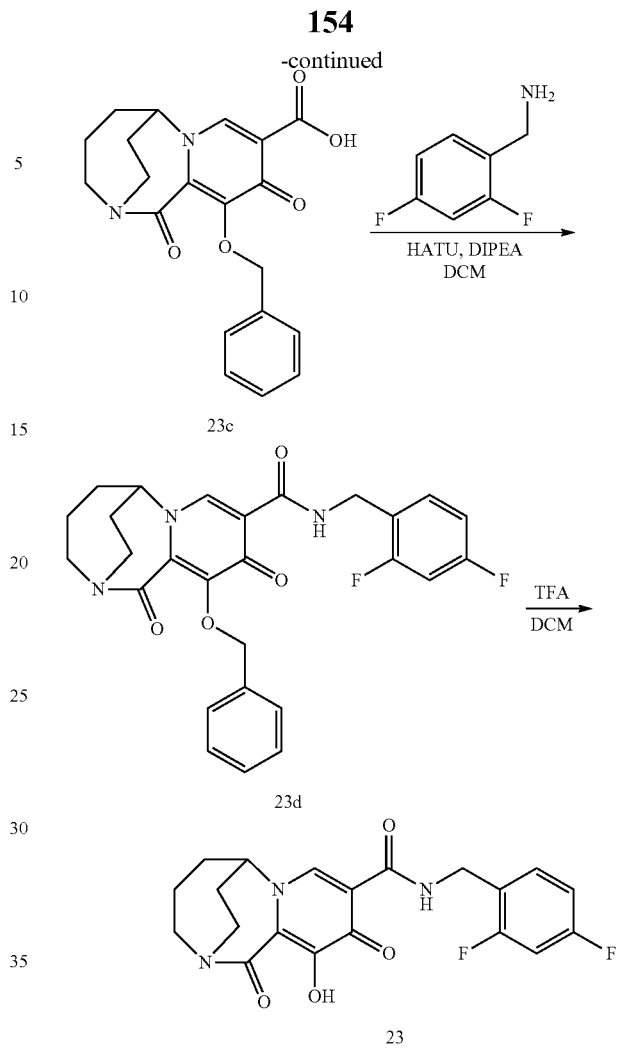

Synthesis of diethyl 1-(azepan-4-yl)-3-(benzyloxy)-4-oxo-1,4-dihydropyridine-2,5-dicarboxylate (23a)

A reactor was charged with tert-butyl 3-aminoazepane-1-carboxylate (588 mg, 3 mmol), NaHCO₃ (576 mg, 7 mmol) in EtOH/Water (9 mL/6 mL) and diethyl 3-(benzyloxy)-4-oxo-4H-pyran-2,5-dicarboxylate (950 mg, 3 mmol) was added. The reaction mixture was heated to 50° C. overnight. The reaction was cooled to room temperature, and extracted with Ethyl Acetate (100 mL). The organic layer was concentrated under vacuum. The residue was used in the next step without purification.

To the above residue in DCM (10 mL) was added 4N HCl in dioxane solution (3 mL). After 2 h at room temperature, remove solvent under vacuum to provide the title compound, which was used in the next step without purification. MS (m/z) 442.945 [M+H]⁺.

Synthesis of ethyl 11-(benzyloxy)-1,10-dioxo-1,3,4,5,6,10-hexahydro-2,6-ethanopyrido[1,2-a][1,4]diazocine-9-carboxylate (23b)

EtOH (20 mL) and DBU (2.2 g, 15 mmol) were added to the above residue. After heating to 110° C. under microwave reactor for 1 h, the reaction mixture was cooled to room temperature and extracted with Ethyl Acetate (100 mL). The organic layer was concentrated under vacuum. The resulting residue was purified by silica gel chromatography to provide the title compound. MS (m/z) 397.113 [M+H]+.

Synthesis of 11-(benzyloxy)-1,10-dioxo-1,3,4,5,6,10-hexahydro-2,6-ethanopyrido[1,2-a][1,4]diazocine-9-carboxylic acid (23c)

To the above residue (114 mg, 0.288 mmol) in MeOH (6 mL) was added 2N LiOH (1 mL) at room temperature. After 2 h, the reaction was diluted with Ethyl Acetate (100 mL) and 1N HCl (20 mL). The organic layer was dried, and concentrated under vacuum. The resulting residue was used in the next step reaction without purification. MS (m/z) 369.131 [M+H]+.

Synthesis of 11-(benzyloxy)-N-(2,4-difluorobenzyl)-1,10-dioxo-1,3,4,5,6,10-hexahydro-2,6-ethanopyrido[1,2-a][1,4]diazocine-9-carboxamide (23d)

To the above residue (57 mg, 0.155 mmol) in DCM (5 mL), was added (2,4-difluorophenyl)methanamine (27.4 mg, 0.17 mmol), DIPEA (60 mg, 0.46 mmol) and HATU (60.2 mg, 0.186 mmol) at room temperature. After 1 h, the reaction was diluted with Ethyl Acetate (100 mL) and washed with brine. The organic layer was dried, and concentrated under vacuum. The resulting residue was used in the next step. MS (m/z) 512.147 [M+H]+.

Synthesis of 11-hydroxy-1,10-dioxo-N-(2,4-difluorobenzyl)-1,3,4,5,6,10-hexahydro-2,6-ethanopyrido[1,2-a][1,4]diazocine-9-carboxamide (23)

To the solution of 11-(benzyloxy)-1,10-dioxo-N-(2,4-difluorobenzyl)-1,3,4,5,6,10-hexahydro-2,6-ethanopyrido[1,2-a][1,4]diazocine-9-carboxamide (163 mg) in DCM (2 mL), was added TFA (1 mL). After 4 h, the solvent was removed. The resulting residue was used purified by RP-HPLC eluting with ACN/water (0.1% TFA) to provide title compound as TFA salt. MS (m/z) 404.154 [M+H]+. $^1$H NMR (400 MHz, DMSO-d6) δ 10.41 (t, J=5.9 Hz, 1H), 8.33 (s, 1H), 7.39 (dd, J=8.6, 6.6 Hz, 2H), 7.22 (ddd, J=10.7, 9.3, 2.6 Hz, 1H), 7.07-7.01 (m, 1H), 4.99 (d, J=11.6 Hz, 1H), 4.59-4.46 (m, 2H), 4.30-4.19 (m, 1H), 3.15-3.07 (m, 1H), 2.42-2.15 (m, 3H), 2.07-1.91 (m, 2H), 1.73 (d, J=46.6 Hz, 3H).

Example 21: Preparation of racemic- and (R)- or (S)-11-hydroxy-1,10-dioxo-N-(2,4,6-trifluorobenzyl)-1,3,4,5,6,10-hexahydro-2,6-ethanopyrido[1,2-a][1,4]diazocine-9-carboxamide (24 and 24-1)

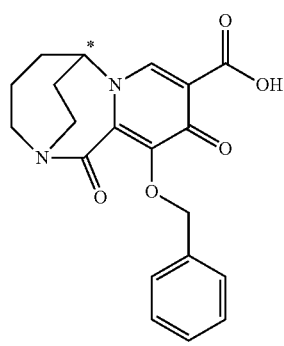

+

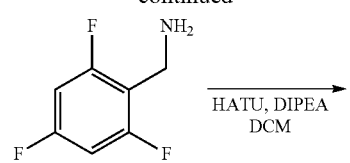

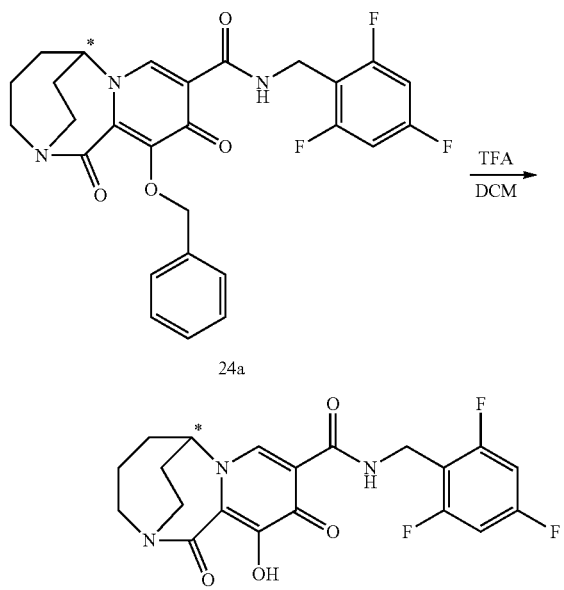

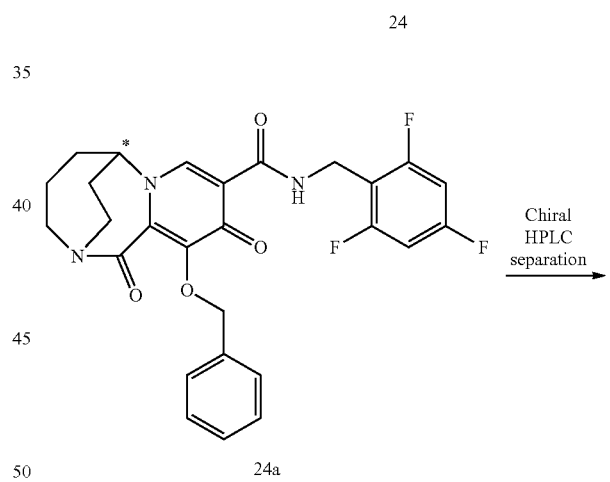

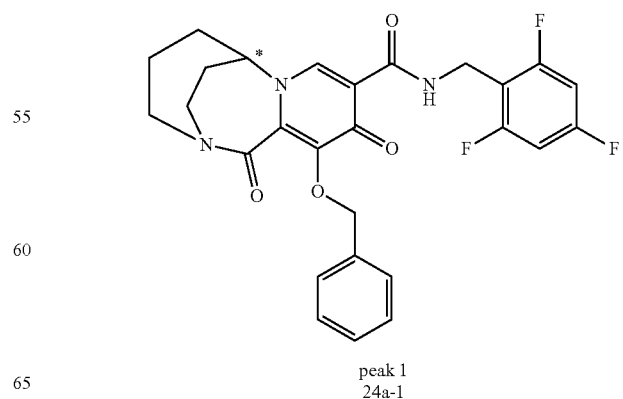

peak 1
24a-1

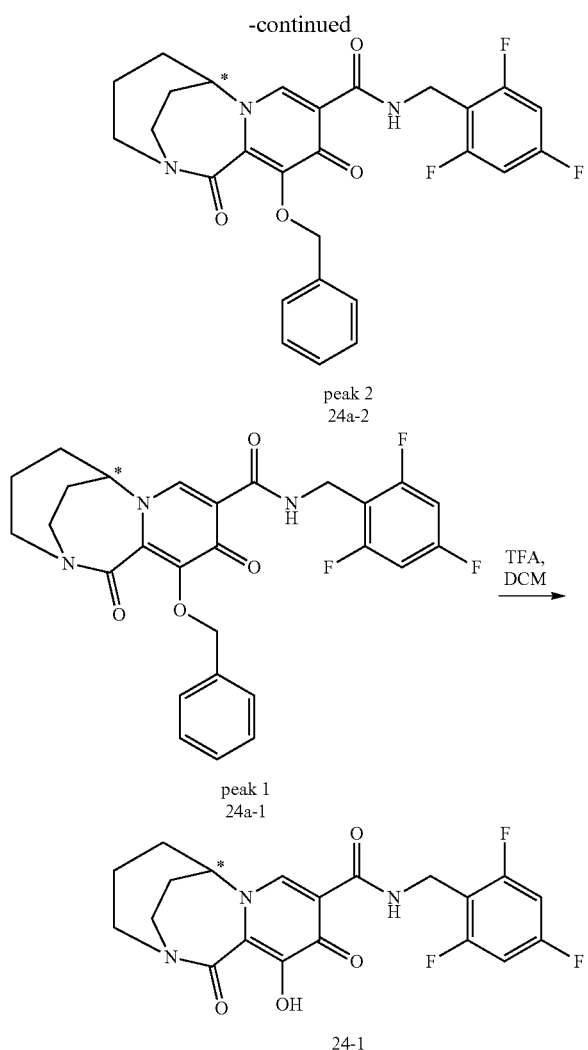

peak 2
24a-2 peak 1
24a-1

24-1

Synthesis of racemic-11-hydroxy-1,10-dioxo-N-(2,4,6-trifluorobenzyl)-1,3,4,5,6,10-hexahydro-2,6-ethanopyrido[1,2-a][1,4]diazocine-9-carboxamide (24)

Racemic 11-hydroxy-1,10-dioxo-N-(2,4,6-trifluorobenzyl)-1,3,4,5,6,10-hexahydro-2,6-ethanopyrido[1,2-a][1,4]diazocine-9-carboxamide (24) was synthesized from 11-(benzyloxy)-1,10-dioxo-1,3,4,5,6,10-hexahydro-2,6-ethanopyrido[1,2-a][1,4]diazocine-9-carboxylic acid and (2,4,6-trifluorophenyl)methanamine similarly to the synthesis of compound 5. MS (m/z) 422.089 [M+H]+. 1H NMR (400 MHz, DMSO-d6) δ 10.41 (t, J=5.9 Hz, 1H), 8.33 (s, 1H), 7.39 (dd, J=8.6, 6.6 Hz, 2H), 7.22 (ddd, J=10.7, 9.3, 2.6 Hz, 1H), 7.07-7.01 (m, 1H), 4.99 (d, J=11.6 Hz, 1H), 4.59-4.46 (m, 2H), 4.30-4.19 (m, 1H), 3.15-3.07 (m, 1H), 2.42-2.15 (m, 2H), 2.07-1.91 (m, 2H), 1.73 (d, J=46.6 Hz, 2H).

Synthesis of (R)- or (S)-11-hydroxy-1,10-dioxo-N-(2,4,6-trifluorobenzyl)-1,3,4,5,6,10-hexahydro-2,6-ethanopyrido[1,2-a][1,4]diazocine-9-carboxamide (24-1)

(R)- or (S)-11-(Benzyloxy)-1,10-dioxo-N-(2,4,6-trifluorobenzyl)-1,3,4,5,6,10-hexahydro-2,6-ethanopyrido[1,2-a][1,4]diazocine-9-carboxamide peak 1 (24a-1) was separated from racemic-11-(benzyloxy)-1,10-dioxo-N-(2,4,6-trifluorobenzyl)-1,3,4,5,6,10-hexahydro-2,6-ethanopyrido[1,2-a][1,4]diazocine-9-carboxamide (24a) by chiral HPLC separation (SFC chromatography on an IB 4.6×100 mm 5mic column using MeOH (20) co-solvent). The separated peak 1 was used to make 11-hydroxy-1,10-dioxo-N-(2,4,6-trifluorobenzyl)-1,3,4,5,6,10-hexahydro-2,6-ethanopyrido[1,2-a][1,4]diazocine-9-carboxamide (24-1). MS (m/z) 422.124 [M+H]+. 1H NMR (400 MHz, DMSO-d6) δ 10.45 (t, J=5.8 Hz, 1H), 8.31 (s, 1H), 7.28-7.10 (m, 2H), 4.97 (d, J=11.3 Hz, 2H), 4.61 (dd, J=14.5, 6.1 Hz, 1H), 4.48 (dd, J=14.6, 5.5 Hz, 1H), 4.24 (d, J=13.0 Hz, 2H), 3.11 (dd, J=13.5, 8.3 Hz, 1H), 2.37-2.21 (m, 2H), 2.00 (d, J=40.1 Hz, 2H), 1.70 (d, J=31.2 Hz, 2H).

Example 22: Preparation of Racemic and (7R)— and (7S)—N-(2,4-difluorobenzyl)-12-hydroxy-1,11-dioxo-1,4,5,6,7,11-hexahydro-3H-2,7-methanopyrido[1,2-a][1,4]diazonine-10-carboxamide (25, 25-1, 25-2)

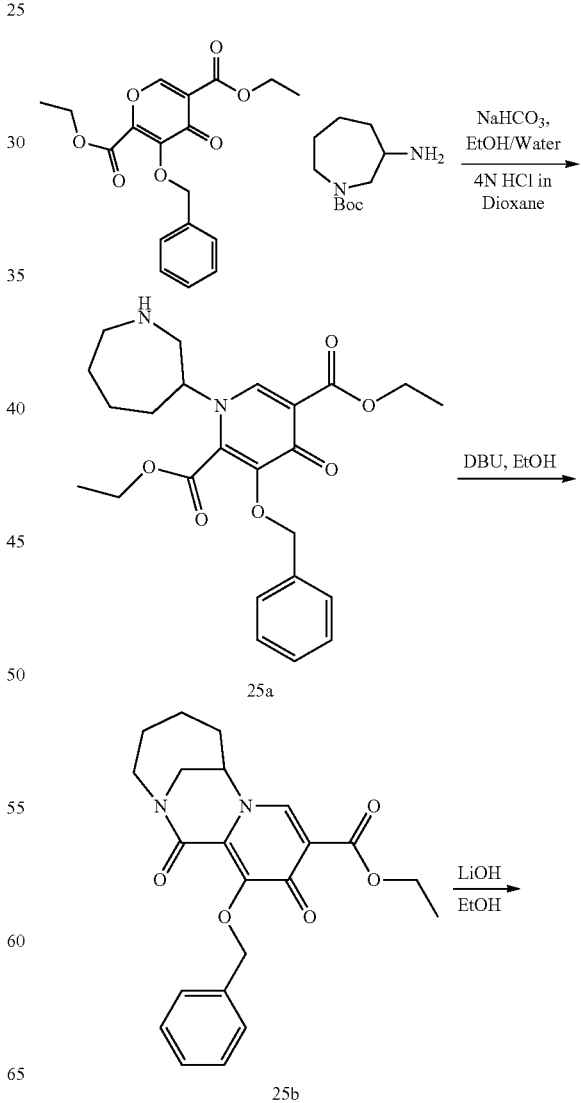

159
-continued
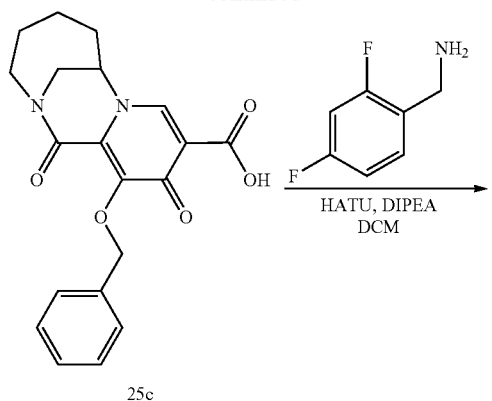
25c
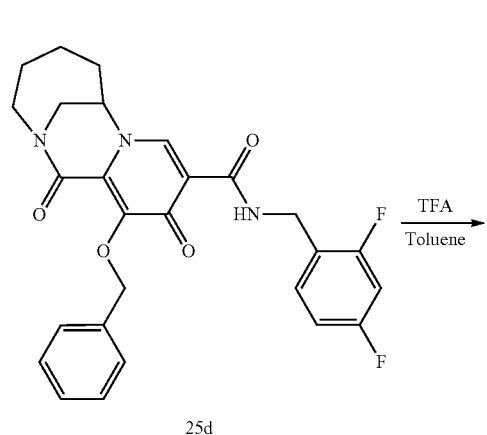
25d
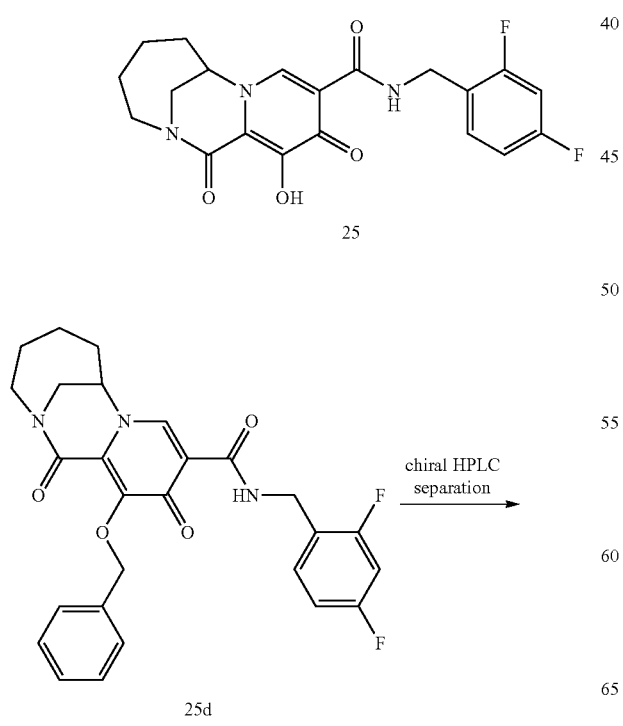
25
25d
160
-continued
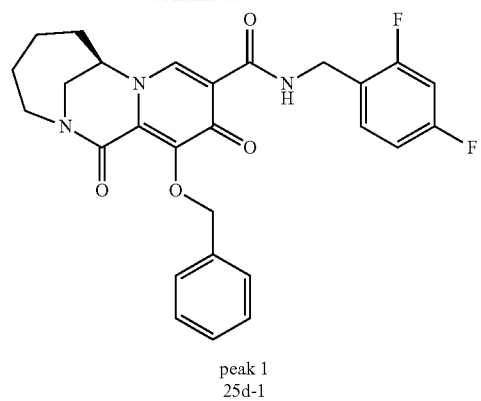
peak 1
25d-1
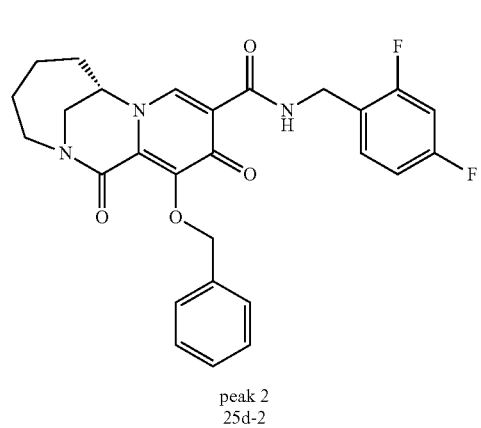
peak 2
25d-2
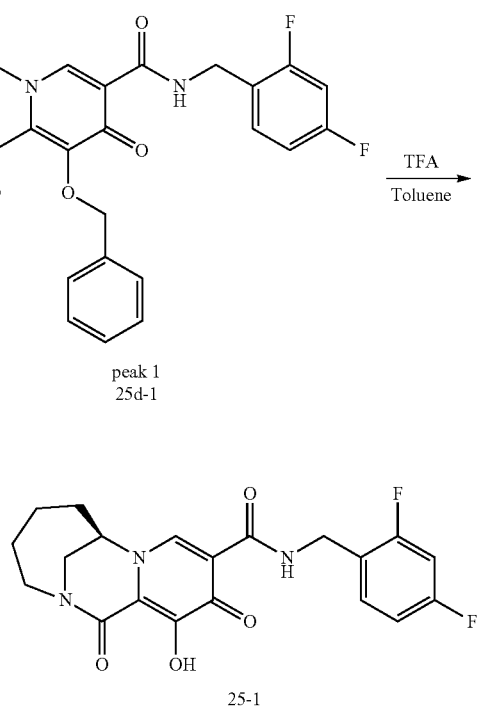
peak 1
25d-1
25-1

-continued

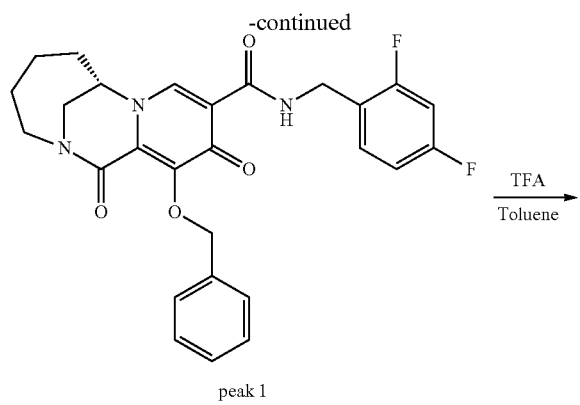

peak 1
25d-1

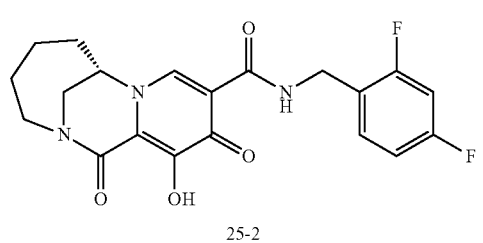

25-2

Synthesis of 12-(benzyloxy)-N-(2,4-difluorobenzyl)-1,11-dioxo-1,4,5,6,7,11-hexahydro-3H-2,7-methanopyrido[1,2-a][1,4]diazonine-10-carboxamide (25d)

12-(Benzyloxy)-N-(2,4-difluorobenzyl)-1,11-dioxo-1,4,5,6,7,11-hexahydro-3H-2,7-methanopyrido[1,2-a][1,4]diazonine-10-carboxamide (25d) was synthesized from diethyl 3-(benzyloxy)-4-oxo-4H-pyran-2,5-dicarboxylate and tert-butyl 3-aminoazepane-1-carboxylate as starting material following a similar procedure as compound 24a. MS (m/z) 494.181 [M+H]$^+$.

Synthesis of racemic N-(2,4-difluorobenzyl)-12-hydroxy-1,11-dioxo-1,4,5,6,7,11-hexahydro-3H-2,7-methanopyrido[1,2-a][1,4]diazonine-10-carboxamide (25)

To a solution of 12-(benzyloxy)-N-(2,4-difluorobenzyl)-1,11-dioxo-1,4,5,6,7,11-hexahydro-3H-2,7-methanopyrido[1,2-a][1,4]diazonine-10-carboxamide (25d) (5.5 mg) in toluene (0.2 mL), was added TFA (0.2 mL) at room temperature. After 4 h, the solvent was removed. The resulting residue was purified by RP-HPLC eluting with ACN/water (0.1% TFA) to provide title compound as TFA salt. MS (m/z) 404.134 [M+H]$^+$. $^1$H NMR (400 MHz, DMSO-d6) δ 10.61 (s, 1H), 10.38 (t, J=6.0 Hz, 1H), 8.47 (s, 1H), 7.38 (td, J=8.7, 6.6 Hz, 1H), 7.22 (ddd, J=10.6, 9.3, 2.6 Hz, 1H), 7.04 (td, J=8.6, 2.6 Hz, 1H), 4.75 (dd, J=5.9, 2.8 Hz, 1H), 4.53 (d, J=5.9 Hz, 2H), 4.12 (d, J=13.3 Hz, 1H), 3.90-3.84 (m, 1H), 3.65 (dd, J=14.7, 1.9 Hz, 1H), 3.07 (td, J=6.6, 3.6 Hz, 1H), 2.02-1.94 (m, 1H), 1.89-1.74 (m, 3H), 1.62 (d, J=7.6 Hz, 1H), 1.12 (d, J=12.1 Hz, 1H).

Synthesis of (7R)-12-(benzyloxy)-N-(2,4-difluorobenzyl)-1,11-dioxo-1,4,5,6,7,11-hexahydro-3H-2,7-methanopyrido[1,2-a][1,4]diazonine-10-carboxamide and (7S)-12-(benzyloxy)-N-(2,4-difluorobenzyl)-1,11-dioxo-1,4,5,6,7,11-hexahydro-3H-2,7-methanopyrido[1,2-a][1,4]diazonine-10-carboxamide (25d-1, 25d-2)

(7R)-12-(Benzyloxy)-N-(2,4-difluorobenzyl)-1,11-dioxo-1,4,5,6,7,11-hexahydro-3H-2,7-methanopyrido[1,2-a][1,4]diazonine-10-carboxamide (25d-1) as peak 1 and (7S)-12-(benzyloxy)-N-(2,4-difluorobenzyl)-1,11-dioxo-1,4,5,6,7,11-hexahydro-3H-2,7-methanopyrido[1,2-a][1,4]diazonine-10-carboxamide (25d-2) as peak 2 were separated from racemic of 12-(benzyloxy)-N-(2,4-difluorobenzyl)-1,11-dioxo-1,4,5,6,7,11-hexahydro-3H-2,7-methanopyrido[1,2-a][1,4]diazonine-10-carboxamide (25d) by chiral HPLC separation (SFC chromatography on an IB 4.6×100 mm 5mic column using MeOH (20) as co-solvent). The peak 1 structure was confirmed by the synthesis starting from (R)-azepan-3-amine.

Synthesis of (7R)—N-(2,4-difluorobenzyl)-12-hydroxy-1,11-dioxo-1,4,5,6,7,11-hexahydro-3H-2,7-methanopyrido[1,2-a][1,4]diazonine-10-carboxamide (25-1) and (7S)—N-(2,4-difluorobenzyl)-12-hydroxy-1,11-dioxo-1,4,5,6,7,11-hexahydro-3H-2,7-methanopyrido[1,2-a][1,4]diazonine-10-carboxamide (25-2)

(7R)—N-(2,4-Difluorobenzyl)-12-hydroxy-1,11-dioxo-1,4,5,6,7,11-hexahydro-3H-2,7-methanopyrido[1,2-a][1,4]diazonine-10-carboxamide (25-1) and (7S)—N-(2,4-difluorobenzyl)-12-hydroxy-1,11-dioxo-1,4,5,6,7,11-hexahydro-3H-2,7-methanopyrido[1,2-a][1,4]diazonine-10-carboxamide (25-2) were synthesized from peak 1 and peak 2 respectively, following similar reaction conditions as those used to prepare compound 25. Compound 25-1: MS (m/z) 404.186 [M+H]$^+$. $^1$H NMR (400 MHz, DMSO-d6) δ 10.59 (s, 1H), 10.38 (t, J=5.9 Hz, 1H), 8.47 (s, 1H), 7.38 (td, J=8.7, 6.6 Hz, 1H), 7.22 (ddd, J=10.6, 9.3, 2.6 Hz, 1H), 7.04 (tdd, J=8.6, 2.6, 1.1 Hz, 1H), 4.75 (d, J=5.4 Hz, 1H), 4.53 (d, J=5.9 Hz, 2H), 4.17-4.05 (m, 1H), 3.86 (d, J=14.6 Hz, 1H), 3.65 (dd, J=14.7, 1.9 Hz, 1H), 3.06 (ddd, J=13.1, 6.9, 3.6 Hz, 1H), 1.99 (s, 1H), 1.89-1.74 (m, 3H), 1.62 (d, J=8.0 Hz, 1H). Compound 25-2: MS (m/z) 404.165 [M+H]$^+$. $^1$H NMR (400 MHz, DMSO-d6) δ 10.61 (s, 1H), 10.38 (t, J=5.9 Hz, 1H), 8.47 (s, 1H), 7.38 (td, J=8.7, 6.6 Hz, 1H), 7.22 (ddd, J=10.5, 9.3, 2.6 Hz, 1H), 7.09-6.99 (m, 1H), 4.75 (s, 1H), 4.53 (d, J=5.9 Hz, 2H), 4.12 (d, J=13.3 Hz, 1H), 3.86 (d, J=14.6 Hz, 1H), 3.69-3.60 (m, 1H), 3.06 (ddd, J=13.1, 6.8, 3.6 Hz, 1H), 1.99 (s, 1H), 1.83 (d, J=13.3 Hz, 3H), 1.67-1.60 (m, 1H).

Example 23: Preparation of racemic-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (26), (7R)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (26-1) and (7S)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (26-2)
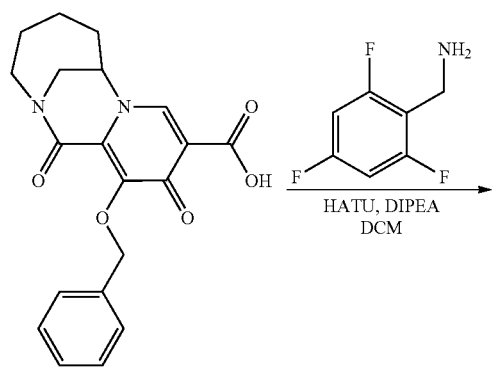
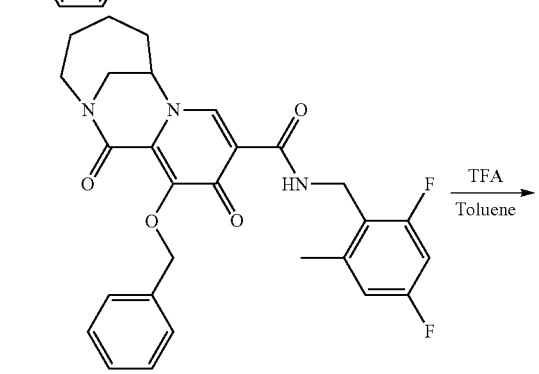
26a
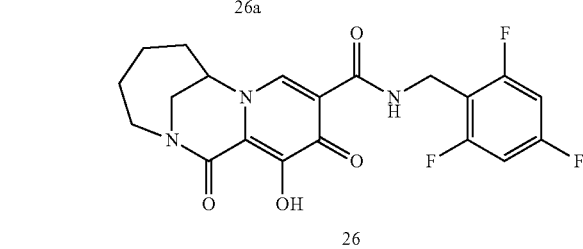
26
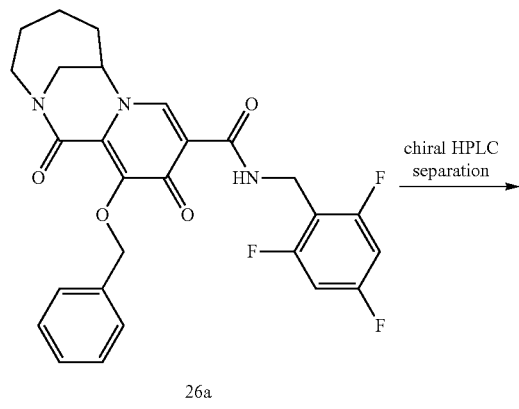
26a
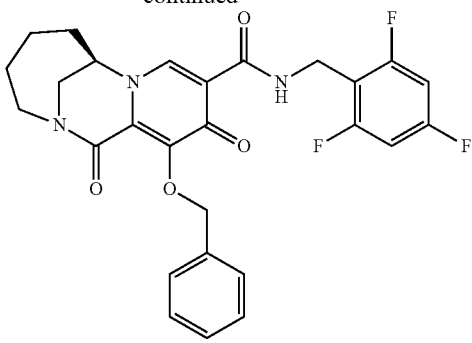
peak 1
26a-1
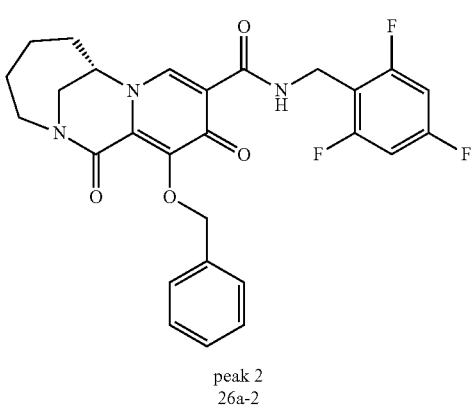
peak 2
26a-2
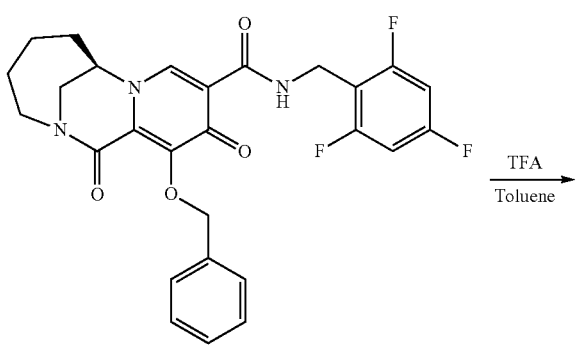
peak 1
26a-1
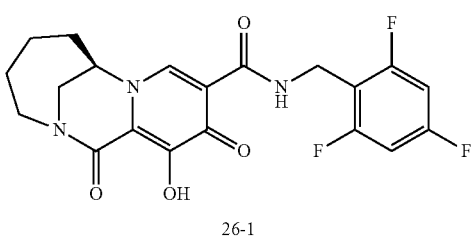
26-1

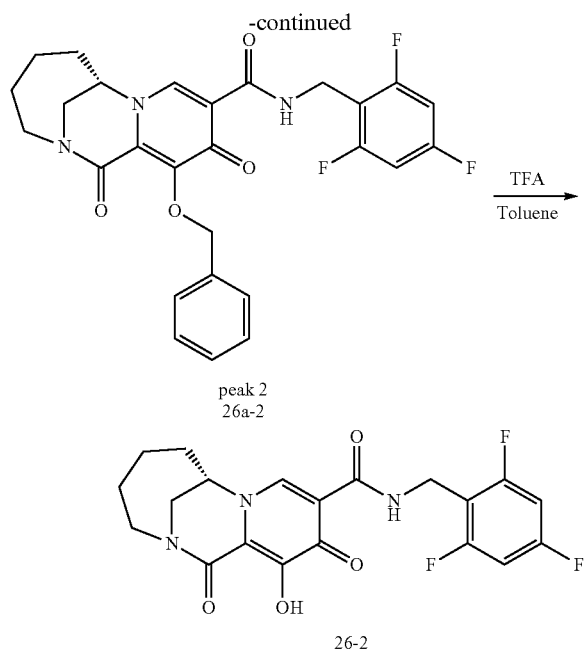

peak 2
26a-2

26-2

Synthesis of 12-Hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (26)

12-(Benzyloxy)-1,11-dioxo-1,4,5,6,7,11-hexahydro-3H-2,7-methanopyrido[1,2-a][1,4]diazonine-10-carboxylic acid (57 mg, 0.155 mmol) was dissolved in DCM (2 mL) with (2,4,6-trifluorophenyl)methanamine (27 mg, 0.17 mmol) and triethylamine (60 mg, 0.464 mmol). HATU (60 mg, 0.186 mmol) was added and the mixture was stirred at room temperature. After overnight reaction, the reaction was concentrated to dryness, purified by silicon gel chromatography to obtain compound 12-(benzyloxy)-1,11-dioxo-N-(2,4,6-trifluorobenzyl)-1,4,5,6,7,11-hexahydro-3H-2,7-methanopyrido[1,2-a][1,4]diazonine-10-carboxamide (26a) MS (m/z) 512.06 [M+H]$^+$.

Compound 12-(benzyloxy)-1,11-dioxo-N-(2,4,6-trifluorobenzyl)-1,4,5,6,7,11-hexahydro-3H-2,7-methanopyrido[1,2-a][1,4]diazonine-10-carboxamide (26a) (7 mg, 0.014 mmol) was dissolved in Tolune (1 mL), then followed by the addition of TFA (1 mL). The resulting mixture was stirred at rt for overnight. The solvent was removed under vacuo an the residue was purified by HPLC to obtain the title compound (26). MS (m/z) 422.091 [M+H]$^+$. $^1$H NMR (400 MHz, DMSO-d6) δ 10.39 (t, J=5.8 Hz, 1H), 8.45 (s, 1H), 7.24-7.11 (m, 2H), 4.72 (dd, J=5.9, 2.9 Hz, 1H), 4.54 (dd, J=6.0, 2.4 Hz, 2H), 4.11 (d, J=13.3 Hz, 1H), 3.88-3.79 (m, 1H), 3.64 (dd, J=14.7, 1.9 Hz, 1H), 3.05 (dq, J=9.5, 3.4 Hz, 1H), 2.06-1.91 (m, 1H), 1.89-1.74 (m, 3H), 1.61 (d, J=7.7 Hz, 1H), 1.11 (d, J=12.7 Hz, 1H).

Synthesis of (7S)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (26-2) and (7R)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (26-1)

Racemic 12-(benzyloxy)-1,11-dioxo-N-(2,4,6-trifluorobenzyl)-1,4,5,6,7,11-hexahydro-3H-2,7-methanopyrido[1,2-a][1,4]diazonine-10-carboxamide (26a) was separated by chiral HPLC separation (SFC chromatography on an IB 4.6×100 mm 5mic column using MeOH (20) as co-solvent) to obtain compounds (7R)-12-(Benzyloxy)-1,11-dioxo-N-(2,4,6-trifluorobenzyl)-1,4,5,6,7,11-hexahydro-3H-2,7-methanopyrido[1,2-a][1,4]diazonine-10-carboxamide (26a-1) and (7S)-12-(benzyloxy)-1,11-dioxo-N-(2,4,6-trifluorobenzyl)-1,4,5,6,7,11-hexahydro-3H-2,7-methanopyrido[1,2-a][1,4]diazonine-10-carboxamide (26a-2)

Compound (7S)-12-(benzyloxy)-1,11-dioxo-N-(2,4,6-trifluorobenzyl)-1,4,5,6,7,11-hexahydro-3H-2,7-methanopyrido[1,2-a][1,4]diazonine-10-carboxamide (26a-2) (20 mg, 0.039 mmol) was dissolved in Tolune (1 mL), then followed by the addition of TFA (1 mL). The resulting mixture was stirred at rt for overnight. The solvent was removed under vacuo an the residue was purified by HPLC to obtain the title compound (26-2). (MS (m/z) 422.123 [M+H]$^+$. $^1$H NMR (400 MHz, DMSO-d6) δ 10.59 (s, 1H), 10.39 (d, J=5.9 Hz, 1H), 8.45 (s, 1H), 7.18 (t, J=8.6 Hz, 2H), 4.72 (s, 1H), 4.59-4.48 (m, 2H), 4.11 (d, J=13.2 Hz, 1H), 3.85 (d, J=14.6 Hz, 1H), 3.69-3.59 (m, 1H), 3.05 (ddd, J=11.3, 6.7, 3.6 Hz, 1H), 1.97 (m, 1H), 1.87-1.71 (m, 3H), 1.67-1.55 (m, 1H), 1.10 (m, 1H).

Compound (7R)-12-(benzyloxy)-1,11-dioxo-N-(2,4,6-trifluorobenzyl)-1,4,5,6,7,11-hexahydro-3H-2,7-methanopyrido[1,2-a][1,4]diazonine-10-carboxamide (26a-1) ((20 mg, 0.039 mmol) was dissolved in Tolune (1 mL), then followed by the addition of TFA (1 mL). The resulting mixture was stirred at rt for overnight. The solvent was removed under vacuo an the residue was purified by HPLC to obtain the title compound (26-1). MS (m/z) 422.116 [M+H]$^+$. $^1$H NMR (400 MHz, DMSO-d6) δ 10.58 (s, 1H), 10.39 (t, J=5.8 Hz, 1H), 8.45 (s, 1H), 7.18 (dd, J=9.2, 8.0 Hz, 2H), 4.73 (s, 1H), 4.58-4.49 (m, 2H), 4.11 (d, J=13.3 Hz, 1H), 3.85 (d, J=14.6 Hz, 1H), 3.65 (d, J=14.2 Hz, 1H), 3.10-3.00 (m, 1H), 1.96 (m, 1H), 1.82 (d, J=12.2 Hz, 3H), 1.61 (d, J=7.4 Hz, 1H), 1.18-1.05 (m, 1H).

Example 24: Preparation of N-(2,4-difluorobenzyl)-7-hydroxy-6,8,15-trioxo-6,8,13,14-tetrahydro-12H-5,12-methanobenzo[e]pyrido[1,2-a][1,4]diazonine-9-carboxamide (27)

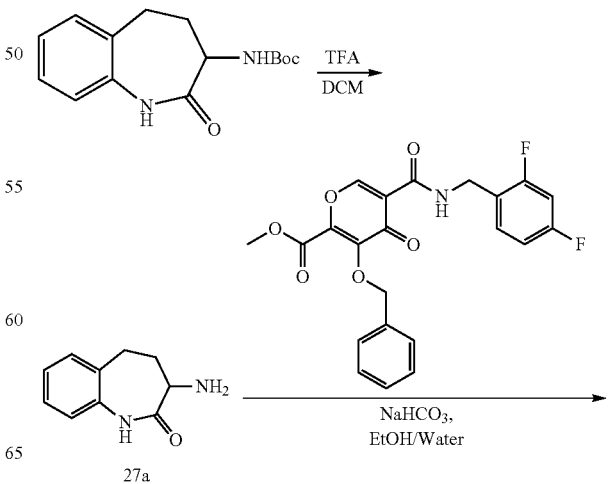

27a

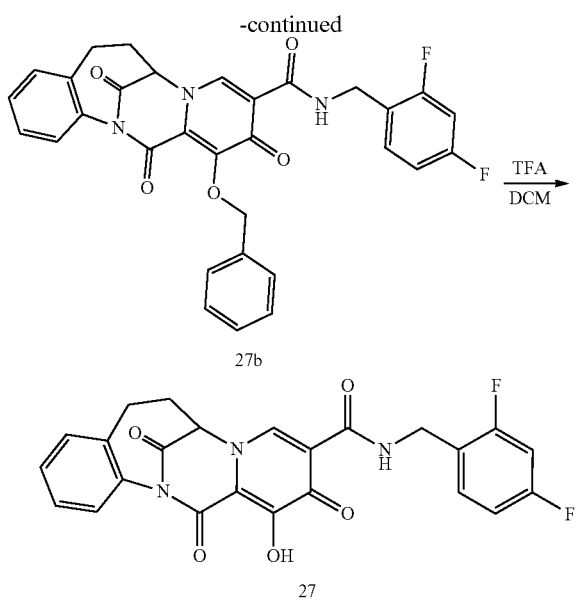

Example 25: Preparation of (7S)—N-(2,4-difluorobenzyl)-12-hydroxy-1,11-dioxo-1,3,4,6,7,11-hexahydro-2,7-methanopyrido[1,2-d][1,4,7]oxadiazonine-10-carboxamide (28)

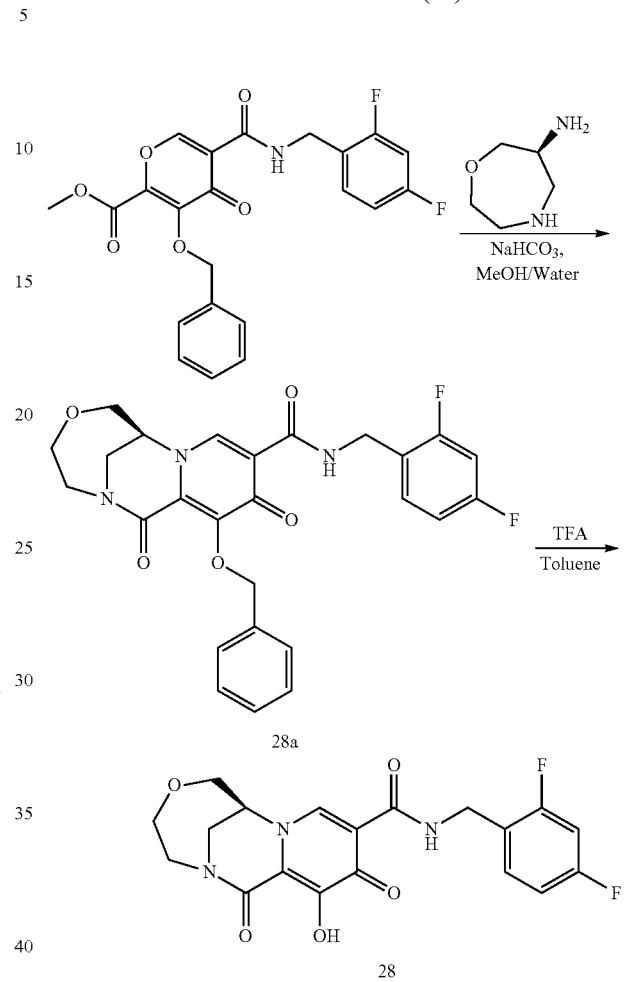

Synthesis of 3-amino-1,3,4,5-tetrahydro-2H-benzo[b]azepin-2-one TFA salt (27a)

To the solution of tert-butyl (2-oxo-2,3,4,5-tetrahydro-1H-benzo[b]azepin-3-yl)carbamate (55 mg, 0.02 mmol) in DCM (3 mL) was added TFA (1 mL) at room temperature. After 4 h, solvent and excess TFA were removed to provide 3-amino-1,3,4,5-tetrahydro-2H-benzo[b]azepin-2-one. MS (m/z) 276.676 [M+H]$^+$.

Synthesis of 7-(benzyloxy)-N-(2,4-difluorobenzyl)-6,8,15-trioxo-6,8,13,14-tetrahydro-12H-5,12-methanobenzo[e]pyrido[1,2-a][1,4]diazonine-9-carboxamide (27b)

7-(Benzyloxy)-N-(2,4-difluorobenzyl)-6,8,15-trioxo-6,8,13,14-tetrahydro-12H-5,12-methanobenzo[e]pyrido[1,2-a][1,4]diazonine-9-carboxamide was prepared from 3-amino-1,3,4,5-tetrahydro-2H-benzo[b]azepin-2-one TFA salt (45 mg, 0.163 mmol) and methyl 3-(benzyloxy)-5-((2,4-difluorobenzyl)carbamoyl)-4-oxo-4H-pyran-2-carboxylate (70 mg, 0.163 mmol) followed the similar procedure as compound 25. MS (m/z) 555.034 [M+H]$^+$.

Synthesis of N-(2,4-difluorobenzyl)-7-hydroxy-6,8,15-trioxo-6,8,13,14-tetrahydro-12H-5,12-methanobenzo[e]pyrido[1,2-a][1,4]diazonine-9-carboxamide (27)

N-(2,4-difluorobenzyl)-7-hydroxy-6,8,15-trioxo-6,8,13,14-tetrahydro-12H-5,12-methanobenzo[e]pyrido[1,2-a][1,4]diazonine-9-carboxamide (27) was prepared followed by same procedure as compound 26, starting from 7-(benzyloxy)-N-(2,4-difluorobenzyl)-6,8,15-trioxo-6,8,13,14-tetrahydro-12H-5,12-methanobenzo[e]pyrido[1,2-a][1,4]diazonine-9-carboxamide (11 mg). MS (m/z) 465.05 [M+H]$^+$. $^1$H NMR (400 MHz, DMSO-d6) δ 10.25 (t, J=5.9 Hz, 1H), 8.61 (s, 1H), 7.42 (d, J=7.1 Hz, 1H), 7.29 (ddd, J=12.1, 9.4, 2.8 Hz, 1H), 7.25-7.18 (m, 2H), 7.14-7.01 (m, 3H), 5.74 (s, 2H), 5.45 (s, 1H), 4.54 (d, J=5.8 Hz, 1H), 3.68 (s, 2H), 3.64 (d, J=2.8 Hz, 1H).

Synthesis of (7S)-12-(benzyloxy)-N-(2,4-difluorobenzyl)-1,11-dioxo-1,3,4,6,7,11-hexahydro-2,7-methanopyrido[1,2-d][1,4,7]oxadiazonine-10-carboxamide (28a)

To the solution of 1,4-oxazepan-6-amine (18.9 mg, 0.16 mmol) in MeOH (6 mL) and water (1 mL), was added sodium bicarbonate (109.6 mg, 1.3 mmol) and methyl 3-(benzyloxy)-5-((2,4-difluorobenzyl)carbamoyl)-4-oxo-4H-pyran-2-carboxylate (70 mg, 0.163 mmol). The reaction mixture was heated to 50° C. overnight. The reaction was cooled to room temperature, and extracted with Ethyl Acetate (100 mL). The organic layer was concentrated under vacuum. The residue was used in the next step without purification. MS (m/z) 496.016 [M+H]$^+$.

Synthesis of (7S)—N-(2,4-difluorobenzyl)-12-hydroxy-1,11-dioxo-1,3,4,6,7,11-hexahydro-2,7-methanopyrido[1,2-d][1,4,7]oxadiazonine-10-carboxamide (28)

To the solution of (7S)-12-(benzyloxy)-N-(2,4-difluorobenzyl)-1,11-dioxo-1,3,4,6,7,11-hexahydro-2,7-methanopyrido[1,2-d][1,4,7]oxadiazonine-10-carboxamide (28a) from the above reaction, was added Toluene (1 mL) and TFA (1 mL). After 4 h at room temperature, solvent and excess TFA were removed under vacuum. The residue was dissolved in DMF and subject to prep. HPLC purification to provide the title compound. MS (m/z) 406.83 [M+H]⁺. ¹H NMR (400 MHz, DMSO-d6) δ 10.36 (t, J=5.9 Hz, 1H), 8.50 (s, 1H), 7.39 (td, J=8.7, 6.6 Hz, 1H), 7.27-7.20 (m, 1H), 7.05 (td, J=7.6, 6.7, 4.0 Hz, 1H), 5.73 (s, 2H), 4.54 (d, J=5.9 Hz, 2H), 4.34-4.23 (m, 1H), 4.10 (d, J=14.3 Hz, 2H), 4.00-3.82 (m, 4H).

Example 26: Preparation of (7R)—N-(2,4-difluorobenzyl)-12-hydroxy-1,11-dioxo-1,3,4,6,7,11-hexahydro-2,7-methanopyrido[1,2-d][1,4,7]oxadiazonine-10-carboxamide (29)

Example 27: Preparation of N-(2,4-difluorobenzyl)-12-hydroxy-1,11-dioxo-1,4,5,6,7,11-hexahydro-3H-2,7-methanopyrido[1,2-a][1,4,7]triazonine-10-carboxamide (30)

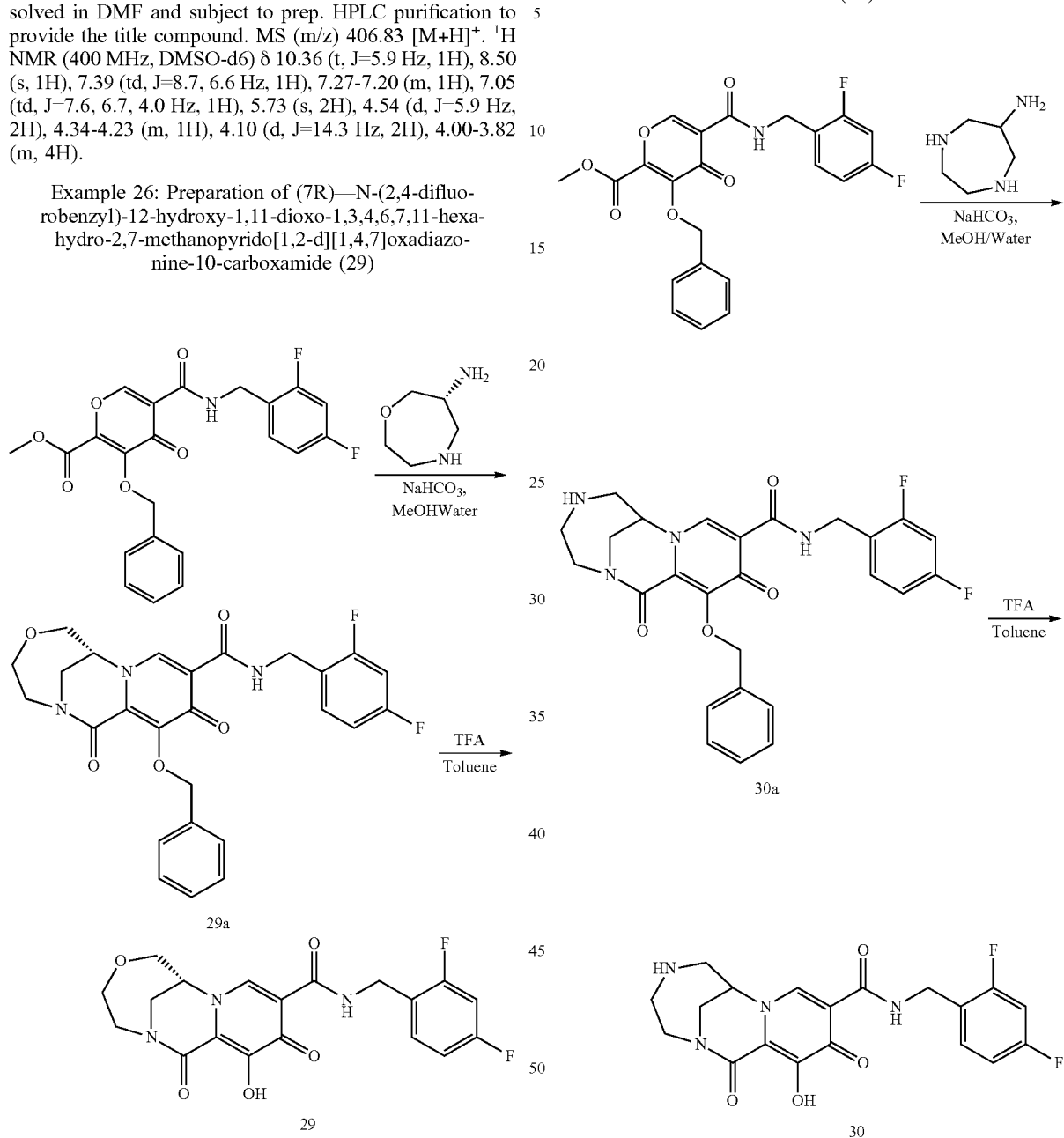

(7R)—N-(2,4-Difluorobenzyl)-12-hydroxy-1,11-dioxo-1,3,4,6,7,11-hexahydro-2,7-methanopyrido[1,2-d][1,4,7]oxadiazonine-10-carboxamide (29) was synthesized from (R)-1,4-oxazepan-6-amine (18.9 mg, 0.163 mmol) and methyl 3-(benzyloxy)-5-((2,4-difluorobenzyl)carbamoyl)-4-oxo-4H-pyran-2-carboxylate (70 mg, 0.163 mmol) followed the similar procedure as compound (28). MS (m/z) 406.136 [M+H]⁺. ¹H NMR (400 MHz, DMSO-d6) δ 10.36 (t, J=5.9 Hz, 1H), 8.51 (s, 1H), 7.42-7.37 (m, 1H), 7.21 (dd, J=9.9, 2.5 Hz, 1H), 7.07-7.02 (m, 1H), 4.70 (s, 1H), 4.54 (d, J=5.9 Hz, 2H), 4.30-4.23 (m, 1H), 4.09 (d, J=5.8 Hz, 1H), 4.00 (d, J=12.0 Hz, 1H), 3.89 (t, J=8.9 Hz, 3H), 3.66 (d, J=10.0 Hz, 2H).

N-(2,4-Difluorobenzyl)-12-hydroxy-1,11-dioxo-1,4,5,6,7,11-hexahydro-3H-2,7-methanopyrido[1,2-a][1,4,7]triazonine-10-carboxamide (30) was synthesized from 1,4-diazepan-6-amine (75.1 mg, 0.652 mmol) and methyl 3-(benzyloxy)-5-((2,4-difluorobenzyl)carbamoyl)-4-oxo-4H-pyran-2-carboxylate (140 mg, 0.326 mmol) followed a similar procedure as compound 28. MS (m/z) 405.183 [M+H]⁺. ¹H NMR (400 MHz, DMSO-d6) δ 10.70 (s, 1H), 10.37 (s, 1H), 8.52 (s, 1H), 7.42-7.34 (m, 1H), 7.22 (s, 1H), 7.05 (d, J=2.6 Hz, 1H), 4.72 (s, 1H), 4.54 (d, J=5.7 Hz, 2H), 4.16 (d, J=12.8 Hz, 2H), 3.92 (d, J=14.8 Hz, 2H), 3.72 (d, J=15.0 Hz, 2H), 3.15 (s, 2H).

Example 28: Preparation of 5-acetyl-N-(2,4-difluorobenzyl)-12-hydroxy-1,11-dioxo-1,4,5,6,7,11-hexahydro-3H-2,7-methanopyrido[1,2-a][1,4,7]triazonine-10-carboxamide (31)

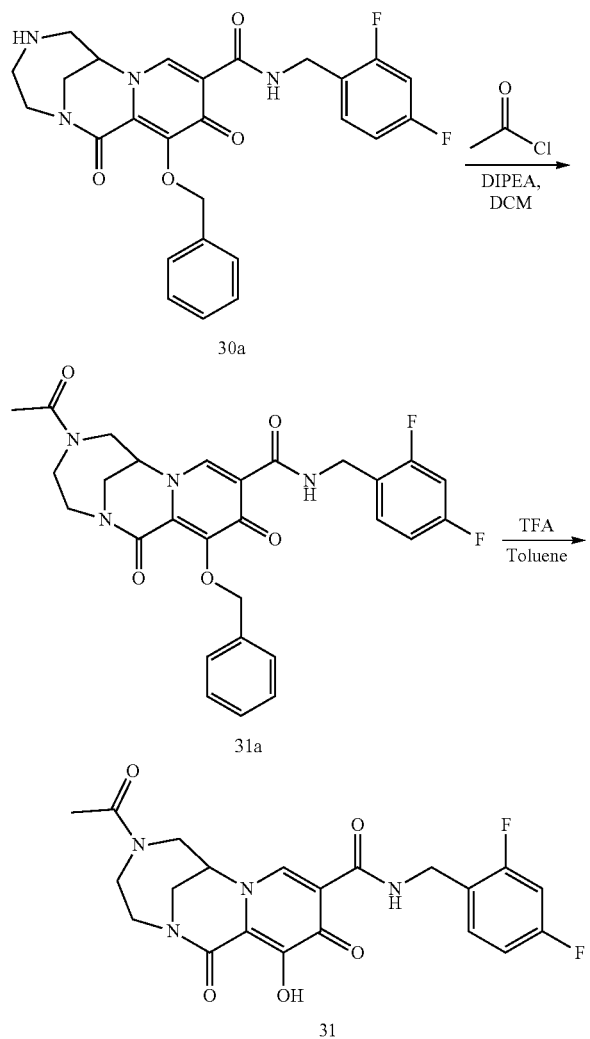

Synthesis of 5-acetyl-12-(benzyloxy)-N-(2,4-difluorobenzyl)-1,11-dioxo-1,4,5,6,7,11-hexahydro-3H-2,7-methanopyrido[1,2-a][1,4,7]triazonine-10-carboxamide (31)

To the solution of 12-(benzyloxy)-N-(2,4-difluorobenzyl)-1,11-dioxo-1,4,5,6,7,11-hexahydro-3H-2,7-methanopyrido[1,2-a][1,4,7]triazonine-10-carboxamide (30a, 26 mg, 0.053 mmol) in DCM (5 mL) was added DIPEA (27.2 mg, 0.21 mmol) and Acetyl chloride (6.2 mg, 0.079 mmol) under ice-water bath cooling. After stirring for 4 h, the reaction was extracted with Ethyl Acetate (100 mL). The organic layer was concentrated under vacuum. The residue was used in the next step without purification. MS (m/z) 537.013 [M+H]$^+$.

5-Acetyl-N-(2,4-difluorobenzyl)-12-hydroxy-1,11-dioxo-1,4,5,6,7,11-hexahydro-3H-2,7-methanopyrido[1,2-a][1,4,7]triazonine-10-carboxamide (31) was synthesized from 5-acetyl-12-(benzyloxy)-N-(2,4-difluorobenzyl)-1,11-dioxo-1,4,5,6,7,11-hexahydro-3H-2,7-methanopyrido[1,2-a][1,4,7]triazonine-10-carboxamide (31a) following similar debenzylation conditions as those used to prepare compound 30. MS (m/z) 447.159 [M+H]$^+$. $^1$H NMR (400 MHz, DMSO-d6) δ 10.36 (t, J=5.9 Hz, 1H), 8.59 (d, J=19.5 Hz, 1H), 7.39 (td, J=8.7, 6.6 Hz, 1H), 7.22 (ddd, J=10.6, 9.4, 2.7 Hz, 1H), 7.05 (ddt, J=10.0, 7.4, 1.3 Hz, 1H), 5.73 (s, 2H), 4.54 (d, J=6.0 Hz, 2H), 4.42-4.32 (m, 1H), 3.97-3.88 (m, 2H), 3.78 (d, J=15.1 Hz, 2H), 3.20-3.15 (m, 1H), 1.86 (s, 3H).

Example 29: Preparation of N-(2,4-difluorobenzyl)-12-hydroxy-5-(methylsulfonyl)-1,11-dioxo-1,4,5,6,7,11-hexahydro-3H-2,7-methanopyrido[1,2-a][1,4,7]triazonine-10-carboxamide (32)

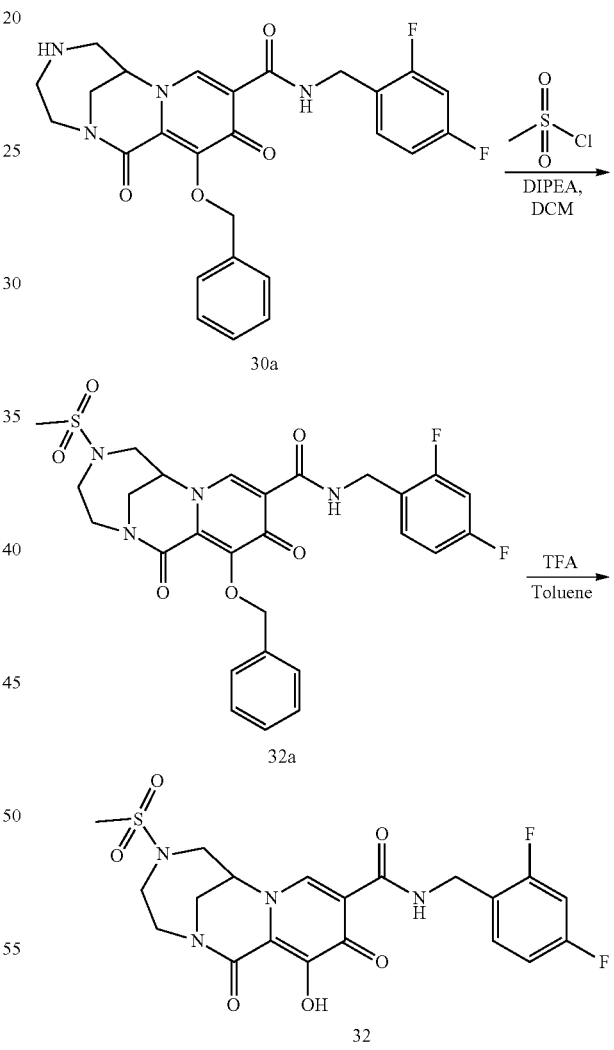

N-(2,4-Difluorobenzyl)-12-hydroxy-5-(methylsulfonyl)-1,11-dioxo-1,4,5,6,7,11-hexahydro-3H-2,7-methanopyrido[1,2-a][1,4,7]triazonine-10-carboxamide (32) was synthesized from 12-(benzyloxy)-N-(2,4-difluorobenzyl)-1,11-dioxo-1,4,5,6,7,11-hexahydro-3H-2,7-methanopyrido[1,2-a][1,4,7]triazonine-10-carboxamide (26 mg, 0.053 mmol) following the same procedure as used to prepare compound 31, and using methanesulfonyl chloride (9 mg, 0.079 mmol). MS (m/z) 483.083 [M+H]⁺. ¹H NMR (400 MHz, DMSO-d6) δ 10.36 (t, J=6.0 Hz, 1H), 8.56 (s, 1H), 7.38 (dd, J=8.7, 6.7 Hz, 1H), 7.22 (ddd, J=10.5, 9.3, 2.6 Hz, 1H), 7.14-6.96 (m, 1H), 4.54 (d, J=5.9 Hz, 2H), 4.21 (dd, J=6.6, 3.3 Hz, 1H), 3.98 (s, 2H), 3.90-3.75 (m, 4H), 3.45 (d, J=15.0 Hz, 1H), 3.29 (d, J=9.2 Hz, 1H), 3.23-3.10 (m, 1H), 2.88 (s, 3H).

Example 30: Preparation of N-(2,4-difluorobenzyl)-12-hydroxy-5-methyl-1,11-dioxo-1,4,5,6,7,11-hexahydro-3H-2,7-methanopyrido[1,2-a][1,4,7]triazonine-10-carboxamide (33)

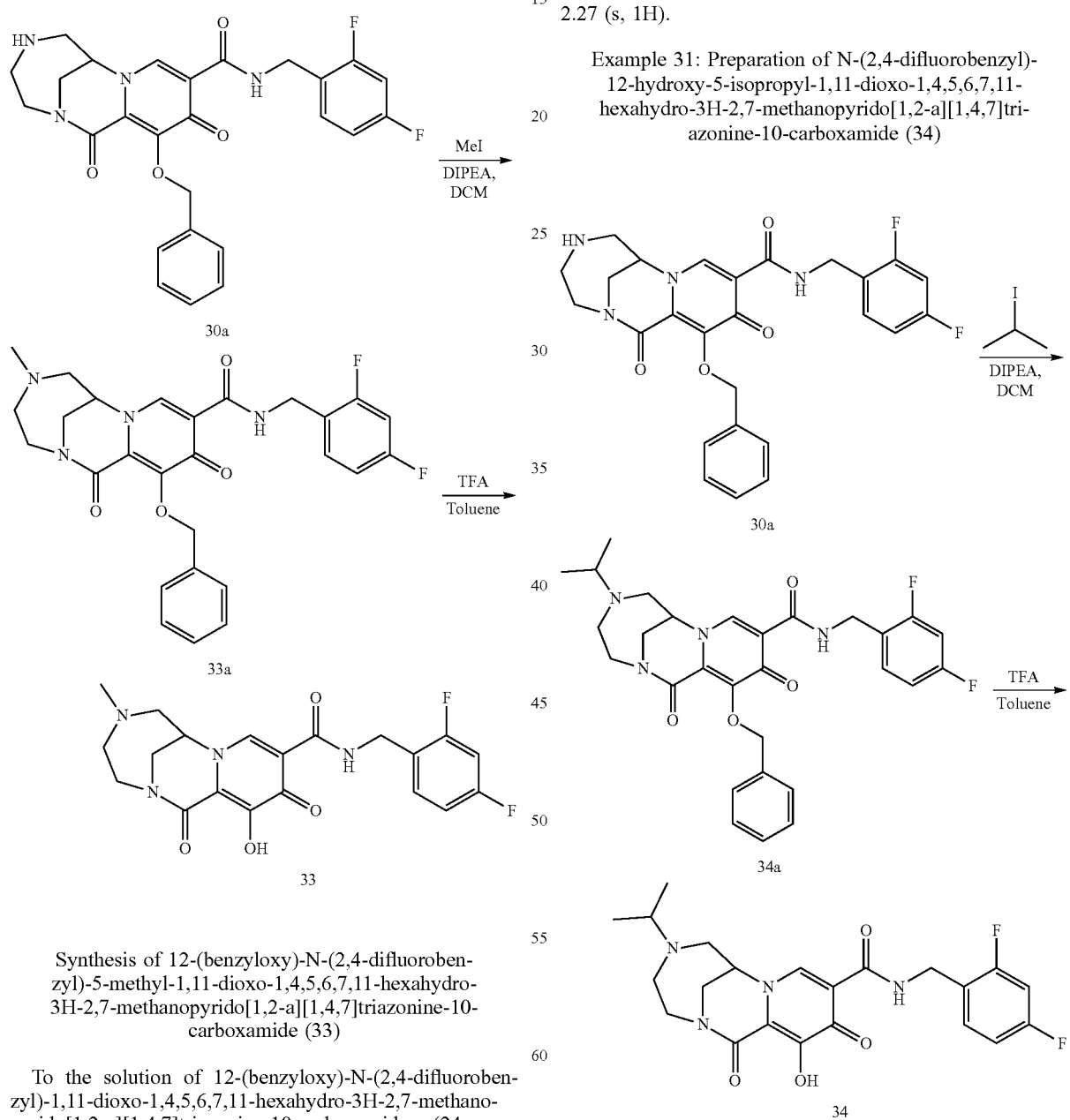

Synthesis of 12-(benzyloxy)-N-(2,4-difluorobenzyl)-5-methyl-1,11-dioxo-1,4,5,6,7,11-hexahydro-3H-2,7-methanopyrido[1,2-a][1,4,7]triazonine-10-carboxamide (33)

To the solution of 12-(benzyloxy)-N-(2,4-difluorobenzyl)-1,11-dioxo-1,4,5,6,7,11-hexahydro-3H-2,7-methanopyrido[1,2-a][1,4,7]triazonine-10-carboxamide (24 mg, 0.049 mmol) in DMF (1.5 mL) was added DIPEA (25.1 mg, 0.194 mmol) and MeI (10.3 mg, 0.073 mmol) at room temperature. After stirring for 4 h, the reaction was extracted with Ethyl Acetate (100 mL). The organic layer was concentrated under vacuum. The residue was used in the next step without purification. MS (m/z) 509.11 [M+H]⁺.

N-(2,4-Difluorobenzyl)-12-hydroxy-5-methyl-1,11-dioxo-1,4,5,6,7,11-hexahydro-3H-2,7-methanopyrido[1,2-a][1,4,7]triazonine-10-carboxamide (33) was synthesized from 12-(benzyloxy)-N-(2,4-difluorobenzyl)-5-methyl-1,11-dioxo-1,4,5,6,7,11-hexahydro-3H-2,7-methanopyrido[1,2-a][1,4,7]triazonine-10-carboxamide (33a) follow the same debenzylation conditions as those used to prepare compound 30. MS (m/z) 419.2 [M+H]⁺. ¹H NMR (400 MHz, DMSO-d6) δ 8.60-8.18 (m, 2H), 7.40 (td, J=8.6, 6.6 Hz, 1H), 7.23 (td, J=9.9, 2.6 Hz, 1H), 7.05 (td, J=8.5, 2.5 Hz, 1H), 4.54 (d, J=5.9 Hz, 2H), 4.17 (dt, J=13.1, 8.1 Hz, 1H), 3.89-3.77 (m, 3H), 3.71-3.60 (m, 1H), 3.28 (d, J=7.3 Hz, 3H), 2.78 (s, 3H), 2.27 (s, 1H).

Example 31: Preparation of N-(2,4-difluorobenzyl)-12-hydroxy-5-isopropyl-1,11-dioxo-1,4,5,6,7,11-hexahydro-3H-2,7-methanopyrido[1,2-a][1,4,7]triazonine-10-carboxamide (34)

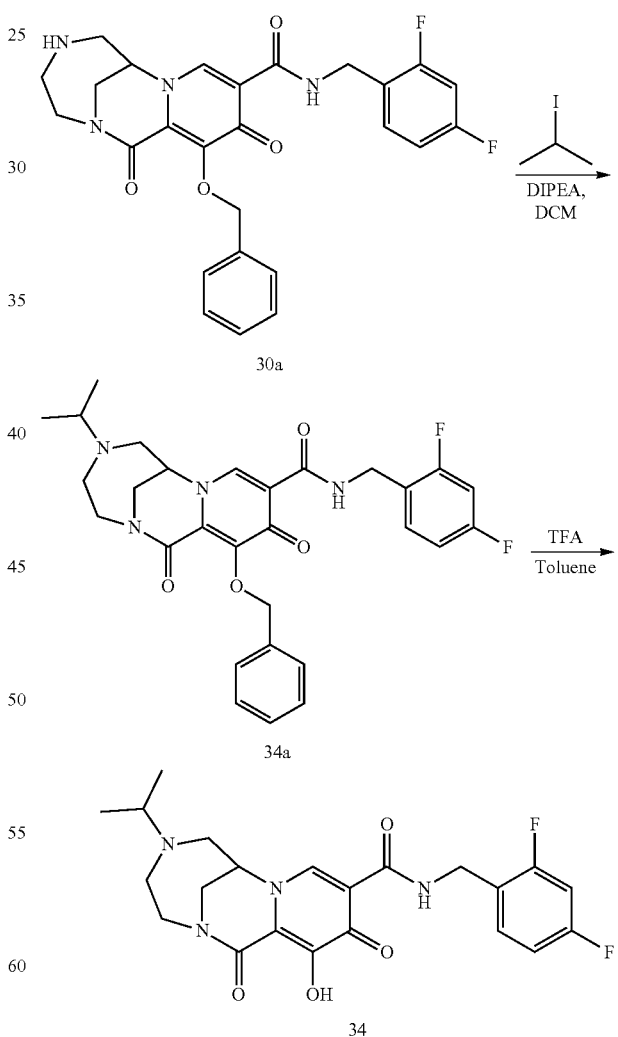

N-(2,4-Difluorobenzyl)-12-hydroxy-5-isopropyl-1,11-dioxo-1,4,5,6,7,11-hexahydro-3H-2,7-methanopyrido[1,2-a][1,4,7]triazonine-10-carboxamide (34) was synthesized from 12-(benzyloxy)-N-(2,4-difluorobenzyl)-1,11-dioxo-1,4,5,6,7,11-hexahydro-3H-2,7-methanopyrido[1,2-a][1,4,7]triazonine-10-carboxamide (24 mg, 0.049 mmol) following a similar procedure as that used to prepare compound 33, using 2-iodopropane (12.38 mg, 0.073 mmol). MS (m/z) 447.2 [M+H]+. $^1$H NMR (400 MHz, DMSO-d6) δ 10.43 (s, 1H), 10.40-10.30 (m, 1H), 8.58 (d, J=17.2 Hz, 1H), 8.50 (s, 1H), 7.81 (d, J=12.3 Hz, 1H), 7.38 (dd, J=9.0, 6.8 Hz, 2H), 7.22 (ddd, J=10.7, 9.3, 2.6 Hz, 2H), 7.05 (td, J=8.5, 2.5 Hz, 2H), 4.53 (d, J=5.7 Hz, 5H), 4.26 (s, 2H), 4.08 (s, 3H), 3.97-3.80 (m, 3H), 3.04 (s, 4H), 2.71 (s, 2H), 0.83 (s, 3H), 0.66 (s, 3H).

Example 32: Preparation of (7R)—N-(3-chloro-2,4-difluorobenzyl)-12-hydroxy-1,11-dioxo-1,4,5,6,7,11-hexahydro-3H-2,7-methanopyrido[1,2-a][1,4]diazonine-10-carboxamide (35)

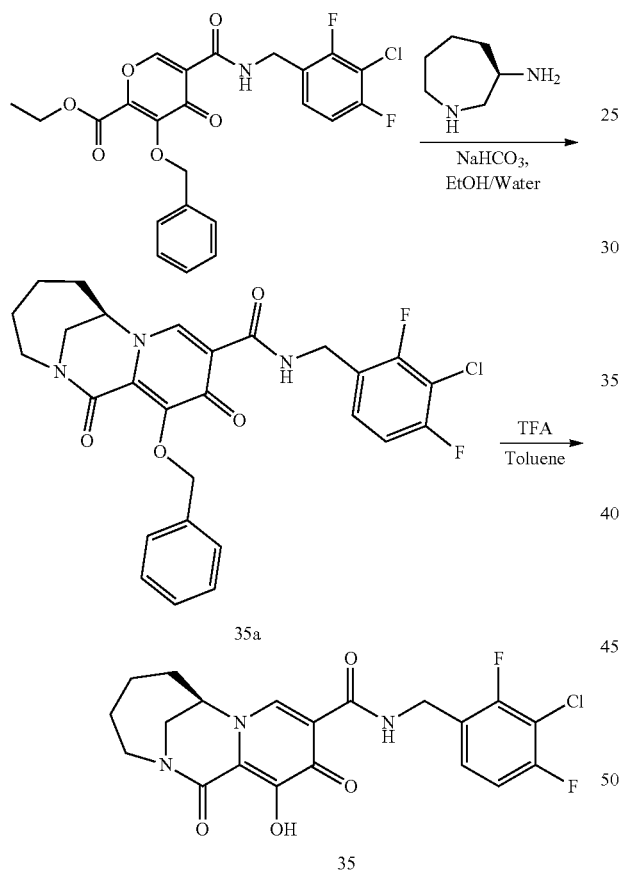

(7R)—N-(3-Chloro-2,4-difluorobenzyl)-12-hydroxy-1,11-dioxo-1,4,5,6,7,11-hexahydro-3H-2,7-methanopyrido[1,2-a][1,4]diazonine-10-carboxamide (35) was synthesized from ethyl 3-(benzyloxy)-5-((3-chloro-2,4-difluorobenzyl)carbamoyl)-4-oxo-4H-pyran-2-carboxylate (170 mg, 0.356 mmol) and (R)-azepan-3-amine (48.7 mg, 0.427 mmol) following the same procedure as that used to prepare compound 28. MS (m/z) 438.1 [M+H]+. $^1$H NMR (400 MHz, DMSO-d6) δ 10.42 (t, J=6.0 Hz, 1H), 8.47 (s, 1H), 7.37 (td, J=8.4, 6.2 Hz, 1H), 7.27 (td, J=8.8, 1.6 Hz, 1H), 4.78-4.70 (m, 1H), 4.57 (d, J=5.9 Hz, 2H), 4.16-4.08 (m, 2H), 3.86 (d, J=14.9 Hz, 1H), 3.65 (dd, J=14.7, 1.8 Hz, 1H), 3.06 (ddd, J=13.2, 6.9, 3.5 Hz, 1H), 1.98 (dd, J=7.5, 4.4 Hz, 1H), 1.90-1.70 (m, 3H), 1.62 (d, J=7.5 Hz, 1H), 1.12 (d, J=12.7 Hz, 1H).

Example 33: Preparation of N-(2,4-difluorobenzyl)-7-hydroxy-6,8-dioxo-6,8,13,14-tetrahydro-12H-5,12-methanobenzo[e]pyrido[1,2-a][1,4]diazonine-9-carboxamide (36)

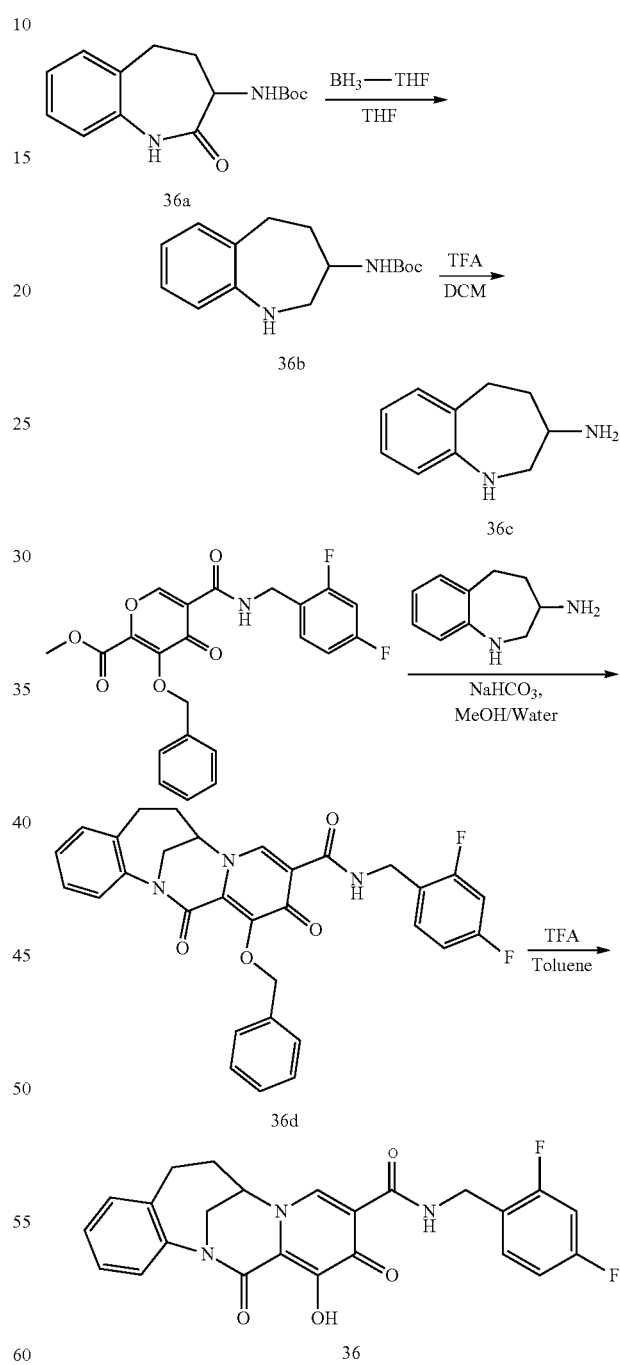

Synthesis of tert-butyl (2,3,4,5-tetrahydro-1H-benzo[b]azepin-3-yl)carbamate (36b)

To the solution of tert-butyl (2-oxo-2,3,4,5-tetrahydro-1H-benzo[b]azepin-3-yl)carbamate (36a) (300 mg, 1.086 mmol) in THF (5 mL) was added BH$_3$-THF solution (6 mL, 1N, 6 mmol) at room temperature. After stirring overnight, the reaction was quenched by adding MeOH and sodium bicarbonate water solution. The resulting mixture was extracted with Ethyl Acetate (100 mL). The organic layer was concentrated under vacuum. The residue was purified by silica gel chromatography to provide tert-butyl (2,3,4,5-tetrahydro-1H-benzo[b]azepin-3-yl)carbamate. MS (m/z) 262.897 [M+H]$^+$.

Synthesis of 2,3,4,5-tetrahydro-1H-benzo[b]azepin-3-amine (36c)

To the solution of tert-butyl (2,3,4,5-tetrahydro-1H-benzo [b]azepin-3-yl)carbamate (36b) (13 mg, 0.05 mmol) in DCM (1 mL), was added TFA (1 mL) at room temperature. After 2 h, the solvent and excess TFA were removed. The residue was used in the next step without purification. MS (m/z) 162.952 [M+H]$^+$.

Synthesis of N-(2,4-difluorobenzyl)-7-hydroxy-6,8-dioxo-6,8,13,14-tetrahydro-12H-5,12-methanobenzo [e]pyrido[1,2-a][1,4]diazonine-9-carboxamide (36)

N-(2,4-Difluorobenzyl)-7-hydroxy-6,8-dioxo-6,8,13,14-tetrahydro-12H-5,12-methanobenzo[e]pyrido[1,2-a][1,4]diazonine-9-carboxamide (36) was synthesized from methyl 3-(benzyloxy)-5-((2,4-difluorobenzyl)carbamoyl)-4-oxo-4H-pyran-2-carboxylate (30 mg, 0.07 mmol) and 2,3,4,5-tetrahydro-1H-benzo[b]azepin-3-amine follow the same procedure as that used to prepare compound 28. MS (m/z) 452.152 [M+H]$^+$. $^1$H NMR (400 MHz, DMSO-d6) δ 10.34 (t, J=5.9 Hz, 1H), 8.59 (s, 1H), 7.41 (s, 1H), 7.36-7.16 (m, 5H), 7.05 (tdd, J=8.5, 2.7, 1.1 Hz, 1H), 4.89 (s, 1H), 4.55 (d, J=6.0 Hz, 2H), 4.18 (s, 1H), 3.74 (d, J=2.1 Hz, 1H), 2.83-2.67 (m, 2H), 2.24 (s, 1H), 2.10 (s, 1H).

Example 34: Preparation of (12R)— and (12S)—N-(2,4-difluorobenzyl)-7-hydroxy-6,8-dioxo-6,8,13,14-tetrahydro-12H-5,12-methanobenzo[e]pyrido[1,2-a] [1,4]diazonine-9-carboxamide (37-1, 37-2)

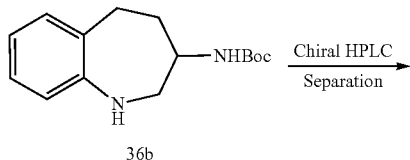

36b

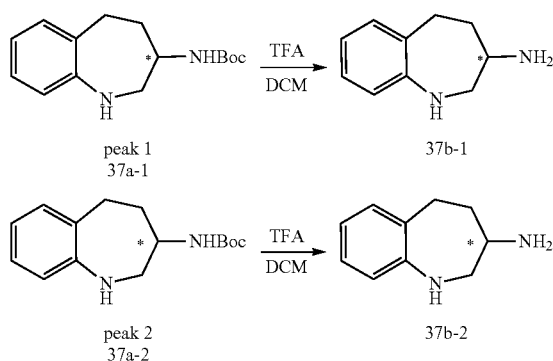

peak 1
37a-1

37b-1 peak 2
37a-2

37b-2

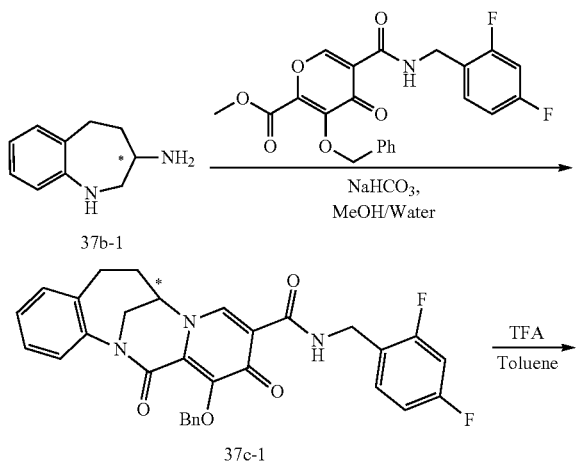

37c-1

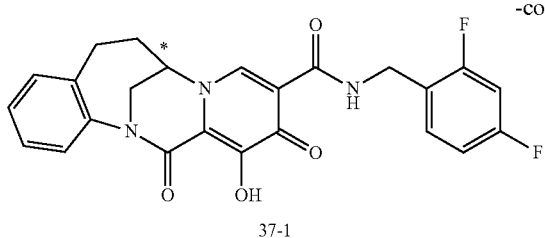

37-1

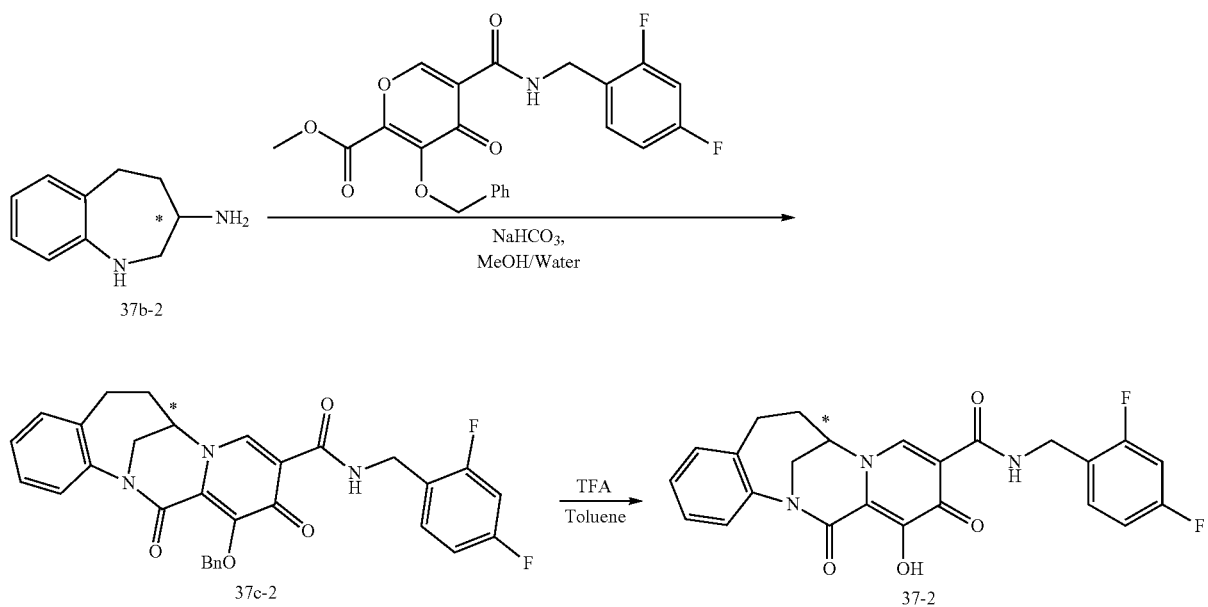

(12R)— and (12S)—N-(2,4-Difluorobenzyl)-7-hydroxy-6,8-dioxo-6,8,13,14-tetrahydro-12H-5,12-methanobenzo[e]pyrido[1,2-a][1,4]diazonine-9-carboxamide (37-1, 37-2) were synthesized from tert-butyl (R)- and (S)-(2,3,4,5-tetrahydro-1H-benzo[b]azepin-3-yl)carbamate (37a-1, 37a-2, 164 mg, 0.625 mmol, for each enantiomer), which were separated from racemic tert-butyl (2,3,4,5-tetrahydro-1H-benzo[b]azepin-3-yl)carbamate (36b) by chiral HPLC separation (SFC chromatography on an IB 4.6×100 mm 5 miccolumn using EtOH (15%) as co-solvent), following the same procedure as that used to prepare compound 28. Peak 1 (37a-1) gave 37-1. MS (m/z) 452.16 [M+H]$^+$. $^1$H NMR (400 MHz, DMSO-d6) δ 10.37 (t, J=5.9 Hz, 1H), 8.62 (s, 1H), 7.48-7.21 (m, 7H), 7.13-7.03 (m, 1H), 4.91 (dq, J=4.9, 2.5 Hz, 1H), 4.58 (d, J=5.9 Hz, 2H), 4.23-4.14 (m, 1H), 3.75 (dd, J=14.8, 2.1 Hz, 1H), 2.79 (dtd, J=17.3, 14.5, 9.6 Hz, 2H), 2.27 (td, J=12.1, 11.6, 4.8 Hz, 1H), 2.15-2.05 (m, 1H). Peak 2 (37a-2) gave 37-2. MS (m/z) 452.2 [M+H]$^+$. $^1$H NMR (400 MHz, DMSO-d6) δ 10.33 (t, J=5.9 Hz, 1H), 8.59 (s, 1H), 7.40 (d, J=6.9 Hz, 1H), 7.36-7.18 (m, 5H), 7.05 (td, J=8.4, 2.5 Hz, 1H), 4.89 (s, 1H), 4.55 (d, J=5.9 Hz, 2H), 4.16 (d, J=14.5 Hz, 1H), 3.86 (s, 1H), 2.81-2.70 (m, 2H), 2.24 (d, J=3.5 Hz, 1H), 2.09 (d, J=8.4 Hz, 1H).

Example 35: Preparation of (12R)- and (12S)-7-hydroxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide (38-1, 38-2)

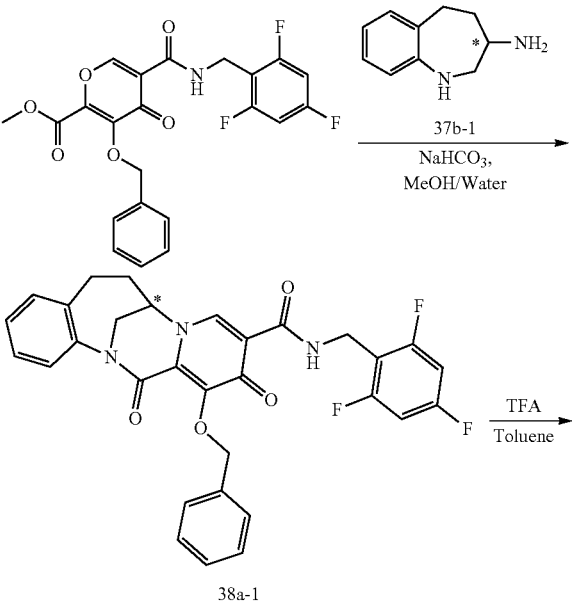

38a-1

-continued

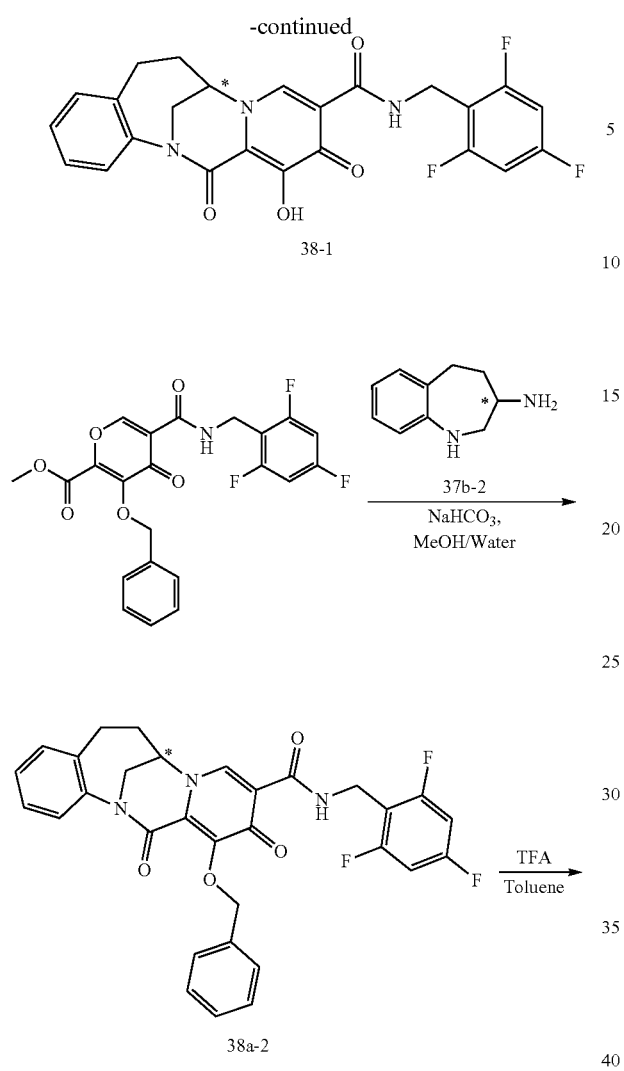

38-1

38a-2

38-2

(12R)- and (12S)-7-Hydroxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide (38-1 and 38-2) were synthesized analogously to 37-1 and 37-2 using methyl 3-(benzyloxy)-4-oxo-5-(((2,4,6-trifluorobenzyl)carbamoyl)-4H-pyran-2-carboxylate in place of methyl 3-(benzyloxy)-5-((2,4-difluorobenzyl)carbamoyl)-4-oxo-4H-pyran-2-carboxylate. MS (m/z) 470.1 [M+H]⁺. ¹H NMR (400 MHz, DMSO-d6) δ 10.36 (t, J=5.8 Hz, 1H), 10.25 (s, 1H), 8.57 (s, 1H), 7.36-7.24 (m, 4H), 7.19 (t, J=8.6 Hz, 2H), 4.86 (s, 1H), 4.56 (d, J=5.8 Hz, 2H), 4.14 (d, J=14.5 Hz, 1H), 3.71 (dd, J=14.8, 2.0 Hz, 1H), 2.81-2.69 (m, 2H), 2.27-2.17 (m, 1H), 2.08 (d, J=9.7 Hz, 1H).

Example 37: Preparation of (4R,7S,8S)- and (4S,7R,8R)-13-hydroxy-1,12-dioxo-N-(2,4,6-trifluorobenzyl)-1,3,4,5,6,7,8,12-octahydro-2,8:4,7-dimethanopyrido[1,2-a][1,4]diazecine-11-carboxamide (40-1, 40-2)

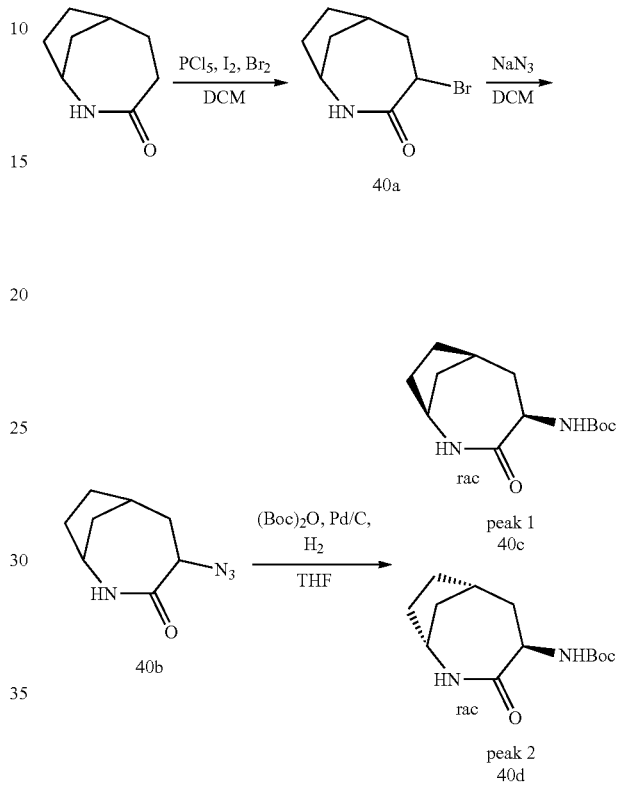

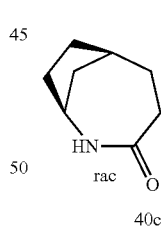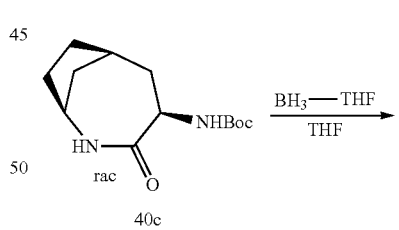

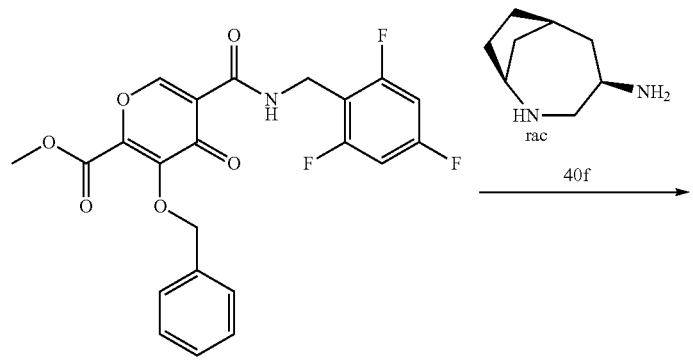
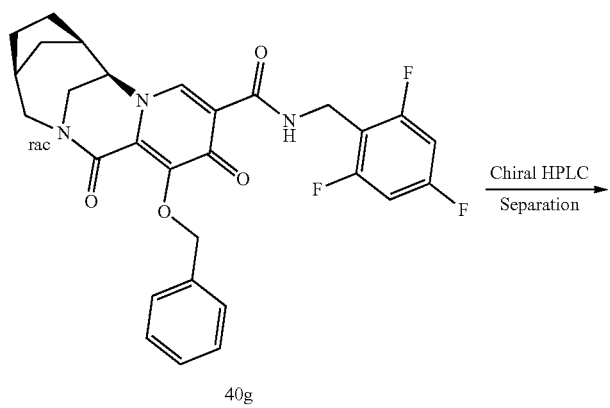
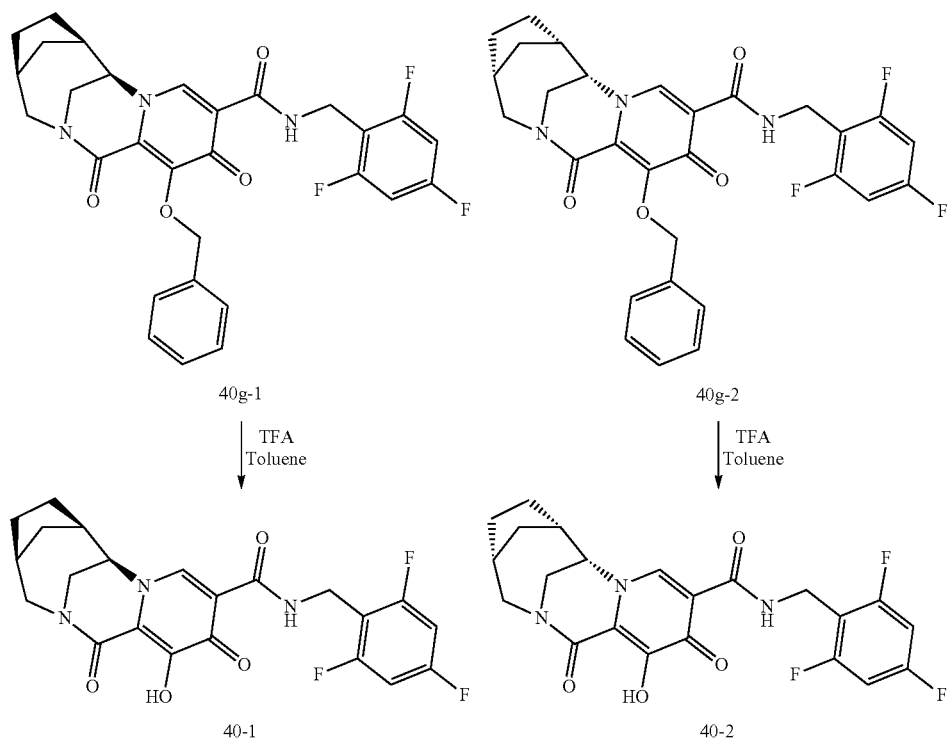

Synthesis of
4-bromo-2-azabicyclo[4.2.1]nonan-3-one (40a)

To a solution of 2-azabicyclo[4.2.1]nonan-3-one (1 g, 7.18 mmol) in DCM (30 mL) was added PCl$_5$ (1.496 g, 7 mmol) at ice-water bath cooling. After stirring at 0-5° C. for 1 h, iodine (18.2 mg, 0.7 mmol) was added and the mixture was stirred for 5 minutes. A solution of bromine (1.148 g, 7 mmol) in DCM (5 mL) was added at −5° C. and the mixture was stirred at room temperature for 1.5 h. Ice-water was added, and stirring was continued for 30 minutes. The mixture was extracted with ethyl acetate (100 mL) and washed with aqueous Na$_2$S$_2$O$_3$ and brine. After drying and solvent removal, the residue was crystalized from DCM and hexane to provide title compound. MS (m/z) 218.1 [M+H]$^+$.

Synthesis of
4-azido-2-azabicyclo[4.2.1]nonan-3-one (40b)

A mixture of 4-bromo-2-azabicyclo[4.2.1]nonan-3-one (40a) (330 mg, 1.513 mmol) and NaN$_3$ (394 mg, 6 mmol) in DMF 10 mL) was heated under microwave reactor at 120° C. overnight. The reaction mixture was extracted with Ethyl acetate (100 mL) and the extracts were washed with brine and dried, and the solvent removed. The residue was purified by silica gel chromatography to provide 4-azido-2-azabicyclo[4.2.1]nonan-3-one (40b). MS (m/z) 181.12 [M+H]$^+$.

Synthesis of rel-tert-butyl ((1R,4S,6S)-3-oxo-2-azabicyclo[4.2.1]nonan-4-yl)carbamate (40c) and rel-tert-butyl ((1R,4R,6S)-3-oxo-2-azabicyclo[4.2.1]nonan-4-yl)carbamate (40d)

A reactor was charged with 4-azido-2-azabicyclo[4.2.1]nonan-3-one (40b) (500 mg, 2.775 mmol), Di-tert-butyl dicarbonate (1.21 g, 6 mmol) and Palladium carbon (10 wt %, wet, 296 mg) in EtOH (30 mL) under argon. The reaction mixture was placed under vacuum and backfilled with Hydrogen gas. After two h of stirring vigorously, the reaction mixture was diluted with EtOH (50 mL), filtered through Celite®, and washed with Ethyl acetate. The solvent was removed and the residue was purified by silica gel chromatography to afford two diastereomers of the product, peak 1 and peak 2. Peak 1, rel-tert-butyl ((1R,4S,6S)-3-oxo-2-azabicyclo[4.2.1]nonan-4-yl)carbamate (40c). MS (m/z) 255.02 [M+H]$^+$. $^1$H NMR (400 MHz, Chloroform-d) δ 6.10-5.84 (m, 2H), 4.12 (d, J=4.9 Hz, 1H), 3.25 (dd, J=14.6, 3.1 Hz, 1H), 3.10 (dddd, J=14.8, 8.4, 6.9, 1.4 Hz, 1H), 2.53 (s, 1H), 2.36 (d, J=6.2 Hz, 1H), 1.99-1.82 (m, 2H), 1.73-1.58 (m, 3H), 1.50 (d, J=1.9 Hz, 1H), 1.45 (s, 9H). Peak 2, rel-tert-butyl ((1R,4R,6S)-3-oxo-2-azabicyclo[4.2.1]nonan-4-yl)carbamate (40d). MS (m/z) 277.2 [M+Na]$^+$. $^1$H NMR (400 MHz, Chloroform-d) δ 5.89 (s, 1H), 5.56 (s, 1H), 4.02 (dd, J=6.9, 4.5 Hz, 1H), 3.36 (ddd, J=15.3, 7.6, 6.0 Hz, 1H), 2.76 (dt, J=15.4, 6.5 Hz, 1H), 2.42-2.31 (m, 1H), 2.17 (s, 1H), 1.97 (s, 2H), 1.75 (d, J=12.7 Hz, 2H), 1.67-1.55 (m, 1H), 1.45 (s, 9H), 1.41 (d, J=5.7 Hz, 1H).

Synthesis of rel-(1R,4S,6R)-2-azabicyclo[4.2.1]nonan-4-amine (40f)

rel-(1R,4S,6R)-2-Azabicyclo[4.2.1]nonan-4-amine (40f) was synthesized from rel-tert-butyl ((1R,4S,6S)-3-oxo-2-azabicyclo[4.2.1]nonan-4-yl)carbamate (40c) analogously to the synthesis of 2,3,4,5-tetrahydro-1H-benzo[b]azepin-3-amine (36c) from tert-butyl (2-oxo-2,3,4,5-tetrahydro-1H-benzo[b]azepin-3-yl)carbamate (36a).

Synthesis of (4S,7R,8R)- and (4R,7S,8S)-13-(benzyloxy)-1,12-dioxo-N-(2,4,6-trifluorobenzyl)-1,3,4,5,6,7,8,12-octahydro-2,8:4,7-dimethanopyrido[1,2-a][1,4]diazecine-11-carboxamide (40g-1, 40g-2)

rel-(4R,7S,8S)-13-(Benzyloxy)-1,12-dioxo-N-(2,4,6-trifluorobenzyl)-1,3,4,5,6,7,8,12-octahydro-2,8:4,7-dimethanopyrido[1,2-a][1,4]diazecine-11-carboxamide (40g) was synthesized from rel-(1R,4S,6R)-2-azabicyclo[4.2.1]nonan-4-amine (40f) and methyl 3-(benzyloxy)-4-oxo-5-((2,4,6-trifluorobenzyl)carbamoyl)-4H-pyran-2-carboxylate by the same procedure as that used to prepare compound 28, followed by chiral HPLC separation to provide peak 1 (40g-1) and peak 2 (40g-2). MS (m/z) 538.2 [M+H]$^+$.

Synthesis of (4R,7S,8S)- and (4S,7R,8R)-13-hydroxy-1,12-dioxo-N-(2,4,6-trifluorobenzyl)-1,3,4,5,6,7,8,12-octahydro-2,8:4,7-dimethanopyrido[1,2-a][1,4]diazecine-11-carboxamide (40-1 and 40-2)

(4R,7S,8S)- and (4S,7R,8R)-13-Hydroxy-1,12-dioxo-N-(2,4,6-trifluorobenzyl)-1,3,4,5,6,7,8,12-octahydro-2,8:4,7-dimethanopyrido[1,2-a][1,4]diazecine-11-carboxamide (40-1, 40-2) were synthesized from compounds 40h-1 and 40h-2, respectively, following the same procedure as used to prepare compound 28. MS (m/z) 448.2 [M+H]$^+$. $^1$H NMR (400 MHz, DMSO-d6) δ 10.37 (t, J=5.8 Hz, 1H), 8.50 (s, 1H), 7.19 (t, J=8.6 Hz, 2H), 4.55 (dd, J=5.9, 2.8 Hz, 2H), 4.51-4.38 (m, 1H), 4.21 (dd, J=13.4, 7.0 Hz, 1H), 3.80 (d, J=15.1 Hz, 1H), 2.90-2.68 (m, 2H), 2.68-2.59 (m, 1H), 2.57-2.50 (m, 1H), 2.15-1.99 (m, 1H), 1.74 (d, J=7.0 Hz, 2H), 1.49 (dd, J=14.1, 6.9 Hz, 2H), 1.16 (d, J=14.4 Hz, 1H).

Example 38: Preparation of (4S,7R,8S)- and (4R,7S,8R)-13-hydroxy-1,12-dioxo-N-(2,4,6-trifluorobenzyl)-1,3,4,5,6,7,8,12-octahydro-2,8:4,7-dimethanopyrido[1,2-a][1,4]diazecine-11-carboxamide (41-1 and 41-2)

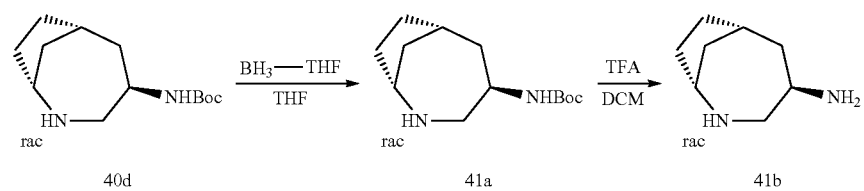

-continued
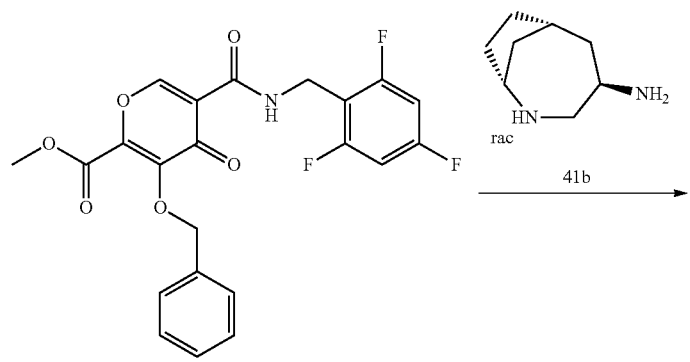
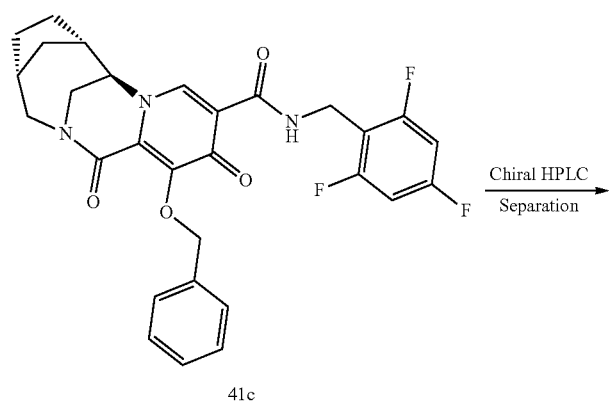
41c
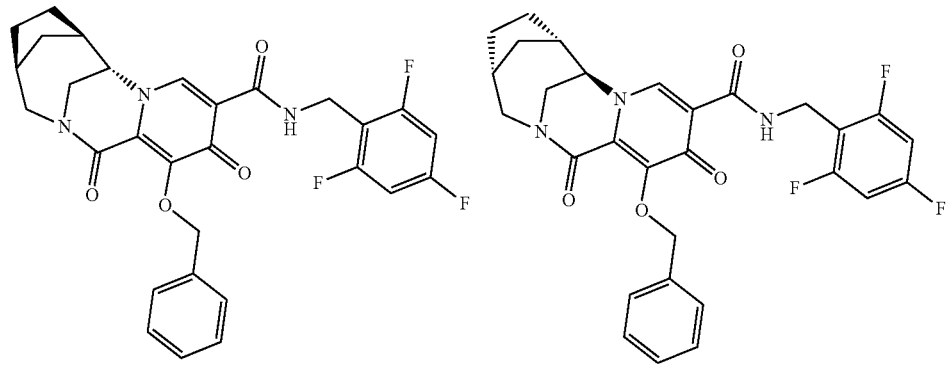
41c-1      41c-2
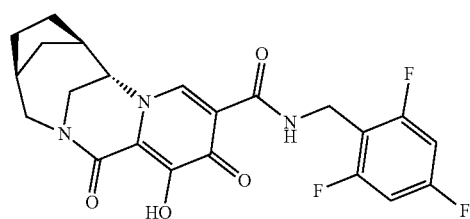 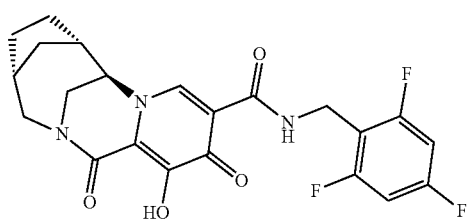
41-1      41-2

(4S,7R,8S)- and (4R,7S,8R)-13-Hydroxy-1,12-dioxo-N-(2,4,6-trifluorobenzyl)-1,3,4,5,6,7,8,12-octahydro-2,8:4,7-dimethanopyrido[1,2-a][1,4]diazecine-11-carboxamide (41-1 and 41-2) were synthesized from rel-tert-butyl ((1R,4R,6S)-3-oxo-2-azabicyclo[4.2.1]nonan-4-yl)carbamate (40d) analogous to the preparation of compounds 40-1 and 40-2. MS (m/z) 448.2 [M+H]+. 1H NMR (400 MHz, DMSO-d6) δ 10.38 (t, J=5.8 Hz, 1H), 8.48 (s, 1H), 7.19 (t, J=8.6 Hz, 2H), 4.78 (d, J=9.2 Hz, 1H), 4.55 (t, J=5.7 Hz, 2H), 4.08 (d, J=13.3 Hz, 1H), 3.82 (d, J=2.5 Hz, 1H), 3.05-2.88 (m, 2H), 2.42 (s, 1H), 2.19 (d, J=14.0 Hz, 1H), 1.63 (dd, J=13.2, 7.2 Hz, 3H), 1.40 (d, J=11.9 Hz, 1H), 0.92 (d, J=3.7 Hz, 1H).

Example 39a: Preparation of N-(2,4-difluorobenzyl)-5-hydroxy-4,6-dioxo-1,1a,2,4,6,10,11,11a-octahydro-3,10-methanocyclopropa[f]pyrido[1,2-a][1,4]diazonine-7-carboxamide (42-1)

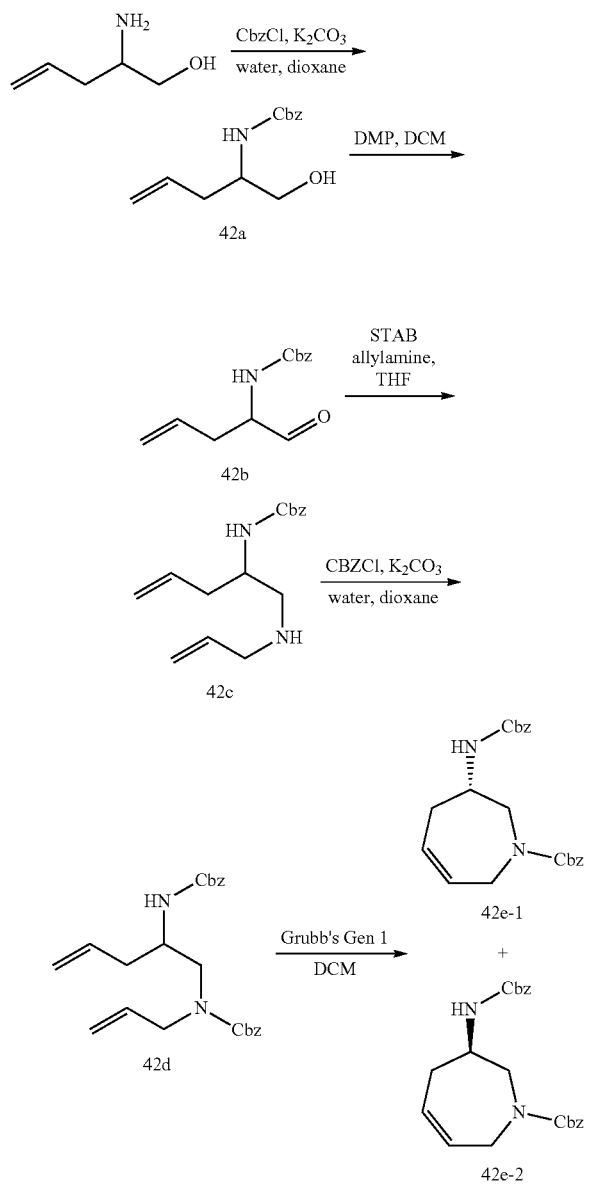

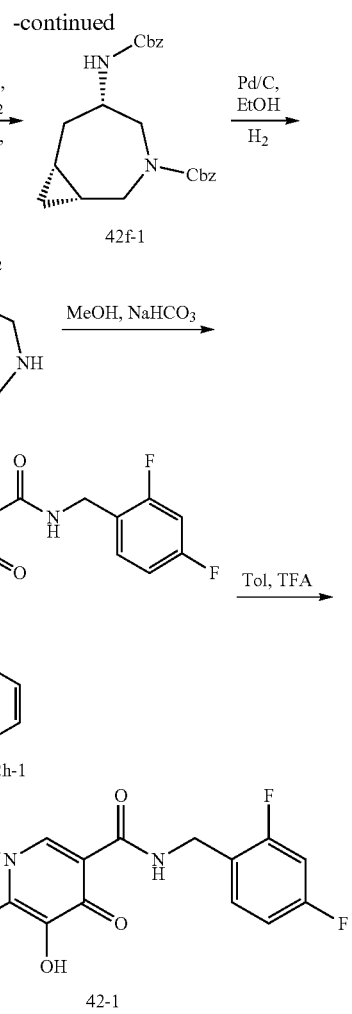

Synthesis of benzyl (1-hydroxypent-4-en-2-yl)carbamate (42a)

To one round-bottom flask was added 2-aminopent-4-en-1-ol (2000 mg, 19.8 mmol), 100 mL water, and potassium carbonate, anhydrous (2.5 g, 40 mmol). To a second round-bottom flask was added 100 mL dioxane and benzyl chloroformate (3.1 mL, 22 mmol). Each mixture was stirred to dissolve. The amine mixture was cooled in an ice bath and the dioxane mixture was added. The reaction mixture was allowed to slowly warm to room temperature while stirring overnight. The reaction mixture was diluted with DCM and extracted twice with DCM. The organic extracts were washed with NH4Cl, dried over sodium sulfate and concentrated. The residue was purified by silica gel chromatography to provide the title compound. MS (m/z) 235.9 [M+H]+.

Synthesis of benzyl (1-oxopent-4-en-2-yl)carbamate (42b)

To a round-bottom flask was added benzyl (1-hydroxypent-4-en-2-yl)carbamate (42a, 3 g, 13 mmol) and 200 mL DCM, followed by Dess Martin periodinane (6 g, 14.2 mmol). After stirring 1 h, more Dess-Martin periodinane (2 g, 4.7 mmol) was added to the reaction mixture and stirring continued for another 30 minutes. The mixture was diluted with DCM, a solution of saturated NaHCO$_3$ and 11 g sodium thiosulfate was added. The resulting mixture was stirred about 10 min and extracted twice with DCM. The organic extracts were washed with a mix of brine, water, and NaHCO$_3$, dried over sodium sulfate, and concentrated to provide the title compound. MS (m/z) 234.0 [M+H]$^+$.

Synthesis of benzyl (1-(allylamino)pent-4-en-2-yl)carbamate (42c)

To a round-bottom flask was added benzyl (1-oxopent-4-en-2-yl)carbamate (6 g, 26 mmol) and THF (100 mL). Allylamine (2.1 mL, 28.3 mmol) and sodium triacetoxyborohydride (8.2 g, 39 mmol) were added and the reaction mixture was stirred overnight. The reaction was quenched with saturated aqueous NaHCO$_3$ (20 mL) and the mixture extracted with EtOAc (100 mL×3). The combined organic extracts were dried over anhydrous sodium sulfate and concentrated in vacuo to provide the title compound. MS (m/z) 275.2 [M+H]$^+$.

Synthesis of benzyl allyl(2-(((benzyloxy)carbonyl)amino)pent-4-en-1-yl)carbamate (42d)

To one round-bottom flask was added benzyl (1-(allylamino)pent-4-en-2-yl)carbamate (42c, 6.3 g, 23.1 mmol), 120 mL water, and potassium carbonate, anhydrous (2.9 g, 46.2 mmol). To a second round-bottom flask was added 120 mL dioxane and benzyl chloroformate (3.6 mL, 25.4 mmol). Each mixture was stirred to dissolve. The amine mixture was cooled in an ice bath and the dioxane mixture was added. The reaction mixture was allowed to slowly warm to room temperature while stirring overnight. The reaction mixture was diluted with DCM and extracted twice with DCM. The organic extracts were washed with NH$_4$Cl, dried over sodium sulfate and concentrated. The residue was purified by silica gel chromatography to provide the title compound. MS (m/z) 409.7 [M+H]$^+$.

Synthesis of benzyl-3-(((benzyloxy)carbonyl)amino)azepane-1-carboxylate (42e-1 and 42e-2)

To a round-bottom flask was added benzyl allyl(2-(((benzyloxy)carbonyl)amino)pent-4-en-1-yl)carbamate (42d, 6.3 mg, 16 mmol), DCM (400 mL), and bis(tricyclohexylphosphine)benzylidine ruthenium (IV) dichloride (Grubbs Catalyst™ 1st Generation) (500 mg, 0.6 mmol). The mixture was heated at reflux overnight, and concentrated. The residue was dissolved in DCM and purified by silica gel chromatography. The mixture of enantiomers was separated into individual enantiomers by preparative SFC chromatography on a Chiralcel® OJ-H column using MeOH co-solvent to provide 42e-1 (peak 1) and 42e-2 (peak 2). MS (m/z) 381.5 [M+H]$^+$.

Synthesis of benzyl 5-(((benzyloxy)carbonyl)amino)-3-azabicyclo[5.1.0]octane-3-carboxylate (42f-1)

To a three neck flask was added 42e-1 (626 mg, 1.6 mmol) and DCM (3 mL). The resulting mixture was cooled to 0 C, and 1M diethylzinc in hexane (3.46 mL) was added slowly, followed by slow addition of diiodomethane (0.5 mL, 6.6 mmol). The reaction mixture was stirred at 0° C. for 10 min, and a second charge of diethylzinc and diiodomethane was added. The mixture was stirred at 0° C. for 2 h, removed from the ice bath stirred and another 2 h. A third charge of diethylzinc and diiodomethane was added and the mixture was stirred overnight. The reaction was quenched with water and extracted twice with DCM. The combined organic extracts were dried over sodium sulfate, filtered, and concentrated. The residue was purified by silica gel chromatography to provide the title compound. MS (m/z) 395.3 [M+H]$^+$.

Synthesis of 5-(benzyloxy)-N-(2,4-difluorobenzyl)-4,6-dioxo-1,1a,2,4,6,10,11,11a-octahydro-3,10-methanocyclopropa[f]pyrido[1,2-a][1,4]diazonine-7-carboxamide (42h-1)

To a round-bottom flask was added 42f-1 (200 mg, 0.5 mmol), Ethanol (20 mL), and Palladium on carbon 10 wt. % loading (dry basis), matrix carbon powder, wet support (216 mg, 0.2 mmol). The mixture was sparged with N$_2$, and a balloon of H$_2$ was added. The reaction mixture was stirred overnight, filtered over Celite®, and concentrated. The residue was combined with methyl 3-benzyloxy-5-[(2,4-difluorophenyl)methylcarbamoyl]-4-oxo-pyran-2-carboxylate (108.9 mg, 0.5 mmol), NaHCO$_3$ (85 mg, 1 mmol), and MeOH (3 mL). The mixture was stirred at 70° C. for approximately 4 h until cyclization was complete. The solids were filtered off and the solution concentrated. The residue was dissolved in DMF/water/TFA and purified by HPLC to provide the major diastereomer of the title compound. MS (m/z) 506.2 [M+H]$^+$.

Synthesis of N-(2,4-difluorobenzyl)-5-hydroxy-4,6-dioxo-1,1a,2,4,6,10,11,11a-octahydro-3,10-methanocyclopropa[f]pyrido[1,2-a][1,4]diazonine-7-carboxamide (42-1)

To a vial was add 5-(benzyloxy)-N-(2,4-difluorobenzyl)-4,6-dioxo-1,1a,2,4,6,10,11,11a-octahydro-3,10-methanocyclopropa[f]pyrido[1,2-a][1,4]diazonine-7-carboxamide (42h-1, 63 mg, 0.12 mmol), toluene (2 mL), and TFA (1 mL). The reaction mixture was stirred until LCMS indicated complete deprotection, concentrated, diluted with DMF, and purified by HPLC to provide the title compound. MS (m/z) 416.2 [M+H]$^+$. $^1$H NMR (400 MHz, Chloroform-d) δ 10.59 (s, 1H), 8.55 (s, 1H), 7.41-7.32 (m, 1H), 6.89-6.78 (m, 2H), 4.67 (d, 2H), 4.64-4.55 (m, 1H), 4.48 (dd, 1H), 4.22 (dd, 1H), 3.94-3.83 (m, 1H), 3.75-3.66 (m, 1H), 2.96-2.84 (m, 1H), 1.38-1.07 (m, 3H), 0.49-0.41 (m, 1H).

Example 39b: Preparation of (1aS,10R,11aS)—N-(2,4-difluorobenzyl)-5-hydroxy-4,6-dioxo-1,1a,2,4,6,10,11,11a-octahydro-3,10-methanocyclopropa[f]pyrido[1,2-a][1,4]diazonine-7-carboxamide (42-2)

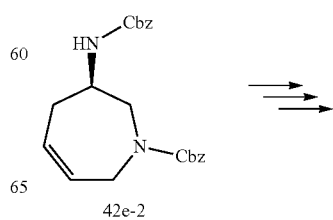

42e-2

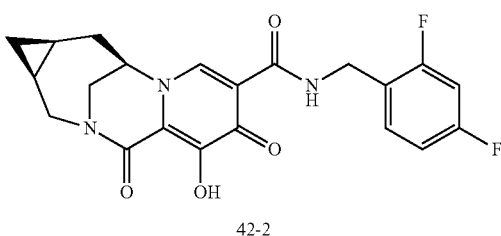

42-2

(1aS,10R,11aS)—N-(2,4-Difluorobenzyl)-5-hydroxy-4,6-dioxo-1,1a,2,4,6,10,11,11a-octahydro-3,10-methanocyclopropa[f]pyrido[1,2-a][1,4]diazonine-7-carboxamide (42-2) was prepared analogous to 42-1, beginning with 42e-2 (peak 2) in place of 42e-1 (peak 1). MS (m/z) 416.2 [M+H]$^+$. $^1$H NMR (400 MHz, Chloroform-d) δ 10.46 (s, 1H), 8.43 (s, 1H), 7.40-7.30 (m, 1H), 6.87-6.75 (m, 2H), 4.64 (d, 2H), 4.56-4.50 (m, 1H), 4.50-4.40 (m, 1H), 4.18 (dd, 1H), 3.86 (dd, 1H), 3.67 (d, 1H), 2.93-2.80 (m, 1H), 1.37-1.04 (m, 3H), 0.91-0.76 (m, 1H), 0.47-0.34 (m, 1H).

Example 40: Preparation of (7S)-2,4,6-trifluorobenzyl 12-methoxy-1,11-dioxo-1,3,4,5,6,11-hexahydro-7I3-2,7-methanopyrido[2,1-c][1,4]diazonine-10-carboxylate and (7R)-2,4,6-trifluorobenzyl 12-methoxy-1,11-dioxo-1,3,4,5,6,11-hexahydro-7I3-2,7-methanopyrido[2,1-c][1,4]diazonine-10-carboxylate (43-1, 43-2)

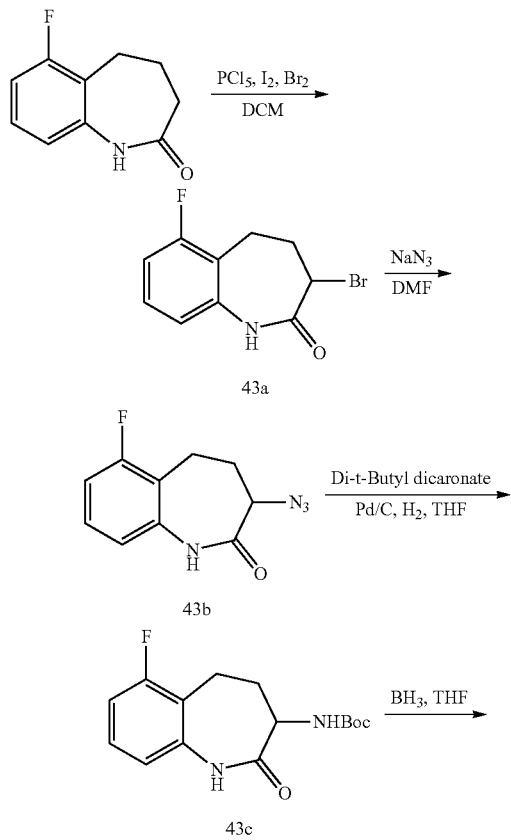

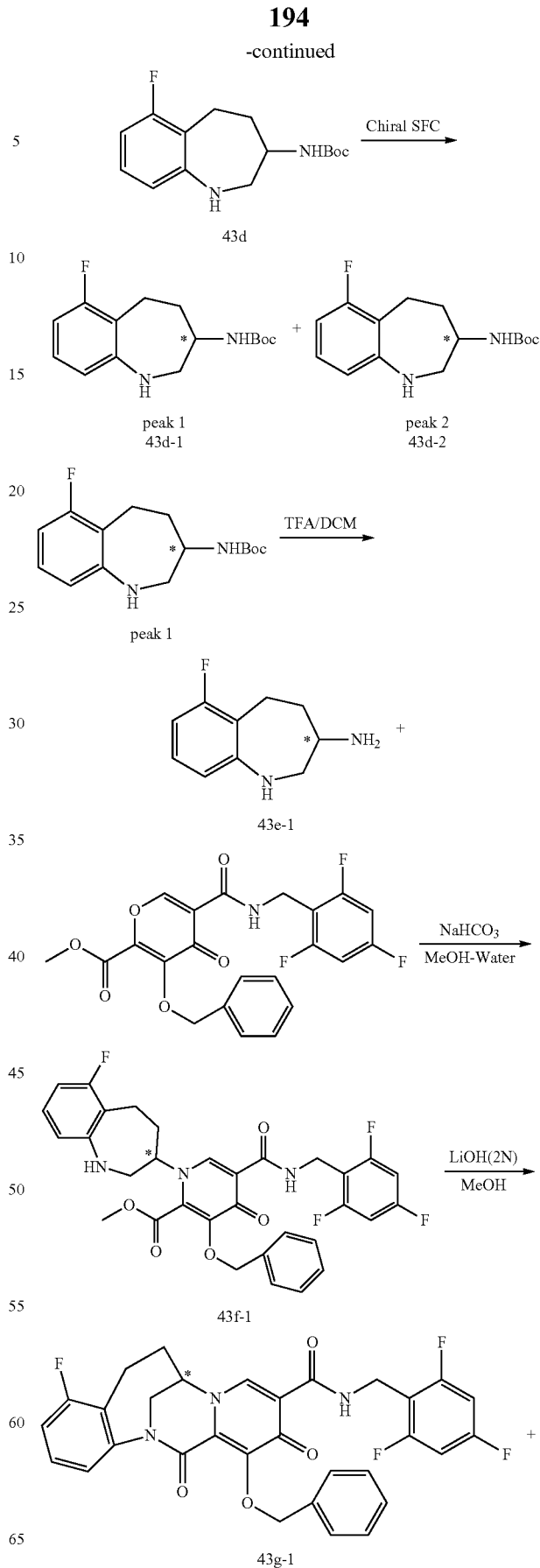

-continued

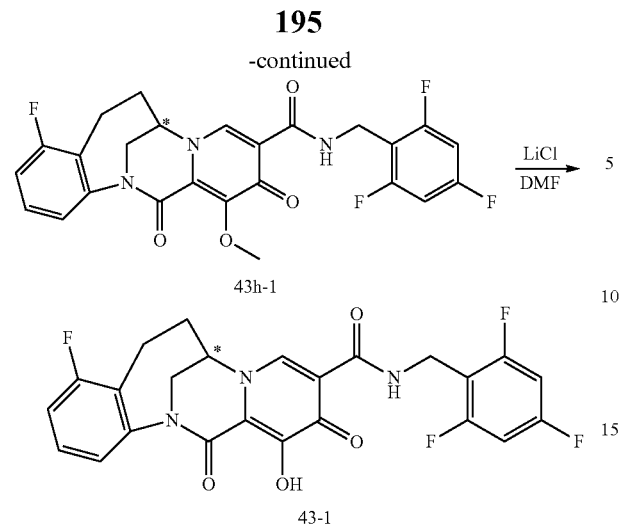

43h-1

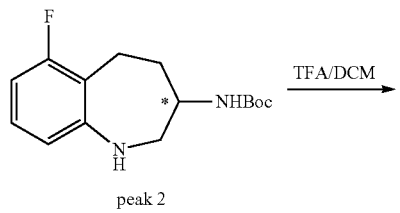

peak 2

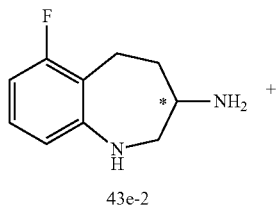

43e-2

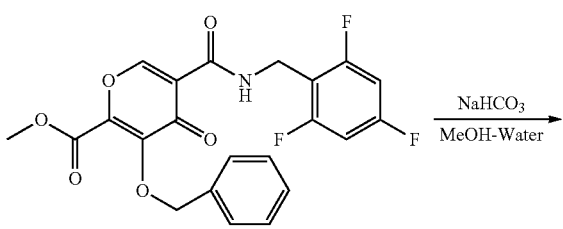

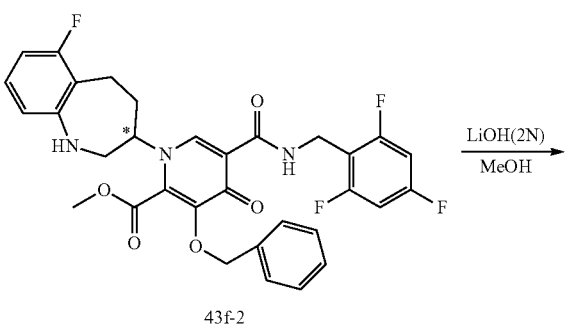

43f-2

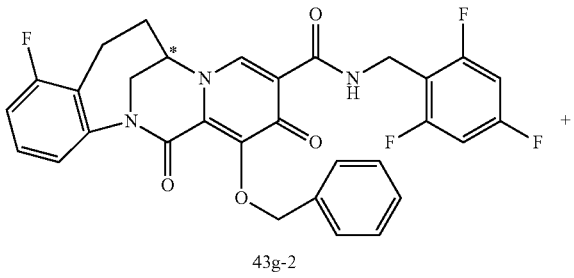

43g-2

-continued

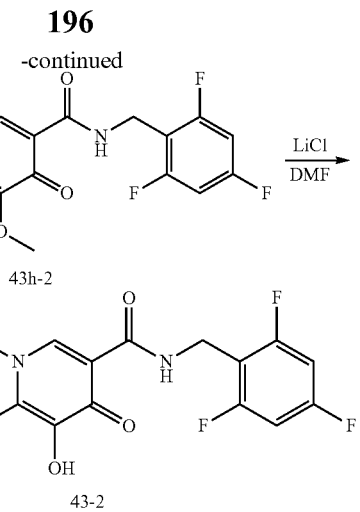

Synthesis of 3-bromo-6-fluoro-1,3,4,5-tetrahydro-2H-benzo[b]azepin-2-one (43a)

Into a solution of 6-fluoro-1,3,4,5-tetrahydro-2H-benzo[b]azepin-2-one (1 g, 5.58 mmol) in DCM (25 mL), phosphorus pentachloride (1.16 g, 5.58 mmol) was added under ice cooling bath. After the reaction mixture was stirred for 5 hrs, iodine (14.2 mg, 0.558 mmol) was added, followed by bromine (0.892 g, 5.58 mmol). The reaction mixture was allowed to warm to rt and was stirred for 1.5 hr. The reaction mixture was extracted with ethyl acetate and washed with a water solution of $Na_2S_2SO_3$ and brine. The organic layer was dried over $MgSO_4$, and the solvent was removed by rotary evaporator. The title compound was crystalized from a mixture of DCM/ethyl acetate. MS (m/z) 260 [M+H]$^+$. $^1$H NMR (400 MHz, DMSO-$d_6$) δ 10.18 (s, 1H), 7.25 (td, J=8.1, 6.3 Hz, 1H), 6.99 (ddd, J=9.4, 8.4, 1.1 Hz, 1H), 6.84 (d, J=7.9 Hz, 1H), 4.65 (dd, J=9.2, 7.3 Hz, 1H), 2.96-2.83 (m, 1H), 2.76-2.59 (m, 2H), 2.47-2.41 (m, 1H).

Synthesis of 3-azido-6-fluoro-1,3,4,5-tetrahydro-2H-benzo[b]azepin-2-one (43b)

Into a solution of 3-bromo-6-fluoro-1,3,4,5-tetrahydro-2H-benzo[b]azepin-2-one (43a, 109 mg, 0.422 mmol) in DMF (5 mL), sodium azide (110 mg, 1.69 mmol) was added. After stirring for 4 hr at 60° C., the reaction mixture was extracted with ethyl acetate and washed with brine. The organic layer was dried over $MgSO_4$, and the solvent removed by rotary evaporator. The residue was purified by silica-gel column to provide the title compound. MS (m/z) 221 [M+H]$^+$.

Synthesis of tert-butyl (6-fluoro-2-oxo-2,3,4,5-tetrahydro-1H-benzo[b]azepin-3-yl)carbamate (43c)

Into a solution of 3-azido-6-fluoro-1,3,4,5-tetrahydro-2H-benzo[b]azepin-2-one (43b, 880 mg, 4 mmol) in THF (30 mL), di-tert-butyl dicarbonate (1.308 g, 5.99 mmol) and 10% Pd/C (425 mg) were added, then the mixture was sparged under a hydrogen atmosphere (balloon pressure). After the reaction was stirred for 2 hr, it was filtered through a pad of Celite® and washed with ethyl acetate, and the filtrate was concentrated in rotary evaporator. The residue was purified by silica-gel column, providing the title compound. MS (m/z) 317.1 [M+Na]$^+$. $^1$H NMR (400 MHz, DMSO-$d_6$) δ 9.87 (s, 1H), 7.32-7.21 (m, 1H), 7.00 (q, J=8.5

Hz, 2H), 6.85 (d, J=7.9 Hz, 1H), 3.91-3.78 (m, 1H), 2.96 (dd, J=14.0, 6.3 Hz, 1H), 2.45-2.28 (m, 1H), 2.23-1.98 (m, 2H), 1.32 (s, 9H).

Synthesis of tert-butyl (S)-(6-fluoro-2,3,4,5-tetrahydro-1H-benzo[b]azepin-3-yl)carbamate and (R)-(6-fluoro-2,3,4,5-tetrahydro-1H-benzo[b]azepin-3-yl)carbamate (43d-1 and 43d-2)

Into a solution of tert-butyl (6-fluoro-2-oxo-2,3,4,5-tetrahydro-1H-benzo[b]azepin-3-yl)carbamate (43c, 800 mg, 2.72 mmol) in THF (30 mL), BH$_3$-THF solution (1 N, 13 mL) was added at room temperature. After the reaction was stirred overnight, the reaction was quenched with MeOH (1 mL) and water solution of sodium bicarbonate. The resulting mixture was extracted with ethyl acetate (100 mL) and washed with brine. The organic layer was dried over MgSO$_4$ and concentrated under vacuum. The residue was purified by silica-gel column, to provide tert-butyl (6-fluoro-2-oxo-2,3,4,5-tetrahydro-1H-benzo[b]azepin-3-yl)carbamate (43d). MS (m/z) 281.2 [M+H]$^+$.

43d was separated into individual enantiomers by chiral HPLC (SFC chromatography on an IB 4.6×100 mm 5mic column using EtOH (15%) as co solvent) to provide the title compounds.

Synthesis of (S)-6-fluoro-2,3,4,5-tetrahydro-1H-benzo[b]azepin-3-amine and (R)-6-fluoro-2,3,4,5-tetrahydro-1H-benzo[b]azepin-3-amine (43e-1 and 43e-2)

Into a solution of (S)-(6-fluoro-2,3,4,5-tetrahydro-1H-benzo[b]azepin-3-yl)carbamate or (R)-(6-fluoro-2,3,4,5-tetrahydro-1H-benzo[b]azepin-3-yl)carbamate (65 mg, 0.232 mmol) in DCM (5 mL), TFA (1 mL) was added at rt. After 2 hr, the solvent and excess TFA was removed by rotary evaporator to afford the title compounds (43e-1 or 43e-2), which were carried forward to next step, without further purification. MS (m/z) 181.2 [M+H]$^+$.

Synthesis of methyl (S)-3-(benzyloxy)-1-(6-fluoro-2,3,4,5-tetrahydro-1H-benzo[b]azepin-3-yl)-4-oxo-5-((2,4,6-trifluorobenzyl)carbamoyl)-1,4-dihydropyridine-2-carboxylate and (R)-3-(benzyloxy)-1-(6-fluoro-2,3,4,5-tetrahydro-1H-benzo[b]azepin-3-yl)-4-oxo-5-((2,4,6-trifluorobenzyl)carbamoyl)-1,4-dihydropyridine-2-carboxylate (43f-1 and 43f-2)

Into a solution of (S)-6-fluoro-2,3,4,5-tetrahydro-1H-benzo[b]azepin-3-amine or (R)-6-fluoro-2,3,4,5-tetrahydro-1H-benzo[b]azepin-3-amine (43e-1 or 43e-2, 40 mg, 0.143 mmol) in MeOH/Water (v/v=6/1, 3.5 mL), sodium bicarbonate (59.9 mg, 0.713 mmol) and methyl 3-(benzyloxy)-4-oxo-5-((2,4,6-trifluorobenzyl)carbamoyl)-4H-pyran-2-carboxylate (60 mg, 0.134 mmol) were added. The reaction mixture was stirred overnight at 60° C., extracted with ethyl acetate (100 mL), and washed with brine. The organic layer was dried over MgSO$_4$ and the solvent was removed by rotary evaporator, to give the title compounds (43f-1 or 43f-2), which were carried forward without further purification. MS (m/z) 610.2 [M+H]$^+$.

Synthesis of mixture of (12S)-7-(benzyloxy)-1-fluoro-6,8-dioxo-N-(2,4,6-trifluorobenzyl)-6,8,13,14-tetrahydro-12H-5,12-methanobenzo[e]pyrido[1,2-a][1,4]diazonine-9-carboxamide and (12S)-1-fluoro-7-methoxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide, and (12R)-7-(benzyloxy)-1-fluoro-6,8-dioxo-N-(2,4,6-trifluorobenzyl)-6,8,13,14-tetrahydro-12H-5,12-methanobenzo[e]pyrido[1,2-a][1,4]diazonine-9-carboxamide and (12R)-1-fluoro-7-methoxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide (mixture of 43g-1 and 43h-1) and (mixture of 43g-2 and 43h-2)

Into a solution of crude of (S)- or (R)-2-methyl 5-(2,4,6-trifluorobenzyl) 3-(benzyloxy)-1-(6-fluoro-2,3,4,5-tetrahydro-1H-benzo[b]azepin-3-yl)-4-oxo-1,4-dihydropyridine-2,5-dicarboxylate (43f-1 or 43f-2, 80 mg. 0.131 mmol) in MeOH (6 mL), water solution of LiOH (2 N, 2 mL) was added. After the reaction was stirred for 2 hr, the solvent was removed and extracted with ethyl acetate (100 mL). After the organic layer was dried over MgSO$_4$, the solvent was removed by rotary evaporator affording the title compounds (mixture of 43g-1 and 43h-1 or mixture of 43g-2 and 43h-2), which were taken on crude, without further purification. 43g-1, 43g-2: MS (m/z) 578.2 [M+H]$^+$. 43h-1, 43h-2: MS (m/z) 501.2 [M+H]$^+$.

Synthesis of (12S)-1-fluoro-7-hydroxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide and (12R)-1-fluoro-7-hydroxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide (43-1 and 43-2)

To the mixture of (12S)-7-(benzyloxy)-1-fluoro-6,8-dioxo-N-(2,4,6-trifluorobenzyl)-6,8,13,14-tetrahydro-12H-5,12-methanobenzo[e]pyrido[1,2-a][1,4]diazonine-9-carboxamide with 1-fluoro-7-methoxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide (43g-1/43h-1,198 mg, 0.343 mmol) or (12R)-7-(benzyloxy)-1-fluoro-6,8-dioxo-N-(2,4,6-trifluorobenzyl)-6,8,13,14-tetrahydro-12H-5,12-methanobenzo[e]pyrido[1,2-a][1,4]diazonine-9-carboxamide with 1-fluoro-7-methoxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide (43g-2/43h-2, 98 mg, 0.17 mmol) in DMF (6 mL), LiCl (10 eq.) was added. After stirring at 105° C. for 1.5 hr, the reaction mixture was filtered, and purified by preparative HPLC (Gemini 10u C18 110A), eluting with 15-80% acetonitrile in water (0.1% TFA) over 15 min, to give the title compounds (43-1 or 43-2).

43-1: MS (m/z) 488.2 [M+H]$^+$. $^1$H NMR (400 MHz, DMSO-d$_6$) δ 10.34 (t, J=5.8 Hz, 1H), 8.58 (s, 1H), 7.32 (dd, J=8.1, 6.1 Hz, 1H), 7.19 (td, J=8.3, 3.5 Hz, 4H), 4.95-4.85 (m, 1H), 4.56 (d, J=5.7 Hz, 2H), 4.13 (d, J=14.7 Hz, 1H), 3.85 (dd, J=14.9, 2.1 Hz, 1H), 2.88 (dd, J=17.0, 9.7 Hz, 1H), 2.71 (dd, J=16.9, 9.2 Hz, 1H), 2.42-2.28 (m, 1H), 2.03-1.92 (m, 1H).

43-2: MS (m/z) 488.1 [M+H]$^+$. $^1$H NMR (400 MHz, DMSO-d$_6$) δ 10.34 (t, J=5.8 Hz, 1H), 8.58 (s, 1H), 7.33 (td, J=8.1, 6.1 Hz, 1H), 7.19 (td, J=8.4, 4.0 Hz, 3H), 4.90 (t,

J=5.8 Hz, 1H), 4.56 (d, J=5.7 Hz, 2H), 4.13 (d, J=14.6 Hz, 1H), 3.87 (d, J=2.2 Hz, 1H), 2.88 (dd, J=16.5, 10.1 Hz, 1H), 2.71 (dd, J=16.9, 9.2 Hz, 1H), 2.35 (q, J=7.7, 7.0 Hz, 1H), 1.98 (d, J=8.6 Hz, 1H).

Example 41: Preparation of (8R,Z)—N-(2,4-difluorobenzyl)-13-hydroxy-1,12-dioxo-1,3,4,7,8,12-hexahydro-2,8-methanopyrido[1,2-a][1,4]diazecine-11-carboxamide and (8S,Z)—N-(2,4-difluorobenzyl)-13-hydroxy-1,12-dioxo-1,3,4,7,8,12-hexahydro-2,8-methanopyrido[1,2-a][1,4]diazecine-11-carboxamide (44-1 and 44-2)

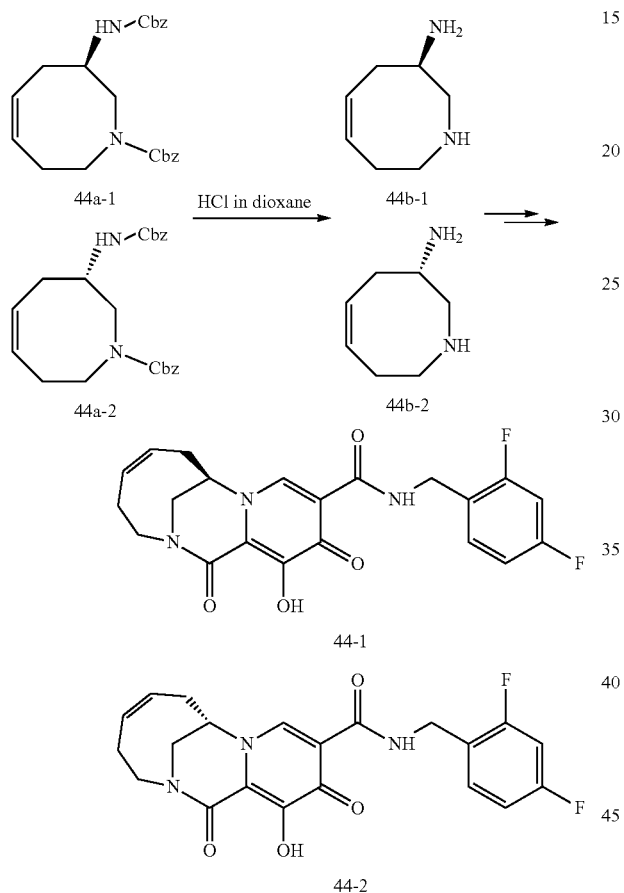

Synthesis of benzyl (R,Z)-3-(((benzyloxy)carbonyl) amino)-3,4,7,8-tetrahydroazocine-1(2H)-carboxylate and (S,Z)-3-(((benzyloxy)carbonyl)amino)-3,4,7,8-tetrahydroazocine-1(2H)-carboxylate (44a-1 and 44a-2)

The title compounds were synthesized from 2-aminopent-4-en-1-ol in a manner analogous to 42e-1 and 42e-2, except that 42-b was reacted with but-3-en-1-amine in place of allylamine. 44a-1: MS (m/z) 395.2 [M+H]$^+$. 44b-1: MS (m/z) 395.2 [M+H]$^+$.

Synthesis of (R,Z)- and (S,Z)-1,2,3,4,7,8-hexahydroazocin-3-amine (44b-1 and 44b-2)

To a vial was added benzyl (R,Z)-3-(((benzyloxy)carbonyl)amino)-3,4,7,8-tetrahydroazocine-1(2H)-carboxylate or (S,Z)-3-(((benzyloxy)carbonyl)amino)-3,4,7,8-tetrahydroazocine-1(2H)-carboxylate (44a-1 or 44a-2, 500 mg, 1.3 mmol) and 4 N HCl in dioxane (6.3 mL, 25 mmol). The reaction was stirred at 95° C. overnight, cooled to rt, and concentrated, to give the title compounds (44b-1 or 44b-2), which were used subsequently without further purification. MS (m/z) 127.2 [M+H]$^+$.

Synthesis of (8R,Z)—N-(2,4-difluorobenzyl)-13-hydroxy-1,12-dioxo-1,3,4,7,8,12-hexahydro-2,8-methanopyrido[1,2-a][1,4]diazecine-11-carboxamide and (8S,Z)—N-(2,4-difluorobenzyl)-13-hydroxy-1,12-dioxo-1,3,4,7,8,12-hexahydro-2,8-methanopyrido[1,2-a][1,4]diazecine-11-carboxamide (44-1 and 44-2)

The title compounds were synthesized from (R,Z)-1,2,3,4,7,8-hexahydroazocin-3-amine or (S,Z)-1,2,3,4,7,8-hexahydroazocin-3-amine (44b-1 or 44b-2, 18.9 mg, 0.163 mmol) and ethyl 3-(benzyloxy)-5-((2,4-difluorobenzyl)carbamoyl)-4-oxo-4H-pyran-2-carboxylate (70 mg, 0.163 mmol) following a procedure similar to the procedure for preparation of compound 28.

44-1: MS (m/z) 416.3 [M+H]$^+$. $^1$H NMR (400 MHz, Chloroform-d) δ 10.71-10.56 (m, 1H), 8.56 (s, 1H), 7.38 (q, 1H), 6.91-6.78 (m, 2H), 6.05 (q, 1H), 5.71 (q, 1H), 4.76-4.61 (m, 2H), 4.55 (ddd, 1H), 4.48-4.34 (m, 1H), 4.02-3.90 (m, 1H), 3.75 (d, 1H), 3.09-2.97 (m, 1H), 2.73-2.64 (m, 1H), 2.63-2.52 (m, 1H), 2.52-2.45 (m, 1H), 2.45-2.32 (m, 1H).

44-2: MS (m/z) 416.2 [M+H]$^+$. $^1$H NMR (400 MHz, Chloroform-d) δ 10.66-10.51 (m, 1H), 8.52 (s, 1H), 7.38 (q, 1H), 6.84 (q, 2H), 6.05 (q, 1H), 5.71 (q, 1H), 4.74-4.62 (m, 2H), 4.56 (ddd, 1H), 4.46-4.35 (m, 1H), 3.97 (dd, 1H), 3.75 (d, 1H), 3.08-2.99 (m, 1H), 2.71-2.63 (m, 1H), 2.63-2.54 (m, 1H), 2.53-2.45 (m, 1H), 2.44-2.32 (m, 1H).

Example 42: Preparation of (12S)-1-chloro-7-hydroxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide and (12R)-1-chloro-7-hydroxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide (45-1 and 45-2)

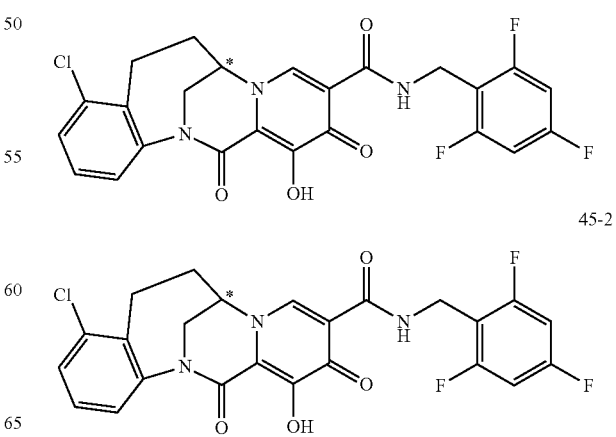

The title compounds were prepared similarly to 43-1 and 43-2, using 6-chloro-1,3,4,5-tetrahydro-2H-benzo[b]azepin-2-one in place of 6-fluoro-1,3,4,5-tetrahydro-2H-benzo[b]azepin-2-one.

45-1: MS (m/z) 504.1 [M+H]$^+$. $^1$H NMR (400 MHz, DMSO-d$_6$) δ 10.38 (t, J=5.8 Hz, 1H), 8.60 (s, 1H), 7.47 (dd, J=6.7, 2.8 Hz, 1H), 7.40-7.30 (m, 2H), 7.29-7.16 (m, 2H), 4.96-4.88 (m, 1H), 4.59 (d, J=5.7 Hz, 2H), 4.15 (dd, J=15.0, 1.9 Hz, 1H), 3.86 (dd, J=14.7, 2.2 Hz, 1H), 3.04 (ddd, J=17.1, 9.7, 2.3 Hz, 1H), 2.86 (ddd, J=15.8, 10.3, 5.6 Hz, 1H), 2.41-2.32 (m, 1H), 2.06 (dd, J=13.4, 6.9 Hz, 1H).

45-2: MS (m/z) 504.1 [M+H]$^+$. $^1$H NMR (400 MHz, DMSO-d$_6$) δ 10.38 (t, J=5.8 Hz, 1H), 10.27 (s, 1H), 8.60 (s, 1H), 7.47 (dd, J=6.7, 2.7 Hz, 1H), 7.41-7.30 (m, 2H), 7.29-7.16 (m, 2H), 4.96-4.88 (m, 1H), 4.59 (d, J=5.7 Hz, 2H), 4.20-4.11 (m, 1H), 3.86 (dd, J=14.7, 2.2 Hz, 1H), 3.04 (ddd, J=17.2, 9.8, 2.3 Hz, 1H), 2.86 (dd, J=16.8, 9.2 Hz, 1H), 2.42-2.33 (m, 1H), 2.04 (q, J=13.0, 9.4 Hz, 1H).

Example 43: Preparation of (12S)-4-fluoro-7-hydroxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide and (12R)-4-fluoro-7-hydroxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide (46-1 and 46-2)

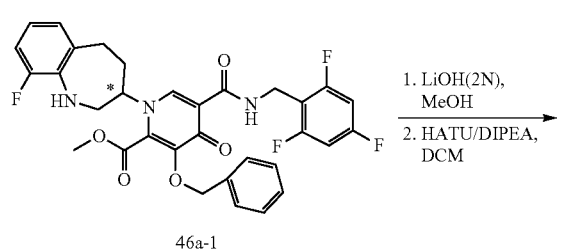

46a-1

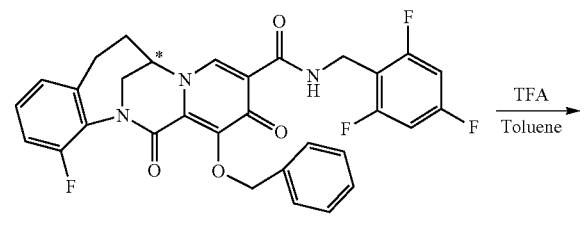

46b-1

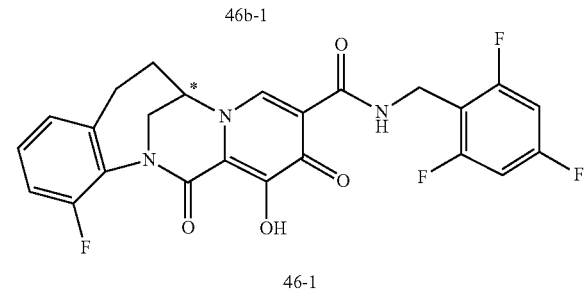

46-1

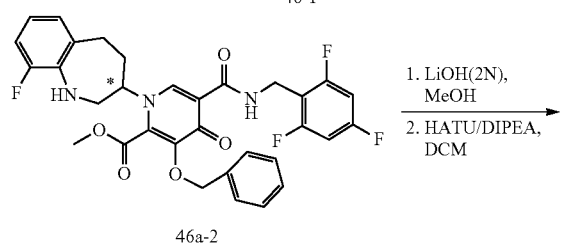

46a-2

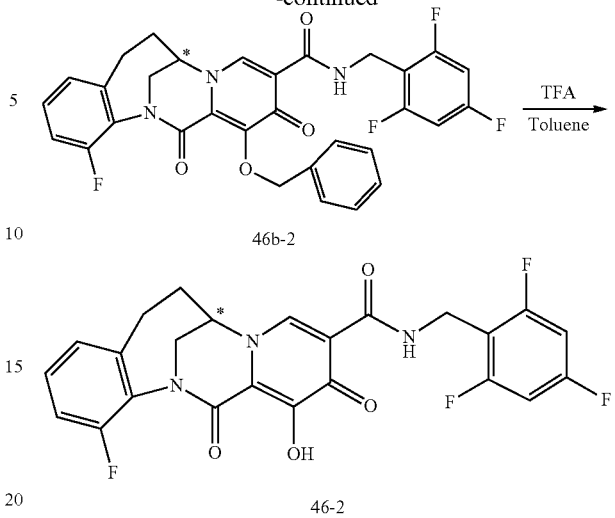

46b-2

46-2

Synthesis of methyl (S)- and (R)-3-(benzyloxy)-1-(9-fluoro-2,3,4,5-tetrahydro-1H-benzo[b]azepin-3-yl)-4-oxo-5-((2,4,6-trifluorobenzyl)carbamoyl)-1,4-dihydropyridine-2-carboxylate (46a-1 and 46a-2)

The title compounds were prepared in a manner similar to methyl (S)-3-(benzyloxy)-1-(6-fluoro-2,3,4,5-tetrahydro-1H-benzo[b]azepin-3-yl)-4-oxo-5-((2,4,6-trifluorobenzyl)carbamoyl)-1,4-dihydropyridine-2-carboxylate and (R)-3-(benzyloxy)-1-(6-fluoro-2,3,4,5-tetrahydro-1H-benzo[b]azepin-3-yl)-4-oxo-5-((2,4,6-trifluorobenzyl)carbamoyl)-1,4-dihydropyridine-2-carboxylate (43f-1 and 43f-2) using 9-fluoro-1,3,4,5-tetrahydro-2H-benzo[b]azepin-2-one in place of 6-fluoro-1,3,4,5-tetrahydro-2H-benzo[b]azepin-2-one.

Synthesis of (12S)-7-(benzyloxy)-4-fluoro-6,8-dioxo-N-(2,4,6-trifluorobenzyl)-6,8,13,14-tetrahydro-12H-5,12-methanobenzo[e]pyrido[1,2-a][1,4]diazonine-9-carboxamide and (12R)-7-(benzyloxy)-4-fluoro-6,8-dioxo-N-(2,4,6-trifluorobenzyl)-6,8,13,14-tetrahydro-12H-5,12-methanobenzo[e]pyrido[1,2-a][1,4]diazonine-9-carboxamide (46b-1 and 46b-2)

Into a solution of methyl (S)-3-(benzyloxy)-1-(9-fluoro-2,3,4,5-tetrahydro-1H-benzo[b]azepin-3-yl)-4-oxo-5-((2,4,6-trifluorobenzyl)carbamoyl)-1,4-dihydropyridine-2-carboxylate or (R)-3-(benzyloxy)-1-(9-fluoro-2,3,4,5-tetrahydro-1H-benzo[b]azepin-3-yl)-4-oxo-5-((2,4,6-trifluorobenzyl)carbamoyl)-1,4-dihydropyridine-2-carboxylate (46a-1 or 46a-2, 80 mg, 0.13 mmol) in MeOH (20 mL), LiOH (2 N, 4 mL) was added at rt. After heating to 50° C. and stirring for 2 hr, a citric acid solution (5% in water) was added and reaction was extracted with ethyl acetate (100 mL). Removal of solvent gave (S)-3-(benzyloxy)-1-(9-fluoro-2,3,4,5-tetrahydro-1H-benzo[b]azepin-3-yl)-4-oxo-5-((2,4,6-trifluorobenzyl)carbamoyl)-1,4-dihydropyridine-2-carboxylic acid or (R)-3-(benzyloxy)-1-(9-fluoro-2,3,4,5-tetrahydro-1H-benzo[b]azepin-3-yl)-4-oxo-5-((2,4,6-trifluorobenzyl)carbamoyl)-1,4-dihydropyridine-2-carboxylic acid, which was carried forward without further purification. MS (m/z) 596.2 [M+H]$^+$.

Into a solution of (S)-3-(benzyloxy)-1-(9-fluoro-2,3,4,5-tetrahydro-1H-benzo[b]azepin-3-yl)-4-oxo-5-((2,4,6-trifluorobenzyl)carbamoyl)-1,4-dihydropyridine-2-carboxylic acid or (R)-3-(benzyloxy)-1-(9-fluoro-2,3,4,5-tetrahydro-1H-benzo[b]azepin-3-yl)-4-oxo-5-((2,4,6-trifluorobenzyl)carbamoyl)-1,4-dihydropyridine-2-carboxylic acid in DCM (5 mL), DIPEA (39 mg, 0.302 mmol) and HATU (86.1 mg, 0.227 mmol) were added at rt. After 1 hr, the reaction mixture was purified by silica-gel column elicited with ethyl acetate to afford the title compounds (46b-1 or 46b-2). MS (m/z) 578.2 [M+H]$^+$.

Synthesis of (12S)-4-fluoro-7-hydroxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide and (12R)-4-fluoro-7-hydroxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide (46-1 and 46-2)

Into a solution of (12S)-7-(benzyloxy)-4-fluoro-6,8-dioxo-N-(2,4,6-trifluorobenzyl)-6,8,13,14-tetrahydro-12H-5,12-methanobenzo[e]pyrido[1,2-a][1,4]diazonine-9-carboxamide or (12R)-7-(benzyloxy)-4-fluoro-6,8-dioxo-N-(2,4,6-trifluorobenzyl)-6,8,13,14-tetrahydro-12H-5,12-methanobenzo[e]pyrido[1,2-a][1,4]diazonine-9-carboxamide (46b-1 or 46b-2, 80 mg, 0.13 mmol) in toluene (4 mL), TFA (1 mL) was added at rt. After stirring overnight, solvent and excess TFA was removed by rotatory evaporation, and the residue was purified by preparative HPLC to afford the title compounds.

46-1: MS (m/z) 488.1 [M+H]$^+$. $^1$H NMR (400 MHz, DMSO-d$_6$) δ 10.35 (t, J=5.8 Hz, 1H), 8.57 (s, 1H), 7.29 (dd, J=7.9, 5.5 Hz, 1H), 7.25-7.03 (m, 4H), 4.90 (s, 1H), 4.57 (d, J=5.7 Hz, 2H), 4.19 (d, J=14.6 Hz, 1H), 3.77 (dd, J=14.9, 2.0 Hz, 1H), 2.90-2.81 (m, 1H), 2.76 (d, J=10.5 Hz, 1H), 2.32-2.19 (m, 1H), 2.07 (d, J=7.8 Hz, 1H).

46-2: MS (m/z) 488.1 [M+H]$^+$. $^1$H NMR (400 MHz, DMSO-d$_6$) δ 10.34 (d, J=5.8 Hz, 1H), 10.27 (s, 1H), 10.22 (s, 1H), 8.57 (s, 1H), 7.34-7.26 (m, 1H), 7.23-7.05 (m, 4H), 4.90 (s, 1H), 4.57 (d, J=5.8 Hz, 2H), 4.19 (d, J=14.6 Hz, 1H), 3.77 (dd, J=14.8, 2.0 Hz, 1H), 2.86 (dd, J=16.8, 7.8 Hz, 1H), 2.77-2.70 (m, 1H), 2.30-2.19 (m, 1H), 2.07 (d, J=7.8 Hz, 1H).

Example 44: Preparation of (7R)—N-(2,4-difluorobenzyl)-12-hydroxy-1,11-dioxo-1,6,7,11-tetrahydro-3H-2,7-methanopyrido[1,2-a][1,4]diazonine-10-carboxamide and (7S)—N-(2,4-difluorobenzyl)-12-hydroxy-1,11-dioxo-1,6,7,11-tetrahydro-3H-2,7-methanopyrido[1,2-a][1,4]diazonine-10-carboxamide (47-1 and 47-2)

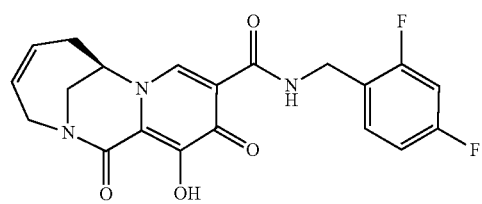

47-1

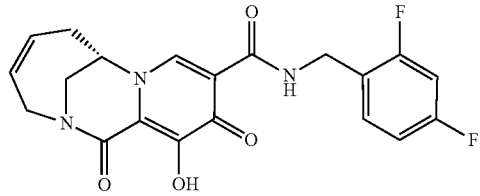

47-2

The title compounds were synthesized in a manner analogous to 44-1 and 44-2, using benzyl-3-(((benzyloxy)carbonyl)amino)azepane-1-carboxylate (42e-1 or 42e-2) in place of benzyl (R,Z)-3-(((benzyloxy)carbonyl)amino)-3,4,7,8-tetrahydroazocine-1(2H)- or (S,Z)-3-(((benzyloxy)carbonyl)amino)-3,4,7,8-tetrahydroazocine-1(2H)-carboxylate (44a-1 or 44a-2).

47-1: MS (m/z) 402.4 [M+H]$^+$. $^1$H NMR (400 MHz, Acetonitrile-d$_3$) δ 10.38 (s, 1H), 8.41 (s, 1H), 7.60-7.23 (m, 1H), 7.15-6.90 (m, 2H), 5.79-5.50 (m, 2H), 5.17-4.87 (m, 1H), 4.78 (d, J=9.2 Hz, 1H), 4.60 (d, J=5.9 Hz, 2H), 3.96-3.83 (m, 1H), 3.82-3.66 (m, 2H), 3.14-2.86 (m, 1H), 2.61-2.34 (m, 1H), 2.15-2.13 (m, 1H).

47-1: MS (m/z) 402.3 [M+H]$^+$. $^1$H NMR (400 MHz, Acetonitrile-d$_3$) δ 10.37 (s, 1H), 8.42 (s, 1H), 7.43 (td, J=8.7, 6.4 Hz, 1H), 7.06-6.87 (m, 2H), 5.69-5.54 (m, 2H), 4.96 (dd, J=18.1, 3.2 Hz, 1H), 4.79 (ddt, J=9.1, 4.5, 2.1 Hz, 1H), 4.60 (d, J=5.8 Hz, 2H), 3.88 (dd, J=14.2, 1.7 Hz, 1H), 3.82-3.68 (m, 2H), 3.11-2.93 (m, 1H), 2.50-2.36 (m, 1H).

Example 45: Preparation of (12S)-2-chloro-7-hydroxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide and (12R)-2-chloro-7-hydroxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide (48-1 and 48-2)

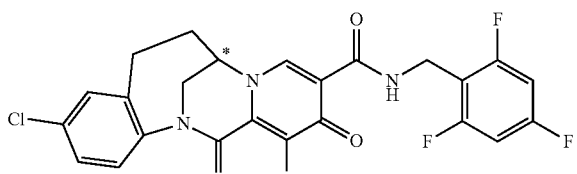

48-1

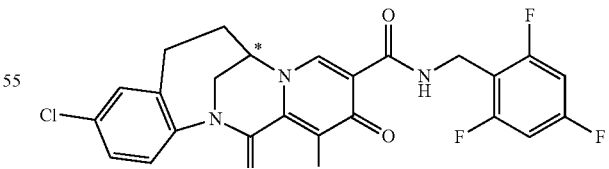

48-2

The title compounds were prepared in a manner analogous to 43-1 and 43-2, using 7-chloro-1,3,4,5-tetrahydro-2H-benzo[b]azepin-2-one in place of 6-fluoro-1,3,4,5-tetrahydro-2H-benzo[b]azepin-2-one.

48-1: MS (m/z) 505.2 [M+H]$^+$. $^1$H NMR (400 MHz, DMSO-d$_6$) δ 10.38 (t, J=5.8 Hz, 1H), 8.59 (s, 1H), 7.47 (d, J=1.8 Hz, 1H), 7.38 (d, J=1.8 Hz, 2H), 7.30-7.04 (m, 2H), 4.89 (td, J=5.0, 2.4 Hz, 1H), 4.59 (d, J=5.8 Hz, 2H), 2.95-2.64 (m, 2H), 2.40-2.24 (m, 1H), 2.15-1.98 (m, 1H).

48-2: MS (m/z) 504.1 [M+H]+. 1H NMR (400 MHz, DMSO-d6) δ 10.38 (t, J=5.8 Hz, 1H), 8.59 (s, 1H), 7.47 (d, J=1.8 Hz, 1H), 7.37 (s, 1H), 7.22 (t, J=8.6 Hz, 2H), 4.89 (s, 1H), 4.59 (d, J=5.7 Hz, 2H), 4.15 (d, J=14.4 Hz, 1H), 3.76 (dd, J=14.7, 2.0 Hz, 1H), 2.92-2.79 (m, 1H), 2.73 (dd, J=9.9, 6.6 Hz, 1H), 2.27 (s, 2H), 2.07 (d, J=10.2 Hz, 2H).

Example 46: Preparation of (12S)-2-chloro-N-(2,4-difluorobenzyl)-7-hydroxy-6,8-dioxo-6,8,13,14-tetrahydro-12H-5,12-methanobenzo[e]pyrido[1,2-a][1,4]diazonine-9-carboxamide and (12R)-2-chloro-N-(2,4-difluorobenzyl)-7-hydroxy-6,8-dioxo-6,8,13,14-tetrahydro-12H-5,12-methanobenzo[e]pyrido[1,2-a][1,4]diazonine-9-carboxamide (49-1 and 49-2)

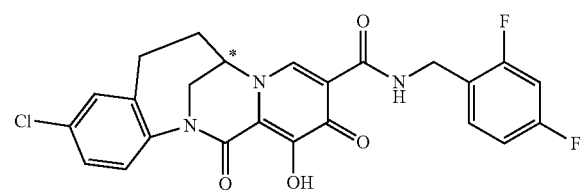

49-1

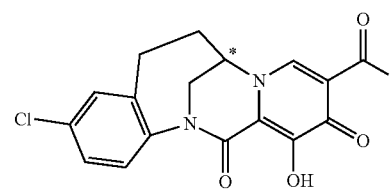

49-2

The title compounds were prepared in a manner analogous to 43-1 and 43-2, using 7-chloro-1,3,4,5-tetrahydro-2H-benzo[b]azepin-2-one in place of 6-fluoro-1,3,4,5-tetrahydro-2H-benzo[b]azepin-2-one, and methyl 3-(benzyloxy)-5-((2,4-difluorobenzyl)carbamoyl)-4-oxo-4H-pyran-2-carboxylate in place of methyl 3-(benzyloxy)-4-oxo-5-((2,4,6-trifluorobenzyl)carbamoyl)-4H-pyran-2-carboxylate.

49-1: MS (m/z) 487.1 [M+H]+. 1H NMR (400 MHz, DMSO-d6) δ 10.35 (t, J=5.9 Hz, 1H), 8.61 (s, 1H), 7.55-7.33 (m, 4H), 7.29-7.18 (m, 1H), 7.12-6.97 (m, 1H), 4.97-4.83 (m, 1H), 4.58 (d, J=5.8 Hz, 2H), 4.22-4.10 (m, 1H), 2.97-2.59 (m, 2H), 2.30 (m, 1H), 2.08 (m, 1H).

49-2: MS (m/z) 486.1 [M+H]+. 1H NMR (400 MHz, DMSO-d6) δ 10.35 (t, J=5.9 Hz, 1H), 10.06 (s, 1H), 8.61 (s, 1H), 7.50-7.38 (m, 2H), 7.38 (d, J=1.4 Hz, 2H), 7.26 (ddd, J=10.5, 9.4, 2.6 Hz, 1H), 7.08 (tt, J=8.6, 1.7 Hz, 1H), 4.91 (dq, J=5.0, 2.5 Hz, 1H), 4.58 (d, J=5.9 Hz, 2H), 4.16 (dd, J=14.8, 2.0 Hz, 1H), 3.82-3.69 (m, 1H), 2.86 (ddd, J=16.8, 9.3, 3.1 Hz, 1H), 2.79-2.68 (m, 1H), 2.29 (s, 1H), 2.12-2.03 (m, 1H).

Example 47: Preparation of (12S)-2,3-difluoro-7-hydroxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide and (12R)-2,3-difluoro-7-hydroxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide (50-1 and 50-2)

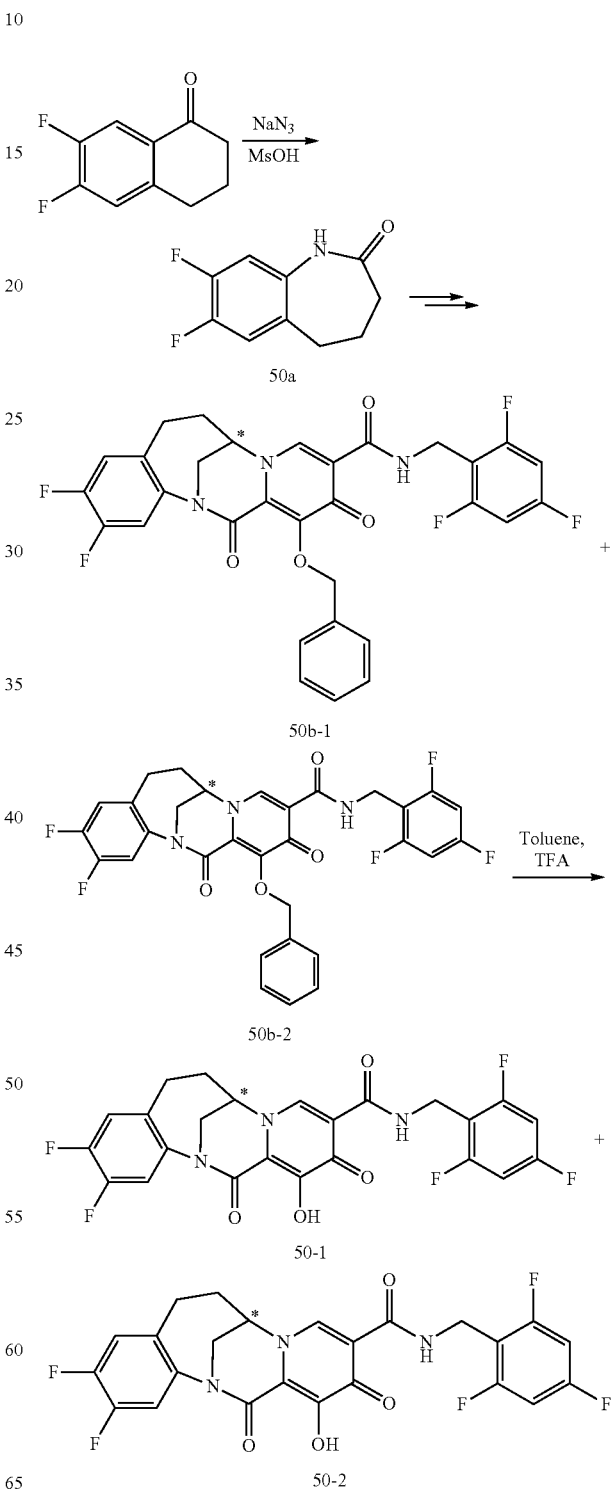

Synthesis of 7,8-difluoro-1,3,4,5-tetrahydro-2H-benzo[b]azepin-2-one (50a)

To a solution of 6,7-difluoro-3,4-dihydronaphthalen-1(2H)-one (1 g, 5.49 mmol) in methane sulfonic acid (7 mL), sodium azide (428 mg, 6.59 mmol) was added in three portions in an ice-cooling bath over 15 min. After 30 min, water (100 mL) was added and product precipitated out of solution. The solid was washed with water and dried, to afford the title compound (50a). MS (m/z) 198 [M+H]$^+$. $^1$H NMR (400 MHz, Chloroform-d) δ 7.88 (s, 1H), 7.04 (dd, J=10.4, 8.4 Hz, 1H), 6.85 (dd, J=10.5, 7.1 Hz, 1H), 2.75 (t, J=7.2 Hz, 2H), 2.36 (t, J=7.3 Hz, 2H), 2.22 (t, J=7.3 Hz, 2H).

Synthesis of (12R)-7-(benzyloxy)-2,3-difluoro-6,8-dioxo-N-(2,4,6-trifluorobenzyl)-6,8,13,14-tetrahydro-12H-5,12-methanobenzo[e]pyrido[1,2-a][1,4]diazonine-9-carboxamide and (12S)-7-(benzyloxy)-2,3-difluoro-6,8-dioxo-N-(2,4,6-trifluorobenzyl)-6,8,13,14-tetrahydro-12H-5,12-methanobenzo[e]pyrido[1,2-a][1,4]diazonine-9-carboxamide (50b-1 and 50b-2)

The title compounds were prepared in a manner analogous to 43g-1 and 43g-2, using 7,8-difluoro-1,3,4,5-tetrahydro-2H-benzo[b]azepin-2-one (50a) in place of 6-fluoro-1,3,4,5-tetrahydro-2H-benzo[b]azepin-2-one.

Synthesis of (12S)-2,3-difluoro-7-hydroxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide and (12R)-2,3-difluoro-7-hydroxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide (50-1 and 50-2)

The title compounds were prepared in a manner analogous to 46-1 and 46-2, using (12R)-7-(benzyloxy)-2,3-difluoro-6,8-dioxo-N-(2,4,6-trifluorobenzyl)-6,8,13,14-tetrahydro-12H-5,12-methanobenzo[e]pyrido[1,2-a][1,4]diazonine-9-carboxamide or (12S)-7-(benzyloxy)-2,3-difluoro-6,8-dioxo-N-(2,4,6-trifluorobenzyl)-6,8,13,14-tetrahydro-12H-5,12-methanobenzo[e]pyrido[1,2-a][1,4]diazonine-9-carboxamide (50b-1 or 50b-2) in place of (S)- or (R)-3-(benzyloxy)-1-(9-fluoro-2,3,4,5-tetrahydro-1H-benzo[b]azepin-3-yl)-4-oxo-5-((2,4,6-trifluorobenzyl)carbamoyl)-1,4-dihydropyridine-2-carboxylate (46a-1 or 46a-2).

50-1: MS (m/z) 488.1 [M+H]$^+$. $^1$H NMR (400 MHz, DMSO-d$_6$) δ 10.31 (t, J=6.0 Hz, 1H), 8.58 (s, 1H), 7.54-7.42 (m, 2H), 7.40 (d, J=6.7 Hz, 1H), 7.22 (td, J=9.9, 2.6 Hz, 1H), 7.05 (td, J=8.6, 2.5 Hz, 1H), 4.89 (d, J=5.1 Hz, 1H), 4.55 (d, J=5.8 Hz, 2H), 4.13 (d, J=14.6 Hz, 1H), 3.76 (s, 1H), 2.79 (d, J=8.1 Hz, 1H), 2.70 (d, J=10.3 Hz, 1H), 2.24 (s, 1H), 2.07 (d, J=8.6 Hz, 1H).

50-2: MS (m/z) 488.1 [M+H]$^+$. $^1$H NMR (400 MHz, DMSO-d$_6$) δ 10.31 (t, J=5.9 Hz, 1H), 8.58 (s, 1H), 7.48 (dt, J=11.6, 8.5 Hz, 2H), 7.39 (dd, J=8.7, 6.7 Hz, 1H), 7.22 (td, J=10.0, 2.6 Hz, 1H), 7.05 (td, J=8.6, 2.5 Hz, 1H), 4.89 (s, 1H), 4.55 (d, J=5.9 Hz, 2H), 4.13 (d, J=14.6 Hz, 1H), 3.80 (d, J=2.0 Hz, 1H), 2.79 (d, J=8.1 Hz, 1H), 2.75-2.62 (m, 1H), 2.24 (s, 1H), 2.13-2.00 (m, 1H).

Example 48: Preparation of (7S)—N-(3-chloro-2,4-difluorobenzyl)-12-hydroxy-1,11-dioxo-1,4,5,6,7,11-hexahydro-3H-2,7-methanopyrido[1,2-a][1,4]diazonine-10-carboxamide (51)

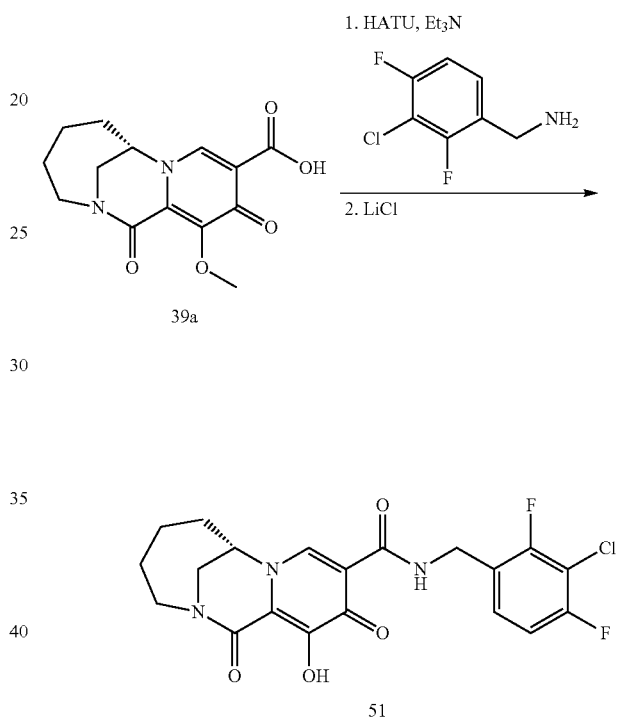

To a solution of (7S)-12-methoxy-1,11-dioxo-1,4,5,6,7,11-hexahydro-3H-2,7-methanopyrido[1,2-a][1,4]diazonine-10-carboxylic acid (39a, 100 mg, 0.31 mmol), (3-chloro-2,4-difluorophenyl)methanamine (82 mg, 0.46 mmol), and triethylamine (0.128 mL, 0.924 mmol) in DCM (2 mL) was added HATU (152 mg, 0.400 mmol). The mixture was stirred at rt for 15 min, then the organic layer was rinsed with 3×1 M HCl, 3×1 M NaOH, and 1×sat aq NaHCO$_3$. The organics were dried over sodium sulfate, filtered, and concentrated to dryness. The residue was dissolved in DMF (1 mL) and lithium chloride (261 mg, 6.16 mmol) was added. The mixture was stirred at 100° C. for 30 minutes, then cooled to room temperature, diluted with aqueous TFA, purified by preparative HPLC (MeCN/water with 0.1% TFA), and lyophilized to provide the title compound (51). MS (m/z) 438.9 [M+H]$^+$. $^1$H NMR (400 MHz, Acetonitrile-d$_3$) δ 10.41 (s, 1H), 8.46 (s, 1H), 7.37 (td, J=8.4, 6.1 Hz, 1H), 7.09 (td, J=8.7, 1.8 Hz, 1H), 4.73-4.53 (m, 3H), 4.24 (ddd, J=13.3, 9.3, 7.3 Hz, 1H), 3.91 (dt, J=14.7, 1.9 Hz, 1H), 3.60 (dd, J=14.8, 1.8 Hz, 1H), 3.18 (ddd, J=13.3, 7.2, 2.7 Hz, 1H), 2.09-1.99 (m, 3H), 1.89-1.59 (m, 2H), 1.38-1.09 (m, 1H).

Example 49: Preparation of (3R,7S)—N-(2,4-difluorobenzyl)-12-hydroxy-3-methyl-1,11-dioxo-1,4,5,6,7,11-hexahydro-3H-2,7-methanopyrido[1,2-a][1,4]diazonine-10-carboxamide, (3S,7R)—N-(2,4-difluorobenzyl)-12-hydroxy-3-methyl-1,11-dioxo-1,4,5,6,7,11-hexahydro-3H-2,7-methanopyrido[1,2-a][1,4]diazonine-10-carboxamide, (3R,7R)—N-(2,4-difluorobenzyl)-12-hydroxy-3-methyl-1,11-dioxo-1,4,5,6,7,11-hexahydro-3H-2,7-methanopyrido[1,2-a][1,4]diazonine-10-carboxamide, and (3S,7S)—N-(2,4-difluorobenzyl)-12-hydroxy-3-methyl-1,11-dioxo-1,4,5,6,7,11-hexahydro-3H-2,7-methanopyrido[1,2-a][1,4]diazonine-10-carboxamide (52-1, 52-2, 52-3, and 52-4)

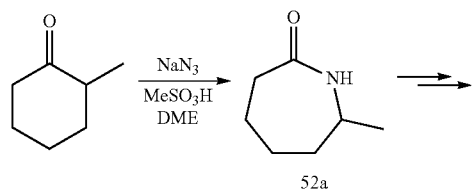

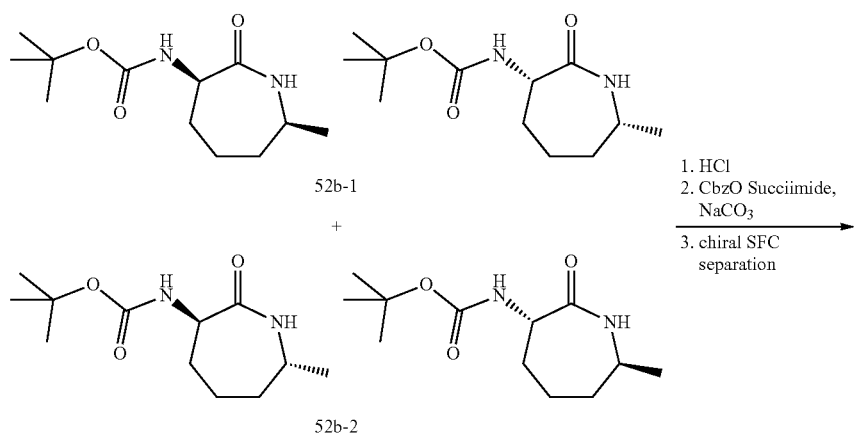

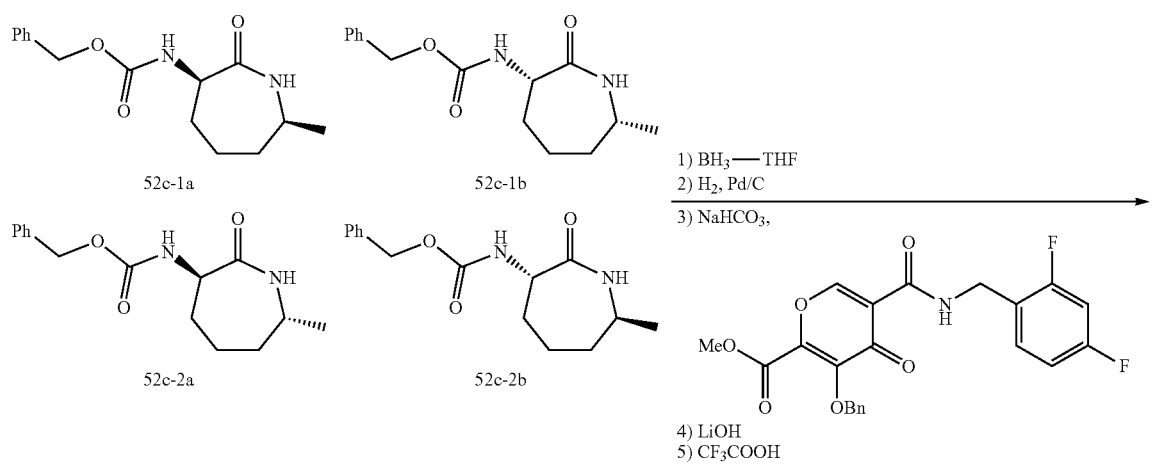

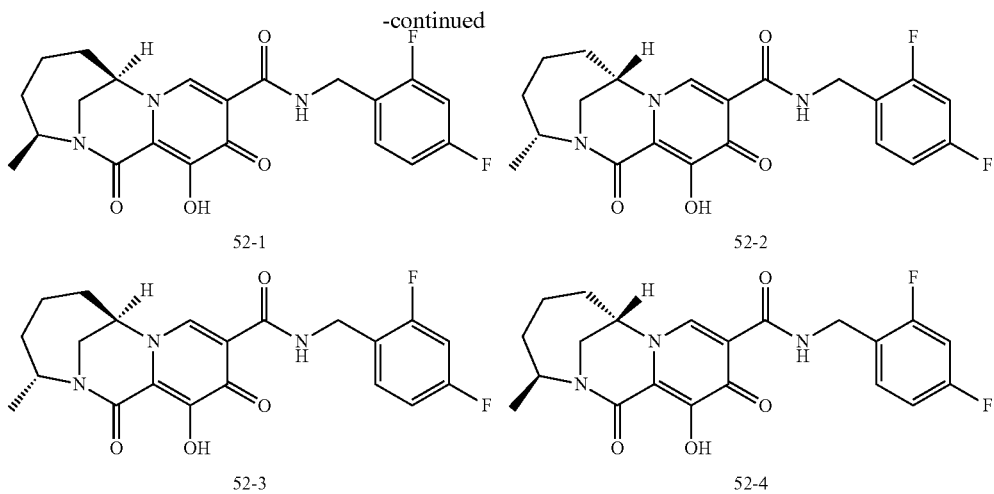

52-1  52-2

52-3  52-4

Synthesis of 7-methylazepan-2-one (52a)

The title compound was prepared in a manner analogous to 50a, using 2-methylcyclohexanone in place of 6,7-difluoro-3,4-dihydronaphthalen-1(2H)-one. MS (m/z) 171.74 [M+H-C$_4$H$_8$]$^+$.

Synthesis of tert-butyl ((syn)- and (trans)-7-methyl-2-oxoazepan-3-yl)carbamate (52b-1 and 52b-2)

The title compounds were prepared in a manner analogous to 43c, using 7-methylazepan-2-one (52a) in place of 6-fluoro-1,3,4,5-tetrahydro-2H-benzo[b]azepin-2-one. Diastereoisomers 52b-1 and 52b-2 were separated via silica gel column chromatography. 52b-1: MS (m/z) 242.73 [M+H]$^+$; 52b-2: MS (m/z) 242.73 [M+H]$^+$.

Synthesis of benzyl ((3S,7R)-, (3R,7S)-, (3R,7R)-, and (3S,7S)-7-methyl-2-oxoazepan-3-yl)carbamate (52c-1a, 52c-1b, 52c-2b, and 52c-2b)

A suspension of tert-butyl ((Z)-7-methyl-2-oxoazepan-3-yl)carbamate (52b-1, 480 mg, 1.981 mmol) in dichloromethane (2 mL) was stirred at rt as 4 N HCl in dioxane (5 mL) was added. After 1 h, the reaction mixture was concentrated and dried under vacuum. A mixture of the resulting residue, N-carbobenzoxyoxysuccinimide (598.3 mg, 2.401 mmol), and sodium carbonate (743.9 mg, 7.019 mmol) in dioxane (5 mL) and water (5 mL) was stirred at rt. After 18 h, the reaction mixture was diluted with ethyl acetate (~60 mL), and washed with water (~10 mL), and brine (~50 mL). The aqueous layer was extracted with ethyl acetate (~60 mL). The organic fractions were washed with brine, combined, dried over MgSO$_4$, and concentrated. The residue was purified by column chromatography on silica gel eluting 0-100% ethyl acetate in hexane to get the racemic benzyl ((Z)-7-methyl-2-oxoazepan-3-yl)carbamate. MS (m/z) 276.94 [M+H]$^+$.

Benzyl ((Z)-7-methyl-2-oxoazepan-3-yl)carbamate was separated into its individual enantiomers by preparative SFC chromatography on an AZ-H column using ethanol-trifluoroacetic acid co-solvent to provide benzyl ((3S,7R)-7-methyl-2-oxoazepan-3-yl)carbamate and benzyl (3R,7S)-7-methyl-2-oxoazepan-3-yl)carbamate (52c-1a and 52c-1b).

Benzyl ((3R,7R)-7-methyl-2-oxoazepan-3-yl)carbamate and benzyl (3S,7S)-7-methyl-2-oxoazepan-3-yl)carbamate (52c-2a, and 52c-2b) were prepared in a similar manner from ((E)-7-methyl-2-oxoazepan-3-yl)carbamate (52b-2).

Synthesis of (3S,7R)—N-(2,4-difluorobenzyl)-12-hydroxy-3-methyl-1,11-dioxo-1,4,5,6,7,11-hexahydro-3H-2,7-methanopyrido[1,2-a][1,4]diazonine-10-carboxamide, (3R,7S)—N-(2,4-difluorobenzyl)-12-hydroxy-3-methyl-1,11-dioxo-1,4,5,6,7,11-hexahydro-3H-2,7-methanopyrido[1,2-a][1,4]diazonine-10-carboxamide, (3R,7R)—N-(2,4-difluorobenzyl)-12-hydroxy-3-methyl-1,11-dioxo-1,4,5,6,7,11-hexahydro-3H-2,7-methanopyrido[1,2-a][1,4]diazonine-10-carboxamide, and (3S,7S)—N-(2,4-difluorobenzyl)-12-hydroxy-3-methyl-1,11-dioxo-1,4,5,6,7,11-hexahydro-3H-2,7-methanopyrido[1,2-a][1,4]diazonine-10-carboxamide (52-1, 52-2, 52-3, and 52-4)

A solution of benzyl (3R,7S)-7-methyl-2-oxoazepan-3-yl)carbamate (52c-2b, 244 mg, 0.883 mmol) in tetrahydrofuran (6 mL) was stirred in ice bath as 1 M borane-THF complex in THF (7.1 mL, 7.1 mmol) was added. The solution was stirred at rt. After 20 h, the reaction mixture was stirred in ice bath, diluted with ethyl acetate (10 mL) and methanol (7-8 mL) was slowly added. After 5 min, the mixture was concentrated to 3 mL, diluted with ethyl acetate (30 mL) and washed with saturated sodium bicarbonate (30 mL) and water. The aqueous fractions were extracted with ethyl acetate (30 mL), the organic fractions were combined, dried over MgSO$_4$, and concentrated.

The crude amine was dissolved in ethanol (5 mL), and 10% palladium on carbon (38.8 mg) was added. The resulting mixture was stirred under H$_2$ atmosphere for 1 h. The mixture was filtered through celite, the pad washed with ethanol, and the filtrate concentrated to get the crude diamine.

A mixture of methyl 3-(benzyloxy)-5-((2,4-difluorobenzyl)carbamoyl)-4-oxo-4H-pyran-2-carboxylate (385.8 mg, 0.846 mmol), the crude diamine, and sodium bicarbonate (171.5 mg, 2.042 mmol) in water (2 mL) and methanol (10 mL) was stirred at rt overnight, and then at 50° C. for 2 h. The reaction mixture was concentrated to remove most of the solvent and diluted with ethyl acetate (40 mL) and brine (40 mL), and two fractions were separated. The aqueous layer was extracted with ethyl acetate (40 mL), and combined organic layer was washed with brine, dried over MgSO₄, and concentrated. To the solution of the residue in methanol (10 mL) was added 1N lithium hydroxide (5 mL) and the resulting mixture was stirred in 50° C. bath for 1 h. The reaction mixture was neutralized with 2 N HCl (~2.5 mL), concentrated to remove methanol, and the remained aqueous residue was diluted with water before extracting with ethyl acetate (40 mL×2). The organic extracts were washed with brine (×1), combined, dried (MgSO₄) and concentrated. The residue was purified by column chromatography on silica gel eluting 0-6% methanol in dichloromethane to get (3S,7R)-12-(benzyloxy)-N-(2,4-difluorobenzyl)-3-methyl-1,11-dioxo-1,4,5,6,7,11-hexahydro-3H-2,7-methanopyrido[1,2-a][1,4]diazonine-10-carboxamide. MS (m/z) 508.20 [M+H]⁺.

(3S,7R)-12-(Benzyloxy)-N-(2,4-difluorobenzyl)-3-methyl-1,11-dioxo-1,4,5,6,7,11-hexahydro-3H-2,7-methanopyrido[1,2-a][1,4]diazonine-10-carboxamide (238.4 mg, 0.470 mmol) was dissolved in toluene (1 mL) and trifluoroacetic acid (4 mL) and stirred at rt for 30 min. The reaction mixture was concentrated and the residue was purified by preparative HPLC, eluting 20-53% acetonitrile (0.1% trifluoroacetic acid) in water (0.1% trifluoroacetic acid)) followed by freeze-drying to afford (3R,7S)—N-(2,4-difluorobenzyl)-12-hydroxy-3-methyl-1,11-dioxo-1,4,5,6,7,11-hexahydro-3H-2,7-methanopyrido[1,2-a][1,4]diazonine-10-carboxamide (52-1).

(3S,7R)—N-(2,4-difluorobenzyl)-12-hydroxy-3-methyl-1,11-dioxo-1,4,5,6,7,11-hexahydro-3H-2,7-methanopyrido[1,2-a][1,4]diazonine-10-carboxamide, (3R,7R)—N-(2,4-difluorobenzyl)-12-hydroxy-3-methyl-1,11-dioxo-1,4,5,6,7,11-hexahydro-3H-2,7-methanopyrido[1,2-a][1,4]diazonine-10-carboxamide, and (3S,7S)—N-(2,4-difluorobenzyl)-12-hydroxy-3-methyl-1,11-dioxo-1,4,5,6,7,11-hexahydro-3H-2,7-methanopyrido[1,2-a][1,4]diazonine-10-carboxamide (52-2, 52-3, and 52-4) were prepared in an analogous manner from benzyl (3R,7S)-7-methyl-2-oxoazepan-3-yl)carbamate, benzyl (3R,7R)-7-methyl-2-oxoazepan-3-yl)carbamate, and benzyl (3S,7S)-7-methyl-2-oxoazepan-3-yl)carbamate (52c-1b, 52c-2b, and 52c-2b), respectively.

52-1: MS (m/z) 418.23 [M+H]⁺. ¹H NMR (400 MHz, Methanol-d₄) δ 8.43 (s, 1H), 7.52-7.28 (m, 1H), 7.05-6.80 (m, 2H), 4.61 (s, 3H), 3.92 (d, J=14.7 Hz, 1H), 3.68 (dd, J=14.8, 2.6 Hz, 1H), 3.53 (s, 1H), 2.64 (dd, J=16.0, 7.9 Hz, 1H), 2.09-1.95 (m, 1H), 1.84-1.72 (m, 3H), 1.76 (d, J=7.1 Hz, 3H), 1.59-1.43 (m, 1H). ¹⁹F NMR (376 MHz, Methanol-d₄) δ −114.00 (q, J=7.8 Hz), −116.90 (q, J=8.8 Hz).

52-2: MS (m/z) 418.23 [M+H]⁺. ¹H NMR (400 MHz, Methanol-d₄) δ 8.43 (s, 1H), 7.41 (q, J=8.2 Hz, 1H), 6.93 (q, J=9.5, 9.1 Hz, 2H), 4.61 (s, 3H), 3.92 (d, J=14.9 Hz, 1H), 3.68 (dd, J=14.9, 2.6 Hz, 1H), 3.61-3.49 (m, 1H), 2.64 (dd, J=16.1, 7.9 Hz, 1H), 2.03 (t, J=7.4 Hz, 1H), 1.86-1.72 (m, 3H), 1.76 (d, J=7.1 Hz, 3H), 1.52 (s, 1H). ¹⁹F NMR (376 MHz, Methanol-d₄) δ −113.99 (t, J=7.9 Hz), −116.90 (q, J=8.6 Hz).

52-3: MS (m/z) 418.24 [M+H]⁺. ¹H NMR (400 MHz, Methanol-d₄) δ 8.46 (s, 1H), 7.41 (td, J=8.5, 6.4 Hz, 1H), 7.03-6.83 (m, 2H), 4.67 (s, 1H), 4.62 (s, 2H), 4.57 (ddd, J=13.3, 8.7, 5.4 Hz, 1H), 3.74 (s, 2H), 2.15 (td, J=15.9, 15.1, 8.0 Hz, 2H), 2.01-1.85 (m, 1H), 1.74 (ddt, J=15.4, 7.7, 4.0 Hz, 1H), 1.52 (dt, J=14.8, 11.1 Hz, 1H), 1.27 (d, J=6.7 Hz, 3H), 1.23-1.07 (m, 1H). ¹⁹F NMR (376 MHz, Methanol-d₄) δ −78.26, −113.94 (ddd, J=15.4, 8.7, 6.9 Hz), −116.87 (q, J=8.4 Hz).

52-4: MS (m/z) 418.23 [M+H]⁺. ¹H NMR (400 MHz, Methanol-d₄) δ 8.46 (s, 1H), 7.41 (td, J=8.5, 6.3 Hz, 1H), 7.02-6.84 (m, 2H), 4.72-4.63 (m, 1H), 4.61 (s, 2H), 4.60-4.52 (m, 1H), 3.75 (t, J=1.6 Hz, 2H), 2.15 (td, J=15.7, 14.9, 7.9 Hz, 2H), 1.93 (ddt, J=18.8, 15.6, 4.3 Hz, 1H), 1.74 (ddt, J=15.3, 7.7, 3.9 Hz, 1H), 1.51 (dt, J=14.8, 11.1 Hz, 1H), 1.27 (d, J=6.7 Hz, 3H), 1.22-1.04 (m, 1H). ¹⁹F NMR (376 MHz, Methanol-d₄) δ −78.28, −113.93 (ddd, J=15.4, 8.5, 6.7 Hz), −116.86 (q, J=8.4 Hz).

Example 50a: Preparation of (4R,7S)—N-(2,4-difluorobenzyl)-4-fluoro-12-hydroxy-1,11-dioxo-1,4,5,6,7,11-hexahydro-3H-2,7-methanopyrido[1,2-a][1,4]diazonine-10-carboxamide and (4S,7S)—N-(2,4-difluorobenzyl)-4-fluoro-12-hydroxy-1,11-dioxo-1,4,5,6,7,11-hexahydro-3H-2,7-methanopyrido[1,2-a][1,4]diazonine-10-carboxamide (53-1 and 53-2) (SDS1, Diastereomer 1)

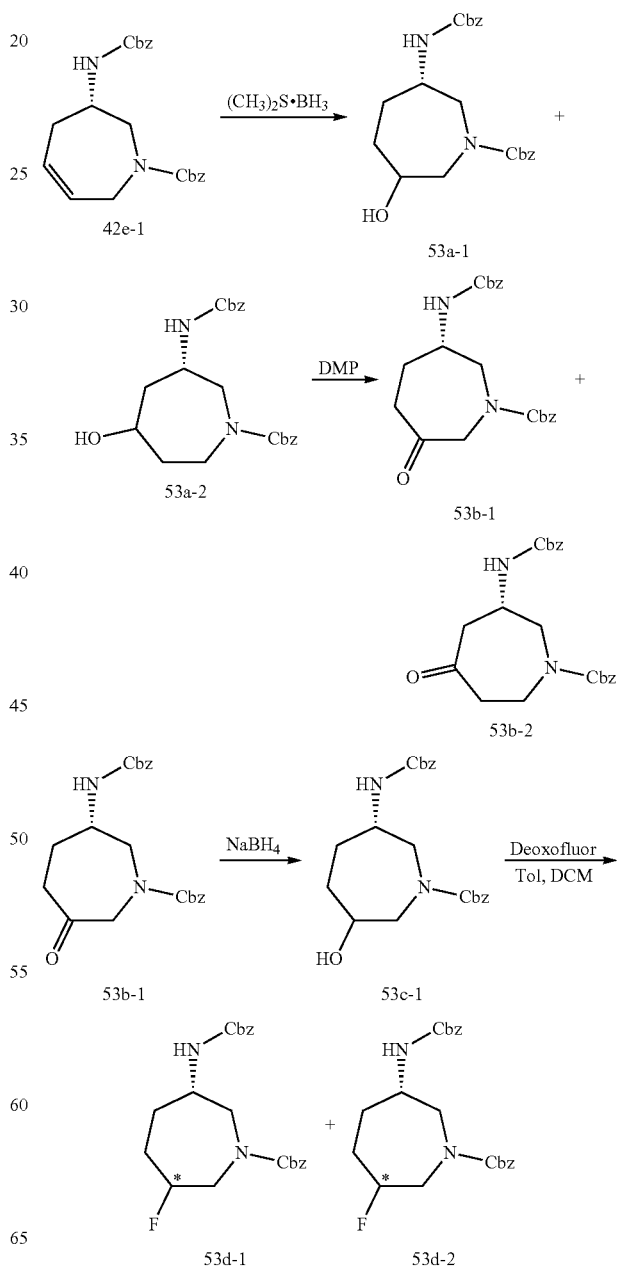

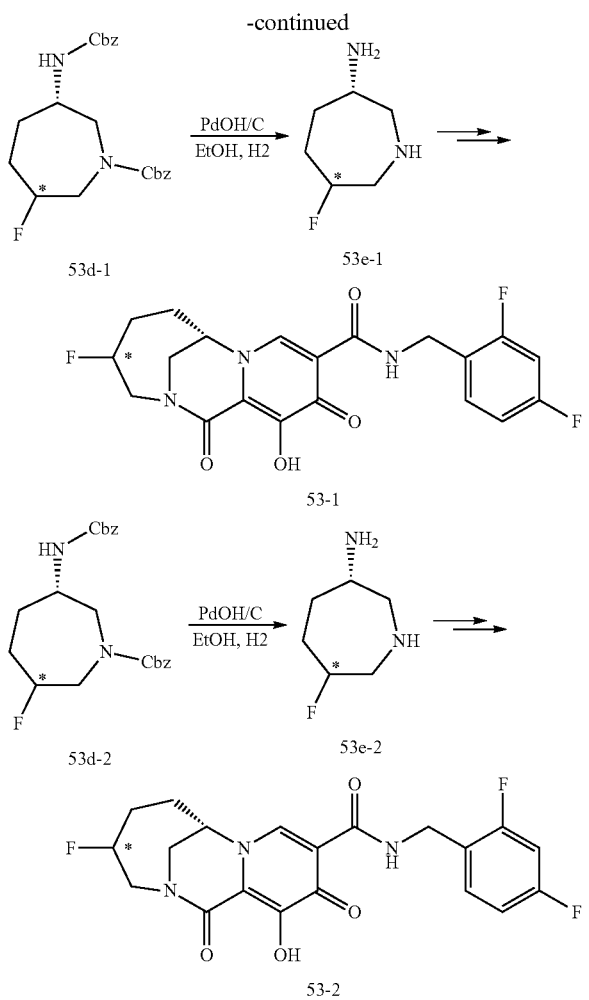

Synthesis of benzyl (3S)-3-(((benzyloxy)carbonyl)amino)-6-hydroxyazepane-1-carboxylate and benzyl (3S)-3-(((benzyloxy)carbonyl)amino)-5-hydroxyazepane-1-carboxylate (53a-1 and 53a-2)

To a solution of benzyl (S)-3-(((benzyloxy)carbonyl)amino)-2,3,4,7-tetrahydro-1H-azepine-1-carboxylate (42e-1, 6.0 g, 15.8 mmol) in THF (100 mL) at 0° C., borane dimethyl sulfide complex (4.5 mL, 47.3 mmol) was added. The solution was allowed to warm to rt, stirred overnight, and quenched with 2 M sodium hydroxide (9.5 mL) and hydrogen peroxide (2.7 mL, 78.9 mmol) at 0° C., stirring for 3 hr. The peroxide was quenched with sodium thiosulfate. The reaction was extracted twice with EtOAc, and the organic layer was dried over sodium sulfate, concentrated, and purified by silica gel chromatography to give the title compounds (53a-1 and 53a-2), as a mixture of regioisomers. MS (m/z) 399.4 [M+H]$^+$.

Synthesis of benzyl (S)-3-(((benzyloxy)carbonyl)amino)-6-oxoazepane-1-carboxylate (53b-1) and benzyl (S)-3-(((benzyloxy)carbonyl)amino)-5-oxoazepane-1-carboxylate (53b-2)

To a solution of the mixture of benzyl (3S)-3-(((benzyloxy)carbonyl)amino)-5-hydroxyazepane-1-carboxylate and benzyl (3S)-3-(((benzyloxy)carbonyl)amino)-6-hydroxyazepane-1-carboxylate (53a-1 and 53a-2, 4.2 g, 10.6 mmol) in DCM (100 mL) at 0° C., was added Dess Martin periodinane (5.4 g, 12.8 mmol). The reaction was allowed to warm to rt, and stirred overnight. The reaction was quenched with sat. sodium sulfite and extracted twice with EtOAc. The organic layer was dried over sodium sulfate, concentrated, and purified by silica gel chromatography to give 53b-1 as the earlier eluting isomer, and 53b-2 as the later. 53b-1: MS (m/z) 397.3 [M+H]$^+$; 53b-2: MS (m/z) 397.0 [M+H]$^+$.

Synthesis of benzyl (3S)-3-(((benzyloxy)carbonyl)amino)-6-hydroxyazepane-1-carboxylate (53c-1)

A solution of benzyl (S)-3-(((benzyloxy)carbonyl)amino)-6-oxoazepane-1-carboxylate (53b-1, 400 mg, 1 mmol) and NaBH$_4$ (76 mg, 2 mmol) in methanol (10 mL) was stirred at rt for 1 hr. It was quenched with saturated NH$_4$Cl and extracted twice with EtOAc. The organic layer was dried over sodium sulfate, filtered, and concentrated, to give the title compound (53c-1), which was used subsequently without further purification. MS (m/z) 399.3 [M+H]$^+$.

Synthesis of benzyl (3S,6R)- and (3S,6S)-3-(((benzyloxy)carbonyl)amino)-6-fluoroazepane-1-carboxylate (53d-1 and 53d-2)

To a solution of benzyl (3S)-3-(((benzyloxy)carbonyl)amino)-6-fluoroazepane-1-carboxylate (53c-1, 300 mg, 0.8 mmol) in DCM (10 mL) at 0° C. in a Teflon bottle was slowly added deoxofluor (50% in toluene, 1.4 mL, 3.8 mmol). The mixture was allowed to warm to rt and stirred overnight. The mixture was cooled to 0° C., quenched with sat. sodium bicarbonate and stirred for 15 minutes, before extracting twice with DCM. Organic layer was dried over sodium sulfate and purified by silica gel chromatography to obtain the title compounds, stereochemistry assigned arbitrarily. 53d-1: MS (m/z) 401.7 [M+H]$^+$; 53d-2: MS (m/z) 401.7 [M+H]$^+$.

Synthesis of (3S,6R)-6-fluoroazepan-3-amine and (3S,6S)-6-fluoroazepan-3-amine (53e-1 and 53e-2)

To a solution of (3S,6R)-6-fluoroazepan-3-amine or (3S,6S)-3-(((benzyloxy)carbonyl)amino)-6-fluoroazepane-1-carboxylate (53d-1 or 53d-2, 82 mg, 0.2 mmol), in ethanol (8 mL), was added PdOH/C (28.8 mg, 0.04 mmol). The mixture was sparged with N$_2$, and a balloon of H$_2$ was added. It was stirred 2 hr, then the mixture was filtered over Celite®. Mixture was concentrated to give the title compounds (53e-1 or 53e-2), which were used subsequently without further purification. MS (m/z) 133.7 [M+H]$^+$.

Synthesis of (4R,7S)—N-(2,4-difluorobenzyl)-4-fluoro-12-hydroxy-1,11-dioxo-1,4,5,6,7,11-hexahydro-3H-2,7-methanopyrido[1,2-a][1,4]diazonine-10-carboxamide and (4S,7S)—N-(2,4-difluorobenzyl)-4-fluoro-12-hydroxy-1,11-dioxo-1,4,5,6,7,11-hexahydro-3H-2,7-methanopyrido[1,2-a][1,4]diazonine-10-carboxamide (53-1 and 53-2)

The title compounds were prepared analogously to 44-1 and 44-2, using (3S,6R)-6-fluoroazepan-3-amine and (3S,6S)-6-fluoroazepan-3-amine (53e-1 and 53e-2) in place of benzyl (R,Z)-3-(((benzyloxy)carbonyl)amino)-3,4,7,8-tetrahydroazocine-1(2H)-carboxylate or benzyl (S,Z)-3-(((benzyloxy)carbonyl)amino)-3,4,7,8-tetrahydroazocine-1(2H)-carboxylate (44a-2 and 44b-2).

53-1: MS (m/z) 422.2 [M+H]+. 1H NMR (400 MHz, Chloroform-d) δ 10.45 (s, 1H), 8.52 (s, 1H), 7.43-7.34 (m, 1H), 6.91-6.76 (m, 2H), 5.31-5.11 (m, 1H), 4.78-4.61 (m, 1H), 4.70-4.66 (m, 2H), 4.53 (s, 1H), 4.02 (d, 1H), 3.80-3.72 (m, 1H), 3.49 (dd, 1H), 2.55-2.40 (m, 1H), 2.38-2.25 (m, 1H), 2.14-2.00 (m, 1H), 1.68-1.41 (m, 1H).

53-2: MS (m/z) 422.2 [M+H]+. 1H NMR (400 MHz, Chloroform-d) δ 10.50 (t, 1H), 8.51 (s, 1H), 7.42-7.32 (m, 1H), 6.88-6.75 (m, 2H), 5.13-4.91 (m, 1H), 4.86-4.73 (m, 1H), 4.72-4.59 (m, 2H), 4.58-4.47 (m, 1H), 4.00 (dd, 1H), 3.49 (dd, 1H), 3.29 (ddd, 1H), 2.47-2.33 (m, 1H), 2.31-2.20 (m, 1H), 2.13-1.99 (m, 1H), 1.98-1.84 (m, 1H).

Example 50b: Preparation of (4S,7R)—N-(2,4-difluorobenzyl)-4-fluoro-12-hydroxy-1,11-dioxo-1,4,5,6,7,11-hexahydro-3H-2,7-methanopyrido[1,2-a][1,4]diazonine-10-carboxamide and (4R,7S)—N-(2,4-difluorobenzyl)-4-fluoro-12-hydroxy-1,11-dioxo-1,4,5,6,7,11-hexahydro-3H-2,7-methanopyrido[1,2-a][1,4]diazonine-10-carboxamide (53-3 and 53-4)

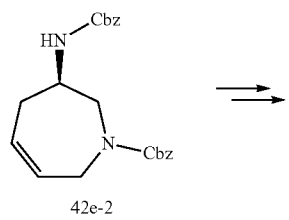

42e-2

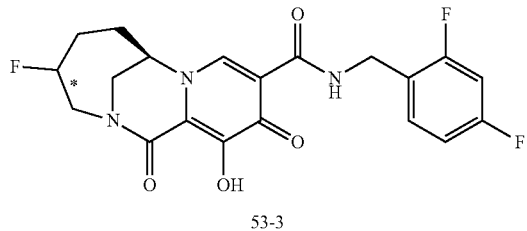

53-3

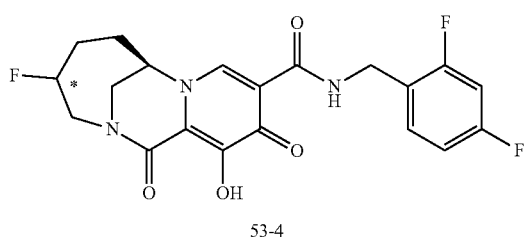

53-4

The title compounds were prepared analogously to 53-1 and 53-2, using benzyl (R)-3-(((benzyloxy)carbonyl)amino)-2,3,4,7-tetrahydro-1H-azepine-1-carboxylate (42e-2) in place of benzyl (S)-3-(((benzyloxy)carbonyl)amino)-2,3,4,7-tetrahydro-1H-azepine-1-carboxylate (42e-1).

53-3: MS (m/z) 422.2 [M+H]+. 1H NMR (400 MHz, Chloroform-d) δ 10.37 (t, 1H), 8.47 (s, 1H), 7.43-7.32 (m, 1H), 6.90-6.76 (m, 2H), 5.34-5.09 (m, 1H), 4.78-4.61 (m, 1H), 4.69-4.65 (m, 2H), 4.57-4.44 (m, 1H), 4.07-3.95 (m, 1H), 3.75 (dd, 1H), 3.49 (dd, 1H), 2.48 (dddd, 1H), 2.31 (ddt, 1H), 2.15-2.01 (m, 1H), 1.55 (dddd, 1H).

53-4: MS (m/z) 422.2 [M+H]+. 1H NMR (400 MHz, Chloroform-d) δ 10.44 (s, 1H), 8.46 (s, 1H), 7.44-7.34 (m, 1H), 6.90-6.77 (m, 2H), 5.14-4.92 (m, 1H), 4.90-4.74 (m, 1H), 4.74-4.57 (m, 2H), 4.56-4.41 (m, 1H), 4.07-3.90 (m, 1H), 3.49 (dd, 1H), 3.29 (ddd, 1H), 2.46-2.32 (m, 1H), 2.32-2.15 (m, 1H), 2.15-1.80 (m, 2H).

Example 51: Preparation of (7S)—N-(2-fluoro-3-methoxybenzyl)-12-methoxy-1,11-dioxo-1,4,5,6,7,11-hexahydro-3H-2,7-methanopyrido[1,2-a][1,4]diazonine-10-carboxamide (54)

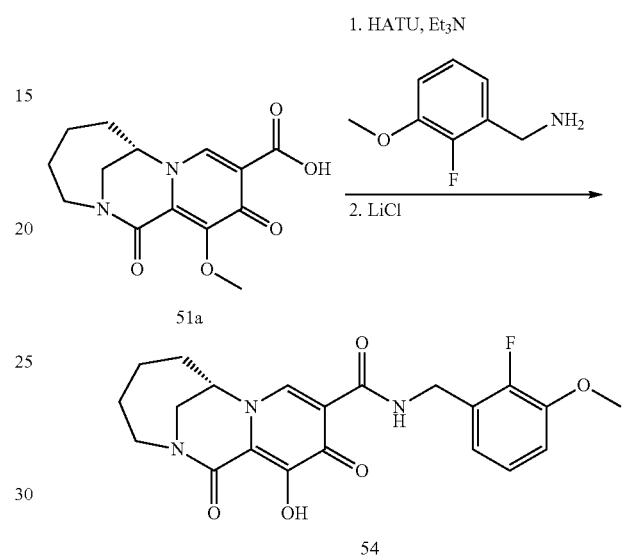

54

The title compound was prepared from (7S)-12-methoxy-1,11-dioxo-1,4,5,6,7,11-hexahydro-3H-2,7-methanopyrido[1,2-a][1,4]diazonine-10-carboxylic acid (51a) and (2-fluoro-3-methoxyphenyl)methanamine according to the method described for compound 51. MS (m/z) 416.2 [M+H]+. 1H NMR (400 MHz, Acetonitrile-d3) δ 10.19 (s, 1H), 8.44 (s, 1H), 7.11 (td, J=7.9, 1.4 Hz, 1H), 7.03 (td, J=8.2, 1.7 Hz, 1H), 6.99-6.90 (m, 1H), 4.67-4.57 (m, 3H), 4.25 (ddd, J=13.3, 9.3, 7.4 Hz, 1H), 3.96-3.83 (m, 4H), 3.61 (dd, J=14.8, 1.9 Hz, 1H), 3.18 (ddd, J=13.3, 7.2, 2.7 Hz, 1H), 2.07-2.00 (m, 2H), 1.90-1.68 (m, 2H), 1.40-1.15 (m, 1H).

Example 52: Preparation of (12S)-2-fluoro-7-hydroxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide and (12R)-2-fluoro-7-hydroxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide (55-1 and 55-2)

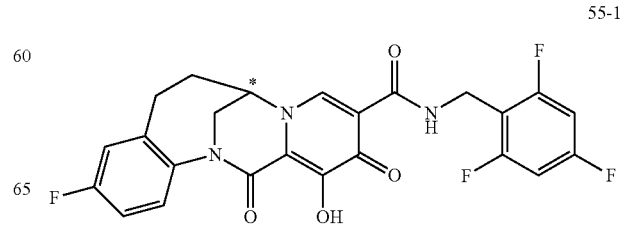

55-1

-continued

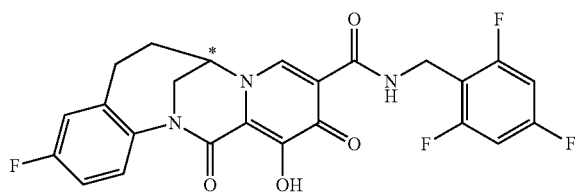
55-2

The title compounds were prepared similarly to compounds 50-1 and 50-2 using 7-fluoro-1,3,4,5-tetrahydro-2H-benzo[b]azepin-2-one in place of 6-fluoro-1,3,4,5-tetrahydro-2H-benzo[b]azepin-2-one.

55-1: MS (m/z) 470.1 [M+H]⁺. ¹H NMR (400 MHz, DMSO-d₆) δ 10.32 (t, J=5.9 Hz, 1H), 8.58 (s, 1H), 7.38 (td, J=9.7, 8.8, 6.2 Hz, 2H), 7.23 (ddd, J=9.5, 7.1, 2.8 Hz, 2H), 7.15-7.09 (m, 1H), 7.08-7.02 (m, 1H), 4.88 (d, J=5.0 Hz, 1H), 4.55 (d, J=5.9 Hz, 2H), 4.14 (d, J=14.6 Hz, 1H), 3.72 (dd, J=14.7, 2.0 Hz, 1H), 2.85-2.76 (m, 1H), 2.70 (dd, J=14.7, 12.0 Hz, 1H), 2.30-2.20 (m, 1H), 2.12-1.99 (m, 1H).

55-2: MS (m/z) 470 [M+H]⁺. ¹H NMR (400 MHz, DMSO-d₆) δ 10.32 (t, J=5.9 Hz, 1H), 8.58 (s, 1H), 7.46-7.32 (m, 2H), 7.22 (ddt, J=9.8, 5.9, 2.7 Hz, 2H), 7.16-7.07 (m, 1H), 7.08-6.99 (m, 1H), 4.88 (t, J=2.5 Hz, 1H), 4.55 (d, J=5.9 Hz, 2H), 4.14 (d, J=14.5 Hz, 1H), 3.74 (d, J=2.0 Hz, 1H), 2.80 (ddd, J=10.8, 8.3, 4.0 Hz, 1H), 2.75-2.66 (m, 1H), 2.30-2.20 (m, 1H), 2.10 (t, J=6.8 Hz, 1H).

Example 53a: (5S,7S)—N-(2,4-difluorobenzyl)-5-fluoro-12-hydroxy-1,11-dioxo-1,4,5,6,7,11-hexahydro-3H-2,7-methanopyrido[1,2-a][1,4]diazonine-10-carboxamide and (5R,7S)—N-(2,4-difluorobenzyl)-5-fluoro-12-hydroxy-1,11-dioxo-1,4,5,6,7,11-hexahydro-3H-2,7-methanopyrido[1,2-a][1,4]diazonine-10-carboxamide (56-1 and 56-2)

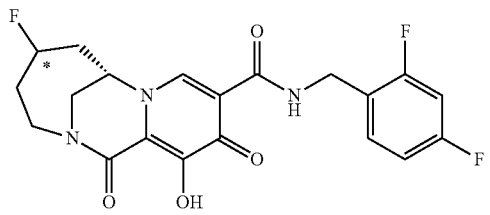
56-1

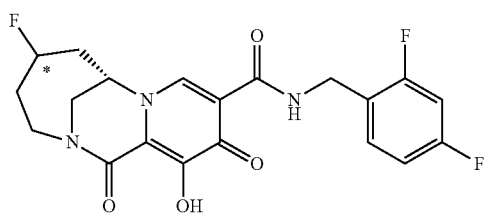
56-2

The title compounds were synthesized in a manner similar to 53-1 and 53-2, using benzyl (S)-3-(((benzyloxy)carbonyl)amino)-5-oxoazepane-1-carboxylate (53b-2) in place of benzyl (S)-3-(((benzyloxy)carbonyl)amino)-6-oxoazepane-1-carboxylate (53b-1), and separating the stereoisomers as the benzyl protected alcohol instead of prior to amide coupling.

56-1: MS (m/z) 422.3 [M+H]⁺. ¹H NMR (400 MHz, Chloroform-d) δ 10.53 (t, 1H), 8.52 (s, 1H), 7.43-7.32 (m, 1H), 6.88-6.71 (m, 2H), 5.26-4.99 (m, 1H), 4.73-4.59 (m, 3H), 4.51 (ddd, 1H), 4.10-3.96 (m, 1H), 3.57 (dd, 1H), 3.27 (ddd, 1H), 2.57-2.42 (m, 2H), 2.38-2.24 (m, 1H), 2.24-2.05 (m, 1H).

56-2: MS (m/z) 422.3 [M+H]⁺. ¹H NMR (400 MHz, Chloroform-d) δ 10.33 (t, 1H), 8.46 (s, 1H), 7.42-7.32 (m, 1H), 6.92-6.75 (m, 2H), 5.02-4.84 (m, 1H), 4.74-4.61 (m, 2H), 4.61-4.48 (m, 2H), 4.03-3.94 (m, 1H), 3.81 (dd, 1H), 3.26-3.08 (m, 1H), 2.90-2.72 (m, 1H), 2.37-2.23 (m, 1H), 2.23-1.94 (m, 2H).

Example 53b: (5S,7R)—N-(2,4-difluorobenzyl)-5-fluoro-12-hydroxy-1,11-dioxo-1,4,5,6,7,11-hexahydro-3H-2,7-methanopyrido[1,2-a][1,4]diazonine-10-carboxamide and (5R,7R)—N-(2,4-difluorobenzyl)-5-fluoro-12-hydroxy-1,11-dioxo-1,4,5,6,7,11-hexahydro-3H-2,7-methanopyrido[1,2-a][1,4]diazonine-10-carboxamide (56-3 and 56-4)

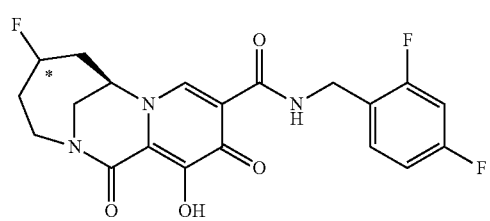
56-3

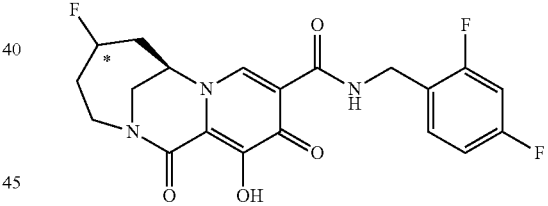
56-4

The title compounds were synthesized in a manner similar to 56-1 and 56-2, using benzyl (R)-3-(((benzyloxy)carbonyl)amino)-2,3,4,7-tetrahydro-1H-azepine-1-carboxylate (42e-2) in place of benzyl (S)-3-(((benzyloxy)carbonyl)amino)-2,3,4,7-tetrahydro-1H-azepine-1-carboxylate (42e-1), and separating the stereoisomers as the benzyl protected alcohol instead of prior to amide coupling.

56-3: MS (m/z) 422.1 [M+H]⁺. ¹H NMR (400 MHz, Chloroform-d) δ 10.54 (t, 1H), 8.50 (s, 1H), 7.41-7.34 (m, 1H), 6.89-6.70 (m, 1H), 5.13 (dt, 1H), 4.76-4.62 (m, 2H), 4.60-4.46 (m, 2H), 4.04 (d, 1H), 3.57 (dd, 1H), 3.27 (ddd, 1H), 2.60-2.43 (m, 2H), 2.42-2.26 (m, 1H), 2.25-1.97 (m, 1H).

56-4: MS (m/z) 422.2 [M+H]⁺. ¹H NMR (400 MHz, Chloroform-d) δ 10.39 (s, 1H), 8.49 (s, 1H), 7.44-7.33 (m, 1H), 6.90-6.76 (m, 2H), 5.08-4.87 (m, 1H), 4.67 (d, 2H), 4.61-4.55 (m, 1H), 4.54 (d, 1H), 3.99 (d, 1H), 3.82 (dd, 1H), 3.19 (dt, 1H), 2.90-2.72 (m, 1H), 2.40-2.23 (m, 1H), 2.23-2.13 (m, 1H), 2.13-1.87 (m, 1H).

Example 54: Preparation of (7'S)—N-(2,4-difluorobenzyl)-12'-hydroxy-1',11'-dioxo-1',4',5',11'-tetrahydro-3'H,7'H-spiro[cyclopropane-1,6'-[2,7]methanopyrido[1,2-a][1,4]diazonine]-10'-carboxamide and (7'R)—N-(2,4-difluorobenzyl)-12'-hydroxy-1',11'-dioxo-1',4',5',11'-tetrahydro-3'H,7'H-spiro[cyclopropane-1,6'-[2,7]methanopyrido[1,2-a][1,4]diazonine]-10'-carboxamide (57-1 and 57-2)

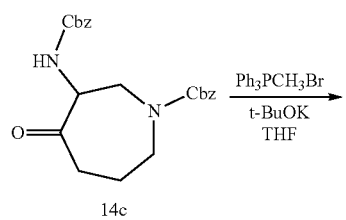

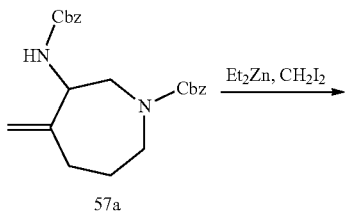

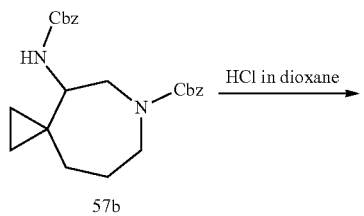

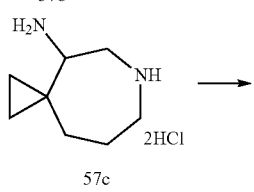

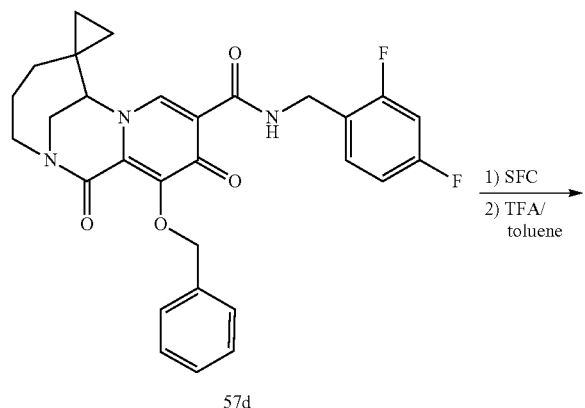

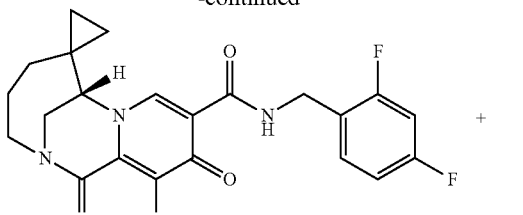

peak 1
57-1

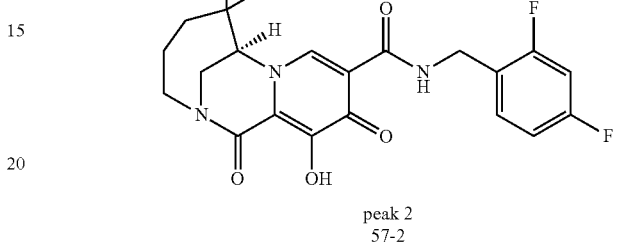

peak 2
57-2

Synthesis of benzyl 3-(((benzyloxy)carbonyl)amino)-4-methyleneazepane-1-carboxylate (57a)

To a suspension of methyltriphenylphosphonium bromide (1.44 g, 4.04 mmol) in anhydrous THF (15 mL) in ice-water bath, was added potassium t-butoxide (368 mg, 3.28 mmol) under nitrogen atmosphere. The resulting suspension was stirred at 0° C. for 30 min then at room temperature for 10 min. A solution of benzyl 3-(benzyloxycarbonylamino)-4-oxo-azepane-1-carboxylate (14c, 400 mg, 1.01 mmol) in THF (8 mL) was added. The reaction mixture was allowed to stir for 1 h and brine was added to quench the reaction. It was extracted with ethyl acetate. The organic layer was separated, dried over MgSO$_4$, filtered, and concentrated to dryness. The residue was purified by silica gel chromatography eluting with ethyl acetate in hexane to afford the title product (57a). MS (m/z) 395.66 [M+H]$^+$.

Synthesis of benzyl 4-(((benzyloxy)carbonyl)amino)-6-azaspiro[2.6]nonane-6-carboxylate (57b)

A flask was charged with a solution of CH$_2$I$_2$ (1.97 g, 7.35 mmol) in anhydrous toluene (10 mL) under Argon at 0° C. Diethylzinc solution (5.88 mL, 5.88 mmol, 1.0 M in hexane) was added. The mixture was stirred for 15 min, and a solution of benzyl 3-(benzyloxycarbonylamino)-4-methylene-azepane-1-carboxylate (57a, 290 mg, 0.735 mmol) in toluene (10 mL) was added. The reaction mixture was stirred at room temperature for 3 days, then quenched with aqueous saturated NH$_4$Cl and extracted with ethyl acetate. The organic layer was separated, dried over Na$_2$SO$_4$ and concentrated to dryness. The residue was purified by silica gel chromatography eluting with ethyl acetate in hexane to afford the title product (57b). MS (m/z) 409.89 [M+H]$^+$.

Synthesis of 6-azaspiro[2.6]nonan-4-amine; dihydrochloride (57c)

Benzyl 4-(((benzyloxy)carbonyl)amino)-6-azaspiro[2.6]nonane-6-carboxylate (57b, 95 mg, 0.233 mmol) was charged into in a sealed 40 mL pressure vial. To it was added 5 mL of HCl in dioxane (4 M). The reaction was heated to 95° C. overnight, and cooled to room temperature. Solvent was removed to afford the title product (57c). MS (m/z) 141.15 [M+H]⁺.

Synthesis of 12'-(benzyloxy)-N-(2,4-difluorobenzyl)-1',11'-dioxo-1',4',5',11'-tetrahydro-3'H,7'H-spiro [cyclopropane-1,6'-[2,7]methanopyrido[1,2-a][1,4] diazonine]-10'-carboxamide (57d)

The title product was prepared in a manner similar to 28a using 6-azaspiro[2.6]nonan-4-amine dihydrochloride (57c) instead of 1,4-oxazepan-6-amine. MS (m/z) 520.20 [M+H]⁺.

Synthesis of (7'S)—N-(2,4-difluorobenzyl)-12'-hydroxy-1',11'-dioxo-1',4',5',11'-tetrahydro-3'H,7'H-spiro[cyclopropane-1,6'-[2,7]methanopyrido[1,2-a] [1,4]diazonine]-10'-carboxamide and (7'R)—N-(2,4-difluorobenzyl)-12'-hydroxy-1',11'-dioxo-1',4',5',11'-tetrahydro-3'H,7'H-spiro[cyclopropane-1,6'-[2,7] methanopyrido[1,2-a][1,4]diazonine]-10'-carboxamide (57-1 and 57-2)

12'-(benzyloxy)-N-(2,4-difluorobenzyl)-1',11'-dioxo-1', 4',5',11'-tetrahydro-3'H,7'H-spiro[cyclopropane-1,6'-[2,7] methanopyrido[1,2-a][1,4]diazonine]-10'-carboxamide (57d) was separated into its individual enantiomers by preparative SFC chromatography on an OD-H column using MeOH cosolvent. The separated enantiomers were dissolved in 1 mL of Toluene and 1 mL of TFA and stirred at room temperature for 1 h. The reactions were concentrated, and purified by RP-HPLC eluting with ACN/water (0.1% TFA) to provide the title compounds.

57-1: MS (m/z) 430.24 [M+H]⁺. ¹H NMR (400 MHz, DMSO-d₆) δ 10.84 (s, 1H), 10.40 (t, J=5.9 Hz, 1H), 8.42 (s, 1H), 7.41 (td, J=8.7, 6.6 Hz, 1H), 7.26 (ddd, J=10.5, 9.3, 2.6 Hz, 1H), 7.07 (tdd, J=8.6, 2.6, 1.0 Hz, 1H), 4.55 (d, J=5.9 Hz, 2H), 4.22 (dt, J=13.2, 8.9 Hz, 1H), 4.04 (d, J=2.2 Hz, 1H), 3.96 (dd, J=14.6, 2.7 Hz, 1H), 3.75 (dd, J=14.6, 1.8 Hz, 1H), 3.23-3.13 (m, 1H), 1.95-1.84 (m, 2H), 1.49-1.38 (m, 1H), 0.77 (qt, J=10.6, 5.8 Hz, 3H), 0.55-0.39 (m, 2H).

57-2: MS (m/z) 430.21 [M+H]⁺. ¹H NMR (400 MHz, DMSO-d₆) δ 10.84 (s, 1H), 10.40 (t, J=5.9 Hz, 1H), 8.42 (s, 1H), 7.42 (td, J=8.7, 6.6 Hz, 1H), 7.26 (ddd, J=10.5, 9.3, 2.6 Hz, 1H), 7.07 (tdd, J=8.6, 2.6, 1.1 Hz, 1H), 4.55 (d, J=5.8 Hz, 2H), 4.22 (dt, J=13.2, 8.8 Hz, 1H), 4.04 (d, J=2.2 Hz, 1H), 3.96 (dd, J=14.5, 2.7 Hz, 1H), 3.75 (dd, J=14.5, 1.8 Hz, 1H), 3.18 (ddd, J=13.1, 6.8, 2.5 Hz, 1H), 1.95-1.84 (m, 2H), 1.49-1.38 (m, 1H), 0.85-0.70 (m, 3H), 0.52-0.39 (m, 2H).

Example 55: Preparation of (7S)—N-(3-chloro-2,4-difluorobenzyl)-12-hydroxy-1,11-dioxo-1,6,7,11-tetrahydro-3H-2,7-methanopyrido[1,2-a][1,4]diazonine-10-carboxamide (58)

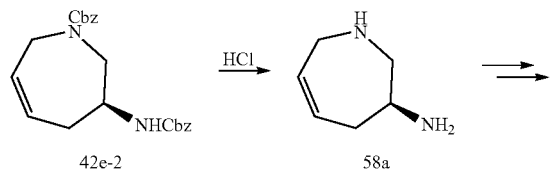

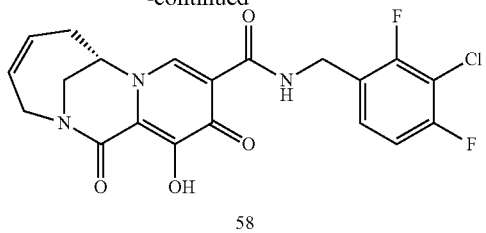

Synthesis of (S)-2,3,4,7-tetrahydro-1H-azepin-3-amine (58a)

Benzyl(S)-3-(((benzyloxy)carbonyl)amino)-2,3,4,7-tetrahydro-1H-azepine-1-carboxylate (42e-2, 648 mg, 1.70 mmol) was dissolved in HCl in dioxane (4 M, 8.5 mL) in a pressure vessel. The mixture was stirred at 95° C. for 3 hours, cooled to rt, diluted with diethyl ether (17 mL), and stirred for 5 minutes. The precipitate was collected by filtration, and rinsed with additional ether to give the title compound (58a), which was used subsequently without further purification.

Synthesis of (7S)—N-(3-chloro-2,4-difluorobenzyl)-12-hydroxy-1,11-dioxo-1,6,7,11-tetrahydro-3H-2,7-methanopyrido[1,2-a][1,4]diazonine-10-carboxamide (58)

The title compound was prepared analogously to 51, using (S)-2,3,4,7-tetrahydro-1H-azepin-3-amine (58a) in place of (3S)-azepan-3-amine. MS (m/z) 436.2 [M+H]⁺. ¹H NMR (400 MHz, Acetonitrile-d₃) δ 10.42 (s, 1H), 8.41 (s, 1H), 7.58-7.25 (m, 1H), 7.10 (td, J=8.8, 1.9 Hz, 1H), 5.70-5.43 (m, 2H), 5.10-4.83 (m, 1H), 4.79 (ddt, J=8.9, 4.4, 2.2 Hz, 1H), 4.63 (dd, J=6.0, 1.4 Hz, 2H), 3.88 (dd, J=14.3, 1.8 Hz, 1H), 3.82-3.61 (m, 2H), 3.22-2.94 (m, 1H), 2.49-2.37 (m, 1H).

Example 56: Preparation of (7S)-12-hydroxy-7-methyl-1,11-dioxo-N-(2,4,6-trifluorobenzyl)-1,4,5,6, 7,11-hexahydro-3H-2,7-methanopyrido[1,2-a][1,4] diazonine-10-carboxamide and (7R)-12-hydroxy-7-methyl-1,11-dioxo-N-(2,4,6-trifluorobenzyl)-1,4,5,6, 7,11-hexahydro-3H-2,7-methanopyrido[1,2-a][1,4] diazonine-10-carboxamide (59-1 and 59-2)

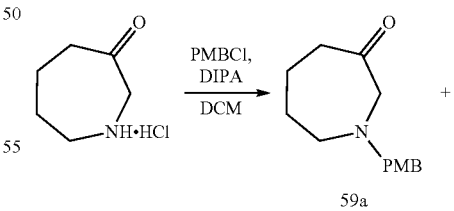

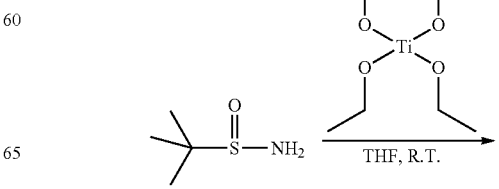

225

-continued

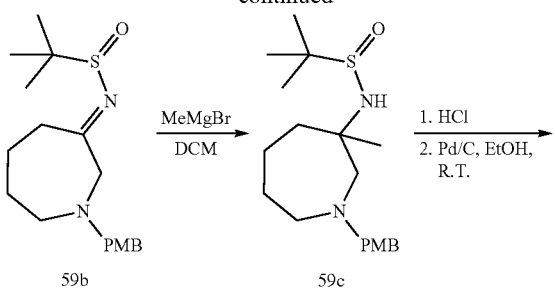

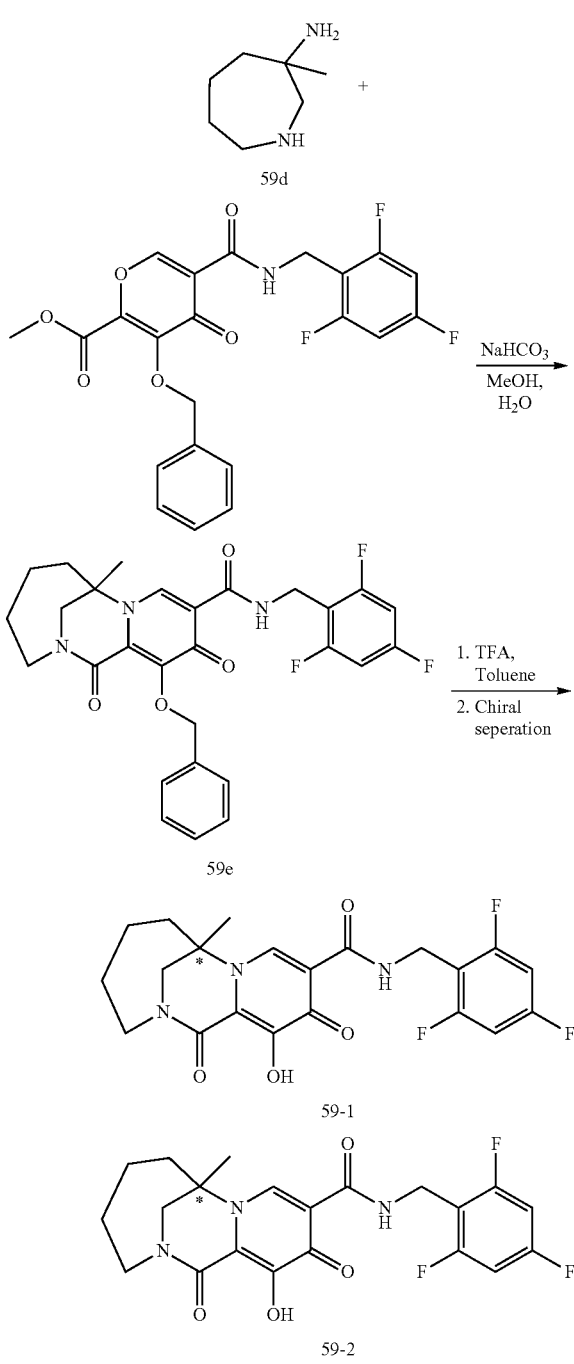

226

Synthesis of 1-(4-methoxybenzyl)azepan-3-one (59a)

PMB-Cl (0.653 g, 4.17 mmol) followed by DIPA (1.18 mL, 6.95 mmol) were added to a suspension of azepan-3-one hydrochloride (0.52g, 3.48 mmol) in DCM (5 mL). The resulting reaction mixture was stirred at room temperature overnight. Solvent was removed under vacuo, and the residue was purified by silica gel column, to afford the title compound (59a). MS (m/z) 234.2 [M+H]$^+$.

Synthesis of N-(1-(4-methoxybenzyl)azepan-3-ylidene)-2-methylpropane-2-sulfinamide (59b)

To a solution of 1-(4-methoxybenzyl)azepan-3-one (59a, 0.809 g, 3.47 mmol) and 2-methylpropane-2-sulfinamide (0.504 g, 4.16 mmol) in THF (10 mL) was added titanium (IV) ethoxide (1.46 mL, 6.98 mmol) at room temperature, and the resulting solution was stirred overnight. The reaction mixture was diluted with ethyl acetate (10 mL), and quenched with aq. NaHCO$_3$ (5 mL). Then Celite was added, the solid was filtered off, and the filter cake was washed with ethyl acetate (10 mL×2). The combined solvent was concentrated under vacuo, and the residue was purified by silica gel chromatography using EtOAc/Hexanes, to afford the title compound (59b). MS (m/z) 337.2 [M+H]$^+$.

Synthesis of N-(1-(4-methoxybenzyl)-3-methylazepan-3-yl)-2-methylpropane-2-sulfinamide (59c)

3 MeMgBr (0.91 mL) was added dropwise to a solution of N-(1-(4-methoxybenzyl)azepan-3-ylidene)-2-methylpropane-2-sulfinamide (59b, 0.23 g, 0.68 mmol) in DCM at −78° C., then the mixture was warmed to room temperature, and stirred overnight. The reaction mixture was diluted with ethyl acetate and was washed with sat. NH$_4$Cl and brine. The mixture was dried over MgSO$_4$, and the solvent was stripped off under vacuum. Crude material was purified by silica gel column with ethyl acetate/hexane to afford the title compound (59c). MS (m/z) 353.2 [M+H]$^+$.

Synthesis of 3-methylazepan-3-amine (59d)

4 M HCl (1 mL) in dioxane was added to solution of N-(1-(4-methoxybenzyl)-3-methylazepan-3-yl)-2-methylpropane-2-sulfinamide (59c, 0.05 g, 0.142 mmol) in DCM (2 mL) at room temperature, and the reaction was stirred for 2 h. The solvent was removed under vacuo, the crude material was dissolved in EtOH (5 mL) and palladium on carbon 10 wt. % loading (dry basis), matrix carbon powder, wet support (15 mg) was added. The resulting mixture was stirred at room temperature for 1 h under N$_2$ to remove the trace amount of S containing by-product, and then black solid was filtered off. Palladium on carbon 10 wt. % loading (dry basis), matrix carbon powder, wet support (15 mg) was recharged to the solution and purged with H$_2$ (3×). Then the reaction mixture was stirred under H$_2$ for 2 h. Black solid was filtered off and solvent was removed under vacuo. The resulting residue was used directly for next step. MS (m/z) 129.2 [M+H]$^+$.

Synthesis of 12-(benzyloxy)-7-methyl-1,11-dioxo-N-(2,4,6-trifluorobenzyl)-1,4,5,6,7,11-hexahydro-3H-2,7-methanopyrido[1,2-a][1,4]diazonine-10-carboxamide (59e)

To a mixture of 3-methylazepan-3-amine (59d, 0.013 g, 0.1 mmol) and sodium bicarbonate (45.07 mg, 0.54 mmol)

in MeOH (2 mL) and H$_2$O (2 mL), was added methyl 3-benzyloxy-4-oxo-5-[(2,4,6-trifluorophenyl)methylcarbamoyl]pyran-2-carboxylate (30 mg, 0.07 mmol) at room temperature. The mixture was stirred at 60° C. for 3 hours. The reaction mixture was diluted with ethyl acetate, washed with H$_2$O and brine, and dried over MgSO$_4$. Solvent was removed under vacuo, and the residue was purified by silica gel column chromatography to afford the title compound (59e). MS (m/z) 526.2 [M+H]$^+$.

Synthesis of (7S)-12-hydroxy-7-methyl-1,11-dioxo-N-(2,4,6-trifluorobenzyl)-1,4,5,6,7,11-hexahydro-3H-2,7-methanopyrido[1,2-a][1,4]diazonine-10-carboxamide and (7R)-12-hydroxy-7-methyl-1,11-dioxo-N-(2,4,6-trifluorobenzyl)-1,4,5,6,7,11-hexahydro-3H-2,7-methanopyrido[1,2-a][1,4]diazonine-10-carboxamide (59-1 and 59-2)

12-(benzyloxy)-7-methyl-1,11-dioxo-N-(2,4,6-trifluorobenzyl)-1,4,5,6,7,11-hexahydro-3H-2,7-methanopyrido[1,2-a][1,4]diazonine-10-carboxamide (59e, 0.03 g, 0.06 mmol) was dissolved in toluene (2 mL) and TFA (2 mL) was added. The reaction mixture was stirred at room temperature for 1 hour. Solvent was removed under vacuo and the residue was purified by HPLC to afford a racemic mixture. The mixture was separated into its enantiomers by preparative SFC chromatography on an IA column using methanol co-solvent to provide the title compounds (59-1 and 59-2).

59-1: MS (m/z) 436.1 [M+H]$^+$. $^1$H NMR (400 MHz, Methanol-d$_4$) 8.57 (s, 1H), 6.90 (m, 2H), 4.69 (s, 2H), 4.39 (m, 1H), 3.80 (m, 1H), 3.70 (m, 1H), 3.20 (m, 1H), 2.15-1.22 (m, 9H).

59-2: MS (m/z) 436.1 [M+H]$^+$. $^1$H NMR (400 MHz, Methanol-d$_4$) 8.57 (s, 1H), 6.90 (m, 2H), 4.69 (s, 2H), 4.38 (m, 1H), 3.80 (m, 1H), 3.71 (m, 1H), 3.19 (m, 1H), 2.15-1.25 (m, 9H).

Example 57a: Preparation of (6S,7R)—N-(2,4-difluorobenzyl)-6-fluoro-12-hydroxy-6-methyl-1,11-dioxo-1,4,5,6,7,11-hexahydro-3H-2,7-methanopyrido[1,2-a][1,4]diazonine-10-carboxamide (60-1)

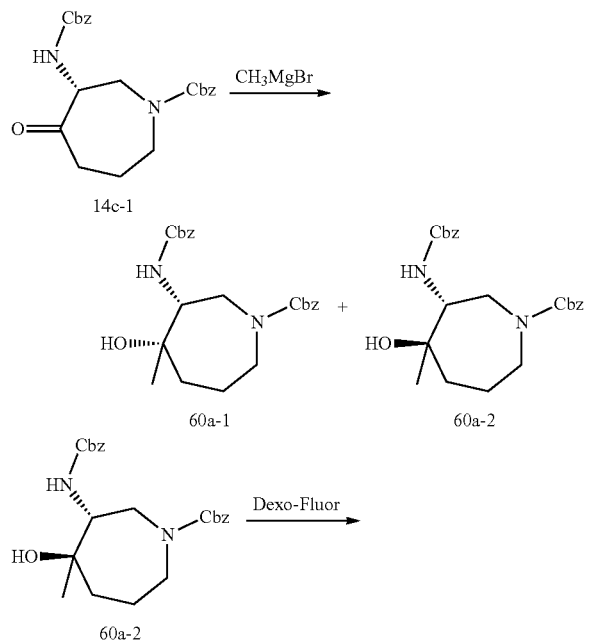

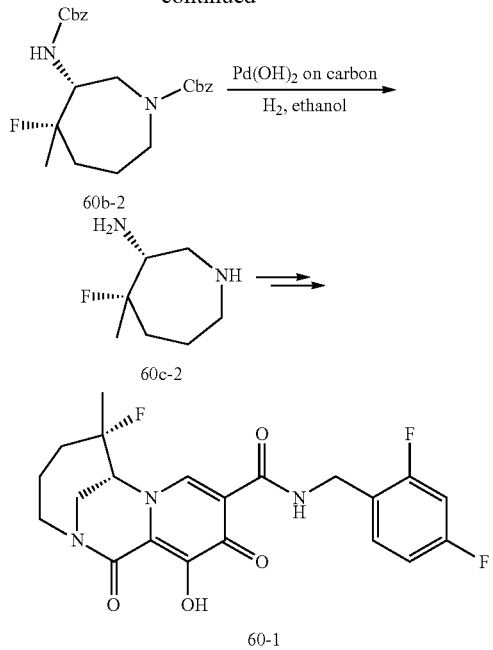

Synthesis of benzyl (3R,4S)-3-(((benzyloxy)carbonyl)amino)-4-hydroxy-4-methylazepane-1-carboxylate (60a-1) and benzyl (3R,4R)-3-(((benzyloxy)carbonyl)amino)-4-hydroxy-4-methylazepane-1-carboxylate (60a-2)

To a flask was added methyl Grignard (3 M in Et$_2$O, 1.02 mL, 3.05 mmol) at 0° C. A solution of benzyl (R)-3-(((benzyloxy)carbonyl)amino)-4-oxoazepane-1-carboxylate (14c-1, 302 mg, 0.76 mmol) in 3 mL THF was added slowly, the reaction was allowed to warm to room temperature, and stirred for 1 h. It was then quenched with NH$_4$Cl (saturated aqueous solution) and extracted into ethyl acetate. The organic layer was washed with brine, dried over MgSO$_4$, filtered, and concentrated to dryness. The residue was purified by silica gel chromatography eluting with ethyl acetate in hexane to afford the title compounds (60a-1 and 60a-2), with stereochemistry arbitrarily assigned. MS (m/z) 413.24 [M+H]$^+$.

Synthesis of benzyl (3R,4S)-3-(((benzyloxy)carbonyl)amino)-4-fluoro-4-methylazepane-1-carboxylate (60b-2)

The title compound was prepared in a manner similar to 13a using benzyl (3R,4R)-3-(((benzyloxy)carbonyl)amino)-4-hydroxy-4-methylazepane-1-carboxylate (60a-2) instead of 12-(benzyloxy)-N-(2,4-difluorobenzyl)-6-hydroxy-1,11-dioxo-1,4,5,6,7,11-hexahydro-3H-2,7-methanopyrido[1,2-a][1,4]diazonine-10-carboxamide (12a). MS (m/z) 415.78 [M+H]$^+$. The structure was confirmed by X-ray Crystallography.

Synthesis of (3R,4S)-4-fluoro-4-methylazepan-3-amine (60c-2)

Benzyl (3R,4S)-3-(((benzyloxy)carbonyl)amino)-4-fluoro-4-methylazepane-1-carboxylate (60b-2, 110 mg, 0.265 mmol) was dissolved in 20 mL of absolute ethanol and was sparged under an argon atmosphere. Palladium hydroxide on carbon (37.3 mg, 0.05 mmol, 20% Pd weight) was added and the mixture was sparged under a hydrogen atmosphere (1 atm, balloon). The mixture was stirred vigorously for 1 day and sparged under an argon atmosphere. It was filtered through a pad of Celite®. The filter cake was washed with absolute ethanol, and the filtrate was concentrated in vacuo to afford the title compound (60c-2). MS (m/z) 147.23 [M+H]$^+$.

Synthesis of (6S,7R)—N-(2,4-difluorobenzyl)-6-fluoro-12-hydroxy-6-methyl-1,11-dioxo-1,4,5,6,7,11-hexahydro-3H-2,7-methanopyrido[1,2-a][1,4]diazonine-10-carboxamide (60-1)

The title compound was prepared in a manner similar to compound 28 using (3R,4S)-4-fluoro-4-methylazepan-3-amine (60c-2) instead of 1,4-oxazepan-6-amine. MS (m/z) 436.18 [M+H]$^+$. $^1$H NMR (400 MHz, DMSO-d$_6$) δ 10.68 (s, 1H), 10.34 (t, J=5.9 Hz, 1H), 8.43 (d, J=1.9 Hz, 1H), 7.41 (td, J=8.7, 6.6 Hz, 1H), 7.25 (ddd, J=10.5, 9.3, 2.6 Hz, 1H), 7.07 (td, J=8.6, 2.6 Hz, 1H), 4.82 (s, 1H), 4.56 (d, J=5.9 Hz, 2H), 4.19 (dt, J=13.2, 8.4 Hz, 1H), 3.96 (ddd, J=15.4, 6.3, 3.0 Hz, 1H), 3.75 (d, J=15.3 Hz, 1H), 3.16-3.06 (m, 1H), 1.95-1.68 (m, 3H), 1.63 (d, J=23.8 Hz, 3H), 1.39 (td, J=13.8, 12.7, 5.2 Hz, 1H).

Example 57b: Preparation of (6S,7S)—N-(2,4-difluorobenzyl)-6-fluoro-12-hydroxy-6-methyl-1,11-dioxo-1,4,5,6,7,11-hexahydro-3H-2,7-methanopyrido[1,2-a][1,4]diazonine-10-carboxamide and (6R,7S)—N-(2,4-difluorobenzyl)-6-fluoro-12-hydroxy-6-methyl-1,11-dioxo-1,4,5,6,7,11-hexahydro-3H-2,7-methanopyrido[1,2-a][1,4]diazonine-10-carboxamide (60-2 and 60-3)

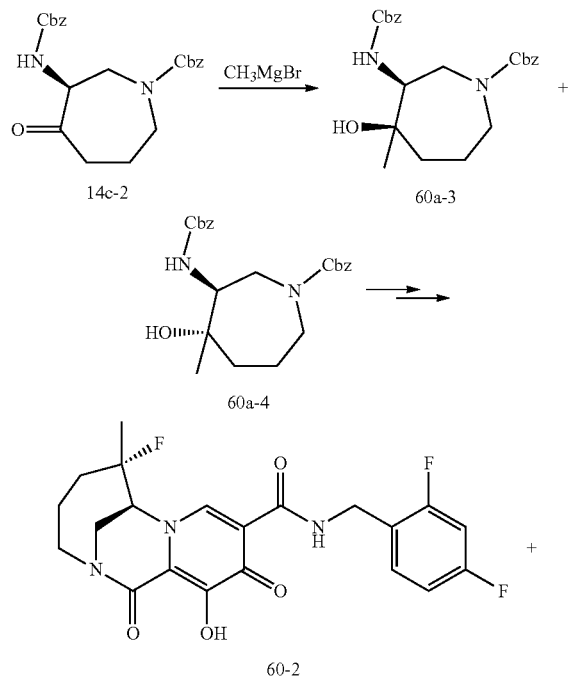

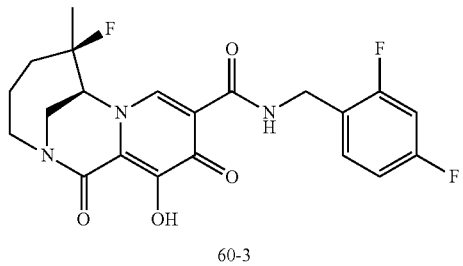

Synthesis of benzyl (3S,4R)-3-(((benzyloxy)carbonyl)amino)-4-hydroxy-4-methylazepane-1-carboxylate and benzyl (3S,4S)-3-(((benzyloxy)carbonyl)amino)-4-hydroxy-4-methylazepane-1-carboxylate (60a-3 and 60a-4)

The title compounds were prepared in a manner similar to benzyl (3R,4S)-3-(((benzyloxy)carbonyl)amino)-4-hydroxy-4-methylazepane-1-carboxylate (60a-1) using benzyl (S)-3-(((benzyloxy)carbonyl)amino)-4-oxoazepane-1-carboxylate (14c-2) instead of benzyl (R)-3-(((benzyloxy)carbonyl)amino)-4-oxoazepane-1-carboxylate (14c-1). MS (m/z) 415.52 [M+H]$^+$.

Synthesis of (6S,7S)- and (6R,7S)—N-(2,4-difluorobenzyl)-6-fluoro-12-hydroxy-6-methyl-1,11-dioxo-1,4,5,6,7,11-hexahydro-3H-2,7-methanopyrido[1,2-a][1,4]diazonine-10-carboxamide (60-2 and 60-3)

The title compounds were prepared in a manner similar to 60-1 using benzyl (3S,4R) 3-(((benzyloxy)carbonyl)amino)-4-hydroxy-4-methylazepane-1-carboxylate- or benzyl (3S,4S)-3-(((benzyloxy)carbonyl)amino)-4-hydroxy-4-methylazepane-1-carboxylate (60a-3 or 60a-4) instead of benzyl (3R,4R)-3-(((benzyloxy)carbonyl)amino)-4-hydroxy-4-methylazepane-1-carboxylate (60a-2).

60-2: MS (m/z) 436.16 [M+H]$^+$. $^1$H NMR (400 MHz, DMSO-d$_6$) δ 10.80 (s, 1H), 10.34 (t, J=6.0 Hz, 1H), 8.65 (s, 1H), 7.47-7.36 (m, 1H), 7.26 (td, J=9.9, 2.6 Hz, 1H), 7.08 (td, J=8.6, 2.6 Hz, 1H), 4.81 (d, J=11.5 Hz, 1H), 4.56 (d, J=5.9 Hz, 2H), 4.16 (q, J=11.3 Hz, 1H), 3.92 (dd, J=15.3, 2.5 Hz, 1H), 3.80 (d, J=14.9 Hz, 1H), 3.16 (dd, J=12.9, 7.7 Hz, 1H), 2.17-2.04 (m, 1H), 1.91 (dd, J=14.9, 7.1 Hz, 1H), 1.74 (dd, J=15.0, 7.6 Hz, 1H), 1.50-1.21 (m, 4H).

60-3: MS (m/z) 436.17 [M+H]$^+$. $^1$H NMR (400 MHz, DMSO-d$_6$) δ 10.68 (s, 1H), 10.34 (t, J=5.9 Hz, 1H), 8.43 (d, J=2.0 Hz, 1H), 7.41 (td, J=8.6, 6.6 Hz, 1H), 7.26 (ddd, J=10.6, 9.4, 2.6 Hz, 1H), 7.12-7.02 (m, 1H), 4.82 (s, 1H), 4.56 (d, J=5.8 Hz, 2H), 4.19 (dt, J=13.1, 8.4 Hz, 1H), 3.96 (ddd, J=15.3, 6.3, 3.0 Hz, 1H), 3.75 (d, J=15.3 Hz, 1H), 3.16-3.05 (m, 1H), 2.00-1.68 (m, 3H), 1.63 (d, J=23.8 Hz, 3H), 1.49-1.26 (m, 1H).

Example 58: Preparation of (6S,7S)-6-fluoro-12-hydroxy-6-methyl-1,11-dioxo-N-(2,4,6-trifluorobenzyl)-1,4,5,6,7,11-hexahydro-3H-2,7-methanopyrido[1,2-a][1,4]diazonine-10-carboxamide and (6R,7S)-6-fluoro-12-hydroxy-6-methyl-1,11-dioxo-N-(2,4,6-trifluorobenzyl)-1,4,5,6,7,11-hexahydro-3H-2,7-methanopyrido[1,2-a][1,4]diazonine-10-carboxamide (61-1 and 61-2)

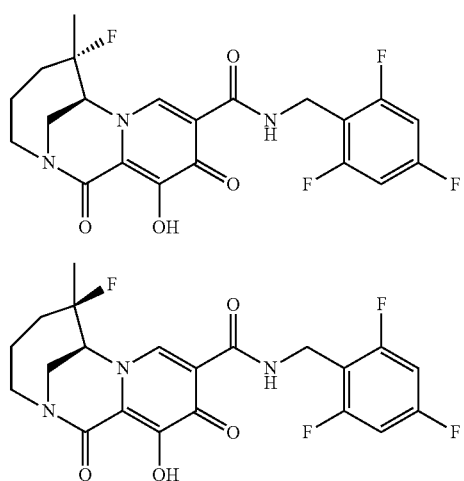

The title compounds were prepared in a similar manner to 60-2 and 60-3 using methyl 3-(benzyloxy)-4-oxo-5-((2,4,6-trifluorobenzyl)carbamoyl)-4H-pyran-2-carboxylate instead of methyl 3-(benzyloxy)-5-((2,4-difluorobenzyl)carbamoyl)-4-oxo-4H-pyran-2-carboxylate.

61-1: MS (m/z) 454.19 [M+H]$^+$. $^1$H NMR (400 MHz, DMSO-d$_6$) δ 10.80 (s, 1H), 10.36 (t, J=5.8 Hz, 1H), 8.63 (s, 1H), 7.22 (t, J=8.6 Hz, 2H), 4.79 (d, J=11.5 Hz, 1H), 4.57 (d, J=5.7 Hz, 2H), 4.22-4.09 (m, 1H), 3.90 (dd, J=15.0, 2.5 Hz, 1H), 3.79 (d, J=15.0 Hz, 1H), 3.15 (dd, J=13.0, 7.7 Hz, 1H), 2.10 (q, J=11.4 Hz, 1H), 1.91 (dt, J=15.6, 6.5 Hz, 1H), 1.73 (dt, J=14.3, 6.6 Hz, 1H), 1.44-1.23 (m, 4H).

61-2: MS (m/z) 454.19 [M+H]$^+$. $^1$H NMR (400 MHz, DMSO-d$_6$) δ 10.63 (s, 1H), 10.36 (t, J=5.8 Hz, 1H), 8.41 (d, J=2.0 Hz, 1H), 7.27-7.17 (m, 2H), 4.80 (s, 1H), 4.57 (d, J=5.7 Hz, 2H), 4.18 (dt, J=13.2, 8.4 Hz, 1H), 3.94 (ddd, J=15.3, 6.2, 3.0 Hz, 1H), 3.74 (d, J=15.4 Hz, 1H), 3.10 (td, J=8.3, 3.8 Hz, 1H), 1.84 (ddt, J=33.9, 13.2, 7.2 Hz, 3H), 1.62 (d, J=23.8 Hz, 3H), 1.38 (t, J=15.3 Hz, 1H).

Example 59: Preparation of (7S)—N-(2,3-dichloro-4-fluorobenzyl)-12-hydroxy-1,11-dioxo-1,4,5,6,7,11-hexahydro-3H-2,7-methanopyrido[1,2-a][1,4]diazonine-10-carboxamide (62)

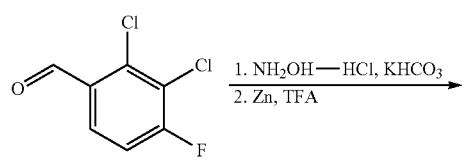

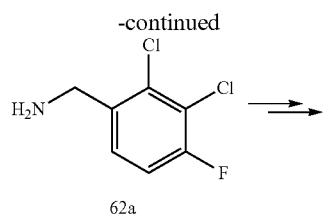

Synthesis of (2,3-dichloro-4-fluorophenyl)methanamine (62a)

A solution of NH$_2$OH—HCl (6.95 g, 0.1 mol) and KHCO$_3$ (5 g, 0.05 mol) in 250 mL water was made. 5.2 mL of the solution was slowly added to 2,3-dichloro-4-fluorobenzaldehyde (1 g, 5 mmol) in ethanol (20 mL). It was stirred for 20 min, an equal volume of water was added (20 mL), and the solid was filtered off. The supernatant was dried to give (Z)-2,3-dichloro-4-fluorobenzaldehyde oxime, which was used as is in the next reaction. MS (m/z) 208.1 [M+H]$^+$.

Zinc powder (1.3 g, 19.2 mmol) was added to a solution of (Z)-2,3-dichloro-4-fluorobenzaldehyde oxime (1 g, 4.8 mmol) in water (1 mL) and TFA (3 mL). The reaction was stirred for 6 hr. Solids were filtered off, and supernatant diluted with EtOAc, followed by sat. NaHCO$_3$ until basic. The mixture was extracted twice with EtOAc, then organic layer was dried over sodium sulfate, filtered, and concentrated to obtain the title compound (62a) which was carried to the next step without further purification. MS (m/z) 194.0 [M+H]$^+$. $^1$H NMR (400 MHz, Chloroform-d) δ 7.37-7.32 (m, 1H), 7.11 (t, 1H), 3.97 (s, 1H), 1.59 (s, 2H).

Synthesis of (7S)—N-(2,3-dichloro-4-fluorobenzyl)-12-hydroxy-1,11-dioxo-1,4,5,6,7,11-hexahydro-3H-2,7-methanopyrido[1,2-a][1,4]diazonine-10-carboxamide (62)

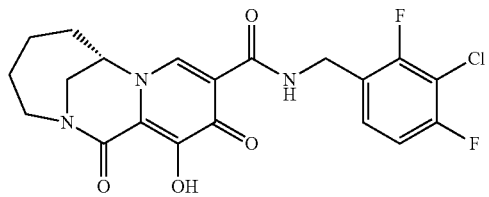

The title compound was prepared analogously to compound 51, using (2,3-dichloro-4-fluorophenyl)methanamine (62a) in place of (3-chloro-2,4-difluorophenyl)methanamine. MS (m/z) 454.1 [M+H]$^+$. $^1$H NMR (400 MHz, Chloroform-d) δ 10.72-10.57 (m, 1H), 8.44 (s, 1H), 7.35 (dd, 1H), 7.07 (t, 1H), 4.82-4.61 (m, 2H), 4.51-4.35 (m, 2H), 4.07-3.90 (m, 1H), 3.54 (dd, 1H), 3.18 (ddd, 1H), 2.22-1.95 (m, 3H), 1.94-1.75 (m, 2H), 1.45-1.33 (m, 1H).

Example 60: Preparation of (13S)-4-hydroxy-3,5-dioxo-N-(2,4,6-trifluorobenzyl)-3,5,8,13-tetrahydro-7H-6,13-methanobenzo[g]pyrido[1,2-a][1,4]diazonine-2-carboxamide and (13R)-4-hydroxy-3,5-dioxo-N-(2,4,6-trifluorobenzyl)-3,5,8,13-tetrahydro-7H-6,13-methanobenzo[g]pyrido[1,2-a][1,4]diazonine-2-carboxamide (63-1 and 63-2)

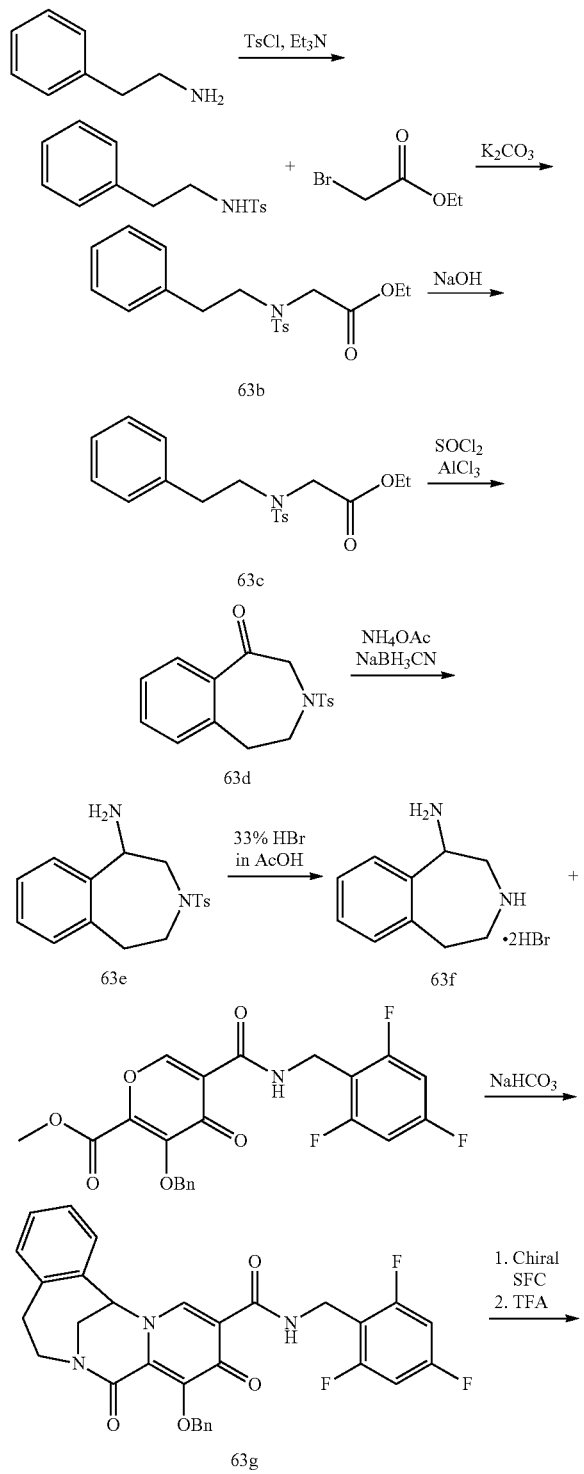

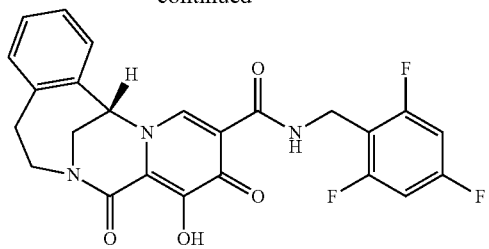

63-1

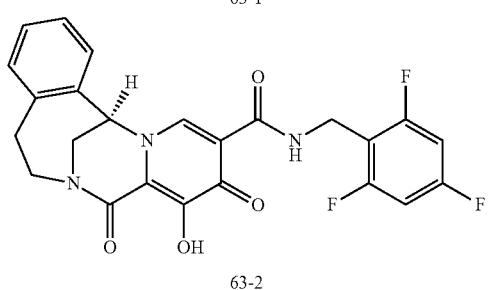

63-2

Synthesis of 4-methyl-N-phenethylbenzenesulfonamide (63a)

To a stirred solution of 2-phenylethan-1-amine (14.55 g, 120 mmol) and Et$_3$N (33 mL, 237 mmol) in DCM (120 mL) under argon at 0° C., was added p-toluenesulfonyl chloride (23.3 g, 122.2 mmol) portion-wise. After addition, the reaction was stirred under argon at 30° C. for 7 h. The reaction mixture was diluted with water (200 mL), and the organic layer was separated. The aqueous layer was extracted with DCM (2×) and the combined organic extracts were concentrated. The residue was dried under vacuo and dissolved in DCM (300 mL), washed with aq. HCl (0.5 M, 100 mL), brine (100 mL), dried over anhydrous Na$_2$SO$_4$ and filtered. The filtrate was concentrated to give the title compound (63a), which was further used without further purification. MS (m/z) 276.3 [M+H]$^+$.

Synthesis of ethyl N-phenethyl-N-tosylglycinate (63b)

To a stirred solution of 4-methyl-N-phenethylbenzenesulfonamide (63a, 33.8 g, 120 mmol) in acetone (360 mL) under argon at room temperature were added K$_2$CO$_3$ (49.8 g, 360 mmol) and ethyl 2-bromoacetate (15.3 mL, 138 mmol). The reaction was stirred under argon at 75° C. for 18 h. The cooled reaction mixture was concentrated. The residue was suspended in water (150 mL) and extracted with EtOAc (3×). The combined organic extracts were washed with brine (100 mL), dried over anhydrous Na$_2$SO$_4$ and filtered. The filtrate was concentrated to give the title compound (63b), which was further used without further purification. MS (m/z) 362.3 [M+H]$^+$.

Synthesis of N-phenethyl-N-tosylglycine (63c)

To a stirred mixture of ethyl N-phenethyl-N-tosylglycinate (63b, 47.1 g, 120 mmol) in EtOH/H$_2$O (120 mL/200 mL) at room temperature, was added NaOH (12.0 g, 300 mmol). The resulting suspension was stirred at 50° C. for 3 h. The reaction mixture was concentrated to remove most of the EtOH, cooled to 0° C., and conc. HCl (30 mL) was added dropwise. The solid precipitate was collected by filtration, rinsed with water (100 mL) and petroleum ether (100 mL), dissolved in EtOAc (500 mL), washed with brine (100 mL), dried over anhydrous $Na_2SO_4$, and filtered. The filtrate was concentrated to give the title compound (63c), which was used without further purification. MS (m/z) 334.2 $[M+H]^+$.

Synthesis of 3-tosyl-2,3,4,5-tetrahydro-1H-benzo[d]azepin-1-one (63d)

To a stirred solution of N-phenethyl-N-tosylglycine (63c, 41.3 g, 120 mmol) in DCM (300 mL) under argon at room temperature, were added $SOCl_2$ (43 mL, 593 mmol) and DMF (0.3 mL). The reaction was stirred under argon at 40° C. for 12 h. The reaction mixture was concentrated to dryness, and then dried under high vacuum for 30 minutes. The residue was dissolved in dry DCM (400 mL) under argon, and cooled to −20° C. $AlCl_3$ (56 g, 420 mmol) was added portion wise. After addition, the reaction was stirred at room temperature for 1 h and then at 30° C. overnight. The cooled reaction mixture was poured into aq. HCl (6 M, 200 mL), which had been cooled to −20° C. The resulting mixture was extracted with DCM (200 mL, 2×) and the combined organic extracts were washed with aq. HCl (1 M, 200 mL), brine (100 mL), dried over anhydrous $Na_2SO_4$, and filtered. The filtrate was concentrated, and the residue purified by silica gel chromatography (20-50% EtOAc/PE, then 50% EtOAc/DCM) to afford the title compound (63d). MS (m/z) 316.3 $[M+H]^+$.

Synthesis of 3-tosyl-2,3,4,5-tetrahydro-1H-benzo[d]azepin-1-one (63e)

To a stirred suspension of 3-tosyl-2,3,4,5-tetrahydro-1H-benzo[d]azepin-1-one (63d, 20.0 g, 63.4 mmol) in i-PrOH (630 mL) under argon at room temperature, was added $NH_4OAc$ (98 g, 1271 mmol). $NaBH_3CN$ (19.95 g, 317.5 mmol) was then added portionwise. The reaction was stirred under argon at 85° C. overnight. The cooled reaction mixture was quenched with water (300 mL), followed by aqueous NaOH (2 M, 100 mL). The suspension was concentrated under reduced pressure to remove most of i-PrOH. The resulting suspension was diluted with DCM (200 mL), filtered, and the filter cake washed with DCM (100 mL). The filter cake was dissolved in MeOH (200 mL), and aq. HCl (3 M, 100 mL) was added dropwise with stirring at room temperature. After addition, the resulting solution was stirred at room temperature overnight. MeOH (100 mL) was added followed by aqueous NaOH (2 M), until pH equaled 11. The resulting mixture was concentrated to remove MeOH, diluted with water (300 mL) and extracted with DCM (300 mL, 2×). The combined organic extracts were filtered through a pad of anhydrous $Na_2SO_4$ and concentrated to give the title compound, which was used without further purification. MS (m/z) 317.3 $[M+H]^+$.

Synthesis of 2,3,4,5-tetrahydro-1H-benzo[d]azepin-1-amine dihydrobromide (63f)

A mixture of 3-tosyl-2,3,4,5-tetrahydro-1H-benzo[d]azepin-1-amine (63e, 11.55 g, 36.5 mmol) and HBr (33 wt % in AcOH) (110 mL) was stirred under argon at 75° C. overnight. The cooled reaction mixture was diluted with EtOAc (1 L), stirred at room temperature for 30 minutes and filtered. The filter cake was washed with EtOAc (100 mL), collected, and dried under vacuo to afford the title compound (63f), which was used without further purification. MS (m/z) 163.5 $[M+H]^+$.

Synthesis of 4-(benzyloxy)-3,5-dioxo-N-(2,4,6-trifluorobenzyl)-3,5,8,13-tetrahydro-7H-6,13-methanobenzo[g]pyrido[1,2-a][1,4]diazonine-2-carboxamide (63g)

To a suspension of methyl 3-(benzyloxy)-4-oxo-5-((2,4,6-trifluorobenzyl)carbamoyl)-4H-pyran-2-carboxylate (0.20 g, 0.45 mmol) and 2,3,4,5-tetrahydro-1H-benzo[d]azepin-1-amine dihydrobromide (63f, 0.145 g, 0.45 mmol) in 6:1 $MeOH/H_2O$ (14 mL) was added $NaHCO_3$ (0.376 g, 4.47 mmol). The suspension was stirred overnight at room temperature. The reaction mixture was concentrated and redissolved in EtOAc and $H_2O$. The organic phase was separated, and the aqueous phase was extracted with EtOAc (2×). The combined organic phases were dried over $Na_2SO_4$, filtered, and concentrated. The residue was purified by column chromatography (25-100% EtOAc/hexanes) to afford the title compound (63g). MS (m/z) 560.07 $[M+H]^+$.

Synthesis of (13S)-4-hydroxy-3,5-dioxo-N-(2,4,6-trifluorobenzyl)-3,5,8,13-tetrahydro-7H-6,13-methanobenzo[g]pyrido[1,2-a][1,4]diazonine-2-carboxamide and (13R)-4-hydroxy-3,5-dioxo-N-(2,4,6-trifluorobenzyl)-3,5,8,13-tetrahydro-7H-6,13-methanobenzo[g]pyrido[1,2-a][1,4]diazonine-2-carboxamide (63-1 and 63-2)

4-(benzyloxy)-3,5-dioxo-N-(2,4,6-trifluorobenzyl)-3,5,8,13-tetrahydro-7H-6,13-methanobenzo[g]pyrido[1,2-a][1,4]diazonine-2-carboxamide (63g) was separated into its individual enantiomers by preparative SFC on an OD-H column using 50% EtOH co-solvent to provide (13S)-4-(benzyloxy)-3,5-dioxo-N-(2,4,6-trifluorobenzyl)-3,5,8,13-tetrahydro-7H-6,13-methanobenzo[g]pyrido[1,2-a][1,4]diazonine-2-carboxamide as the first eluting peak and (13R)-4-(benzyloxy)-3,5-dioxo-N-(2,4,6-trifluorobenzyl)-3,5,8,13-tetrahydro-7H-6,13-methanobenzo[g]pyrido[1,2-a][1,4]diazonine-2-carboxamide as the second eluting peak.

The separated enantiomers were dissolved in 1:1 toluene/TFA (4 mL). The reaction mixture was allowed to stir at rt for 2 h and concentrated. The residue was dissolved in MeCN and purified by preparative HPLC (column, Gemini 10μ C18 110A, AXI/; 250×21.2 mm) eluting with 5-100% acetonitrile (0.1% TFA) in water (0.1% TFA) over 30 minutes to afford the title compounds (63-1 and 63-2).

63-1: MS (m/z) 470.16 $[M+H]^+$. $^1H$ NMR (400 MHz, DMSO-$d_6$) δ 10.39 (t, J=5.8 Hz, 1H), 9.01 (s, 1H), 7.37-7.12 (m, 6H), 6.02 (s, 1H), 4.60 (d, J=5.7 Hz, 2H), 4.45 (dd, J=15.0, 2.7 Hz, 1H), 4.28 (td, J=12.6, 5.5 Hz, 1H), 4.00 (d, J=14.7 Hz, 1H), 3.61 (td, J=14.1, 13.2, 7.4 Hz, 1H), 3.42 (dd, J=12.6, 7.2 Hz, 1H), 2.83 (dd, J=15.3, 5.5 Hz, 1H). $^{19}F$ NMR (376 MHz, DMSO-$d_6$) δ −109.25 (tt, J=9.4, 6.2 Hz), −112.54 (p, J=7.2 Hz).

63-2: MS (m/z) 470.13 $[M+H]^+$. $^1H$ NMR (400 MHz, DMSO-$d_6$) δ 10.39 (t, J=5.8 Hz, 1H), 9.01 (s, 1H), 7.38-7.14 (m, 6H), 6.02 (s, 1H), 4.60 (d, J=5.7 Hz, 2H), 4.45 (dd, J=15.0, 2.7 Hz, 1H), 4.28 (td, J=12.6, 5.5 Hz, 1H), 4.00 (d, J=13.9 Hz, 1H), 3.61 (td, J=14.0, 13.2, 7.3 Hz, 1H), 3.42 (dd, J=12.7, 7.2 Hz, 1H), 2.83 (dd, J=15.3, 5.4 Hz, 1H). $^{19}F$ NMR (376 MHz, DMSO-$d_6$) δ −109.25 (tt, J=9.1, 6.3 Hz), −112.54 (t, J=7.4 Hz).

Example 61: Preparation of (13R)—N-(2,4-difluorobenzyl)-4-hydroxy-3,5-dioxo-3,5,8,13-tetrahydro-7H-6,13-methanobenzo[g]pyrido[1,2-a][1,4]diazonine-2-carboxamide and (13S)—N-(2,4-difluorobenzyl)-4-hydroxy-3,5-dioxo-3,5,8,13-tetrahydro-7H-6,13-methanobenzo[g]pyrido[1,2-a][1,4]diazonine-2-carboxamide (64-1 and 64-2)

Example 62: Preparation of (1aR,11aR)—N-(2,4-difluorobenzyl)-7-hydroxy-6,8-dioxo-1a,2,3,4,6,8-hexahydro-1H-5,11a-methanocyclopropa[h]pyrido[1,2-a][1,4]diazonine-9-carboxamide and (1aS,11aS)—N-(2,4-difluorobenzyl)-7-hydroxy-6,8-dioxo-1a,2,3,4,6,8-hexahydro-1H-5,11a-methanocyclopropa[h]pyrido[1,2-a][1,4]diazonine-9-carboxamide (65-1 and 65-2)

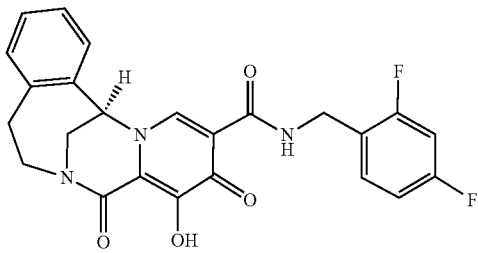

64-1

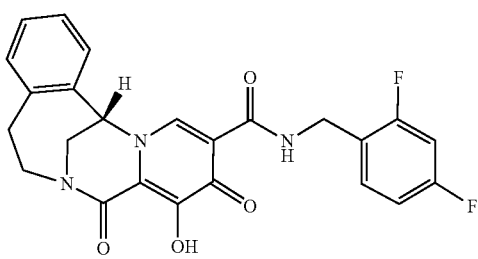

64-2

The title compounds were prepared in a similar manner to 63-1 and 63-2, using methyl 3-(benzyloxy)-5-((2,4-difluorobenzyl)carbamoyl)-4-oxo-4H-pyran-2-carboxylate in place of methyl 3-(benzyloxy)-4-oxo-5-((2,4,6-trifluorobenzyl)carbamoyl)-4H-pyran-2-carboxylate. Chiral separation was carried out before deprotection using preparative SFC on an IA column with 40% MeOH as a co-solvent.

64-1: MS (m/z) 452.14 [M+H]$^+$. $^1$H NMR (400 MHz, DMSO-d$_6$) δ 10.36 (t, J=5.9 Hz, 1H), 9.02 (s, 1H), 7.45 (td, J=8.7, 6.6 Hz, 1H), 7.33-7.18 (m, 5H), 7.09 (td, J=8.4, 2.4 Hz, 1H), 6.05 (s, 1H), 4.67-4.51 (m, 2H), 4.47 (dd, J=15.0, 2.6 Hz, 1H), 4.29 (td, J=12.7, 5.5 Hz, 1H), 4.01 (d, J=15.0 Hz, 1H), 3.71-3.55 (m, 1H), 3.43 (dd, J=12.6, 7.2 Hz, 1H), 2.84 (dd, J=15.3, 5.4 Hz, 1H). $^{19}$F NMR (376 MHz, DMSO-d$_6$) δ -112.30 (p, J=7.9 Hz), -114.92 (q, J=8.9 Hz).

64-2: MS (m/z) 452.17 [M+H]$^+$. $^1$H NMR (400 MHz, DMSO-d$_6$) δ 10.37 (t, J=5.9 Hz, 1H), 9.03 (s, 1H), 7.46 (td, J=8.7, 6.6 Hz, 1H), 7.35-7.18 (m, 5H), 7.10 (td, J=8.6, 2.2 Hz, 1H), 6.06 (s, 1H), 4.67-4.52 (m, 2H), 4.47 (dd, J=15.1, 2.7 Hz, 1H), 4.30 (td, J=12.6, 5.5 Hz, 1H), 4.02 (d, J=14.5 Hz, 1H), 3.63 (td, J=14.2, 13.7, 7.5 Hz, 1H), 3.44 (dd, J=12.6, 7.2 Hz, 1H), 2.85 (dd, J=15.3, 5.5 Hz, 1H). $^{19}$F NMR (376 MHz, DMSO-d$_6$) δ -112.30 (p, J=7.9 Hz), -114.92 (q, J=8.8 Hz).

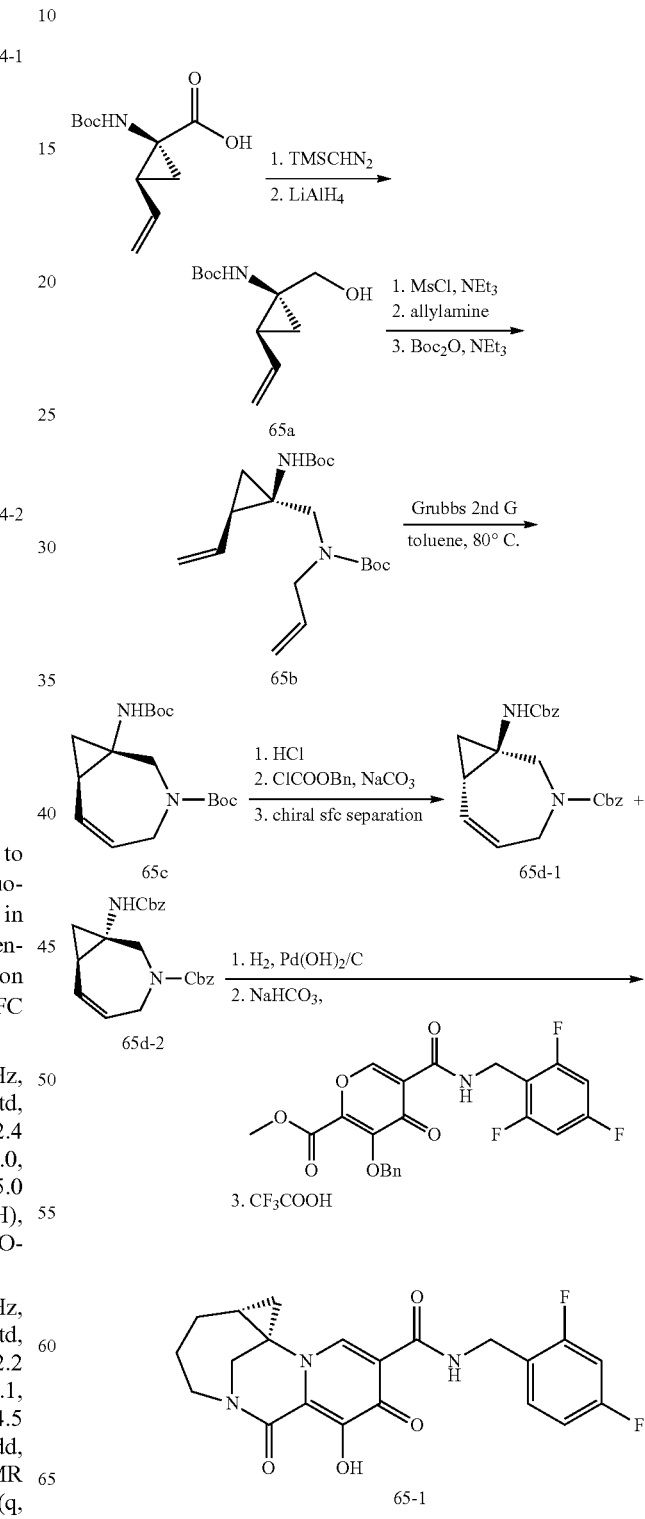

-continued

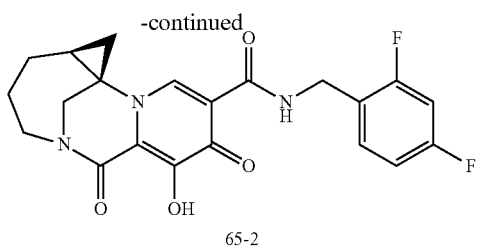

65-2

Synthesis of rel-tert-butyl ((1R,2S)-1-(hydroxymethyl)-2-vinylcyclopropyl)carbamate (65a)

A solution rel-(1R,2S)-1-((tert-butoxycarbonyl)amino)-2-vinylcyclopropane-1-carboxylic acid (993.5 mg, 4.37 mmol) in methanol (20 mL) was stirred at 0° C. as 2 M (trimethylsilyl)diazomethane in diethyl ether (7 mL) was added until yellow color persisted. After 30 min, a solution of acetic acid in methanol was added dropwise until the yellow color disappeared. The resulting solution was concentrated and the residue was co-evaporated with toluene.

The crude residue was dissolved in tetrahydrofuran (15 mL) and stirred at 0° C., as 1M lithium aluminum hydride (5.8 mL, 5.8 mmol) was added dropwise. After 30 min at 0° C., the reaction mixture was diluted with ethyl ether (40 mL) and vigorously stirred at 0° C., as water (0.22 mL), 15% sodium hydroxide (0.22 mL), and water (0.66 mL) were sequentially added dropwise. After 30 min stirring at 0° C., anhydrous sodium sulfate was added to the mixture and filtered through celite. After the filtrate was concentrated, the resulting residue was purified by column chromatography on silica gel eluting with 0-100% ethyl acetate in hexane to obtain the title compound (65a). MS (m/z) 157.76 [M+H-$C_4H_8$]$^+$.

Synthesis of rel-tert-butyl allyl(((1R,2R)-1-((tert-butoxycarbonyl)amino)-2-vinylcyclopropyl)methyl)carbamate (65b)

A solution of rel-tert-butyl ((1R,2S)-1-(hydroxymethyl)-2-vinylcyclopropyl)carbamate (65a, 627.6 mg, 2.943 mmol) in dichloromethane (10 mL) and triethylamine (0.62 mL, 4.448 mmol) was stirred at an ice-salt bath, as methanesulfonyl chloride (0.26 mL, 3.359 mmol) was added dropwise. After 30 min in the cold bath, the reaction mixture was diluted with ice-cold dichloromethane and washed with cold saturated sodium bicarbonate solution and cold brine. After the aqueous fractions were extracted with dichloromethane, the combined organic fractions were dried over MgSO$_4$, and concentrated.

The crude residue was dissolved in acetonitrile (2 mL), and prop-2-en-1-amine (0.2 mL, 2.666 mmol) was added to the solution at rt, and stirred for 88 h. The reaction mixture was concentrated to remove most of the acetonitrile and the residue was diluted with saturated sodium bicarbonate (30 mL), before the product was extracted with ethyl acetate (30 mL×2). After the extracts were washed with brine, the organic fractions were combined, dried over MgSO$_4$, and concentrated to get the crude product.

To a solution of the crude amine and triethylamine (1 mL, 7.174 mmol) in tetrahydrofuran (10 mL) was added di-tert-butyl dicarbonate (1.6 g, 7.14 mmol) and the resulting solution was stirred at rt overnight. The reaction mixture was concentrated and the residual oil was dissolved in ethyl acetate (40 mL), and washed with water. After the aqueous fraction was extracted with ethyl acetate (40 mL), the organic fractions were combined, dried over MgSO$_4$, and concentrated. The residue was purified by column chromatography on silica gel eluting with 0-30% ethyl acetate in hexane to obtain the title compound (65b). MS (m/z) 352.78 [M+H]$^+$.

Synthesis of rel-tert-butyl (1S,7R)-1-((tert-butoxycarbonyl)amino)-3-azabicyclo[5.1.0]oct-5-ene-3-carboxylate (65c)

A solution of rel-tert-butyl allyl(((1R,2R)-1-((tert-butoxycarbonyl)amino)-2-vinylcyclopropyl)methyl)carbamate (65b, 837.7 mg, 2.377 mmol) and Grubbs catalyst 2$^{nd}$ generation (100.89 mg, 118.98 umol) in toluene (800 mL) was purged with Ar gas for 30 min, and stirred at 80° C. for 3 h. The reaction mixture was concentrated, and the residue purified by column chromatography on silica gel, eluting with 0-30% ethyl acetate/hexane to afford the title compound (65c). MS (m/z) 324.75 [M+H]$^+$.

Synthesis of (1R,7S)-1-(((benzyloxy)carbonyl)amino)-3-azabicyclo[5.1.0]oct-5-ene-3-carboxylate and (1S,7R)-1-(((benzyloxy)carbonyl)amino)-3-azabicyclo[5.1.0]oct-5-ene-3-carboxylate (65d-1 and 65d-2)

A solution of rel-tert-butyl allyl(((1R,2R)-1-((tert-butoxycarbonyl)amino)-2-vinylcyclopropyl)methyl)carbamate (65c, 677.9 mg, 2.090 mmol) in dichloromethane (5.5 mL) was stirred at 0° C., as 4 M HCl in dioxane (5.3 mL, 21.20 mmol) was added. After addition, the mixture was stirred at rt for 1 h, additional 4 N HCl in dioxane (5.3 mL) was added, and the mixture was stirred for 2 h, and concentrated to dryness. A suspension of the residue and sodium carbonate (1.3 g, 12.56 mmol) in dioxane (8 mL) and water (8 mL) was stirred at 0° C., as benzyl chloroformate (0.75 mL, 5.04 mmol) was added. After stirring for 3 h at rt, the reaction mixture was diluted with ethyl acetate (40 mL) and washed with water (×2). The aqueous fractions were extracted with ethyl acetate (~30 mL), and the organic fractions were combined, dried over MgSO$_4$, and concentrated. The residue was purified by column chromatography on silica gel eluting with 0-80% ethyl acetate in hexane to afford rel-benzyl (1R,7S)-1-(((benzyloxy)carbonyl)amino)-3-azabicyclo[5.1.0]oct-5-ene-3-carboxylate. MS (m/z) 392.99 [M+H]$^+$.

Benzyl rel-(1R,7S)-1-(((benzyloxy)carbonyl)amino)-3-azabicyclo[5.1.0]oct-5-ene-3-carboxylate was separated into its individual enantiomers by preparative SFC chromatography on an Cell 2 column using 15% IPA-NH$_3$ co-solvent to provide the title compounds (65d-1 and 65d-2).

Synthesis of (1aR,11aR)- and (1aS,11aS)—N-(2,4-difluorobenzyl)-7-hydroxy-6,8-dioxo-1a,2,3,4,6,8-hexahydro-1H-5,11a-methanocyclopropa[h]pyrido[1,2-a][1,4]diazonine-9-carboxamide (65-1 and 65-2)

A mixture of benzyl (1R,7S)-1-(((benzyloxy)carbonyl)amino)-3-azabicyclo[5.1.0]oct-5-ene-3-carboxylate or (1S,7R)-1-(((benzyloxy)carbonyl)amino)-3-azabicyclo[5.1.0]oct-5-ene-3-carboxylate (65d-1 or 65d-2, 96.4 mg, 0.246 mmol) and 20% palladium hydroxide on carbon (9.9 mg) in ethanol (2 mL) and ethyl acetate (4 mL) was stirred under H$_2$ atmosphere for 3 h. The reaction mixture was filtered through celite, washed with ethanol, and the filtrate was concentrated to dryness to get the crude hydrogenated product.

Methyl 3-(benzyloxy)-5-((2,4-difluorobenzyl)carbamoyl)-4-oxo-4H-pyran-2-carboxylate (52.9 mg, 0.123 mmol) and sodium bicarbonate (273 mg, 0.325 mmol) were added to the crude product, followed by water (0.5 mL) and methanol (2.5 mL), before stirring at 50° C. for 17 h. The reaction mixture was concentrated to remove most of solvent and the residue was dissolved in ethyl acetate (15 mL) and brine (15 mL), and the fractions were separated. The aqueous fraction was extracted with ethyl acetate (15 mL), and the two organic fractions were washed with brine, combined, dried over MgSO$_4$, and concentrated. The residue was dissolved in methanol (2 mL) and 1 N lithium hydroxide (1 mL), and stirred vigorously at 50° C. for 30 min. The resulting reaction mixture was neutralized with 1 N HCl and diluted with ethyl acetate (15 mL) before washing with water (15 mL×2). After the aqueous fractions were extracted with ethyl acetate (15 mL), the combined organic fractions were dried over MgSO$_4$ and concentrated. MS (m/z) 506.16 [M+H]$^+$.

The above residue was dissolved in toluene (0.2 mL) and trifluoroacetic acid (1 mL) before stirring at rt. After 2 h, the reaction mixture was concentrated and the residue was purified by preparative HPLC (column, Gemini 10u C18 110A, AXI; 250×21.2 mm) eluting with 10-70% acetonitrile in water (0.1% TFA) to get the title compounds (65-1 or 65-2).

65-1: MS (m/z) 416.21 [M+H]$^+$. $^1$H NMR (400 MHz, Acetonitrile-d$_3$) δ 10.28 (s, 1H), 8.20 (s, 1H), 7.39 (td, J=8.7, 6.4 Hz, 1H), 7.04-6.81 (m, 2H), 4.56 (d, J=5.8 Hz, 2H), 4.43 (dd, J=13.7, 4.6 Hz, 1H), 4.05 (dt, J=14.9, 1.0 Hz, 1H), 3.29 (d, J=14.9 Hz, 1H), 3.00 (ddd, J=13.7, 12.3, 3.4 Hz, 1H), 2.34 (dd, J=15.0, 5.6 Hz, 1H), 2.28 (dd, J=9.5, 7.9 Hz, 1H), 1.86-1.73 (m, 1H), 1.73-1.62 (m, 1H), 1.41 (dd, J=7.8, 6.5 Hz, 1H), 1.39-1.31 (m, 1H), 1.25 (tt, J=10.3, 5.8 Hz, 1H). $^{19}$F NMR (376 MHz, Acetonitrile-d$_3$) δ −77.35, −114.10 (p, J=7.6 Hz), −116.63 (q, J=8.8, 8.3 Hz).

65-2: MS (m/z) 416.21 [M+H]$^+$. $^1$H NMR (400 MHz, Acetonitrile-d$_3$) δ 10.30 (s, 1H), 8.23 (s, 1H), 7.42 (td, J=8.8, 6.6 Hz, 1H), 7.06-6.87 (m, 2H), 4.59 (d, J=5.8 Hz, 2H), 4.46 (dt, J=13.8, 3.2 Hz, 1H), 4.15-3.98 (m, 1H), 3.32 (d, J=14.9 Hz, 1H), 3.03 (ddd, J=13.7, 12.3, 3.4 Hz, 1H), 2.42-2.33 (m, 1H), 2.31 (dd, J=9.5, 7.8 Hz, 1H), 1.82 (dtdd, J=14.4, 12.4, 4.7, 2.0 Hz, 1H), 1.72 (dddd, J=12.5, 5.4, 3.4, 1.7 Hz, 1H), 1.45 (dd, J=7.9, 6.4 Hz, 1H), 1.42-1.33 (m, 1H), 1.34-1.23 (m, 1H). $^{19}$F NMR (376 MHz, Acetonitrile-d$_3$) δ −77.35, −114.04 (ddd, J=15.6, 8.8, 6.8 Hz), −116.45, −116.76 (m).

Example 63: Preparation of (1aR,11aR)—N-(2,4,6-trifluorobenzyl)-7-hydroxy-6,8-dioxo-1a,2,3,4,6,8-hexahydro-1H-5,11a-methanocyclopropa[h]pyrido[1,2-a][1,4]diazonine-9-carboxamide and (1aS,11aS)—N-(2,4,6-trifluorobenzyl)-7-hydroxy-6,8-dioxo-1a,2,3,4,6,8-hexahydro-1H-5,11a-methanocyclopropa[h]pyrido[1,2-a][1,4]diazonine-9-carboxamide (66-1 and 66-2)

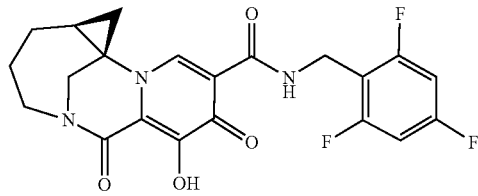

66-1

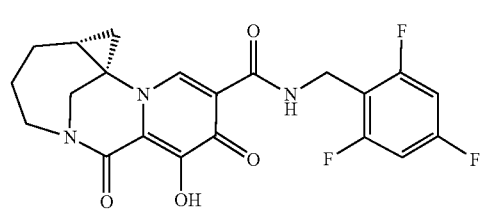

66-2

The title compounds were synthesized analogously to 65-1 and 65-2 using methyl 3-(benzyloxy)-4-oxo-5-((2,4,6-trifluorobenzyl)carbamoyl)-4H-pyran-2-carboxylate in place of methyl 3-(benzyloxy)-5-((2,4-difluorobenzyl)carbamoyl)-4-oxo-4H-pyran-2-carboxylate.

66-1: MS (m/z) 434.19 [M+H]$^+$. $^1$H NMR (400 MHz, Acetonitrile-d$_3$) δ 10.28 (s, 1H), 8.18 (s, 1H), 6.94-6.72 (m, 2H), 4.68-4.49 (m, 2H), 4.42 (dd, J=13.7, 4.5 Hz, 1H), 4.03 (dd, J=14.6, 1.4 Hz, 1H), 3.28 (d, J=14.8 Hz, 1H), 2.99 (ddd, J=13.8, 12.3, 3.4 Hz, 1H), 2.32 (d, J=9.2 Hz, 1H), 2.28 (dd, J=9.6, 7.8 Hz, 1H), 1.86-1.72 (m, 1H), 1.72-1.62 (m, 1H), 1.40 (dd, J=7.9, 6.5 Hz, 1H), 1.38-1.29 (m, 1H), 1.24 (tt, J=10.6, 5.7 Hz, 1H). $^{19}$F NMR (376 MHz, Acetonitrile-d$_3$) δ −77.32, −111.22 (tt, J=9.4, 6.2 Hz), −113.94 (t, J=7.3 Hz).

66-2: MS (m/z) 434.22 [M+H]$^+$. $^1$H NMR (400 MHz, Acetonitrile-d$_3$) δ 10.28 (s, 1H), 8.18 (s, 1H), 6.92-6.74 (m, 2H), 4.67-4.49 (m, 2H), 4.42 (dd, J=13.6, 4.5 Hz, 1H), 4.10-3.97 (m, 1H), 3.28 (d, J=14.9 Hz, 1H), 2.99 (ddd, J=13.8, 12.3, 3.4 Hz, 1H), 2.38-2.21 (m, 1H), 2.31-2.21 (m, 1H), 1.86-1.72 (m, 1H), 1.72-1.61 (m, 1H), 1.40 (dd, J=7.9, 6.4 Hz, 1H), 1.38-1.29 (m, 1H), 1.24 (tt, J=10.6, 5.7 Hz, 1H). $^{19}$F NMR (376 MHz, Acetonitrile-d$_3$) δ −77.37, −111.21 (tt, J=9.0, 6.0 Hz), −113.95 (q, J=5.8, 4.4 Hz).

Example 64: Preparation of N-(3-chloro-2,4-difluorobenzyl)-4-fluoro-7-hydroxy-6,8-dioxo-6,8,13,14-tetrahydro-12H-5,12-methanobenzo[e]pyrido[1,2-a][1,4]diazonine-9-carboxamide (67)

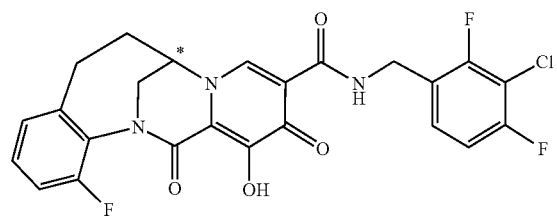 [SMILES: O=C(NCc1ccc(F)c(Cl)c1F)c1cn2c(c(O)c1=O)C(=O)N1CC2CCc2cccc(F)c21]

The title compound was prepared similarly to 50-2 using 9-fluoro-1,3,4,5-tetrahydro-2H-benzo[b]azepin-2-one in place of 7,8-difluoro-1,3,4,5-tetrahydro-2H-benzo[b]azepin-2-one (50a), and methyl 3-(benzyloxy)-5-((3-chloro-2,4-difluorobenzyl)carbamoyl)-4-oxo-4H-pyran-2-carboxylate in place of methyl 3-(benzyloxy)-4-oxo-5-((2,4,6-trifluorobenzyl)carbamoyl)-4H-pyran-2-carboxylate. MS (m/z) 504.1 [M+H]$^+$. $^1$H NMR (400 MHz, DMSO-d$_6$) δ 10.36 (t, J=6.0 Hz, 1H), 8.59 (s, 1H), 7.43-7.35 (m, 1H), 7.35-7.24 (m, 2H), 7.19 (dd, J=23.5, 8.2 Hz, 2H), 4.92 (s, 1H), 4.60 (d, J=6.0 Hz, 2H), 4.27-4.15 (m, 1H), 3.78 (dd, J=14.8, 2.0 Hz, 1H), 2.85 (d, J=8.2 Hz, 1H), 2.77 (d, J=10.6 Hz, 1H), 2.29 (d, J=16.2 Hz, 1H), 2.15-2.00 (m, 1H).

Example 65: Preparation of N-(3-chloro-2,4-difluorobenzyl)-2-fluoro-7-hydroxy-6,8-dioxo-6,8,13,14-tetrahydro-12H-5,12-methanobenzo[e]pyrido[1,2-a][1,4]diazonine-9-carboxamide (68)

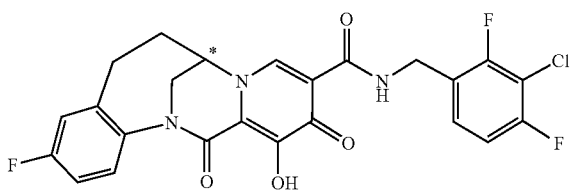 [SMILES: O=C(NCc1ccc(F)c(Cl)c1F)c1cn2c(c(O)c1=O)C(=O)N1CC2CCc2cc(F)ccc21]

The title compound was prepared similarly to 50-2 using 7-fluoro-1,3,4,5-tetrahydro-2H-benzo[b]azepin-2-one in place of 7,8-difluoro-1,3,4,5-tetrahydro-2H-benzo[b]azepin-2-one (50a), and methyl 3-(benzyloxy)-5-((3-chloro-2,4-difluorobenzyl)carbamoyl)-4-oxo-4H-pyran-2-carboxylate in place of methyl 3-(benzyloxy)-4-oxo-5-((2,4,6-trifluorobenzyl)carbamoyl)-4H-pyran-2-carboxylate. MS (m/z) 504.1 [M+H]$^+$. $^1$H NMR (400 MHz, DMSO-d$_6$) δ 10.37 (t, J=6.0 Hz, 1H), 8.58 (s, 1H), 7.48-7.30 (m, 3H), 7.30-7.18 (m, 2H), 7.18-7.00 (m, 1H), 4.90-4.85 (m, 1H), 4.60 (d, J=6.0 Hz, 2H), 4.14 (d, J=14.4 Hz, 1H), 3.72 (dd, J=14.7, 2.0 Hz, 1H), 2.80 (dt, J=8.4, 4.1 Hz, 1H), 2.74-2.69 (m, 1H), 2.22 (d, J=4.8 Hz, 1H), 2.08 (dd, J=11.9, 5.3 Hz, 1H).

Example 66: Preparation of N-(3-chloro-2,4-difluorobenzyl)-2,3-difluoro-7-hydroxy-6,8-dioxo-6,8,13,14-tetrahydro-12H-5,12-methanobenzo[e]pyrido[1,2-a][1,4]diazonine-9-carboxamide (69)

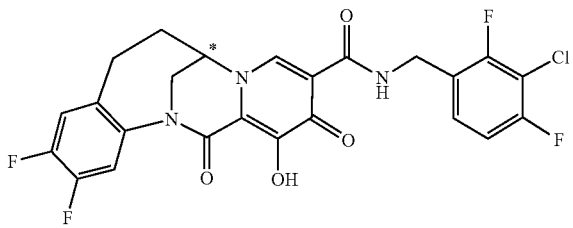 [SMILES: O=C(NCc1ccc(F)c(Cl)c1F)c1cn2c(c(O)c1=O)C(=O)N1CC2CCc2cc(F)c(F)cc21]

The title compound was prepared similarly to 50-2 using methyl 3-(benzyloxy)-5-((3-chloro-2,4-difluorobenzyl)carbamoyl)-4-oxo-4H-pyran-2-carboxylate in place of methyl 3-(benzyloxy)-4-oxo-5-((2,4,6-trifluorobenzyl)carbamoyl)-4H-pyran-2-carboxylate. MS (m/z) 522 [M+H]$^+$. $^1$H NMR (400 MHz, DMSO-d$_6$) δ 10.35 (t, J=6.0 Hz, 1H), 8.57 (s, 1H), 7.48 (dt, J=11.5, 8.7 Hz, 2H), 7.44-7.35 (m, 1H), 7.28 (td, J=8.8, 1.7 Hz, 1H), 4.89 (t, J=2.5 Hz, 1H), 4.60 (d, J=5.9 Hz, 2H), 4.13 (d, J=14.9 Hz, 1H), 3.78 (dd, J=14.8, 2.0 Hz, 1H), 2.85-2.73 (m, 1H), 2.73-2.64 (m, 1H), 2.24 (s, 1H), 2.12-2.03 (m, 1H).

Example 67: Preparation of (6S)-1-hydroxy-2,14-dioxo-N-(2,4,6-trifluorobenzyl)-2,7,12,14-tetrahydro-6H-6,13-methanobenzo[f]pyrido[1,2-a][1,4]diazonine-3-carboxamide (70)

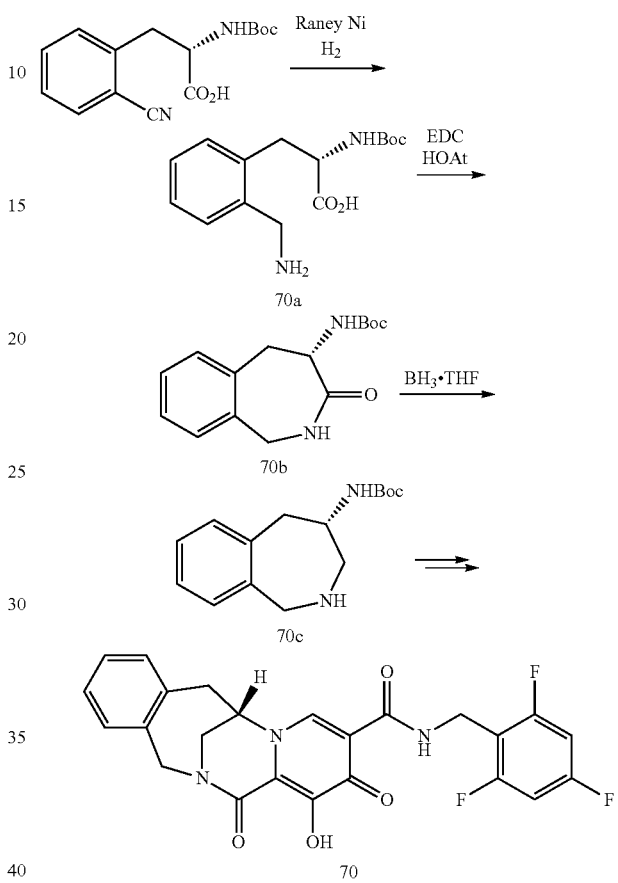

Synthesis of (S)-3-(2-(aminomethyl)phenyl)-2-((tert-butoxycarbonyl)amino)propanoic acid (70a)

A solution of (S)-2-((tert-butoxycarbonyl)amino)-3-(2-cyanophenyl)propanoic acid (1.00 g, 3.44 mmol) in EtOH (34 mL) was added to a Parr shaker pressure vessel. Raney nickel (0.142 g, 2.42 mmol) was added, and the reaction mixture was hydrogenated at 55 psi for 24 h. The reaction mixture was filtered through Celite, rinsing with EtOH then CH$_2$Cl$_2$. The filtrate was concentrated to afford the title compound (70a), which was used in the next step without further purification. MS (m/z) 294.93 [M+H]$^+$.

Synthesis of tert-butyl (S)-(3-oxo-2,3,4,5-tetrahydro-1H-benzo[c]azepin-4-yl)carbamate (70b)

To a suspension of crude (S)-3-(2-(aminomethyl)phenyl)-2-((tert-butoxycarbonyl)amino) propanoic acid (70a, 1.20 g, 4.08 mmol) in CH$_2$Cl$_2$ (17 mL) and DMF (3.4 mL) was added HOAt (0.703 g, 5.17 mmol) and EDC (0.660 g, 3.44 mmol). The reaction mixture was stirred at rt for 1 h and concentrated. EtOAc was added, and the organic phase was washed with 1 M HCl, 1 M NaOH, water, and brine. The organic phase was dried over Na$_2$SO$_4$, filtered, concentrated, and purified by column chromatography (25-100% EtOAc/heptane) to afford the title compound (70b). MS (m/z) 299.03 [M+Na]+.

Synthesis of tert-butyl (S)-(2,3,4,5-tetrahydro-1H-benzo[c]azepin-4-yl)carbamate (70c)

To a solution of tert-butyl (S)-(3-oxo-2,3,4,5-tetrahydro-1H-benzo[c]azepin-4-yl)carbamate (70b, 0.42 g, 1.52 mmol) in THF (5 mL) at 0° C., was added a 1 M borane-THF solution (6.1 mL, 6.1 mmol). The reaction mixture was allowed to warm to rt and stir for 2 h. The reaction mixture was cooled to 0° C., and quenched with MeOH (3 mL). After stirring for 5 min, the mixture was concentrated, diluted with EtOAc, and washed with saturated aqueous NaHCO3 and water. The combined aqueous phase was extracted with EtOAc. The combined organic phase was dried over Na2SO4, and concentrated to afford the title compound (70c), which was used in the next step without further purification. MS (m/z) 262.99 [M+H]+.

Synthesis of (6S)-1-hydroxy-2,14-dioxo-N-(2,4,6-trifluorobenzyl)-2,7,12,14-tetrahydro-6H-6,13-methanobenzo[f]pyrido[1,2-a][1,4]diazonine-3-carboxamide (70)

The title compound was synthesized in the same manner as compound 27, using tert-butyl (S)-(2,3,4,5-tetrahydro-1H-benzo[c]azepin-4-yl)carbamate (70c) in place of tert-butyl (2-oxo-2,3,4,5-tetrahydro-1H-benzo[b]azepin-3-yl) carbamate and methyl 3-(benzyloxy)-4-oxo-5-((2,4,6-trifluorobenzyl)carbamoyl)-4H-pyran-2-carboxylate in place of methyl 3-(benzyloxy)-5-((2,4-difluorobenzyl)carbamoyl)-4-oxo-4H-pyran-2-carboxylate. MS (m/z) 470.19 [M+H]+. 1H NMR (400 MHz, DMSO-d6) δ 10.37 (t, J=5.8 Hz, 1H), 8.54 (s, 1H), 7.34-7.26 (m, 2H), 7.25-7.18 (m, 3H), 7.17 (d, J=7.4 Hz, 1H), 5.53 (d, J=16.4 Hz, 1H), 4.99 (dt, J=8.4, 4.2 Hz, 1H), 4.58 (d, J=5.7 Hz, 2H), 4.45 (d, J=16.6 Hz, 1H), 3.77 (d, J=14.5 Hz, 1H), 3.55 (dd, J=14.7, 2.8 Hz, 1H), 3.36 (dd, J=15.0, 7.5 Hz, 1H), 2.87 (dd, J=14.9, 7.7 Hz, 1H). 19F NMR (376 MHz, DMSO-d6) δ -109.27 (tt, J=9.2, 6.3 Hz), -112.59 (t, J=7.3 Hz).

Example 68: Preparation of (6S)—N-(2,4-difluorobenzyl)-1-hydroxy-2,14-dioxo-2,7,12,14-tetrahydro-6H-6,13-methanobenzo[f]pyrido[1,2-a][1,4]diazonine-3-carboxamide (71)

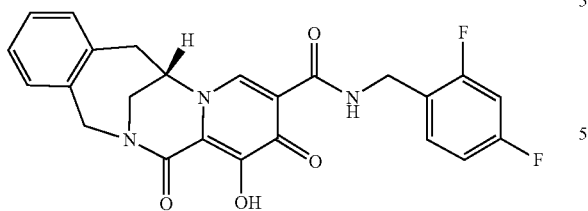

The title compound was prepared in a similar manner to compound 70 using methyl 3-(benzyloxy)-5-((2,4-difluorobenzyl)carbamoyl)-4-oxo-4H-pyran-2-carboxylate instead of methyl 3-(benzyloxy)-4-oxo-5-((2,4,6-trifluorobenzyl)carbamoyl)-4H-pyran-2-carboxylate. MS (m/z) 452.14 [M+H]+. 1H NMR (400 MHz, DMSO-d6) δ 10.34 (t, J=5.9 Hz, 1H), 8.56 (s, 1H), 7.41 (td, J=8.7, 6.5 Hz, 1H), 7.32-7.20 (m, 4H), 7.17 (d, J=7.4 Hz, 1H), 7.11-7.02 (m, 1H), 5.54 (d, J=16.5 Hz, 1H), 5.07-4.92 (m, 1H), 4.56 (d, J=6.0 Hz, 2H), 4.46 (d, J=16.6 Hz, 1H), 3.78 (d, J=14.5 Hz, 1H), 3.56 (dd, J=14.7, 2.8 Hz, 1H), 3.40-3.39 (m, 1H), 2.89 (dd, J=14.9, 7.7 Hz, 1H). 19F NMR (376 MHz, DMSO-d6) δ -112.36 (p, J=7.7 Hz), -114.98 (q, J=8.8 Hz).

Example 69: Preparation of (6S,7R)-6-chloro-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide and (6R,7R)-6-chloro-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (72-1 and 72-2)

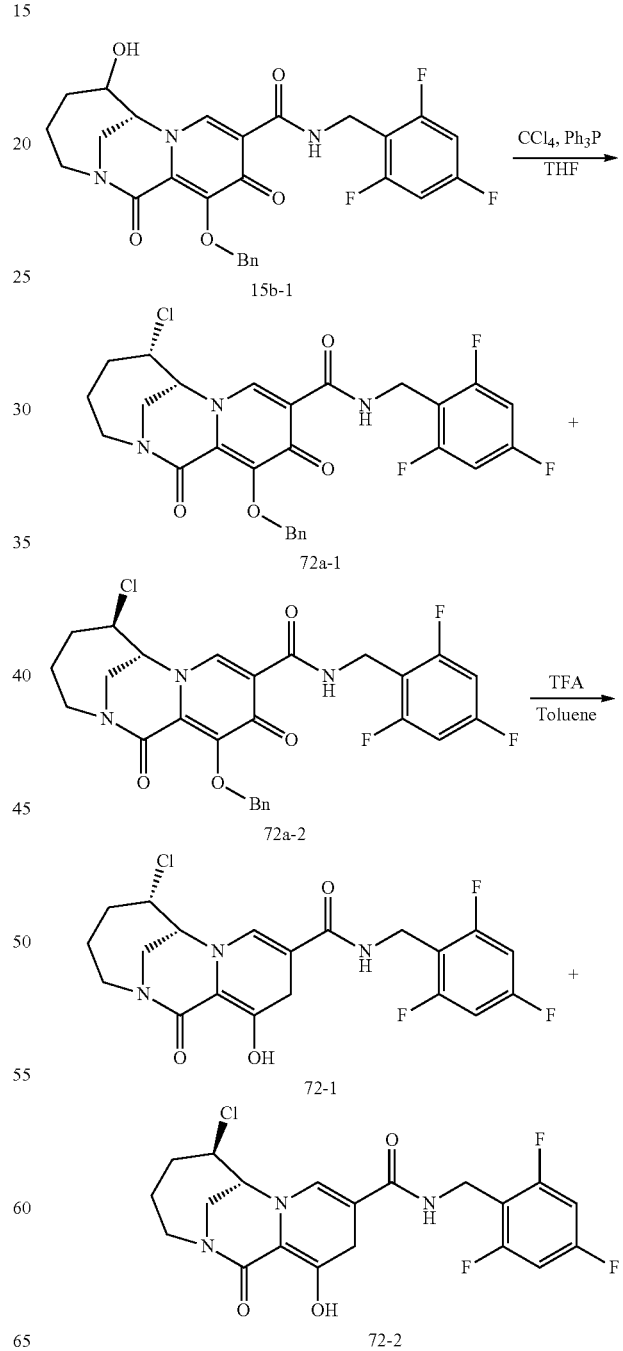

Synthesis of (6S,7R)-12-(benzyloxy)-6-chloro-1,11-dioxo-N-(2,4,6-trifluorobenzyl)-1,4,5,6,7,11-hexahydro-3H-2,7-methanopyrido[1,2-a][1,4]diazonine-10-carboxamide and (6R,7R)-12-(benzyloxy)-6-chloro-1,11-dioxo-N-(2,4,6-trifluorobenzyl)-1,4,5,6,7,11-hexahydro-3H-2,7-methanopyrido[1,2-a][1,4]diazonine-10-carboxamide (72a-1 and 72a-2)

(7R)-12-(benzyloxy)-6-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (15b-1, 150 mg, 0.284 mmol) and Ph₃P (186 mg, 0.711 mmol) were mixed with CCl₄ (3 mL) and DCM (3 mL) at room temperature. Reaction mixture was then heated in a seal tube at 37° C. for 17 hr. The reaction mixture was purified on silica gel column with 0-100% EtOAc/hexane to afford product as a mixture of two diastereomers. Subsequent chiral separation with SFC-IA 45 with MeOH as co-solvent afforded the title compounds (72a-1 and 72a-2), stereochemistry assigned speculatively. MS (m/z) 546.10 [M+H]⁺.

Synthesis of (6S,7R)-6-chloro-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide and (6R,7R)-6-chloro-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (72-1 and 72-2)

(6S,7R)-12-(benzyloxy)-6-chloro-1,11-dioxo-N-(2,4,6-trifluorobenzyl)-1,4,5,6,7,11-hexahydro-3H-2,7-methanopyrido[1,2-a][1,4]diazonine-10-carboxamide or (6R,7R)-12-(benzyloxy)-6-chloro-1,11-dioxo-N-(2,4,6-trifluorobenzyl)-1,4,5,6,7,11-hexahydro-3H-2,7-methanopyrido[1,2-a][1,4]diazonine-10-carboxamide (72a-1 or 72a-2, 31 mg, 0.0568 mmol) was mixed with toluene (4 mL) at rt. and TFA (4 mL) was added. Reaction was stirred at room temperature for 17 hours, and was concentrated to dryness. The residue was put under high vacuum for 10 hours. The residue was taken up in MeOH. After filtering the solution, the filtrate was purified by preparative HPLC (column, Gemini 10μ C18 110A, AXI/; 250×21.2 mm) eluting with 5-100% acetonitrile in water (0.1% TFA) over 20 minutes. Combined fractions were freeze-dried to afford the title compound (72-1 or 72-2).

72-1: MS (m/z) 456.20 [M+]+. ¹H NMR (400 MHz, DMSO-d₆) δ 10.62 (s, 1H), 10.31 (t, J=5.8 Hz, 1H), 8.49 (s, 1H), 7.18 (dd, J=9.2, 8.1 Hz, 2H), 6.49 (s, 1H), 4.91 (d, J=2.6 Hz, 1H), 4.71 (td, J=3.6, 1.7 Hz, 1H), 4.65-4.46 (m, 2H), 4.19-4.03 (m, 1H), 3.95-3.69 (m, 2H), 3.11 (ddd, J=13.2, 7.5, 2.8 Hz, 1H), 2.13 (dt, J=15.0, 5.5 Hz, 1H), 2.06-1.91 (m, 1H), 1.88-1.72 (m, 1H), 1.55 (dd, J=16.0, 10.9 Hz, 1H).

72-2: MS (m/z) 456.20 [M+]+. ¹H NMR (400 MHz, DMSO-d₆) δ 10.62 (s, 1H), 10.31 (t, J=5.8 Hz, 1H), 8.49 (s, 1H), 7.18 (t, J=8.6 Hz, 2H), 6.50 (s, 1H), 4.91 (s, 1H), 4.71 (d, J=5.5 Hz, 1H), 4.64-4.45 (m, 2H), 4.11 (dt, J=13.1, 8.0 Hz, 1H), 3.97-3.69 (m, 2H), 3.11 (ddd, J=13.2, 7.5, 2.7 Hz, 1H).

Example 70: (5R,7S)-5-fluoro-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide and (5R,7R)-5-fluoro-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (73-1 and 73-2)

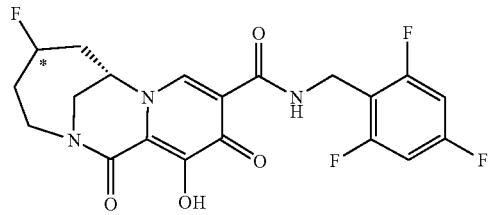

73-1

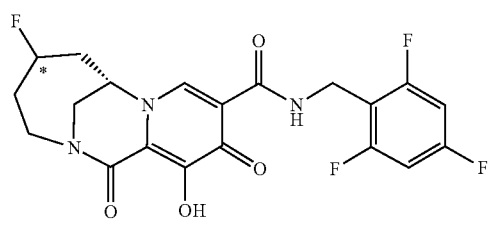

73-2

The title compounds were prepared analogously to 56-1 and 56-2, using methyl 3-(benzyloxy)-4-oxo-5-((2,4,6-trifluorobenzyl)carbamoyl)-4H-pyran-2-carboxylate in place of methyl 3-(benzyloxy)-5-((2,4-difluorobenzyl)carbamoyl)-4-oxo-4H-pyran-2-carboxylate.

73-1: MS (m/z) 440.1 [M+H]⁺. ¹H NMR (400 MHz, Chloroform-d) δ 10.45 (s, 1H), 8.47 (s, 1H), 6.75-6.58 (m, 2H), 5.24-5.01 (m, 1H), 4.83-4.63 (m, 2H), 4.60-4.42 (m, 2H), 4.12-3.94 (m, 1H), 3.56 (dd, 1H), 3.30-3.16 (m, 1H), 2.50 (s, 2H), 2.36-2.05 (m, 1H), 1.27 (s, 1H).

73-2: MS (m/z) 440.1 [M+H]⁺. ¹H NMR (400 MHz, Chloroform-d) δ 10.45 (s, 1H), 8.58 (s, 1H), 6.77-6.61 (m, 2H), 4.97 (dt, 1H), 4.79-4.61 (m, 2H), 4.61-4.50 (m, 2H), 3.99 (d, 1H), 3.83 (dd, 1H), 3.20 (dt, 1H), 2.90-2.66 (m, 1H), 2.38-2.21 (m, 1H), 2.21-2.11 (m, 1H), 2.11-1.94 (m, 1H).

Example 71: (7S)—N-(3-chloro-2,4,6-trifluorobenzyl)-12-hydroxy-1,11-dioxo-1,4,5,6,7,11-hexahydro-3H-2,7-methanopyrido[1,2-a][1,4]diazonine-10-carboxamide (74)

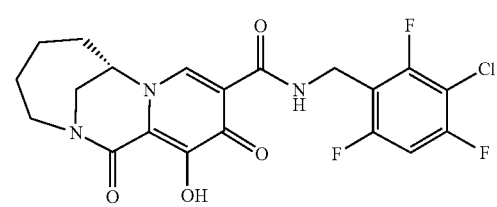 [SMILES: O=C(NCc1c(F)cc(F)c(Cl)c1F)c1cn2c(c(O)c1=O)C(=O)N1CCCC[C@H]2C1]

The title compound was prepared analogously to 62, using 3-chloro-2,4,6-trifluorobenzaldehyde in place of 2,3-dichloro-4-fluorobenzaldehyde. MS (m/z) 456.3 [M+H]⁺. ¹H NMR (400 MHz, Chloroform-d) δ 10.45 (s, 1H), 8.39 (s, 1H), 6.81 (td, 1H), 4.71 (qd, 2H), 4.49-4.33 (m, 2H), 3.97 (d, 1H), 3.53 (dd, 1H), 3.16 (ddd, 1H), 2.22-1.98 (m, 3H), 1.94-1.74 (m, 1H), 1.45-1.29 (m, 2H).

Example 72: Preparation of (7S)-6-fluoro-12-hydroxy-1,11-dioxo-N-(2,4,6-trifluorobenzyl)-1,4,7,11-tetrahydro-3H-2,7-methanopyrido[1,2-a][1,4]diazonine-10-carboxamide and (7R)-6-fluoro-12-hydroxy-1,11-dioxo-N-(2,4,6-trifluorobenzyl)-1,4,7,11-tetrahydro-3H-2,7-methanopyrido[1,2-a][1,4]diazonine-10-carboxamide (75-1 and 75-2)

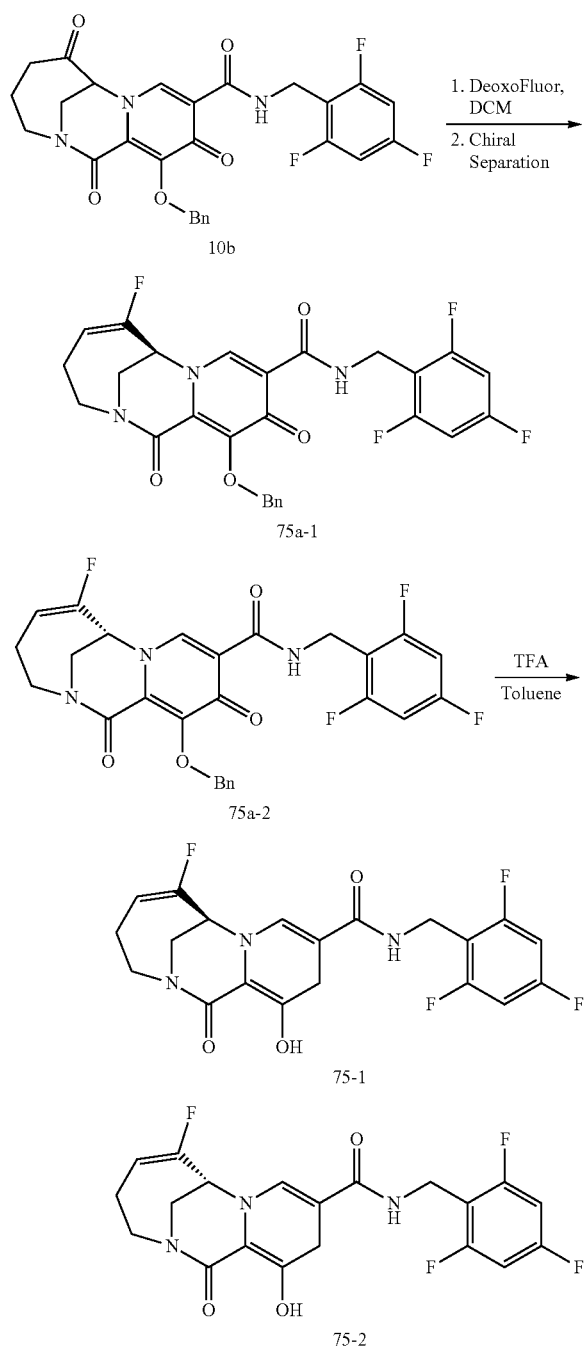

Synthesis of (7S)-12-(benzyloxy)-6-fluoro-1,11-dioxo-N-(2,4,6-trifluorobenzyl)-1,4,7,11-tetrahydro-3H-2,7-methanopyrido[1,2-a][1,4]diazonine-10-carboxamide and (7R)-12-(benzyloxy)-6-fluoro-1,11-dioxo-N-(2,4,6-trifluorobenzyl)-1,4,7,11-tetrahydro-3H-2,7-methanopyrido[1,2-a][1,4]diazonine-10-carboxamide (75a-1 and 75a-2)

Neat DeoxoFluor (3.7 mL, 20.2 mmol) was added dropwise to a solution of 12-(benzyloxy)-1,6,11-trioxo-N-(2,4,6-trifluorobenzyl)-1,4,5,6,7,11-hexahydro-3H-2,7-methanopyrido[1,2-a][1,4]diazonine-10-carboxamide (10b, 1.06 g, 2.02 mmol) in DCM (9 mL) at 0° C. Reaction was stirred without recharging cold bath for 17 hours. Then a second portion of DeoxoFluor (3.7 mL, 20.2 mmol) was added at room temperature. Reaction mixture was stirred at room temperature for 17 hours. The reaction mixture was added to a well stirred saturated $NaHCO_3$/water slurry. It was stirred at room temperature for 20-30 min, and EtOAc (200 mL) was added. The mixture was filtered through celite plug. The organic phase was concentrated, and the residue was purified on silica gel column with 0-100% EtOAc/Hex to afford racemic fluoro-olefin product. The two enantiomers were separated with SFC separation using IG 35 Isopropanol-$NH_3$ to afford of the title products, stereochemistry assigned arbitrarily. 75a-1: MS (m/z) 528.06 $[M+H]^+$; 75a-2: MS (m/z) 528.03 $[M+H]^+$.

Synthesis of (7S)- and (7R)-6-fluoro-12-hydroxy-1,11-dioxo-N-(2,4,6-trifluorobenzyl)-1,4,7,11-tetrahydro-3H-2,7-methanopyrido[1,2-a][1,4]diazonine-10-carboxamide (75-1 and 75-2)

TFA (2 mL) was added to a solution of (7S)- or (7R)-12-(benzyloxy)-6-fluoro-1,11-dioxo-N-(2,4,6-trifluorobenzyl)-1,4,7,11-tetrahydro-3H-2,7-methanopyrido[1,2-a][1,4]diazonine-10-carboxamide (75a-1 or 75a-2, 65 mg, 0.123 mmol) in toluene (2 mL) at rt. Reaction was stirred at room temperature for 17 hours and was concentrated to dryness. The residue was taken up in MeOH, filtered, and the filtrate was purified by preparative HPLC (column, Gemini 10μ C18 110A, AXI; 250×21.2 mm) eluting with 5-100% acetonitrile in water (0.1% TFA) over 20 minutes, to afford the title compounds.

75-1: MS (m/z) 438.20 $[M+H]^+$; $^1H$ NMR (400 MHz, DMSO-$d_6$) δ 10.27 (t, J=5.8 Hz, 1H), 8.47 (s, 1H), 7.18 (dd, J=9.2, 8.1 Hz, 2H), 5.77-5.47 (m, 2H), 4.55 (d, J=5.8 Hz, 2H), 4.19 (ddd, J=12.9, 11.5, 6.7 Hz, 1H), 4.07 (dt, J=15.1, 1.9 Hz, 1H), 3.89 (ddd, J=15.4, 8.5, 1.8 Hz, 1H), 3.29 (dd, J=13.0, 8.2 Hz, 1H), 2.80 (tq, J=10.4, 6.6, 6.0 Hz, 1H), 2.20 (ddd, J=16.2, 10.0, 6.6 Hz, 1H).

75-2: MS (m/z): 438.20 $[M+H]^+$. $^1H$ NMR (400 MHz, DMSO-$d_6$) δ 10.27 (t, J=5.8 Hz, 1H), 8.47 (s, 1H), 7.19 (t, J=8.6 Hz, 2H), 5.82-5.42 (m, 2H), 4.55 (d, J=5.8 Hz, 2H), 4.25-4.13 (m, 1H), 4.07 (dt, J=15.2, 1.9 Hz, 1H), 3.89 (ddd, J=15.3, 8.4, 1.7 Hz, 1H), 3.29 (dd, J=13.0, 8.2 Hz, 1H), 2.98-2.67 (m, 1H), 2.20 (ddd, J=16.3, 9.9, 6.6 Hz, 1H).

Example 73: Preparation of (7R)—N-(2,4-difluorobenzyl)-6-(difluoromethyl)-6,12-dihydroxy-1,11-dioxo-1,4,5,6,7,11-hexahydro-3H-2,7-methanopyrido[1,2-a][1,4]diazonine-10-carboxamide (76)

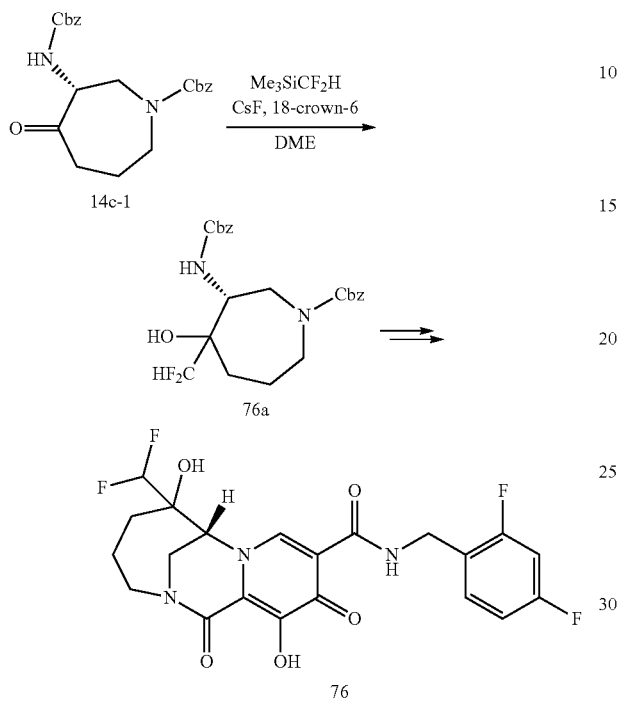

Synthesis of benzyl (3R)-3-(((benzyloxy)carbonyl)amino)-4-(difluoromethyl)-4-hydroxyazepane-1-carboxylate (76a)

Under argon atmosphere, CsF (29 mg, 0.19 mmol) and 18-crown-6 (50 mg, 0.19 mmol) were added to a solution of benzyl (R)-3-(((benzyloxy)carbonyl)amino)-4-oxoazepane-1-carboxylate (14c-1, 250 mg, 0.63 mmol) in 1,2-dimethoxyethane (3 mL). Me$_3$SiCF$_2$H (235 mg, 1.89 mmol) was added, and the mixture was stirred at room temperature overnight. HCl aq. (1 M, 1.0 mL) was added and the mixture was extracted with ethyl acetate (20 mL×3). The organic phase was washed with brine and then dried over Na$_2$SO$_4$. After filtration, and evaporation under vacuum, the residue was subjected to silica gel column chromatography using hexane/ethyl acetate to give the title compound (76a). MS (m/z) 449.17 [M+H]$^+$.

Synthesis of (7R)—N-(2,4-difluorobenzyl)-6-(difluoromethyl)-6,12-dihydroxy-1,11-dioxo-1,4,5,6,7,11-hexahydro-3H-2,7-methanopyrido[1,2-a][1,4]diazonine-10-carboxamide (76)

The title compound was prepared in a manner similar to 60-1, using benzyl (3R)-3-(((benzyloxy)carbonyl)amino)-4-(difluoromethyl)-4-hydroxyazepane-1-carboxylate (76a) in place of benzyl (3R,4S)-3-(((benzyloxy)carbonyl)amino)-4-fluoro-4-methylazepane-1-carboxylate (60b-2). MS (m/z) 470.18 [M+H]$^+$. $^1$H NMR (400 MHz, DMSO-d$_6$) δ 10.48-10.37 (m, 2H), 8.29 (s, 1H), 7.41 (td, J=8.7, 6.6 Hz, 1H), 7.26 (ddd, J=10.6, 9.3, 2.6 Hz, 1H), 7.08 (dt, J=9.4, 4.6 Hz, 1H), 6.55 (s, 2H), 6.01 (t, J=55.3 Hz, 1H), 5.85 (s, 1H), 4.84 (s, 1H), 4.55 (d, J=5.8 Hz, 2H), 4.15 (d, J=12.7 Hz, 1H), 3.88 (s, 2H), 2.93-3.05 (m, 1H), 2.13-1.99 (m, 2H), 1.74-1.59 (m, 2H).

Example 74: Preparation of (6S,7R)—N-(2,4-difluorobenzyl)-6-ethyl-6,12-dihydroxy-1,11-dioxo-1,4,5,6,7,11-hexahydro-3H-2,7-methanopyrido[1,2-a][1,4]diazonine-10-carboxamide (77)

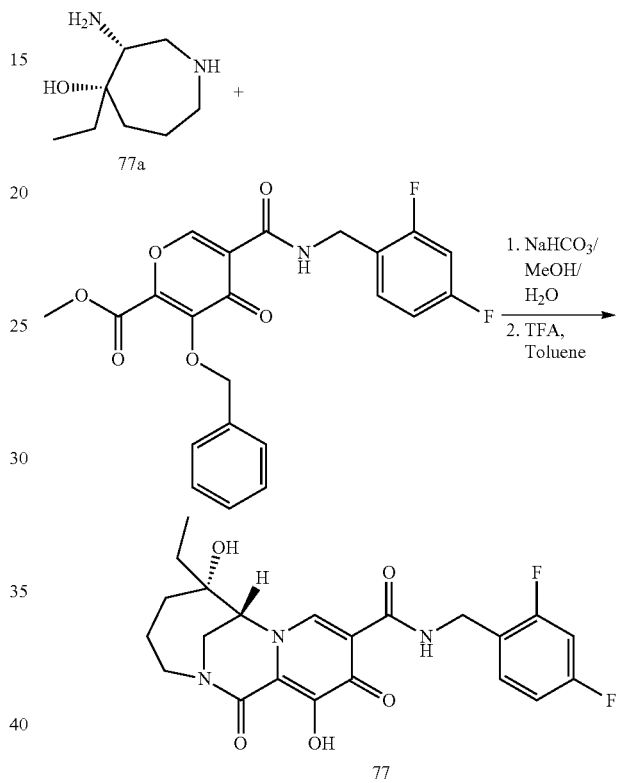

Synthesis of (3R,4S)-3-amino-4-ethylazepan-4-ol (77a)

The title compound was prepared in a manner similar to 14d-1 using ethyl Grignard in place of methyl Grignard.

Preparation of (6S,7R)—N-(2,4-difluorobenzyl)-6-ethyl-6,12-dihydroxy-1,11-dioxo-1,4,5,6,7,11-hexahydro-3H-2,7-methanopyrido[1,2-a][1,4]diazonine-10-carboxamide (77)

The title compound was prepared in a manner similar to compound 28 using (3R,4S)-3-amino-4-ethylazepan-4-ol (77a) instead of 1,4-oxazepan-6-amine. MS (m/z) 448.22 [M+H]$^+$. $^1$H NMR (400 MHz, DMSO-d$_6$) δ 10.79 (s, 1H), 10.46 (t, J=6.0 Hz, 1H), 8.27 (s, 1H), 7.46-7.35 (m, 1H), 7.30-7.20 (m, 1H), 7.12-7.03 (m, 1H), 4.79 (s, 1H), 4.55 (d, J=6.1 Hz, 2H), 4.24 (s, 1H), 4.19-4.06 (m, 1H), 3.84 (dd, J=15.3, 2.9 Hz, 1H), 3.70 (d, J=15.0 Hz, 1H), 1.77 (dt, J=16.7, 8.2 Hz, 3H), 1.56 (dt, J=14.5, 7.1 Hz, 2H), 1.17-1.05 (m, 1H), 0.89 (t, J=7.3 Hz, 3H).

Example 75: Preparation of (7S)-12-hydroxy-1,4,11-trioxo-N-(2,4,6-trifluorobenzyl)-1,4,5,6,7,11-hexahydro-3H-2,7-methanopyrido[1,2-a][1,4]diazonine-10-carboxamide (78)

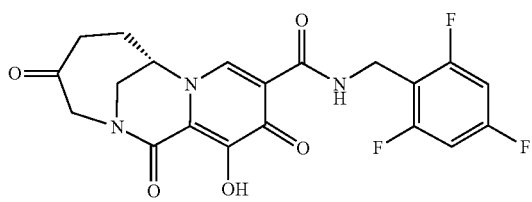 [SMILES: O=C1CC[C@H]2CN(C1)C(=O)c1c(O)c(=O)c(C(=O)NCc3c(F)cc(F)cc3F)cn12]

The title compound was synthesized in a manner similar to compound 60-1, using benzyl (S)-3-(((benzyloxy)carbonyl)amino)-6-oxoazepane-1-carboxylate in place of benzyl (3R,4S)-3-(((benzyloxy)carbonyl)amino)-4-fluoro-4-methylazepane-1-carboxylate (60b-2). MS (m/z) 436.23 [M+H]$^+$. $^1$H NMR (400 MHz, Acetonitrile-d$_3$) δ 10.31 (s, 1H), 8.47 (s, 1H), 7.03-6.80 (m, 2H), 4.86 (d, J=17.4 Hz, 1H), 4.65 (dd, J=21.0, 4.9 Hz, 3H), 4.10 (d, J=14.9 Hz, 1H), 3.63 (d, J=17.4 Hz, 1H), 3.48 (dd, J=15.0, 1.7 Hz, 1H), 2.68-2.56 (m, 1H), 2.34-2.11 (m, 3H).

Example 76: Preparation of (4S,7S)-4,12-dihydroxy-1,11-dioxo-N-(2,4,6-trifluorobenzyl)-1,4,5,6,7,11-hexahydro-3H-2,7-methanopyrido[1,2-a][1,4]diazonine-10-carboxamide and (4R,7S)-4,12-dihydroxy-1,11-dioxo-N-(2,4,6-trifluorobenzyl)-1,4,5,6,7,11-hexahydro-3H-2,7-methanopyrido[1,2-a][1,4]diazonine-10-carboxamide (79-1 and 79-2)

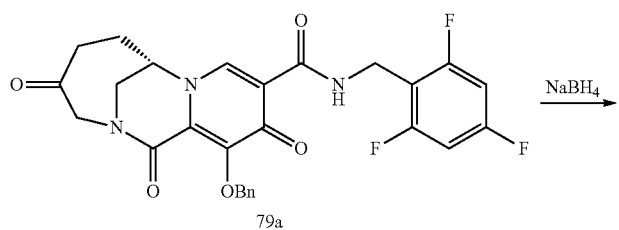

79a

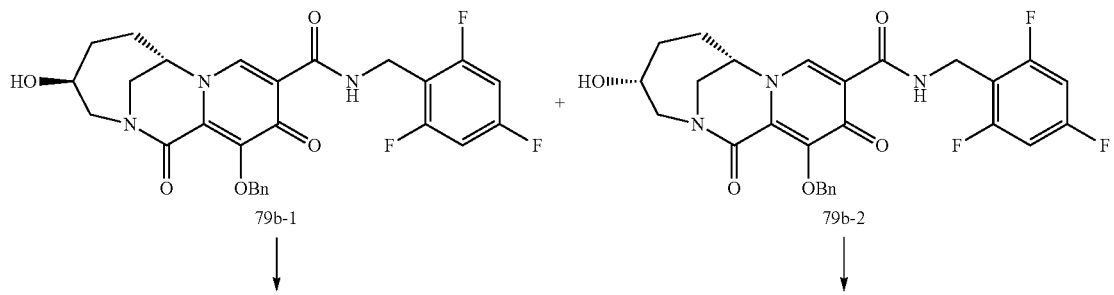

79b-1   79b-2

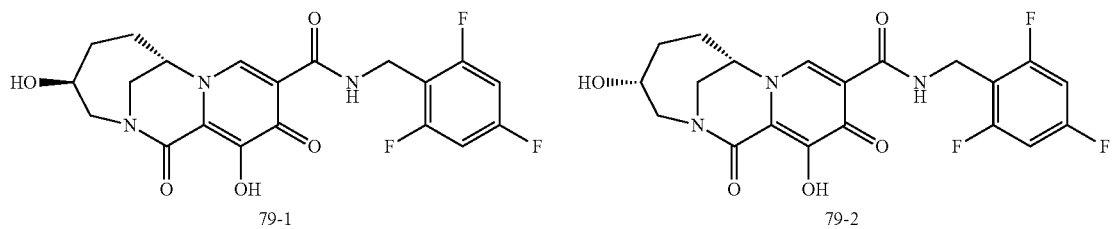

79-1   79-2

Synthesis of (7S)-12-(benzyloxy)-1,4,11-trioxo-N-(2,4,6-trifluorobenzyl)-1,4,5,6,7,11-hexahydro-3H-2,7-methanopyrido[1,2-a][1,4]diazonine-10-carboxamide (79a)

The title compound was prepared in a manner similar to compound 78, and isolated as the benzyl-protected alcohol, before TFA deprotection.

Synthesis of (4S,7S)-12-(benzyloxy)-4-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide and (4R,7S)-12-(benzyloxy)-4-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (79b-1 and 79b-2)

NaBH$_4$ (4 mg) was added to a solution of (7S)-12-(benzyloxy)-1,4,11-trioxo-N-(2,4,6-trifluorobenzyl)-1,4,5,6,7,11-hexahydro-3H-2,7-methanopyrido[1,2-a][1,4]diazonine-10-carboxamide (79a, 27 mg, 0.051 mmol) in methanol (2 mL), at rt. It was stirred for 20 min, and purified via preparative HPLC, eluting with 0-60% acetonitrile (0.1% TFA) in water (0.1% TFA) to give the titled compounds (79b-1 and 79b-2) as separated diastereomers, stereochemistry tentatively assigned. MS (m/z) 528.18 [M+H]$^+$.

Synthesis of (4S,7S)-4,12-dihydroxy-1,11-dioxo-N-(2,4,6-trifluorobenzyl)-1,4,5,6,7,11-hexahydro-3H-2,7-methanopyrido[1,2-a][1,4]diazonine-10-carboxamide and (4R,7S)-4,12-dihydroxy-1,11-dioxo-N-(2,4,6-trifluorobenzyl)-1,4,5,6,7,11-hexahydro-3H-2,7-methanopyrido[1,2-a][1,4]diazonine-10-carboxamide (79-1 and 79-2)

The titled compounds were synthesized in a manner similar to compound 28, using (4S,7S)-12-(benzyloxy)-4-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide or (4R,7S)-12-(benzyloxy)-4-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (79b-1 or 79b-2) in place of (7S)-12-(benzyloxy)-N-(2,4-difluorobenzyl)-1,11-dioxo-1,3,4,6,7,11-hexahydro-2,7-methanopyrido[1,2-d][1,4,7]oxadiazonine-10-carboxamide (28a), and methyl 3-(benzyloxy)-4-oxo-5-((2,4,6-trifluorobenzyl)carbamoyl)-4H-pyran-2-carboxylate in place of methyl 3-(benzyloxy)-5-((2,4-difluorobenzyl)carbamoyl)-4-oxo-4H-pyran-2-carboxylate.

79-1: MS (m/z) 438.22 [M+H]$^+$. $^1$H NMR (400 MHz, Methanol-d$_4$) δ 8.49 (d, J=12.7 Hz, 1H), 7.01-6.82 (m, 2H), 6.74 (t, J=8.3 Hz, 1H), 4.68 (s, 3H), 4.35-4.11 (m, 2H), 3.94 (d, J=14.5 Hz, 1H), 3.69 (d, J=14.7 Hz, 1H), 3.44 (dd, J=12.7, 4.5 Hz, 1H), 2.24 (s, 2H), 2.09 (t, J=11.6 Hz, 1H), 1.90-1.58 (m, 3H).

79-2: MS (m/z) 438.22 [M+H]$^+$. $^1$H NMR (400 MHz, Methanol-d$_4$) δ 8.49 (s, 1H), 6.92 (t, J=8.4 Hz, 2H), 4.68 (s, 2H), 4.56 (dd, J=13.9, 6.1 Hz, 1H), 4.20 (s, 1H), 3.95 (s, 2H), 3.10 (dd, J=13.9, 3.5 Hz, 1H), 2.59 (d, J=14.4 Hz, 1H), 1.95 (d, J=5.1 Hz, 1H), 1.89-1.70 (m, 1H), 1.57 (t, J=13.3 Hz, 1H).

Example 77a: Preparation of (6S)-1-hydroxy-2,15-dioxo-N-(2,4,6-trifluorobenzyl)-2,6,7,8,9,15-hexahydro-6,14-methanobenzo[e]pyrido[1,2-a][1,4]diazecine-3-carboxamide (80-1)

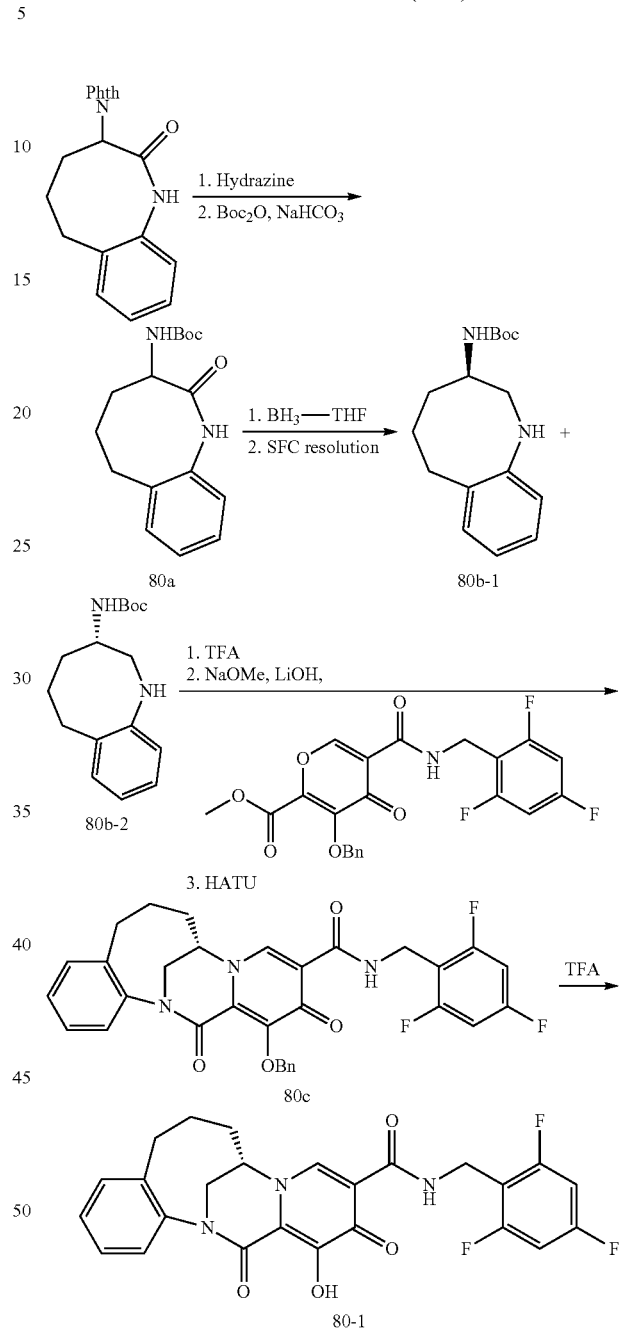

Synthesis of tert-butyl (2-oxo-1,2,3,4,5,6-hexahydrobenzo[b]azocin-3-yl)carbamate (80a)

To a solution of 2-(2-oxo-3,4,5,6-tetrahydro-1H-1-benzazocin-3-yl)isoindoline-1,3-dione, (prepared according to U.S. Pat. No. 4,537,885, 1.5 grams, 4.68 mmol) in ethanol (30 mL) was added hydrazine (0.22 mL, 7.0 mmol). After 3 hours, the reaction mixture was filtered, and the filtrate was concentrated, and purified by CombiFlash (24 g, 0-20%

MeOH/CH$_2$Cl$_2$) to give 3-amino-3,4,5,6-tetrahydro-1H-1-benzazocin-2-one that was used in next step without further purification.

A mixture of 3-amino-3,4,5,6-tetrahydro-1H-1-benzazocin-2-one from above and di-tert-butyl dicarbonate (1.53 g, 7.0 mmol) in saturated sodium bicarbonate (10 mL) and THF (20 mL) was stirred overnight at room temperature. Reaction mixture was diluted with ethyl acetate and washed with brine. Aqueous layer was back-extracted with ethyl acetate. The combined organic layer was dried over MgSO$_4$, filtered, concentrated, and crystallized from refluxing DCM/Hex to give tert-butyl (2-oxo-1,2,3,4,5,6-hexahydrobenzo[b]azocin-3-yl)carbamate (80a). MS (m/z) 290.82 [M+H]$^+$.

Synthesis of tert-butyl (R)-(1,2,3,4,5,6-hexahydrobenzo[b]azocin-3-yl)carbamate and (S)-(1,2,3,4,5,6-hexahydrobenzo[b]azocin-3-yl)carbamate (80b-1 and 80b-2)

To a mixture of tert-butyl (2-oxo-1,2,3,4,5,6-hexahydrobenzo[b]azocin-3-yl)carbamate (80a, 1.09 g, 3.75 mmol) in THF (10 mL) at 0° C., was added 1.0 M borane-THF complex in THF (22.5 mL, 22.5 mmol). After 5 minutes, the reaction mixture was warmed to room temperature, and stirred overnight. Reaction mixture was cooled to 0° C., quenched with methanol, and ethyl acetate, concentrated, dissolved in water and extracted with ethyl acetate (2×). Combined organic layer was washed with brine, dried over MgSO$_4$, filtered, concentrated, and purified by CombiFlash (40 g, 0-100% EtOAc/Hept) to give a racemic mixture. MS (m/z) 277.00 [M+H]$^+$.

Racemic tert-butyl N-(1,2,3,4,5,6-hexahydro-1-benzazocin-3-yl)carbamate (260 mg) was resolved using chiral SFC (AZ-H column, 15% MeOH) to give the title compounds, assigned tentatively. 80b-1: peak 1, MS (m/z) 277.00 [M+H]$^+$; 80b-2: peak 2, MS (m/z) 277.00 [M+H]$^+$.

Synthesis of (6S)-1-(benzyloxy)-2,15-dioxo-N-(2,4,6-trifluorobenzyl)-2,6,7,8,9,15-hexahydro-6,14-methanobenzo[e]pyrido[1,2-a][1,4]diazecine-3-carboxamide (80c)

A solution of tert-butyl (S)-(1,2,3,4,5,6-hexahydrobenzo[b]azocin-3-yl)carbamate (80b-1, 119 mg, 0.430 mmol) and trifluoroacetic acid (1.0 mL) in dichloromethane (3 mL) was stirred for 1.5 hours. The reaction mixture was concentrated and dried under high vacuum, and used in the next step without further purification.

The above residue was dissolved in methanol (0.5 mL) and methyl 3-benzyloxy-4-oxo-5-[(2,4,6-trifluorophenyl)methylcarbamoyl]pyran-2-carboxylate (62.6 mg, 0.14 mmol) was added, followed by 0.5 M sodium methoxide (1.4 mL, 0.70 mmol). Reaction mixture was heated at 50° C. for 2 hours. 2 M LiOH (0.35 mL, 0.70 mmol) was added and the reaction was stirred at 50° C. until ester intermediate was consumed. Reaction mixture was concentrated to ~0.5 mL, diluted with acetonitrile, and lyophilized to give crude 3-benzyloxy-4-oxo-1-[(3S)-1,2,3,4,5,6-hexahydro-1-benzazocin-3-yl]-5-[(2,4,6-trifluorophenyl)methylcarbamoyl]pyridine-2-carboxylic acid that was used in next step without further purification.

To a solution of crude 3-benzyloxy-4-oxo-1-[(3S)-1,2,3,4,5,6-hexahydro-1-benzazocin-3-yl]-5-[(2,4,6-trifluorophenyl)methylcarbamoyl]pyridine-2-carboxylic acid in DMF (2.0 mL), was added HATU (66 mg, 0.28 mmol). The reaction mixture was stirred for 30 minutes. Reaction mixture was diluted with ethyl acetate, washed with 5% lithium chloride solution (3×), brine, dried over MgSO$_4$, filtered and concentrated. Purification by CombiFlash (12 g, 30-100% EtOAc/Hept) gave the title compound (80c). MS (m/z) 574.13 [M+H]$^+$.

Synthesis of (6S)-1-hydroxy-2,15-dioxo-N-(2,4,6-trifluorobenzyl)-2,6,7,8,9,15-hexahydro-6,14-methanobenzo[e]pyrido[1,2-a][1,4]diazecine-3-carboxamide (80-1)

(6S)-1-(benzyloxy)-2,15-dioxo-N-(2,4,6-trifluorobenzyl)-2,6,7,8,9,15-hexahydro-6,14-methanobenzo[e]pyrido[1,2-a][1,4]diazecine-3-carboxamide (80c, 44 mg, 0.077 mmol) and trifluoroacetic acid (0.80 mL, 10.45 mmol) in dichloromethane (2.0 mL) was stirred at room temperature for 1.5 hours. Reaction mixture was concentrated and purified by HPLC (Gemini, 5-100% ACN/H$_2$O+0.1% TFA) to give the title compound (80-1). MS (m/z) 574.13 [M+H]$^+$. $^1$H NMR (400 MHz, Methanol-d$_4$) δ 8.54 (s, 1H), 7.36 (dd, J=20.3, 3.4 Hz, 4H), 6.92 (t, J=8.3 Hz, 2H), 4.79 (s, 1H), 4.70 (s, 2H), 4.46 (d, J=13.0 Hz, 1H), 4.05-3.87 (m, 1H), 3.07 (ddd, J=40.0, 17.6, 9.1 Hz, 2H), 2.54 (t, J=13.0 Hz, 1H), 2.12 (dd, J=16.1, 6.2 Hz, 1H), 1.95 (q, J=11.3, 9.8 Hz, 2H).

Example 77b: Preparation of (6R)-1-hydroxy-2,15-dioxo-N-(2,4,6-trifluorobenzyl)-2,6,7,8,9,15-hexahydro-6,14-methanobenzo[e]pyrido[1,2-a][1,4]diazecine-3-carboxamide (80-2)

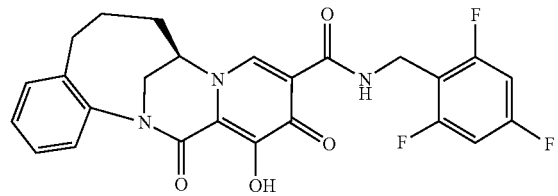 [SMILES: O=C(NCc1c(F)cc(F)cc1F)c1cn2c(c(O)c1=O)C(=O)N1C[C@H]2CCCc2ccccc21]

The title compound was prepared in a manner similar to 80-1 using tert-butyl (R)-(1,2,3,4,5,6-hexahydrobenzo[b]azocin-3-yl)carbamate (80b-2) instead of tert-butyl (S)-(1,2,3,4,5,6-hexahydrobenzo[b]azocin-3-yl)carbamate (80b-1). MS (m/z) 484.21 [M+H]$^+$. $^1$H NMR (400 MHz, Methanol-d$_4$) δ 8.53 (s, 1H), 7.36 (dd, J=22.3, 5.0 Hz, 4H), 6.92 (t, J=8.3 Hz, 2H), 4.80 (s, 1H), 4.69 (s, 2H), 4.46 (d, J=13.2 Hz, 1H), 4.03-3.87 (m, 1H), 3.07 (ddt, J=25.1, 17.5, 9.6 Hz, 2H), 2.63-2.43 (m, 1H), 2.21-2.05 (m, 1H), 1.96 (p, J=11.3, 9.6 Hz, 2H).

Example 78: Preparation of (5R,8S)-5-fluoro-13-hydroxy-1,12-dioxo-N-(2,4,6-trifluorobenzyl)-1,3,4,5,6,7,8,12-octahydro-2,8-methanopyrido[1,2-a][1,4]diazecine-11-carboxamide and (5S,8S)-5-fluoro-13-hydroxy-1,12-dioxo-N-(2,4,6-trifluorobenzyl)-1,3,4,5,6,7,8,12-octahydro-2,8-methanopyrido[1,2-a][1,4]diazecine-11-carboxamide (81-1 and 81-2)

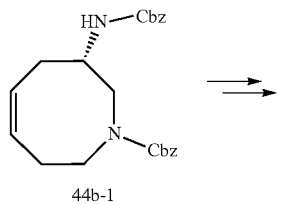

44b-1

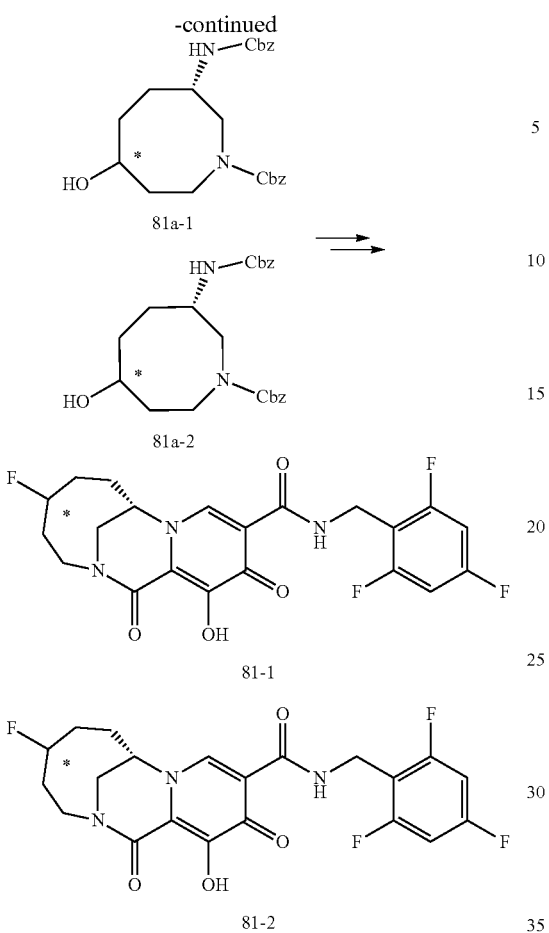

Synthesis of benzyl (3S,6S)-3-(((benzyloxy)carbonyl)amino)-6-hydroxyazocane-1-carboxylate and (3S,6R)-3-(((benzyloxy)carbonyl)amino)-6-hydroxyazocane-1-carboxylate (81a-1 and 81a-2)

The title compounds were prepared analogously to 53d-1 and 53d-2, using (S,Z)-3-(((benzyloxy)carbonyl)amino)-3,4,7,8-tetrahydroazocine-1(2H)-carboxylate (44b-1) in place of benzyl (S)-3-(((benzyloxy)carbonyl)amino)-2,3,4,7-tetrahydro-1H-azepine-1-carboxylate (42e-1). MS (m/z) 413.3 [M+H]+.

Synthesis of (5R,8S)-5-fluoro-13-hydroxy-1,12-dioxo-N-(2,4,6-trifluorobenzyl)-1,3,4,5,6,7,8,12-octahydro-2,8-methanopyrido[1,2-a][1,4]diazecine-11-carboxamide and (5S,8S)-5-fluoro-13-hydroxy-1,12-dioxo-N-(2,4,6-trifluorobenzyl)-1,3,4,5,6,7,8,12-octahydro-2,8-methanopyrido[1,2-a][1,4]diazecine-11-carboxamide (81-1 and 81-2)

The title compounds were prepared analogously to 53-1 and 53-2, using benzyl (3 S,6S)-3-(((benzyloxy)carbonyl)amino)-6-hydroxyazocane-1-carboxylate or (3S,6R)-3-(((benzyloxy)carbonyl)amino)-6-hydroxyazocane-1-carboxylate (81a-1 or 81a-2) in place of benzyl (3 S)-3-(((benzyloxy)carbonyl)amino)-6-hydroxyazepane-1-carboxylate (53c-1), and methyl 3-(benzyloxy)-4-oxo-5-((2,4,6-trifluorobenzyl)carbamoyl)-4H-pyran-2-carboxylate in place of methyl 3-(benzyloxy)-5-((2,4-difluorobenzyl)carbamoyl)-4-oxo-4H-pyran-2-carboxylate.

81-1: MS (m/z) 454.2 [M+H]+. 1H NMR (400 MHz, Chloroform-d) δ 10.65-10.43 (m, 1H), 8.55 (s, 1H), 6.75-6.60 (m, 2H), 4.99-4.79 (m, 1H), 4.79-4.52 (m, 3H), 4.52-4.35 (m, 1H), 4.09 (dd, 1H), 3.54 (dd, 1H), 3.07 (ddd, 1H), 2.55-2.32 (m, 1H), 2.29-2.14 (m, 1H), 2.11-1.72 (m, 3H).

81-2: MS (m/z) 454.2 [M+H]+. 1H NMR (400 MHz, Chloroform-d) δ 10.49-10.37 (m, 1H), 8.43 (s, 1H), 6.75-6.63 (m, 2H), 4.99-4.80 (m, 1H), 4.68 (qd, 2H), 4.52-4.43 (m, 1H), 4.42-4.33 (m, 1H), 4.06-3.96 (m, 1H), 3.80 (dd, 1H), 3.21-3.09 (m, 1H), 2.45-2.35 (m, 1H), 2.32-2.19 (m, 2H), 2.17-1.87 (m, 2H), 1.80 (q, 1H).

Example 79: Preparation of (6S,8S)-6,13-dihydroxy-1,12-dioxo-N-(2,4,6-trifluorobenzyl)-1,3,4,5,6,7,8,12-octahydro-2,8-methanopyrido[1,2-a][1,4]diazecine-11-carboxamide and (6R,8S)-6,13-dihydroxy-1,12-dioxo-N-(2,4,6-trifluorobenzyl)-1,3,4,5,6,7,8,12-octahydro-2,8-methanopyrido[1,2-a][1,4]diazecine-11-carboxamide (82-1 and 82-2)

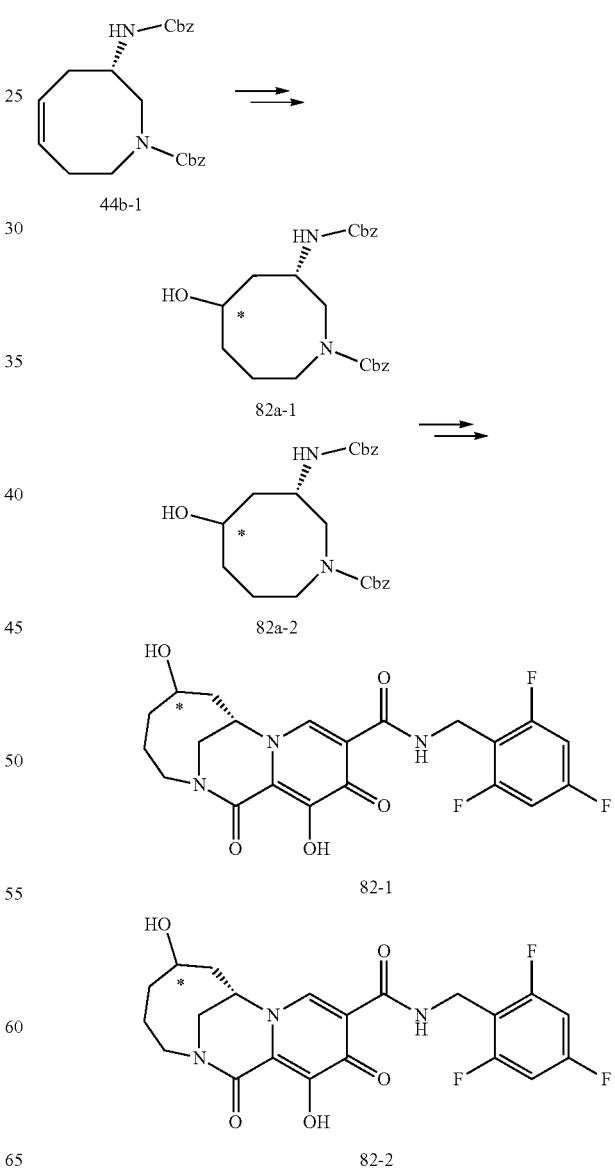

Synthesis of rac-benzyl (3S)-3-(((benzyloxy)carbonyl)amino)-5-hydroxyazocane-1-carboxylate and rac-benzyl (3S)-3-(((benzyloxy)carbonyl)amino)-6-hydroxyazocane-1-carboxylate (82a-1 and 82a-2)

The title compounds were prepared analogously to 53c-1, using (S,Z)-3-(((benzyloxy)carbonyl)amino)-3,4,7,8-tetrahydroazocine-1(2H)-carboxylate (44b-1) in place of benzyl (S)-3-(((benzyloxy)carbonyl)amino)-2,3,4,7-tetrahydro-1H-azepine-1-carboxylate (42e-1). MS (m/z) 413.3 [M+H]+.

Synthesis of (6S,8S)-6,13-dihydroxy-1,12-dioxo-N-(2,4,6-trifluorobenzyl)-1,3,4,5,6,7,8,12-octahydro-2,8-methanopyrido[1,2-a][1,4]diazecine-11-carboxamide and (6R,8S)-6,13-dihydroxy-1,12-dioxo-N-(2,4,6-trifluorobenzyl)-1,3,4,5,6,7,8,12-octahydro-2,8-methanopyrido[1,2-a][1,4]diazecine-11-carboxamide (82-1 and 82-2)

The title compounds were prepared analogously to 53-1 and 53-2, using rac-benzyl (3S)-3-(((benzyloxy)carbonyl)amino)-5-hydroxyazocane-1-carboxylate (82a-1) in place of benzyl (3S,6R)-3-(((benzyloxy)carbonyl)amino)-6-fluoroazepane-1-carboxylate or benzyl (3S,6S)-3-(((benzyloxy)carbonyl)amino)-6-fluoroazepane-1-carboxylate (53d-1 or 53d-2), and methyl 3-(benzyloxy)-4-oxo-5-((2,4,6-trifluorobenzyl)carbamoyl)-4H-pyran-2-carboxylate in place of methyl 3-(benzyloxy)-5-((2,4-difluorobenzyl)carbamoyl)-4-oxo-4H-pyran-2-carboxylate, separating stereoisomers as the benzyl protected alcohol instead of prior to amide coupling.

82-1: MS (m/z) 452.2 [M+H]+. 1H NMR (400 MHz, Acetonitrile-d3) δ 10.45 (s, 1H), 8.36 (s, 1H), 6.86 (t, 2H), 4.69-4.50 (m, 3H), 4.31-4.16 (m, 1H), 3.89-3.71 (m, 2H), 3.65 (dd, 1H), 3.04-2.91 (m, 1H), 2.39-2.24 (m, 1H), 2.13-1.78 (m, 4H), 1.73-1.52 (m, 1H).

82-2: MS (m/z) 452.2 [M+H]+. 1H NMR (400 MHz, Chloroform-d) δ 10.46 (s, 1H), 8.44 (s, 1H), 6.75-6.58 (m, 1H), 4.69 (d, 2H), 4.51-4.35 (m, 2H), 4.26-4.13 (m, 1H), 4.04-3.76 (m, 1H), 3.08-2.85 (m, 1H), 2.59-2.47 (m, 1H), 2.27-1.61 (m, 7H).

Example 80: Preparation of (5S,8S)-5,13-dihydroxy-1,12-dioxo-N-(2,4,6-trifluorobenzyl)-1,3,4,5,6,7,8,12-octahydro-2,8-methanopyrido[1,2-a][1,4]diazecine-11-carboxamide and (5R,8S)-5,13-dihydroxy-1,12-dioxo-N-(2,4,6-trifluorobenzyl)-1,3,4,5,6,7,8,12-octahydro-2,8-methanopyrido[1,2-a][1,4]diazecine-11-carboxamide (83-1 and 83-2)

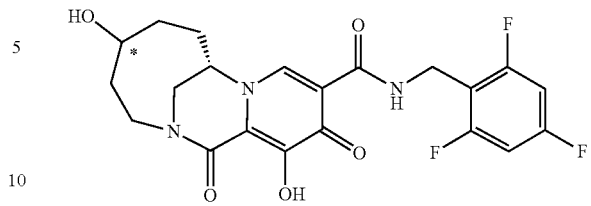

83-2

The title compounds were prepared analogously to 53-1 and 53-2, using benzyl (3S,6S)-3-(((benzyloxy)carbonyl)amino)-6-hydroxyazocane-1-carboxylate or benzyl (3S,6R)-3-(((benzyloxy)carbonyl)amino)-6-hydroxyazocane-1-carboxylate (81a-2) in place of benzyl (3S,6R)-3-(((benzyloxy)carbonyl)amino)-6-fluoroazepane-1-carboxylate or benzyl (3S,6S)-3-(((benzyloxy)carbonyl)amino)-6-fluoroazepane-1-carboxylate (53d-1 or 53d-2), and methyl 3-(benzyloxy)-4-oxo-5-((2,4,6-trifluorobenzyl)carbamoyl)-4H-pyran-2-carboxylate in place of methyl 3-(benzyloxy)-5-((2,4-difluorobenzyl)carbamoyl)-4-oxo-4H-pyran-2-carboxylate, separating stereoisomers as the benzyl protected alcohol instead of prior to amide coupling.

83-1: MS (m/z) 452.2 [M+H]+. 1H NMR (400 MHz, Acetonitrile-d3) δ 11.33 (s, 1H), 9.17 (s, 1H), 7.79-7.61 (m, 2H), 5.50-5.40 (m, 2H), 5.32-5.17 (m, 2H), 4.91-4.79 (m, 1H), 4.70 (d, 1H), 4.50 (d, 1H), 3.89-3.74 (m, 1H), 3.20-2.40 (m, 6H).

83-1: MS (m/z) 452.2 [M+H]. 1H NMR (400 MHz, Chloroform-d) δ 10.59-10.42 (m, 1H), 8.43 (s, 1H), 6.77-6.50 (m, 2H), 4.69 (qd, 2H), 4.49-4.38 (m, 1H), 4.34-4.26 (m, 1H), 4.19-4.08 (m, 1H), 3.95 (d, 2H), 3.19 (ddd, 1H), 2.55-2.35 (m, 1H), 2.24-2.08 (m, 1H), 2.09-1.55 (m, 3H), 1.27 (s, 1H).

Example 81: (3S,7S)-5-fluoro-12-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (84)

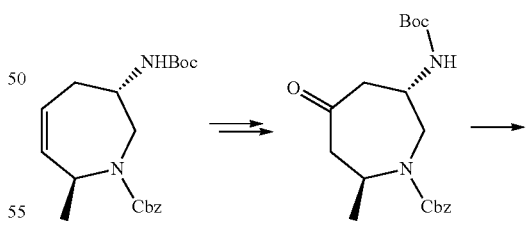

83-1

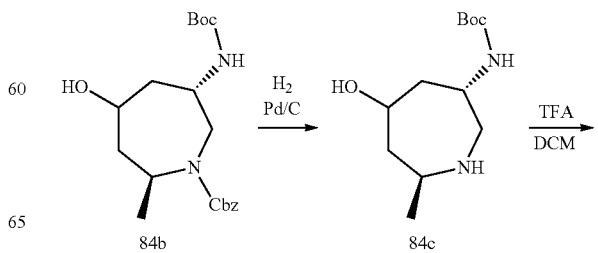

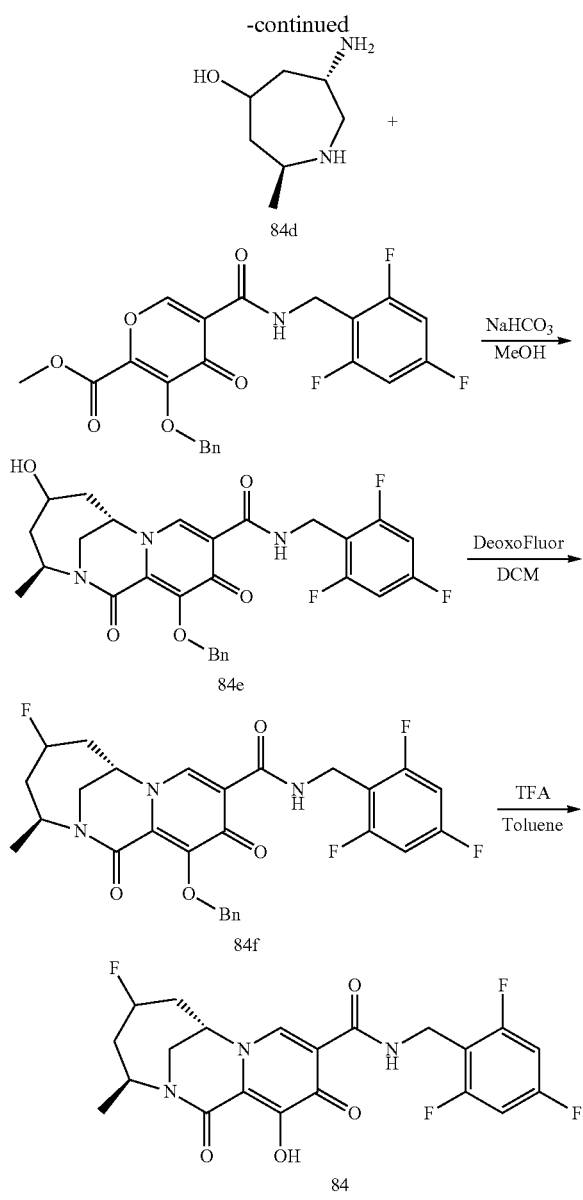

place of benzyl (S)-3-(((benzyloxy)carbonyl)amino)-6-oxoazepane-1-carboxylate (53b-1). MS (m/z) 378.7 [M+H].

Synthesis of (2S,6S)-6-amino-2-methylazepan-4-ol (84d)

Benzyl (2S,6S)-6-((tert-butoxycarbonyl)amino)-4-hydroxy-2-methylazepane-1-carboxylate (84b) (174 mg, 0.46 mmol) was dissolved in MeOH (5 mL). The reaction was fitted with a hydrogen balloon, and evacuated and backfilled three times. The reaction was stirred vigorously at room temperature for around 17 hrs under atmospheric pressure of hydrogen. The reaction mixture was then filtered through a celite plug, the filtrate was concentrated to dryness. The residue was put under hose vacuum overnight. The resulting product (84c) was obtained. MS (m/z) 245.0 [M+H].

Crude product of tert-butyl ((3S,7S)-5-hydroxy-7-methylazepan-3-yl)carbamate (84c) was dissolved in DCM (3 mL) at rt. TFA (3 mL) was added. Reaction mixture was stirred at room temperature for 2 hrs. TFA and DCM was removed in vacuum to afford crude (2S,6S)-6-amino-2-methylazepan-4-ol which was used directly for next step. MS (m/z) 145.0 [M+H].

Synthesis of (3S,7S)-12-(benzyloxy)-5-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (84e)

(2S,6S)-6-amino-2-methylazepan-4-ol (84d, 64 mg, 0.444 mmol) and methyl 3-(benzyloxy)-4-oxo-5-((2,4,6-trifluorobenzyl)carbamoyl)-4H-pyran-2-carboxylate (218 mg, 0.488 mmol) were mixed with MeOH (5 mL), and NaHCO₃ (1.3 g, 15 mmol) was added. Reaction mixture was stirred at room temperature for 17 hours. LiOH (5 M) (0.44 mL) was added, and the reaction mixture was heated at 60° C. for 6 hours. Reaction mixture was diluted with EtOAc (10 mL) and was treated with saturated NH₄Cl/water (10 mL). Organic phase was separated. Aqueous layer was extracted with EtOAc (10 mL). The combined organic phases were washed with water and brine, concentrated, and purified on silica gel column (0-100% EtOAc/heptane) to afford the title compound (84e). MS (m/z) 542.15 [M+H]⁺.

Synthesis of (3 S,7S)-12-(benzyloxy)-5-fluoro-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (84f)

(3S,7S)-12-(benzyloxy)-5-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (84e, 90 mg, 0.166 mmol) was dissolved in DCM (1.8 mL) at room temperature. DeoxoFluor (367 mg, 1.66 mmol) was added dropwise. The reaction mixture was stirred at room temperature for 17 hours, and then was diluted with EtOAc (5 mL). The resulting solution was poured carefully to well stirred solution of NaHCO₃/water at 0° C. The resulting bi-phase mixture was stirred for 30 min. The organic phase was concentrated, and the residue purified on preparative TLC plates with EtOAc/heptane (1/3) to afford the title compound (84f). MS (m/z) 544.20 [M+H]⁺.

Synthesis of (3S,7S)-5-fluoro-12-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (84)

(3S,7S)-12-(benzyloxy)-5-fluoro-3-methyl-1,11-dioxo-N-(2,4,6-trifluorobenzyl)-1,4,5,6,7,11-hexahydro-3H-2,7-

Synthesis of benzyl (2S,6S)-6-((tert-butoxycarbonyl)amino)-2-methyl-4-oxoazepane-1-carboxylate (84a)

The title compound was synthesized in a similar manner to compound 53b-2, using benzyl (2S,6S)-6-((tert-butoxycarbonyl)amino)-2-methyl-4-oxoazepane-1-carboxylate in place of benzyl (S)-3-(((benzyloxy)carbonyl)amino)-2,3,4,7-tetrahydro-1H-azepine-1-carboxylate (42e-1). MS (m/z) 377.1 [M+H]⁺.

Synthesis of benzyl (2S,6S)-6-((tert-butoxycarbonyl)amino)-4-hydroxy-2-methylazepane-1-carboxylate (84b)

The title compound was synthesis in the similar manner to compound 53c-1 using (2S,6S)-6-((tert-butoxycarbonyl)amino)-2-methyl-4-oxoazepane-1-carboxylate (84a) in methanopyrido[1,2-a][1,4]diazonine-10-carboxamide (84f, 3 mg, 0.0055 mmol) was mixed with toluene (1.7 mL) at room temperature. TFA (1.76 mL) was added dropwise. Reaction mixture was stirred at room temperature for 17 hours, and was concentrated to dryness. The residue was taken up in MeOH. After filtering the solution, the filtrate was purified by preparative HPLC (column, Gemini 10μ C18 110A, AXI/; 250×21.2 mm) eluting with 5-100% acetonitrile in water (0.1% TFA) over 20 minutes to afford the title compound (84). MS (m/z) 454.30 [M+H]+. 1H NMR (400 MHz, Acetonitrile-d3) δ 10.38 (s, 1H), 8.43 (s, 1H), 5.5-5.2 (m, 1H), 5.00-4.32 (m, 4H), 3.69 (s, 2H), 2.5-2.1 (m, 4H), 1.25 (d, J=6.6 Hz, 3H).

Example 82: (11S)-6-hydroxy-1-methyl-5,7-dioxo-N-(2,4,6-trifluorobenzyl)-1,5,7,11,12,13-hexahydro-4,11-methanopyrazolo[4,3-e]pyrido[1,2-a][1,4]diazonine-8-carboxamide and (11S)-6-hydroxy-2-methyl-5,7-dioxo-N-(2,4,6-trifluorobenzyl)-2,5,7,11,12,13-hexahydro-4,11-methanopyrazolo[4,3-e]pyrido[1,2-a][1,4]diazonine-8-carboxamide (85-1 and 85-2)

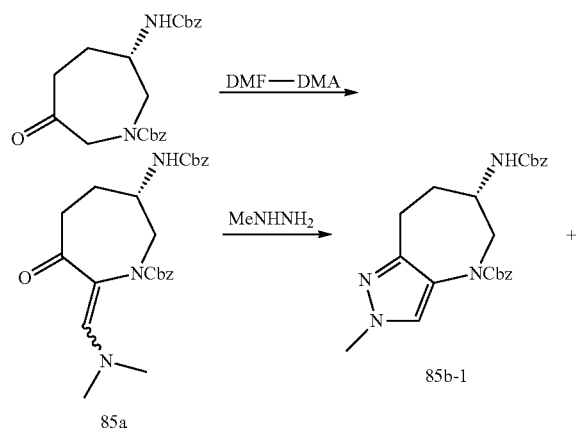

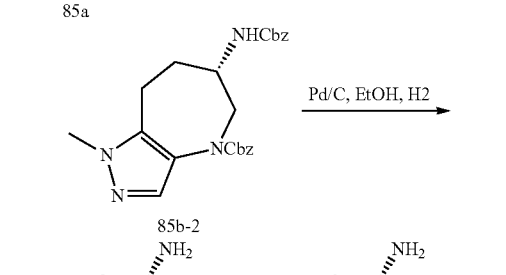

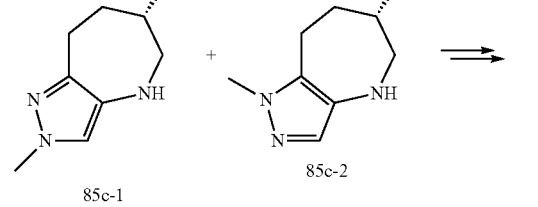

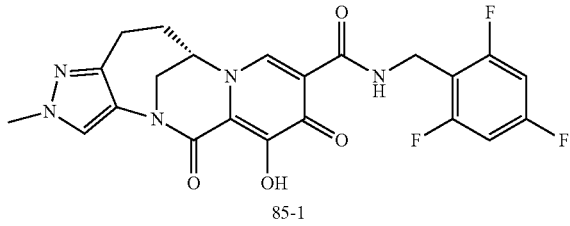

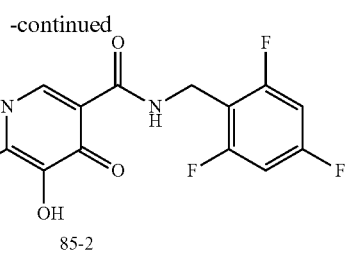

Synthesis of benzyl (S)-6-(((benzyloxy)carbonyl)amino)-2-((dimethylamino)methylene)-3-oxoazepane-1-carboxylate (85a)

Benzyl (3S)-3-(benzyloxycarbonylamino)-6-oxo-azepane-1-carboxylate (500 mg, 1.26 mmol) was dissolved in EtOH (3.5 mL) at room temperature and treated with 1,1-dimethoxy-N,N-dimethyl-methanamine (DMF-DMA) (3.0 g, 25.2 mmol). The resulting mixture was heated at 80° C. for 16 hr. The reaction was cooled to room temperature, concentrated, and used directly in the next step. MS (m/z) 452.20 [M+H]+.

Synthesis of benzyl (S)-6-(((benzyloxy)carbonyl)amino)-2-methyl-5,6,7,8-tetrahydropyrazolo[4,3-b]azepine-4(2H)-carboxylate and benzyl (S)-6-(((benzyloxy)carbonyl)amino)-1-methyl-5,6,7,8-tetrahydropyrazolo[4,3-b]azepine-4(1H)-carboxylate (85b-1 and 85b-2)

Benzyl (S)-6-(((benzyloxy)carbonyl)amino)-2-((dimethylamino)methylene)-3-oxoazepane-1-carboxylate (85a) was dissolved in EtOH (15.0 mL), methyl hydrazine (2.61g, 56.7 mmol) was added, and the resulting mixture was heated at 84° C. for 2 hrs. The mixture was cooled to room temperature, and concentrated. The resulting residue was diluted with EtOAc, washed with sat. NH4Cl twice, dried over sodium sulfate, filtered, and concentrated. The residue was re-dissolved in EtOAc, mixed with silica gel, concentrated to dryness, and purified by normal phase chromatography (40 g silica gel, dry loading, 0-100% EtOAc/Hexanes then 0-10% MeOH/EtOAc) to give the title compounds (85b-1 and 85b-2) as a mixture of regioisomers. MS (m/z) 435.20 [M+H]+.

Synthesis of (S)-2-methyl-2,4,5,6,7,8-hexahydropyrazolo[4,3-b]azepin-6-amine and (S)-1-methyl-1,4,5,6,7,8-hexahydropyrazolo[4,3-b]azepin-6-amine (85c-1 and 85c-2)

A mixture of benzyl (S)-6-(((benzyloxy)carbonyl)amino)-2-methyl-5,6,7,8-tetrahydropyrazolo[4,3-b]azepine-4(2H)-carboxylate and benzyl (S)-6-(((benzyloxy)carbonyl)amino)-1-methyl-5,6,7,8-tetrahydropyrazolo[4,3-b]azepine-4(1H)-carboxylate (85b-1 and 85b-2, 305 mg) was dissolved in EtOH (20.0 mL) at room temperature, 20% Pd/C (60.0 mg) was added, and the resulting mixture was degassed and flushed with hydrogen three times, before it was hydrogenated under hydrogen balloon overnight. The reaction was degassed and flushed with nitrogen, filtered through Celite, filter cake rinsed with EtOH, and concentrated to give the title compounds (85c-1 and 85c-2), used in next step without further purification. MS (m/z) 167.11 [M+H]+.

Synthesis of (11S)-6-hydroxy-2-methyl-5,7-dioxo-N-(2,4,6-trifluorobenzyl)-2,5,7,11,12,13-hexahydro-4,11-methanopyrazolo[4,3-e]pyrido[1,2-a][1,4]diazonine-8-carboxamide and (11S)-6-hydroxy-1-methyl-5,7-dioxo-N-(2,4,6-trifluorobenzyl)-1,5,7,11,12,13-hexahydro-4,11-methanopyrazolo[4,3-e]pyrido[1,2-a][1,4]diazonine-8-carboxamide (85-1 and 85-2)

The title compounds were synthesized in the same manner as compound 28, using (S)-2-methyl-2,4,5,6,7,8-hexahydropyrazolo[4,3-b]azepin-6-amine or (S)-1-methyl-1,4,5,6,7,8-hexahydropyrazolo[4,3-b]azepin-6-amine (85c-1 or 85c-2) in place of 1,4-oxazepan-6-amine, and methyl 3-(benzyloxy)-4-oxo-5-((2,4,6-trifluorobenzyl)carbamoyl)-4H-pyran-2-carboxylate in place of methyl 3-(benzyloxy)-5-((2,4-difluorobenzyl)carbamoyl)-4-oxo-4H-pyran-2-carboxylate, with the regiochemistry of 85-1 confirmed by 2D-NMR.

85-1: MS (m/z) 474.10 [M+H]⁺. ¹H NMR (400 MHz, DMSO-d₆) δ 10.36 (t, J=5.8 Hz, 1H), 8.59 (s, 1H), 7.81 (s, 1H), 7.28-7.17 (m, 2H), 4.92 (t, J=7.9 Hz, 1H), 4.58 (d, J=5.7 Hz, 2H), 4.09 (dd, J=14.9, 1.6 Hz, 1H), 3.89 (dd, J=14.8, 2.5 Hz, 1H), 3.73 (s, 3H), 2.83-2.66 (m, 2H), 2.64-2.54 (m, 1H), 1.66-1.52 (m, 1H).

85-2: MS (m/z) 474.10 [M+H]⁺. ¹H NMR (400 MHz, DMSO-d₆) δ 10.37 (t, J=5.9 Hz, 1H), 8.58 (s, 1H), 7.41 (s, 1H), 7.28-7.16 (m, 2H), 4.94 (t, J=8.3 Hz, 1H), 4.58 (d, J=5.8 Hz, 2H), 4.08 (d, J=14.7 Hz, 1H), 3.88 (d, J=12.9 Hz, 1H), 3.68 (s, 3H), 2.97-2.70 (m, 2H), 2.62-2.68 (m, 1H) 1.73-1.56 (m, 1H).

Example 83: Preparation of (12R)-3-fluoro-7-hydroxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide and (12S)-3-fluoro-7-hydroxy-6,8-dioxo-N-(2,4,6-trifluorobenzyl)-6,8,13,14-tetrahydro-12H-5,12-methanobenzo[e]pyrido[1,2-a][1,4]diazonine-9-carboxamide (86-1 and 86-2)

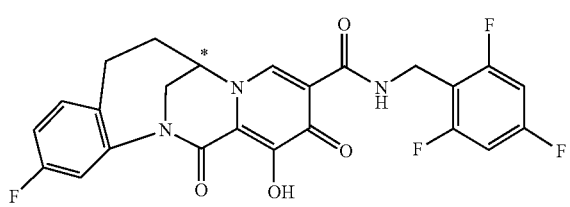

86-1

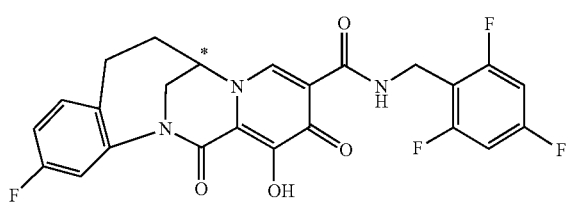

86-2

The title compounds were prepared similarly to compounds 43-1 and 43-2 using 8-fluoro-1,3,4,5-tetrahydro-2H-benzo[b]azepin-2-one in place of 6-fluoro-1,3,4,5-tetrahydro-2H-benzo[b]azepin-2-one.

86-1: MS (m/z) 488.1 [M+H]⁺. ¹H NMR (400 MHz, DMSO-d₆) δ 10.38 (t, J=5.8 Hz, 1H), 8.59 (s, 1H), 7.39 (m, 1H), 7.29-7.15 (m, 4H), 4.89 (m, 1H), 4.59 (m, 2H), 4.15 (dd, J=14.8, 2.0 Hz, 1H), 3.80 (dd, J=14.8, 2.1 Hz, 1H), 2.89-2.77 (m, 1H), 2.71 (m, 1H), 2.30-2.20 (m, 1H), 2.12-2.01 (m, 1H).

86-2: MS (m/z) 488.1 [M+H]⁺. ¹H NMR (400 MHz, DMSO-d₆) δ 10.38 (t, J=5.8 Hz, 1H), 10.10 (s, 1H), 8.59 (s, 1H), 7.39 (dd, J=8.5, 6.2 Hz, 1H), 7.29-7.20 (m, 2H), 7.24-7.10 (m, 2H), 4.93-4.86 (m, 1H), 4.59 (d, J=5.8 Hz, 2H), 4.15 (dd, J=14.8, 2.0 Hz, 1H), 3.80 (dd, J=14.8, 2.1 Hz, 1H), 2.92-2.77 (m, 1H), 2.77-2.65 (m, 1H), 2.25 (s, 1H), 2.06 (dd, J=15.2, 6.7 Hz, 1H).

Example 84: (12S)-7-hydroxy-2-methyl-6,8-dioxo-N-(2,4,6-trifluorobenzyl)-2,4,6,8,12,13-hexahydro-5,12-methanopyrazolo[4,3-f]pyrido[1,2-a][1,4]diazonine-9-carboxamide and (12S)-7-hydroxy-1-methyl-6,8-dioxo-N-(2,4,6-trifluorobenzyl)-1,4,6,8,12,13-hexahydro-5,12-methanopyrazolo[4,3-f]pyrido[1,2-a][1,4]diazonine-9-carboxamide (87-1 and 87-2)

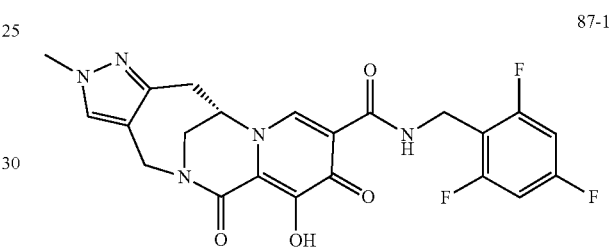

87-1

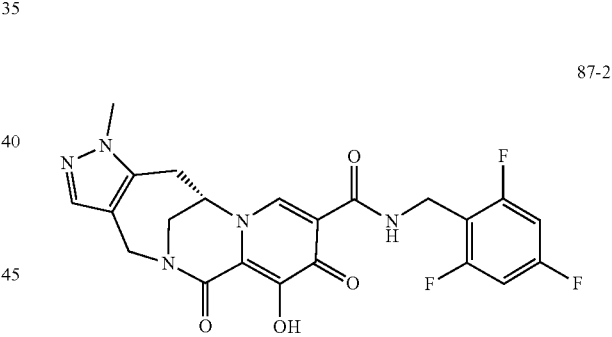

87-2

The title compounds were synthesized in a similar manner to compounds 85-1 and 85-2 using benzyl (3S)-3-(benzyloxycarbonylamino)-5-oxo-azepane-1-carboxylate in place of benzyl (3S)-3-(benzyloxycarbonylamino)-6-oxo-azepane-1-carboxylate, and regiochemistry based off the assignment of 85-1 and 85-2.

87-1: MS (m/z) 474.10 [M+H]⁺. ¹H NMR (400 MHz, DMSO-d₆) δ 10.38 (t, J=5.8 Hz, 1H), 8.55 (d, J=19.1 Hz, 1H), 7.58 (s, 1H), 7.30-7.14 (m, 2H), 5.20 (t, J=15.6 Hz, 1H), 5.01 (dd, J=8.0, 5.5 Hz, 1H), 4.58 (d, J=5.7 Hz, 2H), 4.20-3.76 (m, 2H), 3.74-3.63 (m, 4H), 3.53 (dd, J=16.3, 8.5 Hz, 1H), 2.73 (dd, J=16.4, 5.5 Hz, 1H).

87-2: MS (m/z) 474.16 [M+H]⁺. ¹H NMR (400 MHz, Methanol-d₄) δ 8.56 (s, 1H), 7.53 (s, 1H), 6.92 (t, J=8.4 Hz, 2H), 5.43 (d, J=15.5 Hz, 1H), 4.69 (s, 2H), 4.29 (d, J=15.6 Hz, 1H), 4.10-3.95 (m, 1H), 3.90-3.81 (m, 5H), 3.71-3.55 (m, 1H), 3.00-2.82 (m, 1H).

Example 85: Preparation of (6S)-9,10-difluoro-1-hydroxy-2,14-dioxo-N-(2,4,6-trifluorobenzyl)-2,7,12,14-tetrahydro-6H-6,13-methanobenzo[f]pyrido[1,2-a][1,4]diazonine-3-carboxamide (88)

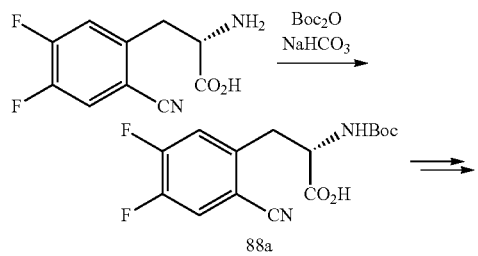

88a

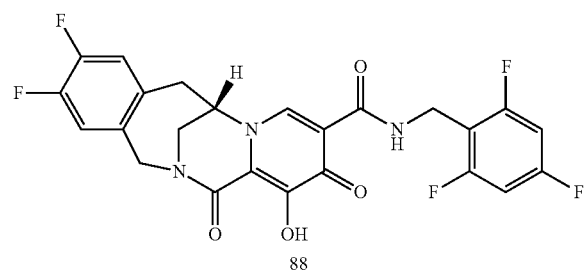

88

Synthesis of (S)-2-((tert-butoxycarbonyl)amino)-3-(2-cyano-4,5-difluorophenyl)propanoic acid (88a)

To a solution of (S)-2-amino-3-(2-cyano-4,5-difluorophenyl)propanoic acid (0.500 g, 2.21 mmol) and Boc$_2$O (0.724 g, 3.32 mmol) in THF (13 mL), was added NaHCO$_3$ (0.680 g, 8.09 mmol) and water (40 mL). The suspension was stirred overnight at rt. The reaction mixture was diluted with Et$_2$O and the phases separated. The aqueous phase was acidified with 0.5 M HCl and extracted with EtOAc (2×). The combined organic phases were washed with brine, dried over Na$_2$SO$_4$, filtered, and concentrated to afford the title compound, which was used without further purification. MS (m/z) 325.17 [M−H]$^-$.

Synthesis of (6S)-9,10-difluoro-1-hydroxy-2,14-dioxo-N-(2,4,6-trifluorobenzyl)-2,7,12,14-tetrahydro-6H-6,13-methanobenzo[f]pyrido[1,2-a][1,4]diazonine-3-carboxamide (88)

The title compound was prepared in a similar manner to compound 70, using (S)-2-((tert-butoxycarbonyl)amino)-3-(2-cyano-4,5-difluorophenyl)propanoic acid (88a) in place of (S)-2-((tert-butoxycarbonyl)amino)-3-(2-cyanophenyl)propanoic acid. MS (m/z) 506.20 [M+H]$^+$. $^1$H NMR (400 MHz, DMSO-d$_6$) δ 10.36 (t, J=5.8 Hz, 1H), 8.51 (s, 1H), 7.41 (dd, J=11.6, 8.2 Hz, 1H), 7.29 (dd, J=11.6, 8.2 Hz, 1H), 7.22 (t, J=8.6 Hz, 2H), 5.47 (d, J=16.7 Hz, 1H), 4.98 (t, J=7.1 Hz, 1H), 4.58 (d, J=5.8 Hz, 2H), 4.44 (d, J=16.7 Hz, 1H), 3.80 (d, J=14.5 Hz, 1H), 3.62 (dd, J=14.8, 2.8 Hz, 1H), 3.37 (dd, J=15.1, 7.3 Hz, 1H), 2.86 (dd, J=15.2, 7.6 Hz, 1H). $^{19}$F NMR (376 MHz, DMSO-d$_6$) δ −109.26 (tt, J=8.9, 6.3 Hz), −112.59 (t, J=7.2 Hz), −141.08 (ddd, J=20.0, 11.1, 8.3 Hz), −141.92 (dt, J=21.0, 10.0 Hz).

Example 86: Preparation of (6S)—N-(2,4-difluorobenzyl)-9,10-difluoro-1-hydroxy-2,14-dioxo-2,7,12,14-tetrahydro-6H-6,13-methanobenzo[f]pyrido[1,2-a][1,4]diazonine-3-carboxamide (89)

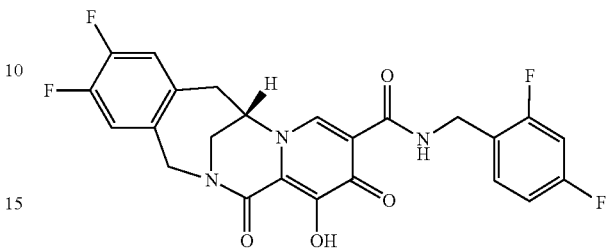

The title compound was prepared in a similar manner to compound 88, using methyl 3-(benzyloxy)-5-((2,4-difluorobenzyl)carbamoyl)-4-oxo-4H-pyran-2-carboxylate instead of methyl 3-(benzyloxy)-4-oxo-5-((2,4,6-trifluorobenzyl)carbamoyl)-4H-pyran-2-carboxylate. MS (m/z) 488.17 [M+H]$^+$. $^1$H NMR (400 MHz, DMSO-d$_6$) δ 10.31 (t, J=5.9 Hz, 1H), 8.52 (s, 1H), 7.42 (ddt, J=11.7, 7.6, 3.7 Hz, 2H), 7.31-7.23 (m, 2H), 7.07 (td, J=7.8, 2.2 Hz, 1H), 5.47 (d, J=16.7 Hz, 1H), 5.00 (t, J=7.3 Hz, 1H), 4.56 (d, J=5.7 Hz, 2H), 4.44 (d, J=16.7 Hz, 1H), 3.80 (d, J=14.6 Hz, 1H), 3.62 (dd, J=14.7, 2.8 Hz, 1H), 3.38 (dd, J=15.1, 7.3 Hz, 1H), 2.87 (dd, J=15.1, 7.5 Hz, 1H). $^{19}$F NMR (376 MHz, DMSO-d$_6$) δ −112.37 (q, J=7.7 Hz), −114.99 (q, J=8.7 Hz), −141.07 (dt, J=20.8, 9.9 Hz), −141.90 (dd, J=22.7, 10.5 Hz).

Example 87: Preparation of (12R)—N-(3-chloro-2,4-difluorobenzyl)-3-fluoro-7-hydroxy-6,8-dioxo-6,8,13,14-tetrahydro-12H-5,12-methanobenzo[e]pyrido[1,2-a][1,4]diazonine-9-carboxamide and (12S)—N-(3-chloro-2,4-difluorobenzyl)-3-fluoro-7-hydroxy-6,8-dioxo-6,8,13,14-tetrahydro-12H-5,12-methanobenzo[e]pyrido[1,2-a][1,4]diazonine-9-carboxamide (90-1 and 90-2)

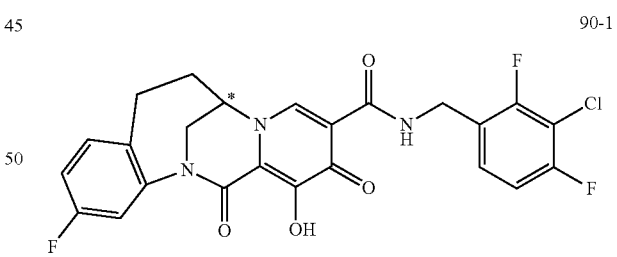

90-1

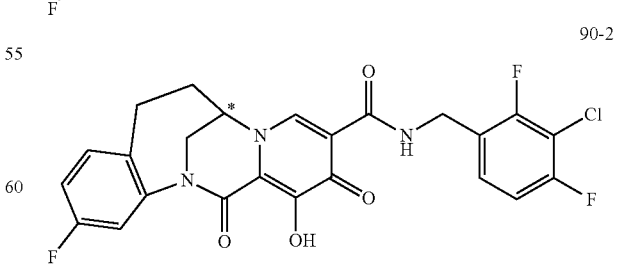

90-2

The title compounds were prepared similarly to compounds 86-1 and 86-2, using methyl 3-(benzyloxy)-5-((3-chloro-2,4-difluorobenzyl)carbamoyl)-4-oxo-4H-pyran-2- carboxylate in place of methyl 3-(benzyloxy)-4-oxo-5-((2,4,6-trifluorobenzyl)carbamoyl)-4H-pyran-2-carboxylate.

90-1: MS (m/z) 504.1 [M+H]+. 1H NMR (400 MHz, DMSO-d6) δ 7.33 (m, 3H), 7.14 (m, 3H), 4.79 (m, 1H), 4.58 (m, 2H), 3.97 (m, 1H), 3.75 (m, 1H), 2.74 (m, 2H), 2.23 (m, 1H), 2.00 (m, 1H).

90-2: MS (m/z) 504.1 [M+H]+. 1H NMR (400 MHz, DMSO-d6) δ 7.32 (m, 3H), 7.14 (m, 3H), 4.80 (m, 1H), 4.58 (m, 2H), 4.00 (m, 1H), 3.75 (m, 1H), 2.74 (m, 2H), 2.23 (m, 1H), 2.00 (m, 1H).

Example 88: Preparation of (4S,7S)-12-hydroxy-4-methoxy-1,11-dioxo-N-(2,4,6-trifluorobenzyl)-1,4,5,6,7,11-hexahydro-3H-2,7-methanopyrido[1,2-a][1,4]diazonine-10-carboxamide (91)

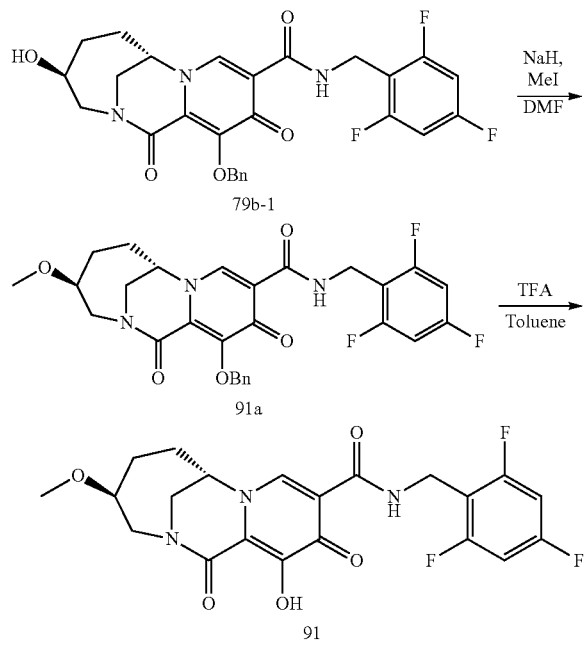

Synthesis of (4S,7S)-12-(benzyloxy)-4-methoxy-1,11-dioxo-N-(2,4,6-trifluorobenzyl)-1,4,5,6,7,11-hexahydro-3H-2,7-methanopyrido[1,2-a][1,4]diazonine-10-carboxamide (91a)

NaH (60%, 3.3 mg) was added to a solution of (4S,7S)-12-(benzyloxy)-4-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (79b-1, 11 mg, 0.021 mmol) in DMF (1 mL), at 0° C. After 20 minutes, MeI (7 µL, 0.027 mmol, 1.3 eq.) was added, and the reaction was stirred at 0° C. for 20 minutes. The reaction crude was diluted with EtOAc, and washed with sat. NaHCO3 solution. The organic layer was concentrated, and purified via preparative HPLC, eluting with 10-60% acetonitrile (0.1% TFA) in water (0.1% TFA) to give the title compound. MS (m/z) 542.27 [M+H]+.

Synthesis of (4S,7S)-12-hydroxy-4-methoxy-1,11-dioxo-N-(2,4,6-trifluorobenzyl)-1,4,5,6,7,11-hexahydro-3H-2,7-methanopyrido[1,2-a][1,4]diazonine-10-carboxamide (91)

TFA (0.5 mL) was added to a solution of (4S,7S)-12-(benzyloxy)-4-methoxy-1,11-dioxo-N-(2,4,6-trifluorobenzyl)-1,4,5,6,7,11-hexahydro-3H-2,7-methanopyrido[1,2-a][1,4]diazonine-10-carboxamide (91a, 2 mg) in toluene (0.5 mL). The reaction was stirred at r.t. for one hour. The reaction mixture was concentrated, purified via preparative HPLC, eluting with 10-60% acetonitrile in water (0.1% TFA) to afford the title compound (91). MS (m/z) 452.22 [M+H]+. 1H NMR (400 MHz, Acetonitrile-d3) δ 8.39 (d, J=7.4 Hz, 1H), 6.87 (t, J=8.5 Hz, 1H), 6.68 (t, J=8.5 Hz, 1H), 4.88-4.51 (m, 2H), 4.37-4.21 (m, 1H), 3.84 (d, J=14.9 Hz, 1H), 3.71 (s, 1H), 3.60-3.46 (m, 1H), 3.30 (d, J=36.8 Hz, 3H), 2.11 (s, 2H), 1.92-1.76 (m, 2H).

Example 89: Preparation of (6R)— and (6S)—N-(2,4-difluorobenzyl)-10,11-difluoro-1-hydroxy-2,14-dioxo-2,6,7,14-tetrahydro-6,13-methanobenzo[b]pyrido[2,1-f][1,4,7]oxadiazonine-3-carboxamide (92-1, 92-2)

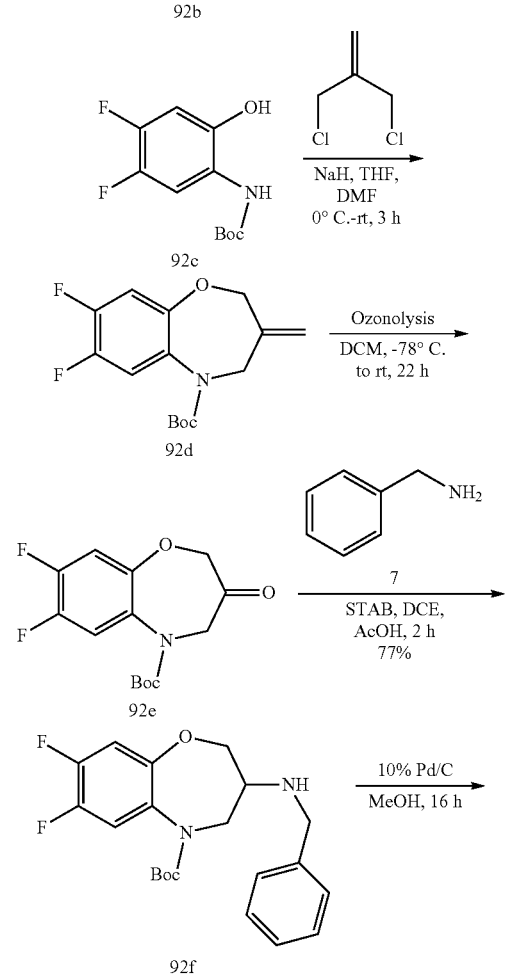

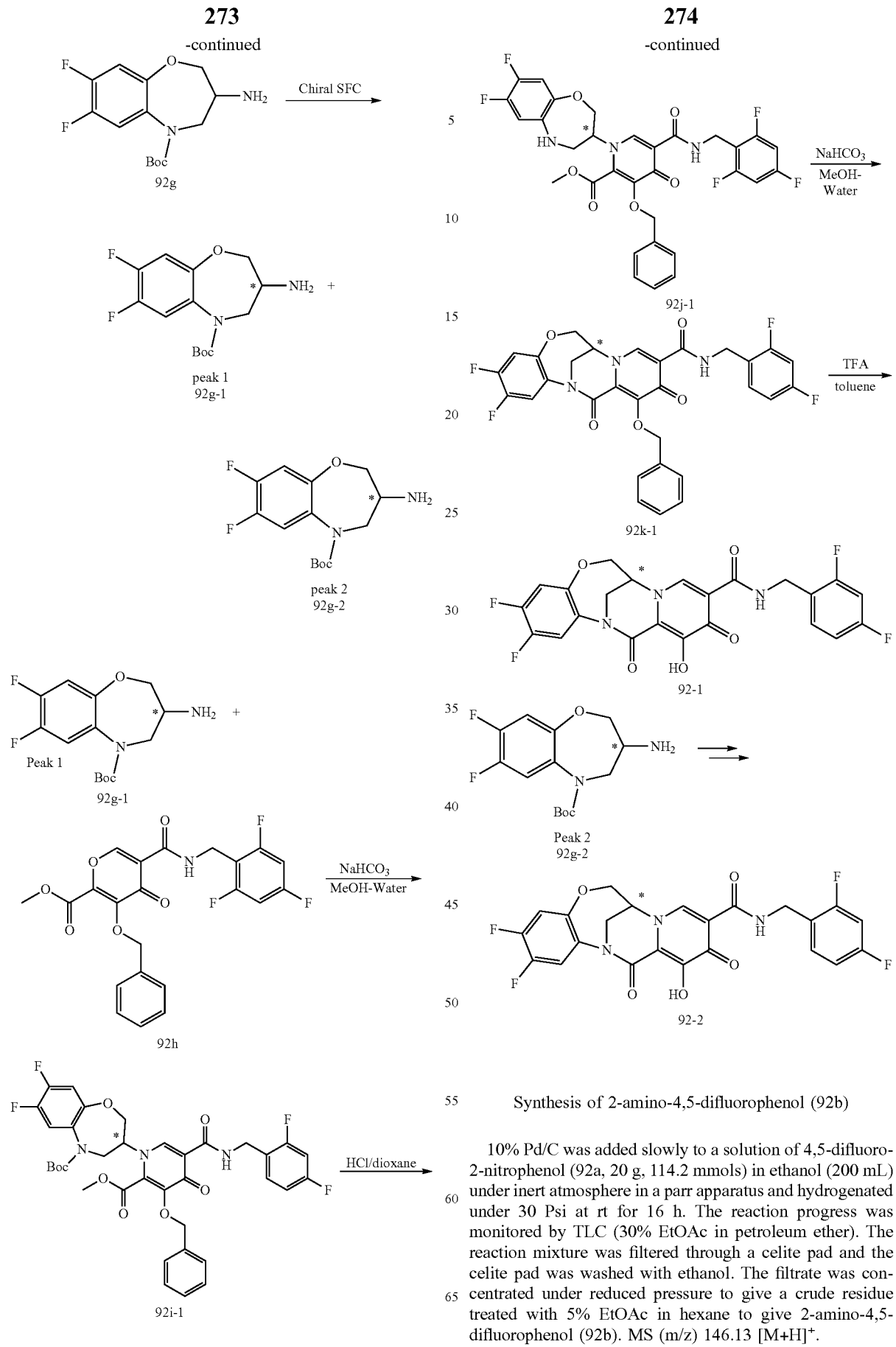

Synthesis of 2-amino-4,5-difluorophenol (92b)

10% Pd/C was added slowly to a solution of 4,5-difluoro-2-nitrophenol (92a, 20 g, 114.2 mmols) in ethanol (200 mL) under inert atmosphere in a parr apparatus and hydrogenated under 30 Psi at rt for 16 h. The reaction progress was monitored by TLC (30% EtOAc in petroleum ether). The reaction mixture was filtered through a celite pad and the celite pad was washed with ethanol. The filtrate was concentrated under reduced pressure to give a crude residue treated with 5% EtOAc in hexane to give 2-amino-4,5-difluorophenol (92b). MS (m/z) 146.13 [M+H]$^+$.

Synthesis of tert-butyl (4,5-difluoro-2-hydroxyphenyl)carbamate (92c)

Boc anhydride (136.45 mmols, 31.3 mL, 1.5 equiv) was added to a stirred solution of 2-amino-4,5-difluorophenol (92b) (90.96 mmols, 13.20 g) in THF (132 mL) at room temperature. The resulting reaction mixture was stirred at 60° C. for 16 h. The reaction mixture was concentrated under vacuum, and purified by column chromatography (using 100-200 silica gel, 8% EtOAc/Hexane as an eluent) to obtain tert-butyl (4,5-difluoro-2-hydroxyphenyl)carbamate (92c). MS (m/z) 244.16 [M+H]$^+$.

Synthesis of tert-butyl 7,8-difluoro-3-methylene-3,4-dihydrobenzo[b][1,4]oxazepine-5(2H)-carboxylate (92d)

NaH (60% in oil, 158.5 mmols, 6.3 g, 2.4 equiv) was added in one portion to a stirred solution of 3-chloro-2-(chloromethyl)prop-1-ene (79.5 mmols, 9.2 mL, 1.2 equiv) in DMF (178 mL) at 0° C. To the reaction mixture was added a solution of tert-butyl (4,5-difluoro-2-hydroxyphenyl)carbamate (92c, 66.23 mmols, 16.2 g) in THF (162 mL) dropwise at 5-10° C. The resulting reaction mixture was stirred at rt for 3 h. The mixture was diluted with cold water and extracted with MTBE twice. The combined organic layer was washed with brine, dried over Na$_2$SO$_4$, concentrated, and purified by column chromatography (using 100-200 silica gel, eluent 5% EtOAc/Hexane) to obtain tert-butyl 7,8-difluoro-3-methylene-3,4-dihydrobenzo[b][1,4]oxazepine-5(2H)-carboxylate (92d). MS (m/z) 298.24 [M+H]$^+$.

Synthesis of tert-butyl 7,8-difluoro-3-oxo-3,4-dihydrobenzo[b][1,4]oxazepine-5(2H)-carboxylate (92e)

Ozone gas was bubbled through a solution of tert-butyl 7,8-difluoro-3-methylene-3,4-dihydrobenzo[b][1,4]oxazepine-5(2H)-carboxylate (92d, 30.45 mmols, 12g) in DCM (1800 mL) at −78° C. until blue color persisted. Then, oxygen gas passed through the reaction mixture to remove of excess of O$_3$ until the solution become colorless. To the reaction mixture was added dimethyl sulfide at −78° C. The resulting reaction mixture was stirred at rt for 16 h. The reaction mixture was concentrated, and purified by column chromatography (using 100-200 silica gel, 10% EtOAc/Hexane) to obtain tert-butyl 7,8-difluoro-3-oxo-3,4-dihydrobenzo[b][1,4]oxazepine-5(2H)-carboxylate (92e). $^1$H NMR (400 MHz, Chloroform-d) δ 7.52-7.47 (m, 1H), 7.26-7.22 (m, 1H), 4.63 (s, 2H), 4.39 (s, 2H), 1.40 (s, 9H).

Synthesis of tert-butyl 3-(benzylamino)-7,8-difluoro-3,4-dihydrobenzo[b][1,4]oxazepine-5(2H)-carboxylate (92f)

Benzylamine (53.5 mmols, 5.83 mL, 2 equiv) and acetic acid (2.96 mL) were added to a stirred solution of tert-butyl 7,8-difluoro-3-oxo-3,4-dihydrobenzo[b][1,4]oxazepine-5(2H)-carboxylate (92e, 26.73 mmols, 8 g) in dichloroethane (80 mL) and stirred at rt for 30 min. Sodium triacetoxy borohydride (53.46 mmols 11.3 g, 2 equiv) was added in one portion under N$_2$ atmosphere, and the resulting solution was stirred at rt for 2 h. The reaction mass was cooled to 0° C. and quenched with cold water and diluted with dichloromethane. The organic layer was separated and the aqueous layer was extracted with dichloromethane. The combined organic layer was washed with brine solution, dried over anhydrous Na$_2$SO$_4$, filtered and evaporated. The crude was purified by column on silica gel (100-200 mesh) with 20% EtOAc in pet ether to give tert-butyl 3-(benzylamino)-7,8-difluoro-3,4-dihydrobenzo[b][1,4]oxazepine-5(2H)-carboxylate (92f). MS (m/z) 391.37 [M+H]$^+$.

Synthesis of tert-butyl 3-amino-7,8-difluoro-3,4-dihydrobenzo[b][1,4]oxazepine-5(2H)-carboxylate (92g)

10% Pd/C (1.0 g) was added slowly to a stirred solution of tert-butyl 3-(benzylamino)-7,8-difluoro-3,4-dihydrobenzo[b][1,4]oxazepine-5(2H)-carboxylate (92f, 13.3 mmols, 5.2 g) in methanol (52 mL) under inert atmosphere. The reaction mixture was stirred at rt under hydrogen gas balloon pressure for 16 h. The reaction mixture was filtered through celite pad. The celite pad was washed with methanol and the filtrate was concentrated and purified by column on silica gel (using 100-200 silica gel, 3% MeOH in DCM), to give tert-butyl 3-amino-7,8-difluoro-3,4-dihydrobenzo[b][1,4]oxazepine-5(2H)-carboxylate (92g). MS (m/z) 301.15 [M+H]$^+$.

92g was separated into individual enantiomers by chiral HPLC (SFC chromatography on IG 4.6×100 mm 5 mic eluting with 15% EtOH-NH$_3$, 3 mL/min flow rate, 100 bar, 40° C., 5 uL) to provide 92g-1 and 92g-2.

Synthesis of tert-butyl 3-(3-(benzyloxy)-5-((2,4-difluorobenzyl)carbamoyl)-2-(methoxycarbonyl)-4-oxopyridin-1(4H)-yl)-7,8-difluoro-3,4-dihydrobenzo[b][1,4]oxazepine-5(2H)-carboxylate (92i-1)

A mixture of tert-butyl 3-amino-7,8-difluoro-3,4-dihydro-2H-1,5-benzoxazepine-5-carboxylate (92g-1, 0.200 g, 0.666 mmol), methyl 3-benzyloxy-5-[(2,4-difluorophenyl)methylcarbamoyl]-4-oxo-pyran-2-carboxylate (92h, 286 mg, 0.666 mmol) and sodium bicarbonate (559 mg, 6.66 mmol) in water (10 mL) and MeOH (25 mL) was stirred at rt. After 2 hours, the mixture was concentrated, the residue was diluted with water (40 mL), and the product was extracted with ethyl acetate (40 mL×3). The organic extracts were combined, dried with magnesium sulfate, and concentrated. The crude product was used for the next reaction without further purification assuming 100% yield. MS (m/z) 711.95 [M+H]$^+$.

Synthesis of methyl 3-(benzyloxy)-1-(7,8-difluoro-2,3,4,5-tetrahydrobenzo[b][1,4]oxazepin-3-yl)-5-((2,4-difluorobenzyl)carbamoyl)-4-oxo-1,4-dihydropyridine-2-carboxylate (92j-1)

To a solution of the crude tert-butyl 3-[3-benzyloxy-5-[(2,4-difluorophenyl)methylcarbamoyl]-2-methoxycarbonyl-4-oxo-1-pyridyl]-7,8-difluoro-3,4-dihydro-2H-1,5-benzoxazepine-5-carboxylate (92i-1, 0.473 g, 0.665 mmol) in DCM (3 mL) was added 4 N HCl (4 M, 1.64 mL, 6.57 mmol) in dioxane and the solution was stirred at room temperature for 2 hours. The solution was concentrated and the crude product was used subsequently without further purification. MS (m/z) 611.98 [M+H]$^+$.

N-(2,4-difluorobenzyl)-10,11-difluoro-1-hydroxy-2,14-dioxo-2,6,7,14-tetrahydro-6,13-methanobenzo[b]pyrido[2,1-f][1,4,7]oxadiazonine-3-carboxamide (92-1)

The crude methyl 3-benzyloxy-5-[(2,4-difluorophenyl)methylcarbamoyl]-1-(7,8-difluoro-2,3,4,5-tetrahydro-1,5-benzoxazepin-3-yl)-4-oxo-pyridine-2-carboxylate (92j-1, 0.406 g, 0.664 mmol) was dissolved in methanol (50 mL). To the solution was added DBU (0.505 g, 3.32 mmol) and the resulting solution was stirred at 50° C. After 2 hours, the crude was concentrated. The residue was dissolved in DCM (1 mL), and purified by silica gel column (40 g) eluting with DCM/MeOH to give 1-(benzyloxy)-N-(2,4-difluorobenzyl)-10,11-difluoro-2,14-dioxo-2,6,7,14-tetrahydro-6,13-methanobenzo[b]pyrido[2,1-f][1,4,7]oxadiazonine-3-carboxamide (92k-1). MS (m/z) 580.01 [M+H]$^+$.

The product (92k-1) was then diluted in toluene (5 mL) and TFA was added (5 mL). The reaction was stirred overnight. The mixture was concentrated, diluted in MeOH, filtered, and purified by reverse phase column chromatography eluting with 0-100% acetonitrile/water (0.1% TFA) to afford N-[(2,4-difluorophenyl)methyl]-4,5-difluoro-15-hydroxy-14,17-dioxo-8-oxa-1,11-diazatetracyclo[8.7.1.02,7.011,16]octadeca-2(7),3,5,12,15-pentaene-13-carboxamide (92-1). MS (m/z) 488.38 [M+H]$^+$. $^1$H NMR (400 MHz, Chloroform-d) δ 10.06 (s, 1H), 8.44 (s, 1H), 7.46-7.31 (m, 2H), 7.20-7.06 (m, 1H), 7.01-6.92 (m, 1H), 6.87-6.77 (m, 2H), 4.69 (s, 1H), 4.65 (d, J=6.3 Hz, 2H), 4.22-4.10 (m, 2H), 4.07-3.92 (m, 2H).

92-2 was made in a similar fashion to 92-1, using 92g-2 instead of 92g-1.

MS (m/z) 490.16 [M+H]$^+$. $^1$H NMR (400 MHz, Chloroform-d) δ 10.06 (s, 1H), 8.44 (s, 1H), 7.46-7.32 (m, 2H), 7.02-6.92 (m, 1H), 6.87-6.72 (m, 2H), 4.77-4.56 (m, 4H), 4.21-4.09 (m, 2H), 4.08-3.96 (m, 1H), 3.11 (dd, J=7.4, 4.9 Hz, 1H).

Example 90: Preparation of 6S,7R)-6-ethyl-6,12-dihydroxy-1,11-dioxo-N-(2,4,6-trifluorobenzyl)-1,4,5,6,7,11-hexahydro-3H-2,7-methanopyrido[1,2-a][1,4]diazonine-10-carboxamide (93)

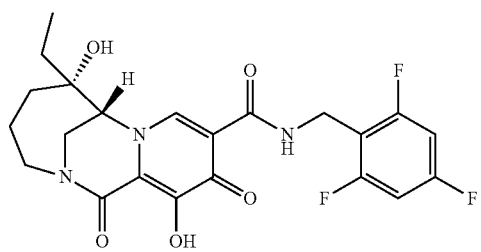 [SMILES: CC[C@]1(O)CCCN2C[C@H]1n1cc(C(=O)NCc3c(F)cc(F)cc3F)c(=O)c(O)c1C2=O]

The title compound was synthesized in a similar manner to compound 77, using methyl 3-(benzyloxy)-4-oxo-5-((2,4,6-trifluorobenzyl)carbamoyl)-4H-pyran-2-carboxylate in place of methyl 3-(benzyloxy)-5-((2,4-difluorobenzyl)carbamoyl)-4-oxo-4H-pyran-2-carboxylate. MS (m/z) 466.46 [M+H]$^+$. $^1$H NMR (400 MHz, DMSO-d$_6$) δ 10.46 (t, J=5.8 Hz, 1H), 8.24 (s, 1H), 7.27-7.14 (m, 2H), 4.64-4.46 (m, 2H), 4.21 (s, 1H), 4.11 (dt, J=12.8, 8.6 Hz, 1H), 3.82 (dd, J=15.3, 2.9 Hz, 1H), 3.68 (dd, J=15.2, 1.8 Hz, 1H), 3.14-2.93 (m, 1H), 1.76 (dt, J=17.2, 8.5 Hz, 3H), 1.55 (dt, J=14.3, 6.9 Hz, 2H), 1.09 (dd, J=14.6, 11.8 Hz, 1H), 0.88 (t, J=7.3 Hz, 3H).

Example 91: Preparation of (6R)-1-hydroxy-2,14-dioxo-N-(2,4,6-trifluorobenzyl)-2,6,7,14-tetrahydro-6,13-methanobenzo[b]pyrido[2,1-f][1,4,7]thiadiazonine-3-carboxamide (94)

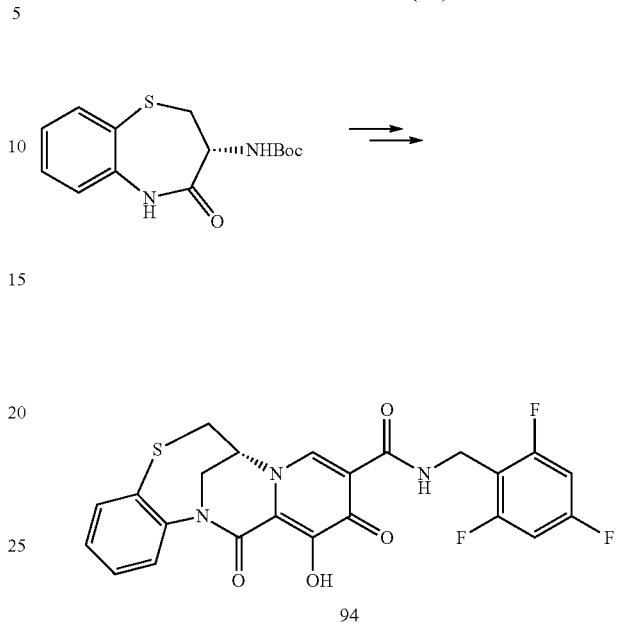

The title compound was prepared similarly to compound 43-1, using tert-butyl (R)-(4-oxo-2,3,4,5-tetrahydrobenzo[b][1,4]thiazepin-3-yl)carbamate (Organic Preparation and Procedures International, 34(4), 405-415, 2002) in place of 6-fluoro-2-oxo-2,3,4,5-tetrahydro-1H-benzo[b]azepin-3-yl)carbamate (43c). MS (m/z) 488.1 [M+H]$^+$. $^1$H NMR (400 MHz, Chloroform-d) δ 10.33 (s, 1H), 8.53 (s, 1H), 7.54 (ddd, J=10.7, 7.8, 1.4 Hz, 2H), 7.43-7.34 (m, 1H), 7.31 (dd, J=7.7, 1.4 Hz, 1H), 6.66 (t, J=8.1 Hz, 2H), 4.77 (s, 1H), 4.67 (tt, J=14.5, 7.1 Hz, 2H), 4.29-4.12 (m, 2H), 3.39 (dd, J=15.3, 4.5 Hz, 1H), 3.24 (dd, J=15.3, 6.0 Hz, 1H).

Example 92: Preparation of (6R)-1-hydroxy-2,14-dioxo-N-(2,4,6-trifluorobenzyl)-2,6,7,14-tetrahydro-6,13-methanobenzo[b]pyrido[2,1-f][1,4,7]thiadiazonine-3-carboxamide 8-oxide (95)

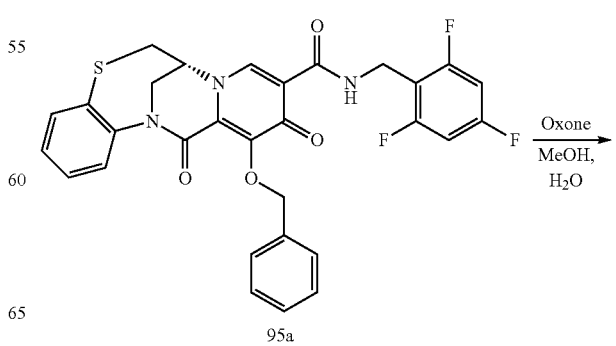

-continued

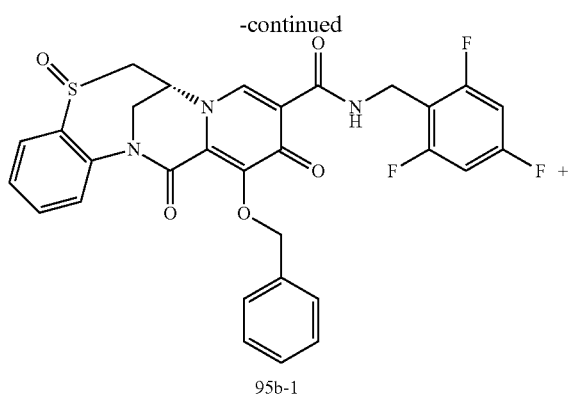

95b-1

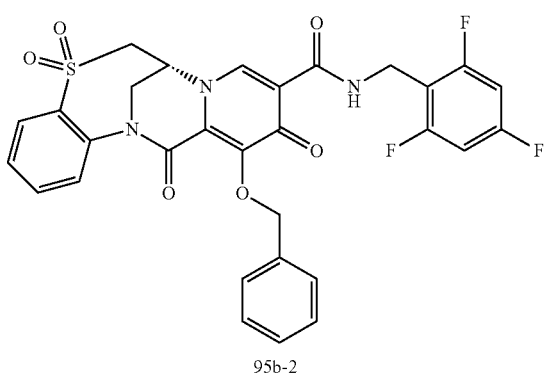

95b-2

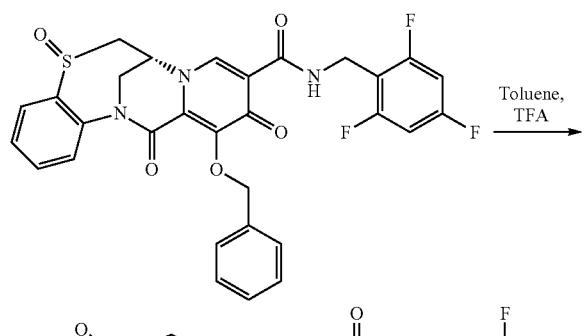

Toluene, TFA →

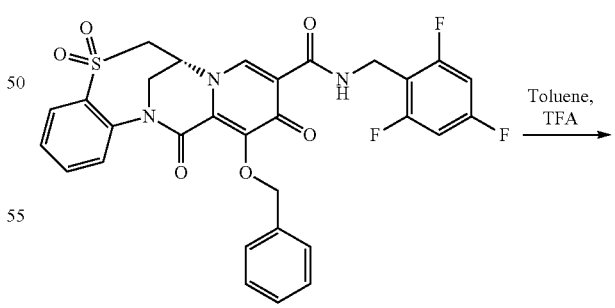

95

Synthesis of (6R)-1-(benzyloxy)-2,14-dioxo-N-(2,4,6-trifluorobenzyl)-2,6,7,14-tetrahydro-6,13-methanobenzo[b]pyrido[2,1-f][1,4,7]thiadiazonine-3-carboxamide (95a)

The title compound was prepared in a similar manner to compound 94, and isolated as the benzyl-protected alcohol, before TFA deprotection.

Synthesis of (6R)-1-(benzyloxy)-2,14-dioxo-N-(2,4,6-trifluorobenzyl)-2,6,7,14-tetrahydro-6,13-methanobenzo[b]pyrido[2,1-f][1,4,7]thiadiazonine-3-carboxamide 8-oxide and (6R)-1-(benzyloxy)-2,14-dioxo-N-(2,4,6-trifluorobenzyl)-2,6,7,14-tetrahydro-6,13-methanobenzo[b]pyrido[2,1-f][1,4,7]thiadiazonine-3-carboxamide 8,8-dioxide (95b-1 and 95b-2)

Into the solution of (6R)-1-(benzyloxy)-2,14-dioxo-N-(2,4,6-trifluorobenzyl)-2,6,7,14-tetrahydro-6,13-methanobenzo[b]pyrido[2,1-f][1,4,7]thiadiazonine-3-carboxamide (95a, 135 mg, 0.235 mmol) in MeOH (16 mL), was added a solution of Oxone (395 mg) in water (10 mL) at rt. After 1 hr, solvent was removed and extracted with ethyl acetate (100 mL). After removing the solvent, the residue was purified by silica-gel column to provide the title compounds (95b-1 and 95b-2). 95b-1: MS (m/z) 594.1 [M+H]$^+$; 95b-2: MS (m/z) 610.1 [M+H]$^+$.

Synthesis of (6R)-1-hydroxy-2,14-dioxo-N-(2,4,6-trifluorobenzyl)-2,6,7,14-tetrahydro-6,13-methanobenzo[b]pyrido[2,1-f][1,4,7]thiadiazonine-3-carboxamide 8-oxide (95)

To a solution of (6R)-1-(benzyloxy)-2,14-dioxo-N-(2,4,6-trifluorobenzyl)-2,6,7,14-tetrahydro-6,13-methanobenzo[b]pyrido[2,1-f][1,4,7]thiadiazonine-3-carboxamide 8-oxide (95a-1, 78 mg, 0.131 mmol) in toluene (4 mL), was added TFA (1 mL) at rt. After stirring overnight, the solvent and excess TFA was removed, and the residue was purified by preparative HPLC to provide the title compound (95). MS (m/z) 504.1 [M+H]$^+$. $^1$H NMR (400 MHz, Chloroform-d) δ 10.08 (s, 1H), 8.60 (s, 1H), 7.86 (d, J=7.4 Hz, 1H), 7.66 (dt, J=11.3, 3.7 Hz, 3H), 7.21-7.13 (m, 1H), 7.14-7.08 (m, 1H), 6.67 (t, J=8.1 Hz, 2H), 5.03 (s, 1H), 4.68 (d, J=5.8 Hz, 2H), 4.35-4.28 (m, 1H), 3.88 (dd, J=14.3, 4.4 Hz, 1H), 3.39 (dd, J=14.3, 5.9 Hz, 1H).

Example 93: Preparation of (6R)-1-hydroxy-2,14-dioxo-N-(2,4,6-trifluorobenzyl)-2,6,7,14-tetrahydro-6,13-methanobenzo[b]pyrido[2,1-f][1,4,7]thiadiazonine-3-carboxamide 8,8-dioxide (96)

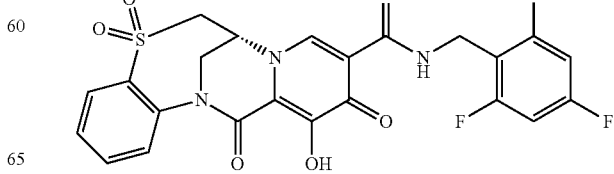

Toluene, TFA →

The title compound was prepared similarly to compound 95, using (6R)-1-(benzyloxy)-2,14-dioxo-N-(2,4,6-trifluorobenzyl)-2,6,7,14-tetrahydro-6,13-methanobenzo[b]pyrido[2,1-f][1,4,7]thiadiazonine-3-carboxamide 8,8-dioxide (95b-2) in place of (6R)-1-(benzyloxy)-2,14-dioxo-N-(2,4,6-trifluorobenzyl)-2,6,7,14-tetrahydro-6,13-methanobenzo[b]pyrido[2,1-f][1,4,7]thiadiazonine-3-carboxamide 8-oxide (95b-1). MS (m/z) 520.1 [M+H]$^+$. $^1$H NMR (400 MHz, Chloroform-d) δ 10.16 (s, 1H), 8.61 (s, 1H), 8.12 (d, J=7.8 Hz, 1H), 7.78 (d, J=7.6 Hz, 1H), 7.73 (d, J=7.7 Hz, 1H), 7.66 (t, J=7.8 Hz, 1H), 6.67 (t, J=8.1 Hz, 2H), 4.90 (s, 1H), 4.68 (t, J=4.7 Hz, 2H), 4.48 (d, J=15.0 Hz, 1H), 4.15 (d, J=15.1 Hz, 1H), 3.89 (s, 2H).

Example 94: Preparation of (6S)—N-(3-chloro-2,4-difluorobenzyl)-1-hydroxy-2,15-dioxo-2,6,7,8,9,15-hexahydro-6,14-methanobenzo[e]pyrido[1,2-a][1,4]diazecine-3-carboxamide and (6R)—N-(3-chloro-2,4-difluorobenzyl)-1-hydroxy-2,15-dioxo-2,6,7,8,9,15-hexahydro-6,14-methanobenzo[e]pyrido[1,2-a][1,4]diazecine-3-carboxamide (97-1 and 97-2)

97-1

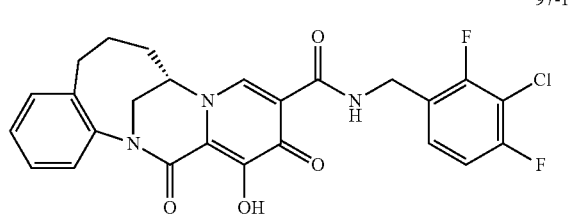

97-2

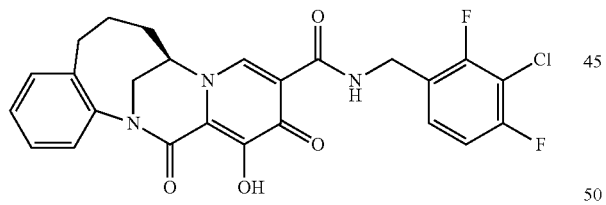

The title compounds were prepared in a manner similar to compounds 80-1 and 80-2, using methyl 3-(benzyloxy)-5-((3-chloro-2,4-difluorobenzyl)carbamoyl)-4-oxo-4H-pyran-2-carboxylate instead of methyl 3-(benzyloxy)-4-oxo-5-((2,4,6-trifluorobenzyl)carbamoyl)-4H-pyran-2-carboxylate.

97-1: MS (m/z) 500.21 [M+H]$^+$. $^1$H NMR (400 MHz, Methanol-d$_4$) δ 8.52 (s, 1H), 7.44-7.27 (m, 5H), 7.09 (td, J=8.7, 1.6 Hz, 1H), 4.77 (s, 1H), 4.67 (s, 2H), 4.50-4.39 (m, 1H), 3.95 (d, J=14.6 Hz, 1H), 3.17-2.94 (m, 2H), 2.59-2.45 (m, 1H), 2.17-2.05 (m, 1H), 1.92 (t, J=9.9 Hz, 2H).

97-2: MS (m/z) 500.21 [M+H]$^+$. $^1$H NMR (400 MHz, Methanol-d$_4$) δ 8.52 (s, 1H), 7.44-7.27 (m, 5H), 7.09 (td, J=8.7, 1.6 Hz, 1H), 4.77 (s, 1H), 4.67 (s, 2H), 4.50-4.39 (m, 1H), 3.95 (d, J=14.6 Hz, 1H), 3.17-2.94 (m, 2H), 2.59-2.45 (m, 1H), 2.17-2.05 (m, 1H), 1.92 (t, J=9.9 Hz, 2H).

Example 95: Preparation of (3S,7S)-12-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (98)

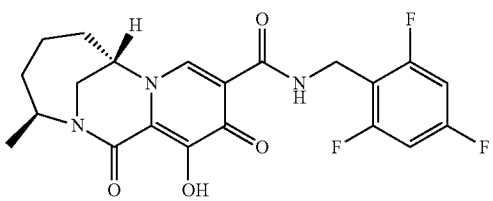 [SMILES: C[C@H]1CCC[C@H]2CN1C(=O)c1c(O)c(=O)c(C(=O)NCc3c(F)cc(F)cc3F)cn12]

The title compound was synthesized in a manner similar to compound 52-1, using methyl 3-(benzyloxy)-4-oxo-5-((2,4,6-trifluorobenzyl)carbamoyl)-4H-pyran-2-carboxylate in place of methyl 3-(benzyloxy)-5-((2,4-difluorobenzyl)carbamoyl)-4-oxo-4H-pyran-2-carboxylate. MS (m/z) 418.23 [M+H]$^+$. $^1$H NMR (400 MHz, Methanol-d$_4$) δ 8.46 (s, 1H), 7.41 (td, J=8.5, 6.3 Hz, 1H), 7.02-6.84 (m, 2H), 4.72-4.63 (m, 1H), 4.61 (s, 2H), 4.60-4.52 (m, 1H), 3.75 (t, J=1.6 Hz, 2H), 2.15 (td, J=15.7, 14.9, 7.9 Hz, 2H), 1.93 (ddt, J=18.8, 15.6, 4.3 Hz, 1H), 1.74 (ddt, J=15.3, 7.7, 3.9 Hz, 1H), 1.51 (dt, J=14.8, 11.1 Hz, 1H), 1.27 (d, J=6.7 Hz, 3H), 1.22-1.04 (m, 1H). $^{19}$F NMR (376 MHz, Methanol-d$_4$) δ −78.28, −113.93 (ddd, J=15.4, 8.5, 6.7 Hz), −116.86 (q, J=8.4 Hz).

Example 96: Preparation of (7S)-12-hydroxy-6-methoxy-1,11-dioxo-N-(2,4,6-trifluorobenzyl)-1,4,5,6,7,11-hexahydro-3H-2,7-methanopyrido[1,2-a][1,4]diazonine-10-carboxamide and (7R)-12-hydroxy-6-methoxy-1,11-dioxo-N-(2,4,6-trifluorobenzyl)-1,4,5,6,7,11-hexahydro-3H-2,7-methanopyrido[1,2-a][1,4]diazonine-10-carboxamide (99-1 and 99-2)

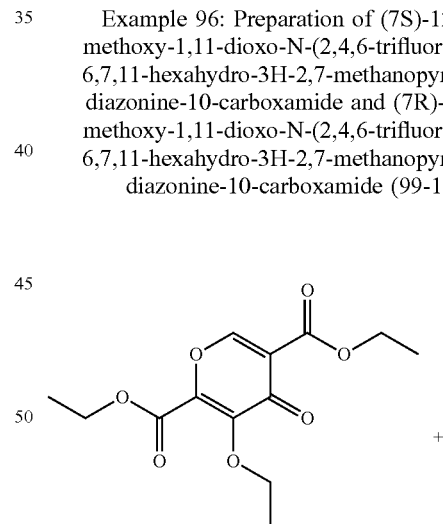

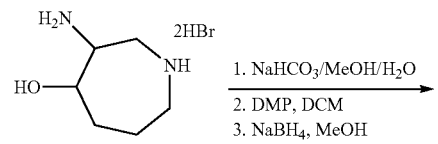

1. NaHCO$_3$/MeOH/H$_2$O
2. DMP, DCM
3. NaBH$_4$, MeOH

283
-continued

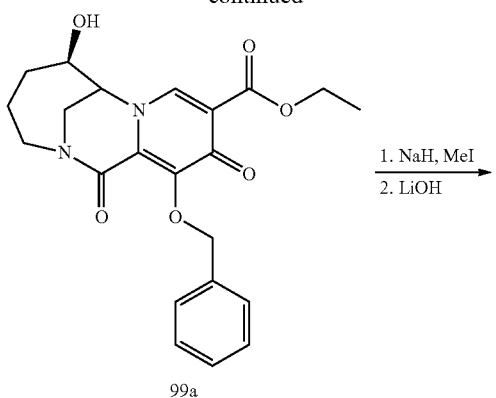

99a

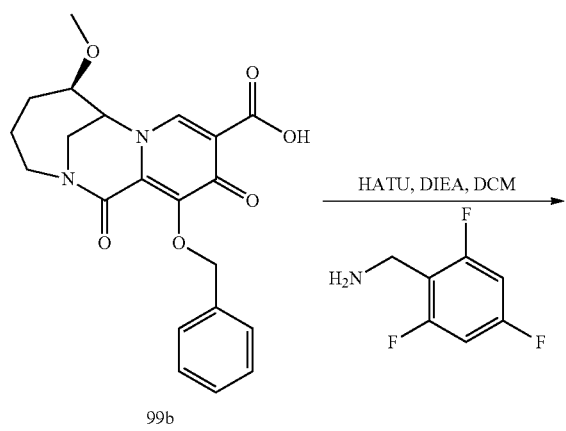

99b

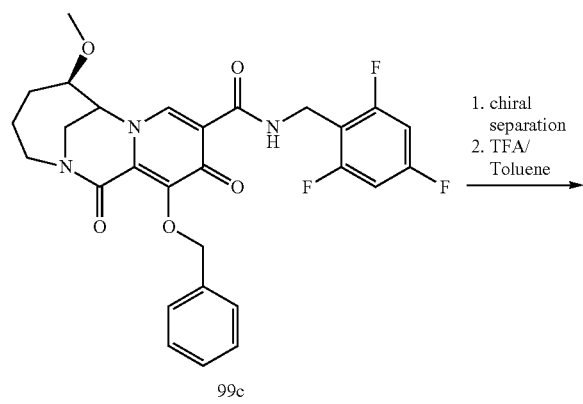

99c

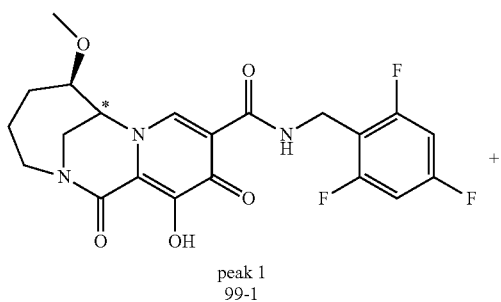

peak 1
99-1

284
-continued

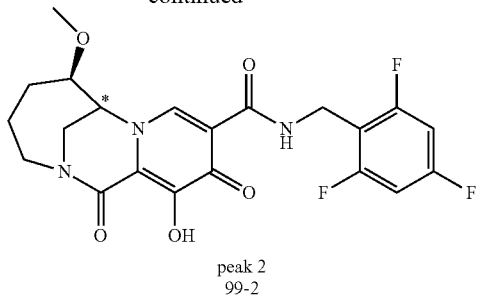

peak 2
99-2

Synthesis of ethyl 12-(benzyloxy)-6-hydroxy-1,11-dioxo-1,4,5,6,7,11-hexahydro-3H-2,7-methanopyrido[1,2-a][1,4]diazonine-10-carboxylate (99a)

Ethyl 12-(benzyloxy)-6-hydroxy-1,11-dioxo-1,4,5,6,7,11-hexahydro-3H-2,7-methanopyrido[1,2-a][1,4]diazonine-10-carboxylate was prepared in a manner similar to compound 28a, using 3-aminoazepan-4-ol dihydrobromide in place of 1,4-oxazepan-6-amine, and diethyl 3-(benzyloxy)-4-oxo-4H-pyran-2,5-dicarboxylate in place of methyl 3-(benzyloxy)-5-((3-chloro-2,4-difluorobenzyl)carbamoyl)-4-oxo-4H-pyran-2-carboxylate, then follow up DMP oxidation and NaBH$_4$ reduction (selectively) to afford 99a as a racemic mixture. MS (m/z) 413.24 [M+H]$^+$.

Synthesis of 12-(benzyloxy)-6-methoxy-1,11-dioxo-1,4,5,6,7,11-hexahydro-3H-2,7-methanopyrido[1,2-a][1,4]diazonine-10-carboxylic acid (99b)

Ethyl (6R)-12-(benzyloxy)-6-hydroxy-1,11-dioxo-1,4,5,6,7,11-hexahydro-3H-2,7-methanopyrido[1,2-a][1,4]diazonine-10-carboxylate (99a, 255 mg, 0.62 mmol) was dissolved in dry DMF (10 mL) and cooled to 0° C. NaH (60% dispersion in mineral oil, 50 mg, 1.24 mmol) was added, and the mixture was stirred for 30 min, before iodomethane (0.077 mL, 1.24 mmol) was added. The reaction mixture was stirred at 0° C. for 20 min, then quenched with saturated aqueous NH$_4$Cl, and extracted with EtOAc. The combined organic extracts were dried over MgSO$_4$, filtered, and concentrated. The residue was purified by RP-HPLC eluting with ACN/water (w/0.1% TFA) to afford ethyl 12-(benzyloxy)-6-methoxy-1,11-dioxo-1,4,5,6,7,11-hexahydro-3H-2,7-methanopyrido[1,2-a][1,4]diazonine-10-carboxylate. This product was stirred with LiOH (67 mg, 1.6 mmol) in THF/MeOH/water (3 mL/2 mL/1 mL). After 20 minutes, the pH was adjusted to 3 with 1 N hydrochloric acid and the product was extracted into EtOAc. The combined organic extracts were dried over MgSO$_4$, filtered, and concentrated to dryness to afford the title product (99b), which was carried forward without further purification. MS (m/z) 399.22 [M+H]$^+$.

Synthesis of 12-(benzyloxy)-6-methoxy-1,11-dioxo-N-(2,4,6-trifluorobenzyl)-1,4,5,6,7,11-hexahydro-3H-2,7-methanopyrido[1,2-a][1,4]diazonine-10-carboxamide (99c)

12-(benzyloxy)-6-methoxy-1,11-dioxo-1,4,5,6,7,11-hexahydro-3H-2,7-methanopyrido[1,2-a][1,4]diazonine-10-carboxylic acid (99b, 115 mg, 0.29 mmol) and HATU (219 mg, 0.58 mmol) in 5 mL of methylene chloride was stirred at room temperature as N,N-Diisopropylethylamine (0.25 mL, 1.44 mmol) was added slowly, followed by slow addition of (2,4,6-trifluorophenyl)methanamine (46.5 mg, 0.29 mmol) in 0.2 mL of DMF. After completion of the reaction, the mixture was partitioned between methylene chloride and water. The organic layer was separated, and washed with brine, dried over MgSO$_4$, filtered, and concentrated. The residue was purified by preparatory HPLC eluting with (MeCN/water with 0.1% TFA), and lyophilized to provide the title compound (99c). MS (m/z) 542.32 [M+H]$^+$.

Synthesis of (7S)- and (7R)-12-hydroxy-6-methoxy-1,11-dioxo-N-(2,4,6-trifluorobenzyl)-1,4,5,6,7,11-hexahydro-3H-2,7-methanopyrido[1,2-a][1,4]diazonine-10-carboxamide (99-1 and 99-2)

12-(benzyloxy)-6-methoxy-1,11-dioxo-N-(2,4,6-trifluorobenzyl)-1,4,5,6,7,11-hexahydro-3H-2,7-methanopyrido[1,2-a][1,4]diazonine-10-carboxamide (98c) was separated into its individual diastereomers by preparative SFC chromatography on an OD-H column using EtOH-NH$_3$ cosolvent. The separated enantiomers were dissolved in 1.5 mL of toluene and 1.5 mL of TFA and stirred at room temperature for 1 h. After concentration, purification by preparatory HPLC eluting with (MeCN/water with 0.1% TFA), provided the title compounds.

99-1: MS (m/z) 452.18 [M+H]$^+$. $^1$H NMR (400 MHz, DMSO-d$_6$) δ 10.71 (s, 1H), 10.40 (t, J=5.8 Hz, 1H), 8.24 (s, 1H), 7.20 (q, J=8.7 Hz, 2H), 4.87 (s, 1H), 4.56 (d, J=5.7 Hz, 2H), 4.20-4.10 (m, 1H), 3.94-3.85 (m, 1H), 3.63 (d, J=15.1 Hz, 1H), 3.53 (d, J=11.4 Hz, 1H), 3.33 (s, 1H), 3.12 (dd, J=13.0, 7.4 Hz, 1H), 1.89 (d, J=12.3 Hz, 2H), 1.81 (s, 1H), 0.87 (t, J=12.1 Hz, 1H).

99-2: MS (m/z) 452.19 [M+H]$^+$. $^1$H NMR (400 MHz, DMSO-d$_6$) δ 10.71 (s, 1H), 10.40 (t, J=5.8 Hz, 1H), 8.24 (s, 1H), 7.28-7.15 (m, 2H), 4.87 (s, 1H), 4.56 (d, J=5.8 Hz, 2H), 4.20-4.08 (m, 1H), 3.90 (dd, J=15.0, 3.1 Hz, 1H), 3.63 (dd, J=15.1, 1.7 Hz, 1H), 3.56-3.46 (m, 1H), 3.35 (s, 3H), 3.12 (dd, J=12.9, 7.3 Hz, 1H), 1.89 (d, J=12.6 Hz, 2H), 1.86-1.73 (m, 1H), 0.89 (q, J=12.0 Hz, 1H).

Example 97: Preparation of (6S,7R)-6-ethyl-12-hydroxy-6-methoxy-1,11-dioxo-N-(2,4,6-trifluorobenzyl)-1,4,5,6,7,11-hexahydro-3H-2,7-methanopyrido[1,2-a][1,4]diazonine-10-carboxamide (100)

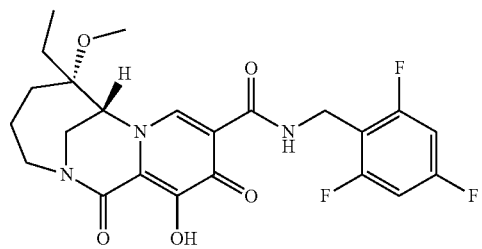 [SMILES: CC[C@]1(OC)CCCN2C[C@H]1n1cc(C(=O)NCc3c(F)cc(F)cc3F)c(=O)c(O)c1C2=O]

The title compound was prepared in a manner similar to compounds 99-1 and 99-2 using (3R,4S)-3-amino-4-ethylazepan-4-ol (77a) in place of 3-aminoazepan-4-ol; dihydrobromide, stereoisomer confirmed by crystal structure. MS (m/z) 480.17 [M+H]$^+$. $^1$H NMR (400 MHz, DMSO-d$_6$) δ 10.71 (s, 1H), 10.39 (t, J=5.8 Hz, 1H), 8.21 (s, 1H), 7.19 (t, J=8.7 Hz, 2H), 4.53 (d, J=5.0 Hz, 2H), 4.49 (s, 1H), 4.20-4.06 (m, 1H), 3.74 (t, J=16.4 Hz, 2H), 3.07 (s, 1H), 2.93 (s, 4H), 1.75 (ddd, J=46.6, 16.0, 9.3 Hz, 5H), 1.10 (s, OH), 0.89 (t, J=7.2 Hz, 3H).

Example 98: Preparation of (7S)-12-hydroxy-1,11-dioxo-N-(2,4,6-trifluorobenzyl)-1,6,7,11-tetrahydro-3H-2,7-methanopyrido[1,2-a][1,4]diazonine-10-carboxamide (101)

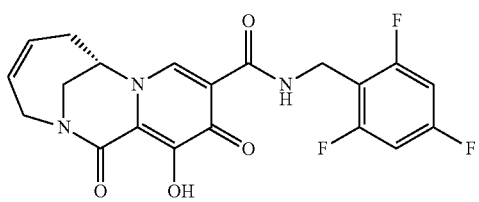 [SMILES: O=C(NCc1c(F)cc(F)cc1F)c1cn2c(c(O)c1=O)C(=O)N1CC=CC[C@H]2C1]

The title compound was prepared in a manner similar to compound 47-1, using methyl 3-(benzyloxy)-4-oxo-5-((2,4,6-trifluorobenzyl)carbamoyl)-4H-pyran-2-carboxylate in place of methyl 3-(benzyloxy)-5-((2,4-difluorobenzyl)carbamoyl)-4-oxo-4H-pyran-2-carboxylate. MS (m/z) 420.21 [M+H]$^+$. $^1$H NMR (400 MHz, Acetonitrile-d$_3$) δ 10.34 (s, 1H), 8.41 (s, 1H), 6.86 (t, J=8.5 Hz, 2H), 5.61 (m, 2H), 4.95 (d, J=18.1 Hz, 1H), 4.77 (d, J=9.1 Hz, 1H), 4.61 (d, J=4.7 Hz, 2H), 3.89 (m, 1H), 3.83-3.65 (m, 2H), 3.03 (dt, J=16.7, 8.0 Hz, 1H), 2.40 (d, J=18.6 Hz, 1H).

Example 99: Preparation of (7S)-12-hydroxy-1,4,11-trioxo-N-(2,4,6-trifluorobenzyl)-1,4,5,6,7,11-hexahydro-3H-2,7-methanopyrido[1,2-a][1,4]diazonine-10-carboxamide (102)

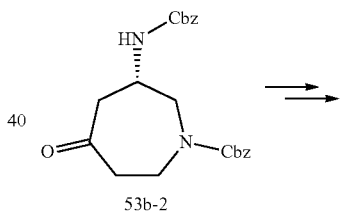

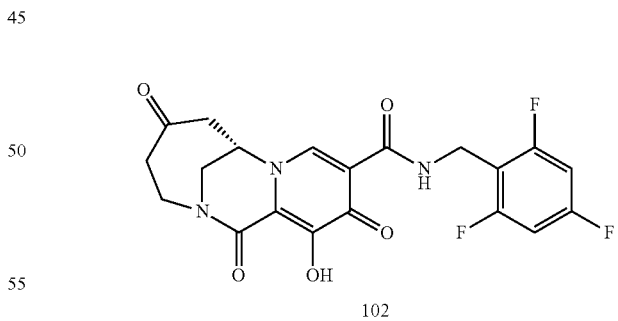

The title compound was synthesized using a procedure similar to compound 78, starting with benzyl (S)-3-(((benzyloxy)carbonyl)amino)-5-oxoazepane-1-carboxylate (53b-2) in place of benzyl (S)-3-(((benzyloxy)carbonyl)amino)-6-oxoazepane-1-carboxylate (53b-1). MS (m/z) 436.25 [M+H]$^+$. $^1$H NMR (400 MHz, Acetonitrile-d$_3$) δ 10.29 (s, 1H), 8.41 (s, 1H), 7.06-6.77 (m, 2H), 4.62 (d, J=5.8 Hz, 2H), 4.39 (dt, J=10.6, 7.9 Hz, 1H), 4.10 (d, J=14.9 Hz, 1H), 3.96 (d, J=15.0 Hz, 1H), 3.32-3.08 (m, 2H), 2.90-2.44 (m, 4H).

Example 100: Preparation of (5R,7S)-12-hydroxy-5-methoxy-1,11-dioxo-N-(2,4,6-trifluorobenzyl)-1,4,5,6,7,11-hexahydro-3H-2,7-methanopyrido[1,2-a][1,4]diazonine-10-carboxamide and (5S,7S)-12-hydroxy-5-methoxy-1,11-dioxo-N-(2,4,6-trifluorobenzyl)-1,4,5,6,7,11-hexahydro-3H-2,7-methanopyrido[1,2-a][1,4]diazonine-10-carboxamide (103-1 and 103-2)

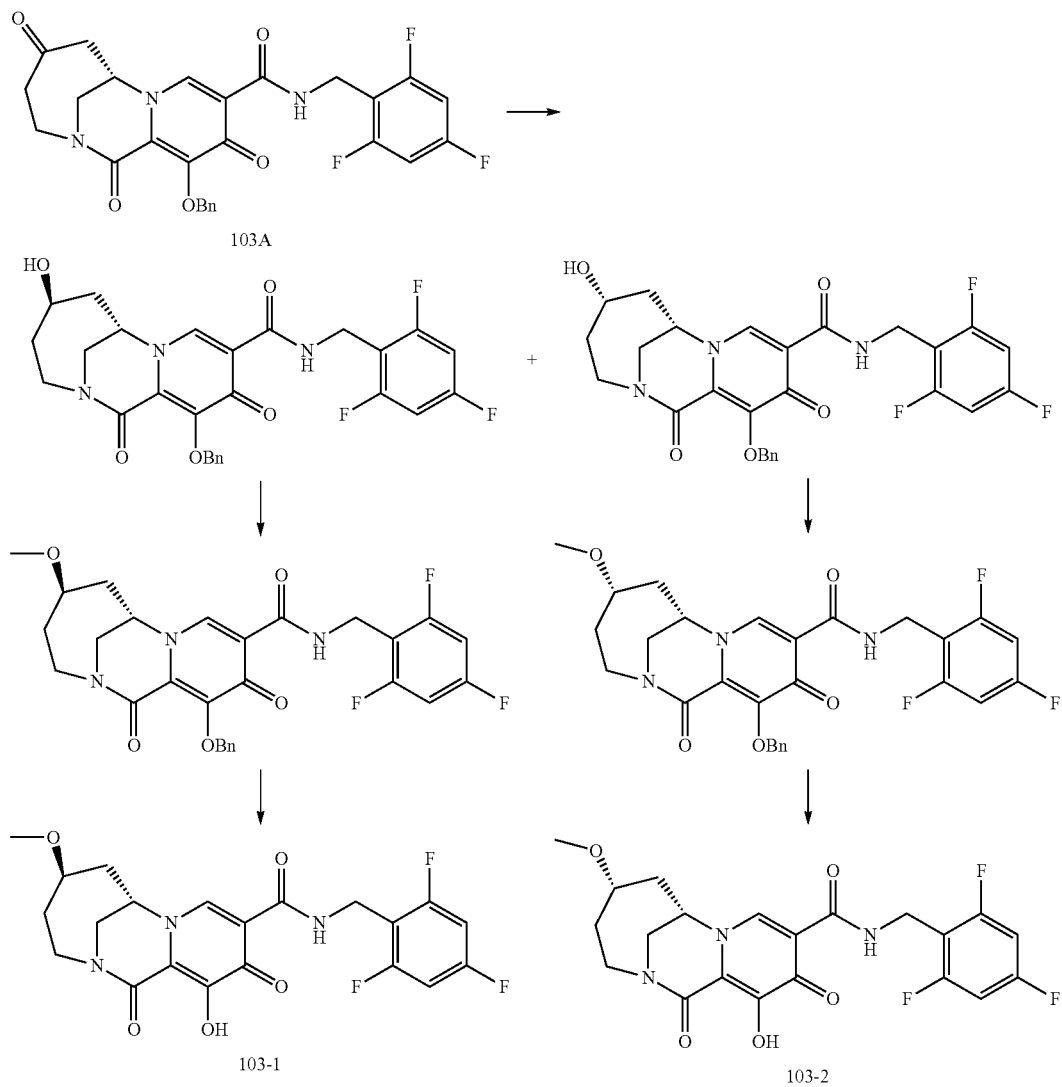

(7S)-12-(benzyloxy)-1,5,11-trioxo-N-(2,4,6-trifluorobenzyl)-1,4,5,6,7,11-hexahydro-3H-2,7-methanopyrido[1,2-a][1,4]diazonine-10-carboxamide (103a) was prepared in a manner similar to compound 102, and isolated as the benzyl-protected alcohol, before TFA deprotection.

The title compounds were synthesized using sequential procedures similar to compounds 79b-1 and 79b-2, followed by compound 91 starting with (7S)-12-(benzyloxy)-1,5,11-trioxo-N-(2,4,6-trifluorobenzyl)-1,4,5,6,7,11-hexahydro-3H-2,7-methanopyrido[1,2-a][1,4]diazonine-10-carboxamide (103a) in place of (7S)-12-(benzyloxy)-1,4,11-trioxo-N-(2,4,6-trifluorobenzyl)-1,4,5,6,7,11-hexahydro-3H-2,7-methanopyrido[1,2-a][1,4]diazonine-10-carboxamide (79a), stereochemistry drawn arbitrarily.

103-1: MS (m/z) 452.22 [M+H]$^+$. $^1$H NMR (400 MHz, Acetonitrile-d$_3$) δ 8.39 (d, J=7.4 Hz, 1H), 6.87 (t, J=8.5 Hz, 1H), 6.68 (t, J=8.5 Hz, 1H), 4.88-4.51 (m, 2H), 4.37-4.21 (m, 1H), 3.84 (d, J=14.9 Hz, 1H), 3.71 (s, 1H), 3.60-3.46 (m, 1H), 3.30 (d, J=36.8 Hz, 3H), 2.11 (s, 2H), 1.92-1.76 (m, 2H).

103-2: MS (m/z) 452.22 [M+H]$^+$. $^1$H NMR (400 MHz, Acetonitrile-d$_3$) δ 8.39 (d, J=7.4 Hz, 1H), 6.87 (t, J=8.5 Hz, 1H), 6.68 (t, J=8.5 Hz, 1H), 4.88-4.51 (m, 2H), 4.37-4.21 (m, 1H), 3.84 (d, J=14.9 Hz, 1H), 3.71 (s, 1H), 3.60-3.46 (m, 1H), 3.30 (d, J=36.8 Hz, 3H), 2.11 (s, 2H), 1.92-1.76 (m, 2H).

Example 101: Preparation of (11S)-6-hydroxy-5,7-dioxo-N-(2,4,6-trifluorobenzyl)-5,7,12,13-tetrahydro-11H-4,11-methanopyrido[1,2-a]thieno[3,2-e][1,4]diazonine-8-carboxamide and (11S)-6-hydroxy-5,7-dioxo-N-(2,4,6-trifluorobenzyl)-5,7,12,13-tetrahydro-11H-4,11-methanopyrido[1,2-a]thieno[3,2-e][1,4]diazonine-8-carboxamide (104-1 and 104-2)

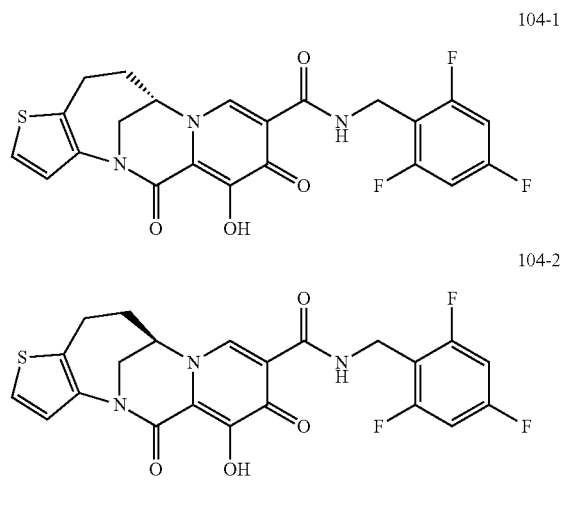

104-1

104-2

The title compounds were prepared in a manner similar to compounds 80-1 and 80-2, using tert-butyl (S)- or (R)-(5,6,7,8-tetrahydro-4H-thieno[3,2-b]azepin-6-yl)carbamate (resolved using SFC (AZ-H column, 15% MeOH)) in place of tert-butyl (S)- or (R)-(1,2,3,4,5,6-hexahydrobenzo[b]azocin-3-yl)carbamate (80b-1 or 80b-2).

104-1: MS (m/z) 476.16 [M+H]⁺. ¹H NMR (400 MHz, DMSO-$d_6$) δ 10.41-10.15 (m, 1H), 8.59 (s, 1H), 7.34 (d, J=5.3 Hz, 1H), 7.22 (t, J=8.7 Hz, 2H), 7.05 (d, J=5.3 Hz, 1H), 4.95 (t, J=7.5 Hz, 1H), 4.58 (s, 2H), 4.14-3.92 (m, 2H), 3.05-2.83 (m, 2H), 2.72-2.55 (m, 2H), 1.86-1.69 (m, 1H).

104-2: MS (m/z) 476.21 [M+H]⁺. ¹H NMR (400 MHz, DMSO-$d_6$) δ 10.52-10.09 (m, 1H), 8.59 (s, 1H), 7.39-7.28 (m, 1H), 7.22 (t, J=8.6 Hz, 2H), 7.05 (d, J=5.1 Hz, 1H), 4.95 (t, J=8.3 Hz, 1H), 4.58 (s, 2H), 4.13-3.93 (m, 2H), 3.06-2.82 (m, 2H), 2.72-2.55 (m, 2H), 1.87-1.66 (m, 1H).

Example 102: Preparation of N-(2,4-difluorobenzyl)-6-fluoro-12-hydroxy-6-methyl-1,11-dioxo-1,4,5,6,7,11-hexahydro-3H-2,7-methanopyrido[1,2-a][1,4]diazonine-10-carboxamide (105)

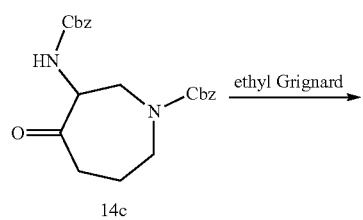

14c

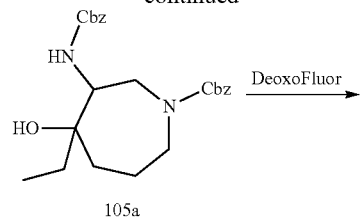

105a

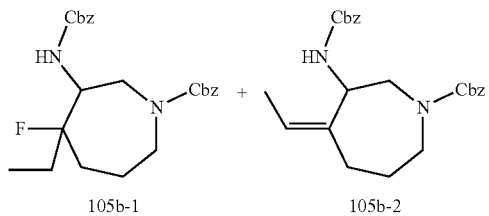

105b-1    105b-2

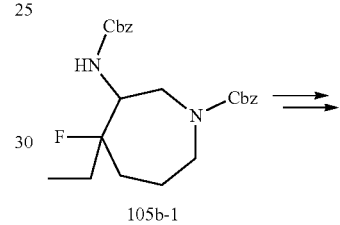

105b-1

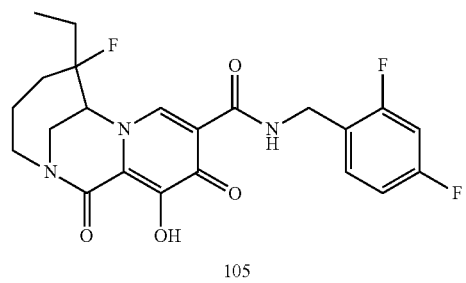

105

Synthesis of benzyl 3-(((benzyloxy)carbonyl)amino)-4-ethyl-4-hydroxyazepane-1-carboxylate (105a)

Ethyl Grignard (1 M in THF, 5.17 mL, 5.17 mmol) was added to a solution of benzyl 3-(((benzyloxy)carbonyl)amino)-4-oxoazepane-1-carboxylate (14c, 820 mg, 2.07 mmol) in THE (10 mL) at 0° C. The reaction was stirred for 30 min and stored in the refrigerator overnight. The reaction was allowed to warm to room temperature, stirred for 1 h, then quenched with saturated aqueous NH₄Cl. It was extracted into ethyl acetate, washed with brine, dried over MgSO₄, filtered, and evaporated to dryness. The residue was purified by silica gel chromatography eluting with ethyl acetate in hexane to afford the title product (105a). MS (m/z) 427.53 [M+H]⁺.

Synthesis of benzyl 3-(((benzyloxy)carbonyl)amino)-4-ethyl-4-fluoroazepane-1-carboxylate and benzyl (Z)-3-(((benzyloxy)carbonyl)amino)-4-ethylideneazepane-1-carboxylate (105b-1 and 105b-2)

The title compounds were prepared in a manner similar to compound 13a, using benzyl 3-(((benzyloxy)carbonyl)amino)-4-ethyl-4-hydroxyazepane-1-carboxylate (105a) in place of 12-(benzyloxy)-N-(2,4-difluorobenzyl)-6-hydroxy-1,11-dioxo-1,4,5,6,7,11-hexahydro-3H-2,7-methanopyrido[1,2-a][1,4]diazonine-10-carboxamide (12a), olefin regiochemistry drawn arbitrarily. 105b-1: MS (m/z) 429.39 [M+H]$^+$; 105b-2: 409.88 [M+H]$^+$.

Synthesis of N-(2,4-difluorobenzyl)-6-ethyl-6-fluoro-12-hydroxy-1,11-dioxo-1,4,5,6,7,11-hexahydro-3H-2,7-methanopyrido[1,2-a][1,4]diazonine-10-carboxamide (105)

The title compound was prepared in a manner similar to compound 60-1, using benzyl 3-(((benzyloxy)carbonyl)amino)-4-ethyl-4-fluoroazepane-1-carboxylate (105b-1) in place of benzyl (3R,4S)-3-(((benzyloxy)carbonyl)amino)-4-fluoro-4-methylazepane-1-carboxylate (60b-2). MS (m/z) 450.15 [M+H]$^+$. $^1$H NMR (400 MHz, DMSO-d$_6$) δ 10.83 (s, 1H), 10.32 (t, J=5.9 Hz, 1H), 8.62 (s, 1H), 7.42 (td, J=8.7, 6.6 Hz, 1H), 7.25 (ddd, J=10.6, 9.3, 2.6 Hz, 1H), 7.13-7.03 (m, 1H), 4.81 (d, J=11.8 Hz, 1H), 4.63-4.48 (m, 2H), 4.17 (q, J=11.2 Hz, 1H), 3.92 (dd, J=15.0, 2.6 Hz, 1H), 3.81 (dd, J=14.9, 1.9 Hz, 1H), 3.17 (dd, J=13.0, 7.7 Hz, 1H), 2.09 (dd, J=14.9, 8.0 Hz, 2H), 1.93-1.72 (m, 2H), 1.36 (ddd, J=29.4, 14.4, 7.3 Hz, 1H), 1.26-1.04 (m, 1H), 0.80 (t, J=7.3 Hz, 3H).

Example 103: Preparation of N-(2,4-difluorobenzyl)-6-ethyl-12-hydroxy-1,11-dioxo-1,4,5,6,7,11-hexahydro-3H-2,7-methanopyrido[1,2-a][1,4]diazonine-10-carboxamide (106)

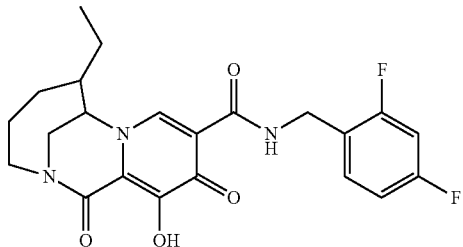 [SMILES: CCC1CCCN2CC1n1cc(C(=O)NCc3ccc(F)cc3F)c(=O)c(O)c1C2=O]

The title compound was prepared in a manner similar to compound 60-1, using benzyl (Z)-3-(((benzyloxy)carbonyl)amino)-4-ethylideneazepane-1-carboxylate (105b-2) in place of benzyl (3R,4S)-3-(((benzyloxy)carbonyl)amino)-4-fluoro-4-methylazepane-1-carboxylate (60b-2). MS (m/z) 432.22 [M+H]$^+$. $^1$H NMR (400 MHz, DMSO-d$_6$) δ 10.40 (t, J=5.9 Hz, 1H), 8.44 (s, 1H), 7.42 (td, J=8.7, 6.6 Hz, 1H), 7.25 (ddd, J=10.6, 9.3, 2.6 Hz, 1H), 7.12-7.02 (m, 1H), 4.55 (d, J=5.9 Hz, 2H), 4.46-4.40 (m, 1H), 4.16 (dt, J=12.3, 5.8 Hz, 1H), 3.79 (qd, J=15.0, 2.3 Hz, 2H), 3.04 (dt, J=13.0, 6.2 Hz, 1H), 1.83 (s, 1H), 1.66 (d, J=13.4 Hz, 4H), 1.50-1.29 (m, 2H), 0.92 (t, J=7.2 Hz, 3H).

Example 104: Preparation of (5S,7S)-5,12-dihydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide and (5R,7S)-5,12-dihydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide (107-1 and 107-2)

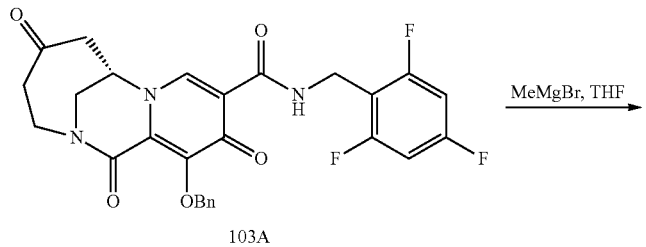

103A

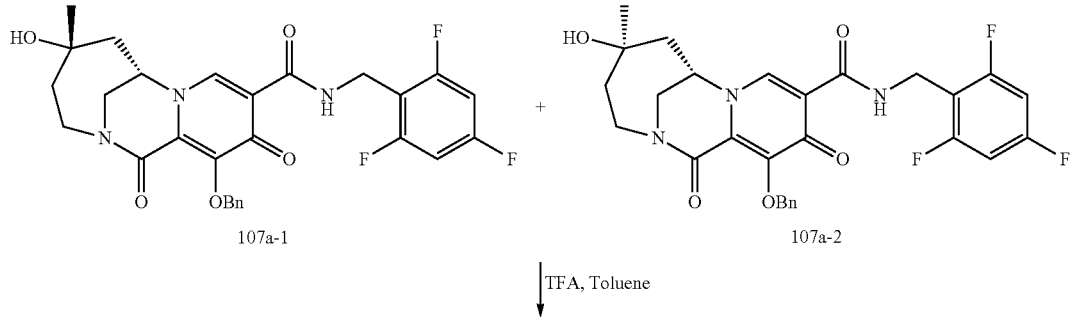

107a-1

107a-2

TFA, Toluene

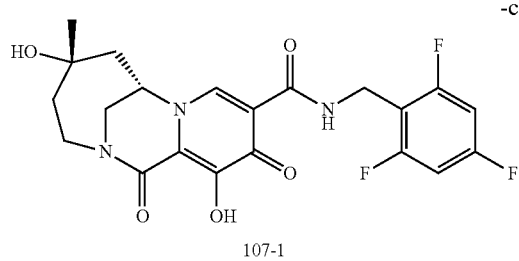 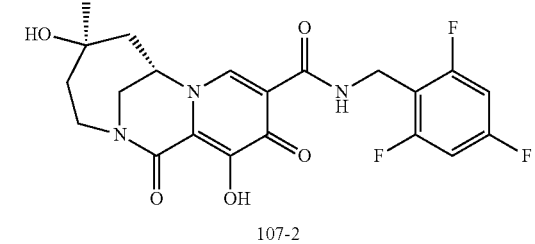

107-1     107-2

Synthesis of (5S,7S)-12-(benzyloxy)-5-hydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide and (5R,7S)-12-(benzyloxy)-5-hydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide (107a-1 and 107a-2)

At 0° C., MeMgBr (1.4 M in THF, 0.124 mL, 0.37 mmol) was added to (5R,7S)-5,12-dihydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide (103a, 65 mg, 0.124 mmol) in anhydrous THF (3 mL), and stirred for 3 hours. The reaction was quenched with water, and diluted with EtOAc. The organic layer was concentrated and purified via preparative HPLC, eluting with 10-60% acetonitrile in water (0.1% TFA) to give the title compounds (107a-1 and 107a-2) as separated diastereomers, stereoisomers assigned speculatively. MS (m/z) 542.17 [M+H]$^+$.

Synthesis of (5S,7S)-5,12-dihydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide and (5R,7S)-5,12-dihydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide (107-1 and 107-2)

TFA (0.5 mL) was added to a solution of (5S,7S)-12-(benzyloxy)-5-hydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide or (5R,7S)-12-(benzyloxy)-5-hydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide (107a-1 or 107a-2, 3 mg) in toluene (0.5 mL) at rt. The reaction was stirred for one hour, concentrated down, and purified via preparative HPLC, eluting with 10-60% acetonitrile in water (0.1% TFA), to give the title compounds (107-1 and 107-2), stereoisomers assigned speculatively.

107-1: MS (m/z) 452.15 [M+H]$^+$. $^1$H NMR (400 MHz, Acetonitrile-d$_3$) δ 10.46 (s, 1H), 8.37 (s, 1H), 7.00-6.78 (m, 2H), 4.61 (d, J=5.3 Hz, 2H), 4.56 (m, 1H), 4.19 (td, J=12.3, 6.6 Hz, 1H), 3.85 (d, J=14.8 Hz, 1H), 3.68 (d, J=14.7 Hz, 1H), 3.21 (dd, J=13.2, 7.4 Hz, 1H), 2.26-2.06 (m, 2H), 2.02 (d, J=5.4 Hz, 1H), 1.95-1.79 (m, 1H), 1.22 (s, 3H).

107-2: MS (m/z) 452.15 [M+H]$^+$. $^1$H NMR (400 MHz, Acetonitrile-d$_3$) δ 10.36 (s, 1H), 8.37 (s, 1H), 6.87 (t, J=8.5 Hz, 1H), 4.62 (m, 2H), 4.46-4.12 (m, 2H), 3.79 (d, J=14.0 Hz, 1H), 3.16 (m, 2H), 2.63 (dd, J=15.9, 9.2 Hz, 1H), 1.94-1.67 (m, 2H), 1.58 (dd, J=15.9, 4.3 Hz, 1H), 1.24 (s, 3H).

Example 105: Preparation of (3S,4R,7S)-12-hydroxy-3,4-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide and (3S,4S,7S)-12-hydroxy-3,4-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide (108-1 and 108-2)

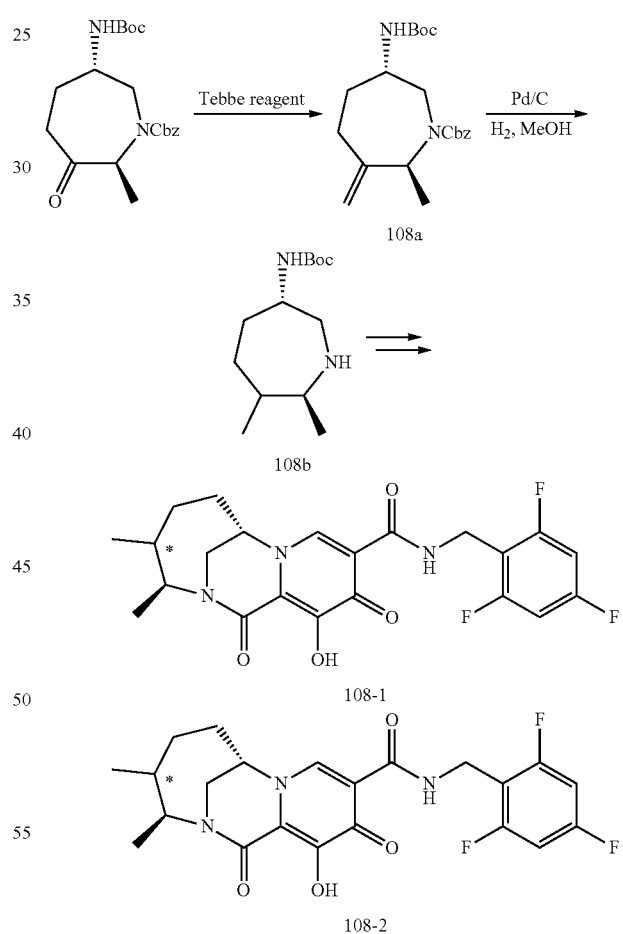

Synthesis of benzyl (2S,6S)-6-((tert-butoxycarbonyl)amino)-2-methyl-3-methyleneazepane-1-carboxylate (108a)

To a solution of benzyl (2S,6S)-6-((tert-butoxycarbonyl)amino)-2-methyl-3-oxoazepane-1-carboxylate (240 mg, 0.638 mmol) in THF (10 mL) at 0° C., was added Tebbe reagent (6.4 mL, 0.5M in toluene). The reaction mixture was allowed to warm to rt and stirred overnight. The reaction mixture was cooled to 0° C., and was quenched by adding sat. NaHCO$_3$ slowly. The mixture was extracted with EtOAc. The organic phase was dried over MgSO$_4$, filtered and concentrated down. The residue was purified by silica gel column chromatography, eluting with 0-50% EtOAc/hexane to give the title compound (108a).

Synthesis of tert-butyl ((3S,7S)-6,7-dimethylazepan-3-yl)carbamate (108b)

A mixture of benzyl (2S,6S)-6-((tert-butoxycarbonyl)amino)-2-methyl-3-methyleneazepane-1-carboxylate (108a, 90 mg, 0.24 mmol) and Pd/C (23.5 mg, 0.22 mmol) in MeOH (5 mL) under H$_2$ balloon was stirred at rt for 1 h. The reaction mixture was filtered, the filtrate was concentrated down and the residue used subsequently, without further purification.

Synthesis of (3S,4R,7S)- and (3S,4S,7S)-12-hydroxy-3,4-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide (108-1 and 108-2)

The title compounds were synthesized in a manner similar to compounds 40-1 and 40-2, using tert-butyl ((3S,7S)-6,7-dimethylazepan-3-yl)carbamate (108b) in place of tert-butyl ((1S,6R)-2-azabicyclo[4.2.1]nonan-4-yl)carbamate (40e).

108-1: MS (m/z) 450.24 [M+H]$^+$. $^1$H NMR (400 MHz, Methanol-d$_4$) δ 8.43 (s, 1H), 6.89 (t, J=8.5 Hz, 2H), 4.66 (s, 3H), 4.19-4.01 (m, 1H), 3.89-3.67 (m, 2H), 2.06 (q, J=16.0, 15.5 Hz, 2H), 1.74 (h, J=6.7 Hz, 1H), 1.50 (d, J=15.3 Hz, 1H), 1.32 (d, J=6.7 Hz, 3H), 1.29-1.20 (m, 1H), 1.05 (d, J=6.7 Hz, 3H).

108-2: MS (m/z) 450.22 [M+H]$^+$. $^1$H NMR (400 MHz, Methanol-d$_4$) δ 8.42 (s, 1H), 6.88 (t, J=8.5 Hz, 2H), 4.78 (t, J=6.9 Hz, 2H), 4.65 (s, 2H), 3.87 (d, J=14.2 Hz, 1H), 3.60 (d, J=14.5 Hz, 1H), 2.59 (s, 1H), 2.06 (q, J=7.8 Hz, 1H), 1.86-1.68 (m, 1H), 1.48 (t, J=13.7 Hz, 2H), 1.23 (d, J=7.1 Hz, 3H), 0.95 (d, J=7.1 Hz, 3H).

Example 106a: Preparation of (7R)-12-hydroxy-1,11-dioxo-N-(2,4,6-trifluorobenzyl)-1,4,7,11-tetrahydro-3H-2,7-methanopyrido[1,2-a][1,4]diazonine-10-carboxamide (109-1)

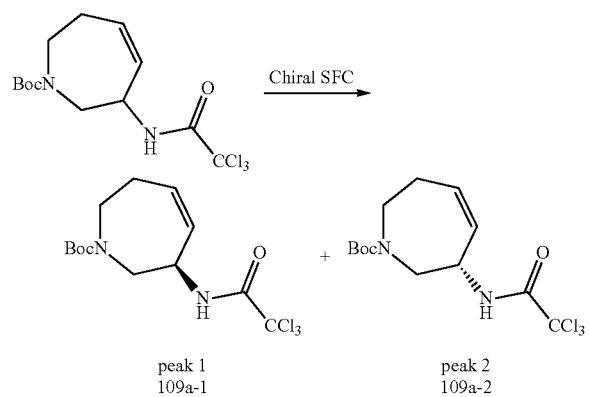

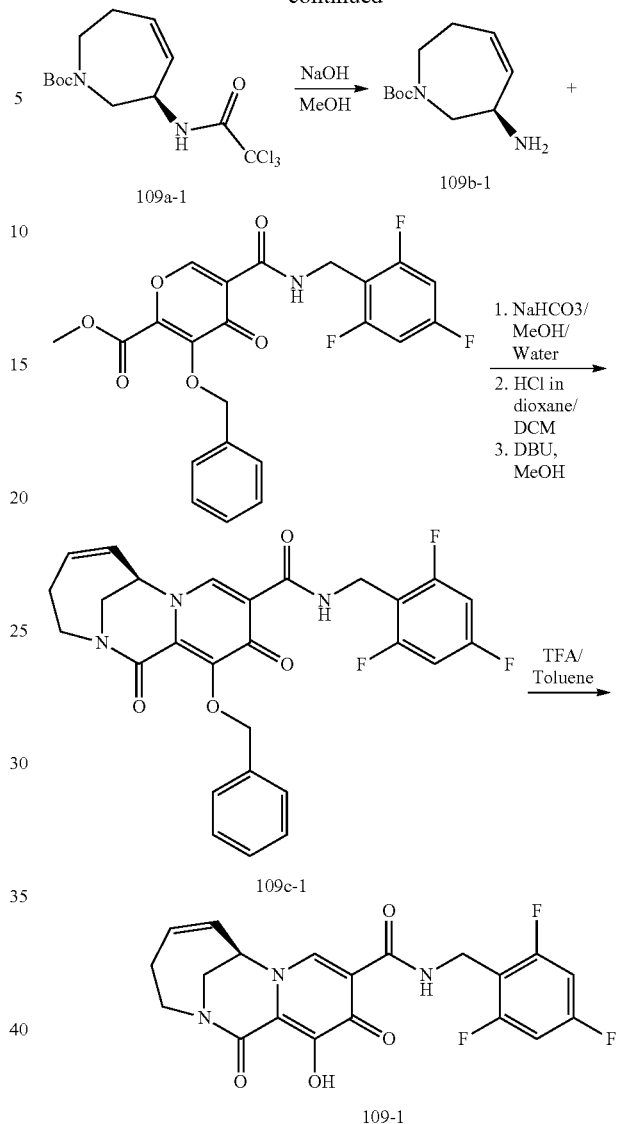

Synthesis of tert-butyl (R)-3-(2,2,2-trichloroacetamido)-2,3,6,7-tetrahydro-1H-azepine-1-carboxylate (109a-1) and tert-butyl (S)-3-(2,2,2-trichloroacetamido)-2,3,6,7-tetrahydro-1H-azepine-1-carboxylate (109a-2)

tert-butyl 3-(2,2,2-trichloroacetamido)-2,3,6,7-tetrahydro-1H-azepine-1-carboxylate (prepared according to procedure in *Org. Biomol. Chem.*, 2012, 10, 8251-8259) was separated into its individual enantiomers by chiral SFC using CHIRALPAK IG column to afford the title compounds (109a-1 and 109a-2).

109a-1, peak 1: MS (m/z): 301.0, 303.0 [M+H]$^+$, ee: 99.66%. [α]20D=−110.18 (c0.50, CHCl3). $^1$H NMR (400 MHz, CDCl$_3$): δ 8.44 (br, 0.65H), 6.80 (br, 0.30H) 5.92-5.67 (m, 2H), 4.65-4.55 (m, 1H), 4.13-4.10 (m, 0.68H), 3.84-3.37 (m, 2.7H), 3.18-3.15 (m, 0.70H), 2.38-2.25 (m, 2H), 1.46 (s, 9H).

109a-2, peak 2: MS (m/z): 301.0, 302.9 [M+H]$^+$, ee: 97.64%. [α]20D=+135.94 (c0.50, CHCl3). $^1$H NMR (400 MHz, CDCl$_3$): δ 8.44 (br, 0.65H), 6.80 (br, 0.29H) 5.92-5.67

(m, 2H), 4.65-4.55 (m, 1H), 4.13-4.10 (m, 0.70H), 3.84-3.37 (m, 2.74H), 3.18-3.15 (m, 0.70H), 2.38-2.25 (m, 2H), 1.47 (s, 9H).

Synthesis of tert-butyl (R)-3-amino-2,3,6,7-tetrahydro-1H-azepine-1-carboxylate (109b-1)

To solution of tert-butyl (R)-3-(2,2,2-trichloroacetamido)-2,3,6,7-tetrahydro-1H-azepine-1-carboxylate (109a-1, 100 mg; 0.28 mmol) in methanol (2 mL) was added sodium hydroxide (1.5N, 1.9 mL). The resulting mixture was stirred at 40° C. overnight. The mixture was diluted with water (10 mL), and extracted with methylene chloride. The organic layer was washed with brine, dried over anhydrous sodium sulfate, filtered, and concentrated to afford the title compound (109b-1). MS (m/z) 212.91 [M+H]$^+$.

Synthesis of (7R)-12-(benzyloxy)-1,11-dioxo-N-(2, 4,6-trifluorobenzyl)-1,4,7,11-tetrahydro-3H-2,7-methanopyrido[1,2-a][1,4]diazonine-10-carboxamide (109c-1)

The title compound was prepared in a method similar to compound 10a in Example 9 using tert-butyl (R)-3-amino-2,3,6,7-tetrahydro-1H-azepine-1-carboxylate (109b-1) instead of tert-butyl 3-amino-4-hydroxyazepane-1-carboxylate. MS (m/z) 510.47 [M+H]$^+$.

Synthesis of (7R)-12-hydroxy-1,11-dioxo-N-(2,4,6-trifluorobenzyl)-1,4,7,11-tetrahydro-3H-2,7-methanopyrido[1,2-a][1,4]diazonine-10-carboxamide (109-1)

The title compound was prepared in a manner similar to compound 11 in Example 10 using (7R)-12-(benzyloxy)-1, 11-dioxo-N-(2,4,6-trifluorobenzyl)-1,4,7,11-tetrahydro-3H-2,7-methanopyrido [1,2-a][1,4]diazonine-10-carboxamide (109c-1) in place of 12-(Benzyloxy)-6-hydroxy-1,11-dioxo-N-(2,4,6-trifluorobenzyl)-1,4,5,6,7,11-hexahydro-3H-2,7-methanopyrido[1,2-a][1,4] diazonine-10-carboxamide (10a). MS (m/z) 420.16 [M+H]$^+$. $^1$H NMR (400 MHz, DMSO-d$_6$) δ 10.39 (t, J=5.7 Hz, 1H), 8.57 (s, 1H), 7.28-7.15 (m, 2H), 5.85-5.73 (m, 1H), 5.64-5.54 (m, 1H), 5.34 (s, 1H), 4.57 (d, J=5.7 Hz, 2H), 4.20 (td, J=12.2, 6.6 Hz, 1H), 4.08 (dd, J=14.9, 2.5 Hz, 1H), 3.84-3.75 (m, 1H), 3.29 (dd, J=12.9, 8.4 Hz, 1H), 2.84 (d, J=9.4 Hz, 1H), 2.29 (ddd, J=15.7, 9.0, 6.4 Hz, 1H).

Example 106b: Preparation of (7S)-12-hydroxy-1, 11-dioxo-N-(2,4,6-trifluorobenzyl)-1,4,7,11-tetrahydro-3H-2,7-methanopyrido[1,2-a][1,4]diazonine-10-carboxamide (109-2)

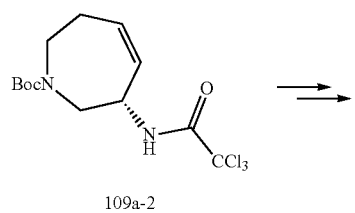

109a-2

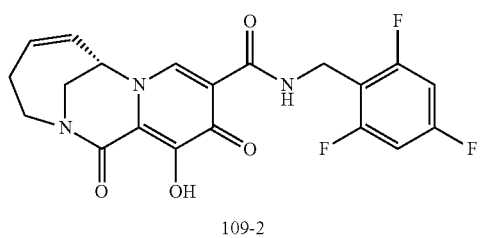

109-2

The title compound was prepared in a manner similar to 109-1, using tert-butyl (S)-3-(2,2,2-trichloroacetamido)-2,3, 6,7-tetrahydro-1H-azepine-1-carboxylate (109a-2) in place of tert-butyl (R)-3-(2,2,2-trichloroacetamido)-2,3,6,7-tetrahydro-1H-azepine-1-carboxylate (109a-1). MS (m/z) 420.14 [M+H]$^+$. $^1$H NMR (400 MHz, DMSO-d$_6$) δ 10.39 (t, J=5.8 Hz, 1H), 8.57 (s, 1H), 7.22 (t, J=8.6 Hz, 2H), 5.85-5.74 (m, 1H), 5.64-5.54 (m, 1H), 5.34 (s, 1H), 4.57 (d, J=5.7 Hz, 2H), 4.20 (td, J=12.1, 6.5 Hz, 1H), 4.08 (dd, J=14.9, 2.5 Hz, 1H), 3.84-3.75 (m, 1H), 3.29 (dd, J=12.9, 8.4 Hz, 1H), 2.90-2.80 (m, 1H), 2.29 (ddd, J=15.7, 9.1, 6.6 Hz, 1H).

Example 107: Preparation of (13S)-10,11-difluoro-4-hydroxy-3,5-dioxo-N-(2,4,6-trifluorobenzyl)-3,5,8, 13-tetrahydro-7H-6,13-methanobenzo[g]pyrido[1,2-a][1,4]diazonine-2-carboxamide and (13R)-10,11-difluoro-4-hydroxy-3,5-dioxo-N-(2,4,6-trifluorobenzyl)-3,5,8,13-tetrahydro-7H-6,13-methanobenzo[g]pyrido[1,2-a][1,4]diazonine-2-carboxamide (110-1 and 110-2)

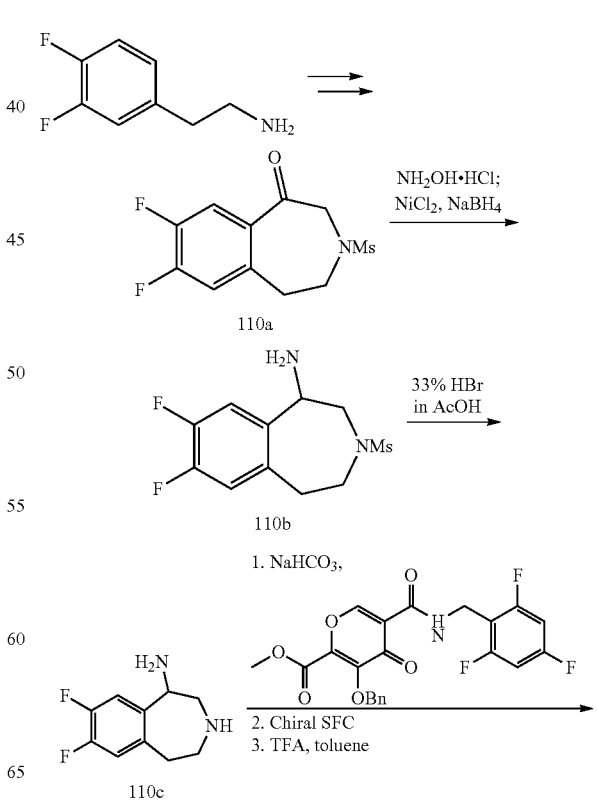

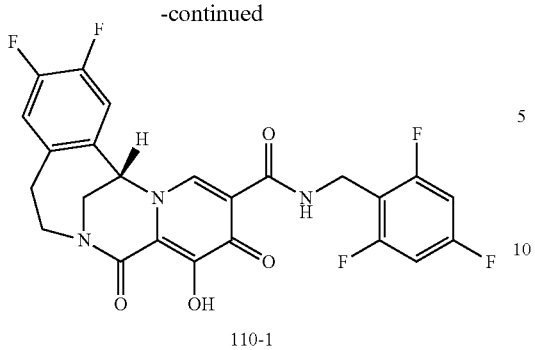

110-1

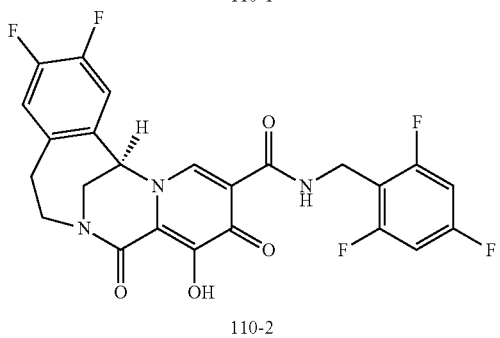

110-2

Synthesis of 7,8-difluoro-3-(methylsulfonyl)-2,3,4,5-tetrahydro-1H-benzo[d]azepin-1-one (110a)

The title compound was synthesized in a manner similar to compound 63d, using 2-(3,4-difluorophenyl)ethan-1-amine in place of 2-phenylethan-1-amine, and methanesulfonyl chloride in place of p-toluenesulfonyl chloride.

Synthesis of 7,8-difluoro-3-(methylsulfonyl)-2,3,4,5-tetrahydro-1H-benzo[d]azepin-1-amine (110b)

To a stirred suspension of 7,8-difluoro-3-(methylsulfonyl)-2,3,4,5-tetrahydro-1H-benzo[d]azepin-1-one (110a, 0.189 g, 0.687 mmol) in MeOH (7 mL) was added NaOAc (0.225 g, 2.75 mmol) and hydroxylamine hydrochloride (0.143 g, 2.06 mmol) at room temperature. The mixture was heated to reflux overnight. The resulting solution was concentrated and saturated NaHCO$_3$ (aq) and EtOAc were added. The phases were separated and the aqueous phase was extracted with EtOAc (2×). The combined organic phase was dried over Na$_2$SO$_4$, filtered, and concentrated.

The crude residue was dissolved in MeOH (6 mL) and nickel (II) chloride (0.174 g, 1.34 mmol) was added. The reaction mixture was cooled to −15° C. and NaBH$_4$ (0.374 g, 9.87 mmol) was added portion-wise over a period of 2 h. The resulting mixture was warmed to room temperature and stirred overnight. The reaction mixture was quenched with water and stirred. The solution was concentrated to remove most of the MeOH and the resulting residue was extracted with DCM (3×). The combined organic phase was washed with brine, dried over anhydrous Na$_2$SO$_4$, filtered, and concentrated to afford the title compound (110b), which was used in the next step without further purification. MS (m/z) 276.97 [M+H]$^+$.

Synthesis of 7,8-difluoro-2,3,4,5-tetrahydro-1H-benzo[d]azepin-1-amine (110c)

A solution of 7,8-difluoro-3-(methylsulfonyl)-2,3,4,5-tetrahydro-1H-benzo[d]azepin-1-amine (110b, 0.157 g, 0.568 mmol) in 33% HBr in AcOH (1.99 mL, 11.4 mmol) was heated to 90° C. overnight in a sealed tube. After cooling to room temperature the cap was removed and the suspension was concentrated. The residue was basified with 1 M NaOH and extracted with DCM (3×). The combined organic phases were dried over Na$_2$SO$_4$, filtered, and concentrated to afford the title compound (110c), which was used without further purification. MS (m/z) 198.96 [M+H]$^+$.

Synthesis of (13S)- and (13R)-10,11-difluoro-4-hydroxy-3,5-dioxo-N-(2,4,6-trifluorobenzyl)-3,5,8,13-tetrahydro-7H-6,13-methanobenzo[g]pyrido[1,2-a][1,4]diazonine-2-carboxamide (110-1 and 110-2)

The title compounds were prepared in a similar manner to compounds 63-1 and 63-2, using 7,8-difluoro-2,3,4,5-tetrahydro-1H-benzo[d]azepin-1-amine (110c) in place of 2,3,4,5-tetrahydro-1H-benzo[d]azepin-1-amine dihydrobromide. Chiral separation was carried out using preparative SFC (IB, 35% MeOH containing 0.1% diethylamine) prior to benzyl deprotection.

110-1, peak 1: MS (m/z) 506.18 [M+H]$^+$. $^1$H NMR (400 MHz, DMSO-d$_6$) δ 10.36 (t, J=5.7 Hz, 1H), 9.03 (s, 1H), 7.40 (dd, J=11.9, 8.3 Hz, 1H), 7.34-7.11 (m, 3H), 5.93 (s, 1H), 4.60 (d, J=5.8 Hz, 2H), 4.43 (dd, J=15.2, 2.8 Hz, 1H), 4.27 (td, J=12.6, 5.6 Hz, 1H), 3.99 (d, J=15.3 Hz, 1H), 3.60-3.56 (m, 1H), 3.40-3.38 (m, 1H), 2.88 (dd, J=15.4, 5.5 Hz, 1H). $^{19}$F NMR (376 MHz, DMSO-d$_6$) δ −109.23 (ddd, J=15.6, 9.4, 6.2 Hz), −112.53 (t, J=7.2 Hz), −138.95 (ddd, J=23.7, 11.8, 8.1 Hz), −140.25 (ddd, J=21.3, 11.9, 8.3 Hz).

110-2, peak 2: MS (m/z) 506.17 [M+H]$^+$. $^1$H NMR (400 MHz, DMSO-d$_6$) δ 10.36 (t, J=5.7 Hz, 1H), 9.03 (s, 1H), 7.40 (dd, J=11.9, 8.3 Hz, 1H), 7.31-7.16 (m, 3H), 5.93 (s, 1H), 4.60 (d, J=5.7 Hz, 2H), 4.43 (dd, J=15.4, 2.7 Hz, 1H), 4.27 (td, J=12.6, 5.5 Hz, 1H), 3.99 (d, J=15.2 Hz, 1H), 3.56-3.50 (m, 1H), 3.40 (dd, J=12.7, 7.2 Hz, 1H), 2.88 (dd, J=15.4, 5.4 Hz, 1H). $^{19}$F NMR (376 MHz, DMSO-d$_6$) δ −109.23 (ddd, J=15.5, 9.3, 6.2 Hz), −112.54 (t, J=7.5 Hz), −138.96 (ddd, J=23.5, 11.8, 8.1 Hz), −140.26 (ddd, J=23.8, 12.1, 8.4 Hz).

Example 108: Preparation of (13S)—N-(2,4-difluorobenzyl)-10,11-difluoro-4-hydroxy-3,5-dioxo-3,5,8,13-tetrahydro-7H-6,13-methanobenzo[g]pyrido[1,2-a][1,4]diazonine-2-carboxamide and (13R)—N-(2,4-difluorobenzyl)-10,11-difluoro-4-hydroxy-3,5-dioxo-3,5,8,13-tetrahydro-7H-6,13-methanobenzo[g]pyrido[1,2-a][1,4]diazonine-2-carboxamide (111-1 and 111-2)

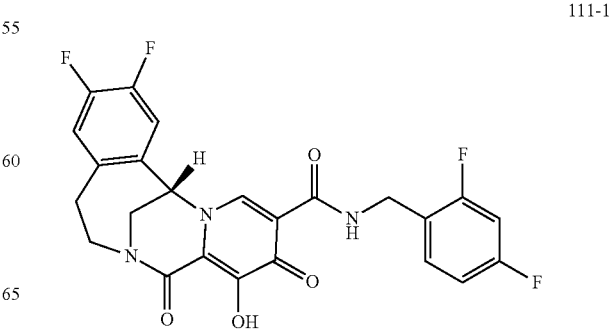

111-1

-continued

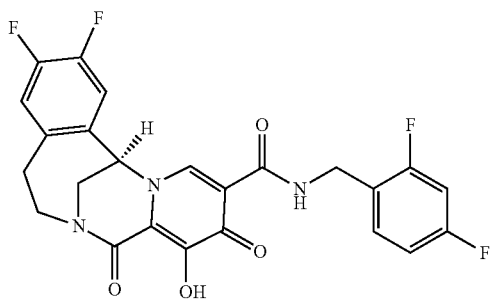

111-2

The title compounds were prepared in a manner similar to compounds 110-1 and 110-2, using methyl 3-(benzyloxy)-5-((2,4-difluorobenzyl)carbamoyl)-4-oxo-4H-pyran-2-carboxylate in place of methyl 3-(benzyloxy)-4-oxo-5-((2,4,6-trifluorobenzyl)carbamoyl)-4H-pyran-2-carboxylate.

111-1, peak 1: MS (m/z) 488.18 [M+H]+. $^1$H NMR (400 MHz, DMSO-d$_6$) δ 10.33 (t, J=5.9 Hz, 1H), 9.05 (s, 1H), 7.55-7.35 (m, 2H), 7.33-7.19 (m, 2H), 7.09 (td, J=8.5, 1.7 Hz, 1H), 5.96 (s, 1H), 4.67-4.51 (m, 2H), 4.44 (dd, J=15.2, 2.7 Hz, 1H), 4.28 (td, J=12.5, 5.5 Hz, 1H), 4.01 (d, J=15.1 Hz, 1H), 3.56 (dt, J=21.1, 10.3 Hz, 1H), 3.41 (dd, J=12.6, 7.2 Hz, 1H), 2.89 (dd, J=15.4, 5.4 Hz, 1H). $^{19}$F NMR (376 MHz, DMSO-d$_6$) δ –112.30 (ddd, J=15.8, 8.9, 6.9 Hz), –114.93 (q, J=8.9 Hz), –138.95 (ddd, J=23.7, 11.8, 8.0 Hz), –140.25 (ddd, J=21.4, 11.9, 8.4 Hz).

111-2, peak 2: MS (m/z) 488.17 [M+H]+. $^1$H NMR (400 MHz, DMSO-d$_6$) δ 10.33 (t, J=5.9 Hz, 1H), 9.05 (s, 1H), 7.53-7.35 (m, 2H), 7.34-7.20 (m, 2H), 7.09 (td, J=8.4, 2.7 Hz, 1H), 5.96 (s, 1H), 4.67-4.50 (m, 2H), 4.44 (dd, J=15.2, 2.7 Hz, 1H), 4.28 (td, J=12.5, 5.5 Hz, 1H), 4.01 (d, J=15.2 Hz, 1H), 3.55-3.49 (m, 1H), 3.41 (dd, J=12.6, 7.2 Hz, 1H), 2.89 (dd, J=15.4, 5.4 Hz, 1H). $^{19}$F NMR (376 MHz, DMSO-d$_6$) δ –112.30 (p, J=7.6 Hz), –114.93 (q, J=8.6 Hz), –138.95 (ddd, J=23.7, 11.9, 8.2 Hz), –140.25 (ddd, J=21.2, 11.7, 8.3 Hz).

Example 109: Synthesis of (7S)-5-fluoro-12-hydroxy-7-methyl-1,11-dioxo-N-(2,4,6-trifluorobenzyl)-1,4,5,6,7,11-hexahydro-3H-2,7-methanopyrido[1,2-a][1,4]diazonine-10-carboxamide (112)

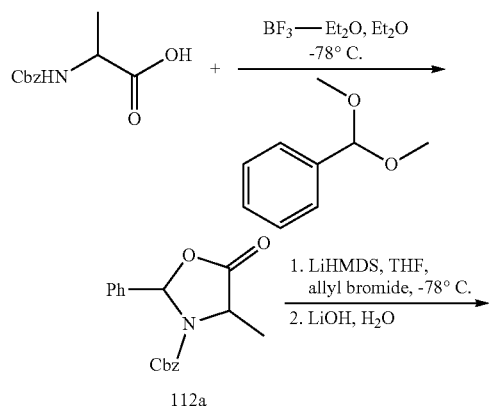

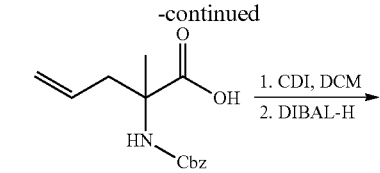

112b

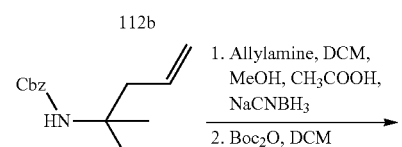

112c

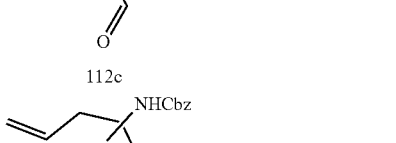

112d

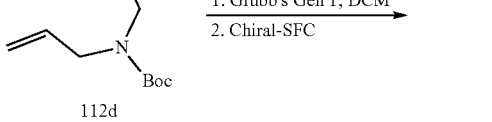

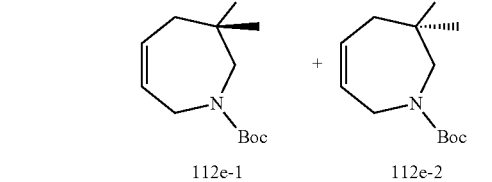

112

Synthesis of benzyl 4-methyl-5-oxo-2-phenyloxazolidine-3-carboxylate (112a)

((Benzyloxy)carbonyl)alanine (380 g, 1.69 mol, 1.0 eq) and (dimethoxymethyl)benzene (386.2 g, 2.54 mol, 1.5 eq) was dissolved in Et$_2$O (3.8 L) and cooled to –78° C. under Ar (g), and a solution of BF$_3$-Et$_2$O (2161 g, 15.22 mol, 9.0 eq) was added dropwise. After the addition completed, the mixture was allowed to stir at room temperature for 12 h. Then the reaction mixture was cooled to 0° C. and aq. NaHCO$_3$ solution (7.6 L) was added dropwise. The reaction mixture was extracted with EtOAc (2×2 L). The combined organic layers were washed with brine, dried over Na$_2$SO$_4$, concentrated to give crude product, which was purified by silica gel column (eluted with Petroleum Ether:Ethyl Acetate=10:1) to give the title compound (112a). MS (m/z): 334.20 [M+Na]$^+$.

Synthesis of 2-(((benzyloxy)carbonyl)amino)-2-methylpent-4-enoic acid (112b)

Benzyl 4-methyl-5-oxo-2-phenyloxazolidine-3-carboxylate (112a, 491 g, 1.58 mol, 1.0 eq) and allyl bromide (248.0 g, 2.05 mol, 1.3 eq) were dissolved in THF/MPA (4:1, 4.9 L), cooled to −78° C. under Ar (g), and a solution of LiHMDS (1 M, 3154 mL, 2.0 eq) was added dropwise. After addition, the mixture was allowed to stir at −78° C. for 2 h. H$_2$O (1.2 L) and LiOH H$_2$O (132.5 g, 3.16 mol, 2.0 eq) were added, and the mixture was allowed to stir at room temperature for 12 h. Then aq. NaHCO$_3$ solution (2.5 L) was added dropwise. The resulting mixture was extracted with MTBE (3×500 mL). The organic extracts were discarded, and the aqueous layer was adjusted to pH=2 with 2 N HCl, extracted with MTBE (1 L×2). The combined organic layers were washed with brine, dried over Na$_2$SO$_4$, and concentrated to give crude product, which was purified by silica gel column (eluted with Petroleum Ether:Ethyl Acetate=5:1) to give the title compound (112b). MS (m/z): 264.10 [M+H]$^+$.

Synthesis of benzyl (2-methyl-1-oxopent-4-en-2-yl)carbamate (112c)

2-(((Benzyloxy)carbonyl)amino)-2-methylpent-4-enoic acid (112b, 213 g, 809.0 mmol, 1.0 eq) was dissolved in DCM (2.1 L) and cooled to 0° C. under Ar (g), and CDI (144.3 g, 889.8 mmol, 1.1 eq) was added in portions. The mixture was allowed to stir at 0° C. for 1.5 h then was cooled to −30° C., and DIBAL-H (3.4 L, 3.4 mol, 4.2 eq) was added dropwise. After addition, the mixture was allowed to stir at −30° C. for 2 h before being carefully quenched with H$_2$O (64 mL), 15% aq. NaOH (64 mL) and H$_2$O (108 mL) dropwise at −30° C. The cooling bath was removed and mixture was stirred for 10 min. Na$_2$SO$_4$ (1300 g) was added and stirred for 10 mins, filtered, and the filtrate was concentrated in vacuo. The crude product was purified by silica gel column (eluted with Petroleum Ether:Ethyl Acetate=30:1 to 5:1) to give the title compound (112c). MS (m/z): 248.10 [M+H]$^+$.

Synthesis of tert-butyl allyl(2-(((benzyloxy)carbonyl)amino)-2-methylpent-4-en-1-yl)carbamate (112d)

To a solution of benzyl (2-methyl-1-oxopent-4-en-2-yl)carbamate (112c, 34.7 g, 140 mmol, 1.0 eq) in DCM (700 mL) was added allylamine (136 g, 2.37 mol, 17 eq) and MgSO$_4$ (67.5 g, 561 mmol, 4.0 eq) under Ar (g). Then the reaction mixture was stirred at 40° C. overnight. The reaction mixture was cooled to room temperature, filtered and the filtrate was concentrated in vacuo. The resulting residue was dissolved in MeOH (1.4 L) and AcOH (31.4 g, 168.3 mmol, 1.2 eq) and NaBH$_3$CN (12.37 g, 196.3 mmol, 1.4 eq) were added. The mixture was allowed to stir at room temperature for 3 h, then aq. NaHCO$_3$ solution (1.4 L) was added and extracted with EtOAc (3×600 mL). The combined organic layers were washed with brine, dried over Na$_2$SO$_4$, and concentrated in vacuo to give benzyl (1-(allylamino)-2-methylpent-4-en-2-yl)carbamate, which was used directly to the next step without further purification. MS (m/z): 289.20 [M+H]$^+$.

The residue (43 g, 149.3 mmol, 1.0 eq) was dissolved in DCM (900 mL) and Boc$_2$O (85.3 g, 224 mmol, 1.5 eq) was added at 0° C., followed by Et$_3$N (22.6 g, 224 mmol, 1.5 eq) and DMAP (1.82 g, 14.9 mmol, 0.1 eq). After the addition, the mixture was allowed to stir at room temperature for 3 h. The reaction mixture was washed with brine (700 mL×2). The organic layer was dried over Na$_2$SO$_4$, concentrated, and purified by silica gel column (eluted with Heptane:Ethyl Acetate=50:1) to give the title compound (112d). MS (m/z): 411.20 [M+Na]$^+$.

Synthesis of tert-butyl (S)- and (R)-3-(((benzyloxy)carbonyl)amino)-3-methyl-2,3,4,7-tetrahydro-1H-azepine-1-carboxylate (112e-1 and 112e-2)

To a solution of tert-butyl allyl(2-(((benzyloxy)carbonyl)amino)-2-methylpent-4-en-1-yl)carbamate (112d, 28 g, 72.2 mmol, 1.0 eq) in DCM (850 mL) was added bis(tricyclohexylphosphine) benzylidine ruthenium (IV) dichloride (5.33 g, 6.5 mmol, 0.09 eq). The reaction mixture was heated to 40° C., and stirred for 3 h. The reaction was concentrated, diluted with DCM and purified by silica gel column chromatography (eluted with heptane:ethyl acetate=5:1) to give the title compound as a mixture of enantiomers. MS (m/z): 361.20 [M+H]$^+$.

The two enantiomers were separated by chiral SFC using an IG-3 column and eluting with 0.1% DEA in IPA/CO$_2$=20:80 to give the title compounds (112e-1 (first eluting compound) and 112e-2 (second eluting compound)). MS (m/z): 361.20 [M+H]$^+$. ee: 96.66%.

Synthesis of tert-butyl (3S)-3-(((benzyloxy)carbonyl)amino)-5-fluoro-3-methylazepane-1-carboxylate (112f)

The title compound was synthesized in a similar manner to compounds 53d-1 and 53d-2, using tert-butyl (S)-3-(((benzyloxy)carbonyl)amino)-3-methyl-2,3,4,7-tetrahydro-1H-azepine-1-carboxylate (112e-1) (single enantiomer, stereochemistry arbitrarily assigned) in place of benzyl (S)-3-(((benzyloxy)carbonyl)amino)-2,3,4,7-tetrahydro-1H-azepine-1-carboxylate. MS (m/z): 380.7 [M+H]$^+$ (42e-1).

Synthesis of (7S)-5-fluoro-12-hydroxy-7-methyl-1,11-dioxo-N-(2,4,6-trifluorobenzyl)-1,4,5,6,7,11-hexahydro-3H-2,7-methanopyrido[1,2-a][1,4]diazonine-10-carboxamide (112)

The title product was prepared in a similar manner to compound 27, using tert-butyl (3S)-3-(((benzyloxy)carbonyl)amino)-5-fluoro-3-methylazepane-1-carboxylate (112f) in place of tert-butyl (2-oxo-2,3,4,5-tetrahydro-1H-benzo[b]azepin-3-yl)carbamate and methyl 3-(benzyloxy)-4-oxo-5-((2,4,6-trifluorobenzyl)carbamoyl)-4H-pyran-2-carboxylate in place of methyl 3-(benzyloxy)-5-((2,4-difluorobenzyl)carbamoyl)-4-oxo-4H-pyran-2-carboxylate. MS (m/z): 454.30 [M+H]$^+$. $^1$H NMR (400 MHz, Acetonitrile-d$_3$) δ 10.38 (s, 1H), 8.52 (s, 1H), 6.86 (dd, J=9.1, 8.0 Hz, 2H), 4.97-4.74 (m, 1H), 4.62 (d, J=5.7 Hz, 2H), 4.39 (dt, J=13.6, 6.8 Hz, 1H), 3.84-3.61 (m, 2H), 3.26-3.15 (m, 1H), 2.48-2.06 (m, 4H), 1.74 (s, 3H).

Example 110: Preparation of (3S,7S)-5,5-difluoro-12-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (113)

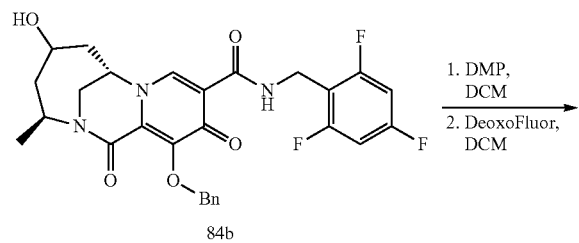
84b

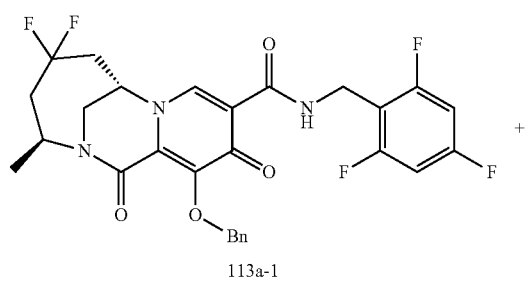
113a-1

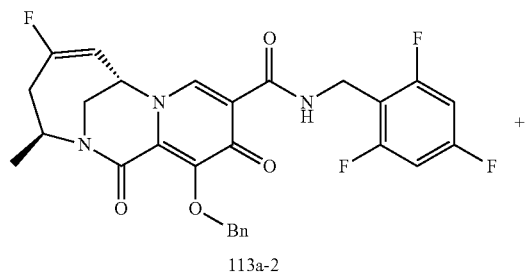
113a-2

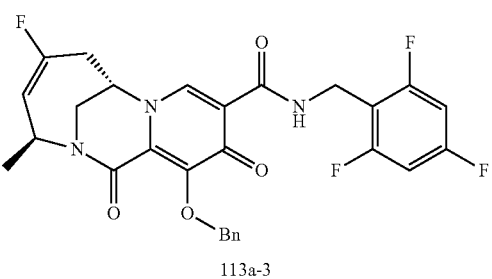
113a-3

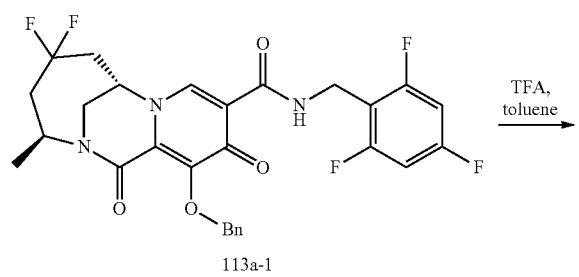
113a-1

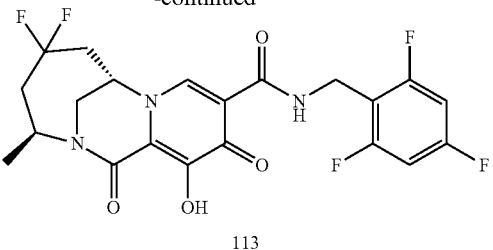
113

Synthesis of (3S,7S)-12-(benzyloxy)-5,5-difluoro-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide, (3S,7S)-12-(benzyloxy)-5-fluoro-3-methyl-1,11-dioxo-N-(2,4,6-trifluorobenzyl)-1,4,7,11-tetrahydro-3H-2,7-methanopyrido[1,2-a][1,4]diazonine-10-carboxamide and (3S,7S)-12-(benzyloxy)-5-fluoro-3-methyl-1,11-dioxo-N-(2,4,6-trifluorobenzyl)-1,6,7,11-tetrahydro-3H-2,7-methanopyrido[1,2-a][1,4]diazonine-10-carboxamide (113a-1, 113a-2, and 113a-3)

DMP (86.4 mg, 0.204 mmol) was added to a solution of (3S,7S)-12-(benzyloxy)-5-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (84b, 92 mg, 0.170 mmol) in DCM (2 mL) at rt, and the reaction mixture was stirred for 17 hours. The mixture was concentrated to dryness, diluted with EtOAc (10 mL), and washed with sat. NaHCO$_3$ (10 mL) and Na$_2$S$_2$O$_3$ (1N, 10 mL). This two wash process was repeated thrice, and the organic phase was then washed with water, dried over Na$_2$SO$_4$, filtered, and concentrated to give (3S,7S)-12-(benzyloxy)-3-methyl-1,5,11-trioxo-N-(2,4,6-trifluorobenzyl)-1,4,5,6,7,11-hexahydro-3H-2,7-methanopyrido[1,2-a][1,4]diazonine-10-carboxamide, which was carried forward without further purification. MS (m/z): 540.12 [M+H]$^+$.

The product (90 mg, 0.167 mmol) was dissolved in DCM (2 mL) at rt. DeoxoFluor (442 mg, 2 mmol) was added dropwise, and the reaction mixture was stirred for 17 hours. The reaction mixture was diluted with EtOAc (10 mL), and treated with sat. NaHCO$_3$ (10 mL). The resulting mixture was stirred at room temperature for 30 min. The organic phase was separated, concentrated, and the residue purified by silica gel eluted with 0-100% EtOAc/heptane to afford the title products (113a-1, 113a-2, and 113a-3), olefin regiochemistry assigned arbitrarily. 113a-1: MS (m/z): 562.20 [M+H]$^+$; 113a-2: MS (m/z): 542.14 [M+H]$^+$; 113a-3: MS (m/z): 542.14 [M+H]$^+$.

Synthesis of (3 S,7S)-5,5-difluoro-12-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (113)

The title compound was prepared in a similar manner to compound 28, using (3S,7S)-12-(benzyloxy)-5,5-difluoro-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (113a-1) in place of (7S)-12-(benzyloxy)-N-(2,4-difluorobenzyl)-1,11-dioxo-1,3,4,6,7,11-hexahydro-2,7-methanopyrido[1,2-d][1,4,7]oxadiazonine-10-carboxamide (28a). MS (m/z): 472.20 [M+H]$^+$. $^1$H NMR (400 MHz, DMSO-d$_6$) δ 10.95-10.58 (br, 1H), (10.36 (t, J=5.8 Hz, 1H), 8.56 (s, 1H), 7.21 (t, J=8.7 Hz, 2H), 4.88 (d, J=5.0 Hz, 1H), 4.54 (dt, J=24.1, 8.0 Hz, 3H), 3.99 (dd, J=15.0, 1.6 Hz, 1H), 3.81 (dd, J=15.0, 2.8 Hz, 1H), 2.72-2.35 (m, 4H), 1.20 (d, J=6.7 Hz, 3H).

Example 111: Preparation of (7S)-5,5-difluoro-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (114)

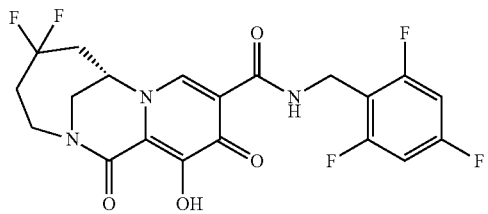 [SMILES: O=C(NCc1c(F)cc(F)cc1F)c1cn2c(c(O)c1=O)C(=O)N1CCC(F)(F)C[C@H]2C1]

The title compound was prepared in a similar manner to 113, using (7S)-12-(benzyloxy)-1,5,11-trioxo-N-(2,4,6-trifluorobenzyl)-1,4,5,6,7,11-hexahydro-3H-2,7-methanopyrido[1,2-a][1,4]diazonine-10-carboxamide (103a) in place of (3S,7S)-12-(benzyloxy)-3-methyl-1,5,11-trioxo-N-(2,4,6-trifluorobenzyl)-1,4,5,6,7,11-hexahydro-3H-2,7-methanopyrido[1,2-a][1,4]diazonine-10-carboxamide (113a-1). MS (m/z): 458.22 [M+H]$^+$. $^1$H NMR (400 MHz, Acetonitrile-d$_3$) δ 10.32 (s, 1H), 8.43 (s, 1H), 6.86 (t, J=8.5 Hz, 2H), 4.78-4.49 (m, 3H), 4.31 (dt, J=14.7, 7.9 Hz, 1H), 3.98 (d, J=14.8 Hz, 1H), 3.78 (d, J=14.8 Hz, 1H), 3.23 (dd, J=13.6, 6.5 Hz, 1H), 2.70-2.00 (m, 4H).

Example 112a: Preparation of (5S,7S)-5-fluoro-12-hydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide (115-1)

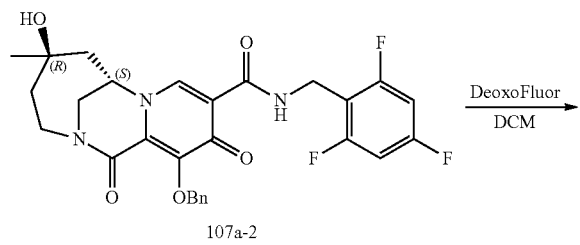

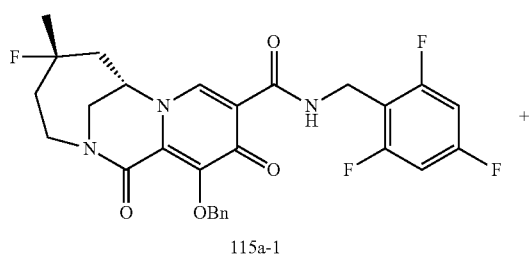

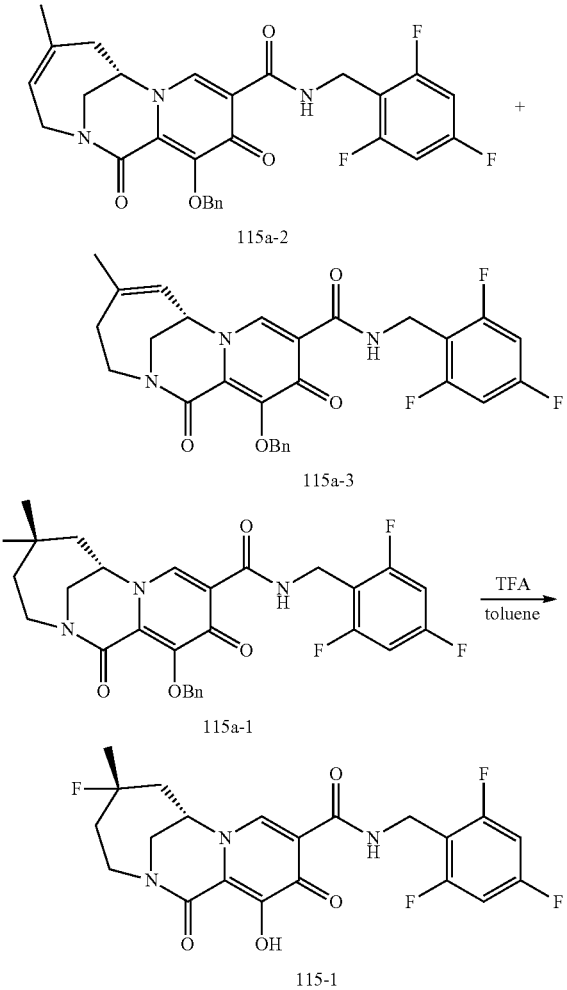

Synthesis of (5S,7S)-12-(benzyloxy)-5-fluoro-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide, (7S)-12-(benzyloxy)-5-methyl-1,11-dioxo-N-(2,4,6-trifluorobenzyl)-1,6,7,11-tetrahydro-3H-2,7-methanopyrido[1,2-a][1,4]diazonine-10-carboxamide and (7S)-12-(benzyloxy)-5-methyl-1,11-dioxo-N-(2,4,6-trifluorobenzyl)-1,4,7,11-tetrahydro-3H-2,7-methanopyrido[1,2-a][1,4]diazonine-10-carboxamide (115a-1, 115a-2, and 115a-3)

Deoxo-Fluor (0.022 mL, 2 eq.) was added to a solution of (5R,7S)-12-(benzyloxy)-5-hydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide (107a-2, 32 mg, 0.006 mmol) in DCM (1 mL) at 0° C., and stirred for 90 min. The reaction was quenched with water, diluted with EtOAc, and washed with sat. NaHCO$_3$ solution. The organic layer was concentrated, and purified via preparative HPLC, eluting with 10-60% acetonitrile in water (0.1% TFA) to give the title compounds (115a-1, 115a-2, and 115a-3). 115a-1: MS (m/z) 544.18 [M+H]$^+$; 115a-2: MS (m/z) 524.15 [M+H]$^+$; 115a-3: MS (m/z) 524.15 [M+H]$^+$.

Synthesis of (5S,7S)-5-fluoro-12-hydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide (115-1)

TFA (0.5 mL) was added to a solution of (5S,7S)-12-(benzyloxy)-5-fluoro-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide (115a-1, 3 mg) in toluene (0.5 mL) at rt, and stirred for one hour. The reaction mixture was concentrated down, and purified by preparative HPLC, eluting with 10-60% acetonitrile (0.1% TFA) in water (0.1% TFA) to afford the title compound (115-1). MS (m/z) 454.22 [M+H]$^+$. $^1$H NMR (400 MHz, Acetonitrile-d$_3$) δ 10.31 (s, 1H), 8.39 (s, 1H), 6.96-6.80 (m, 2H), 4.62 (d, J=5.5 Hz, 2H), 4.36-4.22 (m, 1H), 3.91 (m, 2H), 3.17 (ddd, J=13.9, 11.5, 4.4 Hz, 1H), 2.97-2.78 (m, 1H), 2.23-2.00 (m, 1H), 2.00-1.90 (m, 2H), 1.83 (ddd, J=37.1, 16.5, 4.0 Hz, 1H), 1.40 (d, J=22.5 Hz, 3H).

Example 112b: Preparation of (5R,7S)-5-fluoro-12-hydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide (115-2)

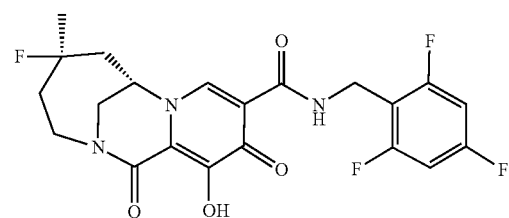 [SMILES: C[C@@]1(F)CCN2C[C@H](C1)n1cc(C(=O)NCc3c(F)cc(F)cc3F)c(=O)c(O)c1C2=O]

The title compound was prepared in a manner similar to compound 115-1, using (5S,7S)-12-(benzyloxy)-5-hydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide (107a-1) instead of (5R,7S)-12-(benzyloxy)-5-hydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide (107a-2). MS (m/z) 454.22 [M+H]$^+$ $^1$H NMR (400 MHz, Acetonitrile-d$_3$) δ 8.38 (d, J=5.0 Hz, 1H), 6.87 (t, J=8.5 Hz, 1H), 6.68 (t, J=8.5 Hz, 1H), 4.93-4.73 (m, 1H), 4.62 (d, J=5.7 Hz, 1H), 4.53-4.12 (m, 2H), 3.90 (m, 1H), 3.21-3.06 (m, 1H), 2.91 (m, 1H), 2.11 (m, 4H), 1.41 (dd, J=22.4, 6.7 Hz, 3H).

Example 113: Preparation of (7S)-12-hydroxy-5-methyl-1,11-dioxo-N-(2,4,6-trifluorobenzyl)-1,6,7,11-tetrahydro-3H-2,7-methanopyrido[1,2-a][1,4]diazonine-10-carboxamide and (7S)-12-hydroxy-5-methyl-1,11-dioxo-N-(2,4,6-trifluorobenzyl)-1,4,7,11-tetrahydro-3H-2,7-methanopyrido[1,2-a][1,4]diazonine-10-carboxamide (116-1 and 116-2)

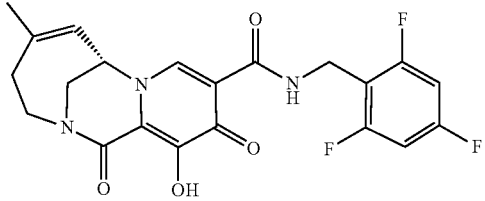

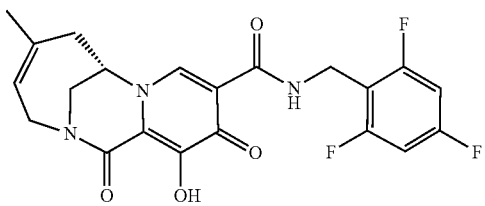

The title compounds were prepared in a manner similar to 115-1, using (7S)-12-(benzyloxy)-5-methyl-1,11-dioxo-N-(2,4,6-trifluorobenzyl)-1,6,7,11-tetrahydro-3H-2,7-methanopyrido[1,2-a][1,4]diazonine-10-carboxamide or (7S)-12-(benzyloxy)-5-methyl-1,11-dioxo-N-(2,4,6-trifluorobenzyl)-1,4,7,11-tetrahydro-3H-2,7-methanopyrido[1,2-a][1,4]diazonine-10-carboxamide (115a-2 or 115a-3) in place of (5S,7S)-12-(benzyloxy)-5-fluoro-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide (115a-1).

116-1: MS (m/z) 434.21 [M+H]$^+$. $^1$H NMR (400 MHz, Acetonitrile-d$_3$) δ 8.38 (s, 1H), 6.97-6.82 (m, 2H), 5.39 (s, 1H), 4.97-4.66 (m, 2H), 4.62 (d, J=5.6 Hz, 1H), 3.89-3.53 (m, 3H), 2.79 (dd, J=17.3, 8.8 Hz, 3H), 1.77 (s, 3H).

116-2: MS (m/z) 434.21 [M+H]$^+$. $^1$H NMR (400 MHz, Acetonitrile-d$_3$) δ 10.35 (s, 1H), 8.42 (s, 1H), 7.03-6.76 (m, 2H), 5.38 (s, 1H), 5.00 (s, 1H), 4.62 (d, J=5.5 Hz, 2H), 4.30 (td, J=12.7, 6.2 Hz, 1H), 4.05 (dd, J=15.1, 2.3 Hz, 1H), 3.76 (d, J=14.8 Hz, 1H), 3.37 (dd, J=13.1, 8.1 Hz, 1H), 3.00 (q, J=12.3, 11.1 Hz, 1H), 2.16 (dd, J=15.8, 6.0 Hz, 1H), 1.81 (s, 3H).

Example 114: Preparation of (7R)—N-(3-chloro-2,4-difluorobenzyl)-6,6-difluoro-12-hydroxy-1,11-dioxo-1,4,5,6,7,11-hexahydro-3H-2,7-methanopyrido[1,2-a][1,4]diazonine-10-carboxamide and (7S)—N-(3-chloro-2,4-difluorobenzyl)-6,6-difluoro-12-hydroxy-1,11-dioxo-1,4,5,6,7,11-hexahydro-3H-2,7-methanopyrido[1,2-a][1,4]diazonine-10-carboxamide (117-1 and 117-2)
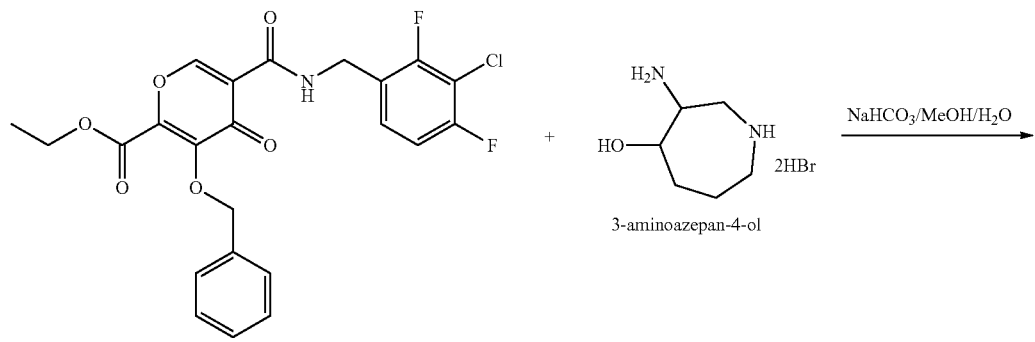
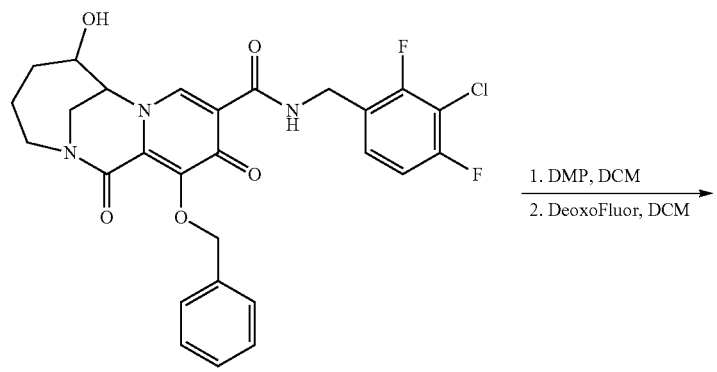
117a
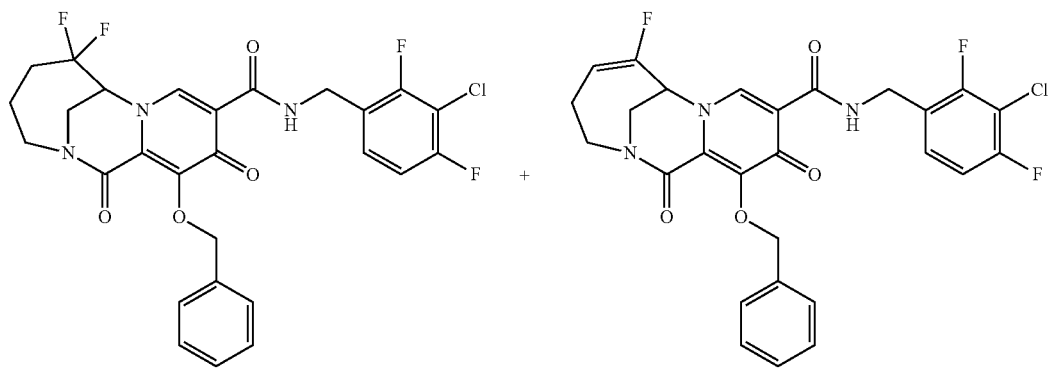
117b-1      117b-2
1. chiral separation
2. TFA/Toluene

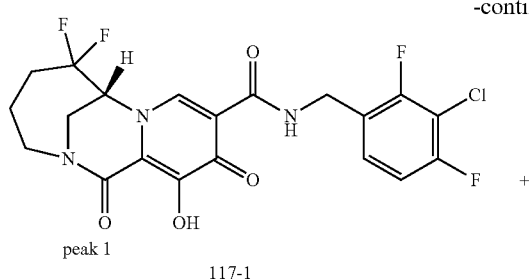

peak 1
117-1

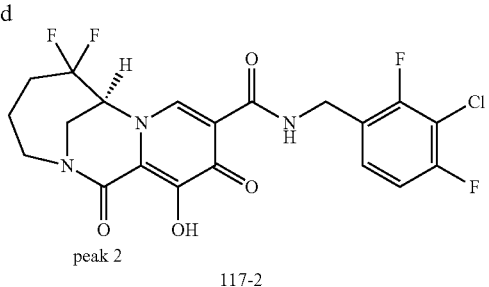

peak 2
117-2

Synthesis of 12-(benzyloxy)-N-(3-chloro-2,4-difluorobenzyl)-6-hydroxy-1,11-dioxo-1,4,5,6,7,11-hexahydro-3H-2,7-methanopyrido[1,2-a][1,4]diazonine-10-carboxamide (117a)

The title compound was prepared in a manner similar to compound 28a using 3-aminoazepan-4-ol; dihydrobromide in place of 1,4-oxazepan-6-amine and ethyl 3-benzyloxy-5-[(3-chloro-2,4-difluoro-phenyl)methylcarbamoyl]-4-oxo-pyran-2-carboxylate in place of methyl 3-(benzyloxy)-5-((2,4-difluorobenzyl)carbamoyl)-4-oxo-4H-pyran-2-carboxylate. MS (m/z): 544.28 [M+H]$^+$.

Synthesis of 12-(benzyloxy)-N-(3-chloro-2,4-difluorobenzyl)-6,6-difluoro-1,11-dioxo-1,4,5,6,7,11-hexahydro-3H-2,7-methanopyrido[1,2-a][1,4]diazonine-10-carboxamide and 12-(benzyloxy)-N-(3-chloro-2,4-difluorobenzyl)-6-fluoro-1,11-dioxo-1,4,7,11-tetrahydro-3H-2,7-methanopyrido[1,2-a][1,4]diazonine-10-carboxamide (117b-1 and 117b-2)

The title compounds were prepared in a manner similar to compounds 113a-1, 113a-2, and 113a-3 using 12-(benzyloxy)-N-(3-chloro-2,4-difluorobenzyl)-6-hydroxy-1,11-dioxo-1,4,5,6,7,11-hexahydro-3H-2,7-methanopyrido[1,2-a][1,4]diazonine-10-carboxamide (117a) in place of (5R,7S)-12-(benzyloxy)-5-hydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide (107a-2). 117b-1: MS (m/z) 564.29 [M+H]$^+$; 117b-2: MS (m/z) 544.31 [M+H]$^+$.

Synthesis of (7R)—N-(3-chloro-2,4-difluorobenzyl)-6,6-difluoro-12-hydroxy-1,11-dioxo-1,4,5,6,7,11-hexahydro-3H-2,7-methanopyrido[1,2-a][1,4]diazonine-10-carboxamide and (7S)—N-(3-chloro-2,4-difluorobenzyl)-6,6-difluoro-12-hydroxy-1,11-dioxo-1,4,5,6,7,11-hexahydro-3H-2,7-methanopyrido[1,2-a][1,4]diazonine-10-carboxamide (117-1 and 117-2)

12-(benzyloxy)-N-(3-chloro-2,4-difluorobenzyl)-6,6-difluoro-1,11-dioxo-1,4,5,6,7,11-hexahydro-3H-2,7-methanopyrido[1,2-a][1,4]diazonine-10-carboxamide (71c, 145 mg) was separated into its individual enantiomers by preparative SFC chromatography on an IB column using MeOH cosolvent. The separated enantiomers were dissolved in 3 mL of Toluene and 3 mL of TFA and stirred at room temperature for 1 h. After concentration, purification by RP-HPLC eluting with ACN/water (0.1% TFA) provided the title compounds (117-1 and 117-2), stereochemistry drawn arbitrarily.

117-1 (peak 1): MS (m/z) 474.18 [M+H]$^+$. $^1$H NMR (400 MHz, DMSO-d$_6$) δ 10.67 (s, 1H), 10.28 (t, J=6.0 Hz, 1H), 8.50 (s, 1H), 7.40 (q, J=7.8 Hz, 1H), 7.30 (t, J=8.9 Hz, 1H), 5.24 (t, J=7.2 Hz, 1H), 4.61 (d, J=5.9 Hz, 2H), 4.27-4.15 (m, 1H), 4.03 (dd, J=16.4, 4.1 Hz, 1H), 3.88 (d, J=15.5 Hz, 1H), 3.19 (dd, J=13.7, 6.7 Hz, 1H), 2.22 (s, 1H), 1.95 (dd, J=18.6, 12.1 Hz, 2H), 1.69-1.54 (m, 1H).

117-2 (peak 2): MS (m/z) 474.16 [M+H]$^+$. $^1$H NMR (400 MHz, DMSO-d$_6$) δ 10.28 (t, J=6.0 Hz, 1H), 8.50 (s, 1H), 7.40 (td, J=8.5, 6.3 Hz, 1H), 7.30 (td, J=8.8, 1.7 Hz, 1H), 5.25 (d, J=7.6 Hz, 1H), 4.61 (d, J=6.0 Hz, 2H), 4.27-4.15 (m, 1H), 4.04 (dd, J=15.6, 4.1 Hz, 1H), 3.88 (dd, J=15.5, 2.0 Hz, 1H), 3.19 (dd, J=13.5, 6.5 Hz, 1H), 2.23 (d, J=12.2 Hz, 1H), 1.96 (d, J=20.5 Hz, 2H), 1.61 (dt, J=28.6, 14.3 Hz, 1H).

Example 115: Preparation of (3S,7S)-5-fluoro-12-hydroxy-3-methyl-1,11-dioxo-N-(2,4,6-trifluorobenzyl)-1,4,7,11-tetrahydro-3H-2,7-methanopyrido[1,2-a][1,4]diazonine-10-carboxamide and (3S,7S)-5-fluoro-12-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (118-1 and 118-2)

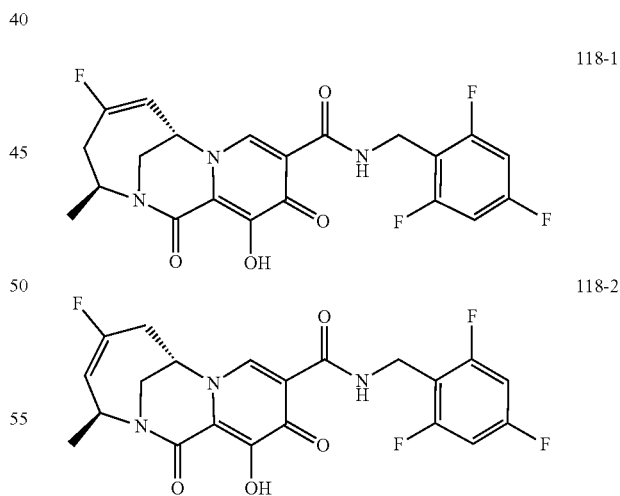

118-1

118-2

The title compounds were prepared in a similar manner to compound 113, using (3S,7S)-12-(benzyloxy)-5-fluoro-3-methyl-1,11-dioxo-N-(2,4,6-trifluorobenzyl)-1,4,7,11-tetrahydro-3H-2,7-methanopyrido[1,2-a][1,4]diazonine-10-carboxamide or (3S,7S)-12-(benzyloxy)-5-fluoro-3-methyl-1,11-dioxo-N-(2,4,6-trifluorobenzyl)-1,6,7,11-tetrahydro-3H-2,7-methanopyrido[1,2-a][1,4]diazonine-10-carboxamide (113a-2 or 113a-3) in place of (3S,7S)-12-(benzyloxy)-5,5- difluoro-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (113a-1).

118-1: MS (m/z): 452.20 [M+H]+. 1H NMR (400 MHz, Acetonitrile-d3) δ 10.31 (s, 1H), 8.41 (s, 1H), 6.86 (t, J=8.5 Hz, 2H), 5.33 (dt, J=24.1, 2.5 Hz, 1H), 5.33-5.24 (m, 1H), 4.86 (d, J=9.6 Hz, 1H), 4.61 (d, J=5.2 Hz, 2H), 3.90 (d, J=14.3 Hz, 1H), 3.70 (d, J=14.4 Hz, 1H), 3.12 (td, J=18.8, 9.1 Hz, 1H), 2.79 (d, J=18.7 Hz, 1H), 1.33 (d, J=6.9 Hz, 3H).

118-2: MS (m/z): 452.20 [M+H]+. 1H NMR (400 MHz, Acetonitrile-d3) δ 10.30 (s, 1H), 8.43 (s, 1H), 6.86 (t, J=8.5 Hz, 2H), 5.41 (d, J=21.1 Hz, 1H), 5.06 (s, 1H), 4.80 (dt, J=12.2, 6.5 Hz, 1H), 4.61 (d, J=5.5 Hz, 2H), 3.92 (d, J=15.1 Hz, 1H), 3.74 (d, J=15.1 Hz, 1H), 2.93 (d, J=12.0 Hz, 1H), 2.66-2.55 (m, 1H), 1.28 (dd, J=6.6, 1.0 Hz, 3H).

Example 116: Preparation of (7S)-7-ethyl-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide and (7R)-7-ethyl-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (119-1 and 119-2)

119-1

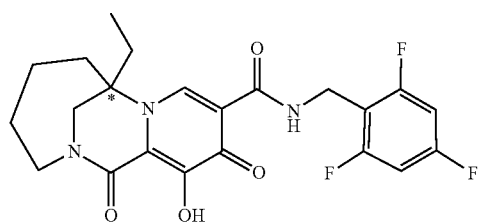

119-2

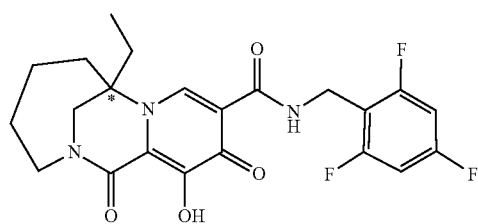

The title compounds were prepared similarly to compounds 59-1 and 59-2, using EtMgBr in place of MeMgBr.

119-1: MS (m/z) 432.1 [M+H]+. 1H NMR (400 MHz, Methanol-d4) δ 8.50 (s, 1H), 6.93 (m, 2H), 4.69 (s, 2H), 4.39 (m, 1H), 4.12 (m, 1H), 3.91 (m, 1H), 3.17 (m, 1H), 2.31 (m, 1H), 2.12 (m, 2H), 1.87 (m, 3H), 1.55 (m, 1H), 0.98 (m, 3H).

119-2: MS (m/z) 432.1 [M+H]+. 1H NMR (400 MHz, Methanol-d4) δ 8.50 (s, 1H), 6.91 (m, 2H), 4.69 (s, 2H), 4.39 (m, 1H), 3.91 (m, 1H), 3.72 (m, 2H), 3.17 (m, 1H), 2.31 (m, 1H), 2.12 (m, 2H), 1.91 (m, 2H), 1.78 (m, 1H), 1.55 (m, 1H), 0.98 (m, 3H).

Example 117: Preparation of (13S)-10,11-difluoro-4-hydroxy-13-methyl-3,5-dioxo-N-(2,4,6-trifluorobenzyl)-3,5,8,13-tetrahydro-7H-6,13-methanobenzo[g]pyrido[1,2-a][1,4]diazonine-2-carboxamide and (13R)-10,11-difluoro-4-hydroxy-13-methyl-3,5-dioxo-N-(2,4,6-trifluorobenzyl)-3,5,8,13-tetrahydro-7H-6,13-methanobenzo[g]pyrido[1,2-a][1,4]diazonine-2-carboxamide (120-1 and 120-2)

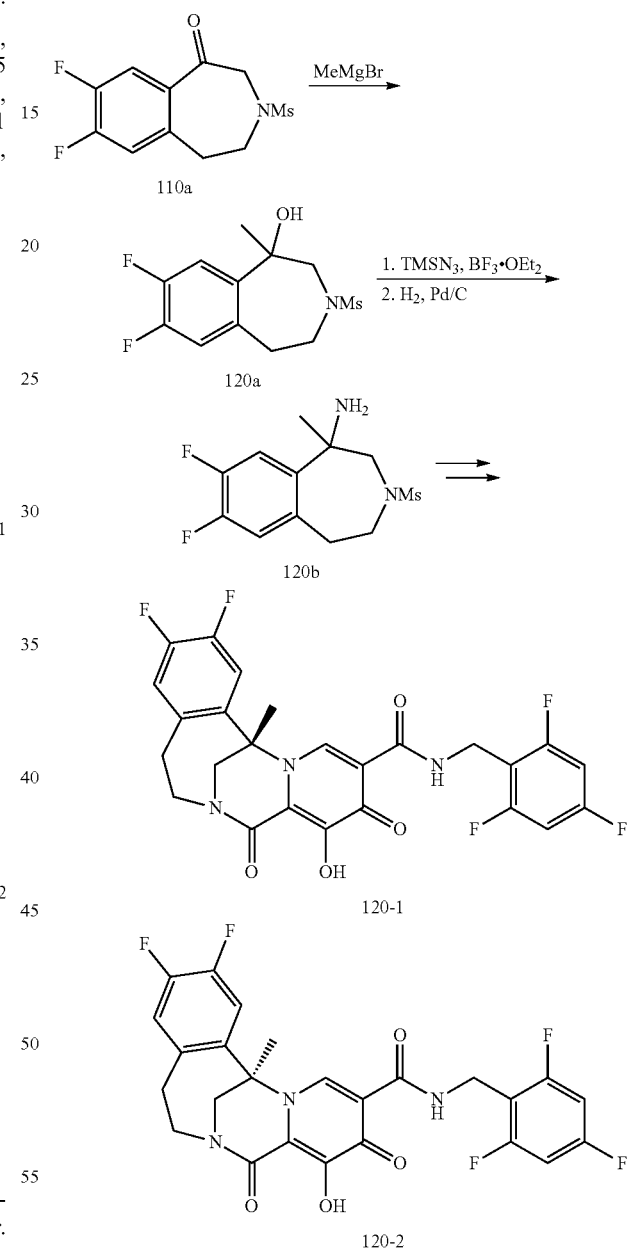

Synthesis of 7,8-difluoro-1-methyl-3-(methylsulfonyl)-2,3,4,5-tetrahydro-1H-benzo[d]azepin-1-ol (120a)

To a solution of 7,8-difluoro-3-(methylsulfonyl)-2,3,4,5-tetrahydro-1H-benzo[d]azepin-1-one (110a, 0.102 g, 0.371 mmol) in Et2O (1 mL) and THF (2 mL) at −78° C. was added a 3 M solution of MeMgBr in THF (0.25 mL, 0.741 mmol). The reaction mixture was stirred for 30 min then warmed to rt. The reaction was quenched with brine and extracted with EtOAc. The organic phase was dried over Na$_2$SO$_4$, filtered, concentrated, and purified by column chromatography (0-100% EtOAc/heptane) to afford the title compound (120a). MS (m/z) 291.96 [M+H]$^+$.

Synthesis of 7,8-difluoro-1-methyl-3-(methylsulfonyl)-2,3,4,5-tetrahydro-1H-benzo[d]azepin-1-amine (120b)

To a solution of 7,8-difluoro-1-methyl-3-(methylsulfonyl)-2,3,4,5-tetrahydro-1H-benzo[d]azepin-1-ol (120a, 0.11 g, 0.38 mmol) and azidotrimethylsilane (0.13 mL, 0.953 mmol) in CHCl$_3$ (5 mL) at 0° C., was added boron trifluoride diethyl etherate (0.24 mL, 1.91 mmol). The reaction mixture was allowed to warm to rt, and stirred overnight. The reaction mixture was concentrated, and purified by column chromatography (0-100% EtOAc/heptane) to afford 1-azido-7,8-difluoro-1-methyl-3-(methylsulfonyl)-2,3,4,5-tetrahydro-1H-benzo[d]azepine. MS (m/z) 315.88 [M+H]$^+$.

To a solution of 1-azido-7,8-difluoro-1-methyl-3-(methylsulfonyl)-2,3,4,5-tetrahydro-1H-benzo[d]azepine (0.084 g, 0.266 mmol) in EtOH (5 mL) was added 10% Pd/C (0.056 g, 0.053 mmol). A hydrogen balloon was introduced and hydrogen gas was bubbled into the reaction mixture for 5 min. The outlet needle was removed and the reaction mixture left to stir under hydrogen atmosphere. After 3 h, the reaction mixture was filtered through Celite and concentrated to afford the title compound (120b), which was carried forward without further purification. MS (m/z) 290.91 [M+H]$^+$.

Synthesis of (13S)- and (13R)-10,11-difluoro-4-hydroxy-13-methyl-3,5-dioxo-N-(2,4,6-trifluorobenzyl)-3,5,8,13-tetrahydro-7H-6,13-methanobenzo[g]pyrido[1,2-a][1,4]diazonine-2-carboxamide (120-1 and 120-2)

The title compounds were prepared in a similar manner to compounds 110-1 and 110-2 using 7,8-difluoro-1-methyl-3-(methylsulfonyl)-2,3,4,5-tetrahydro-1H-benzo[d]azepin-1-amine (120b) in place of 7,8-difluoro-3-(methylsulfonyl)-2,3,4,5-tetrahydro-1H-benzo[d]azepin-1-amine (110b). Chiral separation was carried out using preparative SFC (IB, 35% MeOH), prior to deprotection.

120-1, peak 1: MS (m/z) 520.20 [M+H]$^+$. $^1$H NMR (400 MHz, DMSO-d$_6$) δ 10.39 (t, J=5.8 Hz, 1H), 8.74 (s, 1H), 7.37 (dd, J=11.7, 8.3 Hz, 1H), 7.31 (dd, J=12.2, 8.0 Hz, 1H), 7.26-7.14 (m, 2H), 4.60 (d, J=5.8 Hz, 2H), 4.28 (d, J=15.3 Hz, 1H), 4.21 (td, J=12.6, 5.4 Hz, 1H), 3.92 (d, J=15.4 Hz, 1H), 3.61 (td, J=14.4, 13.2, 7.0 Hz, 1H), 3.40 (dd, J=12.6, 7.0 Hz, 1H), 2.87 (dd, J=15.3, 5.3 Hz, 1H), 1.98 (s, 3H). $^{19}$F NMR (376 MHz, DMSO-d$_6$) δ −109.35 (ddd, J=15.5, 9.4, 6.2 Hz), −112.52 (t, J=7.3 Hz), −139.13 (ddd, J=23.7, 11.7, 8.0 Hz), −139.67 (ddd, J=21.6, 12.1, 8.2 Hz).

120-2, peak 2: MS (m/z) 520.17 [M+H]$^+$. $^1$H NMR (400 MHz, DMSO-d$_6$) δ 10.39 (t, J=5.8 Hz, 1H), 8.74 (s, 1H), 7.37 (dd, J=11.7, 8.3 Hz, 1H), 7.31 (dd, J=12.3, 8.1 Hz, 1H), 7.26-7.17 (m, 2H), 4.60 (d, J=5.7 Hz, 2H), 4.28 (d, J=15.3 Hz, 1H), 4.21 (td, J=12.6, 5.3 Hz, 1H), 3.92 (d, J=15.4 Hz, 1H), 3.61 (td, J=14.0, 7.2 Hz, 1H), 3.40 (dd, J=12.7, 7.0 Hz, 1H), 2.87 (dd, J=15.2, 5.2 Hz, 1H), 1.98 (s, 3H). $^{19}$F NMR (376 MHz, DMSO-d$_6$) δ −109.35 (tt, J=9.4, 6.3 Hz), −112.52 (t, J=7.2 Hz), −139.13 (ddd, J=23.5, 11.6, 7.9 Hz), −139.67 (ddd, J=23.7, 12.1, 8.3 Hz).

Example 118: Preparation of (7S)-5-fluoro-12-hydroxy-1,11-dioxo-N-(2,4,6-trifluorobenzyl)-1,4,7,11-tetrahydro-3H-2,7-methanopyrido[1,2-a][1,4]diazonine-10-carboxamide (121)

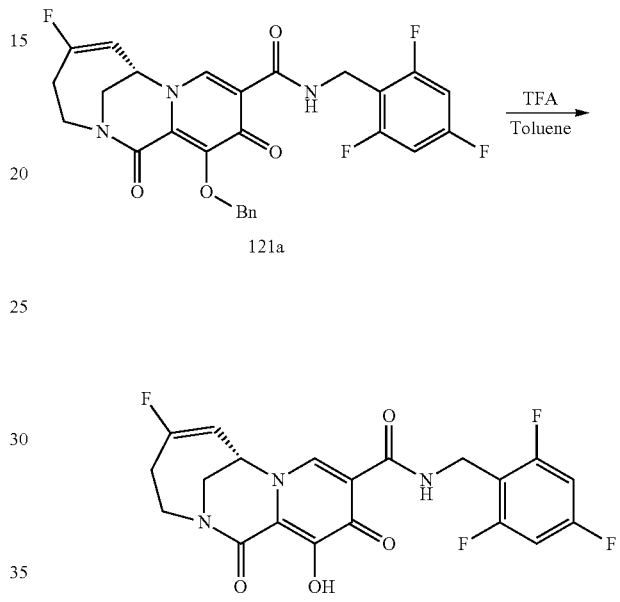

(7S)-12-(benzyloxy)-5-fluoro-1,11-dioxo-N-(2,4,6-trifluorobenzyl)-1,4,7,11-tetrahydro-3H-2,7-methanopyrido[1,2-a][1,4]diazonine-10-carboxamide (121a) was prepared in a similar manner to 113a-2, using (7S)-12-(benzyloxy)-1,5,11-trioxo-N-(2,4,6-trifluorobenzyl)-1,4,5,6,7,11-hexahydro-3H-2,7-methanopyrido[1,2-a][1,4]diazonine-10-carboxamide (103a) in place of (3S,7S)-12-(benzyloxy)-5-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (84b).

The title compound (121) was prepared in a similar manner to compound 113, using (7S)-12-(benzyloxy)-5-fluoro-1,11-dioxo-N-(2,4,6-trifluorobenzyl)-1,4,7,11-tetrahydro-3H-2,7-methanopyrido[1,2-a][1,4]diazonine-10-carboxamide (121a) in place of (3S,7S)-12-(benzyloxy)-5,5-difluoro-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (113a-1). MS (m/z): 438.20 [M+H]$^+$. $^1$H NMR (400 MHz, Acetonitrile-d$_3$) δ 10.30 (s, 1H), 8.42 (s, 1H), 6.86 (t, J=8.5 Hz, 2H), 5.44 (d, J=24.6 Hz, 1H), 4.88-4.77 (m, 1H), 4.72-4.55 (m, 2H), 4.36-4.24 (m, 1H), 3.97 (d, J=14.4 Hz, 1H), 3.76 (d, J=14.3 Hz, 1H), 3.65 (d, J=17.3 Hz, 1H), 3.35-3.13 (m, 1H), 2.83-2.73 (m, 1H).

319

Example 119: Preparation of (13S)-11-bromo-4-hydroxy-3,5-dioxo-N-(2,4,6-trifluorobenzyl)-3,5,8,13-tetrahydro-7H-6,13-methanobenzo[g]pyrido[1,2-a][1,4]diazonine-2-carboxamide and (13R)-11-bromo-4-hydroxy-3,5-dioxo-N-(2,4,6-trifluorobenzyl)-3,5,8,13-tetrahydro-7H-6,13-methanobenzo[g]pyrido[1,2-a][1,4]diazonine-2-carboxamide (122-1 and 122-2)

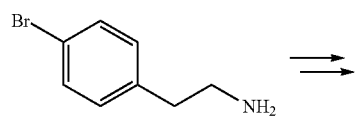

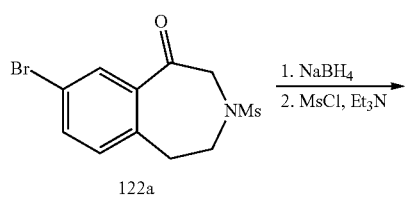
122a

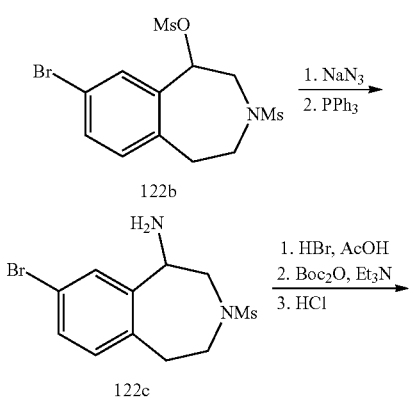
122b

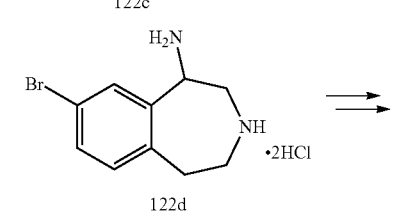
122c

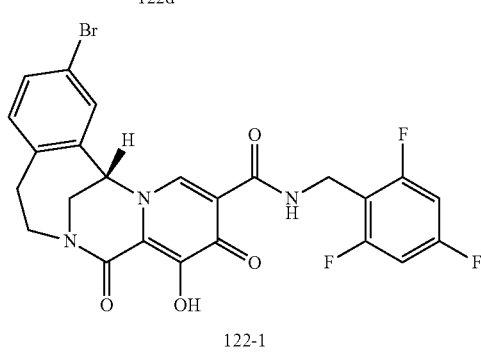
122d 122-1

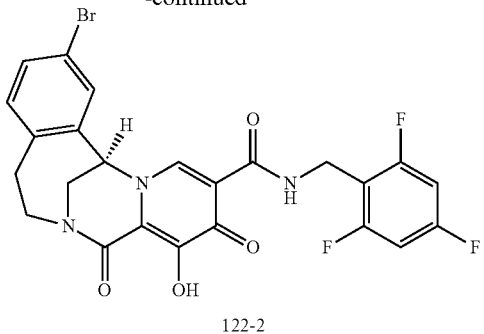
122-2

Synthesis of 8-bromo-3-(methylsulfonyl)-2,3,4,5-tetrahydro-1H-benzo[d]azepin-1-one (122a)

The title compound was synthesized in a manner similar to compound 110a, using 2-(4-bromophenyl)ethan-1-amine in place of 2-(3,4-difluorophenyl)ethan-1-amine. MS (m/z) 318.2 [M+H]$^+$.

Synthesis of 8-bromo-3-(methylsulfonyl)-2,3,4,5-tetrahydro-1H-benzo[d]azepin-1-yl methanesulfonate (122b)

To a stirred suspension of 8-bromo-3-(methylsulfonyl)-2,3,4,5-tetrahydro-1H-benzo[d]azepin-1-one (122a, 14.0 g, 44.0 mmol) in MeOH (50 mL) was added NaBH$_4$ (3.3 g, 88.0 mmol) and heated at 80° C. for 1 h. The mixture was cooled to rt, quenched with water (200 mL) and extracted with EtOAc (200 mL×3). The combined organic layers were washed with brine, dried over Na$_2$SO$_4$, filtered and concentrated. The residue was purified by column chromatography (1:1 petroleum ether/EtOAc) to give 8-bromo-3-(methylsulfonyl)-2,3,4,5-tetrahydro-1H-benzo[d]azepin-1-ol. MS (m/z) 302.0 [M+H-H$_2$O].

To a stirred suspension of 8-bromo-3-(methylsulfonyl)-2,3,4,5-tetrahydro-1H-benzo[d]azepin-1-ol (13.0 g, 40.6 mmol) in DCM (100 mL), was added Et$_3$N (12.3 g, 122 mmol) and methanesulfonyl chloride (9.3 g, 81.2 mmol) at rt. The reaction mixture was stirred at room temperature for 1 h. The mixture was washed with brine (100 mL×5), dried over Na$_2$SO$_4$, filtered and concentrated to give the title compound (122b), which was used in the next step without further purification. MS (m/z) 302.0 [M+H-MsOH]$^+$.

Synthesis of 8-bromo-3-(methylsulfonyl)-2,3,4,5-tetrahydro-1H-benzo[d]azepin-1-amine (122c)

To a stirred suspension of 8-bromo-3-(methylsulfonyl)-2,3,4,5-tetrahydro-1H-benzo[d]azepin-1-yl methanesulfonate (122b, 17.0 g, 42.7 mmol) in DMF (50 mL) was added NaN$_3$ (5.3 g, 81.2 mmol) at rt. The resulting mixture was stirred at 80° C. overnight. The mixture was diluted with EtOAc (200 mL), washed with brine (200 mL×3), dried over Na$_2$SO$_4$, filtered, and concentrated to afford 1-azido-8-bromo-3-(methylsulfonyl)-2,3,4,5-tetrahydro-1H-benzo[d]azepine, which was used in the next step without further purification. MS (m/z) 317.2 [M+H-N$_2$]+.

To a stirred suspension of 1-azido-8-bromo-3-(methylsulfonyl)-2,3,4,5-tetrahydro-1H-benzo[d]azepine (17.0 g, 49.2 mmol) in THF (50 mL)/H$_2$O (10 mL) was added PPh$_3$ (21.3 g, 81.2 mmol) at rt. The mixture was stirred at 60° C. overnight. The mixture was concentrated to dryness, and the residue purified by column chromatography (100% EtOAc, then 10:1 DCM/MeOH) to afford the title compound (122c). MS (m/z) 319.0 [M+H]$^+$.

Synthesis of 8-bromo-2,3,4,5-tetrahydro-1H-benzo[d]azepin-1-amine dihydrochloride (122d)

A mixture of 8-bromo-3-(methylsulfonyl)-2,3,4,5-tetrahydro-1H-benzo[d]azepin-1-amine (122c, 8.0 g, 25.1 mmol) in 33 wt % HBr/AcOH (50 mL) was stirred at 75° C. for 48 h. The mixture was concentrated to dryness, and the residue basified with 7 M NH$_3$/MeOH to pH>7. The mixture was filtered and washed with MeOH (200 mL). The filtrate was concentrated and dissolved in DCM (100 mL). Et$_3$N (23.7 g, 235 mmol) and Boc$_2$O (30.6 g, 141 mmol) were added and the reaction mixture was stirred at room temperature for 1 h. The mixture was washed with 1 N HCl (100 mL) and brine (100 mL). The organic layer was dried over Na$_2$SO$_4$, filtered, and concentrated. The residue was purified by silica gel column (10:1 petroleum ether/EtOAc) to give tert-butyl 8-bromo-1-((tert-butoxycarbonyl)amino)-1,2,4,5-tetrahydro-3H-benzo[d]azepine-3-carboxylate. MS (m/z) 441.2 [M+H]$^+$.

A mixture of tert-butyl 8-bromo-1-((tert-butoxycarbonyl)amino)-1,2,4,5-tetrahydro-3H-benzo[d]azepine-3-carboxylate (12.0 g, 27.2 mmol), 4 M HCl in MeOH (50 mL, 200 mmol) and MeOH (100 mL) was stirred at room temperature for 4 h. The mixture was concentrated to remove solvent and EtOAc (200 mL) was added. The solid was filtered and dried to afford the title compound, which was carried forward without further purification. MS (m/z) 241.2 [M+H]$^+$.

Synthesis of (13S)- and (13R)-11-bromo-4-hydroxy-3,5-dioxo-N-(2,4,6-trifluorobenzyl)-3,5,8,13-tetrahydro-7H-6,13-methanobenzo[g]pyrido[1,2-a][1,4]diazonine-2-carboxamide (122-1 and 122-2)

The title compounds were prepared in a similar manner to compounds 63-1 and 63-2, using 8-bromo-2,3,4,5-tetrahydro-1H-benzo[d]azepin-1-amine; dihydrochloride (122d) in place of 2,3,4,5-tetrahydro-1H-benzo[d]azepin-1-amine dihydrobromide (63f). Chiral separation was carried using SFC (IB, 45% MeOH containing 0.1% diethylamine), prior to deprotection.

122-1, peak 1: MS (m/z) 548.09 [M+H]$^+$. $^1$H NMR (400 MHz, DMSO-d$_6$) δ 10.37 (t, J=5.7 Hz, 1H), 9.07 (s, 1H), 7.47 (dd, J=8.2, 2.2 Hz, 1H), 7.39 (d, J=2.1 Hz, 1H), 7.29-7.15 (m, 3H), 5.98 (s, 1H), 4.61 (qd, J=14.5, 5.7 Hz, 2H), 4.43 (dd, J=15.2, 2.7 Hz, 1H), 4.28 (td, J=12.6, 5.6 Hz, 1H), 3.99 (d, J=15.2 Hz, 1H), 3.58-3.56 (m, 1H), 3.41 (dd, J=12.8, 7.3 Hz, 1H), 2.86 (dd, J=15.4, 5.4 Hz, 1H). $^{19}$F NMR (376 MHz, DMSO-d$_6$) δ −109.23 (ddd, J=15.1, 9.4, 6.2 Hz), −112.53 (t, J=7.4 Hz).

122-2, peak 2: MS (m/z) 548.09 [M+H]$^+$. $^1$H NMR (400 MHz, DMSO-d$_6$) δ 10.37 (t, J=5.7 Hz, 1H), 9.07 (s, 1H), 7.47 (dd, J=8.2, 2.2 Hz, 1H), 7.39 (d, J=2.1 Hz, 1H), 7.31-7.12 (m, 3H), 5.98 (s, 1H), 4.61 (qd, J=14.5, 5.7 Hz, 2H), 4.43 (dd, J=15.2, 2.7 Hz, 1H), 4.28 (td, J=12.5, 5.5 Hz, 1H), 3.99 (d, J=15.1 Hz, 1H), 3.59-3.57 (m, 1H), 3.44-3.38 (m, 1H), 2.86 (dd, J=15.3, 5.4 Hz, 1H). $^{19}$F NMR (376 MHz, DMSO-d$_6$) δ −109.23 (tt, J=9.4, 6.4 Hz), −112.53 (t, J=7.5 Hz).

Example 120: Preparation of (7R)—N-(3-chloro-2,4-difluorobenzyl)-6-fluoro-12-hydroxy-1,11-dioxo-1,4,7,11-tetrahydro-3H-2,7-methanopyrido[1,2-a][1,4]diazonine-10-carboxamide and (7S)—N-(3-chloro-2,4-difluorobenzyl)-6-fluoro-12-hydroxy-1,11-dioxo-1,4,7,11-tetrahydro-3H-2,7-methanopyrido[1,2-a][1,4]diazonine-10-carboxamide (123-1 and 123-2)

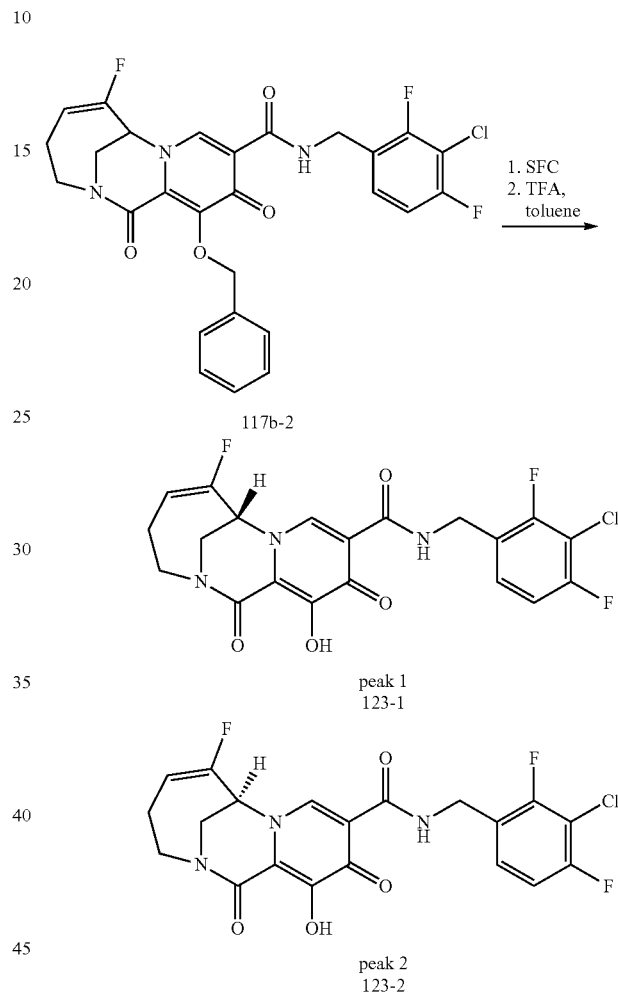

12-(benzyloxy)-N-(3-chloro-2,4-difluorobenzyl)-6-fluoro-1,11-dioxo-1,4,7,11-tetrahydro-3H-2,7-methanopyrido[1,2-a][1,4]diazonine-10-carboxamide (117b-2.35 mg) was separated into its individual enantiomers by preparative SFC chromatography on an IB column using methanol as co-solvent. The separated enantiomers were individually dissolved in 1 mL of toluene and 1 mL of TFA and stirred at room temperature for 1 h. After concentration, purification of each by RP-HPLC eluting with ACN/water (0.1% TFA) provided the title compounds.

123-1, from peak 1: MS (m/z) 454.11 [M+H]$^+$. $^1$H NMR (400 MHz, DMSO-d$_6$) δ 10.32 (t, J=6.0 Hz, 1H), 8.51 (s, 1H), 7.41 (td, J=8.5, 6.2 Hz, 1H), 7.30 (td, J=8.8, 1.7 Hz, 1H), 5.63 (s, 1H), 5.69-5.55 (m, 1H), 4.61 (d, J=6.0 Hz, 2H), 4.22 (td, J=12.2, 6.7 Hz, 1H), 4.11 (d, J=14.9 Hz, 1H), 3.93 (dd, J=15.0, 8.4 Hz, 1H), 3.38-3.21 (m, 1H), 2.88-2.80 (m, 1H), 2.23 (ddd, J=16.3, 10.0, 6.7 Hz, 1H).

123-2, from peak 2: MS (m/z) 454.11 [M+H]$^+$. $^1$H NMR (400 MHz, DMSO-d$_6$) δ 10.32 (t, J=6.0 Hz, 1H), 8.51 (s, 1H), 7.41 (td, J=8.5, 6.3 Hz, 1H), 7.30 (td, J=8.8, 1.7 Hz, 1H), 5.63 (s, 1H), 5.69-5.55 (m, 1H), 4.61 (d, J=6.1 Hz, 2H), 4.22 (td, J=12.2, 6.7 Hz, 1H), 4.11 (d, J=14.9 Hz, 1H), 3.93 (dd, J=15.0, 8.4 Hz, 1H), 3.33 (dd, J=13.1, 8.2 Hz, 1H), 2.94-2.76 (m, OH), 2.23 (ddd, J=16.2, 9.8, 6.5 Hz, 1H).

Example 121: Preparation of (7S)-12-hydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide (124)

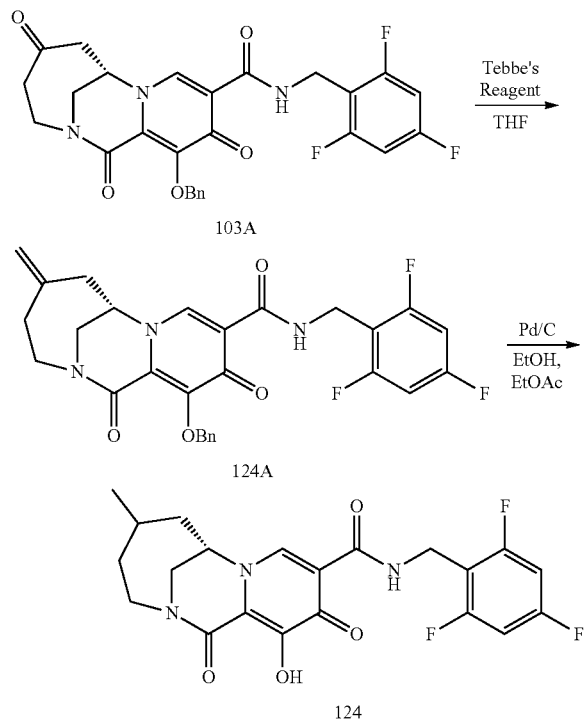

Synthesis of (7S)-12-(benzyloxy)-5-methylene-1,11-dioxo-N-(2,4,6-trifluorobenzyl)-1,4,5,6,7,11-hexahydro-3H-2,7-methanopyrido[1,2-a][1,4]diazonine-10-carboxamide (124a)

Tebbe's reagent (0.5 M in toluene, 1.9 mL) was added to a solution of (7S)-12-(benzyloxy)-1,5,11-trioxo-N-(2,4,6-trifluorobenzyl)-1,4,5,6,7,11-hexahydro-3H-2,7-methanopyrido[1,2-a][1,4]diazonine-10-carboxamide (103a, 166 mg, 0.316 mmol) in THF (4 mL), at 0° C., and stirred for 2 hours. The reaction was quenched with water, diluted with EtOAc, and washed with sat. NaHCO₃ solution. The organic layer was concentrated, and purified by silica gel chromatography to give the title compound (124a). MS (m/z) 524.21 [M+H]⁺.

Synthesis of (7S)-12-hydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide (124)

10% Pd/C (10 mg) was added to a solution of (7S)-12-(benzyloxy)-5-methylene-1,11-dioxo-N-(2,4,6-trifluorobenzyl)-1,4,5,6,7,11-hexahydro-3H-2,7-methanopyrido[1,2-a][1,4]diazonine-10-carboxamide (22 mg) in EtOH (5 mL) and EtOAc (5 mL). A H₂ balloon was affixed to the reaction, and the reaction was stirred at rt for 2 hours, before being filtered through celite. The filtrate was concentrated and purified via preparative HPLC, eluting with 10-60% acetonitrile (0.1% TFA) in water (0.1% TFA) to afford the title compound (124). MS (m/z) 436.24 [M+H]⁺. ¹H NMR (400 MHz, Acetonitrile-d₃) δ 10.37 (s, 1H), 8.37 (s, 1H), 6.87 (t, J=8.5 Hz, 2H), 4.73-4.47 (m, 2H), 4.35 (dd, J=13.8, 6.0 Hz, 1H), 3.85 (d, J=14.6 Hz, 1H), 3.67 (d, J=14.4 Hz, 1H), 3.11-2.91 (m, 1H), 2.45 (dd, J=15.6, 9.1 Hz, 1H), 2.11-1.95 (m, 1H), 1.77 (m, 2H), 1.58-1.37 (m, 1H), 1.26 (t, J=14.6 Hz, 1H), 0.94 (dd, J=11.3, 6.6 Hz, 3H).

Example 122: (7S)-12-hydroxy-1,11-dioxo-N-(2,3,4,6-tetrafluorobenzyl)-1,4,5,6,7,11-hexahydro-3H-2,7-methanopyrido[1,2-a][1,4]diazonine-10-carboxamide (125)

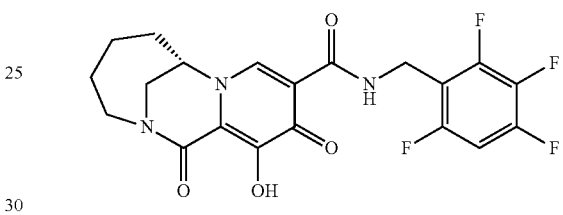

The title compound was prepared in a similar manner to compound 51, using (2,3,4,6-tetrafluorophenyl)methanamine in place of (3-chloro-2,4-difluorophenyl)methanamine. MS (m/z) 440.2 [M+H]⁺. ¹H NMR (400 MHz, DMSO-d₆) δ 10.48 (t, J=5.9 Hz, 1H), 8.48 (s, 1H), 7.76-7.42 (m, 1H), 4.75 (dd, J=6.0, 2.9 Hz, 1H), 4.60 (d, J=5.9 Hz, 2H), 4.13 (dt, J=13.1, 7.8 Hz, 1H), 3.97-3.81 (m, 1H), 3.67 (dd, J=14.7, 1.9 Hz, 1H), 3.07 (ddd, J=13.2, 6.8, 3.6 Hz, 1H), 2.16-1.47 (m, 5H), 1.14 (q, J=11.9 Hz, 1H).

Example 123: (7S)—N-(3-chloro-2-fluorobenzyl)-12-hydroxy-1,11-dioxo-1,4,5,6,7,11-hexahydro-3H-2,7-methanopyrido[1,2-a][1,4]diazonine-10-carboxamide (126)

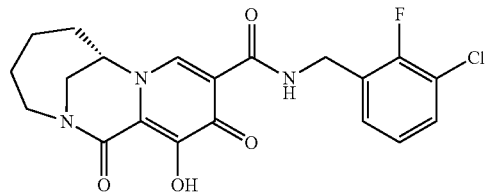 [SMILES: O=C(NCc1cccc(Cl)c1F)c1cn2c(c(O)c1=O)C(=O)N1CCCC[C@H]2C1]

The title compound was prepared in a similar manner to compound 51, using (3-chloro-2-fluorophenyl)methanamine in place of (3-chloro-2,4-difluorophenyl)methanamine. MS (m/z) 418.85 [M]⁻. ¹H NMR (400 MHz, DMSO-d₆) δ 10.53-10.36 (m, 1H), 8.72-8.39 (m, 1H), 7.66-7.06 (m, 3H), 4.77 (s, 1H), 4.63 (d, J=6.1 Hz, 2H), 4.14 (dt, J=15.0, 7.7 Hz, 1H), 3.89 (d, J=14.5 Hz, 1H), 3.68 (dd, J=14.6, 1.9 Hz, 1H), 3.08 (ddd, J=12.0, 6.8, 3.6 Hz, 1H), 2.08-1.59 (m, 5H), 1.19-1.00 (m, 1H).

Example 124: Synthesis of (6S)-9-chloro-1-hydroxy-2,14-dioxo-N-(2,4,6-trifluorobenzyl)-2,7,12,14-tetrahydro-6H-6,13-methanobenzo[f]pyrido[1,2-a][1,4]diazonine-3-carboxamide and (6R)-9-chloro-1-hydroxy-2,14-dioxo-N-(2,4,6-trifluorobenzyl)-2,7,12,14-tetrahydro-6H-6,13-methanobenzo[f]pyrido[1,2-a][1,4]diazonine-3-carboxamide (127-1 and 127-2)

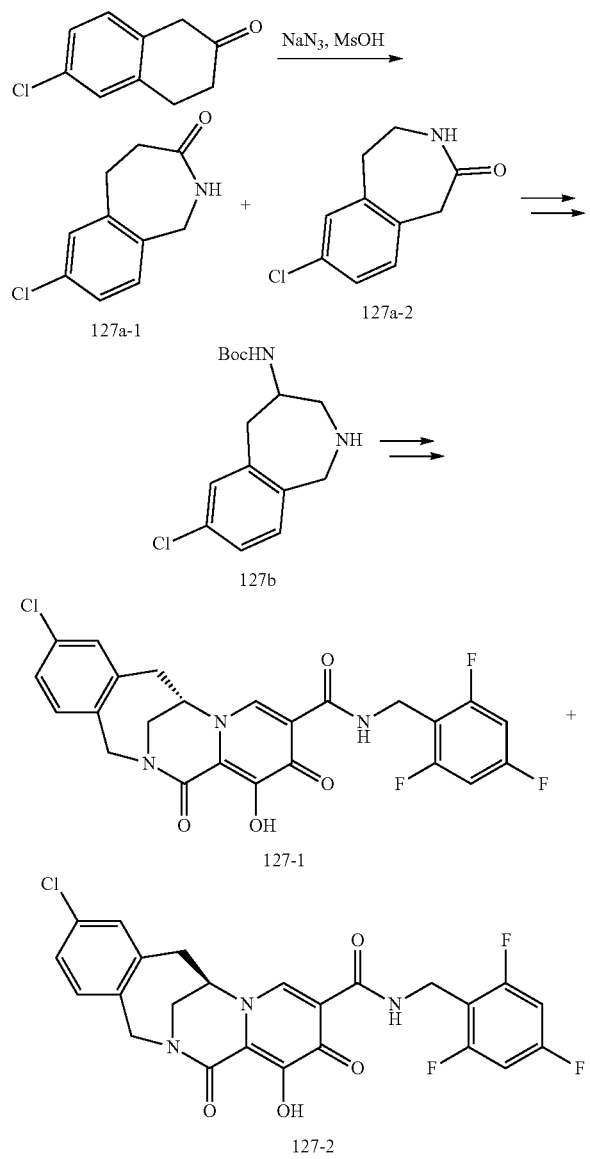

Synthesis of 7-chloro-1,2,4,5-tetrahydro-3H-benzo[c]azepin-3-one and 7-chloro-1,3,4,5-tetrahydro-2H-benzo[d]azepin-2-one (127a-1 and 127a-2)

Into a solution of 6-chloro-3,4-dihydronaphthalen-2(1H)-one (2 g, 11.1 mmol) in MsOH (10 mL) was added sodium azide (828 mg, 12.7 mmol) in three portions over 15 min in an ice-salt bath. The reaction mixture was stirred at 0° C. for 15 min, then at rt for 3 h. The reaction mixture was quenched with sat. NaHCO$_3$ at 0° C. until the mixture was slightly basic. The reaction mixture was then extracted with EtOAc, the organic phase was separated, dried over MgSO$_4$, filtered, concentrated down, and purified by silica gel column chromatography, eluting with 0-100% EtOAc/hexane and then 0-20% DCM/MeOH. The title compounds (127a-1 and 127a-2) were separated after multiple chromatographies.

127a-1: $^1$H NMR (400 MHz, Chloroform-d) δ 7.23 (d, J=2.1 Hz, 1H), 7.18 (d, J=7.5 Hz, 1H), 7.08 (d, J=8.0 Hz, 1H), 6.27 (s, 1H), 4.37 (s, 2H), 3.18-3.01 (m, 2H), 2.84 (t, J=6.6 Hz, 2H).

127a-2: $^1$H NMR (400 MHz, Chloroform-d) δ 7.21-7.13 (m, 2H), 7.10 (d, J=8.0 Hz, 1H), 5.84 (s, 1H), 3.84 (s, 2H), 3.66-3.57 (m, 2H), 3.17-3.09 (m, 2H).

Synthesis of tert-butyl (7-chloro-2,3,4,5-tetrahydro-1H-benzo[c]azepin-4-yl)carbamate (127b)

The title compound was prepared in a similar manner to compound 43d, using 7-chloro-1,2,4,5-tetrahydro-3H-benzo[c]azepin-3-one (127a-1) in place of 6-fluoro-1,3,4,5-tetrahydro-2H-benzo[b]azepin-2-one, and platinum (IV) oxide in place of Pd/C.

Synthesis of (6S)- and (6R)-9-chloro-1-hydroxy-2,14-dioxo-N-(2,4,6-trifluorobenzyl)-2,7,12,14-tetrahydro-6H-6,13-methanobenzo[f]pyrido[1,2-a][1,4]diazonine-3-carboxamide (127-1 and 127-2)

The title compounds were prepared in a manner similar to compounds 40-1 and 40-2, using tert-butyl (7-chloro-2,3,4,5-tetrahydro-1H-benzo[c]azepin-4-yl)carbamate (127b) in place of tert-butyl ((1S,6R)-2-azabicyclo[4.2.1]nonan-4-yl)carbamate (40e).

127-1, from peak 1: MS (m/z) 504.22 [M+H]$^+$. $^1$H NMR (400 MHz, DMSO-d$_6$) δ 10.36 (t, J=5.8 Hz, 1H), 8.51 (s, 1H), 7.44-7.14 (m, 5H), 5.49 (d, J=16.6 Hz, 1H), 4.99 (td, J=7.6, 2.3 Hz, 1H), 4.59 (d, J=5.2 Hz, 2H), 4.46 (d, J=16.7 Hz, 1H), 3.79 (d, J=14.6 Hz, 1H), 3.58 (dd, J=14.9, 2.8 Hz, 1H), 3.40 (d, J=7.6 Hz, 2H), 2.94-2.85 (m, 1H).

127-2, from peak 2: MS (m/z) 504.14 [M+H]$^+$. $^1$H NMR (400 MHz, DMSO-d$_6$) δ 10.36 (t, J=5.8 Hz, 1H), 8.51 (s, 1H), 7.37 (dd, J=8.2, 2.3 Hz, 1H), 7.31 (d, J=8.3 Hz, 1H), 7.28-7.16 (m, 3H), 5.49 (d, J=16.6 Hz, 1H), 5.03-4.94 (m, 1H), 4.59 (d, J=5.8 Hz, 2H), 4.46 (d, J=16.7 Hz, 1H), 3.79 (d, J=14.6 Hz, 1H), 3.58 (dd, J=14.8, 2.8 Hz, 2H), 3.40 (s, 1H), 2.98-2.82 (m, 1H).

Example 125: Preparation of (6S)-9-chloro-N-(2,4-difluorobenzyl)-1-hydroxy-2,14-dioxo-2,7,12,14-tetrahydro-6H-6,13-methanobenzo[f]pyrido[1,2-a][1,4]diazonine-3-carboxamide and (6R)-9-chloro-N-(2,4-difluorobenzyl)-1-hydroxy-2,14-dioxo-2,7,12,14-tetrahydro-6H-6,13-methanobenzo[f]pyrido[1,2-a][1,4]diazonine-3-carboxamide (128-1 and 128-2)

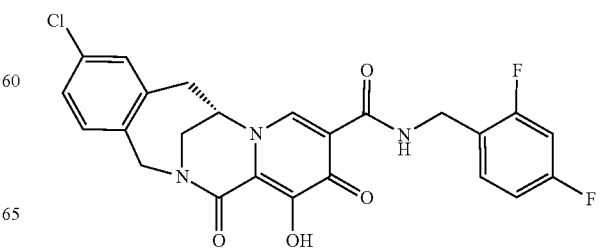

128-1

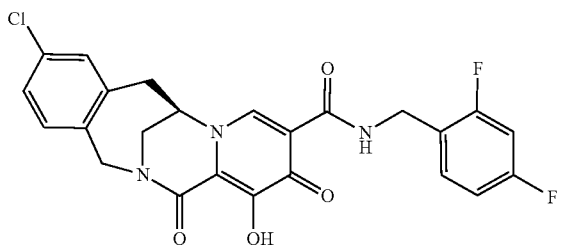

The title compounds were prepared in a manner similar to compounds 127-1 and 127-2, using methyl 3-(benzyloxy)-5-((2,4-difluorobenzyl)carbamoyl)-4-oxo-4H-pyran-2-carboxylate in place of methyl 3-(benzyloxy)-4-oxo-5-((2,4,6-trifluorobenzyl)carbamoyl)-4H-pyran-2-carboxylate.

128-1, from peak 1: MS (m/z) 486.13 [M+H]⁺. ¹H NMR (400 MHz, DMSO-d₆) δ 10.33 (t, J=5.9 Hz, 1H), 8.53 (s, 1H), 7.48-7.19 (m, 5H), 7.08 (td, J=8.5, 2.6 Hz, 1H), 5.50 (d, J=16.6 Hz, 1H), 5.02 (d, J=8.5 Hz, 1H), 4.57 (d, J=5.9 Hz, 2H), 4.47 (d, J=16.7 Hz, 1H), 3.80 (d, J=14.6 Hz, 1H), 3.59 (dd, J=14.8, 2.7 Hz, 1H), 3.43 (s, 2H), 2.90 (dd, J=14.9, 7.5 Hz, 1H).

128-2, from peak 2: MS (m/z) 486.27 [M+H]⁺. ¹H NMR (400 MHz, DMSO-d₆) δ 10.33 (t, J=5.9 Hz, 1H), 8.53 (s, 1H), 7.50-7.20 (m, 5H), 7.08 (td, J=8.6, 2.5 Hz, 1H), 5.50 (d, J=16.6 Hz, 1H), 5.01 (s, 1H), 4.57 (d, J=5.9 Hz, 2H), 4.47 (d, J=16.7 Hz, 1H), 3.80 (d, J=14.6 Hz, 1H), 3.59 (dd, J=14.7, 2.6 Hz, 1H), 3.42 (d, J=7.5 Hz, 2H), 2.90 (dd, J=14.9, 7.6 Hz, 1H).

Example 126: Preparation of (7'S)-12'-hydroxy-1',11'-dioxo-N-(2,4,6-trifluorobenzyl)-1',4',5',6',7',11'-hexahydrospiro[cyclopropane-1,3'-[2,7]methano-pyrido[1,2-a][1,4]diazonine]-10'-carboxamide (129)

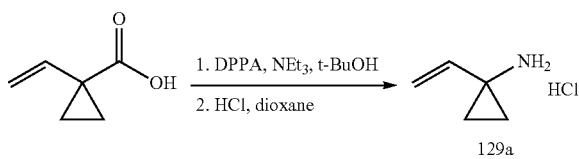

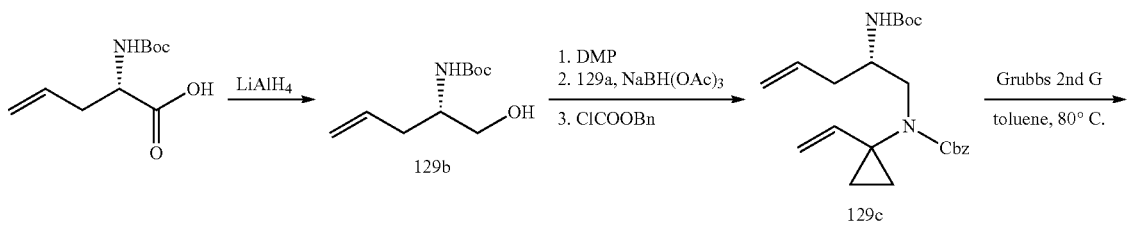

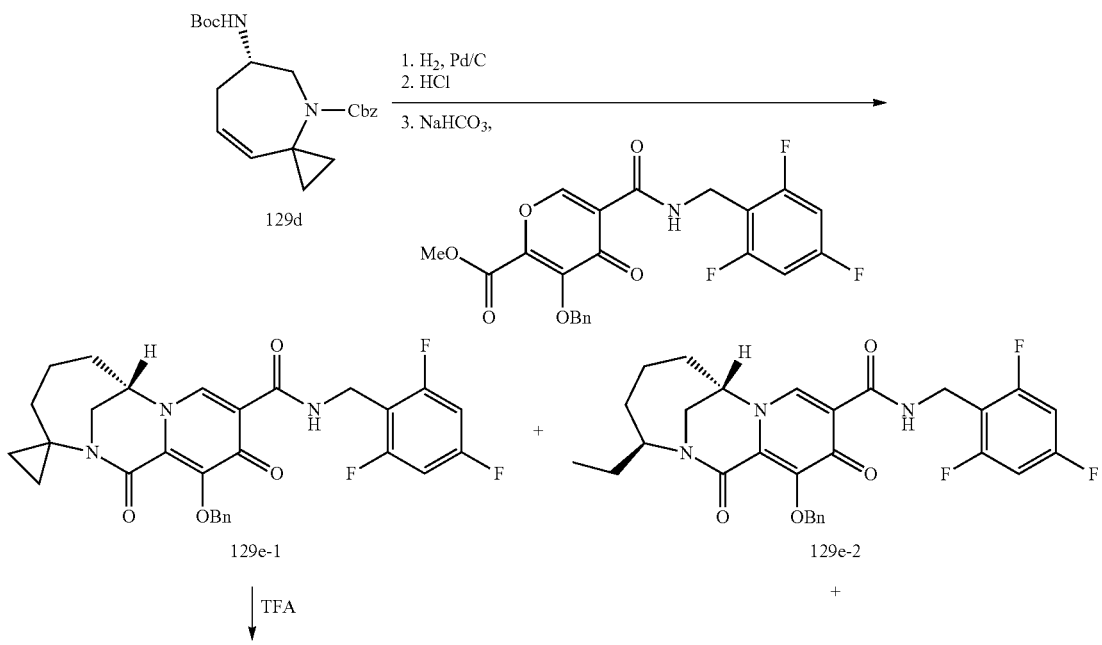

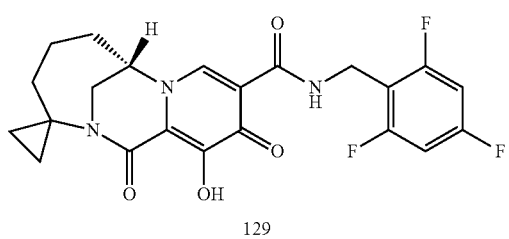

129

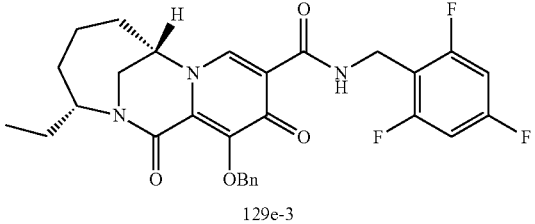

129e-3

Synthesis of 1-vinylcyclopropan-1-amine hydrochloride (129a)

A solution of 1-vinylcyclopropanecarboxylic acid (974.0 mg, 8.687 mmol) and triethylamine (1.25 mL, 8.968 mmol) in tert-butanol (40 mL) was stirred at rt as diphenyl phosphoryl azide (2.1 mL, 9.744 mmol) was added. After addition, the reaction mixture was stirred in an 87° C. bath for 18 h. The reaction mixture was concentrated, and the residue was dissolved in ethyl acetate (50 mL), before the solution was washed with saturated sodium bicarbonate (50 mL) and water (50 mL). The aqueous fractions were extracted with ethyl acetate (30 mL), and the organic fractions were combined, dried over MgSO$_4$, and concentrated. The residue was purified by column chromatography on silica gel eluting with 0-30% ethyl acetate in hexane to get tert-butyl (1-vinylcyclopropyl)carbamate. $^1$H NMR (400 MHz, Chloroform-d) δ 5.43 (dd, J=17.0, 10.4 Hz, 1H), 5.16-4.85 (m, 3H), 1.45 (s, 9H), 1.08 (s, 2H), 0.91 (s, 2H).

A solution of tert-butyl N-(1-vinylcyclopropyl)carbamate (1.2 g, 6.573 mmol) and 4 M HCl in dioxane (16.5 mL) was stirred at rt for 1.5 h and then concentrated completely to get the title compound (129a), which was carried forward without further purification.

Synthesis of tert-butyl (S)-(1-hydroxypent-4-en-2-yl)carbamate (129b)

A solution of (S)-2-((tert-butoxycarbonyl)amino)pent-4-enoic acid (6.0 g, 26.2 mmol) in tetrahydrofuran (90 mL) was stirred at 0° C., as 1 M lithium aluminum hydride (34.1 mL) was added dropwise. After 30 min, the reaction mixture was diluted with ethyl ether (150 mL) and vigorously stirred at 0° C., as water (1.3 mL), 15% sodium hydroxide (1.3 mL), and water (3.9 mL) were sequentially added dropwise. After 30 min, anhydrous sodium sulfate was added to the mixture and filtered through celite after 2 min. The filtrate was concentrated, and the resulting residue was purified by column chromatography on silica gel, eluting with 0-100% ethyl acetate in hexane, to obtain the title compound (129b). MS (m/z) 201.83 [M+H]$^+$.

Synthesis of benzyl (S)-(2-((tert-butoxycarbonyl)amino)pent-4-en-1-yl)(1-vinylcyclopropyl)carbamate (129c)

A solution of tert-butyl (S)-(1-hydroxypent-4-en-2-yl)carbamate (129b, 1.5 g, 6.195 mmol) in dichloromethane (80 mL) was stirred at 0° C. bath as Dess-Martin periodinane (3.9 g, 9.094 mmol) was added. After 10 min, the reaction mixture was warmed to rt, and stirred for 1.5 h. Additional Dess-Martin periodinane (750 mg, 1.768 mmol) was added and the resulting solution was stirred at rt for 1 h. The reaction mixture was cooled to 0° C. and saturated sodium bicarbonate (100 mL) was added. After separating the two fractions, the aqueous fraction was extracted with dichloromethane (100 mL). The organic fractions were washed with 10% sodium thiosulfate solution (100 mL), and brine (70 mL), combined, dried over MgSO$_4$, and concentrated. The residue was purified by column chromatography on silica gel, eluting with 0-50% ethyl acetate in hexane, to get tert-butyl (S)-(1-oxopent-4-en-2-yl)carbamate.

A suspension of tert-butyl (S)-(1-oxopent-4-en-2-yl)carbamate (1.2 g, 6.254 mmol) and 1-vinylcyclopropanamine; hydrochloride (129a, 6.574 mmol) in tetrahydrofuran (38 mL) was stirred at rt, as triethylamine (1.75 mL, 12.56 mmol) and sodium triacetoxyborohydride (2.0 g, 9.424 mmol) were added. The resulting reaction mixture was stirred at rt for 19 h. The reaction mixture was concentrated to remove most of the tetrahydrofuran, and diluted with saturated sodium bicarbonate (100 mL), and extracted with ethyl acetate (100 mL×3). The extracts were washed with brine, and the organic fractions were combined, dried over MgSO$_4$, and concentrated to get tert-butyl (S)-(1-((1-vinylcyclopropyl)amino)pent-4-en-2-yl)carbamate.

A mixture of tert-butyl (S)-(1-((1-vinylcyclopropyl)amino)pent-4-en-2-yl)carbamate, and potassium carbonate (1.0 g, 16.38 mmol) in 1,4-dioxane (40 mL) and water (40 mL) was stirred at 0° C., as benzyl chloroformate (1.3 mL, 8.852 mmol) was added. The resulting mixture was stirred at 0° C. for 2 h and then at rt overnight. The reaction mixture was diluted with saturated ammonium chloride (100 mL) and the product was extracted with ethyl acetate (100 mL×2). The extracts were combined, dried over MgSO$_4$, concentrated, and the residue purified by column chromatography on silica gel, eluting with 0-30% ethyl acetate in hexane, to get the title compound (129c). MS (m/z) 400.80 [M+H]$^+$.

Synthesis of benzyl (S)-6-((tert-butoxycarbonyl)amino)-4-azaspiro[2.6]non-8-ene-4-carboxylate (129d)

The title compound was synthesized in a manner similar to compound 65c, using benzyl (S)-(2-((tert-butoxycarbonyl)amino)pent-4-en-1-yl)(1-vinylcyclopropyl)carbamate (129c) in place of benzyl allyl(((E)-1-((tert-butoxycarbonyl)amino)-2-vinylcyclopropyl)methyl)carbamate (65b). MS (m/z) 395.19 [M+H]$^+$. Benzyl (S)-6-((tert-butoxycarbonyl)amino)-4-azaspiro[2.6]non-8-ene-4-carboxylate (129d) was further purified by preparative SFC chromatography on an ID-5 um column using 30% IPA-NH$_3$ co-solvent.

Synthesis of (7'S)-12'-(benzyloxy)-1' 11'-dioxo-N-(2,4,6-trifluorobenzyl)-1',4',5',6',7',11'-hexahydrospiro[cyclopropane-1,3'-[2,7]methanopyrido[1,2-a][1,4]diazonine]-10'-carboxamide, (3S,7S)-12-(benzyloxy)-3-ethyl-1,11-dioxo-N-(2,4,6-trifluorobenzyl)-1,4,5,6,7,11-hexahydro-3H-2,7-methanopyrido[1,2-a][1,4]diazonine-10-carboxamide, and (3R,7S)-12-(benzyloxy)-3-ethyl-1,11-dioxo-N-(2,4,6-trifluorobenzyl)-1,4,5,6,7,11-hexahydro-3H-2,7-methanopyrido[1,2-a][1,4]diazonine-10-carboxamide (129e-1, 129e-2, and 129e-3)

A mixture of benzyl (S)-6-((tert-butoxycarbonyl)amino)-4-azaspiro[2.6]non-8-ene-4-carboxylate (129d, 107.5 mg, 288.62 μmol) and 10% palladium on carbon (12.2 mg) in ethyl acetate (4 mL) and ethanol (2 mL) was stirred under $H_2$ atmosphere. After 1 h, the reaction mixture was filtered and the filtrate was concentrated.

The residue was dissolved in 4 N HCl in 1,4-dioxane (4 mL) and stirred at rt for 1 h before the reaction mixture was concentrated.

The above residue, methyl 3-(benzyloxy)-4-oxo-5-((2,4,6-trifluorobenzyl)carbamoyl)-4H-pyran-2-carboxylate (129.1 mg, 288.58 umol), and sodium bicarbonate (96.2 mg, 1.145 mmol) in water (1.2 mL) and methanol (6 mL) was stirred at 50° C. After 22 h, the reaction mixture was heated at 60° C. for 6 h. The reaction mixture was concentrated to remove most of the solvent, and the residue was dissolved in ethyl acetate (25 mL) and brine (25 mL), and separated. The aqueous fraction was extracted with ethyl acetate (25 mL), and the organic fractions were washed with brine, combined, dried over $MgSO_4$, and concentrated. The residue was purified by preparative HPLC (column, Gemini 10u C18 110A, AXI; 250×21.2 mm) eluting with 30-90% acetonitrile in water (0.1% TFA), to obtain the title compounds, stereochemistry drawn arbitrarily. 129e-1: MS (m/z) 538.14 [M+H]$^+$; 129e-2: MS (m/z) 540.16 [M+H]$^+$; 129e-3: MS (m/z) 540.17 [M+H]$^+$.

Synthesis of (7'S)-12'-hydroxy-1' 11'-dioxo-N-(2,4,6-trifluorobenzyl)-1',4',5',6',7',11'-hexahydrospiro[cyclopropane-1,3'-[2,7]methanopyrido[1,2-a][1,4]diazonine]-10'-carboxamide (129)

(7'S)-12'-(benzyloxy)-1',11'-dioxo-N-(2,4,6-trifluorobenzyl)-1',4',5',6',7',11'-hexahydrospiro[cyclopropane-1,3'-[2,7]methanopyrido[1,2-a][1,4]diazonine]-10'-carboxamide (129e-1, 56.5 mg, 105 umol) was dissolved in TFA (2 mL) and stirred at rt for 2 h. The reaction mixture was concentrated and the residue was purified by preparative HPLC (column, Gemini 10u C18 110A, AXI/; 250×21.2 mm) eluting with 10-65% acetonitrile in water (0.1% TFA) to afford the title compound. MS (m/z) 448.21 [M+H]$^+$. $^1$H NMR (400 MHz, Acetonitrile-d$_3$) δ 10.34 (s, 1H), 8.37 (s, 1H), 6.91-6.76 (m, 2H), 4.58 (m, 3H), 3.83-3.67 (m, 2H), 2.53 (dt, J=15.9, 8.0 Hz, 1H), 2.17-2.05 (m, 1H), 1.85-1.51 (m, 4H), 1.42 (ddd, J=14.2, 6.4, 2.2 Hz, 1H), 0.99 (ddd, J=9.7, 6.8, 5.6 Hz, 1H), 0.72 (dddd, J=10.5, 6.5, 5.0, 1.2 Hz, 1H), 0.50 (ddd, J=9.7, 6.9, 5.0 Hz, 1H). $^{19}$F NMR (376 MHz, Acetonitrile-d$_3$) δ -77.36, -111.24 (ddd, J=15.0, 9.2, 6.2 Hz), -113.93 (t, J=7.1 Hz).

Example 127: Synthesis of (3R,7S)-3-ethyl-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide and (3S,7S)-3-ethyl-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (130-1 and 130-2)

130-1

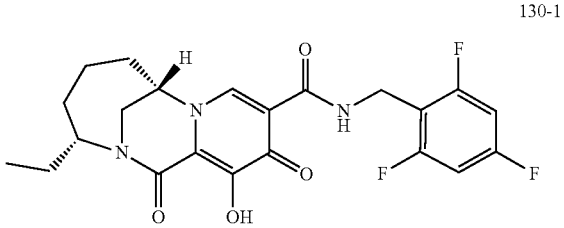

130-2

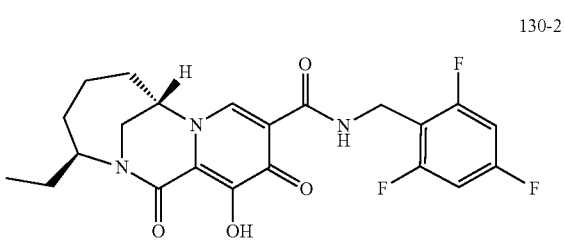

The title compounds were synthesized in a similar manner to compound 129, using (3R,7S)-12-(benzyloxy)-3-ethyl-1,11-dioxo-N-(2,4,6-trifluorobenzyl)-1,4,5,6,7,11-hexahydro-3H-2,7-methanopyrido[1,2-a][1,4]diazonine-10-carboxamide or (3S,7S)-12-(benzyloxy)-3-ethyl-1,11-dioxo-N-(2,4,6-trifluorobenzyl)-1,4,5,6,7,11-hexahydro-3H-2,7-methanopyrido[1,2-a][1,4]diazonine-10-carboxamide (129e-2 or 129e-3) in place of (7'S)-12'-(benzyloxy)-1',11'-dioxo-N-(2,4,6-trifluorobenzyl)-1',4',5',6',7',11'-hexahydrospiro [cyclopropane-1,3'-[2,7]methanopyrido[1,2-a][1,4]diazonine]-10'-carboxamide (129e-1)

130-1: MS (m/z) 450.23 [M+H]$^+$. $^1$H NMR (400 MHz, Acetonitrile-d$_3$) δ 10.43 (s, 1H), 8.37 (s, 1H), 6.91-6.76 (m, 2H), 4.59 (d, J=5.8 Hz, 2H), 4.53 (d, J=3.8 Hz, 1H), 4.25 (tt, J=10.9, 6.0 Hz, 1H), 3.64 (dt, J=14.8, 2.7 Hz, 1H), 3.52 (dd, J=14.7, 1.8 Hz, 1H), 2.18-2.01 (m, 2H), 1.88-1.73 (m, 1H), 1.67 (ddt, J=15.3, 7.7, 4.0 Hz, 1H), 1.62-1.45 (m, 2H), 1.40 (dt, J=14.5, 11.3 Hz, 1H), 1.19-1.04 (m, 1H), 0.96 (t, J=7.3 Hz, 3H). $^{19}$F NMR (376 MHz, Acetonitrile-d$_3$) δ -77.34, -111.27 (ddd, J=15.3, 9.3, 6.3 Hz), -113.92 (t, J=7.1 Hz).

130-2: MS (m/z) 450.22 [M+H]$^+$. $^1$H NMR (400 MHz, Acetonitrile-d$_3$) δ 10.38 (s, 1H), 8.34 (d, J=5.7 Hz, 1H), 6.84 (t, J=8.5 Hz, 2H), 4.58 (d, J=5.4 Hz, 2H), 4.50 (s, 1H), 3.85 (d, J=14.7 Hz, 1H), 3.50 (dd, J=14.8, 2.5 Hz, 1H), 3.19 (d, J=10.1 Hz, 1H), 2.57 (dt, J=15.6, 7.8 Hz, 1H), 2.48-2.27 (m, 1H), 1.83-1.70 (m, 3H), 1.65 (td, J=10.4, 6.9 Hz, 2H), 1.48 (d, J=9.7 Hz, 1H), 1.05 (t, J=7.2 Hz, 3H). $^{19}$F NMR (376 MHz, Acetonitrile-d$_3$) δ -77.25, -111.28 (ddd, J=15.0, 9.3, 6.0 Hz), -113.95 (q, J=11.7, 9.5 Hz).

Example 128: Preparation of (3R,7S)-3-(difluoromethyl)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (131)

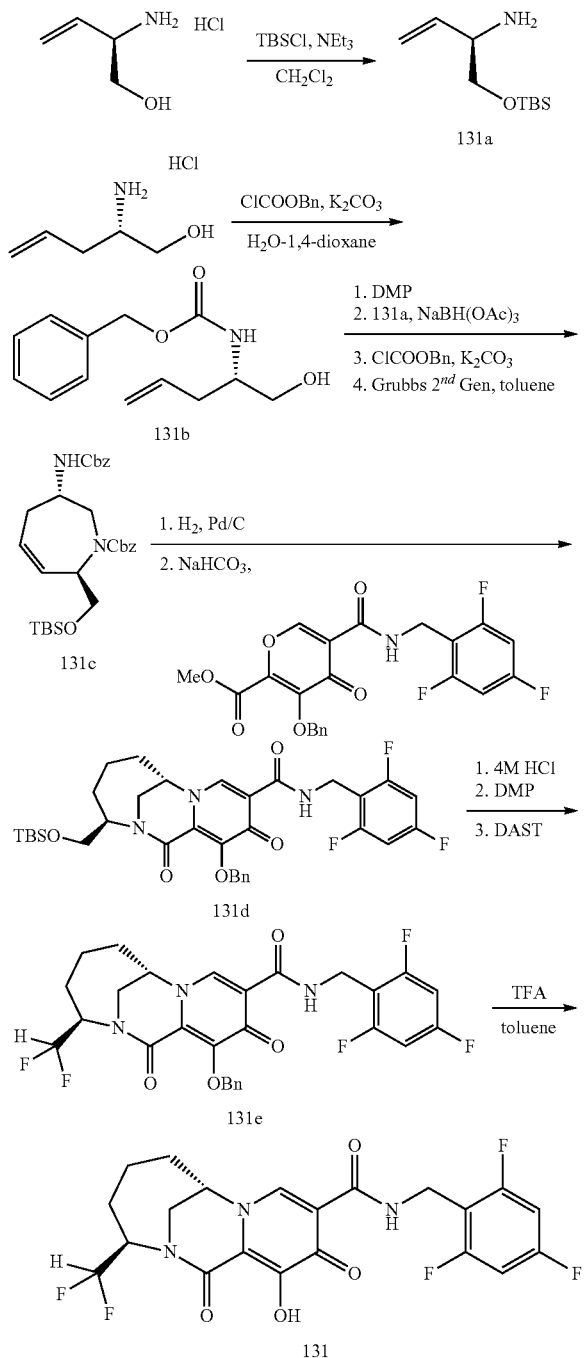

Synthesis of (R)-1-((tert-butyldimethylsilyl)oxy)but-3-en-2-amine (131a)

A suspension of (2R)-2-aminobut-3-en-1-ol hydrochloride (1.0 g, 8.18 mmol) and triethylamine (3.5 mL, 25.11 mmol) in dichloromethane (12 mL) was stirred at 0° C., as tert-butyldimethylsilyl chloride (1.35 g, 8.957 mmol) was added. After addition, the reaction mixture was stirred at rt for 23 h. The reaction mixture was diluted with dichloromethane (30 mL) and washed with saturated sodium bicarbonate solution (50 mL). The aqueous fraction was extracted with dichloromethane (2×30 mL), and the combined organic fractions were washed with brine (30 mL), dried over MgSO$_4$, and concentrated. The residue was dissolved in ethyl ether, filtered, and the filtrate was concentrated to get the crude TBS protected product (131a). MS (m/z) 202.01 [M+H]$^+$.

Synthesis of benzyl (S)-(1-hydroxypent-4-en-2-yl)carbamate (131b)

A solution of (2S)-2-amino-4-penten-1-ol (2.0 g, 14.53 mmol) and potassium carbonate (6.0 g, 43.63 mmol) in water (36 mL) and 1,4-dioxane (36 mL) was stirred at 0° C., as benzyl chloroformate (2.6 mL, 17.52 mmol) was added. The mixture was stirred at 0° C. for 2 h, and then at rt overnight. The reaction mixture was diluted with saturated sodium bicarbonate (150 mL), and the mixture was extracted with ethyl acetate (150 mL×2). After the extracts were washed with water (150 mL), the organic fractions were combined, dried over MgSO$_4$, and concentrated. The residue was purified by column chromatography on silica gel, eluting with 0-70% ethyl acetate in hexane, to obtain the title compound (131b). MS (m/z) 235.84 [M+H]$^+$.

Synthesis of benzyl (3S,7R)-3-(((benzyloxy)carbonyl)amino)-7-(((tert-butyldimethylsilyl)oxy)methyl)-2,3,4,7-tetrahydro-1H-azepine-1-carboxylate (131c)

The title compound was prepared in a similar manner to compound 129d, using (R)-1-((tert-butyldimethylsilyl)oxy)but-3-en-2-amine (131a) in place of 1-vinylcyclopropanamine; hydrochloride (129a), and benzyl (S)-(1-hydroxypent-4-en-2-yl)carbamate (131b) in place of tert-butyl (S)-(1-hydroxypent-4-en-2-yl)carbamate (129b). MS (m/z) 525.01 [M+H]$^+$.

Synthesis of (3R,7S)-12-(benzyloxy)-3-(((tert-butyldimethylsilyl)oxy)methyl)-1,11-dioxo-N-(2,4,6-trifluorobenzyl)-1,4,5,6,7,11-hexahydro-3H-2,7-methanopyrido[1,2-a][1,4]diazonine-10-carboxamide (131d)

A mixture of benzyl (3S,7R)-3-(((benzyloxy)carbonyl)amino)-7-(((tert-butyldimethylsilyl)oxy) methyl)-2,3,4,7-tetrahydro-1H-azepine-1-carboxylate (131c, 262.8 mg, 500.8 µmol) and 10% palladium on carbon (51.26 mg) in ethanol (10 mL) and EtOAc (5 mL) was stirred under H$_2$ atmosphere for 2 h. The reaction mixture was filtered and concentrated to dryness.

A mixture of the above residue, methyl 3-(benzyloxy)-4-oxo-5-((2,4,6-trifluorobenzyl) carbamoyl)-4H-pyran-2-carboxylate (224.5 mg, 501.83 umol), and sodium bicarbonate (96.2 mg, 1.15 mmol) in water (1.2 mL) and methanol (6 mL) was stirred at 50° C. for 22 h followed by at 60° C. for 6 h. The reaction mixture was concentrated to remove most of solvent and the residue was dissolved in ethyl acetate (25 mL) and water (25 mL) before two fractions were separated. After the aqueous fraction was extracted with ethyl acetate (25 mL), two organic fractions were washed with brine, combined, dried over MgSO$_4$, and concentrated. The residue was purified by column chromatography on silica gel, eluting with 0-9.5% methanol in dichloromethane, to get the title compound (131d). MS (m/z) 656.23 [M+H]⁺.

Synthesis of (3R,7S)-12-(benzyloxy)-3-(difluoromethyl)-1,11-dioxo-N-(2,4,6-trifluorobenzyl)-1,4,5,6,7,11-hexahydro-3H-2,7-methanopyrido[1,2-a][1,4]diazonine-10-carboxamide (131e)

(3R,7S)-12-(benzyloxy)-3-(((tert-butyldimethylsilyl)oxy)methyl)-1,11-dioxo-N-(2,4,6-trifluorobenzyl)-1,4,5,6,7,11-hexahydro-3H-2,7-methanopyrido[1,2-a][1,4]diazonine-10-carboxamide (131d, 230.2 mg, 351.03 umol) was dissolved in 4 N HCl in dioxane (3 mL) in 0° C. bath and stirred for 30 min. The reaction mixture was concentrated and the residue was purified by column chromatography on silica gel eluting with 0-20% methanol in dichloromethane to get the deprotected alcohol. MS (m/z) 542.17 [M+H]⁺.

A solution of (3R,7S)-12-(benzyloxy)-3-(hydroxymethyl)-1,11-dioxo-N-(2,4,6-trifluorobenzyl)-1,4,5,6,7,11-hexahydro-3H-2,7-methanopyrido[1,2-a][1,4]diazonine-10-carboxamide (76.9 mg, 142.01 umol) in dichloromethane (10 mL) was stirred at rt as Dess-Martin periodinane (91.9 mg, 216.67 umol) was added. After 30 min at rt, the reaction mixture was cooled to 0° C. and saturated sodium bicarbonate (10 mL), 10% sodium thiosulfate solution (10 mL), and dichloromethane (10 mL) were added, before two fractions were separated. After the aqueous fraction was extracted with ethyl acetate (10 mL×2), the organic fractions were combined, dried over MgSO₄, and concentrated. The crude residue was purified by column chromatography on silica gel eluting with 0-8% methanol in dichloromethane to get (3R,7S)-12-(benzyloxy)-3-formyl-1,11-dioxo-N-(2,4,6-trifluorobenzyl)-1,4,5,6,7,11-hexahydro-3H-2,7-methanopyrido[1,2-a][1,4]diazonine-10-carboxamide. MS (m/z) 540.14 [M+H]⁺.

A solution of (3R,7S)-12-(benzyloxy)-3-formyl-1,11-dioxo-N-(2,4,6-trifluorobenzyl)-1,4,5,6,7,11-hexahydro-3H-2,7-methanopyrido[1,2-a][1,4]diazonine-10-carboxamide (63.4 mg, 118 umol) in dichloromethane (2 mL) was stirred at 0° C. as (diethylamino)sulfur trifluoride (0.017 mL, 129 umol) was added. After 30 min, the reaction mixture was stirred at rt for 22 h. Saturated sodium bicarbonate (20 mL) was added, and the mixture was extracted with dichloromethane (2×20 mL). The combined extracts were dried over MgSO₄, concentrated, and the residue was purified by column chromatography on silica gel, eluting with 0-8% methanol in dichloromethane, to get the title compound (131e). MS (m/z) 562.15 [M+H]⁺.

Synthesis of (3R,7S)-3-(difluoromethyl)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (131)

(3R,7S)-12-(benzyloxy)-3-(difluoromethyl)-1,11-dioxo-N-(2,4,6-trifluorobenzyl)-1,4,5,6,7,11-hexahydro-3H-2,7-methanopyrido[1,2-a][1,4]diazonine-10-carboxamide (131e) (66.3 mg, 118 umol) was dissolved in trifluoroacetic acid (2 mL) and stirred at rt. After 1 h, the reaction mixture was concentrated and the residue was purified by preparative HPLC (column, Gemini 10u C18 110A, AXI; 250×21.2 mm), eluting with 10-60% acetonitrile in water (0.1% trifluoroacetic acid), to get the title compound (131). MS (m/z) 472.20 [M+H]⁺. ¹H NMR (400 MHz, Acetonitrile-d₃) δ 10.32 (s, 1H), 8.39 (d, J=2.9 Hz, 1H), 6.94-6.75 (m, 2H), 6.03 (td, J=54.9, 3.5 Hz, 1H), 4.65 (dt, J=15.0, 3.3 Hz, 1H), 4.59 (s, 2H), 4.55 (s, 1H), 3.83 (d, J=14.8 Hz, 1H), 3.72 (dd, J=15.1, 1.7 Hz, 1H), 2.16 (ddd, J=17.1, 12.3, 5.0 Hz, 2H), 1.92-1.73 (m, 3H), 1.24-1.09 (m, 1H). ¹⁹F NMR (376 MHz, Acetonitrile-d₃) δ −77.36, −111.06--111.40 (m), −113.75-−114.10 (m), −125.91--127.10 (m), −128.45 (ddd, J=286.8, 55.2, 12.6 Hz).

Example 129: Preparation of (4R,7S)-4-fluoro-12-hydroxy-4-methyl-1,11-dioxo-N-(2,4,6-trifluorobenzyl)-1,4,5,6,7,11-hexahydro-3H-2,7-methanopyrido[1,2-a][1,4]diazonine-10-carboxamide, (4S,7S)-4-fluoro-12-hydroxy-4-methyl-1,11-dioxo-N-(2,4,6-trifluorobenzyl)-1,4,5,6,7,11-hexahydro-3H-2,7-methanopyrido[1,2-a][1,4]diazonine-10-carboxamide, and (7S)-12-hydroxy-4-methyl-1,11-dioxo-N-(2,4,6-trifluorobenzyl)-1,6,7,11-tetrahydro-3H-2,7-methanopyrido[1,2-a][1,4]diazonine-10-carboxamide (132-1, 132-2, and 132-3)

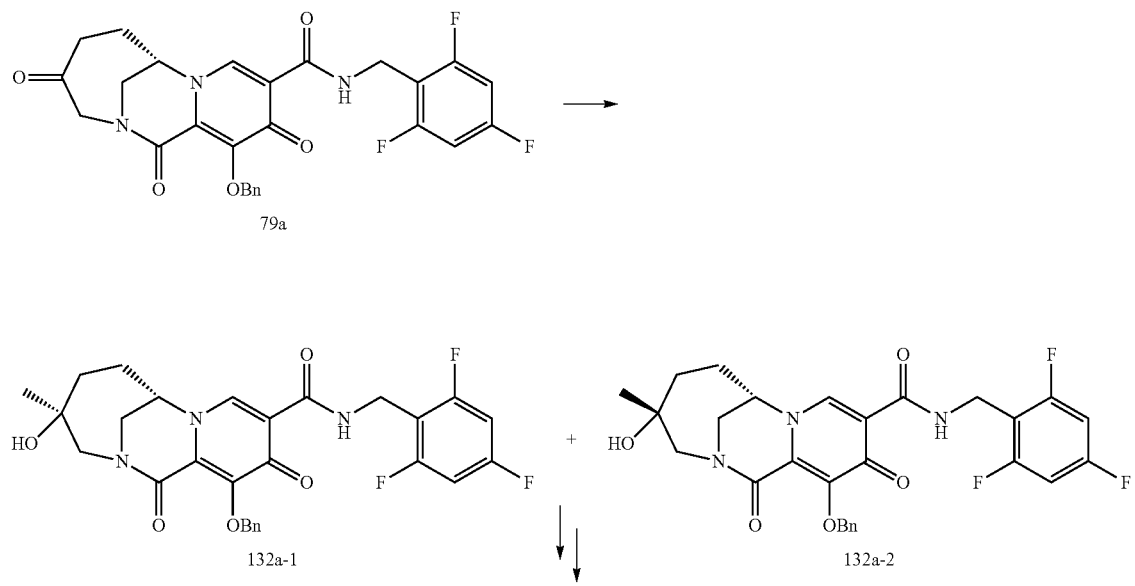

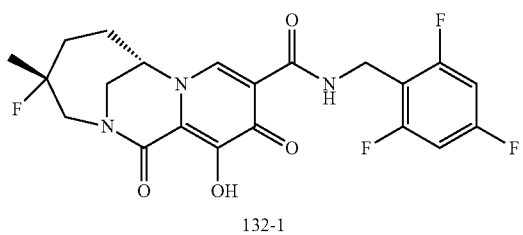

132-1

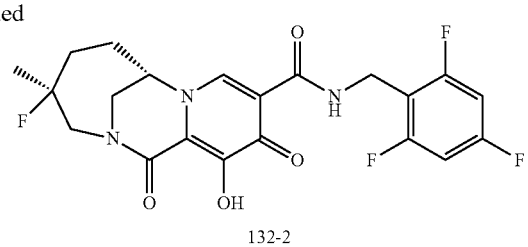

132-2

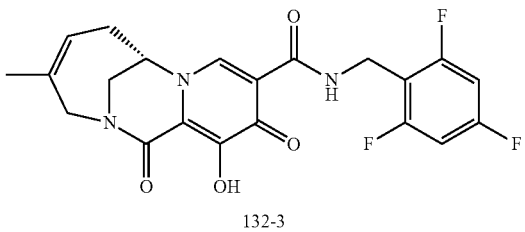

132-3

Synthesis of (4S,7S)-12-(benzyloxy)-4-hydroxy-4-methyl-1,11-dioxo-N-(2,4,6-trifluorobenzyl)-1,4,5,6,7,11-hexahydro-3H-2,7-methanopyrido[1,2-a][1,4]diazonine-10-carboxamide and (4R,7S)-12-(benzyloxy)-4-hydroxy-4-methyl-1,11-dioxo-N-(2,4,6-trifluorobenzyl)-1,4,5,6,7,11-hexahydro-3H-2,7-methanopyrido[1,2-a][1,4]diazonine-10-carboxamide (132a-1 and 132a-2)

The title compounds were synthesized in a similar manner to compounds 107a-1 and 107a-2, using (7S)-12-(benzyloxy)-1,4,11-trioxo-N-(2,4,6-trifluorobenzyl)-1,4,5,6,7,11-hexahydro-3H-2,7-methanopyrido[1,2-a][1,4]diazonine-10-carboxamide (79a), in place of (5R,7S)-5,12-dihydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide (103a).

Synthesis of (4R,7S)-4-fluoro-12-hydroxy-4-methyl-1,11-dioxo-N-(2,4,6-trifluorobenzyl)-1,4,5,6,7,11-hexahydro-3H-2,7-methanopyrido[1,2-a][1,4]diazonine-10-carboxamide, (4S,7S)-4-fluoro-12-hydroxy-4-methyl-1,11-dioxo-N-(2,4,6-trifluorobenzyl)-1,4,5,6,7,11-hexahydro-3H-2,7-methanopyrido[1,2-a][1,4]diazonine-10-carboxamide, and (7S)-12-hydroxy-4-methyl-1,11-dioxo-N-(2,4,6-trifluorobenzyl)-1,6,7,11-tetrahydro-3H-2,7-methanopyrido[1,2-a][1,4]diazonine-10-carboxamide (132-1, 132-2, and 132-3)

The title compounds were prepared in a manner similar to compounds 115-1, 115-2, and 116-1, using (4S,7S)-12-(benzyloxy)-4-hydroxy-4-methyl-1,11-dioxo-N-(2,4,6-trifluorobenzyl)-1,4,5,6,7,11-hexahydro-3H-2,7-methanopyrido[1,2-a][1,4]diazonine-10-carboxamide or (4R,7S)-12-(benzyloxy)-4-hydroxy-4-methyl-1,11-dioxo-N-(2,4,6-trifluorobenzyl)-1,4,5,6,7,11-hexahydro-3H-2,7-methanopyrido[1,2-a][1,4]diazonine-10-carboxamide (132a-1 or 132a-2) in place of (5S,7S)-12-(benzyloxy)-5-hydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide or (5R,7S)-12-(benzyloxy)-5-hydroxy-5-methyl-1,11-dioxo-N-(2,4,6-trifluorobenzyl)-1,4,5,6,7,11-hexahydro-3H-2,7-methanopyrido[1,2-a][1,4]diazonine-10-carboxamide (107a-1 or 107a-2).

132-1: MS (m/z) 454.22 [M+H]$^+$. $^1$H NMR (400 MHz, Acetonitrile-d$_3$) d 9.32 (s, 1H), 8.40 (d, J=5.3 Hz, 1H), 6.87 (t, J=8.5 Hz, 1H), 6.68 (t, J=8.5 Hz, 1H), 4.93-4.69 (m, 2H), 4.58 (q, J=15.7, 14.9 Hz, 2H), 4.42 (dd, J=14.8, 4.8 Hz, 1H), 3.83 (dd, J=14.9, 10.8 Hz, 1H), 3.64 (dd, J=14.9, 6.1 Hz, 1H), 3.11 (td, J=37.5, 15.2 Hz, 2H), 2.11 (m, 2H), 1.48-1.33 (m, 3H).

132-2: MS (m/z) 454.22 [M+H]$^+$. $^1$H NMR (400 MHz, Acetonitrile-d$_3$) d 8.44 (d, J=12.1 Hz, 1H), 6.96-6.82 (m, 1H), 6.69 (t, J=8.5 Hz, 1H), 5.48 (s, 1H), 4.83 (dd, J=15.2, 7.5 Hz, 2H), 4.65 (d, J=16.7 Hz, 2H), 4.54-4.27 (m, 3H), 3.91 (d, J=14.9 Hz, 2H), 3.74 (d, J=14.5 Hz, 2H), 3.51-3.23 (m, 3H), 2.11 (s, 3H), 1.44 (dd, J=22.1, 3.6 Hz, 3H).

132-3: MS (m/z) 434.22 [M+H]$^+$. $^1$H NMR (400 MHz, Acetonitrile-d$_3$) d 10.38 (d, J=25.2 Hz, 1H), 9.30 (s, 1H), 8.39 (d, J=11.5 Hz, 1H), 6.87 (t, J=8.5 Hz, 1H), 6.69 (t, J=8.5 Hz, 1H), 5.39 (s, 1H), 5.15 (d, J=34.3 Hz, 1H), 4.96-4.69 (m, 2H), 4.62 (s, 1H), 4.43 (s, 1H), 4.00-3.64 (m, 2H), 2.85 (m, 2H), 1.72 (s, 3H).

Example 130: Preparation of (7S)-5-fluoro-12-hydroxy-1,11-dioxo-N-(2,4,6-trifluorobenzyl)-1,6,7,11-tetrahydro-3H-2,7-methanopyrido[1,2-a][1,4]diazonine-10-carboxamide (133)

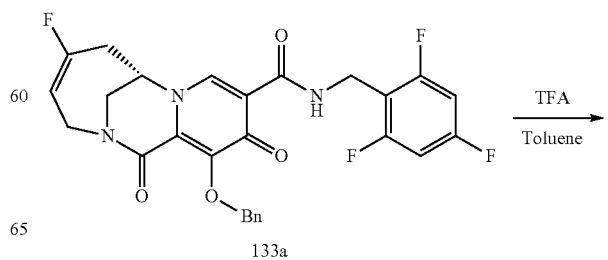

133a

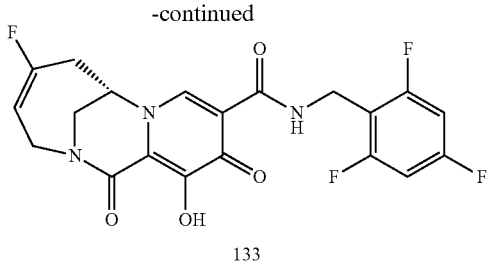

133

(7S)-12-(benzyloxy)-5-fluoro-1,11-dioxo-N-(2,4,6-trifluorobenzyl)-1,6,7,11-tetrahydro-3H-2,7-methanopyrido[1,2-a][1,4]diazonine-10-carboxamide (133a) was prepared in a similar manner to compound 113a-2, using (7S)-12-(benzyloxy)-1,5,11-trioxo-N-(2,4,6-trifluorobenzyl)-1,4,5,6,7,11-hexahydro-3H-2,7-methanopyrido[1,2-a][1,4]diazonine-10-carboxamide (103a) in place of (3S,7S)-12-(benzyloxy)-3-methyl-1,5,11-trioxo-N-(2,4,6-trifluorobenzyl)-1,4,5,6,7,11-hexahydro-3H-2,7-methanopyrido[1,2-a][1,4]diazonine-10-carboxamide.

The title compound was prepared in a similar manner to compound 113, using (7S)-12-(benzyloxy)-5-fluoro-1,11-dioxo-N-(2,4,6-trifluorobenzyl)-1,6,7,11-tetrahydro-3H-2,7-methanopyrido[1,2-a][1,4]diazonine-10-carboxamide (133a) in place of (3S,7S)-12-(benzyloxy)-5,5-difluoro-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (113a-1). MS (m/z): 438.22 [M+H]$^+$. $^1$H NMR (400 MHz, Acetonitrile-d$_3$) δ 10.28 (s, 1H), 8.43 (s, 1H), 6.86 (t, J=8.5 Hz, 2H), 5.46 (d, J=22.3 Hz, 1H), 5.04 (s, 1H), 4.61 (d, J=4.9 Hz, 2H), 4.46 (q, J=10.3, 9.7 Hz, 1H), 3.91 (s, 2H), 3.42-3.31 (m, 1H), 3.29-3.14 (m, 1H), 2.60-2.40 (m, 1H).

Example 131: Preparation of (7S)—N-(2,4-difluorobenzyl)-7-ethyl-12-hydroxy-1,11-dioxo-1,4,5,6,7,11-hexahydro-3H-27-methanopyrido[1,2-a][1,4]diazonine-10-carboxamide and (7R)—N-(2,4-difluorobenzyl)-7-ethyl-12-hydroxy-1,11-dioxo-1,4,5,6,7,11-hexahydro-3H-27-methanopyrido[1,2-a][1,4]diazonine-10-carboxamide (134-1 and 134-2)

134-1

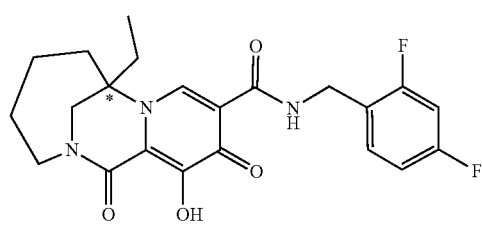

134-2

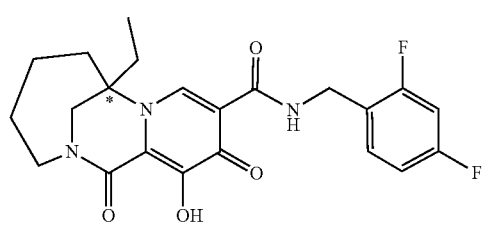

The title compounds were prepared similarly to compounds 59-1 and 59-2, using EtMgBr in place of MeMgBr, and methyl 3-(benzyloxy)-5-((2,4-difluorobenzyl)carbamoyl)-4-oxo-4H-pyran-2-carboxylate in place of methyl 3-(benzyloxy)-4-oxo-5-((2,4,6-trifluorobenzyl)carbamoyl)-4H-pyran-2-carboxylate. The stereoisomers were separated by SFC chromatography on an IA column using methanol co-solvent.

134-1: MS (m/z) 449.9 [M+H]$^+$. $^1$H NMR (400 MHz, Chloroform-d) δ 10.49 (s, 1H), 8.5 (s, 1H), 7.39 (s, 1H), 6.83 (m, 2H), 4.66 (m, 2H), 4.48 (m, 1H), 3.80 (m, 1H), 3.39 (m, 1H), 3.07 (m, 1H), 2.35-0.80 (m, 11H).

134-2: MS (m/z) 449.9 [M+H]$^+$. $^1$H NMR (400 MHz, Chloroform-d) δ 10.48 (s, 1H), 8.5 (s, 1H), 7.39 (s, 1H), 6.83 (m, 2H), 4.7 (m, 2H), 4.62 (m, 1H), 3.81 (m, 1H), 3.39 (m, 1H), 3.07 (m, 1H), 2.31-0.75 (m, 11H).

Example 132: Preparation of (12S)-7-hydroxy-3-methyl-6,8-dioxo-N-(2,4,6-trifluorobenzyl)-6,8,12,13-tetrahydro-4H-5,12-methanoisoxazolo[4,5-f]pyrido[1,2-a][1,4]diazonine-9-carboxamide and (5S)-10-hydroxy-3-methyl-9,11-dioxo-N-(2,4,6-trifluorobenzyl)-4,9,11,13-tetrahydro-5H-5,12-methanoisoxazolo[5,4-f]pyrido[1,2-a][1,4]diazonine-8-carboxamide (135-1 and 135-2)

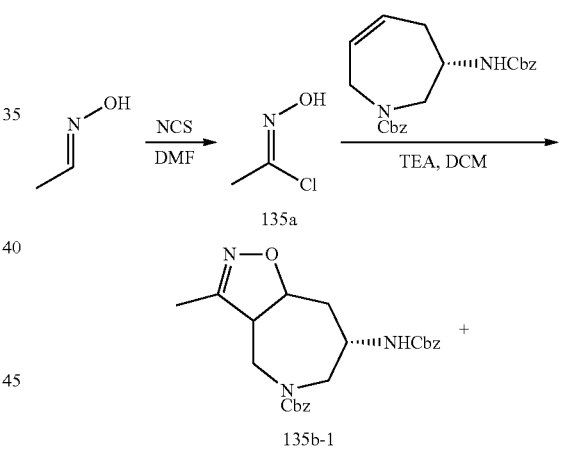

135a 135b-1

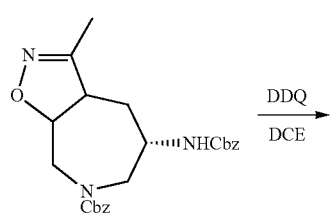

135b-2

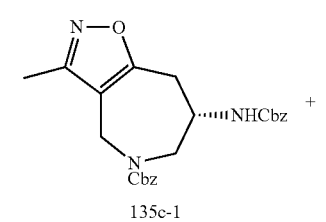

135c-1

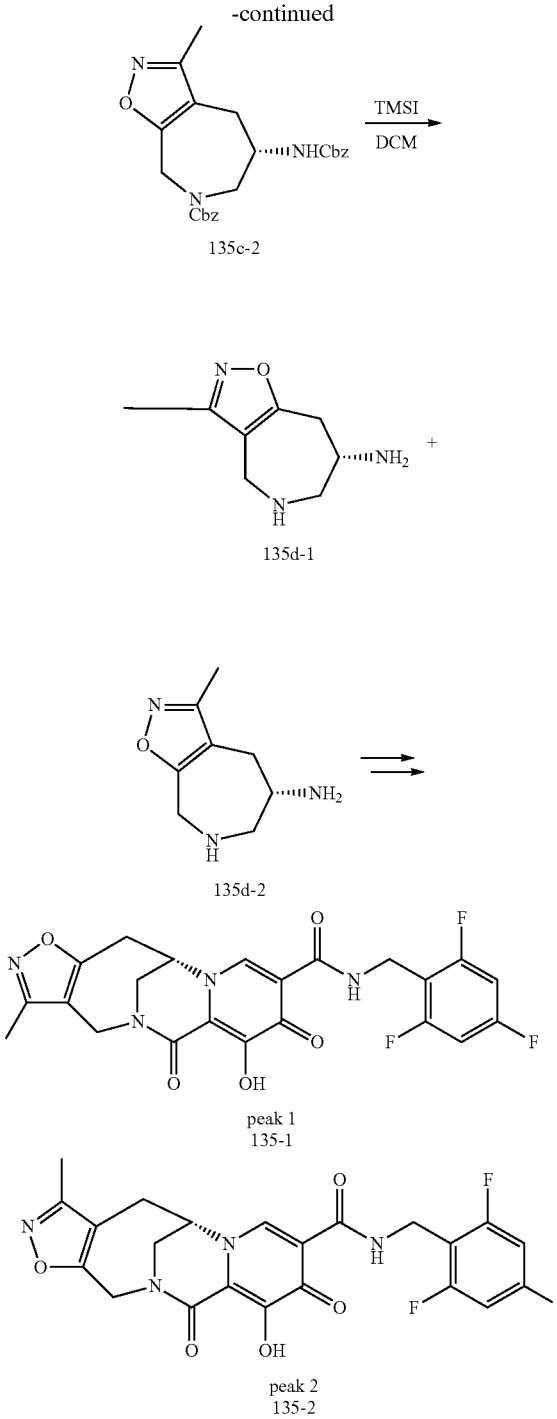

Synthesis of benzyl (7S)-7-(((benzyloxy)carbonyl)amino)-3-methyl-3a,4,6,7,8,8a-hexahydro-5H-isoxazolo[4,5-c]azepine-5-carboxylate and benzyl (5S)-5-(((benzyloxy)carbonyl)amino)-3-methyl-3a,4,5,6,8,8a-hexahydro-7H-isoxazolo[5,4-c]azepine-7-carboxylate (135b-1 and 135b-2)

To a solution of benzyl (S)-3-(((benzyloxy)carbonyl)amino)-2,3,4,7-tetrahydro-1H-azepine-1-carboxylate (1.22 g, 3.21 mmol) and TEA (813 mg, 8.03 mmol) in DCM (50 mL) N-hydroxyacetimidoyl chloride (135a) was added at rt. After the reaction mixture was stirred for 48 hr, it was extracted with ethyl acetate (150 mL), washed with brine, and dried over MgSO$_4$. The solvent was then removed to obtain the title compounds (135b-1 and 135b-2) as a mixture of regioisomers, which were used subsequently without further purification. MS (m/z) 438.2 [M+H]$^+$.

Synthesis of benzyl (S)-7-(((benzyloxy)carbonyl)amino)-3-methyl-4,6,7,8-tetrahydro-5H-isoxazolo[4,5-c]azepine-5-carboxylate and benzyl (S)-5-(((benzyloxy)carbonyl)amino)-3-methyl-4,5,6,8-tetrahydro-7H-isoxazolo[5,4-c]azepine-7-carboxylate (135c-1 and 135c-2)

To a solution of crude mixture of benzyl (7S)-7-(((benzyloxy)carbonyl)amino)-3-methyl-3a,4,6,7,8,8a-hexahydro-5H-isoxazolo[4,5-c]azepine-5-carboxylate and benzyl (5S)-5-(((benzyloxy)carbonyl)amino)-3-methyl-3a,4,5,6,8,8a-hexahydro-7H-isoxazolo[5,4-c]azepine-7-carboxylate (135b-1 and 135b-2, 890 mg) in DCE (100 mL), DDQ (462 mg, 2.03 mmol) was added. The solution was heated to reflux for 4 hr. The reaction was concentrated, and the residue purified by silica-gel column to provide the title compounds (135c-1 and 135c-2) as a mixture of regioisomers. MS (m/z) 436.1 [M+H]$^+$.

Synthesis of (S)-3-methyl-5,6,7,8-tetrahydro-4H-isoxazolo[4,5-c]azepin-7-amine and (S)-3-methyl-5,6,7,8-tetrahydro-4H-isoxazolo[5,4-c]azepin-5-amine (135d-1 and 135d-2)

To a solution of benzyl (S)-7-(((benzyloxy)carbonyl)amino)-3-methyl-4,6,7,8-tetrahydro-5H-isoxazolo[4,5-c]azepine-5-carboxylate and benzyl (S)-5-(((benzyloxy)carbonyl)amino)-3-methyl-4,5,6,8-tetrahydro-7H-isoxazolo[5,4-c]azepine-7-carboxylate (135c-1 and 135c-2, 354 mg) in DCM (10 mL), TMSI (1 mL) was added. After 30 min, HCl (1 N, 2 mL) was added and stirred for 30 min. Concentration gave the title compounds (135d-1 and 135d-2) as a mixture of regioisomers, which were used subsequently without further purification. MS (m/z) 167.95 [M+H]$^+$.

Synthesis of (12S)-7-hydroxy-3-methyl-6,8-dioxo-N-(2,4,6-trifluorobenzyl)-6,8,12,13-tetrahydro-4H-5,12-methanoisoxazolo[4,5-f]pyrido[1,2-a][1,4]diazonine-9-carboxamide and (5S)-10-hydroxy-3-methyl-9,11-dioxo-N-(2,4,6-trifluorobenzyl)-4,9,11,13-tetrahydro-5H-5,12-methanoisoxazolo[5,4-f]pyrido[1,2-a][1,4]diazonine-8-carboxamide (135-1 and 135-2)

The title compounds were prepared similarly to compound 28 using (S)-3-methyl-5,6,7,8-tetrahydro-4H-isoxazolo[4,5-c]azepin-7-amine and (S)-3-methyl-5,6,7,8-tetrahydro-4H-isoxazolo[5,4-c]azepin-5-amine (135d-1 and 135d-2) in place of 1,4-oxazepan-6-amine, and methyl Synthesis of (Z)—N-hydroxyacetimidoyl chloride (135a)

To a solution of acetaldehyde oxime (1.598 g, 27.1 mmol) in DMF (50 mL), NCS (3.61 g, 27.1 mmol) was added at rt, then the reaction was heated to 50° C., and stirred for 2 hr. The reaction mixture was extracted with ethyl acetate (150 mL) and washed with brine. The organic layer was dried over MgSO$_4$, and the solvent removed to obtain the title compound (135a), which was used for the next step of the reaction.

3-(benzyloxy)-4-oxo-5-((2,4,6-trifluorobenzyl)carbamoyl)-4H-pyran-2-carboxylate in place of methyl 3-(benzyloxy)-5-((2,4-difluorobenzyl)carbamoyl)-4-oxo-4H-pyran-2-carboxylate, and separating the regioisomers by normal phase chromatography prior to TFA deprotection.

135-1, from peak 1: MS (m/z) 475.04 [M+H]$^+$. $^1$H NMR (400 MHz, Chloroform-d) δ 10.27 (t, J=5.8 Hz, 1H), 8.54 (s, 1H), 6.67 (t, J=8.1 Hz, 2H), 5.36 (dd, J=16.5, 1.7 Hz, 1H), 4.84 (d, J=9.3 Hz, 1H), 4.67 (t, J=6.4 Hz, 2H), 4.13 (d, J=14.4 Hz, 1H), 4.01-3.74 (m, 4H), 3.05 (d, J=18.3 Hz, 1H), 2.25 (s, 3H).

135-2, from peak 2: MS (m/z) 475.05 [M+H]$^+$. $^1$H NMR (400 MHz, Chloroform-d) δ 10.33 (d, J=6.2 Hz, 1H), 8.59 (s, 1H), 6.67 (t, J=8.1 Hz, 2H), 5.70 (d, J=17.2 Hz, 1H), 4.85 (s, 1H), 4.68 (t, J=5.7 Hz, 2H), 4.34 (d, J=17.2 Hz, 1H), 4.13 (d, J=14.3 Hz, 1H), 3.76 (d, J=14.3 Hz, 1H), 3.34 (d, J=14.8 Hz, 1H), 2.69 (d, J=17.0 Hz, 1H), 2.20 (s, 3H).

Example 133: Preparation of (13S)-10-chloro-4-hydroxy-3,5-dioxo-N-(2,4,6-trifluorobenzyl)-3,5,8,13-tetrahydro-7H-6,13-methanobenzo[g]pyrido[1,2-a][1,4]diazonine-2-carboxamide and (13R)-10-chloro-4-hydroxy-3,5-dioxo-N-(2,4,6-trifluorobenzyl)-3,5,8,13-tetrahydro-7H-6,13-methanobenzo[g]pyrido[1,2-a][1,4]diazonine-2-carboxamide (136-1 and 136-2)

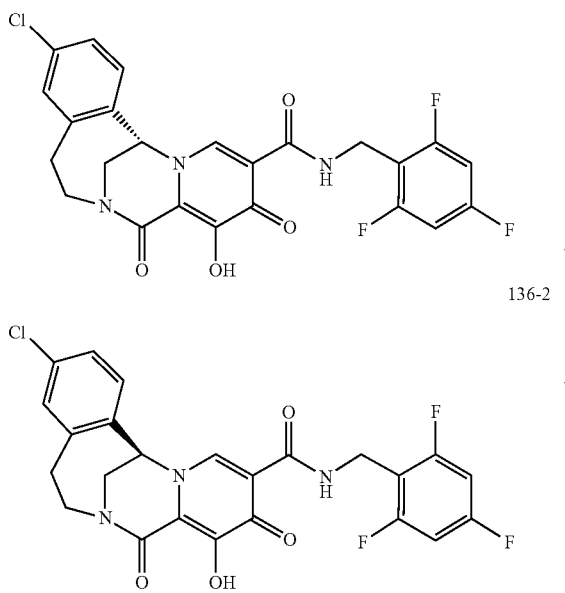

The title compounds were prepared in a manner similar to compounds 127-1 and 127-2, using 7-chloro-1,3,4,5-tetrahydro-2H-benzo[d]azepin-2-one in place of 6-chloro-3,4-dihydronaphthalen-2(1H)-one.

136-1: MS (m/z) 504.20 [M+H]$^+$. $^1$H NMR (400 MHz, DMSO-d$_6$) δ 10.38 (t, J=5.8 Hz, 1H), 10.23 (s, 1H), 9.02 (s, 1H), 7.50-7.31 (m, 2H), 7.31-7.14 (m, 2H), 6.02 (s, 1H), 4.73-4.55 (m, 2H), 4.45 (dd, J=15.1, 2.7 Hz, 1H), 4.29 (td, J=12.6, 5.4 Hz, 1H), 4.00 (d, J=15.1 Hz, 1H), 3.48-3.41 (m, 2H), 2.88 (dd, J=15.4, 5.4 Hz, 1H).

136-2: MS (m/z) 504.21 [M+H]$^+$. $^1$H NMR (400 MHz, DMSO-d$_6$) δ 10.38 (t, J=5.7 Hz, 1H), 10.22 (s, 1H), 9.02 (s, 1H), 7.46-7.30 (m, 2H), 7.30-7.12 (m, 2H), 6.02 (s, 1H), 4.60 (d, J=6.7 Hz, 2H), 4.45 (dd, J=15.1, 2.8 Hz, 1H), 4.29 (td, J=12.6, 5.4 Hz, 1H), 4.00 (d, J=15.1 Hz, 1H), 3.60 (d, J=8.0 Hz, 1H), 3.45 (s, 2H), 2.94-2.82 (m, 1H).

Example 134: Preparation of (4S,7S)-12-hydroxy-4-methyl-1,11-dioxo-N-(2,4,6-trifluorobenzyl)-1,4,5,6,7,11-hexahydro-3H-2,7-methanopyrido[1,2-a][1,4]diazonine-10-carboxamide and (4R,7S)-12-hydroxy-4-methyl-1,11-dioxo-N-(2,4,6-trifluorobenzyl)-1,4,5,6,7,11-hexahydro-3H-2,7-methanopyrido[1,2-a][1,4]diazonine-10-carboxamide (137-1 and 137-2)

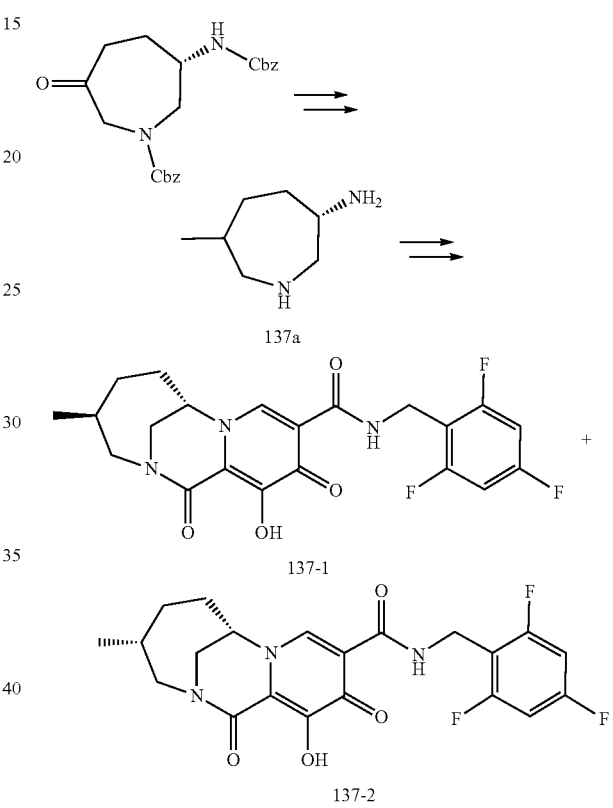

Synthesis of (3S)-6-methylazepan-3-amine (137a)

The title compound was prepared in a method similar to compound 124, using benzyl (S)-3-(((benzyloxy)carbonyl)amino)-6-oxoazepane-1-carboxylate in place of (7S)-12-(benzyloxy)-1,5,11-trioxo-N-(2,4,6-trifluorobenzyl)-1,4,5,6,7,11-hexahydro-3H-2,7-methanopyrido[1,2-a][1,4]diazonine-10-carboxamide (103a), and Pd(OH)$_2$/C in place of Pd/C.

Synthesis of (4S,7S)-12-hydroxy-4-methyl-1,11-dioxo-N-(2,4,6-trifluorobenzyl)-1,4,5,6,7,11-hexahydro-3H-2,7-methanopyrido[1,2-a][1,4]diazonine-10-carboxamide (137-1 and 137-2)

The title compounds were synthesized in a manner similar to compounds 40-1 and 40-2, using (3S)-6-methylazepan-3-amine (137a) in place of rel-(1R,4S,6R)-2-Azabicyclo[4.2.1]nonan-4-amine (40f). Chiral separation was carried out prior to benzyl deprotection.

137-1: MS (m/z) 436.25 [M+H]$^+$. $^1$H NMR (400 MHz, Acetonitrile-d$_3$) δ 10.42 (s, 1H), 8.39 (s, 1H), 6.98-6.75 (m, 2H), 4.71-4.48 (m, 3H), 3.87 (dt, J=14.6, 2.4 Hz, 1H), 3.78 (dd, J=13.2, 10.3 Hz, 1H), 3.62 (dd, J=14.7, 1.5 Hz, 1H), 3.30 (dd, J=13.2, 7.1 Hz, 1H), 2.23-2.04 (m, 2H), 1.50 (dt, J=15.2, 4.1 Hz, 1H), 1.20 (dddd, J=15.6, 13.2, 10.5, 2.7 Hz, 1H), 1.01 (d, J=6.7 Hz, 3H).

137-2: MS (m/z) 436.25 [M+H]$^+$. $^1$H NMR (400 MHz, Acetonitrile-d$_3$) d 10.38 (s, 1H), 8.38 (s, 1H), 6.86 (d, J=10.2 Hz, 2H), 4.58 (d, J=22.0 Hz, 3H), 4.36 (d, J=12.6 Hz, 2H), 3.92-3.53 (m, 4H), 2.65 (s, 2H), 1.82-1.37 (m, 3H), 0.99 (dd, J=18.0, 6.4 Hz, 3H).

Example 135: Preparation of (13S)-11-chloro-4-hydroxy-3,5-dioxo-N-(2,4,6-trifluorobenzyl)-3,5,8,13-tetrahydro-7H-6,13-methanobenzo[g]pyrido[1,2-a][1,4]diazonine-2-carboxamide (138)

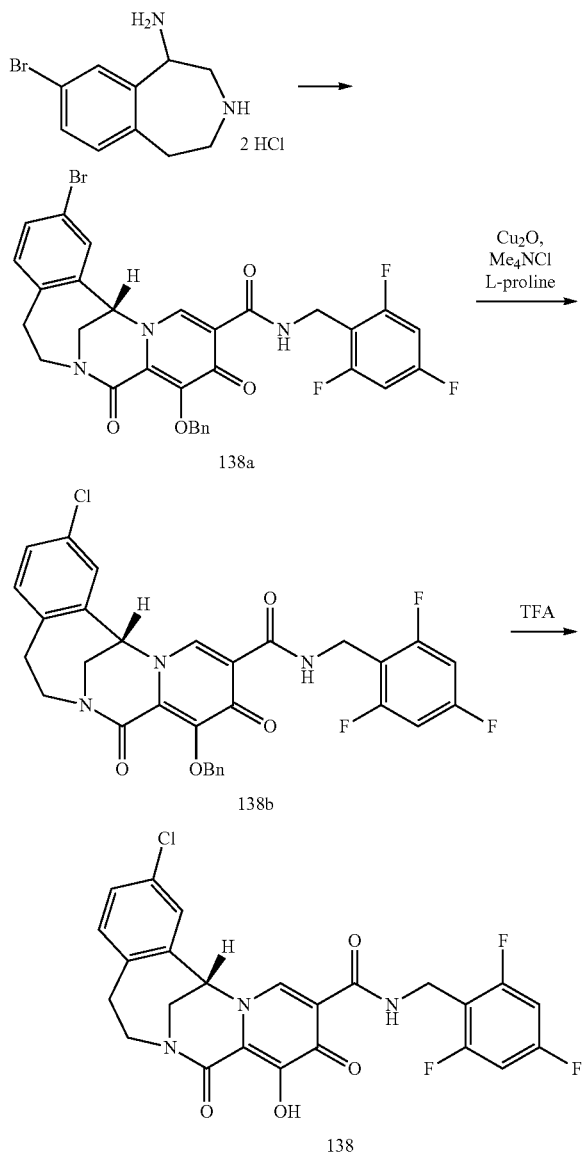

Synthesis of (13S)-4-(benzyloxy)-11-bromo-3,5-dioxo-N-(2,4,6-trifluorobenzyl)-3,5,8,13-tetrahydro-7H-6,13-methanobenzo[g]pyrido[1,2-a][1,4]diazonine-2-carboxamide (138a)

The title compound was prepared in a similar manner to compound 63g, using 8-bromo-2,3,4,5-tetrahydro-1H-benzo[d]azepin-1-amine dihydrochloride (122d) in place of 2,3,4,5-tetrahydro-1H-benzo[d]azepin-1-amine dihydrobromide (63f).

Synthesis of (13S)-4-(benzyloxy)-11-chloro-3,5-dioxo-N-(2,4,6-trifluorobenzyl)-3,5,8,13-tetrahydro-7H-6,13-methanobenzo[g]pyrido[1,2-a][1,4]diazonine-2-carboxamide (138b)

To a microwave tube with a stir bar was added (13S)-4-(benzyloxy)-11-bromo-3,5-dioxo-N-(2,4,6-trifluorobenzyl)-3,5,8,13-tetrahydro-7H-6,13-methanobenzo[g]pyrido[1,2-a][1,4]diazonine-2-carboxamide, (138a, 0.055 g, 0.086 mmol), Me$_4$NCl (0.0094 g, 0.086 mmol), L-proline (0.0020 g, 0.017 mmol), and cuprous oxide (0.0012 g, 0.0086 mmol). The tube was sealed, evacuated, and backfilled with Argon twice. Ethanol (1 mL) was added and the suspension was heated to 100° C. overnight. The reaction mixture was concentrated and purified by column chromatography (0-100% EtOAc/heptane) to give an inseparable mixture of (13S)-4-(benzyloxy)-11-bromo-3,5-dioxo-N-(2,4,6-trifluorobenzyl)-3,5,8,13-tetrahydro-7H-6,13-methanobenzo[g]pyrido[1,2-a][1,4]diazonine-2-carboxamide and (13S)-4-(benzyloxy)-11-chloro-3,5-dioxo-N-(2,4,6-trifluorobenzyl)-3,5,8,13-tetrahydro-7H-6,13-methanobenzo[g]pyrido[1,2-a][1,4]diazonine-2-carboxamide (138a and 138b), which was used without further purification.

Synthesis of (13S)-11-chloro-4-hydroxy-3,5-dioxo-N-(2,4,6-trifluorobenzyl)-3,5,8,13-tetrahydro-7H-6,13-methanobenzo[g]pyrido[1,2-a][1,4]diazonine-2-carboxamide (138)

To a flask containing an inseparable mixture of (13S)-4-(benzyloxy)-11-bromo-3,5-dioxo-N-(2,4,6-trifluorobenzyl)-3,5,8,13-tetrahydro-7H-6,13-methanobenzo[g]pyrido[1,2-a][1,4]diazonine-2-carboxamide and (13S)-4-(benzyloxy)-11-chloro-3,5-dioxo-N-(2,4,6-trifluorobenzyl)-3,5,8,13-tetrahydro-7H-6,13-methanobenzo[g]pyrido[1,2-a][1,4]diazonine-2-carboxamide (138a and 138b, 0.0085 g, 0.014 mmol) was added a 1:1 toluene/TFA solution (2 mL). The reaction mixture was stirred at rt for 3 h. The reaction mixture was concentrated, dissolved in MeCN, filtered, and purified by preparative HPLC (column, Gemini 10μ C18 110A, AXI/; 250×21.2 mm), eluting with 5-100% acetonitrile in water (0.1% TFA) over 30 minutes, to afford the title compound. MS (m/z) 504.14 [M+H]$^+$. $^1$H NMR (400 MHz, DMSO-d$_6$) δ 10.37 (t, J=5.7 Hz, 1H), 9.07 (s, 1H), 7.40-7.18 (m, 5H), 5.98 (s, 1H), 4.61 (qd, J=14.6, 5.7 Hz, 2H), 4.44 (dd, J=15.2, 2.8 Hz, 1H), 4.27 (td, J=12.6, 5.5 Hz, 1H), 4.00 (d, J=15.1 Hz, 1H), 3.62-3.50 (m, 2H), 2.88 (dd, J=15.4, 5.5 Hz, 1H). $^{19}$F NMR (376 MHz, DMSO-d$_6$) δ -109.22 (tt, J=9.6, 6.3 Hz), -112.53 (t, J=7.3 Hz).

Example 136: Preparation of (6R)—N-(3-chloro-2,4-difluorobenzyl)-9,10-difluoro-1-hydroxy-2,14-dioxo-2,7,12,14-tetrahydro-6H-6,13-methanobenzo[f]pyrido[1,2-a][1,4]diazonine-3-carboxamide and (6S)—N-(3-chloro-2,4-difluorobenzyl)-9,10-difluoro-1-hydroxy-2,14-dioxo-2,7,12,14-tetrahydro-6H-6,13-methanobenzo[f]pyrido[1,2-a][1,4]diazonine-3-carboxamide (139-1 and 139-2)

Example 137: Preparation of (13S)-10-chloro-N-(2,4-difluorobenzyl)-4-hydroxy-3,5-dioxo-3,5,8,13-tetrahydro-7H-6,13-methanobenzo[g]pyrido[1,2-a][1,4]diazonine-2-carboxamide and (13R)-10-chloro-N-(2,4-difluorobenzyl)-4-hydroxy-3,5-dioxo-3,5,8,13-tetrahydro-7H-6,13-methanobenzo[g]pyrido[1,2-a][1,4]diazonine-2-carboxamide (140-1 and 140-2)

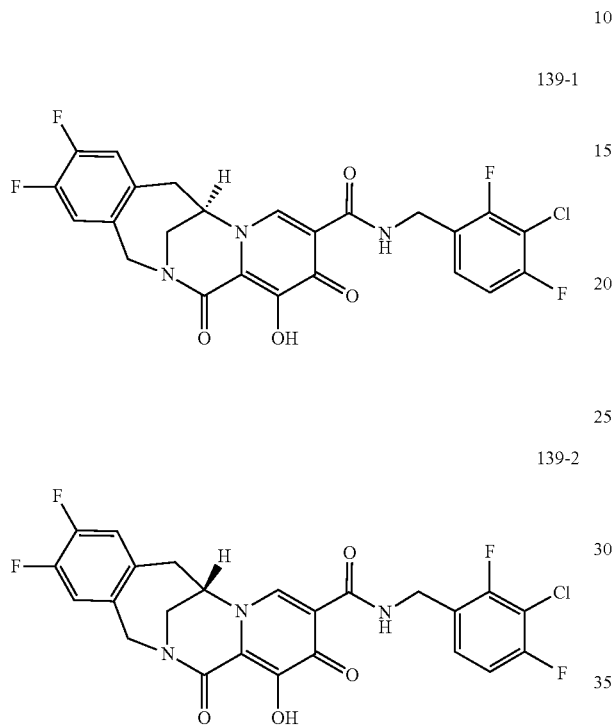

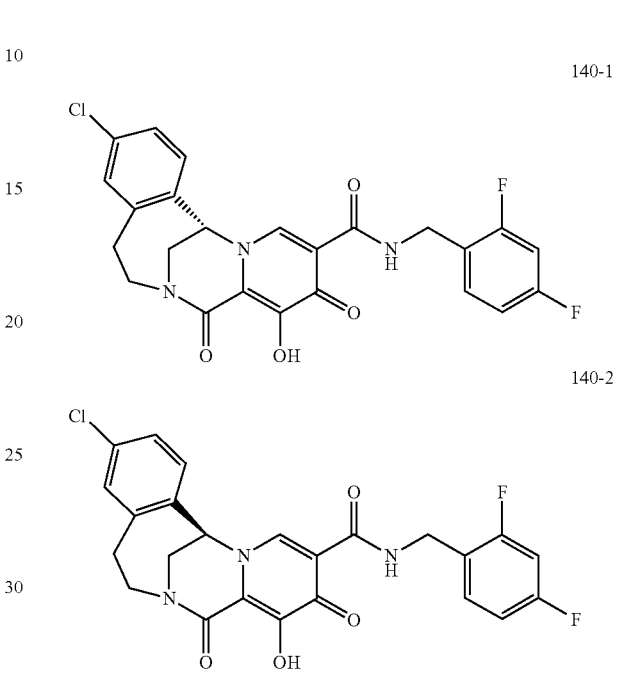

The title compounds were prepared in a similar manner as compounds 127-1 and 127-2, using 6,7-difluoro-3,4-dihydronaphthalen-2(1H)-one in place of 6-chloro-3,4-dihydronaphthalen-2(1H)-one, and ethyl 3-benzyloxy-5-[(3-chloro-2,4-difluoro-phenyl)methylcarbamoyl]-4-oxo-pyran-2-carboxylate in place of methyl 3-(benzyloxy)-4-oxo-5-((2,4,6-trifluorobenzyl)carbamoyl)-4H-pyran-2-carboxylate. Chiral separation was carried out using preparative SFC (IB, 45% MeOH containing 0.1% diethylamine).

139-1: MS (m/z) 522.15 [M+H]$^+$. $^1$H NMR (400 MHz, DMSO-d$_6$) δ 10.36 (t, J=6.0 Hz, 1H), 8.52 (s, 1H), 7.46-7.35 (m, 2H), 7.35-7.22 (m, 2H), 5.47 (d, J=16.6 Hz, 1H), 4.99 (td, J=7.8, 2.3 Hz, 1H), 4.61 (d, J=6.0 Hz, 2H), 4.44 (d, J=16.7 Hz, 1H), 3.80 (d, J=14.7 Hz, 1H), 3.62 (dd, J=14.8, 2.8 Hz, 1H), 3.35-3.35 (m, 1H), 2.87 (dd, J=15.1, 7.6 Hz, 1H). $^{19}$F NMR (376 MHz, DMSO-d$_6$) δ −115.99−−116.39 (m), −118.35 (d, J=8.0 Hz), −141.06 (ddd, J=22.1, 11.2, 8.2 Hz), −141.91 (dt, J=21.1, 9.8 Hz).

139-2: MS (m/z) 522.13 [M+H]$^+$. $^1$H NMR (400 MHz, DMSO-d$_6$) δ 10.36 (t, J=6.0 Hz, 1H), 8.52 (s, 1H), 7.47-7.34 (m, 2H), 7.34-7.22 (m, 2H), 5.47 (d, J=16.6 Hz, 1H), 4.99 (td, J=7.5, 2.2 Hz, 1H), 4.61 (d, J=6.0 Hz, 2H), 4.44 (d, J=16.7 Hz, 1H), 3.80 (d, J=14.6 Hz, 1H), 3.62 (dd, J=14.8, 2.8 Hz, 1H), 3.38 (dd, J=15.2, 7.3 Hz, 1H), 2.86 (dd, J=15.0, 7.6 Hz, 1H). $^{19}$F NMR (376 MHz, DMSO-d$_6$) δ −116.19 (td, J=7.4, 6.2, 2.3 Hz), −118.36 (d, J=8.1 Hz), −141.05 (ddd, J=23.3, 11.7, 8.3 Hz), −141.90 (dt, J=21.0, 9.9 Hz).

The title compounds were prepared in a manner similar to compounds 136-1 and 136-2, using methyl 3-(benzyloxy)-5-((2,4-difluorobenzyl)carbamoyl)-4-oxo-4H-pyran-2-carboxylate in place of methyl 3-(benzyloxy)-4-oxo-5-((2,4,6-trifluorobenzyl)carbamoyl)-4H-pyran-2-carboxylate.

140-1: MS (m/z) 486.19 [M+H]$^+$. $^1$H NMR (400 MHz, DMSO-d$_6$) δ 10.35 (t, J=5.9 Hz, 1H), 9.03 (s, 1H), 7.46 (td, J=8.7, 6.5 Hz, 1H), 7.41-7.32 (m, 2H), 7.32-7.22 (m, 2H), 7.15-7.04 (m, 1H), 6.04 (s, 1H), 4.66-4.51 (m, 2H), 4.46 (dd, J=15.2, 2.7 Hz, 1H), 4.30 (td, J=12.6, 5.4 Hz, 1H), 4.02 (d, J=15.0 Hz, 1H), 3.62 (d, J=13.3 Hz, 2H), 2.89 (dd, J=15.3, 5.4 Hz, 1H).

140-2: MS (m/z) 486.21 [M+H]$^+$. $^1$H NMR (400 MHz, DMSO-d$_6$) δ 10.35 (t, J=5.9 Hz, 1H), 10.23 (s, 1H), 9.03 (s, 1H), 7.46 (td, J=8.7, 6.6 Hz, 1H), 7.42-7.33 (m, 1H), 7.33-7.20 (m, 2H), 7.13-7.02 (m, 1H), 6.55 (s, 1H), 6.04 (s, 1H), 4.70-4.50 (m, 2H), 4.46 (dd, J=15.1, 2.7 Hz, 1H), 4.30 (td, J=12.7, 5.5 Hz, 1H), 4.02 (d, J=15.0 Hz, 1H), 3.69-3.53 (m, 2H), 2.89 (dd, J=15.3, 5.4 Hz, 1H).

Example 138: Preparation of 12-hydroxy-1,11-dioxo-N-(2,4,6-trifluorobenzyl)-5-(trifluoromethyl)-1,4,5,6,7,11-hexahydro-3H-2,7-methanopyrido[1,2-a][1,4,7]triazonine-10-carboxamide (141)

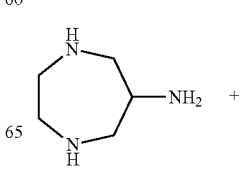

-continued

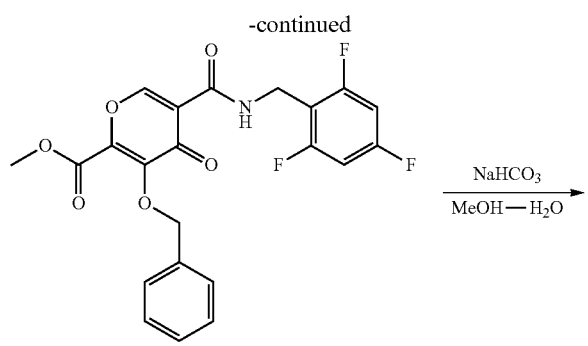

141a

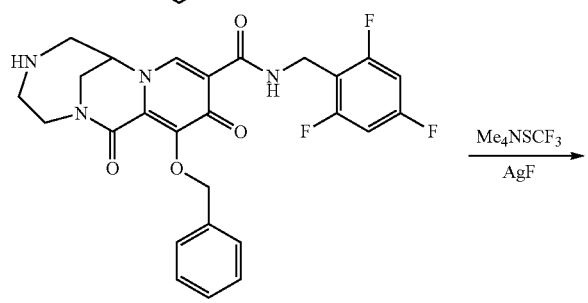

141b

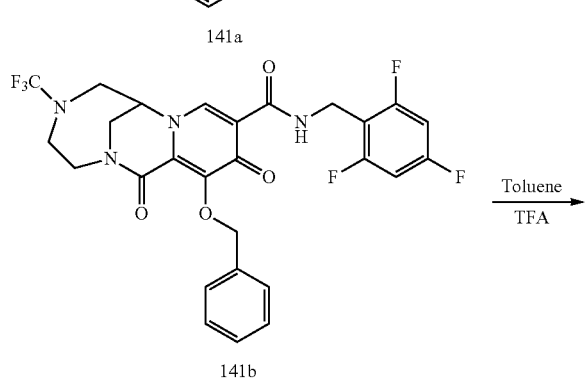

141

Synthesis of 12-(benzyloxy)-1,11-dioxo-N-(2,4,6-trifluorobenzyl)-1,4,5,6,7,11-hexahydro-3H-2,7-methanopyrido[1,2-a][1,4,7]triazonine-10-carboxamide (141a)

To a solution of 1,4-diazepan-6-amine (82.2 mg, 0.714 mmol) in MeOH (3 mL) and H₂O (0.5 mL), sodium bicarbonate (135 mg, 1.61 mmol) and methyl 3-(benzyloxy)-4-oxo-5-((2,4,6-trifluorobenzyl)carbamoyl)-4H-pyran-2-carboxylate (180 mg, 0.402 mmol) were added at rt. The reaction mixture was stirred overnight at 50° C., then extracted with ethyl acetate (100 mL). The organic phase was washed with brine, dried over MgSO₄, and concentrated. The residue was purified by silica-gel column to provide the title compound (141a). MS (m/z) 513.126 [M+H]⁺.

Synthesis of 12-(benzyloxy)-1,11-dioxo-N-(2,4,6-trifluorobenzyl)-5-(trifluoromethyl)-1,4,5,6,7,11-hexahydro-3H-2,7-methanopyrido[1,2-a][1,4,7]triazonine-10-carboxamide (141b)

To a solution of 12-(benzyloxy)-1,11-dioxo-N-(2,4,6-trifluorobenzyl)-1,4,5,6,7,11-hexahydro-3H-2,7-methanopyrido[1,2-a][1,4,7]triazonine-10-carboxamide (141a, 125 mg, 0.244 mmol) in ACN (5 mL), tetramethylammonium trifluormethylthiolate (70 mg, 0.399 mmol) was added at rt. The reaction mixture was stirred for 30 min, then AgF (92.8 mg, 0.73 mmol) was added, and the reaction mixture was stirred at 50° C. for 4 hr. After the reaction was cooled to rt, the reaction mixture was filtered through Celite®, and the solvent was removed. The residue was purified by silica-gel column to provide the title compound (141b). MS (m/z) 581.1 [M+H]⁺.

Synthesis of 12-hydroxy-1,11-dioxo-N-(2,4,6-trifluorobenzyl)-5-(trifluoromethyl)-1,4,5,6,7,11-hexahydro-3H-2,7-methanopyrido[1,2-a][1,4,7]triazonine-10-carboxamide (141)

The title compound was prepared similarly to compound 28, using 12-(benzyloxy)-1,11-dioxo-N-(2,4,6-trifluorobenzyl)-5-(trifluoromethyl)-1,4,5,6,7,11-hexahydro-3H-2,7-methanopyrido[1,2-a][1,4,7] triazonine-10-carboxamide (141b) in place of (7S)-12-(benzyloxy)-N-(2,4-difluorobenzyl)-1,11-dioxo-1,3,4,6,7,11-hexahydro-2,7-methanopyrido[1,2-d][1,4,7]oxadiazonine-10-carboxamide (28a). MS (m/z) 491.1 [M+H]⁺. ¹H NMR (400 MHz, DMSO-d₆) δ 10.33 (dt, J=6.0, 3.9 Hz, 1H), 8.61 (d, J=1.8 Hz, 1H), 7.18 (t, J=8.7 Hz, 2H), 4.78 (s, 1H), 4.56 (t, J=4.5 Hz, 2H), 4.32 (m, 1H), 4.10 (d, J=15.6 Hz, 1H), 4.03-3.92 (m, 1H), 3.85 (d, J=14.7 Hz, 2H), 3.59 (d, J=15.5 Hz, 1H), 3.55-3.42 (m, 1H), 3.17 (dd, J=13.2, 6.2 Hz, 1H).

Example 139: Preparation of (3S,5S,7S)-12-hydroxy-3,5-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide and (3S,5R,7S)-12-hydroxy-3,5-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide (142-1 and 142-2)

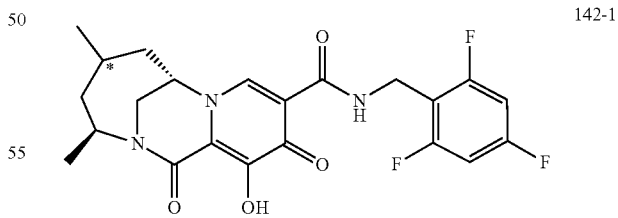

142-1

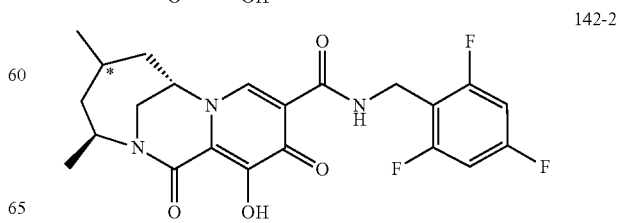

142-2

The title compounds were prepared in a manner similar to compounds 108-1 and 108-2, using benzyl (2S,6S)-6-((tert-butoxycarbonyl)amino)-2-methyl-4-oxoazepane-1-carboxylate in place of benzyl (2S,6S)-6-((tert-butoxycarbonyl)amino)-2-methyl-3-oxoazepane-1-carboxylate.

142-1: MS (m/z) 450.25 [M+H]+. 1H NMR (400 MHz, Methanol-d4) δ 8.47 (s, 1H), 6.92 (t, J=8.5 Hz, 2H), 4.94 (d, J=2.5 Hz, 1H), 4.68 (s, 3H), 3.81 (d, J=17.2 Hz, 2H), 2.04 (d, J=14.2 Hz, 1H), 1.97-1.84 (m, 1H), 1.75 (s, 1H), 1.55 (dd, J=20.7, 10.0 Hz, 2H), 1.27 (d, J=6.6 Hz, 3H), 0.96 (d, J=5.8 Hz, 3H).

142-2: MS (m/z) 450.24 [M+H]+. 1H NMR (400 MHz, Methanol-d4) δ 8.47 (s, 1H), 6.92 (s, 2H), 4.81 (s, 2H), 4.68 (s, 2H), 3.94 (s, 1H), 3.64 (s, 1H), 2.41 (s, 1H), 2.19 (s, 1H), 1.70 (d, J=5.0 Hz, 2H), 1.41 (s, 1H), 1.35 (d, J=6.9 Hz, 3H), 0.94 (d, J=6.0 Hz, 3H).

Example 140: Preparation of (6R)—N-(3-chloro-2-fluorobenzyl)-9,10-difluoro-1-hydroxy-2,14-dioxo-2,7,12,14-tetrahydro-6H-6,13-methanobenzo[f]pyrido[1,2-a][1,4]diazonine-3-carboxamide and (6S)—N-(3-chloro-2-fluorobenzyl)-9,10-difluoro-1-hydroxy-2,14-dioxo-2,7,12,14-tetrahydro-6H-6,13-methanobenzo[f]pyrido[1,2-a][1,4]diazonine-3-carboxamide (143-1 and 143-2)

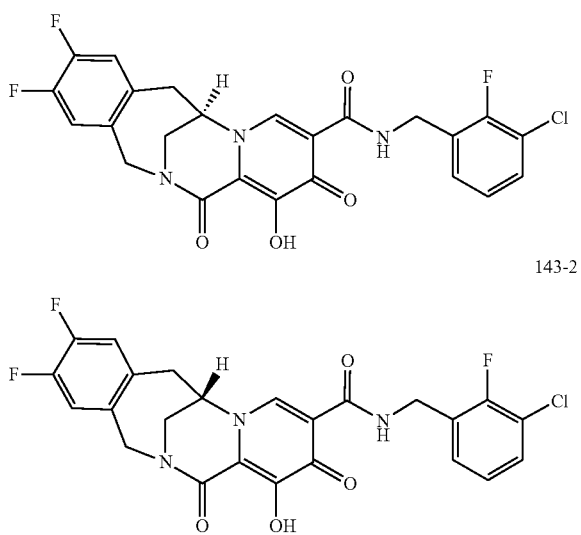

143-1

143-2

The title compounds were prepared in a similar manner to compounds 139-1 and 139-2 using methyl 3-(benzyloxy)-5-((3-chloro-2-fluorobenzyl)carbamoyl)-4-oxo-4H-pyran-2-carboxylate in place of methyl 3-(benzyloxy)-4-oxo-5-((2,4,6-trifluorobenzyl)carbamoyl)-4H-pyran-2-carboxylate. Chiral separation was carried out using preparative SFC (IB, 50% EtOH containing 0.1% TFA).

143-1: MS (m/z) 504.16 [M+H]+. 1H NMR (400 MHz, DMSO-d6) δ 10.37 (t, J=6.0 Hz, 1H), 8.53 (s, 1H), 7.50 (td, J=7.7, 1.7 Hz, 1H), 7.41 (dd, J=11.7, 8.2 Hz, 1H), 7.37-7.24 (m, 2H), 7.20 (td, J=7.9, 1.0 Hz, 1H), 5.47 (d, J=16.6 Hz, 1H), 5.00 (td, J=7.9, 2.2 Hz, 1H), 4.72-4.56 (m, 2H), 4.44 (d, J=16.7 Hz, 1H), 3.80 (d, J=14.6 Hz, 1H), 3.62 (dd, J=14.8, 2.8 Hz, 1H), 3.40 (d, J=7.3 Hz, 1H), 2.87 (dd, J=15.0, 7.7 Hz, 1H). 19F NMR (376 MHz, DMSO-d6) δ −121.99 (t, J=6.9 Hz), −141.06 (ddd, J=22.2, 11.1, 8.3 Hz), −141.90 (dt, J=21.2, 10.1 Hz).

143-2: MS (m/z) 504.14 [M+H]+. 1H NMR (400 MHz, DMSO-d6) δ 10.37 (t, J=6.0 Hz, 1H), 8.53 (s, 1H), 7.50 (td, J=7.7, 1.7 Hz, 1H), 7.41 (dd, J=11.7, 8.2 Hz, 1H), 7.38-7.23 (m, 2H), 7.20 (td, J=7.9, 1.1 Hz, 1H), 5.47 (d, J=16.6 Hz, 1H), 5.00 (dt, J=8.3, 4.1 Hz, 1H), 4.63 (d, J=6.0 Hz, 2H), 4.44 (d, J=16.7 Hz, 1H), 3.80 (d, J=14.6 Hz, 1H), 3.62 (dd, J=14.7, 2.8 Hz, 1H), 3.36 (d, J=7.6 Hz, 1H), 2.87 (dd, J=15.1, 7.6 Hz, 1H). 19F NMR (376 MHz, DMSO-d6) δ −121.99 (t, J=7.1 Hz), −141.06 (ddd, J=23.0, 11.6, 8.1 Hz), −141.91 (dt, J=20.8, 9.8 Hz).

Example 141: Preparation of (3S,7S)-4-fluoro-12-hydroxy-3,4-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide and (3S,7S)-12-hydroxy-3,4-dimethyl-1,11-dioxo-N-(2,4,6-trifluorobenzyl)-1,6,7,11-tetrahydro-3H-2,7-methanopyrido[1,2-a][1,4]diazonine-10-carboxamide (144-1 and 144-2)

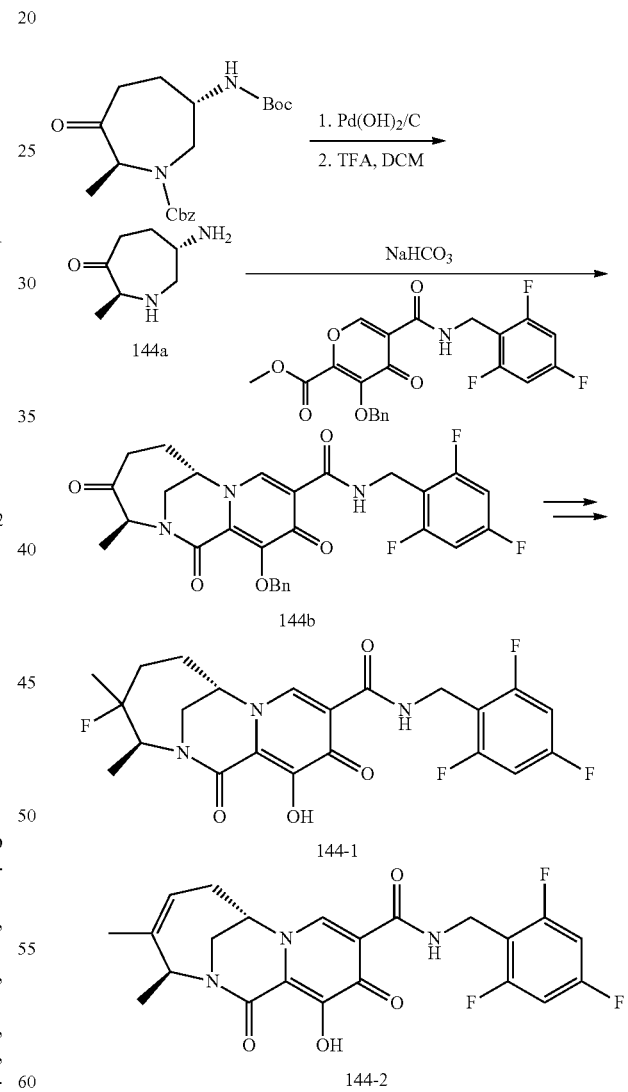

Synthesis of (2S,6S)-6-amino-2-methylazepan-3-one (144a)

To a solution of benzyl (2S,6S)-6-((tert-butoxycarbonyl)amino)-2-methyl-3-oxoazepane-1-carboxylate (130 mg) in ethanol (20 mL) and ethyl acetate (20 mL), was added 10% Pd(OH)$_2$/C (40 mg). The mixture was evacuated several times and a H$_2$ balloon was applied. The reaction was stirred at r.t. overnight, filtered through Celite®, and concentrated, to give tert-butyl ((3S,7S)-7-methyl-6-oxoazepan-3-yl)carbamate, which was used subsequently without further purification.

TFA (1 mL) was added to tert-butyl ((3S,7S)-7-methyl-6-oxoazepan-3-yl)carbamate in DCM (3 mL). The reaction was stirred at r.t. for 2 hours. The reaction was concentrated to give the title compound (144a), which was used subsequently without further purification.

Synthesis of (3S,7S)-12-(benzyloxy)-3-methyl-1,4,11-trioxo-N-(2,4,6-trifluorobenzyl)-1,4,5,6,7,11-hexahydro-3H-2,7-methanopyrido[1,2-a][1,4]diazonine-10-carboxamide (144b)

NaHCO$_3$ (320 mg, 5.2 mmol) was added to a solution of methyl 3-(benzyloxy)-4-oxo-5-((2,4,6-trifluorobenzyl)carbamoyl)-4H-pyran-2-carboxylate (72 mg, 0.52 mmol) and (2S,6S)-6-amino-2-methylazepan-3-one (144a) in methanol (20 mL), and the reaction was stirred at rt overnight. The reaction mixture was concentrated, diluted with ethyl acetate, and washed with saturated ammonium chloride. The organic layer was concentrated, and purified via silica gel chromatography (144b) to give the title compound. MS (m/z) 540.09 [M+H]$^+$.

Synthesis of (3S,7S)-4-fluoro-12-hydroxy-3,4-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide and (3S,7S)-12-hydroxy-3,4-dimethyl-1,11-dioxo-N-(2,4,6-trifluorobenzyl)-1,6,7,11-tetrahydro-3H-2,7-methanopyrido[1,2-a][1,4]diazonine-10-carboxamide (144-1 and 144-2)

The title compounds were prepared in a similar manner to compounds 132-1, 132-2 and 132-3, using (3S,7S)-12-(benzyloxy)-3-methyl-1,4,11-trioxo-N-(2,4,6-trifluorobenzyl)-1,4,5,6,7,11-hexahydro-3H-2,7-methanopyrido[1,2-a][1,4]diazonine-10-carboxamide (144b) in place of (7S)-12-(benzyloxy)-1,4,11-trioxo-N-(2,4,6-trifluorobenzyl)-1,4,5,6,7,11-hexahydro-3H-2,7-methanopyrido[1,2-a][1,4]diazonine-10-carboxamide (79a), and isolating 144-1 as a mixture of stereoisomers.

144-1: MS (m/z) 468.21 [M+H]$^+$. $^1$H NMR (400 MHz, DMSO-d$_6$) δ 10.40 (t, J=5.8 Hz, 1H), 8.49 (s, 1H), 7.30-7.17 (m, 2H), 4.81 (s, 1H), 4.64-4.39 (m, 3H), 3.78-3.58 (m, 3H), 2.17 (d, J=15.8 Hz, 1H), 2.02-1.84 (m, 2H), 1.55 (dt, J=32.2, 14.0 Hz, 2H), 1.37 (d, J=22.4 Hz, 3H), 1.28 (dd, J=7.0, 2.0 Hz, 3H).

144-2: MS (m/z) 448.21 [M+H]$^+$. $^1$H NMR (400 MHz, Acetonitrile-d$_3$) δ 10.40 (d, J=21.2 Hz, 1H), 8.39 (d, J=7.7 Hz, 1H), 6.95-6.79 (m, 2H), 5.35-4.93 (m, 2H), 4.69-4.48 (m, 2H), 3.89-3.60 (m, 2H), 3.38 (dd, J=14.6, 1.6 Hz, 1H), 2.91 (dt, J=17.5, 8.5 Hz, 1H), 2.47-2.27 (m, 2H), 2.21-2.07 (m, 1H), 1.93-1.85 (m, 1H), 1.73 (d, J=2.4 Hz, 1H), 1.39 (dd, J=10.2, 6.9 Hz, 3H).

Example 142: Preparation of (6S)-10-fluoro-1-hydroxy-2,14-dioxo-N-(2,4,6-trifluorobenzyl)-2,7,12,14-tetrahydro-6H-6,13-methanobenzo[f]pyrido[1,2-a][1,4]diazonine-3-carboxamide (145)

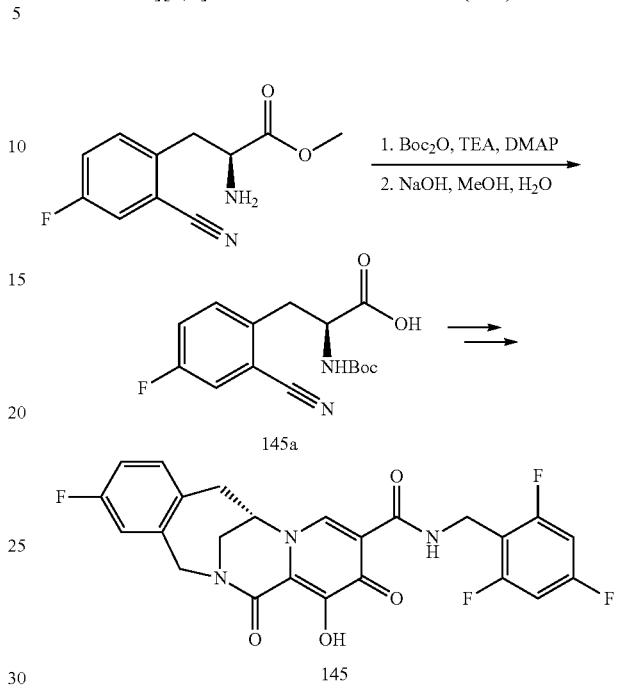

Synthesis of (S)-2-((tert-butoxycarbonyl)amino)-3-(2-cyano-4-fluorophenyl)propanoic acid (145a)

A solution of methyl (S)-2-amino-3-(2-cyano-4-fluorophenyl)propanoate (1 g, 4.5 mmol), di-tert-butyl dicarbonate (1.47 g, 6.75 mmol), trimethylamine (1.9 mL, 13.5 mmol) in THF (10 mL) was stirred at rt for 1 days. To the mixture was added DCM (10 mL) and the reaction mixture was stirred at rt overnight. Then to the mixture was added DMAP (100 mg, 0.82 mmol) and the reaction mixture was stirred at rt for 2 days. The reaction mixture was diluted with DCM, washed with sat. NaHCO$_3$, and extracted with DCM. The organic phase was separated, dried over MgSO$_4$, filtered, concentrated down and the residue purified by silica gel column chromatography, eluting with EtOAc/hexane (0-100%), to give methyl (S)-2-((tert-butoxycarbonyl)amino)-3-(2-cyano-4-fluorophenyl)propanoate.

A mixture of methyl (S)-2-((tert-butoxycarbonyl)amino)-3-(2-cyano-4-fluorophenyl)propanoate (1.15 g, 3.57 mmol) in 2 N NaOH (3.5 mL, 7.0 mmol) and MeOH (10 mL) was stirred at rt for 3 h. The reaction mixture was concentrated down, and the residue dissolved in DCM, and purified by silica gel column chromatography, eluting with 0-100% EtOAc/hexane then 0-20% MeOH/DCM, to give the title compound (145a).

Synthesis of (6S)-10-fluoro-1-hydroxy-2,14-dioxo-N-(2,4,6-trifluorobenzyl)-2,7,12,14-tetrahydro-6H-6,13-methanobenzo[f]pyrido[1,2-a][1,4]diazonine-3-carboxamide (145)

The title compound was prepared in a similar manner to compound 70, using (S)-2-((tert-butoxycarbonyl)amino)-3-(2-cyano-4-fluorophenyl)propanoic acid (145a) in place of (S)-2-((tert-butoxycarbonyl)amino)-3-(2-cyanophenyl)propanoic acid. MS (m/z) 488.17 [M+H]$^+$. $^1$H NMR (400 MHz, DMSO-d$_6$) δ 10.37 (t, J=5.8 Hz, 1H), 8.53 (s, 1H), 7.29-7.12 (m, 4H), 7.06 (td, J=8.4, 2.8 Hz, 1H), 5.52 (d, J=16.7 Hz, 1H), 4.98 (td, J=7.7, 2.4 Hz, 1H), 4.58 (d, J=5.9 Hz, 2H), 4.46 (d, J=16.8 Hz, 1H), 3.79 (d, J=14.6 Hz, 1H), 3.58 (dd, J=14.7, 2.9 Hz, 1H), 3.37 (s, 2H), 2.83 (dd, J=15.0, 7.7 Hz, 1H).

Example 143: Preparation of (6S)—N-(2,4-difluorobenzyl)-10-fluoro-1-hydroxy-2,14-dioxo-2,7,12,14-tetrahydro-6H-6,13-methanobenzo[f]pyrido[1,2-a][1,4]diazonine-3-carboxamide (146)

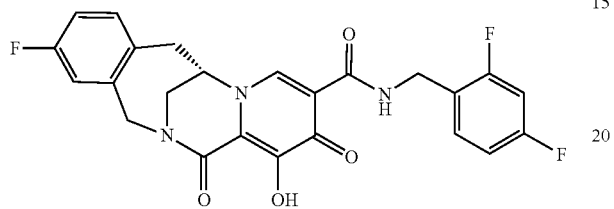

The title compound was prepared in a manner similar to compound 145, using methyl 3-(benzyloxy)-5-((2,4-difluorobenzyl)carbamoyl)-4-oxo-4H-pyran-2-carboxylate in place of methyl 3-(benzyloxy)-4-oxo-5-((2,4,6-trifluorobenzyl)carbamoyl)-4H-pyran-2-carboxylate. MS (m/z) 470.19 [M+H]$^+$. $^1$H NMR (400 MHz, DMSO-d$_6$) δ 10.33 (t, J=5.9 Hz, 1H), 10.26 (s, 1H), 8.56 (s, 1H), 7.42 (td, J=8.6, 6.6 Hz, 1H), 7.30-7.15 (m, 2H), 7.07 (tt, J=8.4, 3.5 Hz, 2H), 5.53 (d, J=16.7 Hz, 1H), 5.00 (t, J=7.3 Hz, 1H), 4.57 (d, J=5.9 Hz, 2H), 4.47 (d, J=16.9 Hz, 1H), 3.80 (d, J=14.6 Hz, 1H), 3.58 (dd, J=14.8, 2.8 Hz, 1H), 3.41 (dd, J=15.1, 7.4 Hz, 1H), 3.31 (s, 1H), 2.84 (dd, J=15.0, 7.7 Hz, 1H).

Example 144: Preparation of (13S)-11-fluoro-4-hydroxy-3,5-dioxo-N-(2,4,6-trifluorobenzyl)-3,5,8,13-tetrahydro-7H-6,13-methanobenzo[g]pyrido[1,2-a][1,4]diazonine-2-carboxamide (147)

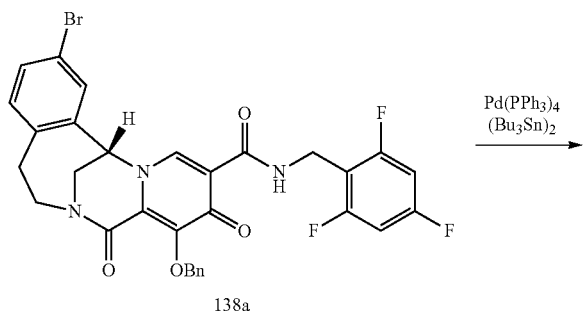

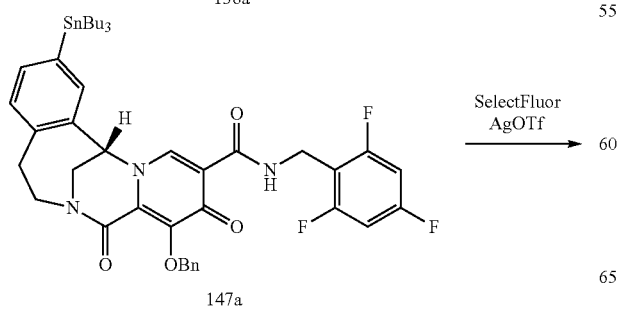

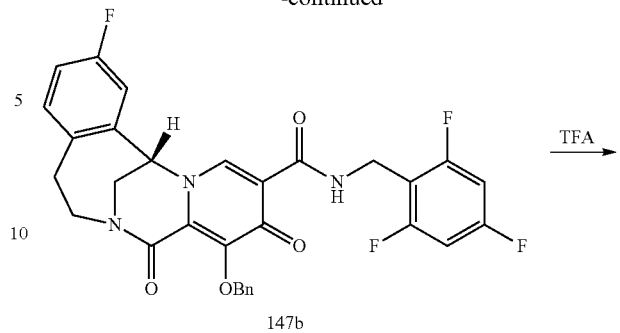

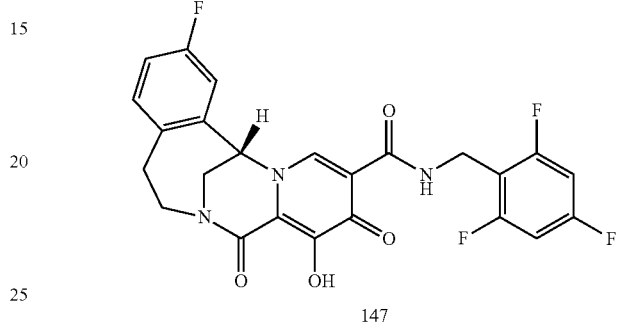

Synthesis of (13S)-4-(benzyloxy)-3,5-dioxo-11-(tributylstannyl)-N-(2,4,6-trifluorobenzyl)-3,5,8,13-tetrahydro-7H-6,13-methanobenzo[g]pyrido[1,2-a][1,4]diazonine-2-carboxamide (147a)

To a suspension of (13S)-4-(benzyloxy)-11-bromo-3,5-dioxo-N-(2,4,6-trifluorobenzyl)-3,5,8,13-tetrahydro-7H-6,13-methanobenzo[g]pyrido[1,2-a][1,4]diazonine-2-carboxamide (138a, 0.030 g, 0.047 mmol) and Pd(PPh$_3$)$_4$ (0.0027 g, 0.0024 mmol) in toluene (0.5 mL) under Ar (g) in a sealed microwave tube, was added hexabutylditin (0.054 g, 0.094 mmol). The reaction mixture was heated to 100° C. overnight. The reaction mixture was concentrated and purified by column chromatography (0-20% EtOAc/heptane, then 100% EtOAc) to afford the title compound (147a). MS (m/z) 848.10 [M+H]$^+$.

Synthesis of (13S)-4-(benzyloxy)-11-fluoro-3,5-dioxo-N-(2,4,6-trifluorobenzyl)-3,5,8,13-tetrahydro-7H-6,13-methanobenzo[g]pyrido[1,2-a][1,4]diazonine-2-carboxamide (147b)

To a solution of (13S)-4-(benzyloxy)-3,5-dioxo-11-(tributylstannyl)-N-(2,4,6-trifluorobenzyl)-3,5,8,13-tetrahydro-7H-6,13-methanobenzo[g]pyrido[1,2-a][1,4]diazonine-2-carboxamide (147a, 0.026 g, 0.031 mmol) in acetone (1 mL) at rt was added silver triflate (0.016 g, 0.062 mmol) and SelectFluor (0.013 g, 0.037 mmol). After 20 min, the reaction mixture was concentrated and purified by column chromatography (0-70% EtOAc/heptane) to afford the title compound (147b). MS (m/z) 578.15 [M+H]$^+$.

Synthesis of (13S)-11-fluoro-4-hydroxy-3,5-dioxo-N-(2,4,6-trifluorobenzyl)-3,5,8,13-tetrahydro-7H-6,13-methanobenzo[g]pyrido[1,2-a][1,4]diazonine-2-carboxamide (147)

To a flask containing (13 S)-4-(benzyloxy)-11-fluoro-3,5-dioxo-N-(2,4,6-trifluorobenzyl)-3,5,8,13-tetrahydro-7H-

6,13-methanobenzo[g]pyrido[1,2-a][1,4]diazonine-2-carboxamide (147b, 0.013 g, 0.022 mmol) was added a 1:1 toluene/TFA solution (4 mL). The reaction mixture was stirred at rt for 4 h. The reaction mixture was concentrated, dissolved in MeCN, filtered, and purified by preparative HPLC (column, Gemini 10μ C18 110A, AXI/; 250×21.2 mm), eluting with 5-100% acetonitrile (0.1% TFA) in water (0.1% TFA) over 30 minutes, to afford the title compound (147). MS (m/z) 488.16 [M+H]⁺. H NMR (400 MHz, DMSO-d₆) δ 10.37 (t, J=5.9 Hz, 1H), 9.05 (s, 1H), 7.32 (dd, J=8.6, 6.1 Hz, 1H), 7.25 (d, J=8.3 Hz, 2H), 7.14 (td, J=8.2, 2.7 Hz, 1H), 7.03 (dd, J=10.3, 2.8 Hz, 1H), 6.01 (d, J=20.4 Hz, 1H), 4.68-4.54 (m, 2H), 4.46 (dd, J=15.2, 2.8 Hz, 1H), 4.37-4.19 (m, 1H), 4.00 (d, J=15.0 Hz, 1H), 3.62-3.48 (m, 1H), 3.45 (s, 1H), 2.89 (dd, J=15.3, 5.4 Hz, 1H). ¹⁹F NMR (376 MHz, DMSO-d₆) δ −109.25 (ddt, J=11.7, 6.3, 2.5 Hz), −112.53 (t, J=7.7 Hz), −115.54 (q, J=8.4, 7.9 Hz).

Example 145: Preparation of (3S,7S)-12-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (148)

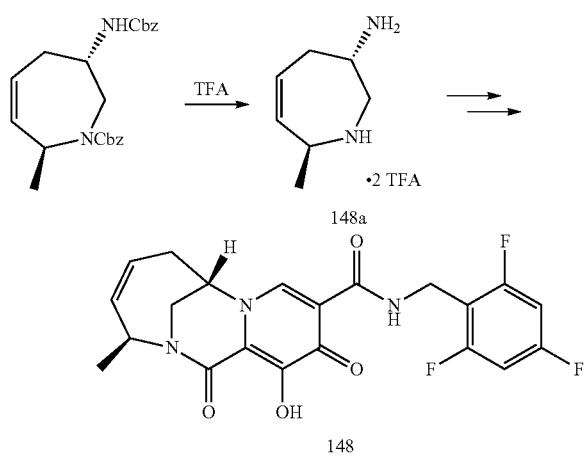

148

Synthesis of (3S,7S)-7-methyl-2,3,4,7-tetrahydro-1H-azepin-3-amine.2TFA (148a)

A solution of benzyl (3S,7S)-3-(((benzyloxy)carbonyl)amino)-7-methyl-2,3,4,7-tetrahydro-1H-azepine-1-carboxylate (0.200 g, 0.507 mmol) in TFA (5 mL) was heated to 100° C. in a sealed vial for 2 h. The solution was concentrated to afford (3S,7S)-7-methyl-2,3,4,7-tetrahydro-1H-azepin-3-amine.2TFA, which was used in the next step without further purification. MS (m/z) 126.95 [M+H]⁺.

Synthesis of (3S,7S)-12-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide (148)

The title compound was prepared similarly to compound 28 using (3S,7S)-7-methyl-2,3,4,7-tetrahydro-1H-azepin-3-amine.2TFA (148a) in place of 1,4-oxazepan-6-amine, and methyl 3-(benzyloxy)-4-oxo-5-((2,4,6-trifluorobenzyl)carbamoyl)-4H-pyran-2-carboxylate in place of methyl 3-(benzyloxy)-5-((2,4-difluorobenzyl)carbamoyl)-4-oxo-4H-pyran-2-carboxylate. MS (m/z) 434.23 [M+H]⁺. ¹H NMR (400 MHz, DMSO-d₆) δ 10.38 (t, J=5.8 Hz, 1H), 8.48 (s, 1H), 7.28-7.11 (m, 2H), 5.59-5.38 (m, 2H), 5.33-5.16 (m, 1H), 4.95 (t, J=7.1 Hz, 1H), 4.56 (d, J=5.8 Hz, 2H), 3.78 (dd, J=14.4, 2.7 Hz, 1H), 3.61 (d, J=14.1 Hz, 1H), 2.89 (dt, J=17.3, 8.5 Hz, 1H), 2.29-2.15 (m, 1H), 1.26 (d, J=7.2 Hz, 3H). ¹⁹F NMR (376 MHz, DMSO-d₆) δ −109.28 (tt, J=9.3, 6.2 Hz), −112.55 (t, J=7.3 Hz).

Example 146: Preparation of (3S,7S)—N-(2,4-difluorobenzyl)-12-hydroxy-3-methyl-1,11-dioxo-1,6,7,11-tetrahydro-3H-2,7-methanopyrido[1,2-a][1,4]diazonine-10-carboxamide (149)

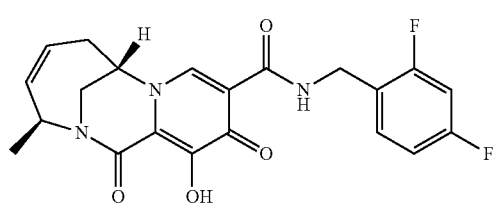 [SMILES: C[C@H]1C=CC[C@H]2CN1C(=O)c1c(O)c(=O)c(C(=O)NCc3ccc(F)cc3F)cn12]

The title compound was prepared similarly to compound 148 using methyl 3-(benzyloxy)-5-((2,4-difluorobenzyl)carbamoyl)-4-oxo-4H-pyran-2-carboxylate in place of methyl 3-(benzyloxy)-4-oxo-5-((2,4,6-trifluorobenzyl)carbamoyl)-4H-pyran-2-carboxylate. MS (m/z) 416.24 [M+H]⁺. ¹H NMR (400 MHz, DMSO-d₆) δ 10.36 (t, J=5.9 Hz, 1H), 8.51 (s, 1H), 7.40 (td, J=8.6, 6.6 Hz, 1H), 7.24 (ddd, J=10.5, 9.3, 2.6 Hz, 1H), 7.06 (ddd, J=10.7, 8.2, 2.5 Hz, 1H), 5.52 (ddt, J=10.3, 7.6, 2.7 Hz, 1H), 5.46 (dt, J=11.6, 2.2 Hz, 1H), 5.31-5.20 (m, 1H), 5.02-4.92 (m, 1H), 4.55 (d, J=5.8 Hz, 2H), 3.79 (dd, J=14.4, 2.8 Hz, 1H), 3.63 (d, J=14.2 Hz, 1H), 2.90 (dt, J=17.3, 8.5 Hz, 1H), 2.30-2.16 (m, 1H), 1.26 (d, J=7.2 Hz, 3H). ¹⁹F NMR (376 MHz, DMSO-d₆) δ −112.38 (p, J=7.8 Hz), −114.98 (q, J=8.4 Hz).

Example 147: Preparation of (1aS,4R,11aS)-7-hydroxy-4-methyl-6,8-dioxo-N-(2,4,6-trifluorobenzyl)-1a,2,3,4,6,8-hexahydro-1H-5,11a-methanocyclopropa[h]pyrido[1,2-a][1,4]diazonine-9-carboxamide (150)

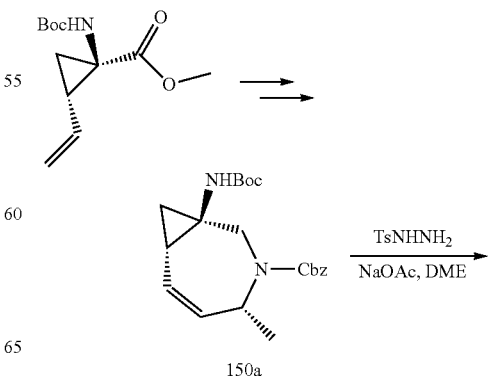

150a

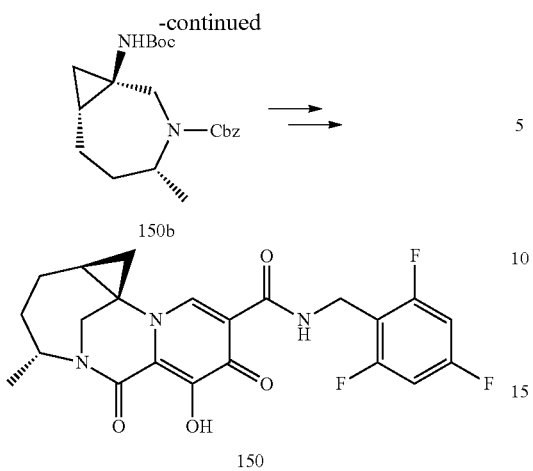

Synthesis of benzyl (1R,4R,7S)-1-((tert-butoxycarbonyl)amino)-4-methyl-3-azabicyclo[5.1.0]oct-5-ene-3-carboxylate (150a)

The title compound was prepared in a similar manner to compound 65c, using (R)-but-3-en-2-amine in place of allylamine, and benzyl chloroformate and potassium carbonate for Cbz protection in place of di-tert-butyl dicarbonate and trimethylamine for Boc protection. MS (m/z) 372.77 [M+H]⁺.

Synthesis of benzyl (1R,4R,7R)-1-((tert-butoxycarbonyl)amino)-4-methyl-3-azabicyclo[5.1.0]octane-3-carboxylate (150b)

A mixture of benzyl (1R,4R,7S)-1-((tert-butoxycarbonyl)amino)-4-methyl-3-azabicyclo[5.1.0] oct-5-ene-3-carboxylate (150a, 171.6 mg, 0.461 mmol), p-toluenesulfonhydrazide (646.6 mg, 3.47 mmol), and sodium acetate (569.1 mg, 6.94 mmol) in 1,2-dimethoxyethane (7.5 mL) and water (0.75 mL) was stirred at 95° C. for 17 h. Additional p-toluenesulfonhydrazide (646.1 mg, 3.47 mmol), sodium acetate (569.5 mg, 6.94 mmol), 1,2-dimethoxyethane (7.5 mL), and water (0.75 mL) were added, before the resulting mixture was stirred at reflux at 95° C. bath for 5 h. The reaction mixture was concentrated to remove most of DME and the residue was dissolved in water (30 mL), and extracted with ethyl acetate (2×30 mL). The extracts were washed with water (30 mL), dried over MgSO₄, and concentrated. The crude residue was subjected to the same condition with p-toluenesulfonhydrazide (1746 mg, 9.38 mmol), sodium acetate (1548 mg, 18.9 mmol), 1,2-dimethoxyethane (20 mL), and water (2 mL) twice and then extracted as described above. The residue was purified by column chromatography on silica gel, eluting with 5-30% ethyl acetate in hexane, to get the title compound (150b). MS (m/z) 374.83 [M+H]⁺.

Synthesis of (aS,4R,11aS)-7-hydroxy-4-methyl-6,8-dioxo-N-(2,4,6-trifluorobenzyl)-1a,2,3,4,6,8-hexahydro-1H-5,11a-methanocyclopropa[h]pyrido[1,2-a][1,4]diazonine-9-carboxamide (150)

The title compound was prepared in a manner similar to compound 65-2, using benzyl (R,4R,7R)-1-((tert-butoxycarbonyl)amino)-4-methyl-3-azabicyclo[5.1.0]octane-3-carboxylate (150b) in place of benzyl (1S,7R)-1-(((benzyloxy)carbonyl)amino)-3-azabicyclo[5.1.0]oct-5-ene-3-carboxylate (65d-2). MS (m/z) 448.19 [M+H]⁺. ¹H NMR (400 MHz, Acetonitrile-d₃) δ 10.27 (s, 1H), 8.16 (s, 1H), 6.89-6.76 (m, 2H), 4.63-4.51 (m, 3H), 4.08 (dd, J=15.0, 1.4 Hz, 1H), 3.42 (dqd, J=11.2, 7.1, 2.6 Hz, 1H), 3.16 (d, J=14.9 Hz, 1H), 2.39-2.28 (m, 1H), 2.28-2.16 (m, 1H), 1.91-1.81 (m, 1H), 1.79-1.71 (m, 1H), 1.69 (d, J=7.1 Hz, 3H), 1.38-1.20 (m, 3H). ¹⁹F NMR (376 MHz, Acetonitrile-d₃) δ −77.36, −111.13 (tt, J=9.0, 6.2 Hz), −113.89 (t, J=7.0 Hz).

Example 148: Preparation of (3R,6S,7R)- and (3R,6R,7S)-12-hydroxy-3,6-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide (151-1 and 151-2)

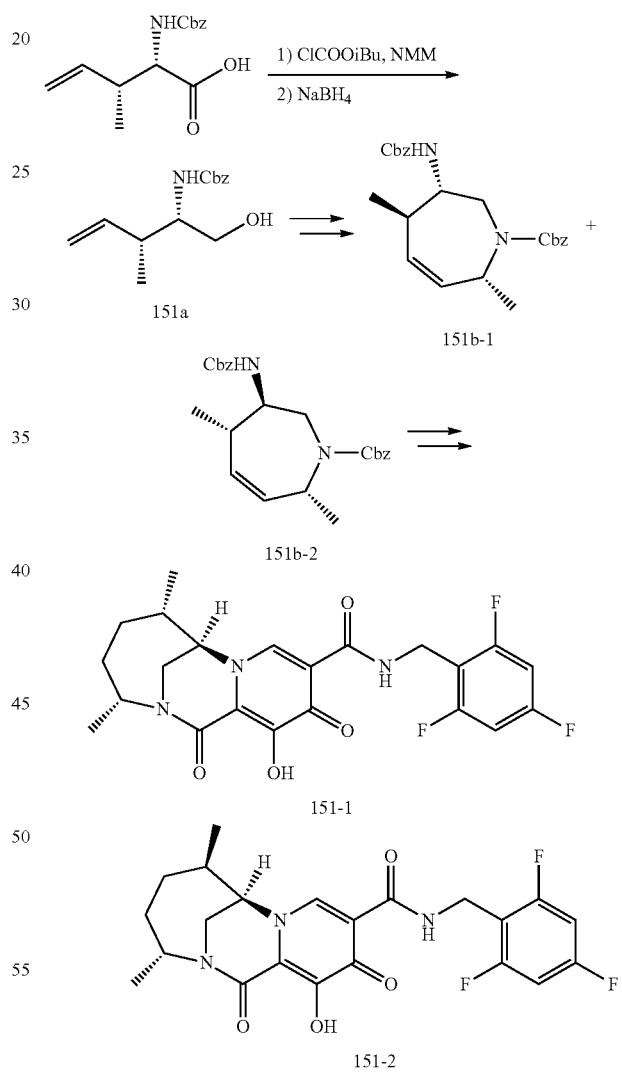

Synthesis of benzyl rac-((2S,3R)-1-hydroxy-3-methylpent-4-en-2-yl)carbamate (151a)

A solution of the racemic (2S,3R)-2-(benzyloxycarbonylamino)-3-methyl-pent-4-enoic acid (2.0 g, 7.60 mmol) and 4-methylmorpholine (1 mL, 9.20 mmol) in tetrahydrofuran (20 mL) was stirred at ice-salt bath as isobutyl chloroformate (1.2 mL, 9.10 mmol) was added dropwise. After 30 min, the reaction mixture was filtered, and the solids were washed with tetrahydrofuran (10 mL).

The filtrate was stirred in an ice-salt bath as a solution of sodium borohydride in water (4 mL) was added dropwise. The reaction mixture was further diluted with water (16 mL) and the resulting reaction mixture was stirred at rt overnight. The reaction mixture was diluted with saturated ammonium chloride solution (50 mL) and water (50 mL) before the product was extracted with ethyl acetate (100 mL×2). The extracts were washed with brine (100 mL), and the organic fractions were combined, dried over MgSO$_4$, and concentrated. The residue was purified by column chromatography on silica gel, eluting with 15-55% ethyl acetate in hexane, to get the title compound (151a). MS (m/z) 249.81 [M+H]$^+$.

Synthesis of benzyl (3R,4S,7R) and (3S,4R,7R)-3-(((benzyloxy)carbonyl)amino)-4,7-dimethyl-2,3,4,7-tetrahydro-1H-azepine-1-carboxylate (151b-1 and 151b-2)

A mixture of the title compounds were prepared analogously to compound 129d, using benzyl rac-((2S,3R)-1-hydroxy-3-methylpent-4-en-2-yl)carbamate (151a) in place of tert-butyl (S)-(1-hydroxypent-4-en-2-yl)carbamate (129b) and (R)-but-3-en-2-amine in place of 1-vinylcyclopropanamine; hydrochloride (129a). Two diastereomers were separated by column chromatography on silica gel eluting with 0-30% ethyl acetate in hexane to obtain the title compounds as separated stereoisomers. 151b-1: MS (m/z) 409.00 [M+H]$^+$; 151b-2: MS (m/z) 409.03 [M+H]$^+$.

Synthesis of (3R,6S,7R)- and (3R,6R,7S)-12-hydroxy-3,6-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide (151-1 and 151-2)

The title compounds were prepared in a manner similar to compounds 65-1 and 65-2 using benzyl (3R,4S,7R)-3-(((benzyloxy)carbonyl)amino)-4,7-dimethyl-2,3,4,7-tetrahydro-1H-azepine-1-carboxylate or (3S,4R,7R)-3-(((benzyloxy)carbonyl)amino)-4,7-dimethyl-2,3,4,7-tetrahydro-1H-azepine-1-carboxylate (151b-1 or 151b-2) in place of benzyl (1R,7S)-1-(((benzyloxy)carbonyl)amino)-3-azabicyclo[5.1.0]oct-5-ene-3-carboxylate or (1S,7R)-1-(((benzyloxy)carbonyl)amino)-3-azabicyclo[5.1.0]oct-5-ene-3-carboxylate (65d-1 or 65d-2).

151-1: MS (m/z) 450.23.19 [M+H]$^+$. $^1$H NMR (400 MHz, Acetonitrile-d$_3$) δ 10.35 (s, 1H), 8.44 (s, 1H), 6.92-6.75 (m, 2H), 4.59 (d, J=5.6 Hz, 2H), 4.50 (dp, J=10.3, 6.8 Hz, 1H), 4.18 (d, J=3.0 Hz, 1H), 3.65-3.48 (m, 2H), 2.18 (d, J=8.3 Hz, 1H), 1.85 (dt, J=14.4, 7.0 Hz, 1H), 1.63-1.46 (m, 2H), 1.38-1.26 (m, 1H), 1.22 (d, J=6.7 Hz, 3H), 1.12 (d, J=7.4 Hz, 3H). 19F NMR (376 MHz, Acetonitrile-d$_3$) δ -77.34, -111.13 (tt, J=9.4, 6.3 Hz), -113.84 (t, J=7.2 Hz).

151-2: MS (m/z) 450.23.19 [M+H]$^+$. $^1$H NMR (400 MHz, Acetonitrile-d$_3$) δ 10.35 (s, 1H), 8.44 (s, 1H), 6.92-6.75 (m, 2H), 4.59 (d, J=5.6 Hz, 2H), 4.50 (dp, J=10.3, 6.8 Hz, 1H), 4.18 (d, J=3.0 Hz, 1H), 3.65-3.48 (m, 2H), 2.18 (d, J=8.3 Hz, 1H), 1.85 (dt, J=14.4, 7.0 Hz, 1H), 1.63-1.46 (m, 2H), 1.38-1.26 (m, 1H), 1.22 (d, J=6.7 Hz, 3H), 1.12 (d, J=7.4 Hz, 3H). $^{19}$F NMR (376 MHz, Acetonitrile-d$_3$) δ -77.34, -111.13 (tt, J=9.4, 6.3 Hz), -113.84 (t, J=7.2 Hz).

Example 149: Preparation of (7S)—N-(2-chloro-4-fluoro-benzyl)-12-hydroxy-1,11-dioxo-1,4,5,6,7,11-hexahydro-3H-2,7-methanopyrido[1,2-a][1,4]diazonine-10-carboxamide (152)

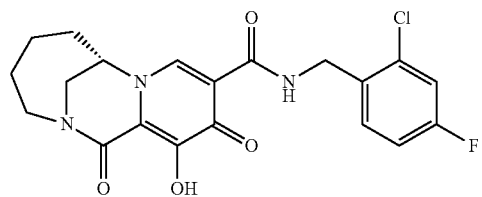 [SMILES: O=C(NCc1ccc(F)cc1Cl)c1cn2c(c(O)c1=O)C(=O)N1CCCC[C@H]2C1]

The title compound was prepared in a manner similar to compound 51, using (2-chloro-4-fluoro-phenyl) methanamine in place of (3-chloro-2,4-difluorophenyl)methanamine. MS (m/z) 420.21 [M+H]$^+$. $^1$H NMR (400 MHz, DMSO-d$_6$) δ 10.48 (t, J=6.0 Hz, 1H), 8.50 (s, 1H), 7.48 (dd, J=8.8, 2.6 Hz, 1H), 7.42 (dd, J=8.6, 6.2 Hz, 1H), 7.22 (td, J=8.5, 2.6 Hz, 1H), 4.79-4.76 (m, 1H), 4.58 (d, J=6.0 Hz, 2H), 4.14 (dt, J=13.2, 7.8 Hz, 1H), 3.95-3.84 (m, 1H), 3.68 (dd, J=14.6, 1.9 Hz, 1H), 3.08 (ddd, J=13.1, 6.8, 3.6 Hz, 1H), 2.09-1.95 (m, 1H), 1.93-1.74 (m, 3H), 1.71-1.59 (m, 1H), 1.15 (q, J=12.0 Hz, 1H).

Example 150: Preparation of (7S)—N-(2,4-dichlorobenzyl)-12-hydroxy-1,11-dioxo-1,4,5,6,7,11-hexahydro-3H-2,7-methanopyrido[1,2-a][1,4]diazonine-10-carboxamide (153)

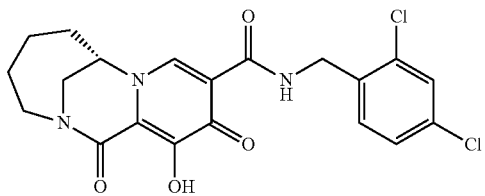 [SMILES: O=C(NCc1ccc(Cl)cc1Cl)c1cn2c(c(O)c1=O)C(=O)N1CCCC[C@H]2C1]

The title compound was prepared analogously to compound 51, using (2,4-di-chloro-phenyl)methanamine in place of (3-chloro-2,4-difluorophenyl)methanamine. MS (m/z) 436.18 [M+H]$^+$. $^1$H NMR (400 MHz, DMSO-d$_6$) δ 10.50 (t, J=6.0 Hz, 1H), 8.50 (s, 1H), 7.65 (d, J=2.1 Hz, 1H), 7.43 (dd, J=8.3, 2.1 Hz, 1H), 7.37 (d, J=8.3 Hz, 1H), 4.78 (s, 1H), 4.59 (d, J=6.0 Hz, 2H), 4.15 (dt, J=15.0, 7.7 Hz, 1H), 3.89 (d, J=14.4 Hz, 2H), 3.14-3.01 (m, 1H), 2.07-1.95 (m, 1H), 1.91-1.77 (m, 3H), 1.71-1.60 (m, 1H), 1.22-1.09 (m, 1H).

Example 151: Preparation of (3S,7S)-4-fluoro-12-hydroxy-3-methyl-1,11-dioxo-N-(2,4,6-trifluorobenzyl)-1,6,7,11-tetrahydro-3H-2,7-methanopyrido[1,2-a][1,4]diazonine-10-carboxamide and (3S,7S)-4,4-difluoro-12-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (154-1 and 154-2)

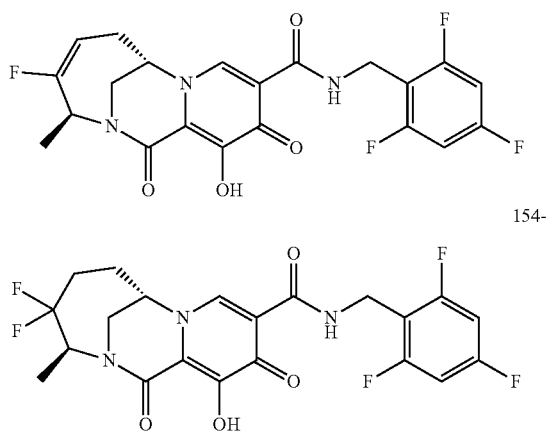

The title compounds were prepared in a manner similar to compounds 118-2 and 113, using (3S,7S)-12-(benzyloxy)-3-methyl-1,4,11-trioxo-N-(2,4,6-trifluorobenzyl)-1,4,5,6,7,11-hexahydro-3H-2,7-methanopyrido[1,2-a][1,4]diazonine-10-carboxamide (144b) in place of (3S,7S)-12-(benzyloxy)-3-methyl-1,5,11-trioxo-N-(2,4,6-trifluorobenzyl)-1,4,5,6,7,11-hexahydro-3H-2,7-methanopyrido[1,2-a][1,4]diazonine-10-carboxamide.

154-1: MS (m/z) 452.22 [M+H]+. 1H NMR (400 MHz, Acetonitrile-d3) δ 8.41 (d, J=4.5 Hz, 1H), 6.97-6.77 (m, 2H), 5.45 (s, 1H), 5.38-5.23 (m, 1H), 4.81 (d, J=9.5 Hz, 1H), 4.62 (d, J=5.8 Hz, 1H), 3.89 (dd, J=14.5, 2.7 Hz, 1H), 3.73 (d, J=14.5 Hz, 1H), 2.93 (dt, J=18.0, 8.8 Hz, 2H), 2.11 (s, 2H), 1.44 (dd, J=7.1, 1.7 Hz, 3H).

154-2: MS (m/z) 472.25 [M+H]+. 1H NMR (400 MHz, Acetonitrile-d3) δ 10.31 (s, 1H), 8.44 (s, 1H), 6.98-6.80 (m, 2H), 4.93-4.79 (m, 1H), 4.62 (d, J=5.6 Hz, 3H), 3.80-3.57 (m, 4H), 2.38-2.23 (m, 1H), 2.23-2.02 (m, 3H), 1.38 (dd, J=7.0, 2.0 Hz, 3H).

Example 152: Preparation of (7S)-12-hydroxy-1,11-dioxo-N-(2,4,6-trifluorobenzyl)-1,3,4,6,7,11-hexahydro-2,7-methanopyrido[1,2-d][1,4,7]thiadiazonine-10-carboxamide and (7R)-12-hydroxy-1,11-dioxo-N-(2,4,6-trifluorobenzyl)-1,3,4,6,7,11-hexahydro-2,7-methanopyrido[1,2-d][1,4,7]thiadiazonine-10-carboxamide (155-1 and 155-2)

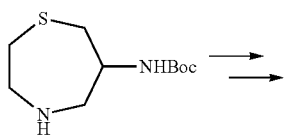

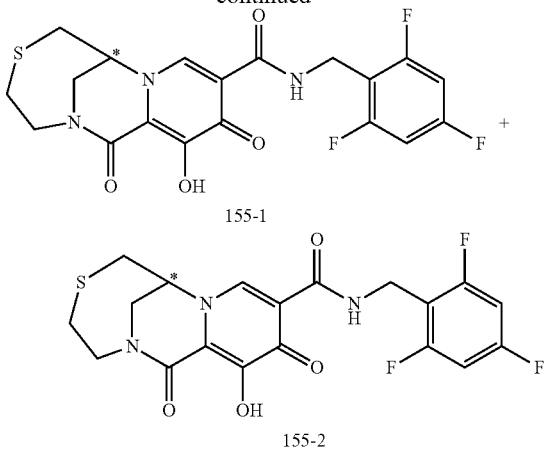

The title compounds were prepared similarly to compound 70, using tert-butyl (1,4-thiazepan-6-yl)carbamate in place of tert-butyl (S)-(2,3,4,5-tetrahydro-1H-benzo[c]azepin-4-yl)carbamate (70c), and isolated as a mixture of stereoisomers. The stereoisomers were separated following benzyl deprotection (SFC chromatography on IB 4.6×100 mm 5 mic eluting with 45% EtOH-TFA, 3 mL/min flow rate, 100 bar, 40° C., 5 uL). MS (m/z) 440.1 [M+H]+.

155-1: 1H NMR (400 MHz, Chloroform-d) δ 10.45 (s, 1H), 8.50 (s, 1H), 6.79-6.62 (m, 2H), 4.77-4.55 (m, 4H), 4.08 (dd, J=14.5, 2.5 Hz, 1H), 3.78 (d, J=14.6 Hz, 1H), 3.37-3.11 (m, 3H), 2.90 (ddd, J=14.5, 8.1, 5.7 Hz, 2H).

155-2: 1H NMR (400 MHz, Chloroform-d) δ 10.45 (s, 1H), 8.50 (s, 1H), 6.79-6.62 (m, 2H), 4.77-4.55 (m, 4H), 4.08 (dd, J=14.5, 2.5 Hz, 1H), 3.78 (d, J=14.6 Hz, 1H), 3.37-3.11 (m, 3H), 2.90 (ddd, J=14.5, 8.1, 5.7 Hz, 2H).

Example 153: Preparation of (7S)-12-hydroxy-7-methyl-1,11-dioxo-N-(2,4,6-trifluorobenzyl)-1,6,7,11-tetrahydro-3H-2,7-methanopyrido[1,2-a][1,4]diazonine-10-carboxamide (156)

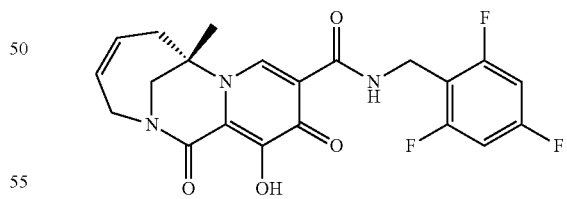

The title compound was prepared in a manner similar to compound 148, using tert-butyl (3S)-3-(benzyloxycarbonylamino)-3-methyl-4,7-dihydro-2H-azepine-1-carboxylate in place of benzyl (3S,7S)-3-(((benzyloxy)carbonyl)amino)-7-methyl-2,3,4,7-tetrahydro-1H-azepine-1-carboxylate. MS (m/z) 434.20 [M+H]+. 1H NMR (400 MHz, DMSO-d6) δ 10.41 (t, J=5.8 Hz, 1H), 8.35 (s, 1H), 7.21 (ddd, J=11.7, 8.7, 3.1 Hz, 2H), 5.73-5.57 (m, 2H), 4.94-4.82 (m, 1H), 4.57 (d, J=5.8 Hz, 2H), 3.80-3.66 (m, 2H), 3.58 (d, J=14.3 Hz, 1H), 2.59-2.52 (m, 1H), 2.43 (d, J=16.3 Hz, 1H), 1.67 (s, 3H).

Example 154: Preparation of (3S,6S,7R)-6-fluoro-12-hydroxy-3-methyl-1,11-dioxo-N-(2,4,6-trifluorobenzyl)-1,4,5,6,7,11-hexahydro-3H-2,7-methano-pyrido[1,2-a][1,4]diazonine-10-carboxamide (157)

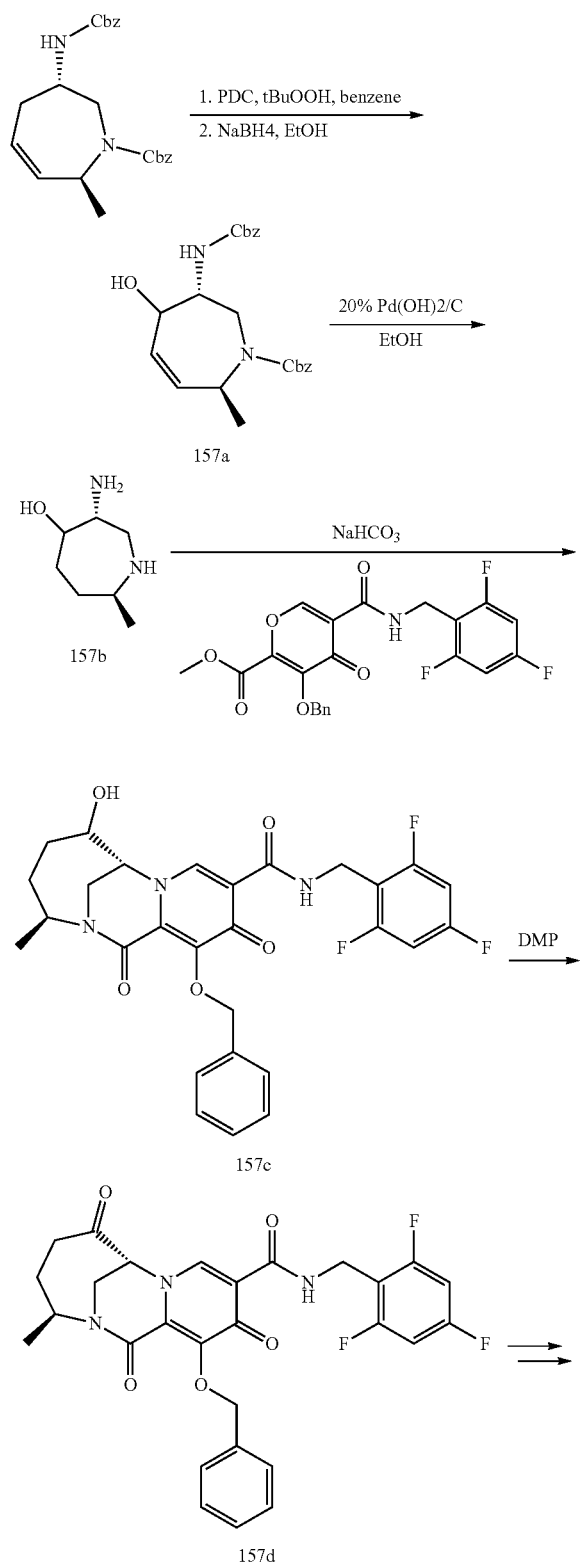

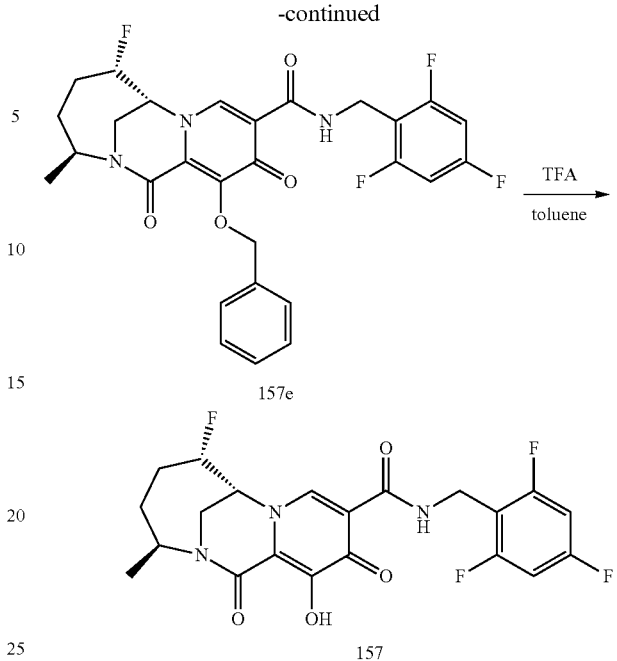

Synthesis of benzyl (3R,7S)-3-(((benzyloxy)carbonyl)amino)-4-hydroxy-7-methyl-2,3,4,7-tetrahydro-1H-azepine-1-carboxylate (157a)

To a solution of benzyl (3S,7S)-3-(benzyloxycarbonylamino)-7-methyl-2,3,4,7-tetrahydroazepine-1-carboxylate (1.06 g, 2.68 mmol) in benzene (28 mL) at rt, was added Celite (1.058 g). To the stirred mixture was added pyridinium dichromate (4.036 g, 10.7 mmol) followed by tert-butyl hydroperoxide (1.03 mL, 10.7 mmol). The resulting mixture was stirred at rt overnight. The reaction was then filtered through a pad of Celite, the filter cake rinsed with EtOAc, and the filtrate was mixed with 1 N sodium thiosulfate and stirred vigorously for 1 hr. The layers were separated, and the organic layer washed with brine, dried over sodium sulfate, filtered, mixed with silica gel, concentrated to dryness, and purified by normal phase chromatography (24 g silica gel, 0-70% EtOAc/Hexanes, dry loading) to give benzyl (3R,7S)-3-(((benzyloxy)carbonyl)amino)-7-methyl-4-oxo-2,3,4,7-tetrahydro-1H-azepine-1-carboxylate. MS (m/z) 408.86 [M+H]$^+$.

Benzyl (3R,7S)-3-(((benzyloxy)carbonyl)amino)-7-methyl-4-oxo-2,3,4,7-tetrahydro-1H-azepine-1-carboxylate was dissolved in EtOH (10.0 mL) at 0° C. Sodium borohydride (97.7 mg, 2.58 mmol) was added, and the mixture was removed from cooling bath and stirred at rt for 1 hr. The reaction was cooled back to 0° C., and quenched with saturated ammonium chloride dropwise. The mixture was then concentrated to remove EtOH, partitioned between EtOAc (50.0 mL) and water (20.0 mL), and the organic layer was washed with brine, dried over sodium sulfate, filtered and concentrated to give the title compound (157a). MS (m/z) 410.89 [M+H]$^+$.

Synthesis of (3R,7S)-3-amino-7-methylazepan-4-ol (157b)

Benzyl (3R,7S)-3-(((benzyloxy)carbonyl)amino)-4-hydroxy-7-methyl-2,3,4,7-tetrahydro-1H-azepine-1-carboxylate (157a, 500 mg, 1.22 mmol) was dissolved in EtOH (10.0 mL) at rt, and 20% Pd(OH)$_2$/C (50 wt % water, 90.0 mg) was added. The resulting mixture was degassed and flushed with nitrogen three times, then degassed and flushed with hydrogen three times, before it was hydrogenated under hydrogen balloon overnight. The reaction was filtered through Celite, filter cake rinsed with EtOH, and the filtrate concentrated to give the title compound (157b), which was carried forward without further purification. MS (m/z) 145.07 [M+H]$^+$.

Synthesis of (3S,6R,7R)-12-(benzyloxy)-6-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (157c)

(3R,7S)-3-amino-7-methylazepan-4-ol (157b, 156 mg, 1.08 mmol) and methyl 3-benzyloxy-4-oxo-5-[(2,4,6-trifluorophenyl)methylcarbamoyl]pyran-2-carboxylate (484 mg, 1.08 mmol) was treated with a mixture of MeOH (10.0 mL) and water (2.0 mL) at room temperature. Sodium bicarbonate (182 mg, 2.16 mmol) was added, and the resulting mixture was heated at 50° C. overnight. The reaction was then concentrated, and the resulting residue partitioned between EtOAc (50 mL) and saturated sodium bicarbonate (20 mL). The organic layer was washed with brine (15 mL), dried over sodium sulfate, filtered, and concentrated. The residue was redissolved in MeOH (10 mL), and treated with 5 M LiOH in water (1 mL) at 50° C. for 1 hr. The reaction was concentrated, redissolved in EtOAc, washed with water and brine, dried over sodium sulfate, filtered, the filtrate mixed with silica gel, concentrated to dryness, and purified by normal phase chromatography (12 g silica gel, 0-100% EtOAc/Hexanes then 0-10% MeOH/EtOAc) to give the title compound (157c). MS (m/z) 542.15 [M+H]$^+$.

Synthesis of (3S,7R)-12-(benzyloxy)-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide (157d)

(3S,6R,7R)-12-(benzyloxy)-6-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (157c, 121 mg, 0.223 mmol) was dissolved in DCM (3.0 mL) at 0° C. DMP (142 mg, 0.335 mmol) was added, and the reaction was removed from the cooling bath and allowed to stir at rt for 1 hr. The reaction was quenched with a 1:1 mixture of sodium thiosulfate (5 mL) and sat. NaHCO$_3$ (5 mL), and stirred vigorously at rt for 20 min. The mixture was diluted with EtOAc (20 mL), the layers were separated, and the organic layer was washed with brine, dried over sodium sulfate, filtered, and concentrated. Purification by normal phase chromatography (12 g silica gel, 0-100% EtOAc/Hexanes, then 0-10% MeOH/EtOAc) gave the title compound (157d). MS (m/z) 540.11 [M+H]$^+$.

Synthesis of (3S,6S,7R)-12-(benzyloxy)-6-fluoro-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (157e)

The title compound was prepared in a manner similar to compound 53d-1, using (3S,7R)-12-(benzyloxy)-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide (157d) in place of benzyl (S)-3-(((benzyloxy)carbonyl)amino)-6-oxoazepane-1-carboxylate (53b-1).

Synthesis of (3S,6S,7R)-6-fluoro-12-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (157)

The title compound was prepared analogously to compound 147, using (3S,6S,7R)-12-(benzyloxy)-6-fluoro-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (157d) in place of (13S)-4-(benzyloxy)-11-fluoro-3,5-dioxo-N-(2,4,6-trifluorobenzyl)-3,5,8,13-tetrahydro-7H-6,13-methanobenzo[g]pyrido[1,2-a][1,4]diazonine-2-carboxamide (147b). MS (m/z) 454.22 [M+H]$^+$. $^1$H NMR (400 MHz, DMSO-d$_6$) δ 12.53 (s, 1H), 10.44 (t, J=5.7 Hz, 1H), 8.31 (s, 1H), 7.30-7.15 (m, 2H), 5.22 (dq, J=50.8, 7.7 Hz, 1H), 4.62-4.51 (m, 3H), 4.38-4.23 (m, 2H), 4.01 (dd, J=12.9, 11.1 Hz, 1H), 2.41-2.30 (m, 1H), 2.30-1.97 (m, 3H), 1.24 (d, J=6.9 Hz, 3H).

Example 155: Preparation of (3S,4R,7S)-4-fluoro-12-hydroxy-3-methyl-1,11-dioxo-N-(2,4,6-trifluorobenzyl)-1,4,5,6,7,11-hexahydro-3H-2,7-methanopyrido[1,2-a][1,4]diazonine-10-carboxamide (158)

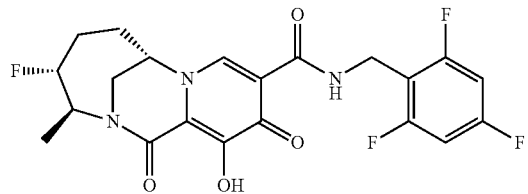 [SMILES: C[C@H]1[C@H](F)CC[C@H]2CN1C(=O)c1c(O)c(=O)c(C(=O)NCc3c(F)cc(F)cc3F)cn12]

The title compound was prepared in a similar manner to compound 157, using (3S,7S)-12-(benzyloxy)-3-methyl-1,4,11-trioxo-N-(2,4,6-trifluorobenzyl)-1,4,5,6,7,11-hexahydro-3H-2,7-methanopyrido[1,2-a][1,4]diazonine-10-carboxamide (144b) in place of (3S,7R)-12-(benzyloxy)-3-methyl-1,6,11-trioxo-N-(2,4,6-trifluorobenzyl)-1,4,5,6,7,11-hexahydro-3H-2,7-methanopyrido[1,2-a][1,4]diazonine-10-carboxamide (157d). MS (m/z) 454.25 [M+H]$^+$. $^1$H NMR (400 MHz, Acetonitrile-d$_3$) δ 8.43 (s, 1H), 6.98-6.80 (m, 2H), 5.02 (ddd, J=48.7, 6.8, 4.7 Hz, 2H), 4.79-4.53 (m, 3H), 3.70 (t, J=2.7 Hz, 2H), 2.28-2.14 (m, 23H), 1.49 (dddd, J=35.8, 16.3, 13.5, 3.0 Hz, 2H), 1.37 (dd, J=7.1, 2.2 Hz, 3H).

Example 156: Preparation of (6R)-9,10-difluoro-1-hydroxy-2,14-dioxo-N-(2,4,6-trifluorobenzyl)-2,7,12,14-tetrahydro-6H-6,13-methanobenzo[f]pyrido[1,2-a][1,4]diazonine-3-carboxamide (159)

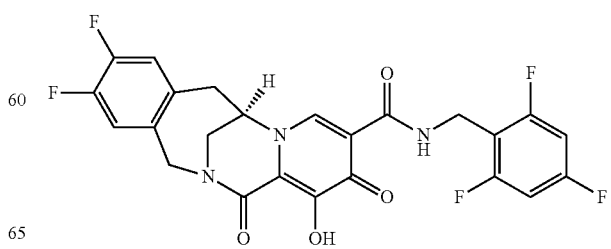

The title compound was prepared in a similar manner to compound 127-2, using 6,7-difluoro-3,4-dihydronaphthalen-2(1H)-one in place of 6-chloro-3,4-dihydronaphthalen-2(1H)-one. Chiral separation using preparative chiral HPLC (1H, 60:40 hexane/EtOAc) gave the title compound (159) after deprotection of the second eluting peak. MS (m/z) 506.15 [M+H]+. 1H NMR (400 MHz, DMSO-d6) δ 10.35 (t, J=5.8 Hz, 1H), 8.50 (s, 1H), 7.40 (dd, J=11.7, 8.1 Hz, 1H), 7.34-7.14 (m, 3H), 5.46 (d, J=16.6 Hz, 1H), 4.98 (td, J=7.4, 2.2 Hz, 1H), 4.58 (d, J=5.8 Hz, 2H), 4.43 (d, J=16.7 Hz, 1H), 3.79 (d, J=14.6 Hz, 1H), 3.61 (dd, J=14.9, 2.8 Hz, 1H), 3.37 (dd, J=15.2, 7.3 Hz, 1H), 2.86 (dd, J=15.1, 7.6 Hz, 1H). 19F NMR (376 MHz, DMSO-d6) δ −109.26 (tt, J=9.4, 6.3 Hz), −112.59 (t, J=7.2 Hz), −141.08 (ddd, J=20.7, 11.6, 8.2 Hz), −141.92 (dt, J=20.8, 10.0 Hz).

Example 157: (7S)—N-(2,3-difluorobenzyl)-12-hydroxy-1,11-dioxo-1,4,5,6,7,11-hexahydro-3H-2,7-methanopyrido[1,2-a][1,4]diazonine-10-carboxamide (160)

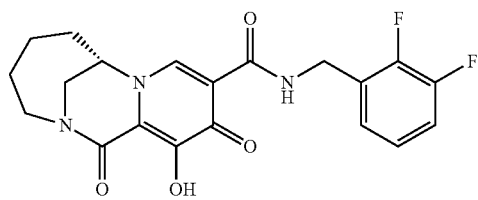 [SMILES: O=C(NCc1cccc(F)c1F)c1cn2c(c(O)c1=O)C(=O)N1CCCC[C@H]2C1]

The title compound was prepared in a similar manner to compound 51, using (2,3-difluorophenyl)methanamine in place of (3-chloro-2,4-difluorophenyl)methanamine. MS (m/z) 404.2 [M+H]+. 1H NMR (400 MHz, Methanol-d4) δ 8.50 (s, 1H), 7.27-7.09 (m, 3H), 4.72 (m, 3H), 4.34 (dt, J=13.3, 8.0 Hz, 1H), 3.99 (d, J=14.8 Hz, 1H), 3.74 (d, J=14.4 Hz, 1H), 3.21 (ddd, J=13.4, 7.1, 3.0 Hz, 1H), 2.09 (m, 3H), 1.96-1.74 (m, 2H), 1.33 (q, J=11.9 Hz, 1H).

Example 158: (7S)-12-hydroxy-1,11-dioxo-N-(2,3,4-trifluorobenzyl)-1,4,5,6,7,11-hexahydro-3H-2,7-methanopyrido[1,2-a][1,4]diazonine-10-carboxamide (161)

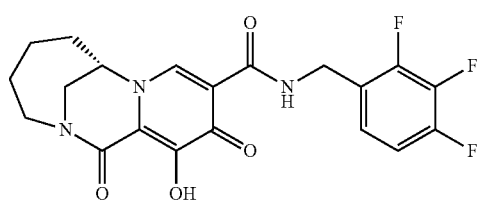 [SMILES: O=C(NCc1ccc(F)c(F)c1F)c1cn2c(c(O)c1=O)C(=O)N1CCCC[C@H]2C1]

The title compound was prepared in a similar manner to compound 51, using (2,3,4-trifluorophenyl)methanamine in place of (3-chloro-2,4-difluorophenyl)methanamine. MS (m/z) 422.2 [M+H]+. 1H NMR (400 MHz, Methanol-d4) δ 8.49 (s, 1H), 7.22 (q, J=6.2 Hz, 1H), 7.17-7.06 (m, 1H), 4.69 (m, 3H), 4.34 (dt, J=13.4, 8.1 Hz, 1H), 3.99 (d, J=14.6 Hz, 1H), 3.74 (dd, J=14.8, 1.9 Hz, 1H), 3.28-3.14 (m, 1H), 2.09 (m, 3H), 1.86 (m, 2H), 1.32 (q, J=12.3 Hz, 1H).

Example 159: Preparation of (7S)—N-(2,4-difluorobenzyl)-7-(fluoromethyl)-12-hydroxy-1,11-dioxo-1,4,5,6,7,11-hexahydro-3H-2,7-methanopyrido[1,2-a][1,4]diazonine-10-carboxamide and (7R)—N-(2,4-difluorobenzyl)-7-(fluoromethyl)-12-hydroxy-1,11-dioxo-1,4,5,6,7,11-hexahydro-3H-2,7-methanopyrido[1,2-a][1,4]diazonine-10-carboxamide (162-1 and 162-2)

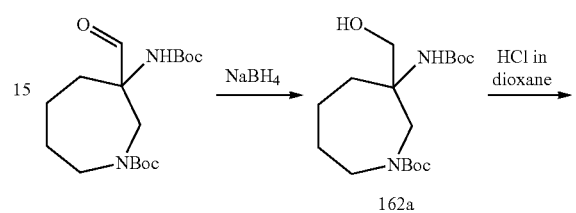

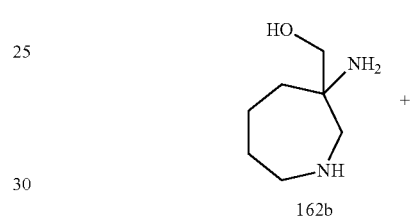

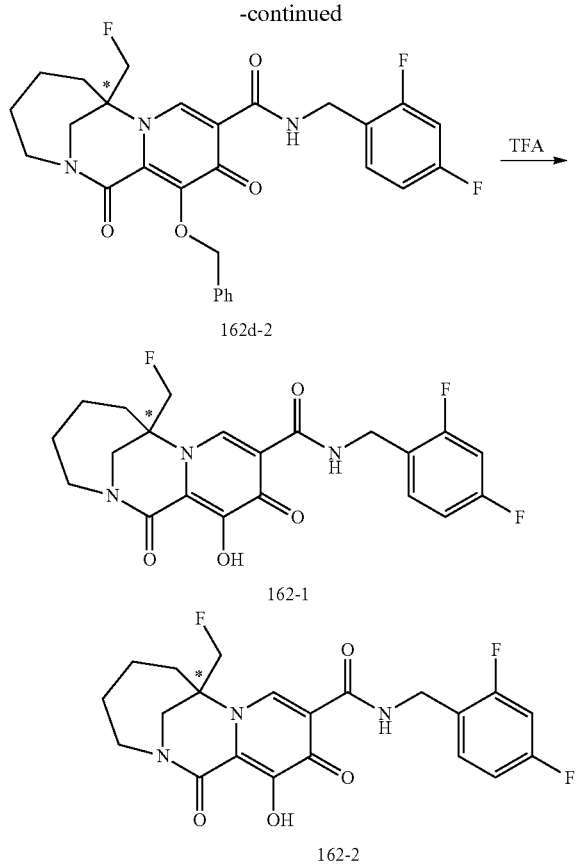

added to a solution of methyl 3-(benzyloxy)-5-((2,4-difluorobenzyl) carbamoyl)-4-oxo-4H-pyran-2-carboxylate (0.05 g, 0.112 mmol) in MeOH (1 mL) and H$_2$O (0.1 mL). The reaction mixture was stirred at rt for 24 hr, then at 45° C. overnight. The reaction mixture was diluted with EtOAc (10 mL), washed with H$_2$O (10 mL), and dried over MgSO$_4$. Solvent was removed, and the residue was purified by silica column to obtain the title compound (162c). MS (m/z) 524.1 [M+H]$^+$.

Synthesis of (7S)- and (7R)-12-(benzyloxy)-N-(2,4-difluorobenzyl)-7-(fluoromethyl)-1,11-dioxo-1,4,5,6,7,11-hexahydro-3H-2,7-methanopyrido[1,2-a][1,4]diazonine-10-carboxamide (162d-1 and 162d-2)

12-(benzyloxy)-N-(2,4-difluorobenzyl)-7-(hydroxymethyl)-1,11-dioxo-1,4,5,6,7,11-hexahydro-3H-2,7-methanopyrido[1,2-a][1,4]diazonine-10-carboxamide (162c) was separated into its individual enantiomers by preparative SFC chromatography on an IA column using methanol co-solvent. The individual enantiomers (0.05 g, 0.09 mmol) were dissolved in DCM at 0° C. under N$_2$, and Deoxo-fluor (0.245 g, 1.1 mmol) was added. The reaction mixture was stirred at rt for 4 days, then quenched with dropwise addition of saturated aqueous NaHCO$_3$ at 0° C., stirring for 1 h. The organic phase was separated and dried over MgSO$_4$, concentrated, and the residue purified by silica gel column to obtain the title compounds (162d-1 and 162d-2). MS (m/z) 526.2 [M+H]$^+$.

Synthesis of tert-butyl 3-((tert-butoxycarbonyl) amino)-3-(hydroxymethyl)azepane-1-carboxylate (162a)

NaBH$_4$ (0.0955g, 2.52 mmol) was added to a solution of tert-butyl 3-((tert-butoxycarbonyl) amino)-3-formylazepane-1-carboxylate (0.56g, 1.68 mmol) in MeOH (6 mL) at 0° C. The mixture solution was stirred at room temperature for 30 minutes, diluted with EtOAc (20 mL), and washed with NaHCO$_3$ (15 mL), H$_2$O, and brine. The organic phase was dried over MgSO$_4$, and concentrated, to give the title compound (162a) without further purification. MS (m/z) 367.2 [M+Na]$^+$.

Synthesis of (3-aminoazepan-3-yl)methanol (162b)

4 M HCl in dioxane (0.84 mL, 3.36 mmol) was added to a solution of tert-butyl 3-((tert-butoxycarbonyl)amino)-3-(hydroxymethyl)azepane-1-carboxylate (162a, 0.579 g, 1.68 mmol) in DCM (5 mL) at rt. The reaction mixture was stirred for 2 h, the solvent was removed under vacuum, and the title compound (162b) was obtained as the HCl salt. MS (m/z) 145.3 [M+H]$^+$.

Synthesis of 12-(benzyloxy)-N-(2,4-difluorobenzyl)-7-(hydroxymethyl)-1,11-dioxo-1,4,5,6,7,11-hexahydro-3H-2,7-methanopyrido[1,2-a][1,4]diazonine-10-carboxamide (162c)

(3-aminoazepan-3-yl)methanol; HCl (162b, 28.5 mg, 0.112 mmol) and NaHCO$_3$ (0.075 g, 0.894 mmol) were Synthesis of (7S)- and (7R)-12-(benzyloxy)-N-(2,4-difluorobenzyl)-7-(fluoromethyl)-1,11-dioxo-1,4,5,6,7,11-hexahydro-3H-2,7-methanopyrido[1,2-a][1,4]diazonine-10-carboxamide (162-1 and 162-2)

To (7S)-12-(benzyloxy)-N-(2,4-difluorobenzyl)-7-(fluoromethyl)-1,11-dioxo-1,4,5,6,7,11-hexahydro-3H-2,7-methanopyrido[1,2-a][1,4]diazonine-10-carboxamide or (7R)-12-(benzyloxy)-N-(2,4-difluorobenzyl)-7-(fluoromethyl)-1,11-dioxo-1,4,5,6,7,11-hexahydro-3H-2,7-methanopyrido[1,2-a][1,4]diazonine-10-carboxamide (162d-1 or 162d-2, 0.03 g, 0.055 mmol) in toluene (1 mL) was added TFA (1 mL). The reaction mixture was stirred at rt overnight. The mixture was concentrated, and the resulting crude material was purified by prep-HPLC to afford the title compounds (162-1 and 162-2). MS (m/z) 436.2 [M+H]$^+$.

162-1: $^1$H NMR (400 MHz, Methanol-d$_4$) δ 8.64 (s, 1H), 7.42 (q, J=8.0, 7.6 Hz, 1H), 6.94 (q, J=9.7 Hz, 2H), 5.19 (d, J=11.6 Hz, 1H), 5.07 (d, J=11.6 Hz, 1H), 4.91 (d, J=11.6 Hz, 1H), 4.78 (d, J=11.6 Hz, 1H), 4.63 (s, 2H), 4.49-4.26 (m, 1H), 3.98 (d, J=14.7 Hz, 1H), 3.78 (d, J=14.7 Hz, 1H), 3.24-3.07 (m, 1H), 2.24-1.41 (m, 6H).

162-2: $^1$H NMR (400 MHz, Methanol-d$_4$) δ 8.64 (s, 1H), 7.42 (q, J=8.0, 7.6 Hz, 1H), 6.94 (q, J=9.7 Hz, 2H), 5.19 (d, J=11.6 Hz, 1H), 5.07 (d, J=11.6 Hz, 1H), 4.91 (d, J=11.6 Hz, 1H), 4.78 (d, J=11.6 Hz, 1H), 4.63 (s, 2H), 4.38 (m, 1H), 3.98 (d, J=14.7 Hz, 1H), 3.78 (d, J=14.7 Hz, 1H), 3.17 (m, 1H), 2.01-1.6 (m, 6H).

373

Example 160: Preparation of (7S)—N-(2,4,6-trifluorobenzyl)-7-(fluoromethyl)-12-hydroxy-1,11-dioxo-1,4,5,6,7,11-hexahydro-3H-2,7-methanopyrido[1,2-a][1,4]diazonine-10-carboxamide and (7R)—N-(2,4,6-trifluorobenzyl)-7-(fluoromethyl)-12-hydroxy-1,11-dioxo-1,4,5,6,7,11-hexahydro-3H-2,7-methanopyrido[1,2-a][1,4]diazonine-10-carboxamide (163-1 and 163-2)

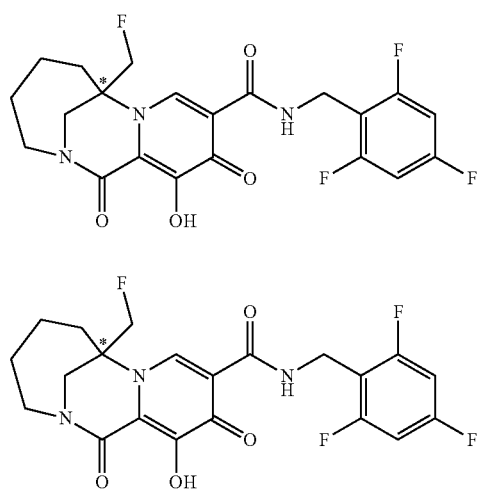

163-1

163-2

The title compounds were prepared similarly to compounds 162-1 and 162-2, using methyl 3-(benzyloxy)-4-oxo-5-((2,4,6-trifluorobenzyl)carbamoyl)-4H-pyran-2-carboxylate in place of methyl 3-(benzyloxy)-5-((2,4-difluorobenzyl)carbamoyl)-4-oxo-4H-pyran-2-carboxylate. MS (m/z) 454.1 [M+H]+.

163-1: $^1$H NMR (400 MHz, Methanol-$d_4$) δ 8.64 (s, 2H), 6.91 (t, J=8.5 Hz, 4H), 5.21 (d, J=11.5 Hz, 1H), 5.09 (d, J=11.5 Hz, 1H), 4.69 (s, 4H), 4.40 (dt, J=13.4, 6.7 Hz, 2H), 4.00 (d, J=14.6 Hz, 2H), 3.80 (d, J=14.6 Hz, 2H), 3.31 (s, 4H), 3.20 (dd, J=13.2, 6.5 Hz, 2H), 2.08-1.77 (m, 7H), 1.54 (td, J=17.4, 16.8, 9.5 Hz, 2H).

163-2: $^1$H NMR (400 MHz, Methanol-$d_4$) δ 8.64 (s, 2H), 6.91 (dd, J=9.0, 7.9 Hz, 3H), 5.21 (d, J=11.4 Hz, 1H), 5.09 (d, J=11.4 Hz, 1H), 4.69 (s, 4H), 4.40 (dt, J=13.4, 6.6 Hz, 2H), 4.00 (d, J=14.5 Hz, 2H), 3.81 (d, J=14.5 Hz, 2H), 3.20 (dd, J=13.2, 6.4 Hz, 2H), 3.08 (s, OH), 2.09-1.79 (m, 6H), 1.61-1.46 (m, 2H).

Example 161: Preparation of (3R,7S)-3-(fluoromethyl)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (164)

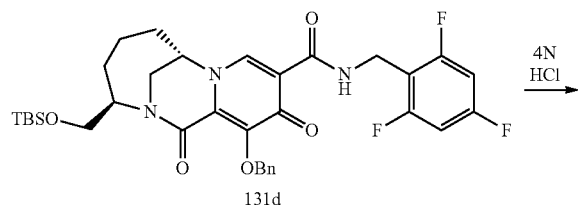

131d

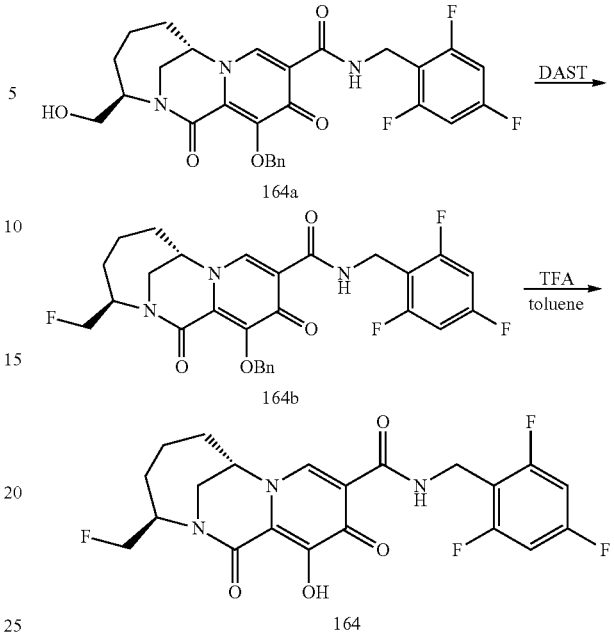

164a

164b

164

(1S,10R)-6-benzyloxy-10-(hydroxymethyl)-5,8-dioxo-N-[(2,4,6-trifluorophenyl)methyl]-2,9-diazatricyclo[7.4.1.02,7]tetradeca-3,6-diene-4-carboxamide (164a) was prepared from (3R,7S)-12-(benzyloxy)-3-(((tert-butyldimethylsilyl)oxy)methyl)-1,11-dioxo-N-(2,4,6-trifluorobenzyl)-1,4,5,6,7,11-hexahydro-3H-2,7-methanopyrido[1,2-a][1,4]diazonine-10-carboxamide (131d, 40.6 mg, 61.9 umol) as was described in the first step of the synthesis of (3R,7S)-12-(benzyloxy)-3-(difluoromethyl)-1,11-dioxo-N-(2,4,6-trifluorobenzyl)-1,4,5,6,7,11-hexahydro-3H-2,7-methanopyrido[1,2-a][1,4]diazonine-10-carboxamide (131e).

A solution of (1S,10R)-6-benzyloxy-10-(hydroxymethyl)-5,8-dioxo-N-[(2,4,6-trifluorophenyl)methyl]-2,9-diazatricyclo[7.4.1.02,7]tetradeca-3,6-diene-4-carboxamide (164a, 61.9 umol) in dichloromethane (2 mL) was stirred at 0° C. as (diethylamino)sulfur trifluoride (DAST, 2 drops) was added. After 30 min, the reaction mixture was stirred at rt overnight. After ~18 h, the reaction mixture was stirred at 0° C. and added saturated sodium bicarbonate (5 mL) and the product was extracted with dichloromethane (2×10 mL). The combined extracts were dried (MgSO$_4$), and concentrated to get a crude (3R,7S)-12-(benzyloxy)-3-(fluoromethyl)-1,11-dioxo-N-(2,4,6-trifluorobenzyl)-1,4,5,6,7,11-hexahydro-3H-2,7-methanopyrido[1,2-a][1,4]diazonine-10-carboxamide (164b). MS (m/z) 544.20 [M+H]+.

The crude (3R,7S)-12-(benzyloxy)-3-(fluoromethyl)-1,11-dioxo-N-(2,4,6-trifluorobenzyl)-1,4,5,6,7,11-hexahydro-3H-2,7-methanopyrido[1,2-a][1,4]diazonine-10-carboxamide (164b) was dissolved in toluene (1 mL) and trifluoroacetic acid (1 mL). After the resulting solution was stirred at rt for 1 h and concentrated, the residue was purified by preparative HPLC (column, Gemini 10u C18 110A, AXI; 250×21.2 mm), eluting with 10-70% acetonitrile in water (0.1% trifluoroacetic acid), to get the title compound (164). MS (m/z) 454.17 [M+H]+. $^1$H NMR (400 MHz, Acetonitrile-$d_3$) δ 10.35 (d, J=6.5 Hz, 1H), 8.39 (s, 1H), 6.84 (t, J=8.5 Hz, 2H), 4.73-4.51 (m, 5H), 4.51-4.41 (m, 1H), 3.77 (dt, J=14.9, 2.7 Hz, 1H), 3.65 (dd, J=15.0, 1.8 Hz, 1H), 2.17-2.08 (m, 1H), 2.05 (dd, J=14.6, 7.2 Hz, 1H), 1.92-1.70 (m, 2H), 1.55 (dt, J=14.4, 11.5 Hz, 1H), 1.24-1.09 (m, 1H).

Example 162: Preparation of (3R,7S)—N-(2,4-difluorobenzyl)-3-(fluoromethyl)-12-hydroxy-1,11-dioxo-1,4,5,6,7,11-hexahydro-3H-2,7-methanopyrido[1,2-a][1,4]diazonine-10-carboxamide (165)
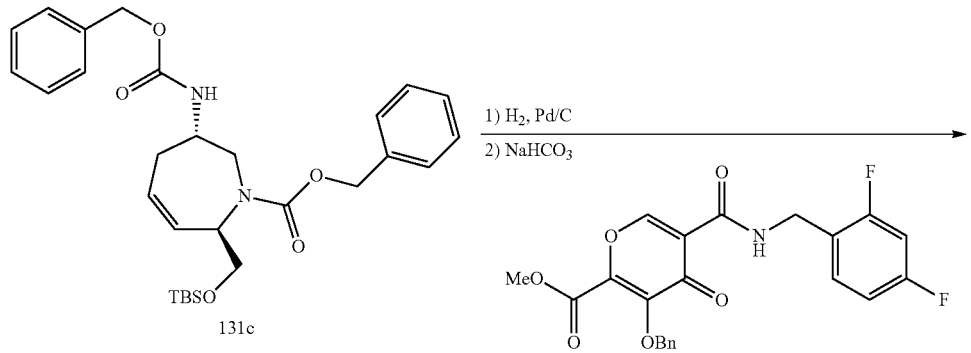
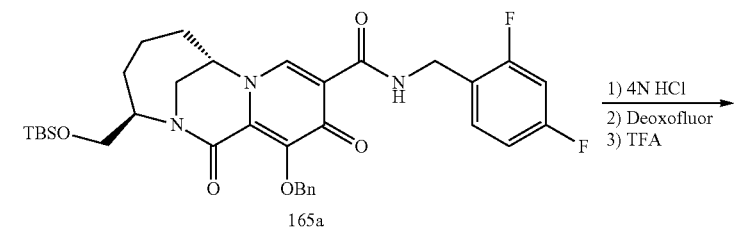
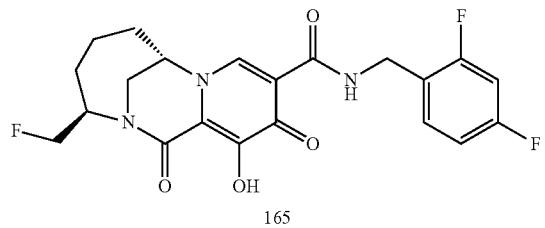

The title compound was prepared analogously to (3R,7S)-3-(fluoromethyl)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (164), using benzyl (3S,7R)-3-(((benzyloxy)carbonyl)amino)-7-(((tert-butyldimethylsilyl)oxy)methyl)-2,3,4,7-tetrahydro-1H-azepine-1-carboxylate (131c) and methyl 3-(benzyloxy)-5-((2,4-difluorobenzyl)carbamoyl)-4-oxo-4H-pyran-2-carboxylate in place of methyl 3-(benzyloxy)-5-((2,4,6-trifluorobenzyl)carbamoyl)-4-oxo-4H-pyran-2-carboxylate.

MS (m/z) 436.19 [M+H]⁺. ¹H NMR (400 MHz, Acetonitrile-d₃) δ 10.37 (d, J=6.7 Hz, 1H), 8.40 (s, 1H), 7.41 (td, J=8.8, 6.5 Hz, 1H), 7.01-6.85 (m, 2H), 4.73-4.61 (m, 1H), 4.58 (m, 4H), 4.52-4.41 (m, 1H), 3.78 (dt, J=15.0, 2.7 Hz, 1H), 3.66 (dd, J=15.0, 1.8 Hz, 1H), 2.12 (dt, J=15.5, 2.3 Hz, 1H), 2.05 (dd, J=14.6, 7.3 Hz, 1H), 1.92-1.69 (m, 2H), 1.56 (dt, J=14.6, 11.6 Hz, 1H), 1.25-1.09 (m, 1H).

Example 163: (7S)—N-(4-fluorobenzyl)-12-hydroxy-1,11-dioxo-1,4,5,6,7,11-hexahydro-3H-2,7-methanopyrido[1,2-a][1,4]diazonine-10-carboxamide (166)

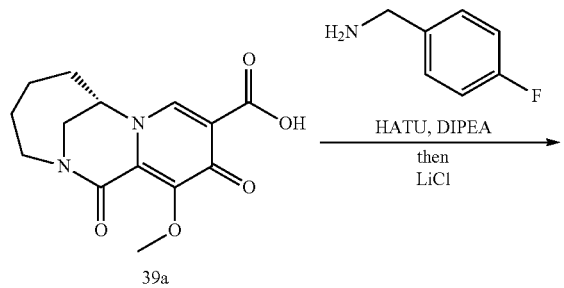

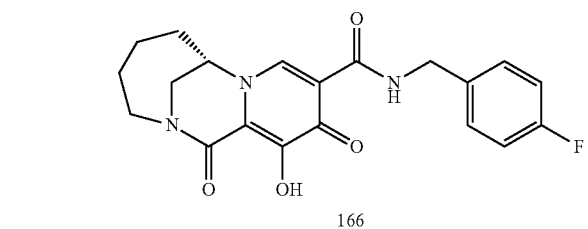

The title compound was prepared in a manner similar to (7S)—N-(3-chloro-2,4-difluorobenzyl)-12-hydroxy-1,11-dioxo 1,4,5,6,7,11-hexahydro-3H-2,7-methanopyrido[1,2-a][1,4]diazonine-10-carboxamide (51) except by using (4-fluorophenyl)methanamine instead of (3-chloro-2,4-difluorophenyl)methanamine. MS (m/z) 386.2 [M+H]⁺. ¹H NMR (400 MHz, Methanol-d₄) δ 8.46 (s, 1H), 7.39-7.22 (m, 2H), 7.09-6.94 (m, 2H), 4.69 (d, J=3.2 Hz, 1H), 4.34 (dt, J=13.4, 8.2 Hz, 1H), 3.98 (d, J=14.8 Hz, 1H), 3.74 (dd, J=14.7, 1.9 Hz, 1H), 3.66 (t, J=7.0 Hz, 2H), 3.21 (ddd, J=13.3, 7.1, 3.0 Hz, 1H), 2.91 (t, J=7.0 Hz, 2H), 2.19-1.98 (m, 2H), 1.95-1.73 (m, 2H), 1.32 (q, J=12.3 Hz, 1H).

Example 164: (7S)—N-benzyl-12-hydroxy-1,11-dioxo-1,4,5,6,7,11-hexahydro-3H-2,7-methanopyrido[1,2-a][1,4]diazonine-10-carboxamide (167)

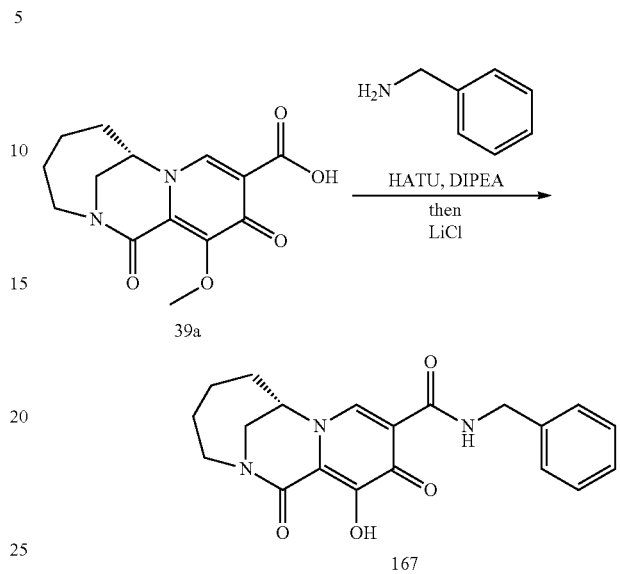

The title compound was prepared in a manner similar to (7S)—N-(3-chloro-2,4-difluorobenzyl)-12-hydroxy-1,11-dioxo 1,4,5,6,7,11-hexahydro-3H-2,7-methanopyrido[1,2-a][1,4]diazonine-10-carboxamide (51) except by using benzylamine instead of (3-chloro-2,4-difluorophenyl)methanamine. MS (m/z) 368.2 [M+H]⁺.

Example 165: Preparation of (7S)—N-(2,4-difluorobenzyl)-12-hydroxy-7-methyl-1,11-dioxo-1,6,7,11-tetrahydro-3H-2,7-methanopyrido[1,2-a][1,4]diazonine-10-carboxamide (168)

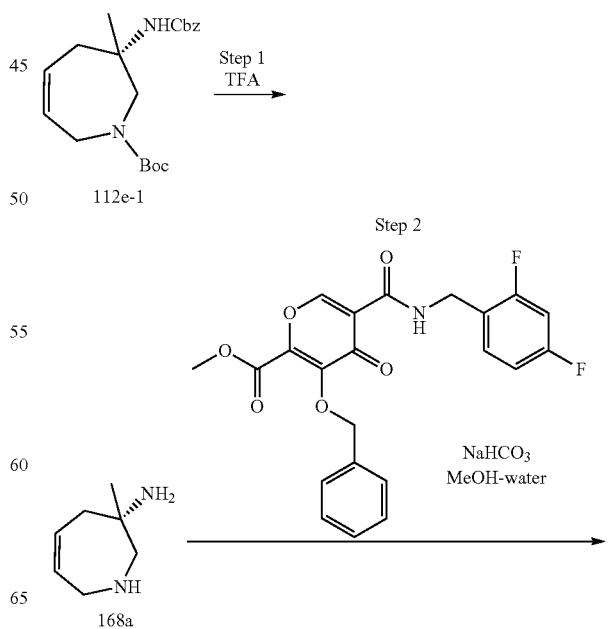

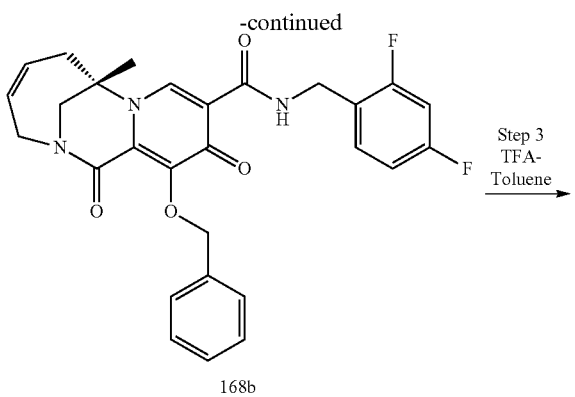

168b

Step 3
TFA-
Toluene

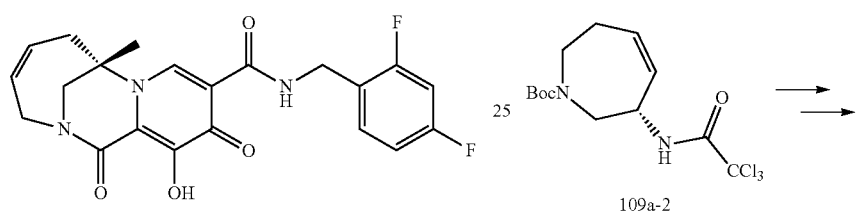

Step 1. Synthesis of (S)-3-methyl-2,3,4,7-tetrahydro-1H-azepin-3-amine (168a)

Tert-butyl (S)-3-(((benzyloxy)carbonyl)amino)-3-methyl-2,3,4,7-tetrahydro-1H-azepine-1-carboxylate (112e-1) (1000 mg, 2.77 mol) was dissolved in TFA (2 mL) at room temperature. The resulting reaction mixture was heated in seal tube at 100° C. for 2 hours. The resulting reaction mixture was concentrated to dryness. The product was then obtained as TFA salt which was used directly in the next step. MS (m/z) 127.18 [M+H]$^+$.

Step 2. Synthesis of (7S)-12-(benzyloxy)-N-(2,4-difluorobenzyl)-7-methyl-1,11-dioxo-1,6,7,11-tetrahydro-3H-2,7-methanopyrido[1,2-a][1,4]diazonine-10-carboxamide (168b)

The title compound was prepared in a manner similar to (7S)-12-(benzyloxy)-N-(2,4-difluorobenzyl)-1,11-dioxo-1,3,4,6,7,11-hexahydro-2,7-methanopyrido[1,2-d][1,4,7]oxadiazonine-10-carboxamide (28a) except by using (S)-3-methyl-2,3,4,7-tetrahydro-1H-azepin-3-amine bis TFA salt (168a) instead of 1,4-oxazepan-6-amine. MS (m/z) 506.20 [M+H]$^+$.

Step 3. Synthesis of (7S)—N-(2,4-difluorobenzyl)-12-hydroxy-7-methyl-1,11-dioxo-1,6,7,11-tetrahydro-3H-2,7-methanopyrido[1,2-a][1,4]diazonine-10-carboxamide (168)

The title compound was prepared in a manner similar to (7S)—N-(2,4-difluorobenzyl)-12-hydroxy-1,11-dioxo-1,3,4,6,7,11-hexahydro-2,7-methanopyrido[1,2-d][1,4,7]oxadiazonine-10-carboxamide (28) using (7S)-12-(benzyloxy)-N-(2,4-difluorobenzyl)-7-methyl-1,11-dioxo-1,6,7,11-tetrahydro-3H-2,7-methanopyrido[1,2-a][1,4]diazonine-10-carboxamide (168b) instead of (7S)-12-(benzyloxy)-N-(2,4-difluorobenzyl)-1,11-dioxo 1,3,4,6,7,11-hexahydro-2,7-methanopyrido [1,2-d][1,4,7]oxadiazonine-10-carboxamide (28a). MS (m/z) 416.18 [M+H]$^+$. $^1$H NMR (400 MHz, Methanol-d$_4$) δ 8.57 (s, 1H), 7.45 (td, J=8.5, 6.3 Hz, 1H), 7.06-6.87 (m, 2H), 5.82-5.60 (m, 1H), 5.18-4.99 (m, 1H), 4.65 (s, 2H), 4.00-3.63 (m, 4H), 2.76-2.45 (m, 2H), 1.79 (s, 3H).

Example 166: Preparation of (7S)—N-(2,4-difluorobenzyl)-12-hydroxy-1,11-dioxo-1,4,7,11-tetrahydro-3H-2,7-methanopyrido[1,2-a][1,4]diazonine-10-carboxamide (169)

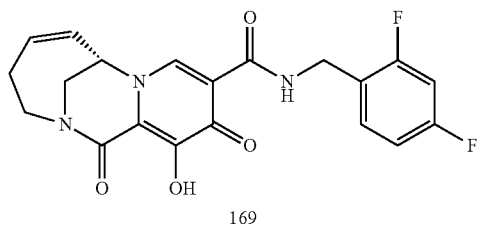

109a-2

169

The title compound was prepared in a manner similar to (7R)-12-hydroxy-1,11-dioxo-N-(2,4,6-trifluorobenzyl)-1,4,7,11-tetrahydro-3H-2,7-methanopyrido[1,2-a][1,4]diazonine-10-carboxamide (84) using tert-butyl (S)-3-(2,2,2-trichloroacetamido)-2,3,6,7-tetrahydro-1H-azepine-1-carboxylate (109a-2) and methyl 3-(benzyloxy)-5-((2,4-difluorobenzyl)carbamoyl)-4-oxo-4H-pyran-2-carboxylate instead of tert-butyl (R)-3-(2,2,2-trichloroacetamido)-2,3,6,7-tetrahydro-1H-azepine-1-carboxylate (109a-1) and methyl 3-(benzyloxy)-4-oxo-5-((2,4,6-trifluorobenzyl)carbamoyl)-4H-pyran-2-carboxylate. MS (m/z) 402.34 [M+H]$^+$. $^1$H NMR (400 MHz, DMSO-d6) δ 10.36 (t, J=5.9 Hz, 1H), 8.59 (s, 1H), 7.42 (td, J=8.7, 6.6 Hz, 1H), 7.25 (ddd, J=10.5, 9.3, 2.5 Hz, 1H), 7.07 (tdd, J=8.6, 2.6, 1.1 Hz, 1H), 5.80 (dddd, J=10.6, 9.1, 4.0, 1.5 Hz, 1H), 5.60 (dt, J=11.6, 2.7 Hz, 1H), 5.36 (s, 1H), 4.56 (d, J=5.9 Hz, 2H), 4.21 (td, J=12.2, 6.6 Hz, 1H), 4.09 (dd, J=14.9, 2.6 Hz, 1H), 3.81 (dt, J=15.0, 1.9 Hz, 1H), 3.31 (dd, J=12.9, 8.4 Hz, 1H), 2.94-2.74 (m, 1H), 2.30 (ddd, J=15.7, 9.1, 6.5 Hz, 1H).

Example 167: Preparation of (6S,7S)-12-hydroxy-6-methyl-1,11-dioxo-N-(2,4,6-trifluorobenzyl)-1,4,5,6,7,11-hexahydro-3H-2,7-methanopyrido[1,2-a][1,4]diazonine-10-carboxamide (170)
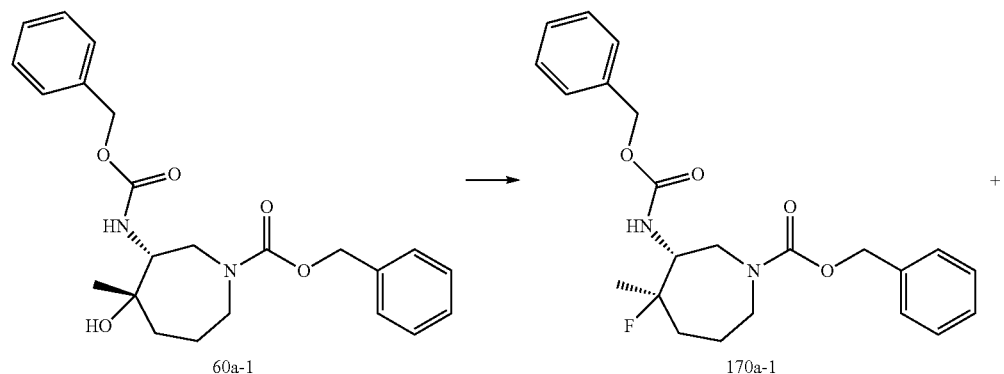
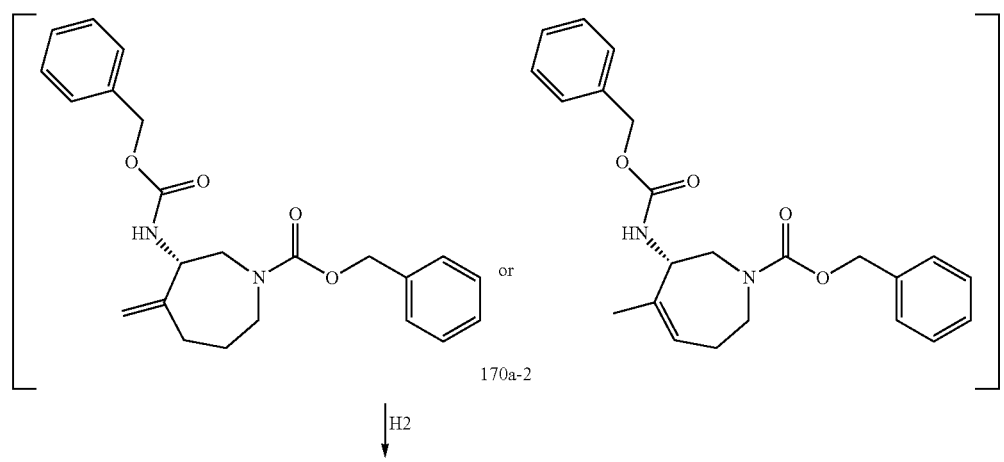
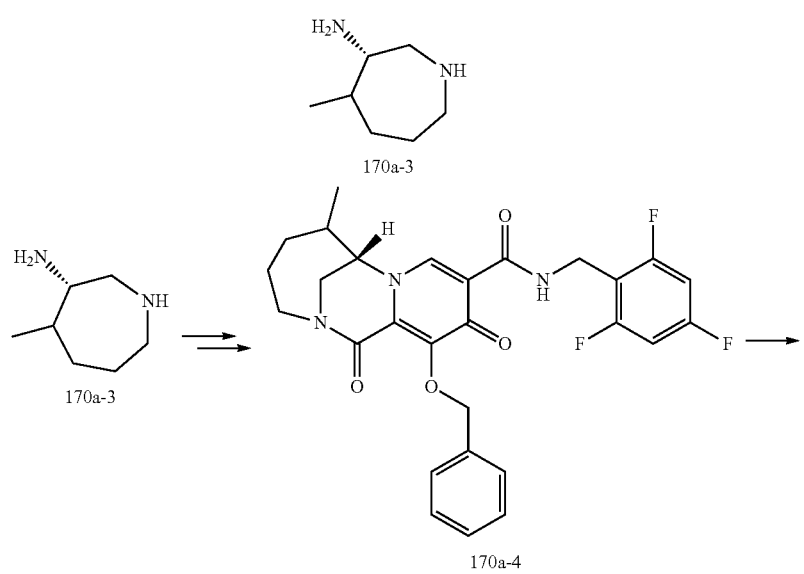

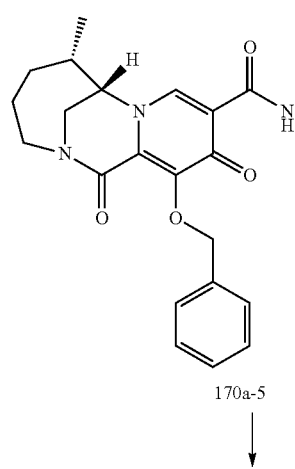

170a-5

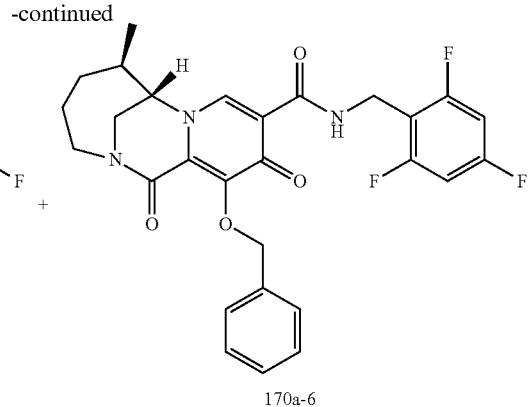

170a-6

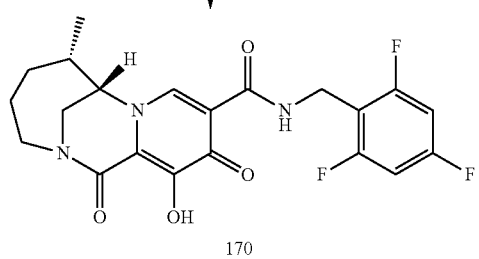

170

Synthesis of benzyl (S)-3-(((benzyloxy)carbonyl)amino)-4-methyleneazepane-1-carboxylate and benzyl (S)-3-(((benzyloxy)carbonyl)amino)-4-methyl-2,3,6,7-tetrahydro-1H-azepine-1-carboxylate (170a-2)

The title compound was prepared in a manner similar to benzyl 3-(((benzyloxy)carbonyl)amino)-4-ethyl-4-fluoroazepane-1-carboxylate (105b-2) in Example 102 except by using benzyl (3R,4S)-3-(((benzyloxy)carbonyl)amino)-4-hydroxy-4-methylazepane-1-carboxylate instead of benzyl 3-(((benzyloxy)carbonyl)amino)-4-ethyl-4-hydroxyazepane-1-carboxylate (105a). MS (m/z) 395.12 [M+H]$^+$.

Synthesis of (3S)-4-methylazepan-3-amine (170a-3)

Benzyl (S)-3-(((benzyloxy)carbonyl)amino)-4-methyleneazepane-1-carboxylate (170a-2, 150 mg, 0.38 mmol) was dissolved in 20 mL of absolute ethanol and was sparged under an argon atmosphere. Palladium hydroxide on carbon (53.4 mg, 0.076 mmol, 20% Pd weight) was added and the mixture was sparged under a hydrogen atmosphere (1 atm, balloon). The mixture was stirred vigorously for overnight and sparged under an argon atmosphere. It was filtered through a pad of Celite®. The Celite® was washed with absolute ethanol and the filtrate was concentrated in vacuo to afford the title compound. MS (m/z) 128.23 [M+H]$^+$.

Synthesis of (6S,7S)-12-(benzyloxy)-6-methyl-1,11-dioxo-N-(2,4,6-trifluorobenzyl)-1,4,5,6,7,11-hexahydro-3H-2,7-methanopyrido[1,2-a][1,4]diazonine-10-carboxamide (170a-5) and (6R,7S)-12-(benzyloxy)-6-methyl-1,11-dioxo-N-(2,4,6-trifluorobenzyl)-1,4,5,6,7,11-hexahydro-3H-2,7-methanopyrido[1,2-a][1,4]diazonine-10-carboxamide (170a-6)

Compounds (7S)-12-(benzyloxy)-6-methyl-1,11-dioxo-N-(2,4,6-trifluorobenzyl)-1,4,5,6,7,11-hexahydro-3H-2,7-methanopyrido[1,2-a][1,4]diazonine-10-carboxamide (170a-4) was prepared in a manner similar to (7S)-12-(benzyloxy)-N-(2,4-difluorobenzyl)-1,11-dioxo-1,3,4,6,7,11-hexahydro-2,7-methanopyrido[1,2-d][1,4,7]oxadiazonine-10-carboxamide (28a) in Example 25 using (3S)-4-methylazepan-3-amine (170a-3) and methyl 3-benzyloxy-4-oxo-5-[(2,4,6-trifluorophenyl)methylcarbamoyl]pyran-2-carboxylate instead of 1,4-oxazepan-6-amine and methyl 3-(benzyloxy)-5-((2,4-difluorobenzyl)carbamoyl)-4-oxo-4H-pyran-2-carboxylate. MS (m/z): 526.21 [M+H]$^+$.

The mixture was separated by silica gel chromatography to afford (6S,7S)-12-(benzyloxy)-6-methyl-1,11-dioxo-N-(2,4,6-trifluorobenzyl)-1,4,5,6,7,11-hexahydro-3H-2,7-methanopyrido[1,2-a][1,4]diazonine-10-carboxamide (170a-5). MS (m/z): 526.13 and (6R,7S)-12-(benzyloxy)-6-methyl-1,11-dioxo-N-(2,4,6-trifluorobenzyl)-1,4,5,6,7,11-hexahydro-3H-2,7-methanopyrido[1,2-a][1,4]diazonine-10-carboxamide (170a-6). MS (m/z): 526.25. The stereo-center on methyl position was arbitrary assigned.

Synthesis of (6S,7S)-12-hydroxy-6-methyl-1,11-dioxo-N-(2,4,6-trifluorobenzyl)-1,4,5,6,7,11-hexahydro-3H-2,7-methanopyrido[1,2-a][1,4]diazonine-10-carboxamide (170)

The title compound was prepared in a manner similar to (7S)—N-(2,4-difluorobenzyl)-12-hydroxy-1,11-dioxo-1,3,4,6,7,11-hexahydro-2,7-methanopyrido[1,2-d][1,4,7]oxadiazonine-10-carboxamide (28) using (6S,7S)-12-(benzyloxy)-6-methyl-1,11-dioxo-N-(2,4,6-trifluorobenzyl)-1,4,5,6,7,11-hexahydro-3H-2,7-methanopyrido[1,2-a][1,4]diazonine-10-carboxamide (170a-5) instead of (7S)-12-(benzyloxy)-N-(2,4-difluorobenzyl)-1,11-dioxo-1,3,4,6,7,11-hexahydro-2,7-methanopyrido[1,2-d][1,4,7]oxadiazonine-10-carboxamide (28a). MS (m/z) 436.23 [M+H]$^+$. $^1$H NMR (400 MHz, DMSO-d6) δ 10.42 (t, J=5.8 Hz, 1H), 8.49 (s, 1H), 7.28-7.15 (m, 2H), 4.64-4.49 (m, 2H), 4.36 (q, J=2.5 Hz, 1H), 4.13 (dd, J=13.1, 6.7 Hz, 1H), 3.80 (dd, J=14.9, 2.2 Hz, 1H), 3.74 (dd, J=14.8, 2.1 Hz, 1H), 3.03 (dt, J=12.7, 5.9 Hz, 1H), 1.90 (d, J=8.1 Hz, 1H), 1.90-1.74 (m, 1H), 1.72-1.57 (m, 2H), 1.39-1.26 (m, 1H), 1.12 (d, J=7.2 Hz, 3H).

Example 168: Synthesis of (7S)—N-(3-chloro-2,4-difluorobenzyl)-12-hydroxy-1,11-dioxo-1,4,7,11-tetrahydro-3H-2,7-methanopyrido[1,2-a][1,4]diazonine-10-carboxamide (171)

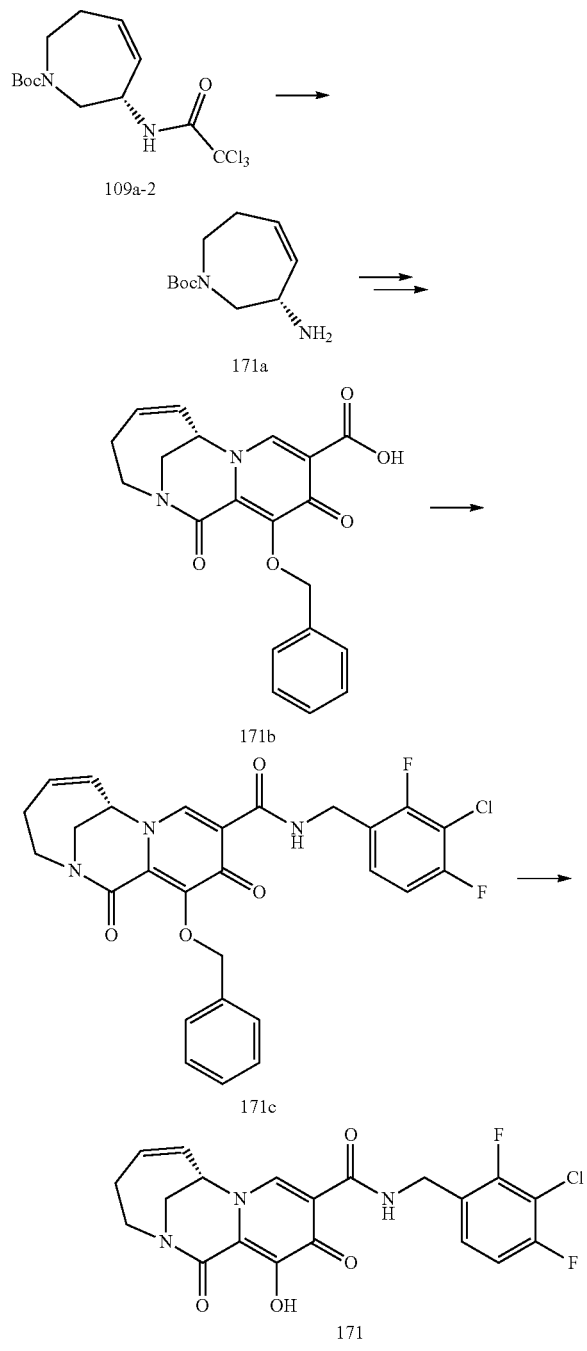

171a was prepared in a manner similar to tert-butyl (R)-3-amino-2,3,6,7-tetrahydro-1H-azepine-1-carboxylate (109b-1) using tert-butyl (S)-3-(2,2,2-trichloroacetamido)-2,3,6,7-tetrahydro-1H-azepine-1-carboxylate (109a-2) instead of tert-butyl (R)-3-(2,2,2-trichloroacetamido)-2,3,6,7-tetrahydro-1H-azepine-1-carboxylate (109a-1). MS (m/z): 213.183 [M+H]$^+$.

Synthesis of (7S)-12-(benzyloxy)-1,11-dioxo-1,4,7,11-tetrahydro-3H-2,7-methanopyrido[1,2-a][1,4]diazonine-10-carboxylic acid (171b)

Prepared in a manner similar to 11-(benzyloxy)-1,10-dioxo-1,3,4,5,6,10-hexahydro-2,6-ethanopyrido[1,2-a][1,4]diazocine-9-carboxylic acid (23c) using tert-butyl (S)-3-amino-2,3,6,7-tetrahydro-1H-azepine-1-carboxylate (171a) instead of tert-butyl 4-aminoazepane-1-carboxylate. MS (m/z): 367.100 [M+H]$^+$.

Synthesis of (7S)-12-(benzyloxy)-N-(3-chloro-2,4-difluorobenzyl)-1,11-dioxo-1,4,7,11-tetrahydro-3H-2,7-methanopyrido[1,2-a][1,4]diazonine-10-carboxamide (171c)

(7S)-12-(benzyloxy)-1,11-dioxo-1,4,7,11-tetrahydro-3H-2,7-methanopyrido[1,2-a][1,4]diazonine-10-carboxylic acid (171b) (75 mg, 0.205 mmol) was dissolved in DMF (2.0 mL) at room temperature, (3-chloro-2,4-difluorophenyl)methanamine (72.7 mg, 0.41 mmol) was added followed by HATU (117 mg, 0.307 mmol) and N,N-diisopropylethylamine (212 mg, 1.64 mmol). The reaction was stirred at room temperature overnight. The reaction was diluted with EtOAc, washed with water, saturated ammonium chloride, brine, dried over sodium sulfate, filtered and concentrated to give a light yellowish oil, used directly in next step without purification. LCMS-ESI+ (m/z): calcd H$^+$ for $C_{27}H_{22}ClF_2N_3O_4$, Theoretical: 525.13, Found: 526.09.

Synthesis of (7S)—N-(3-chloro-2,4-difluorobenzyl)-12-hydroxy-1,11-dioxo-1,4,7,11-tetrahydro-3H-2,7-methanopyrido[1,2-a][1,4]diazonine-10-carboxamide (171)

(1S)-6-benzyloxy-N-[(3-chloro-2,4-difluoro-phenyl)methyl]-5,8-dioxo-2,9-diazatricyclo[7.4.1.02,7]tetradeca-3,6,12-triene-4-carboxamide from previous step was treated with a mixture of Toluene (1.0 mL) and TFA (1.0 mL) at room temperature for overnight. The reaction was concentrated, redissolved in DMF, filtered and purified by reverse phase prep HPLC. LCMS-ESI+ (m/z): calcd H$^+$ for $C_{20}H_{16}ClF_2N_3O_4$, Theoretical: 435.08, Found: 435.99. 1H NMR (400 MHz, DMSO-d6) δ 10.41 (t, J=6.0 Hz, 1H), 8.59 (s, 1H), 7.40 (td, J=8.4, 6.2 Hz, 1H), 7.30 (td, J=8.7, 1.7 Hz, 1H), 5.88-5.71 (m, 1H), 5.60 (dq, J=11.7, 2.7 Hz, 1H), 5.36 (s, 1H), 4.61 (d, J=6.0 Hz, 2H), 4.21 (td, J=12.2, 6.6 Hz, 1H), 4.10 (dd, J=14.9, 2.5 Hz, 1H), 3.81 (dt, J=15.4, 1.9 Hz, 2H), 3.31 (dd, J=12.9, 8.4 Hz, 1H), 2.92-2.78 (m, 1H), 2.30 (ddd, J=15.7, 9.0, 6.5 Hz, 1H).

Example 169-1: Preparation of (6R,7S)—N-(2,4-difluorobenzyl)-6-fluoro-12-hydroxy-1,11-dioxo-1,4,5,6,7,11-hexahydro-3H-2,7-methanopyrido[1,2-a][1,4]diazonine-10-carboxamide (172-1)

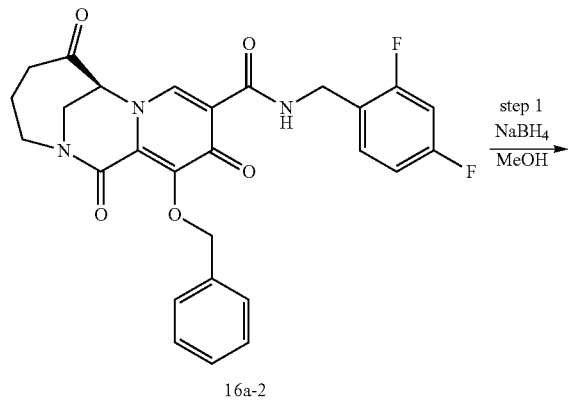

16a-2

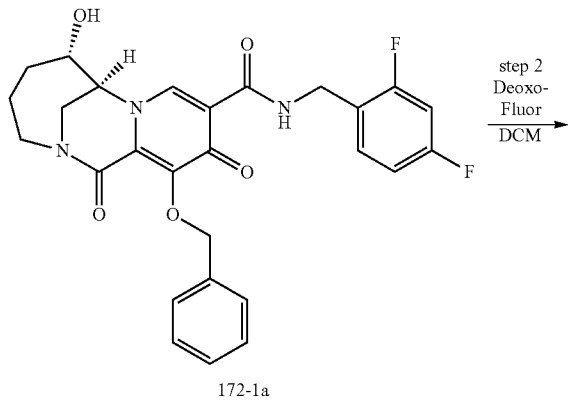

172-1a

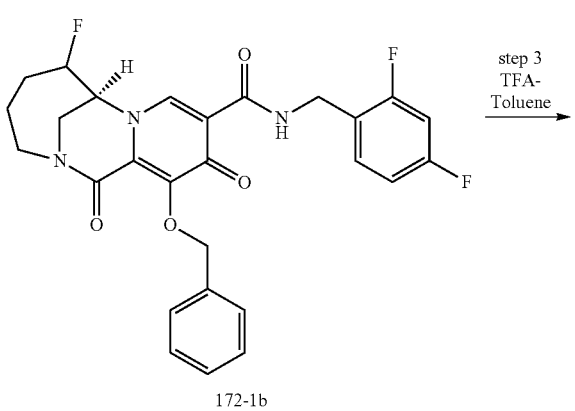

172-1b

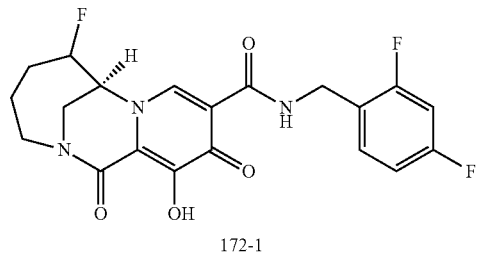

172-1

Step 1: Synthesis of (6S,7S)-12-(benzyloxy)-N-(2,4-difluorobenzyl)-6-hydroxy-1,11-dioxo-1,4,5,6,7,11-hexahydro-3H-2,7-methanopyrido[1,2-a][1,4]diazonine-10-carboxamide (172-1a):

(1S)-6-Benzyloxy-N-[(2,4-difluorophenyl)methyl]-5,8,13-trioxo-2,9-diazatricyclo[7.4.1.02,7]tetradeca-3,6-diene-4-carboxamide (16a-2) (60.0 mg, 0.118 mmol) in anhydrous MeOH (3.0 mL) was treated with sodium borohydride (8.95 mg, 0.236 mmol) at 0° C. for 10 min. The reaction was quenched with saturated ammonium chloride dropwise, extracted with EtOAc, the organic layer was washed with brine, dried over sodium sulfate, filtered and concentrated to give the product. MS (m/z): 510.18 [M+H]+.

Step 2: synthesis of (6R,7S)-12-(benzyloxy)-difluorobenzyl)-6-fluoro-1,11-dioxo-1,4,5,6,7,11-hexahydro-3H-2,7-methanopyrido[1,2-a][1,4]diazonine-10-carboxamide (172-1b)

(6S,7S)-12-(Benzyloxy)-N-(2,4-difluorobenzyl)-6-hydroxy-1,11-dioxo-1,4,5,6,7,11-hexahydro-3H-2,7-methanopyrido[1,2-a][1,4]diazonine-10-carboxamide (172-1a) (50.0 mg, 0.098 mmol) in DCM (5.0 mL) was cooled to 0° C. and treated with Deoxo-Fluor (86.8 mg, 0.393 mmol). The reaction was allowed to warm up to room temperature as ice melted overnight. The reaction was cooled back to 0° C. and quenched with saturated sodium bicarbonate. Extracted with EtOAc, the organic layer was washed with brine, dried over sodium sulfate, filtered and concentrated, used directly in next step. MS (m/z) 512.24 [M+H]+.

Step 3: Synthesis of (6R,7S)—N-(2,4-difluorobenzyl)-6-fluoro-12-hydroxy-1,11-dioxo-1,4,5,6,7,11-hexahydro-3H-2,7-methanopyrido[1,2-a][1,4]diazonine-10-carboxamide (172-1)

(6R,7S)-12-(Benzyloxy)-N-(2,4-difluorobenzyl)-6-fluoro-1,11-dioxo-1,4,5,6,7,11-hexahydro-3H-2,7-methanopyrido[1,2-a][1,4]diazonine-10-carboxamide (172-1b) (50 mg, 0.098 mmol) was treated with a mixture of TFA (0.3 mL) and toluene (0.3 mL) at room temperature for overnight. The reaction was concentrated, re-dissolved in DMF, filtered and purified by Gilson HPLC (Gemini, 5-100% ACN/H2O+0.1% TFA) to give title compound after lyophilization. MS (m/z) 422.27 [M+H]+. 1H NMR (400 MHz, DMSO-d6) δ 10.33 (t, J=6.0 Hz, 1H), 8.60 (s, 1H), 7.41 (td, J=8.7, 6.6 Hz, 1H), 7.25 (ddd, J=10.6, 9.3, 2.6 Hz, 1H), 7.13-6.98 (m, 1H), 5.12-4.89 (m, 2H), 4.56 (d, J=6.0 Hz, 2H), 4.13 (dt, J=13.0, 8.0 Hz, 1H), 3.92-3.84 (m, 2H), 3.13 (ddd, J=13.1, 7.1, 2.9 Hz, 1H), 2.09 (dtd, J=34.8, 19.6, 17.3, 7.8 Hz, 2H), 1.84-1.69 (m, 1H), 1.40 (dt, J=40.8, 13.6 Hz, 1H).

Example 169-2: Preparation of (7R)—N-(2,4-difluorobenzyl)-6-fluoro-12-hydroxy-1,11-dioxo-1,4,5,6,7,11-hexahydro-3H-2,7-methanopyrido[1,2-a][1,4]diazonine-10-carboxamide (172-2)

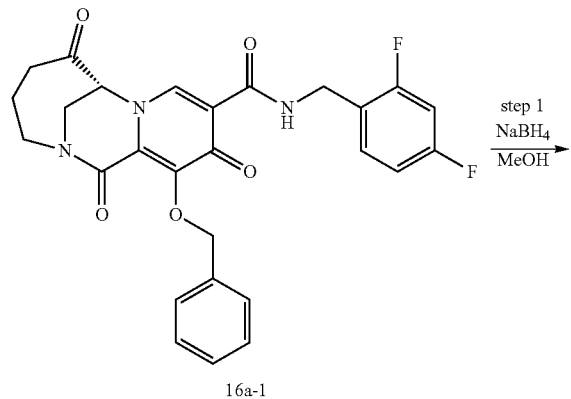

16a-1 step 1
NaBH₄
MeOH

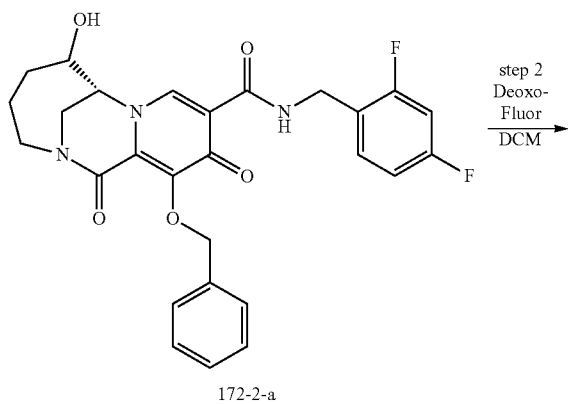

172-2-a step 2
Deoxo-Fluor
DCM

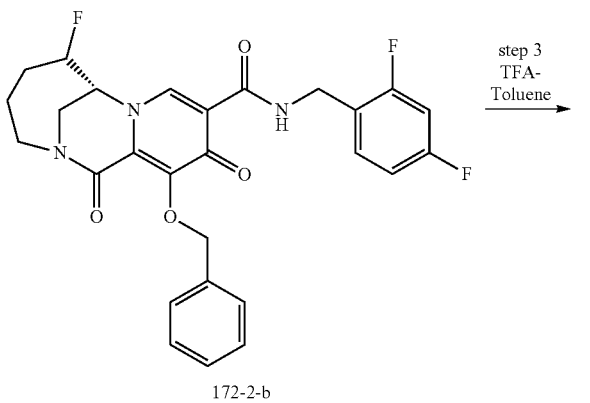

172-2-b step 3
TFA-Toluene

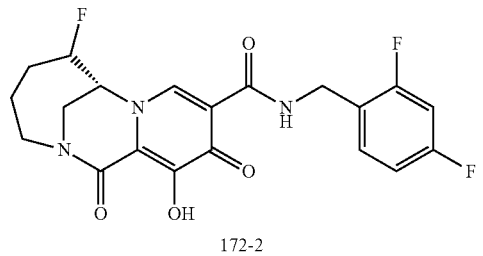

172-2

The title compound was prepared in a manner similar to of (6R,7S)—N-(2,4-difluorobenzyl)-6-fluoro-12-hydroxy-1,11-dioxo-1,4,5,6,7,11-hexahydro-3H-2,7-methanopyrido[1,2-a][1,4]diazonine-10-carboxamide (172-1) except using (1R)-6-Benzyloxy-N-[(2,4-difluorophenyl)methyl]-5,8,13-trioxo-2,9-diazatricyclo[7.4.1.02,7] tetradeca-3,6-diene-4-carboxamide (16a-1) instead of (1R)-6-Benzyloxy-N-[(2,4-difluorophenyl)methyl]-5,8,13-trioxo-2,9-diazatricyclo[7.4.1.02,7]tetradeca-3,6-diene-4-carboxamide (16a-2). MS (m/z) 422.10 [M+H]+. ¹HNMR (400 MHz, DMSO-d6) δ 10.61 (s, 1H), 10.33 (t, J=5.9 Hz, 1H), 8.60 (s, 1H), 7.41 (td, J=8.7, 6.6 Hz, 1H), 7.25 (ddd, J=10.5, 9.3, 2.5 Hz, 1H), 7.12-7.02 (m, 1H), 5.30-4.84 (m, 2H), 4.56 (d, J=5.9 Hz, 2H), 4.13 (dt, J=15.6, 7.9 Hz, 1H), 3.90 (d, J=14.9 Hz, 1H), 3.82 (dd, J=15.0, 2.0 Hz, 1H), 3.13 (ddd, J=13.2, 7.1, 2.8 Hz, 1H), 2.20-1.96 (m, 2H), 1.75 (d, J=15.2 Hz, 1H), 1.40 (ddd, J=41.0, 15.8, 11.2 Hz, 1H).

Example 170: Preparation of (7S)—N-(2,4-difluorobenzyl)-12-hydroxy-7-methyl-1,11-dioxo-1,4,5,6,7,11-hexahydro-3H-2,7-methanopyrido[1,2-a][1,4]diazonine-10-carboxamide (173)

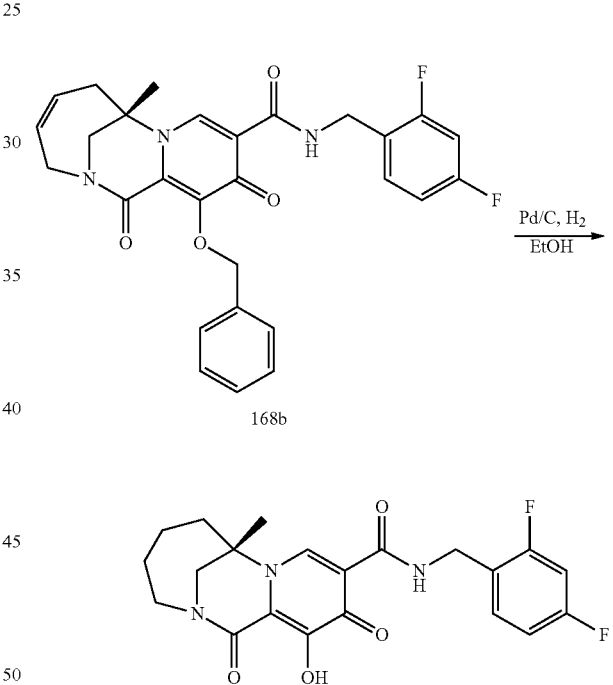

168b

Pd/C, H₂
EtOH (7S)-12-(benzyloxy)-N-(2,4-difluorobenzyl)-7-methyl-1,11-dioxo-1,6,7,11-tetrahydro-3H-2,7-methanopyrido[1,2-a][1,4]diazonine-10-carboxamide (50 mg, 0.1 mmol) was dissolved in EtOH (5 mL). Pd/C (10%) (5 mg) was added. Hydrogenolysis was applied with hydrogen balloon. Reaction was complete after 3 hrs. Reaction mixture was then filtered through celite plug. The filtrate was concentrated and purified by Gilson HPLC (Gemini, 5-100% ACN/H₂O+ 0.1% TFA) to give title compound after lyophilization. MS (m/z) 418.29 [M+H]⁺. ¹H NMR (400 MHz, Methanol-d4) δ 8.59 (s, 1H), 7.45 (td, J=8.5, 6.4 Hz, 1H), 7.05-6.84 (m, 2H), 4.65 (s, 2H), 4.39 (dt, J=13.4, 6.7 Hz, 1H), 3.92-3.51 (m, 2H), 3.18 (dt, J=13.1, 6.4 Hz, 1H), 2.08 (ddd, J=15.4, 10.3, 2.4 Hz, 1H), 2.00-1.84 (m, 4H), 1.73 (s, 3H), 1.62-1.37 (m, 1H).

Example 171: Synthesis of (3S,6R,7S)-12-hydroxy-3,6-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide (174)

tallization from Et₂O (160 mL) and hexane (320 mL) afforded 174b. ¹H NMR (400 MHz, DMSO-d₆) δ 12.64 (br, 1H), 7.54 (s, 1H), 7.36-7.31 (m, 5H), 5.82-5.72 (m, 1H), 5.07-4.99 (m, 4H), 4.05-4.01 (m, 1H), 2.64 (t, J=6.8 Hz, 1H), 0.99 (d, J=6.8 Hz, 3H). MS (m/z): 264.10 [M+H]⁺.

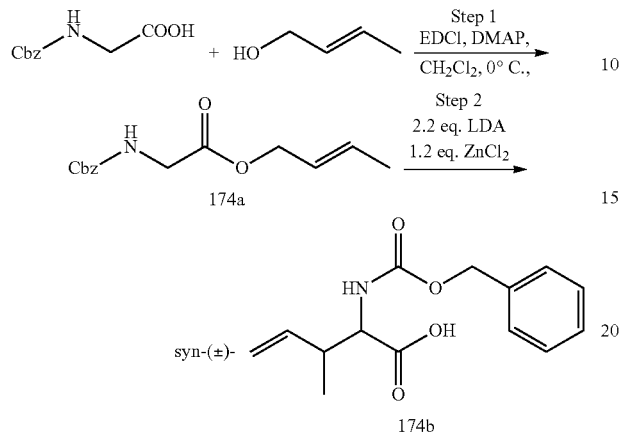

Step 1. Synthesis of (E)-but-2-en-1-yl ((benzyloxy)carbonyl)glycinate (174a)

To a solution of ((benzyloxy)carbonyl)glycine (120.0 g, 574 mmol, 1.0 eq) in DCM (1200 mL) was added (E)-but-2-en-1-ol (49.7 g, 689 mmol, 1.2 eq) and DMAP (14.1 g, 115 mmol, 0.2 eq). The mixture was cooled to 0° C. and EDC.HCl (164.9 g, 860 mmol, 1.5 eq) was added by portion wise. The mixture was stirred at room temperature for 1.5 h. HPLC showed completion. Water (1200 mL) was added and phases were separated. The organic phase was washed with water (500 mL×2). Dried over Na₂SO₄, concentrated to give a crude residue, which was purified by silica gel column chromatography (eluted with PE:EA=5:1) to give compound 174a (140 g, 93%, contain EtOAc) as a colorless oil. ¹H NMR (400 MHz, CDCl₃) δ 7.36-7.28 (m, 5H), 5.86-5.77 (m, 1H), 5.62-5.55 (m, 1H), 5.44 (s, 1H), 5.13 (s, 2H), 4.73 (d, J=6.8 Hz, 2H), 3.98 (d, J=5.6 Hz, 2H), 1.74 (d, J=6.4 Hz, 3H).

Synthesis of syn-(±)-2-(((benzyloxy)carbonyl)amino)-3-methylpent-4-enoic acid (177b)

To a solution of diisopropylamine (161.4 g, 1.60 mol, 3.0 eq) in THF (1500 mL) at −20° C. was added n-BuLi (2.4 M, 552 mL, 1.32 mol, 2.5 eq) by drop with under N₂. The mixture was stirred at −20° C. for 30 mins. Then cooled to −78° C. and a solution of (E)-but-2-en-1-yl ((benzyloxy)carbonyl)glycinate (174a) (140.0 g, 0.53 mol, 1.0 eq) in THE (382 mL) was added by dropwise at −78° C. The mixture was stirred for 30 mins at −78° C. ZnCl₂ (1 M in THF, 600 mL, 0.60 mol, 1.13 eq) was added by dropwise at −78° C. The mixture was warmed to room temperature and stirred for 3-4 h. Adjusted pH=4-5 with 1 N HCl at 0° C. Extracted with MTBE (750 mL×2). Most of THE was removed under vacuo. The organics were washed with 2 N NaOH (500 mL×2). The aqueous phase was adjusted pH=4-5 with 1 N HCl at 0° C. Extracted with MTBE (750 mL×2). Dried over Na₂SO₄, concentrated to give crude product (70 g), which was purified with silica gel column (eluted with PE:EA=1:1) to give compound 174b. Recrys-

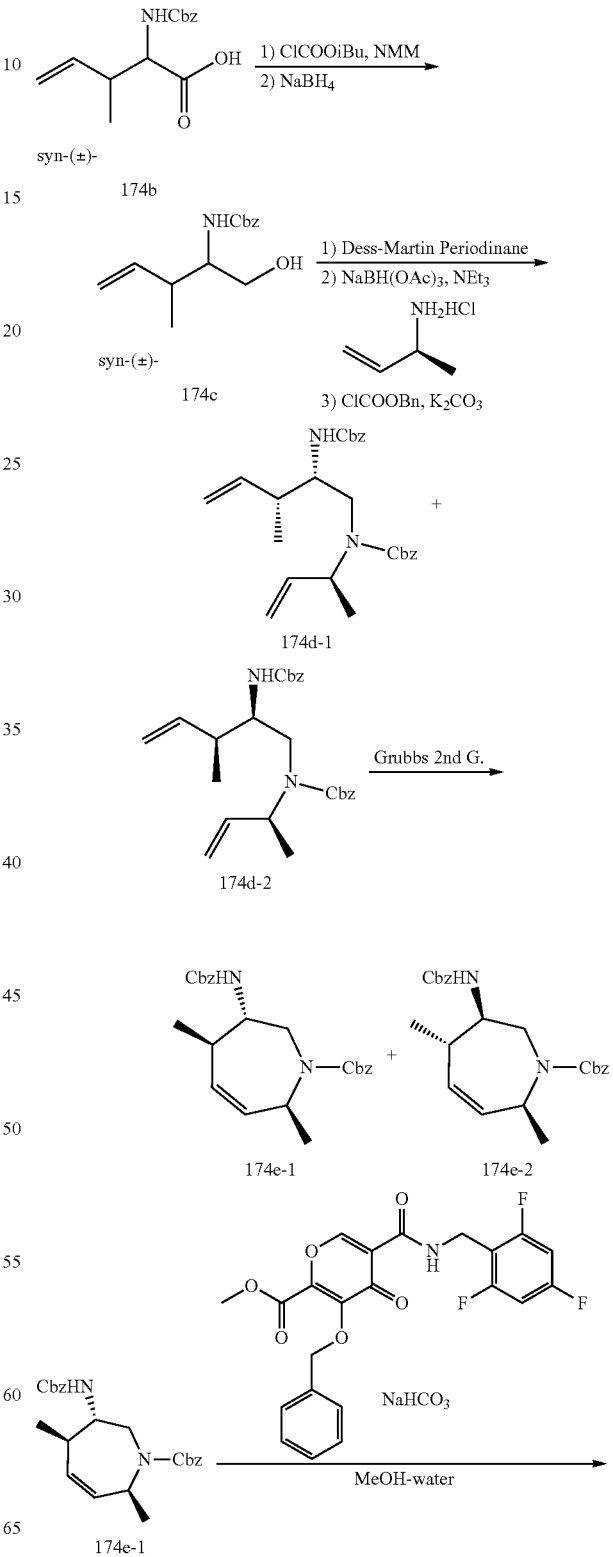

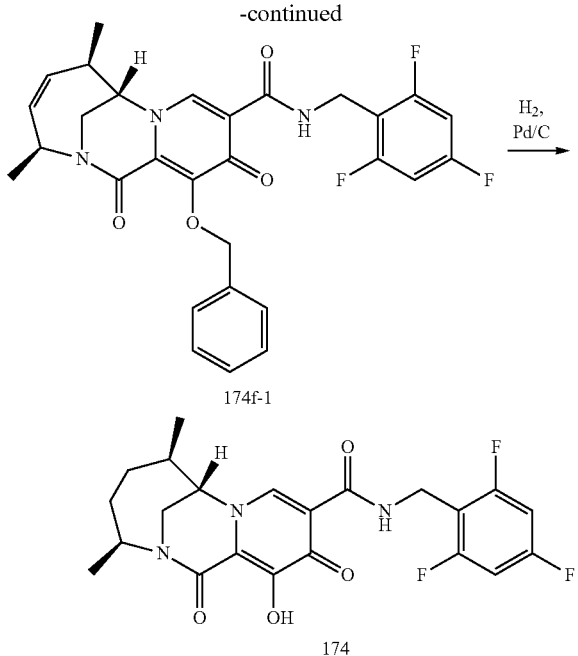

174f-1

174

Synthesis of syn-(±)-benzyl (1-hydroxy-3-methyl-pent-4-en-2-yl)carbamate (174c)

A solution of the syn-(±)-2-(benzyloxycarbonylamino)-3-methyl-pent-4-enoic acid (177b) (2000.1 mg, 7.60 mmol) and 4-methylmorpholine (1 mL, 9.20 mmol) in tetrahydrofuran (20 mL) was stirred at ice-salt bath as isobutyl chloroformate (1.2 mL, 9.10 mmol) was added dropwise. After 30 min, the reaction mixture was filtered, and the solids were washed with tetrahydrofuran (10 mL). The filtrate was stirred in the ice-salt bath as a solution of sodium borohydride (441 mg, 11.7 mmol) in water (4 mL) was added dropwise. The reaction mixture was further diluted with water (16 mL) and the resulting reaction mixture was stirred at rt overnight. The reaction mixture was diluted with saturated ammonium chloride (50 mL) and water (50 mL) before extracted with ethyl acetate (100 mL×2). After the extracts were washed with brine (1×100 mL), the organic fractions were combined, dried (MgSO$_4$) and concentrated. The residue was purified by column chromatography on silica gel eluting 15-55% ethyl acetate in hexane to get the title compound 174c. MS (m/z) 249.81 [M+H]$^+$.

Synthesis of a mixture of benzyl ((2S,3R)-2-(((benzyloxy)carbonyl)amino)-3-methylpent-4-en-1-yl)((S)-but-3-en-2-yl)carbamate (174d-1) and benzyl ((2R,3S)-2-(((benzyloxy)carbonyl)amino)-3-methyl-pent-4-en-1-yl)((S)-but-3-en-2-yl)carbamate (174d-2)

A solution of syn-(±)-benzyl (1-hydroxy-3-methylpent-4-en-2-yl)carbamate (174c) (806.3 mg, 3.23 mmol) in dichloromethane (37 mL) was stirred at 0° C. bath as Dess Martin periodinane (1785.6 mg, 4.21 mmol) was added. After 10 min, the reaction mixture was stirred at rt. After 1.5 h, additional Dess-Martin periodinane (3.45.7 mg, 0.815 mmol) was added at rt and the resulting solution was stirred at rt for 1 h. The reaction mixture was stirred at 0° C. and added saturated sodium bicarbonate (100 mL). After the mixture was transferred to a separatory funnel, 10% sodium thiosulfate solution (1×100 mL), and ethyl acetate (100 mL) were added and two fractions were separated. After the lower aq. fraction was extracted with ethyl acetate (100 mL×1), the two resulting organic fractions were washed with brine (70 mL×1), combined, dried (MgSO$_4$), and concentrated.

A suspension of the residue and (2S)-but-3-en-2-amine hydrochloride (385.6 mg, 3.58 mmol) in tetrahydrofuran (21 mL) was stirred at rt as triethylamine (0.5 mL, 3.59 mmol) and sodium triacetoxyborohydride (1156.7 mg, 5.46 mmol) were added. The resulting reaction mixture was stirred at rt for 22 h. The reaction mixture was concentrated to remove most of tetrahydrofuran and diluted with water (~100 mL) before the product was extracted with ethyl acetate (100 mL×2). After the extracts were washed with water (×1), the organic fractions were combined, dried (MgSO$_4$) and concentrated to get the crude amine.

A mixture of the crude amine and potassium carbonate (500.0 mg, 3.62 mmol) in 1,4-dioxane (15 mL) and water (15 mL) was stirred at 0° C. as benzyl chloroformate (0.525 mL, 3.57 mmol) was added. The resulting mixture was stirred at 0° C. for ~1 h and then at rt overnight. The reaction mixture was diluted with water (100 mL) and the product was extracted with ethyl acetate (100 mL×2). After the extracts were washed with water (150 mL×1), combined, dried (MgSO$_4$), and concentrated, the residue was purified by column chromatography on silica gel eluting 0-30% ethyl acetate in hexane to get the title compounds 174d-1 and 174d-2 as a mixture: MS (m/z) 437.26 [M+H]$^+$.

Synthesis of benzyl (3S,4R,7S) and (3R,4S,7S)-3-(((benzyloxy)carbonyl)amino)-4,7-dimethyl-2,3,4,7-tetrahydro-1H-azepine-1-carboxylate (174e-1 and 174e-2)

A solution of the diastereomeric mixture of reactant (174d-1 & 174d-2, 984.5 mg, 2.26 mmol) and Grubbs catalyst 2nd generation (131.7 mg, 155 umol) in toluene (600 mL) was purged with argon gas for 15 min. The resulting solution was stirred at 80° C. bath for 3 h. The reaction mixture was concentrated, and the residue was purified by column chromatography on silica gel eluting 5-40% ethyl acetate in hexane to get the title compounds 174e-1 and 174e-2, respectively. Compound 174e-1: MS (m/z) 409.20 [M+H]$^+$. Compound 174e-2: MS (m/z) 409.05 [M+H]$^+$.

Synthesis of (3S,6R,7S)-12-(benzyloxy)-3,6-dimethyl-1,11-dioxo-N-(2,4,6-trifluorobenzyl)-1,6,7,11-tetrahydro-3H-2,7-methanopyrido[1,2-a][1,4]diazonine-10-carboxamide (174f-1)

Benzyl (3S,4R,7S)-3-(((benzyloxy)carbonyl)amino)-4,7-dimethyl-2,3,4,7-tetrahydro-1H-azepine-1-carboxylate (174e-1) (238.8 mg, 0.585 mmol) was dissolved in TFA (5 mL) and heated to 100° C. in a sealed vial for 2 h. The reaction mixture was concentrated and co-evaporated with toluene once. A half of the residue was mixed with methyl 3-(benzyloxy)-4-oxo-5-((2,4,6-trifluorobenzyl)carbamoyl)-4H-pyran-2-carboxylate (128.1 mg, 0.286 mmol), and sodium bicarbonate (138 mg, 1.64 mmol) before methanol (5 mL) and water (5 mL) were added. The resulting mixture was heated at 50° C. After 2.5 h, additional methanol (10 mL) and dichloromethane (15 mL) were added and the resulting suspension was stirred at 50° C. bath. After 22 h, the reaction mixture was concentrated to remove most of the organic solvents and the residue was dissolved in dichloromethane (25 mL) and water (25 mL). After separation of two fractions, the aqueous fraction was extracted with dichloromethane (25 mL×1) and the combined two organic extracts were dried (MgSO$_4$) and concentrated. The residue was purified by column chromatography on silica gel eluting 0-30% methanol in dichloromethane to get the title compound 7: MS (m/z) 538.16 [M+H]$^+$.

Synthesis of (3S,6R,7S)-12-hydroxy-3,6-dimethyl-1, 11-dioxo-N-(2,4,6-trifluorobenzyl)-1,4,5,6,7,11-hexahydro-3H-2,7-methanopyrido[1,2-a][1,4]diazonine-10-carboxamide (174)

To a flask containing (3S,6R,7S)-12-(benzyloxy)-3,6-dimethyl-1,11-dioxo-N-(2,4,6-trifluorobenzyl)-1,6,7,11-tetrahydro-3H-2,7-methanopyrido[1,2-a][1,4]diazonine-10-carboxamide (15.1 mg, 28.1 umol) and 10% Pd in C (4.8 mg) was added ethanol (3 mL) and the resulting mixture was stirred under H$_2$ atmosphere for 1 h. The reaction mixture was filtered through celite pad and the filtrate was concentrated. The residue was dissolved in DMF, filtered through a membrane filter, and the filtrate was injected on preparative HPLC (column, Gemini 5 um C18 110A, LC column 100×30 mm) eluting 10-70% acetonitrile (0.1% TFA) in water (0.1% TFA) over 25 min.). The product containing fraction was freeze-dried to get the title compound 174: MS (m/z) 450.23 [M+H]$^+$. $^1$H NMR (400 MHz, Acetonitrile-d$_3$) δ 10.39 (s, 1H), 8.42 (s, 1H), 6.92-6.74 (m, 2H), 4.59 (d, J=5.5 Hz, 2H), 4.50 (dp, J=10.2, 6.7 Hz, 1H), 4.17 (q, J=2.0 Hz, 1H), 3.57 (d, J=1.9 Hz, 2H), 2.18 (p, J=3.8 Hz, 1H), 1.85 (dt, J=14.4, 7.1 Hz, 1H), 1.61-1.45 (m, 2H), 1.31 (ddd, J=15.2, 11.2, 3.4 Hz, 1H), 1.21 (d, J=6.7 Hz, 3H), 1.12 (d, J=7.3 Hz, 3H).

Example 172: Synthesis of (3S,6R,7S)—N-(2,4-difluorobenzyl)-12-hydroxy-3,6-dimethyl-1,11-dioxo-1,4,5,6,7,11-hexahydro-3H-2,7-methanopyrido[1,2-a][1,4]diazonine-10-carboxamide (175)

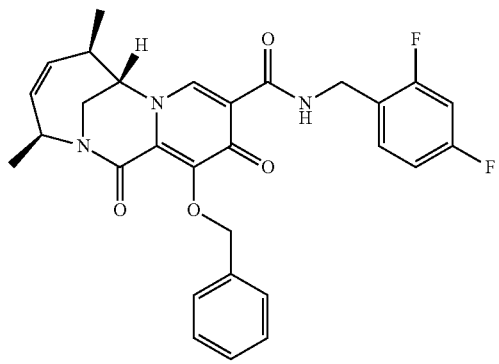

175a

↓ H$_2$, Pd/C

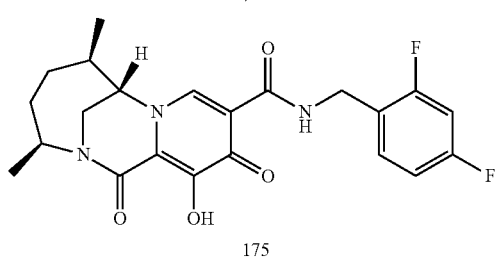

175

The title compound was prepared in a manner similar to compound 174f-1 except using methyl 3-(benzyloxy)-5-((2,4-difluorobenzyl)carbamoyl)-4-oxo-4H-pyran-2-carboxylate instead of using methyl 3-(benzyloxy)-4-oxo-5-((2,4,6-trifluorobenzyl)carbamoyl)-4H-pyran-2-carboxylate. MS (m/z) 432.24 [M+H]$^+$. $^1$H NMR (400 MHz, Acetonitrile-d$_3$) δ 10.43 (s, 1H), 8.47 (s, 1H), 7.43 (q, J=9.1, 8.5 Hz, 1H), 7.04-6.87 (m, 2H), 4.60 (d, J=5.3 Hz, 2H), 4.57-4.45 (m, 1H), 4.21 (s, 1H), 3.60 (d, J=1.9 Hz, 2H), 2.22 (dt, J=7.8, 3.9 Hz, 1H), 1.88 (dt, J=14.5, 7.1 Hz, 1H), 1.67-1.46 (m, 2H), 1.35 (ddd, J=15.4, 11.5, 3.1 Hz, 1H), 1.25 (d, J=6.6 Hz, 3H), 1.16 (d, J=7.3 Hz, 3H).

Example 173: (3S,6R,7S)-12-hydroxy-3,6-dimethyl-1,11-dioxo-N-(2,4,6-trifluorobenzyl)-1,6,7,11-tetrahydro-3H-2,7-methanopyrido[1,2-a][1,4]diazonine-10-carboxamide (176)

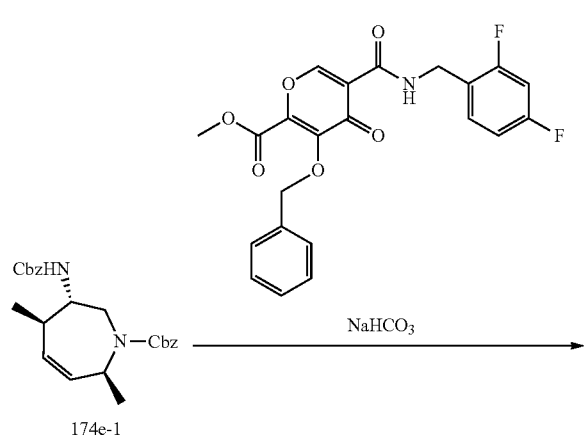

174e-1

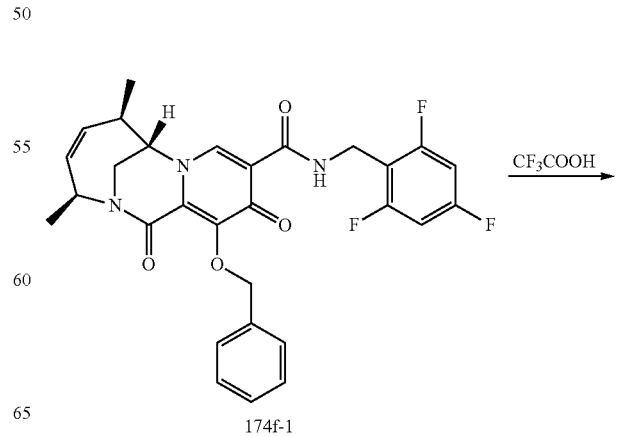

174f-1

-continued

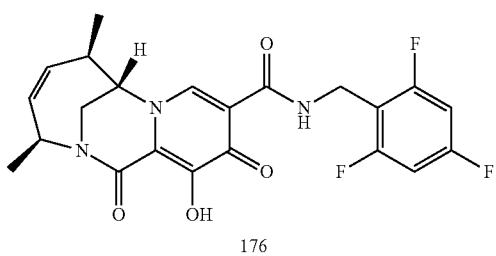

176

To a solution of (3S,6R,7S)-12-(benzyloxy)-3,6-dimethyl-1,11-dioxo-N-(2,4,6-trifluorobenzyl)-1,6,7,11-tetrahydro-3H-2,7-methanopyrido[1,2-a][1,4]diazonine-10-carboxamide (174f-1) (7, 14.2 mg, 26.4 umol) in toluene (0.5 mL) was added 2,2,2-trifluoroacetic acid (1 mL) at rt and the resulting solution was stirred at rt. After 2 h, the reaction mixture was concentrated, and the residue was dissolved in DMF, filtered through a membrane filter. The filtrate was injected on preparative HPLC (column, Gemini 5 um C18 110A, LC column 100×30 mm) eluting 10-70% acetonitrile (0.1% TFA) in water (0.1% TFA) over 25 min.) The product containing fraction was freeze-dried to get the title compound 176: MS (m/z) 448.19 [M+H]+. $^1$H NMR (400 MHz, Acetonitrile-d$_3$) δ 10.31 (s, 1H), 8.35 (s, 1H), 6.84 (t, J=8.5 Hz, 2H), 5.45-5.31 (m, 2H), 5.28 (d, J=7.8 Hz, 1H), 4.59 (d, J=5.2 Hz, 2H), 4.26-4.12 (m, 1H), 3.89 (dd, J=14.3, 2.8 Hz, 1H), 3.54 (d, J=14.2 Hz, 1H), 2.75-2.57 (m, 1H), 1.30 (d, J=7.1 Hz, 3H), 1.18 (d, J=7.1 Hz, 3H).

Example 174: Synthesis of (3S,6R,7S)—N-(2,4-difluorobenzyl)-12-hydroxy-3,6-dimethyl-1,11-dioxo-1,6,7,11-tetrahydro-3H-2,7-methanopyrido[1,2-a][1,4]diazonine-10-carboxamide (177)

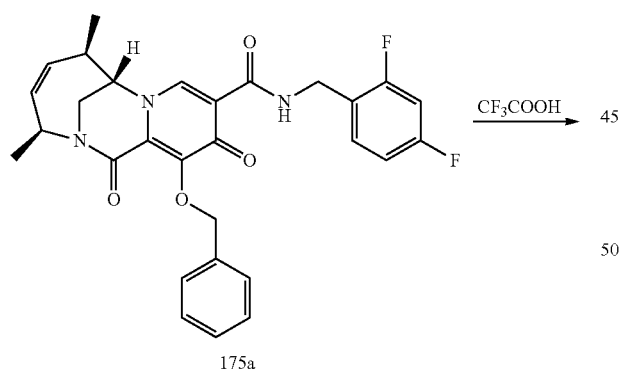

To a solution of (1S,10S,13R)-6-benzyloxy-N-[(2,4-difluorophenyl)methyl]-10,13-dimethyl-5,8-dioxo-2,9-diazatricyclo[7.4.1.02,7]tetradeca-3,6,11-triene-4-carboxamide (175a, 13.1 mg, 25 umol) in toluene (0.5 mL) was added 2,2,2-trifluoroacetic acid (1 mL) at rt and the resulting solution was stirred at rt for 2 h. The reaction mixture was concentrated, and the residue was dissolved in DMF, filtered through a membrane filter before the filtrate was injected on preparative HPLC (column, Gemini 5 um C18 110A, LC column 100×30 mm) eluting 10-70% acetonitrile (0.1% TFA) in water (0.1% TFA) over 25 min.) and freeze-dried to get the title compound 177. MS (m/z) 430.22 [M+H]+. $^1$H NMR (400 MHz, Acetonitrile-d$_3$) δ 10.32 (s, 1H), 8.37 (s, 1H), 7.41 (q, J=8.1 Hz, 1H), 7.03-6.85 (m, 2H), 5.47-5.32 (m, 2H), 5.32-5.23 (m, 1H), 4.58 (d, J=5.0 Hz, 2H), 4.22 (dd, J=5.8, 2.7 Hz, 1H), 3.89 (dd, J=14.3, 2.8 Hz, 1H), 3.55 (d, J=14.2 Hz, 1H), 2.68 (s, 1H), 1.30 (d, J=7.1 Hz, 3H), 1.19 (d, J=7.1 Hz, 3H).

Example 175: Preparation of (7S)-4-fluoro-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (178)

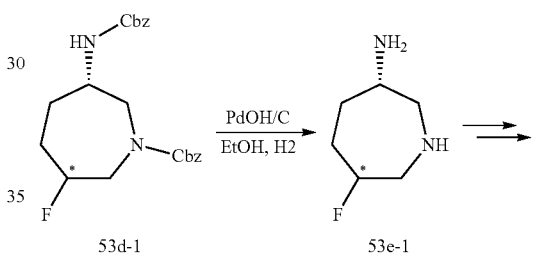

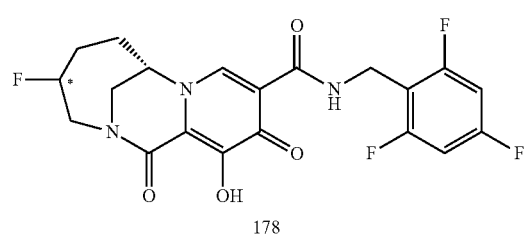

178

The title compounds were prepared analogously to (4R,7S)—N-(2,4-difluorobenzyl)-4-fluoro-12-hydroxy-1,11-dioxo-1,4,5,6,7,11-hexahydro-3H-2,7-methanopyrido[1,2-a][1,4]diazonine-10-carboxamide and (4S,7S)—N-(2,4-difluorobenzyl)-4-fluoro-12-hydroxy-1,11-dioxo-1,4,5,6,7,11-hexahydro-3H-2,7-methanopyrido[1,2-a][1,4]diazonine-10-carboxamide 53-1, using methyl 3-(benzyloxy)-4-oxo-5-((2,4,6-trifluorobenzyl)carbamoyl)-4H-pyran-2-carboxylate in place of methyl 3-(benzyloxy)-5-((2,4-difluorobenzyl)carbamoyl)-4-oxo-4H-pyran-2-carboxylate. MS (m/z) 440.30 [M+H]+. $^1$H NMR (400 MHz, Methanol-d4) δ 8.51 (s, 1H), 6.91 (t, J=8.4 Hz, 2H), 5.23 (t, J=6.2 Hz, 1H), 5.11 (t, J=6.3 Hz, 1H), 4.69 (s, 3H), 4.05 (d, J=14.8 Hz, 1H), 3.76 (d, J=14.6 Hz, 1H), 3.49 (dd, J=21.7, 15.2 Hz, 1H), 2.46 (t, J=14.7 Hz, 1H), 2.29-2.20 (m, 1H), 2.04 (d, J=15.3 Hz, 1H), 1.53 (dd, J=31.1, 16.5 Hz, 1H).

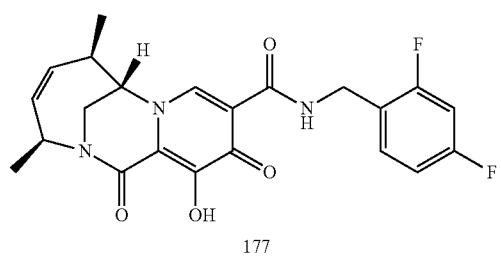

177

Example 176: Preparation of (6S,7R)-6-fluoro-12-hydroxy-6-methyl-1,11-dioxo-N-(2,4,6-trifluorobenzyl)-1,4,5,6,7,11-hexahydro-3H-2,7-methanopyrido[1,2-a][1,4]diazonine-10-carboxamide (179)

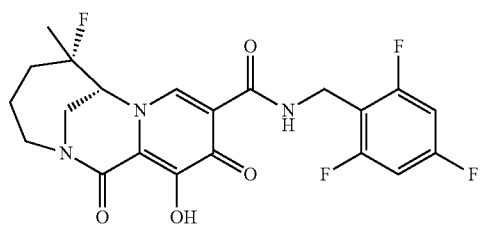

179

Prepared in a manner similar to (6S,7R)—N-(2,4-difluorobenzyl)-6-fluoro-12-hydroxy-6-methyl-1,11-dioxo-1,4,5,6,7,11-hexahydro-3H-2,7-methanopyrido[1,2-a][1,4]diazonine-10-carboxamide (60-1) in Example 57a using methyl 3-benzyloxy-4-oxo-5-[(2,4,6-trifluorophenyl)methylcarbamoyl]pyran-2-carboxylate instead of methyl 3-benzyloxy-5-[(2,4-difluorophenyl)methylcarbamoyl]-4-oxo-pyran-2-carboxylate. MS (m/z) 454.10 [M+H]$^+$. $^1$HNMR (400 MHz, DMSO-d6) δ 10.64 (s, 1H), 10.35 (t, J=5.8 Hz, 1H), 8.41 (d, J=1.9 Hz, 1H), 7.21 (t, J=8.6 Hz, 2H), 4.80 (s, 1H), 4.57 (d, J=5.7 Hz, 2H), 4.18 (dt, J=13.3, 8.4 Hz, 1H), 3.94 (ddd, J=15.5, 6.3, 3.0 Hz, 1H), 3.74 (d, J=15.5 Hz, 3H), 3.10 (dd, J=13.0, 7.3 Hz, 1H), 1.90 (q, J=7.7 Hz, 1H), 1.80 (td, J=13.4, 7.6 Hz, 2H), 1.62 (d, J=23.8 Hz, 3H), 1.45-1.32 (m, 1H).

Example 177: (3R,7S)-3-(fluoromethyl)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (180)

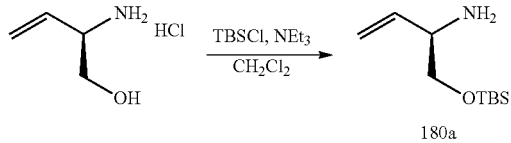

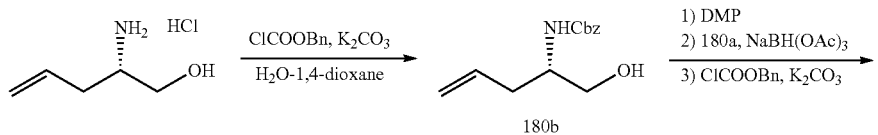

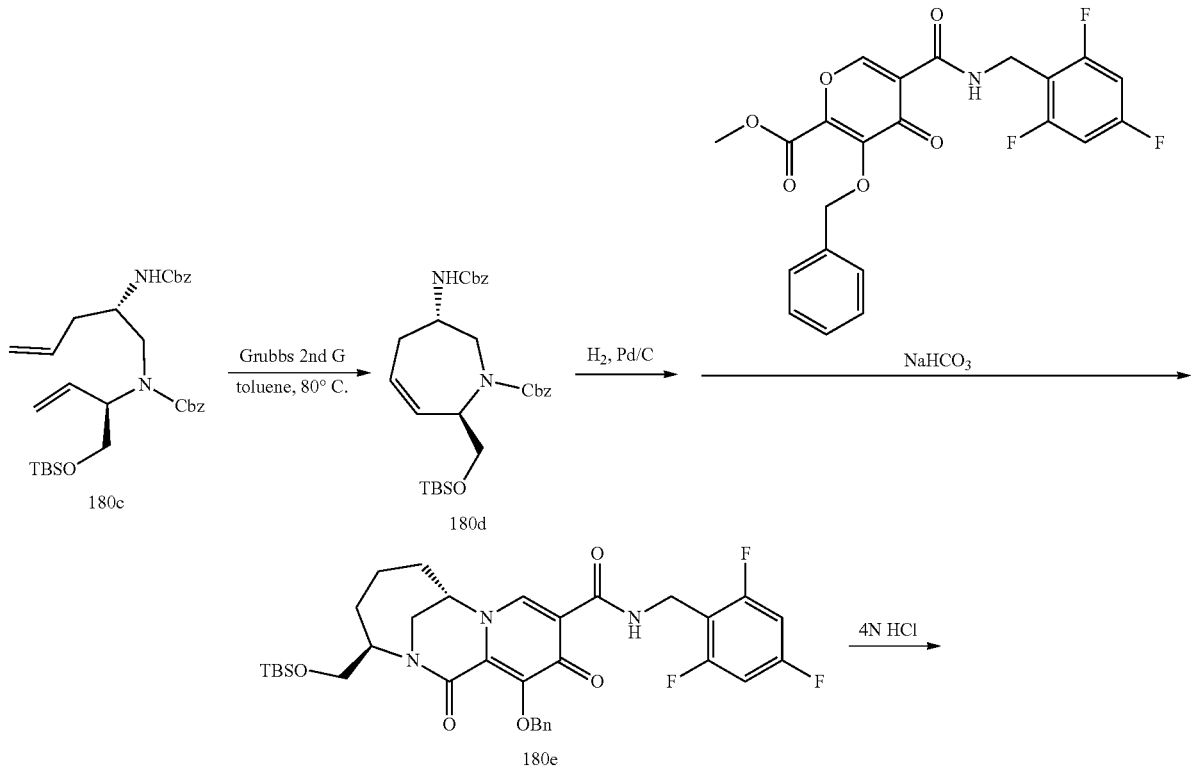

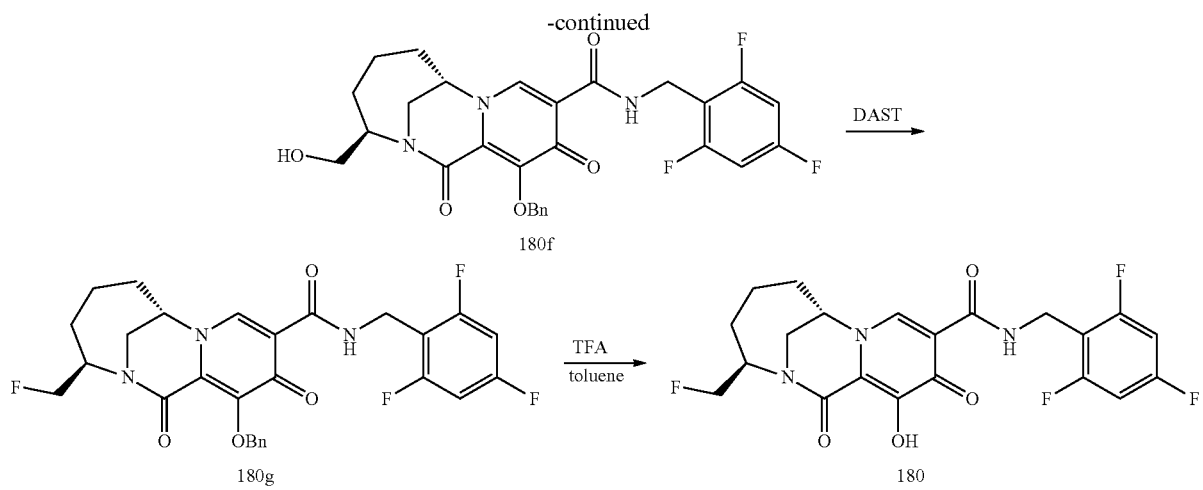

Synthesis of (R)-1-((tert-butyldimethylsilyl)oxy)but-3-en-2-amine (180a)

A suspension of (2R)-2-aminobut-3-en-1-ol hydrochloride (1010.4 mg, 8.176 mmol) and triethylamine (3.5 mL, 25.11 mmol) in dichloromethane (12 mL) was stirred at 0° C. bath as tert-butyldimethylsilyl chloride (1.35 g, 8.957 mmol) was added. After addition, the reaction mixture was stirred at rt. After 23 h, the reaction mixture was diluted with dichloromethane (30 mL) and washed with saturated sodium bicarbonate solution (50 mL). After the aqueous fraction was extracted with dichloromethane (2×30 mL), the organic fractions were washed with brine (30 mL×1), combined, dried (MgSO$_4$), and concentrated. The resulting mixture was dissolved in ethyl ether, filtered, and the filtrate was concentrated to get the crude TBS protected product: MS (m/z) 202.01 [M+H]$^+$.

Synthesis of benzyl (S)-(1-hydroxypent-4-en-2-yl)carbamate (180b)

A solution of (2S)-2-amino-4-penten-1-ol (2000 mg, 14.5 mmol), potassium carbonate (6030 mg, 43.6 mmol) in water (36 mL) and 1,4-dioxane (36 mL) was stirred at 0° C. bath as benzyl chloroformate (2.6 mL, 17.52 mmol) was added. The mixture was stirred at 0° C. for 2 h and then rt overnight. The reaction mixture was diluted with saturated sodium bicarbonate (150 mL) and the product was extracted with ethyl acetate (150 mL×2). After the extracts were washed with water (1×150 mL), the organic fractions were combined, dried (MgSO$_4$), and concentrated. The residue was purified by column chromatography on silica gel eluting 0-70% ethyl acetate in hexane to get the title compound. MS (m/z) 235.84 [M+H]$^+$.

Synthesis of benzyl ((S)-2-(((benzyloxy)carbonyl)amino)pent-4-en-1-yl)((R)-1-((tert-butyldimethylsilyl)oxy)but-3-en-2-yl)carbamate (180c)

The title compound was synthesized in a manner similar to a mixture of benzyl ((2S,3R)-2-(((benzyloxy)carbonyl)amino)-3-methylpent-4-en-1-yl)((S)-but-3-en-2-yl)carbamate (174d-1) and benzyl ((2R,3S)-2-(((benzyloxy)carbonyl)amino)-3-methylpent-4-en-1-yl)((S)-but-3-en-2-yl)carbamate (174d-2) except using (R)-1-((tert-butyldimethylsilyl)oxy)but-3-en-2-amine (180a) and benzyl (S)-(1-hydroxypent-4-en-2-yl)carbamate (180b) instead of syn-(±)-benzyl N-[1-(hydroxymethyl)-2-methyl-but-3-enyl]carbamate (174c) and (2S)-but-3-en-2-amine hydrochloride respectively. MS (m/z) 553.10 [M+H]$^+$.

Synthesis of benzyl (3S,7R)-3-(((benzyloxy)carbonyl)amino)-7-(((tert-butyldimethylsilyl)oxy)methyl)-2,3,4,7-tetrahydro-1H-azepine-1-carboxylate (180d)

The title compound was synthesized in a manner similar to benzyl (3S,4R,7S) and (3R,4S,7S)-3-(((benzyloxy)carbonyl)amino)-4,7-dimethyl-2,3,4,7-tetrahydro-1H-azepine-1-carboxylate (174e-1 and 174e-2) except using benzyl ((S)-2-(((benzyloxy)carbonyl)amino)pent-4-en-1-yl)((R)-1-((tert-butyldimethylsilyl)oxy)but-3-en-2-yl)carbamate (180c) instead of a mixture of benzyl ((2S,3R)-2-(((benzyloxy)carbonyl)amino)-3-methylpent-4-en-1-yl)((S)-but-3-en-2-yl)carbamate (174d-1) and benzyl ((2R,3S)-2-(((benzyloxy)carbonyl)amino)-3-methylpent-4-en-1-yl)((S)-but-3-en-2-yl)carbamate (174d-2). MS (m/z) 525.01 [M+H]$^+$.

Synthesis of (3R,7S)-12-(benzyloxy)-3-(((tert-butyldimethylsilyl)oxy)methyl)-1,11-dioxo-N-(2,4,6-trifluorobenzyl)-1,4,5,6,7,11-hexahydro-3H-2,7-methanopyrido[1,2-a][1,4]diazonine-10-carboxamide (180e)

A mixture of benzyl (3S,7R)-3-(((benzyloxy)carbonyl)amino)-7-(((tert-butyldimethylsilyl)oxy)methyl)-2,3,4,7-tetrahydro-1H-azepine-1-carboxylate (180d) (719.7 mg, 1.37 mmol) and 10% palladium on carbon (140.9 mg) in ethanol (27 mL) and EtOAc (13.5 mL) was stirred under H$_2$ atmosphere. After 3 h, the reaction mixture was filtered through celite, washed with ethanol, and the filtrate was concentrated to get the diamine: MS (m/z) 259.24 [M+H]$^+$.

One third of the above residue was mixed with methyl 3-(benzyloxy)-4-oxo-5-((2,4,6-trifluorobenzyl)carbamoyl)-4H-pyran-2-carboxylate (205.3 mg, 0.459 mmol), and sodium bicarbonate (90.2 mg, 1.07 mmol) before methanol (5 mL) and water (1 mL) were added. The resulting mixture was heated at 50° C. for 22 h and at 60° C. for 24 h. The reaction mixture was concentrated to remove most of solvent and the residue was dissolved in ethyl acetate (25 mL) and water (25 mL), and two fractions were separated. After the aq. fraction was extracted with ethyl acetate (25 mL×1), two organic fractions were washed with brine (×1), combined, dried (MgSO₄) and concentrated. The residue was purified by column chromatography on silica gel eluting 0-15% methanol in dichloromethane to get the title compound: MS (m/z) 656.63 [M+H]⁺.

Synthesis of (3R,7S)-12-(benzyloxy)-3-(hydroxymethyl)-1,11-dioxo-N-(2,4,6-trifluorobenzyl)-1,4,5,6,7,11-hexahydro-3H-2,7-methanopyrido[1,2-a][1,4]diazonine-10-carboxamide (180f)

(3R,7S)-12-(benzyloxy)-3-(((tert-butyldimethylsilyl)oxy)methyl)-1,11-dioxo-N-(2,4,6-trifluorobenzyl)-1,4,5,6,7,11-hexahydro-3H-2,7-methanopyrido[1,2-a][1,4]diazonine-10-carboxamide (41.0 mg, 62.5 umol) was dissolved in 4 N HCl in dioxane (3 mL) in 0° C. bath and stirred at 0° C. for 30 min. The reaction mixture was concentrated, and the residue was co-evaporated with toluene (×1). The residue was purified by column chromatography on silica gel eluting 0-25% methanol in dichloromethane to get the title compound: MS (m/z) 542.15 [M+H]⁺.

Synthesis of (3R,7S)-3-(fluoromethyl)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (180g)

A solution of (3R,7S)-12-(benzyloxy)-3-(hydroxymethyl)-1,11-dioxo-N-(2,4,6-trifluorobenzyl)-1,4,5,6,7,11-hexahydro-3H-2,7-methanopyrido[1,2-a][1,4]diazonine-10-carboxamide (180f, 30.5 mg, 56.3 umol) in dichloromethane (2 mL) was stirred at 0° C. as (Diethylamino)sulfur trifluoride (DAST, 0.01 mL, 75.7 umol) was added. After 30 min, the reaction mixture was stirred at rt overnight. After ~18 h, additional (Diethylamino)sulfur trifluoride (DAST, 0.01 mL, 75.7 umol) was added at rt and stirred at rt for 6 h. After the reaction mixture was stirred at 0° C. and saturated sodium bicarbonate (15 mL) was added, and the product was extracted with ethyl acetate (2×15 mL). The combined extracts were dried (MgSO₄), and concentrated: MS (m/z) 544.15 [M+H]⁺.

Synthesis of (3R,7S)-3-(fluoromethyl)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (180)

The crude residue from the previous step was dissolved in toluene (1 mL) and TFA (1 mL) and stirred at rt for 2 h. The reaction mixture was concentrated, and the residue was dissolved in DMF (1 mL) before filtered. The filtrate was purified by preparative HPLC (column, Gemini 5 um C18 110A, LC column 100×30 mm) eluting 10-70% acetonitrile (0.1% TFA) in water (0.1% TFA) over 20 min.). The purified fraction was freeze-dried to get the title compound: MS (m/z) 454.17 [M+H]⁺. ¹H NMR (400 MHz, Acetonitrile-d₃) δ 10.35 (d, J=6.5 Hz, 1H), 8.39 (s, 1H), 6.84 (t, J=8.5 Hz, 2H), 4.73-4.51 (m, 5H), 4.51-4.41 (m, 1H), 3.77 (dt, J=14.9, 2.7 Hz, 1H), 3.65 (dd, J=15.0, 1.8 Hz, 1H), 2.17-2.08 (m, 1H), 2.05 (dd, J=14.6, 7.2 Hz, 1H), 1.92-1.70 (m, 2H), 1.55 (dt, J=14.4, 11.5 Hz, 1H), 1.24-1.09 (m, 1H).

Example 178: Synthesis of (3R,7S)—N-(2,4-difluorobenzyl)-3-(fluoromethyl)-12-hydroxy-1,11-dioxo-1,4,5,6,7,11-hexahydro-3H-2,7-methanopyrido[1,2-a][1,4]diazonine-10-carboxamide (181)

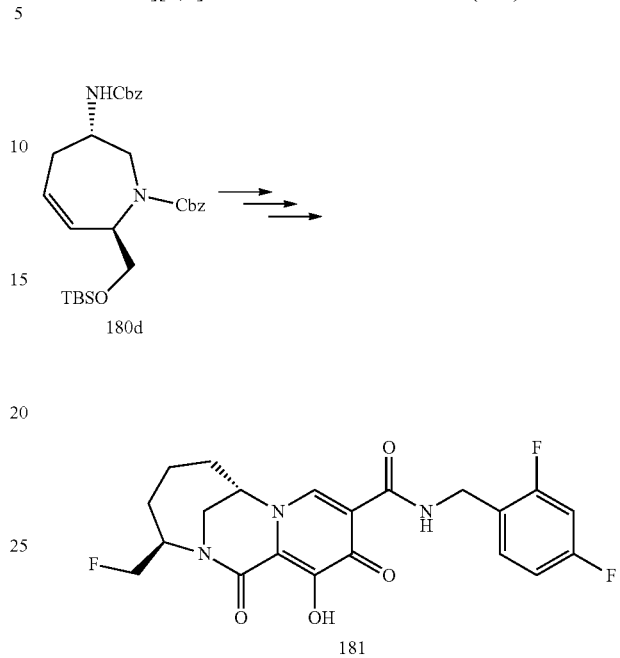

The title compound was prepared in a manner similar to (3R,7S)-3-(fluoromethyl)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (180) using methyl 3-(benzyloxy)-5-((2,4-difluorobenzyl)carbamoyl)-4-oxo-4H-pyran-2-carboxylate instead of methyl 3-(benzyloxy)-4-oxo-5-((2,4,6-trifluorobenzyl)carbamoyl)-4H-pyran-2-carboxylate. MS (m/z) 436.19 [M+H]⁺. ¹H NMR (400 MHz, Acetonitrile-d₃) δ 10.37 (d, J=6.7 Hz, 1H), 8.40 (s, 1H), 7.41 (td, J=8.8, 6.5 Hz, 1H), 7.01-6.85 (m, 2H), 4.73-4.61 (m, 1H), 4.58 (m, 4H), 4.52-4.41 (m, 1H), 3.78 (dt, J=15.0, 2.7 Hz, 1H), 3.66 (dd, J=15.0, 1.8 Hz, 1H), 2.12 (dt, J=15.5, 2.3 Hz, 1H), 2.05 (dd, J=14.6, 7.3 Hz, 1H), 1.92-1.69 (m, 2H), 1.56 (dt, J=14.6, 11.6 Hz, 1H), 1.25-1.09 (m, 1H).

Example 179: Preparation of (7S)—N-(3-chloro-2,4-difluorobenzyl)-12-hydroxy-1,11-dioxo-1,4,5,6,7,11-hexahydro-3H-2,7-methanopyrido[1,2-a][1,4]diazonine-10-carboxamide (182)

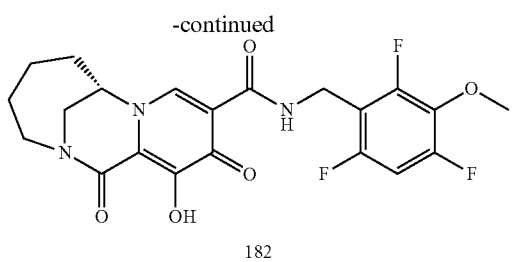

182

The title compound was prepared in a manner similar to (7S)—N-(3-chloro-2,4-difluorobenzyl)-12-hydroxy-1,11-dioxo-1,4,5,6,7,11-hexahydro-3H-2,7-methanopyrido[1,2-a][1,4]diazonine-10-carboxamide (51), except that EDCI was used instead of HATU, DMAP and DIPEA were used instead of TEA, and (2,4,6-trifluoro-3-methoxy-phenyl)methanamine was used instead of (3-chloro-2,4-difluorophenyl)methanamine. MS (m/z) 452.28 [M+H]⁺. ¹H NMR (400 MHz, Methanol-d4) δ 8.47 (s, 1H), 6.96 (t, J=10.0 Hz, 1H), 4.68 (s, 2H), 4.33 (dt, J=14.9, 8.2 Hz, 1H), 3.97 (s, 1H), 3.94 (s, 3H), 3.74 (d, J=12.5 Hz, 1H), 3.26-3.15 (m, 1H), 2.31-1.66 (m, 6H), 1.33 (t, J=13.0 Hz, 1H).

Example 180: Synthesis of (3S,6S,7S)—N-(2,4-difluorobenzyl)-12-hydroxy-3,6-dimethyl-1,11-dioxo-1,6,7,11-tetrahydro-3H-2,7-methanopyrido[1,2-a][1,4]diazonine-10-carboxamide (183)

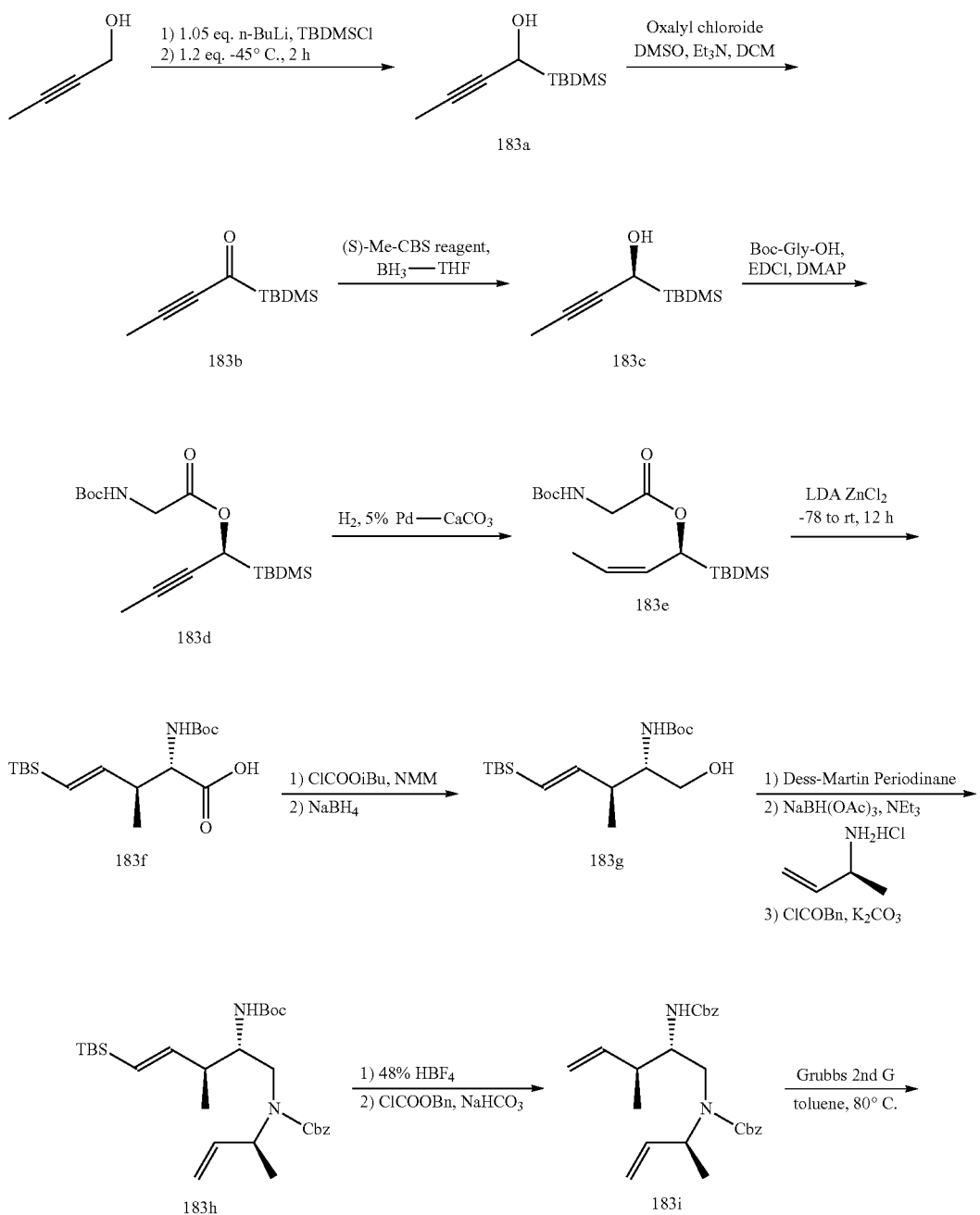

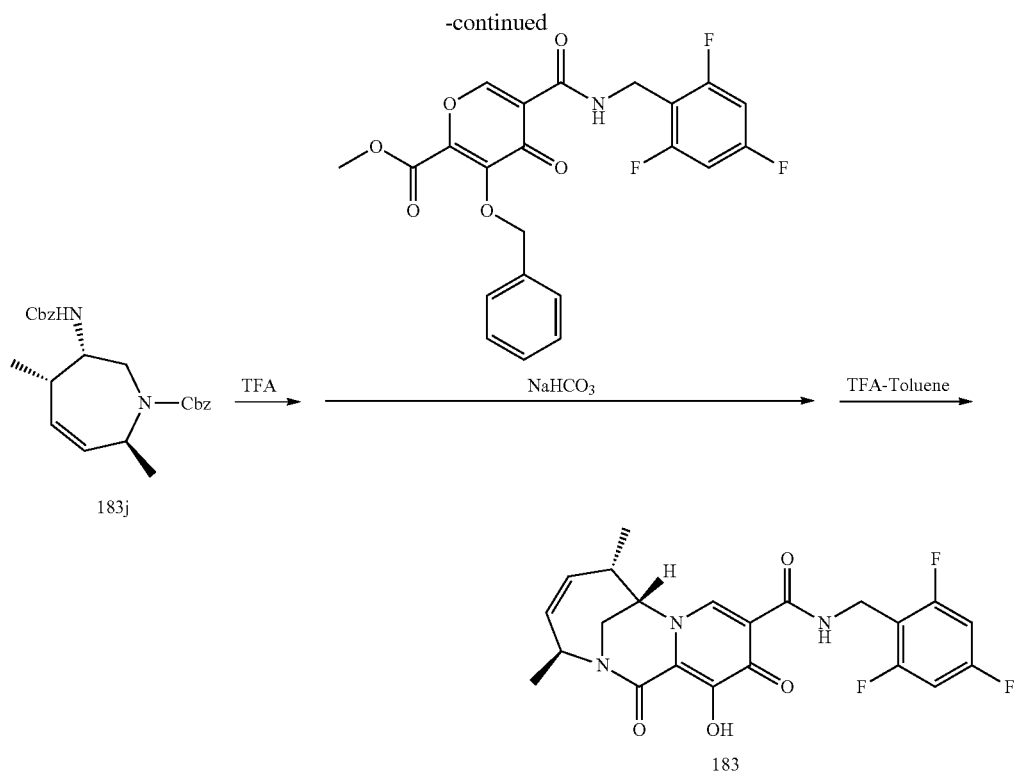

Synthesis of 1-(tert-butyldimethylsilyl)but-2-yn-1-ol (183a)

To a solution of but-2-yn-1-ol (125 g, 1.78 mol, 1.0 eq) in THF (2270 mL) was added n-BuLi (2.5 M in hexane, 892 mL, 2.23 mol, 1.25 eq) at −78° C. by dropwise under Argon. The mixture was stirred for 30 mins at 0° C. under Argon. To the mixture was added a solution of TBS-Cl (335.9 g, 2.23 mol, 1.25 eq) in THF (454 mL) at −78° C. dropwise. After stirring at room temperature for 16 h, n-BuLi (998 mL, 2.5 M in hexane, 2.5 mol, 1.4 eq) was added and the reaction mixture was stirred at −45° C. for 3 h. The reaction was then quenched by addition of AcOH (856 g) in THF (2.5 L) at −78° C. and then water (3.4 L) was added. The mixture was warmed to room temperature and extracted with MTBE (4 L×3). The organic phase was washed with saturated aq. NaHCO$_3$ (2.2 L×4), brine (2.2 L), dried over Na$_2$SO$_4$ and concentrated in vacuo to give crude compound 183a which was directly used into next step without purification. $^1$H NMR (400 MHz, CDCl$_3$) δ 4.18 (q, J=2.8 Hz, 1H), 1.88 (d, J=2.4 Hz, 3H), 0.98 (s, 9H), 0.10 (s, 3H), 0.07 (s, 3H).

Synthesis of 1-(tert-butyldimethylsilyl)but-2-yn-1-one (183b)

To a stirred solution of oxalyl chloride (275.4 g, 2.17 mol, 2.0 eq) in dichloromethane (4000 mL) was added dimethyl sulfoxide (339.0 g, 4.34 mol, 4.0 eq) by dropwise at −78° C. under N$_2$. The reaction mixture was stirred for 0.5 h before 1-(tert-butyldimethylsilyl)but-2-yn-1-ol (183a) (200.0 g, 1.08 mol, 1.0 eq, crude) in dichloromethane (1000 mL) was slowly added. The mixture was stirred for a further 1 h before triethylamine (548.9 g, 5.42 mol, 5.0 eq) was added. This reaction mixture was stirred at −78° C. for 1 h. HPLC showed completion. Saturated aq. NH$_4$Cl (12.0 L) was added below 0° C. and warmed to room temperature. Organic phase was separated and the aqueous phase was extracted with DCM (4 L×2). The combined organic layers were washed with brine (5 L). Dried with Na$_2$SO$_4$ and concentrated to give a crude residue (200 g, crude), which was purified by silica gel column (eluted with PE:EA=50:1) to give the product. $^1$H NMR (400 MHz, CDCl$_3$) δ 2.10 (s, 3H), 0.97 (s, 9H), 0.23 (s, 6H). MS (m/z) 183.20 [M+H]$^+$.

Synthesis of (S)-1-(tert-butyldimethylsilyl)but-2-yn-1-ol (183c)

Borane-tetrahydrofuran complex (1 M in THF, 867 mL, 0.867 mol, 5.0 eq) was added into (S)-Me-CBS reagent (1 M in PhMe, 347 mL, 0.347 mol, 2.0 eq) by dropwise at −78° C. under Ar (g). The mixture was stirred for 30 mins at −78° C. under Ar (g). A solution of 1-(tert-butyldimethylsilyl)but-2-yn-1-one (183b) (50 g, QNMR, 64%, 0.175 mol, 1.0 eq) in THF (900 mL) was added by drop wise. The mixture was stirred for 30 mins at −78° C. under Argon. Methanol (850 mL) was added and the solution allowed to stir for an additional 30 mins at −78° C. Diluted with MTBE (2 L) and allowed to warm to room temperature. The mixture was washed with saturated NaHCO$_3$ (2 L×2), brine (2 L), dried over Na$_2$SO$_4$ and concentrated in vacuo. The residue was purified by silica gel column (eluted with PE:EA=50:1) to give the product. $^1$H NMR (400 MHz, CDCl$_3$) δ 4.18 (q, J=2.8 Hz, 1H), 1.88 (d, J=2.4 Hz, 3H), 0.98 (s, 9H), 0.10 (s, 3H), 0.08 (s, 3H).

Synthesis of (S)-1-(tert-butyldimethylsilyl)but-2-yn-1-yl (tert-butoxycarbonyl)glycinate (183d)

To a solution of (S)-1-(tert-butyldimethylsilyl)but-2-yn-1-ol (183c) (31.0 g, 0.168 mol, 1.0 eq) in dry DCM (626 mL)

was added N-Boc-glycine (87.8 g, 0.504 mol, 3.0 eq), 1-ethyl-3-(3-dimethylaminopropyl)-carbodiimide hydrochloride (54.4 g, 0.284 mol, 1.7 eq) and DMAP (1.02 g, 8.35 mmol, 0.05 eq) at 0° C. The reaction mixture was stirred at 0° C. for 2 h. Then concentrated in vacuo and diluted with MTBE (300 mL) and saturated aq NaHCO$_3$ (300 mL). Separated and washed with saturated aq NaHCO$_3$ (500 mL) and brine (500 mL). The combined organic phases were dried over Na$_2$SO$_4$, concentrated in vacuo to give a crude product (75 g), which was purified by silica gel column (eluted with PE:EA=10:1) to give the product. $^1$H NMR (400 MHz, CDCl$_3$) δ 5.29-5.27 (m, 1H), 5.02 (brs, 1H), 3.94-3.91 (m, 2H), 1.85 (d, J=2.4 Hz, 3H), 1.45 (s, 9H), 0.94 (s, 9H), 0.10 (s, 3H), 0.08 (s, 3H). MS (m/z) 364.20 [M+Na]$^+$.

Synthesis of (S,Z)-1-(tert-butyldimethylsilyl)but-2-en-1-yl (tert-butoxycarbonyl)glycinate (183e)

To a solution of (S)-1-(tert-butyldimethylsilyl)but-2-yn-1-yl (tert-butoxycarbonyl)glycinate (183d) (38 g, 0.11 mol) in EtOAc (286 mL) was added Lindlar's catalyst (Pd/5% wt on CaCO$_3$, 23.5 g), the mixture was stirred at room temperature under H$_2$ (1 atm) for overnight. The suspension was filtered on a pad Celite and washed with DCM. The solvents were removed in vacuo to give crude product, which was purified by silica gel column (eluting with PE:EA=10:1) to give the product. $^1$H NMR (400 MHz, CDCl$_3$) δ 5.67 (d, J=10.4 Hz, 1H), 5.57-5.53 (m, 1H), 5.45-5.39 (m, 1H), 5.02 (brs, 1H), 3.90 (d, J=4.8 Hz, 2H), 1.72 (dd, J=6.8, 1.2 Hz, 3H), 1.46 (s, 9H), 0.94 (s, 9H), 0.06 (s, 3H), 0.00 (s, 3H).

Synthesis of (2S,3S,E)-2-((tert-butoxycarbonyl)amino)-5-(tert-butyldimethylsilyl)-3-methylpent-4-enoic acid (183f)

To a solution of diisopropylamine (46.3 g, 0.45 mol, 4.5 eq) in THF (700 mL) was added n-BuLi (2.4 M, 170 mL, 0.40 mol, 4.0 eq) by drop with at −20° C. under N$_2$. The mixture was stirred at −20° C. for 30 mins. Cooled the mixture to −78° C. A solution of (S,Z)-1-(tert-butyldimethylsilyl)but-2-en-1-yl (tert-butoxycarbonyl)glycinate (183e) (35 g, 0.10 mol, 1.0 eq) in THF (175 mL) was added by dropwise at −78° C. ZnCl$_2$ (1 M in THF, 122 mL, 0.12 mol, 1.13 eq) was added by dropwise at −78° C. The mixture was warmed to room temperature and stirred for overnight. HPLC showed completion. Adjusted pH=4-5 with 1 N HCl at 0° C. Extracted with MTBE (200 mL×2). The organics was washed with brine (200 mL) Dried over Na$_2$SO$_4$, concentrated to give crude product (25 g), which was purified with silica gel column (eluted with PE:EA=10:1) to give the product. $^1$H NMR (400 MHz, CDCl$_3$) δ 5.87 (dd, J=18.4, 6.8 Hz, 1H), 5.77 (d, J=18.4 Hz, 1H), 4.89 (d, J=8.4 Hz, 1H), 4.27-4.23 (m, 1H), 2.81-2.77 (m, 1H), 1.45 (s, 9H), 1.12 (d, J=6.8 Hz, 3H), 0.85 (s, 9H), 0.01 (s, 6H). MS (m/z) 344.20 [M+H]$^+$.

Synthesis of tert-butyl ((2S,3S,E)-5-(tert-butyldimethylsilyl)-1-hydroxy-3-methylpent-4-en-2-yl)carbamate (183g)

The title compound was prepared in a manner similar to syn-(±)-benzyl (1-hydroxy-3-methylpent-4-en-2-yl)carbamate (174c) except using (2S,3S,E)-2-((tert-butoxycarbonyl)amino)-5-(tert-butyldimethylsilyl)-3-methylpent-4-enoic acid (183f) instead of syn-(±)-2-(((benzyloxy)carbonyl)amino)-3-methylpent-4-enoic acid (174b). MS (m/z) 330.20 [M+H]$^+$.

Synthesis of benzyl ((2S,3S,E)-2-(((benzyloxy)carbonyl)amino)-5-(tert-butyldimethylsilyl)-3-methylpent-4-en-1-yl)((S)-but-3-en-2-yl)carbamate (183h)

The title compound was prepared in a manner similar to the preparation of a mixture of benzyl ((2S,3R)-2-(((benzyloxy)carbonyl)amino)-3-methylpent-4-en-1-yl)((S)-but-3-en-2-yl)carbamate (173d-1) and benzyl ((2R,3S)-2-(((benzyloxy)carbonyl)amino)-3-methylpent-4-en-1-yl)((S)-but-3-en-2-yl)carbamate (173d-2) except using tert-butyl ((2S,3S,E)-5-(tert-butyldimethylsilyl)-1-hydroxy-3-methylpent-4-en-2-yl)carbamate (183g) instead of syn-(±)-benzyl (1-hydroxy-3-methylpent-4-en-2-yl)carbamate (173c). MS (m/z) 517.52 [M+H]$^+$.

Synthesis of benzyl ((2S,3S)-2-(((benzyloxy)carbonyl)amino)-3-methylpent-4-en-1-yl)((S)-but-3-en-2-yl)carbamate (183i)

To a solution of benzyl ((2S,3S,E)-2-(((benzyloxy)carbonyl)amino)-5-(tert-butyldimethylsilyl)-3-methylpent-4-en-1-yl)((S)-but-3-en-2-yl)carbamate (183h) (933.2 mg, 1.81 mmol) in 1,4-dioxane (15.5 mL) was added 48% aq. HBF$_4$ (19 mL, 145 mmol) and the resulting mixture was stirred at 70° C. bath. After 22 h, additional 48% aq. HBF$_4$ (19 mL, 145 mmol) was added and the resulting mixture was stirred at 70° C. additional 24 h and the cooled to rt. The reaction mixture transferred to a large flask using some water and was neutralized by cautious addition of solid sodium bicarbonate (~23 g). To the above reaction mixture was added benzyl chloroformate (0.7 mL, 4.77 mmol) at 0° C. and the resulting mixture was stirred vigorously overnight. The reaction mixture was diluted with more water (100 mL) and the product was extracted with ethyl acetate (70 mL×2). After the extracts were washed with water (50 mL×1), combined, dried (MgSO$_4$), and concentrated, the residue was purified by column chromatography on silica gel eluting 0-40% ethyl acetate in hexane to get the title compound: MS (m/z) 437.50 [M+H]$^+$.

Synthesis of benzyl (3S,4S,7S)-3-(((benzyloxy)carbonyl)amino)-4,7-dimethyl-2,3,4,7-tetrahydro-1H-azepine-1-carboxylate (183j)

The title compound was prepared in a manner similar to benzyl (3S,4R,7S) and (3R,4S,7S)-3-(((benzyloxy)carbonyl)amino)-4,7-dimethyl-2,3,4,7-tetrahydro-1H-azepine-1-carboxylate (174e-1 and 174e-2) except using benzyl ((2S,3S)-2-(((benzyloxy)carbonyl)amino)-3-methylpent-4-en-1-yl)((S)-but-3-en-2-yl)carbamate (183i) instead of a mixture of benzyl ((2S,3R)-2-(((benzyloxy)carbonyl)amino)-3-methylpent-4-en-1-yl)((S)-but-3-en-2-yl)carbamate (174d-1) and benzyl ((2R,3S)-2-(((benzyloxy)carbonyl)amino)-3-methylpent-4-en-1-yl)((S)-but-3-en-2-yl)carbamate (174d-2). MS (m/z) 409.20 [M+H]$^+$.

Synthesis of (3S,6S,7S)-12-hydroxy-3,6-dimethyl-1,11-dioxo-N-(2,4,6-trifluorobenzyl)-1,6,7,11-tetrahydro-3H-2,7-methanopyrido[1,2-a][1,4]diazonine-10-carboxamide (183)

The title compounds was prepared in a manner similar to (3S,6R,7S)-12-hydroxy-3,6-dimethyl-1,11-dioxo-N-(2,4,6- trifluorobenzyl)-1,6,7,11-tetrahydro-3H-2,7-methanopyrido[1,2-a][1,4]diazonine-10-carboxamide (example 176) except using benzyl (3S,4S,7S)-3-(((benzyloxy)carbonyl)amino)-4,7-dimethyl-2,3,4,7-tetrahydro-1H-azepine-1-carboxylate (183j) as diamine precursor instead of benzyl (3S,4R,7S)-3-(((benzyloxy)carbonyl)amino)-4,7-dimethyl-2,3,4,7-tetrahydro-1H-azepine-1-carboxylate (174e-1). MS (m/z) 448.11 [M+H]⁺. ¹H NMR (400 MHz, Acetonitrile-d₃) δ 10.35 (s, 1H), 8.42 (s, 1H), 6.91-6.76 (m, 2H), 5.50-5.37 (m, 2H), 5.29 (q, J=7.2 Hz, 1H), 4.81 (dt, J=9.1, 2.4 Hz, 1H), 4.60 (d, J=5.7 Hz, 2H), 3.86 (dd, J=14.4, 2.3 Hz, 1H), 3.70 (dd, J=14.4, 2.3 Hz, 1H), 3.26-3.12 (m, 1H), 1.30 (d, J=7.1 Hz, 3H), 0.76 (d, J=7.6 Hz, 3H).

Example 181: Synthesis of (3S,6S,7S)—N-(2,4-difluorobenzyl)-12-hydroxy-3,6-dimethyl-1,11-dioxo-1,6,7,11-tetrahydro-3H-2,7-methanopyrido[1,2-a][1,4]diazonine-10-carboxamide (184)

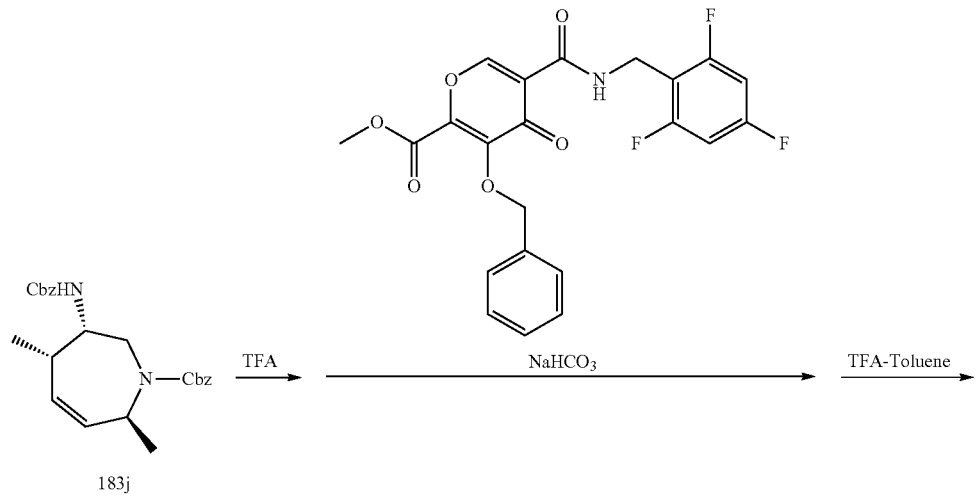

The title compound was prepared in a manner similar to (3S,6S,7S)-12-hydroxy-3,6-dimethyl-1,11-dioxo-N-(2,4,6-trifluorobenzyl)-1,6,7,11-tetrahydro-3H-2,7-methanopyrido[1,2-a][1,4]diazonine-10-carboxamide (example 183) except using methyl 3-(benzyloxy)-4-oxo-5-((2,4-difluorobenzyl)carbamoyl)-4H-pyran-2-carboxylate instead of methyl 3-(benzyloxy)-4-oxo-5-((2,4,6-trifluorobenzyl)carbamoyl)-4H-pyran-2-carboxylate. MS (m/z) 430.10 [M+H]⁺. ¹H NMR (400 MHz, Acetonitrile-d₃) δ 10.36 (s, 1H), 8.45 (s, 1H), 7.41 (td, J=9.2, 8.8, 6.5 Hz, 1H), 6.94 (dddd, J=11.0, 7.2, 5.4, 2.9 Hz, 2H), 5.49-5.37 (m, 2H), 5.30 (q, J=7.2 Hz, 1H), 4.83 (dt, J=9.1, 2.4 Hz, 1H), 4.58 (d, J=5.7 Hz, 2H), 3.87 (dd, J=14.4, 2.3 Hz, 1H), 3.72 (dd, J=14.4, 2.3 Hz, 1H), 3.26-3.12 (m, 1H), 1.31 (d, J=7.2 Hz, 3H), 0.77 (d, J=7.6 Hz, 3H). ¹⁹F NMR (376 MHz, Acetonitrile-d₃) δ −77.34, −114.07 (ddd, J=15.6, 8.9, 6.9 Hz), −116.46–−116.74 (m).

Example 182: Preparation of (7S)-10-(5-(2,4-difluorobenzyl)-1,3,4-thiadiazol-2-yl)-12-hydroxy-4,5,6,7-tetrahydro-3H-2,7-methanopyrido[1,2-a][1,4]diazonine-1,11-dione (185)

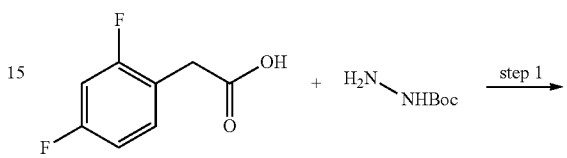

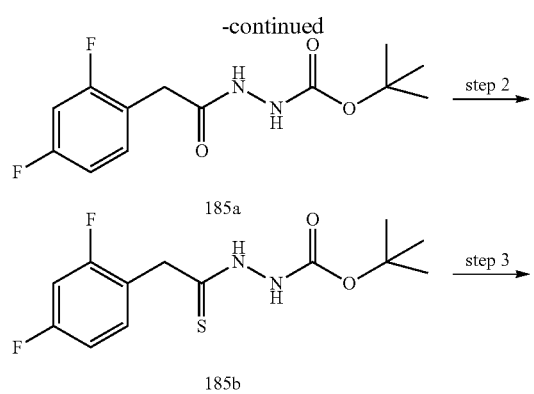

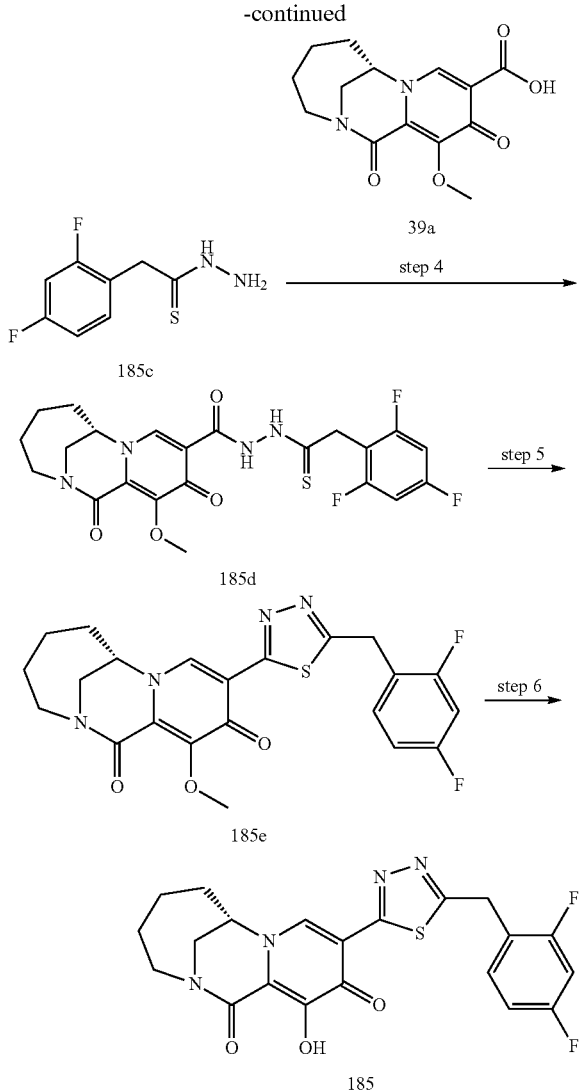

Step 1: Synthesis of tert-butyl 2-(2-(2,4-difluorophenyl)acetyl)hydrazine-1-carboxylate (185a)

To a mixture of 2-(2,4-difluorophenyl)acetic acid (1.62g, 9.22 mmol) and tert-butyl carbazate (1.30g, 9.68 mmol) in DMF (15.0 mL) at room temperature was added 1-hydroxybenzotriazole hydrate (1.73g, 11.1 mmol) and 1-(3-dimethylaminopropyl)-3-ethylcarbodiimide HCl (1.72g, 11.1 mmol). The mixture was stirred for overnight. The reaction was then quenched with saturated sodium bicarbonate solution. After being stirred for 10 min, the precipitate was collected by filtration. The solid was washed with water, then a 1:1 mixture of ether/hexane, followed by hexane to give the product (2.0g). MS (m/z) 288.06 [M+H]$^+$.

Step 2: Synthesis of tert-butyl 2-(2-(2,4-difluorophenyl)ethanethioyl)hydrazine-1-carboxylate (185b)

Tert-butyl 2-(2-(2,4-difluorophenyl)acetyl)hydrazine-1-carboxylate (185a) (2.0g, 6.99 mmol) was suspended in THF (79 mL) at room temperature and treated with Lawson's reagent (8.5g, 21.0 mmol). The resulting mixture was heated to 50° C. for 18 hrs. The reaction was quenched with saturated sodium bicarbonate, extracted with EtOAc twice. Combined organic layer was dried over sodium sulfate, filtered and concentrated. The residue was purified by Combiflash (40 g silica gel, 0-100% EtOAc/Hexanes). Desired fractions were pooled and concentrated to give a light yellowish oil (400 mg). MS (m/z) 303.18 [M+H]$^+$.

Step 3: Synthesis of 2-(2,4-difluorophenyl)ethanethiohydrazide (185c)

Tert-butyl 2-(2-(2,4-difluorophenyl)ethanethioyl)hydrazine-1-carboxylate (185b) (400 mg, 1.32 mmol) was dissolved in DCM (10.0 mL) and treated with 4 N HCl in 1,4-dioxane (10.0 mL) at room temperature for 30 min. The reaction was concentrated, re-dissolved in DMF, filtered and purified by Gilson HPLC (Gemini, 5-100% ACN/H$_2$O+ 0.1% TFA) to give title compound as a TFA salt after lyophilization. MS (m/z) 203.09 [M+H]$^+$.

Step 4: Synthesis of (7S)—N'-(2-(2,4-difluorophenyl)ethanethioyl)-12-methoxy-1,11-dioxo-1,4,5,6,7,11-hexahydro-3H-2,7-methanopyrido[1,2-a][1,4]diazonine-10-carbohydrazide (185d)

To the solution of (1S)-6-methoxy-5,8-dioxo-2,9-diazatricyclo[7.4.1.0 2,7]tetradeca-3,6-diene-4-carboxylic acid (39a) (50.2 mg, 0.172 mmol) in a mixture of THF (1.72 mL) and DMF (0.3 mL) at 0° C. was added N-methyl morpholine (69.4 mg, 0.687 mmol) followed by isobutyl chloroformate (56.3 mg, 0.412 mmol). After stirred at 0° C. for 1 hr, 2-(2,4-difluorophenyl)ethanethiohydrazide TFA salt (185c) (65.2 mg, 0.206 mmol) was added followed by additional N-methyl morpholine (69.4 mg, 0.687 mmol). The reaction was removed from the cooling bath and stirred at room temperature for 3 hrs. The reaction was then diluted with EtOAc (20 mL), washed with saturated sodium bicarbonate, brine, dried over sodium sulfate, filtered and concentrated to give the product. The crude material was purified by Gilson HPLC (Gemini, 5-100% ACN/H$_2$O+0.1% TFA) to give title compound after lyophilization. MS (m/z) 477.13 [M+H]$^+$.

Step 5: Synthesis of (7S)-10-(5-(2,4-difluorobenzyl)-1,3,4-thiadiazol-2-yl)-12-methoxy-4,5,6,7-tetrahydro-3H-2,7-methanopyrido[1,2-a][1,4]diazonine-1,11-dione (185e)

(7S)—N'-(2-(2,4-Difluorophenyl)ethanethioyl)-12-methoxy-1,11-dioxo-1,4,5,6,7,11-hexahydro-3H-2,7-methanopyrido[1,2-a][1,4]diazonine-10-carbohydrazide (185d) (81 mg, 0.17 mmol) was heated at 100° C. in acetic acid (0.3 mL) for 7 hrs. The reaction was cooled to rt, diluted with DMF, filtered and purified by Gilson HPLC (Gemini, 5-100% ACN/H$_2$O+0.1% TFA) to give title compound after lyophilization. MS (m/z) 459.35 [M+H]$^+$.

Step 6: Synthesis of (7S)-10-(5-(2,4-difluorobenzyl)-1,3,4-thiadiazol-2-yl)-12-hydroxy-4,5,6,7-tetrahydro-3H-2,7-methanopyrido[1,2-a][1,4]diazonine-1,11-dione (185)

(7S)-10-(5-(2,4-difluorobenzyl)-1,3,4-thiadiazol-2-yl)-12-methoxy-4,5,6,7-tetrahydro-3H-2,7-methanopyrido[1,2-a][1,4]diazonine-1,11-dione (185d) (15.0 mg, 0.0327 mmol) was dissolved in DMF (0.25 mL) and treated with lithium chloride (13.9 mg, 0.327 mmol) at 100° C. for 2 hrs. The reaction was cooled to rt, diluted with DMF, filtered and purified by Gilson HPLC (Gemini, 5-100% ACN/H$_2$O+ 0.1% TFA) to give title compound after lyophilization. MS (m/z) 445.35 [M+H]$^+$. $^1$H NMR (400 MHz, Methanol-d4) δ 8.87 (s, 1H), 7.55-7.40 (m, 1H), 7.09-6.90 (m, 2H), 4.71-4.84 (m, 1H), 4.51 (s, 2H), 4.35 (dt, J=13.4, 8.1 Hz, 1H), 4.13-3.96 (m, 1H), 3.84-3.67 (m, 1H), 3.23 (ddd, J=13.2, 6.9, 2.6 Hz, 1H), 2.27-2.02 (m, 3H), 2.02-1.74 (m, 2H), 1.35 (q, J=11.3 Hz, 1H).

Example 183: Synthesis of (3S,6S,7S)-12-hydroxy-3,6-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide (186)

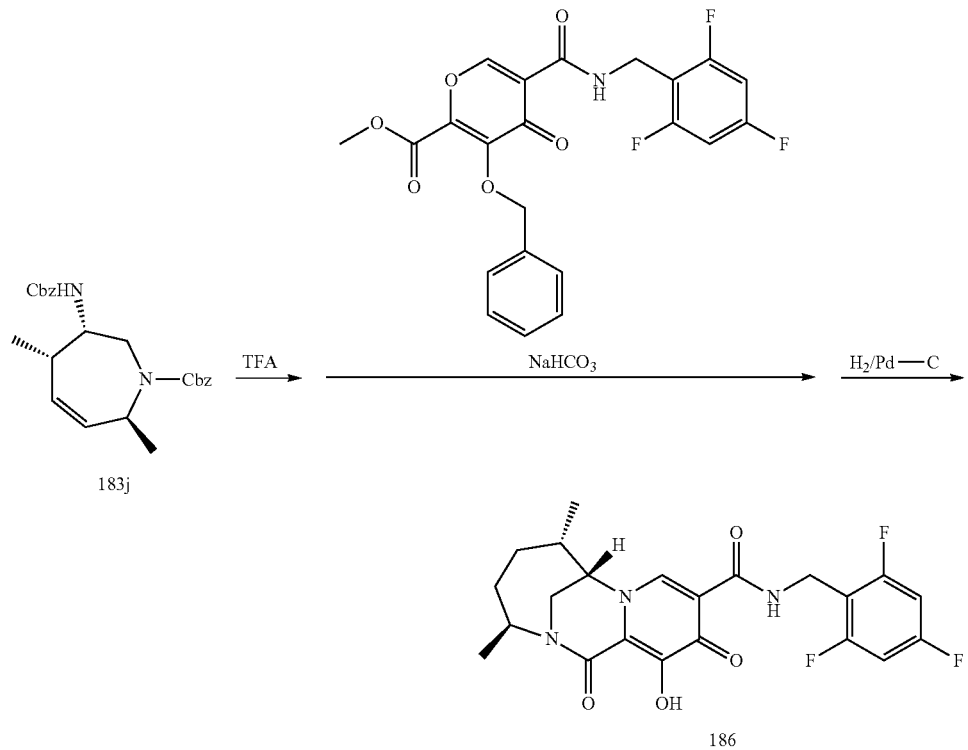

The title compounds was prepared in a manner similar to (3S,6R,7S)-12-hydroxy-3,6-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide (174) except using benzyl (3S,4S,7S)-3-(((benzyloxy)carbonyl)amino)-4,7-dimethyl-2,3,4,7-tetrahydro-1H-azepine-1-carboxylate (183j) instead of benzyl (3S,4R,7S)-3-(((benzyloxy)carbonyl)amino)-4,7-dimethyl-2,3,4,7-tetrahydro-1H-azepine-1-carboxylate (174e-1). MS (m/z) 450.11 [M+H]⁺. ¹H NMR (400 MHz, Acetonitrile-d₃) δ 10.42 (s, 1H), 8.29 (s, 1H), 6.92-6.75 (m, 2H), 4.71-4.46 (m, 3H), 4.39 (dt, J=4.9, 2.2 Hz, 1H), 3.69 (dd, J=14.8, 2.9 Hz, 1H), 3.61 (dd, J=14.8, 1.8 Hz, 1H), 2.13-1.98 (m, 2H), 1.60-1.41 (m, 2H), 1.20 (d, J=6.7 Hz, 3H), 0.96 (dt, J=15.5, 11.9 Hz, 1H), 0.86 (d, J=7.0 Hz, 3H).

Example 184: Synthesis of (3S,6S,7S)—N-(2,4-difluorobenzyl)-12-hydroxy-3,6-dimethyl-1,11-dioxo-1,4,5,6,7,11-hexahydro-3H-2,7-methanopyrido[1,2-a][1,4]diazonine-10-carboxamide (187)

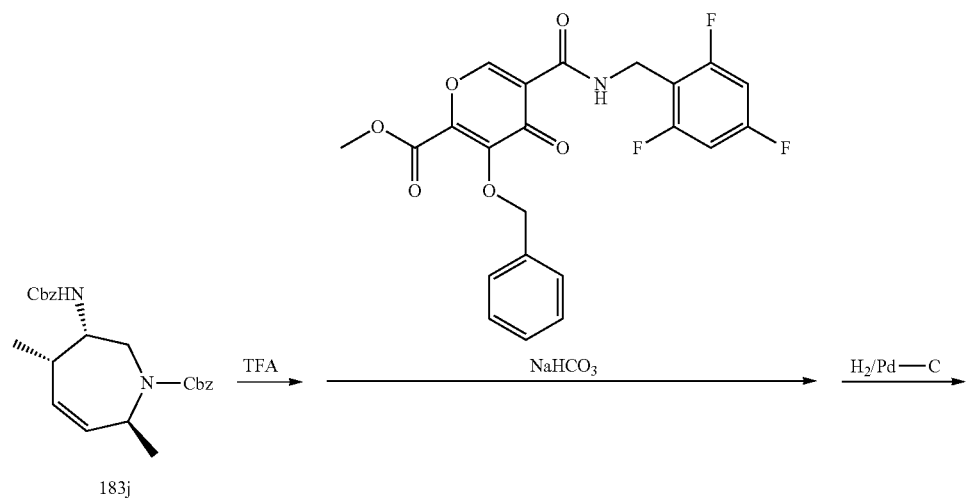

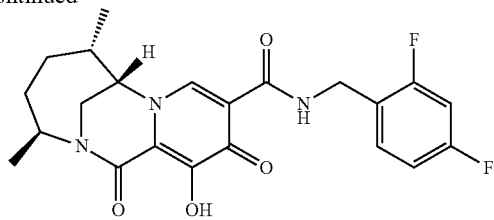

187

The title compounds was prepared in a manner similar to synthesis of (3S,6S,7S)-12-hydroxy-3,6-dimethyl-1,11-dioxo-N-(2,4,6-trifluorobenzyl)-1,4,5,6,7,11-hexahydro-3H-2,7-methanopyrido[1,2-a][1,4]diazonine-10-carboxamide (example 186) except using methyl 3-(benzyloxy)-4-oxo-5-((2,4-difluorobenzyl)carbamoyl)-4H-pyran-2-carboxylate instead of 3-(benzyloxy)-4-oxo-5-((2,4-trifluorobenzyl)carbamoyl)-4H-pyran-2-carboxylate. MS (m/z) 432.11 [M+H]$^+$. $^1$H NMR (400 MHz, Acetonitrile-d$_3$) δ 10.43 (s, 1H), 8.30 (s, 1H), 7.41 (d, J=7.8 Hz, 1H), 6.93 (d, J=9.5 Hz, 2H), 4.57 (s, 3H), 4.40 (s, 1H), 3.70 (d, J=14.8 Hz, 1H), 3.62 (d, J=14.7 Hz, 1H), 2.15-1.97 (m, 2H), 1.61-1.40 (m, 2H), 1.21 (d, J=6.5 Hz, 3H), 1.16-0.91 (m, 1H), 0.87 (d, J=6.9 Hz, 3H).

Example 185: Preparation of (3R,7S)-12-(benzyloxy)-N-(2,4-difluorobenzyl)-3-(fluoromethyl)-1,11-dioxo-1,6,7,11-tetrahydro-3H-2,7-methanopyrido[1,2-a][1,4]diazonine-10-carboxamide (188)

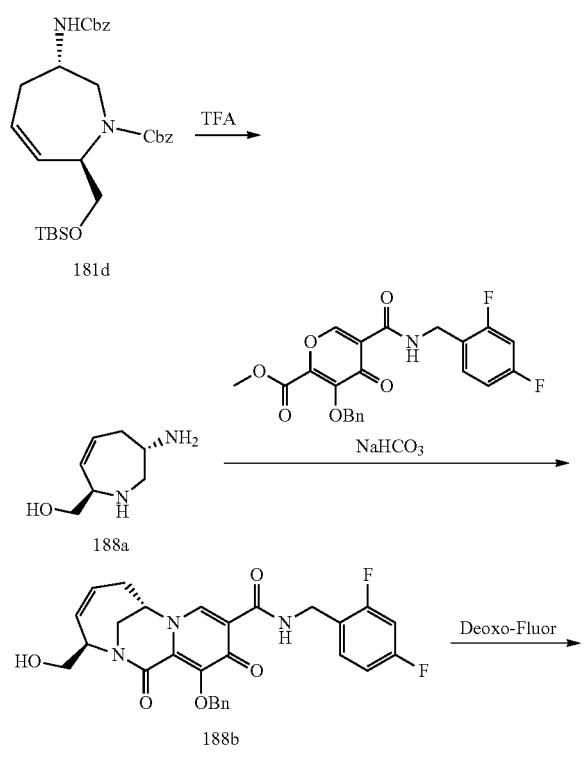

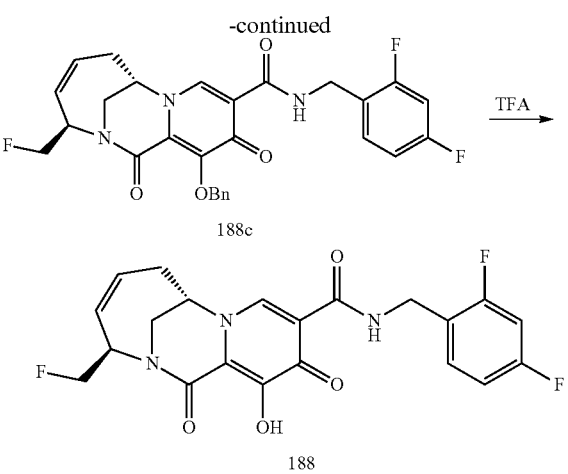

Synthesis of ((2R,6S)-6-aminoazepan-2-yl)methanol (188a)

Trifluoroacetic acid (2 mL) was added to benzyl (3S,7R)-3-(((benzyloxy)carbonyl) amino)-7-(((tert-butyldimethylsilyl)oxy)methyl)-2,3,4,7-tetrahydro-1H-azepine-1-carboxylate (82 mg, 0.156 mmol) and the reaction was heated to 80° C. for 3 hours. The reaction mixture was concentrated down. The crude was used directly in next step. MS (m/z): 143.10 [M+H]$^+$.

Synthesis of (3R,7S)-12-(benzyloxy)-N-(2,4-difluorobenzyl)-3-(hydroxymethyl)-1,11-dioxo-1,6,7,11-tetrahydro-3H-2,7-methanopyrido[1,2-a][1,4]diazonine-10-carboxamide (188b)

Added methanol (4 mL) to methyl 3-(benzyloxy)-4-oxo-5-((2,4-difluorobenzyl) carbamoyl)-4H-pyran-2-carboxylate (66 mg, 0.156 mmol) and ((2R,6S)-6-aminoazepan-2-yl) methanol (191a). At r.t., NaHCO$_3$ (260 mg, 3.09 mmol) was added to the reaction mixture. The reaction was stirred at. r.t. overnight, then heat to 50° C. for 4 hours. The reaction mixture was concentrated down, then added ethyl acetate, washed with saturated ammonium chloride solution. The organic layer was concentrated and purified via silica chromatograph to give (3R,7S)-12-(benzyloxy)-N-(2,4-difluorobenzyl)-3-(hydroxymethyl)-1,11-dioxo-1,6,7,11-tetrahydro-3H-2,7-methanopyrido[1,2-a][1,4]diazonine-10-carboxamide. MS (m/z) 522.2 [M+H]$^+$.

Synthesis of (3R,7S)-12-(benzyloxy)-N-(2,4-difluorobenzyl)-3-(fluoromethyl)-1,11-dioxo-1,6,7,11-tetrahydro-3H-2,7-methanopyrido[1,2-a][1,4]diazonine-10-carboxamide (188c)

Deoxo-Fluor (15 mg, 2 eq.) was added to (3R,7S)-12-(benzyloxy)-N-(2,4-difluorobenzyl)-3-(hydroxymethyl)-1, 11-dioxo-1,6,7,11-tetrahydro-3H-2,7-methanopyrido[1,2-a][1,4]diazonine-10-carboxamide (18 mg, 0.034 mmol) at 0° C., then the reaction was kept at r.t. for 4 hours. The reaction mixture was concentrated down, then add ethyl acetate, washed with saturated ammonium chloride solution. The organic layer was concentrated and purified via silica chromatograph to give (3R,7S)-12-(benzyloxy)-N-(2,4-difluorobenzyl)-3-(fluoromethyl)-1,11-dioxo-1,6,7,11-tetrahydro-3H-2,7-methanopyrido[1,2-a][1,4]diazonine-10-carboxamide. MS (m/z) 524.2 [M+H]⁺.

Synthesis of (3R,7S)-12-(benzyloxy)-N-(2,4-difluorobenzyl)-3-(fluoromethyl)-1,11-dioxo-1,6,7,11-tetrahydro-3H-2,7-methanopyrido[1,2-a][1,4]diazonine-10-carboxamide (188)

(3R,7S)-12-(Benzyloxy)-N-(2,4-difluorobenzyl)-3-(fluoromethyl)-1,11-dioxo-1,6,7,11-tetrahydro-3H-2,7-methanopyrido[1,2-a][1,4]diazonine-10-carboxamide (188c) (8 mg, 0.015 mmol) was dissolved in toluene (1 mL) and then TFA (1 mL) was added. The reaction was stirred at r.t. for overnight. The reaction mixture was concentrated down, purified via preparative HPLC, eluting 10-60% acetonitrile (0.1% TFA) in water (0.1% TFA). Combined fractions were freeze-dried to afford the title compound. MS (m/z) 434.10 [M+H]⁺. ¹H NMR (400 MHz, Acetonitrile-d3) δ 10.31 (s, 1H), 8.42 (s, 1H), 7.53-7.31 (m, 1H), 7.07-6.90 (m, 2H), 5.89-5.74 (m, 1H), 5.58 (dt, J=11.6, 2.5 Hz, 1H), 5.46 (d, J=23.1 Hz, 1H), 4.73 (d, J=5.4 Hz, 2H), 4.61 (dd, J=5.6, 3.1 Hz, 2H), 3.98 (dd, J=14.4, 2.8 Hz, 1H), 3.82-3.69 (m, 1H), 2.99 (dt, J=17.5, 8.8 Hz, 2H), 2.45-2.33 (m, 1H).

Example 186: Preparation of (3R,7S)—N-(2,4-difluorobenzyl)-3-(difluoromethyl)-12-hydroxy-1,11-dioxo-1,4,5,6,7,11-hexahydro-3H-2,7-methanopyrido[1,2-a][1,4]diazonine-10-carboxamide (189)

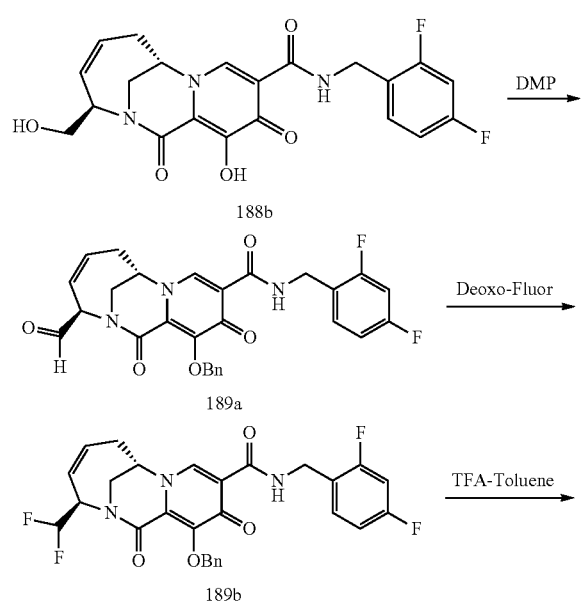

Synthesis of (3R,7S)-12-(benzyloxy)-N-(2,4-difluorobenzyl)-3-formyl-1,11-dioxo-1,6,7,11-tetrahydro-3H-2,7-methanopyrido[1,2-a][1,4]diazonine-10-carboxamide (189a)

Added Dess Martin periodinane (73 mg, 1.2 eq.) to (3R,7S)-12-(benzyloxy)-N-(2,4-difluorobenzyl)-3-(hydroxymethyl)-1,11-dioxo-1,6,7,11-tetrahydro-3H-2,7-methanopyrido[1,2-a][1,4]diazonine-10-carboxamide (189b) (75 mg, 0.1444 mmol) at 0° C. Then the reaction was warmed up to r.t. The reaction was stirred at r.t. for 2 hours. The reaction mixture was concentrated down, then added ethyl acetate, washed with saturated ammonium chloride solution. The organic layer was concentrated and purified via silica chromatography (eluting with 5% MeOH/DCM) to give (3R,7S)-12-(benzyloxy)-N-(2,4-difluorobenzyl)-3-formyl-1,11-dioxo-1,6,7,11-tetrahydro-3H-2,7-methanopyrido[1,2-a][1,4]diazonine-10-carboxamide. MS (m/z) 520.2 [M+H]⁺.

Synthesis of (3R,7S)-12-(benzyloxy)-N-(2,4-difluorobenzyl)-3-(difluoromethyl)-1,11-dioxo-1,6,7,11-tetrahydro-3H-2,7-methanopyrido[1,2-a][1,4]diazonine-10-carboxamide (189b)

Added Deoxo-Fluor (126 mg, 4 eq.) to (3R,7S)-12-(benzyloxy)-N-(2,4-difluorobenzyl)-3-formyl-1,11-dioxo-1,6,7,11-tetrahydro-3H-2,7-methanopyrido[1,2-a][1,4]diazonine-10-carboxamide (189a) in 1 mL DCM solution at 0° C. The reaction was kept at 0° C. for one hour. The reaction mixture was concentrated down, then added ethyl acetate, washed with saturated sodium bicarbonate solution. The organic layer was concentrated and purified via preparative HPLC, eluting with 10-60% acetonitrile (0.1% TFA) in water (0.1% TFA) to give (3R,7S)-12-(benzyloxy)-N-(2,4-difluorobenzyl)-3-(difluoromethyl)-1,11-dioxo-1,6,7,11-tetrahydro-3H-2,7-methanopyrido[1,2-a][1,4]diazonine-10-carboxamide. MS (m/z) 542.1 [M+H]⁺.

Synthesis of (3R,7S)—N-(2,4-difluorobenzyl)-3-(difluoromethyl)-12-hydroxy-1,11-dioxo-1,4,5,6,7,11-hexahydro-3H-2,7-methanopyrido[1,2-a][1,4]diazonine-10-carboxamide (189)

(3R,7S)-12-(benzyloxy)-N-(2,4-difluorobenzyl)-3-(difluoromethyl)-1,11-dioxo-1,6,7,11-tetrahydro-3H-2,7-methanopyrido[1,2-a][1,4]diazonine-10-carboxamide (189b) (8 mg, 0.015 mmol) was dissolved in ethanol, ethyl acetate mixture (10 mL), and 10% Palladium on carbon (3 mg) was added. Hydrogen atmosphere was applied with a balloon. After 2 hours, the reaction mixture was filtered through celite. The filtrate was concentrated down and purified via preparative HPLC, eluting with 10-60% acetonitrile (0.1% TFA) in water (0.1% TFA). Combined fractions were freeze-dried to afford the title compound. MS (m/z)

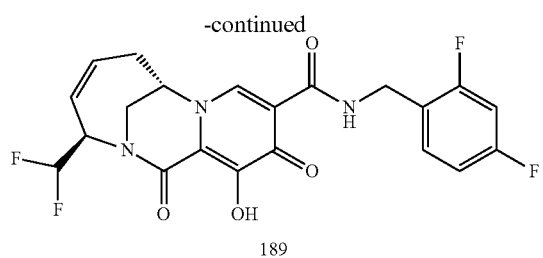

454.10 [M+H]⁺. ¹H NMR (400 MHz, Acetonitrile-d3) d 10.35 (s, 1H), 8.42 (s, 1H), 7.63-7.33 (m, 1H), 6.97 (td, J=9.6, 7.8, 3.5 Hz, 2H), 6.06 (td, J=55.0, 3.5 Hz, 1H), 4.81-4.54 (m, 3H), 3.94-3.68 (m, 3H), 2.27-2.06 (m, 2H), 1.91-1.64 (m, 3H), 1.30-1.03 (m, 1H).

Example 187: Preparation of (6S)-12-hydroxy-6-methyl-1,11-dioxo-N-(2,4,6-trifluorobenzyl)-1,4,5,6,7,11-hexahydro-3H-2,7-methanopyrido[1,2-a][1,4]diazonine-10-carboxamide (190)

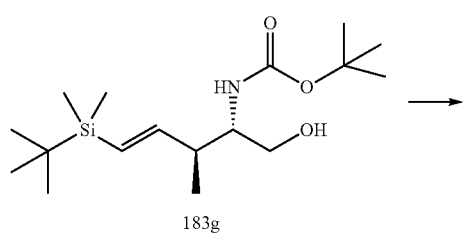

183g

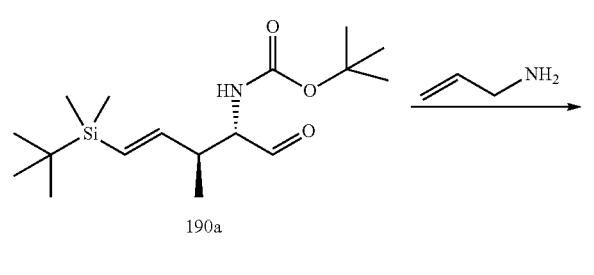

190a

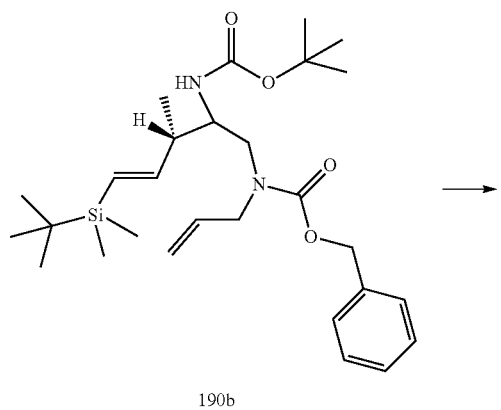

190b

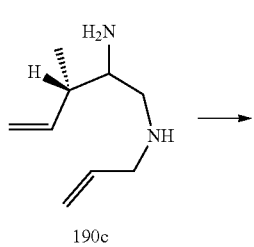

190c

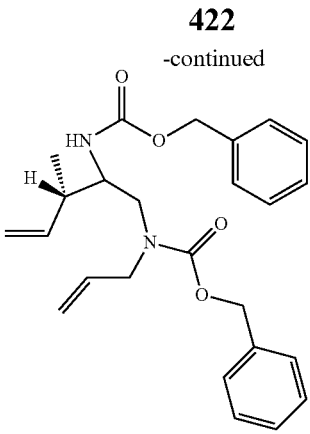

190d

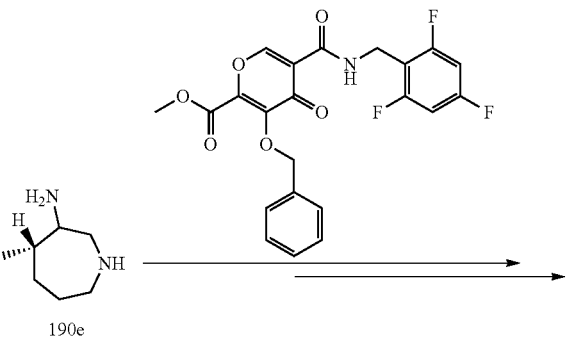

190e

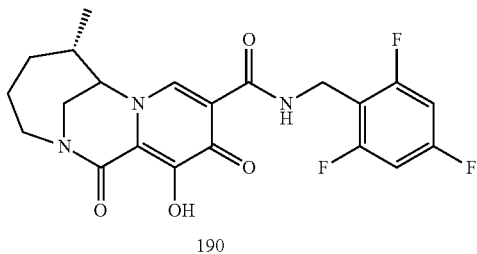

190

Synthesis of tert-butyl ((2S,3S)-5-(tert-butyldimethylsilyl)-3-methyl-1-oxopent-4-en-2-yl)carbamate (190a)

The title compound was prepared in a manner similar to benzyl (1-oxopent-4-en-2-yl)carbamate (42b) using tert-butyl ((2S,3S)-5-(tert-butyldimethylsilyl)-1-hydroxy-3-methylpent-4-en-2-yl)carbamate (183g) instead of benzyl (1-hydroxypent-4-en-2-yl)carbamate (42a). MS (m/z): 328.90 [M+H]⁺.

Synthesis of benzyl allyl((3S)-2-((tert-butoxycarbonyl)amino)-5-(tert-butyldimethylsilyl)-3-methylpent-4-en-1-yl)carbamate (190b)

The title compound was prepared in a manner similar to benzyl (1-(allylamino)pent-4-en-2-yl)carbamate (42c) using tert-butyl ((2S,3S)-5-(tert-butyldimethylsilyl)-3-methyl-1-oxopent-4-en-2-yl)carbamate (193a) instead of benzyl (1-oxopent-4-en-2-yl)carbamate (42b). MS (m/z): 369.30 [M+H]$^+$.

Synthesis of (3S)—N1-allyl-3-methylpent-4-ene-1,2-diamine (190c)

To a solution of benzyl allyl((2S,3S)-2-((tert-butoxycarbonyl)amino)-5-(tert-butyldimethylsilyl)-3-methylpent-4-en-1-yl)carbamate (190b) (1.23 g, 3.34 mmol) in 20 mL of 1,4-dioxane was added tetrafluoroboric acid (48% aqueous solution, 21.8 mL, 167 mmol), and the resulting mixture was stirred at 70° C. bath for overnight. Added additional tetrafluoroboric acid (48% aqueous solution, 21.8 mL, 167 mmol and stirred at 70° C. for additional 24 hours and cooled to room temperature. The reaction mixture was transferred to an Erlenmeyer flask (500 mL) using some water, and stirred as solid NaHCO$_3$ were added until the reaction mixture was not acidic. The resulting mixture was used as such in the next step. MS (m/z): 155.20 [M+H]$^+$.

Synthesis of benzyl allyl((3S)-2-(((benzyloxy)carbonyl)amino)-3-methylpent-4-en-1-yl)carbamate (190d)

To the above reaction mixture was added benzyl chloroformate (2.45 mL, 16.7 mmol) at 0° C. and the resulting mixture was stirred vigorously overnight. The reaction mixture was filtered to remove solid; the filtrate was extracted with EtOAc. After the extracts were washed with water, combined, dried (MgSO$_4$), concentrated, the residue was purified by Silica gel chromatography eluting with EtOAc in hexane to afford the title product. MS (m/z): 423.20 [M+H]$^+$.

Synthesis of (4S)-4-methylazepan-3-amine (190e)

The title compound was prepared in a manner similar to benzyl-3-(((benzyloxy)carbonyl)amino)azepane-1-carboxylate (42e-1 and 42e-2) except using benzyl allyl((3S)-2-(((benzyloxy)carbonyl)amino)-3-methylpent-4-en-1-yl)carbamate (190d) instead of benzyl allyl(2-(((benzyloxy)carbonyl)amino)pent-4-en-1-yl)carbamate (42d). MS (m/z): 128.23 [M+H]$^+$.

Synthesis of (6S)-12-hydroxy-6-methyl-1,11-dioxo-N-(2,4,6-trifluorobenzyl)-1,4,5,6,7,11-hexahydro-3H-2,7-methanopyrido[1,2-a][1,4]diazonine-10-carboxamide (190)

The title compound was prepared in a manner similar to N-(2,4-difluorobenzyl)-5-hydroxy-4,6-dioxo-1,1a,2,4,6,10,11,11a-octahydro-3,10-methanocyclopropa[f]pyrido[1,2-a][1,4]diazonine-7-carboxamide (42-1) except using (4S)-4-methylazepan-3-amine (190e) and methyl 3-(benzyloxy)-4-oxo-5-((2,4,6-trifluorobenzyl)carbamoyl)-4H-pyran-2-carboxylate instead of 42g-1 and methyl 3-benzyloxy-5-[(2,4-difluorophenyl)methylcarbamoyl]-4-oxo-pyran-2-carboxylate). MS (m/z) 436.10 [M+H]$^+$. $^1$H NMR (400 MHz, DMSO-d$_6$) δ 10.42 (q, J=5.5 Hz, 1H), 8.49 (s, 0.6H), 8.41 (s, 0.4H), 7.21 (dd, J=9.2, 7.7 Hz, 2H), 4.74-4.29 (m, 3H), 4.13 (dd, J=13.2, 7.4 Hz, 1H), 3.90 (d, J=2.9 Hz, 1H), 3.85-3.65 (m, 1H), 3.07 (ddd, J=39.9, 12.8, 6.5 Hz, 1H), 2.12-1.16 (m, 5H), 0.98 (dd, J=110.7, 7.0 Hz, 3H).

Example 188: Preparation of (6R)-9,10-difluoro-1-hydroxy-6-methyl-2,14-dioxo-N-(2,4,6-trifluorobenzyl)-2,7,12,14-tetrahydro-6H-6,13-methanobenzo[f]pyrido[1,2-a][1,4]diazonine-3-carboxamide and (6S)-9,10-difluoro-1-hydroxy-6-methyl-2,14-dioxo-N-(2,4,6-trifluorobenzyl)-2,7,12,14-tetrahydro-6H-6,13-methanobenzo[f]pyrido[1,2-a][1,4]diazonine-3-carboxamide (191-1 and 191-2)

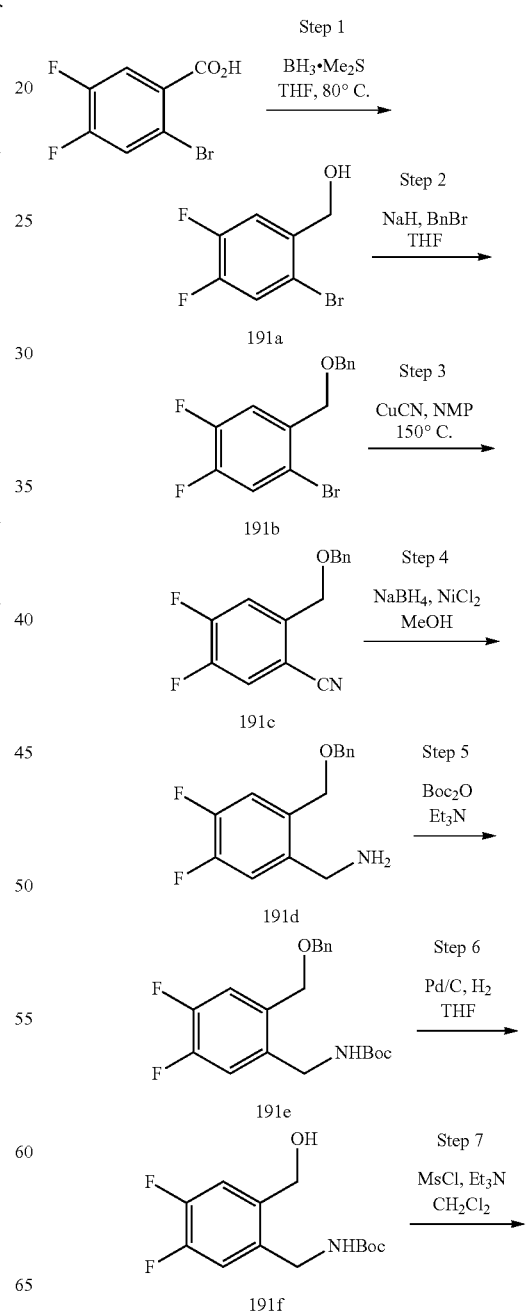

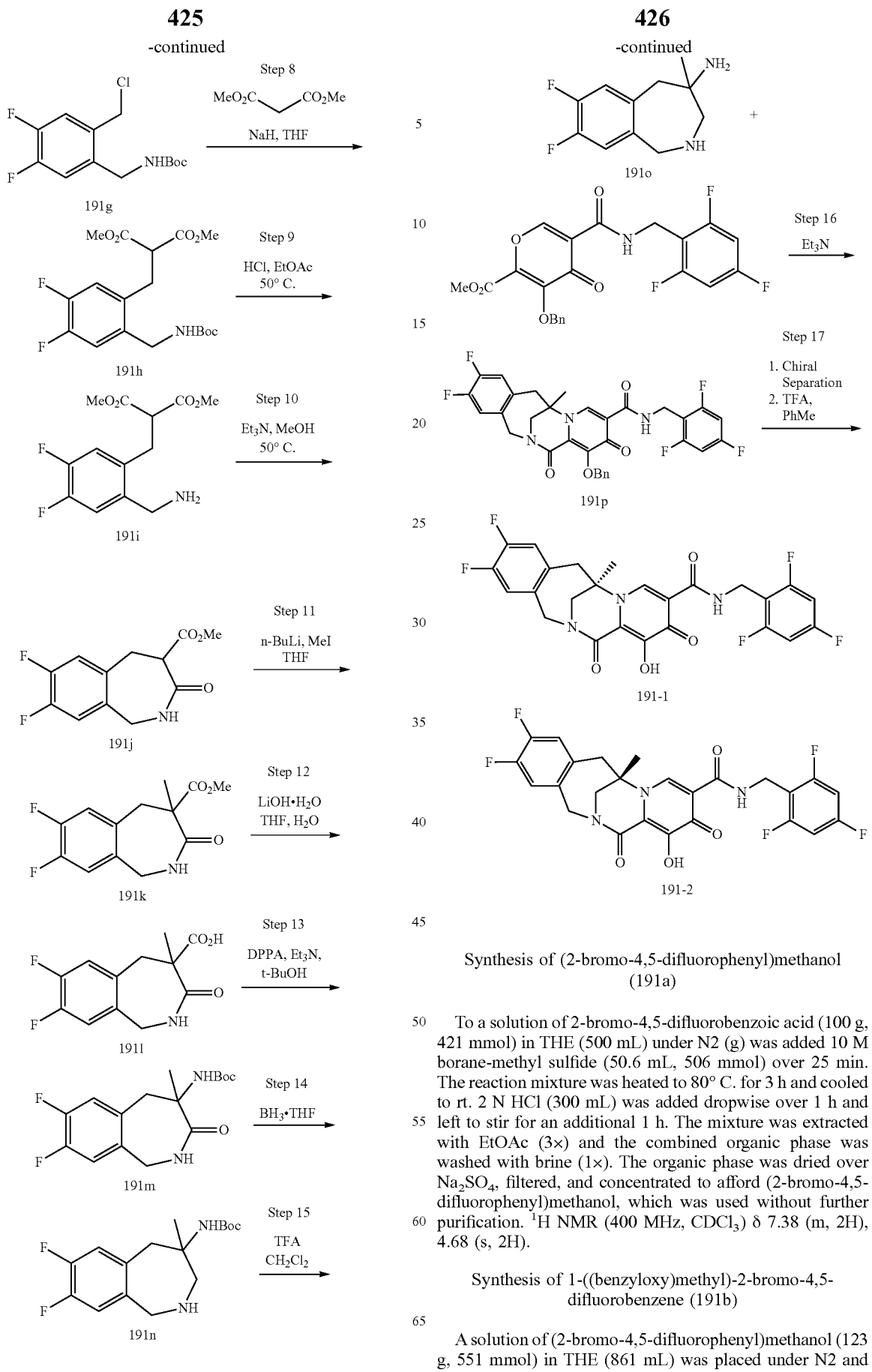

Synthesis of (2-bromo-4,5-difluorophenyl)methanol (191a)

To a solution of 2-bromo-4,5-difluorobenzoic acid (100 g, 421 mmol) in THF (500 mL) under N2 (g) was added 10 M borane-methyl sulfide (50.6 mL, 506 mmol) over 25 min. The reaction mixture was heated to 80° C. for 3 h and cooled to rt. 2 N HCl (300 mL) was added dropwise over 1 h and left to stir for an additional 1 h. The mixture was extracted with EtOAc (3×) and the combined organic phase was washed with brine (1×). The organic phase was dried over $Na_2SO_4$, filtered, and concentrated to afford (2-bromo-4,5-difluorophenyl)methanol, which was used without further purification. $^1$H NMR (400 MHz, $CDCl_3$) δ 7.38 (m, 2H), 4.68 (s, 2H).

Synthesis of 1-((benzyloxy)methyl)-2-bromo-4,5-difluorobenzene (191b)

A solution of (2-bromo-4,5-difluorophenyl)methanol (123 g, 551 mmol) in THF (861 mL) was placed under N2 and cooled to 0° C. 60% sodium hydride (26.4 g, 661 mmol) was added and the reaction mixture was stirred for 1 h. A solution of benzyl bromide (94.3 g, 551 mmol) in THF (65 mL) was added dropwise and the reaction was warmed to rt. After 16 h, the reaction mixture was poured into ice and extracted with EtOAc (3×). The combined organic phase was washed with 10% citric acid (2×) and brine (1×), dried over $Na_2SO_4$, filtered, and concentrated to afford 1-((benzyloxy)methyl)-2-bromo-4,5-difluorobenzene, which was used without further purification. $^1$H NMR (400 MHz, $CDCl_3$) δ 7.20 (m, 7H), 4.47 (s, 2H), 4.36 (s, 2H).

Synthesis of
2-((benzyloxy)methyl)-4,5-difluorobenzonitrile
(191c)

To a solution of 1-((benzyloxy)methyl)-2-bromo-4,5-difluorobenzene (100 g, 319 mmol) in NMP (1 L) was added CuCN (85.8 g, 958 mmol). The reaction mixture was heated to 150° C. for 21 h. After cooling to rt, water was added and the mixture was extracted with EtOAc (3×). The combined organic phase was washed with brine (1×), dried over $Na_2SO_4$, filtered, and concentrated to provide 2-((benzyloxy)methyl)-4,5-difluorobenzonitrile, which was used in the next step without further purification. $^1$H NMR (400 MHz, $CDCl_3$) δ 7.45 (m, 7H), 4.68 (d, J=10.8 Hz, 4H).

Synthesis of (2-((benzyloxy)methyl)-4,5-difluorophenyl)methanamine (191d)

To a suspension of 2-((benzyloxy)methyl)-4,5-difluorobenzonitrile (80.0 g, 308 mmol) and $NiCl_2.6H_2O$ (73.4 g, 308 mmol) in MeOH (1.2 L) at 0° C. was added $NaBH_4$ (35.0 g, 923 mmol) portion-wise over 1 h. The reaction mixture was warmed to rt and stirred for 1 h. 5% HCl was added and the mixture was stirred for 1 h. $Na_2CO_3$ was added to basify and the mixture was filtered. The filtrate was extracted with EtOAc (3×) and the combined organic phase was dried over $Na_2SO_4$ and concentrated to afford (2-((benzyloxy)methyl)-4,5-difluorophenyl) methanamine, which was used without further purification.

Synthesis of tert-butyl (2-((benzyloxy)methyl)-4,5-difluorobenzyl)carbamate (191e)

To a solution of (2-((benzyloxy)methyl)-4,5-difluorophenyl)methanamine (77.4 g, 293 mmol) in $CH_2Cl_2$ (542 mL) was added triethylamine (102.3 mL, 735 mmol). The reaction mixture was cooled to 0° C. and $Boc_2O$ (128 g, 135.07 mmol) was added. The reaction mixture was warmed to rt and stirred for 5 h. Water was added and the mixture was extracted with $CH_2Cl_2$ (3×). The combined organic phase was dried over $Na_2SO_4$, filtered, and concentrated to afford tert-butyl (2-((benzyloxy)methyl)-4,5-difluorobenzyl)carbamate, which was used without further purification. $^1$H NMR (400 MHz, $CDCl_3$) δ 7.26 (m, 5H), 7.08 (m, 2H), 4.95 (s, 1H), 4.48 (s, 2H), 4.42 (s, 2H), 4.18 (d, J=6.0 Hz, 2H), 1.35 (s, 9H).

Synthesis of tert-butyl
(4,5-difluoro-2-(hydroxymethyl)benzyl)carbamate
(191f)

To a mixture of tert-butyl (2-((benzyloxy)methyl)-4,5-difluorobenzyl)carbamate (54.7 g, 151 mmol) and 10% Pd/C (5.47 g) was added THF (820 mL). The suspension was placed under 35 psi of $H_2$ (g) and stirred for 16 h. An additional portion of Pd/C (5.0 g) was added and the reaction mixture was stirred under 35 psi of $H_2$ (g) for an additional 36 h. The reaction mixture was filtered and concentrated to provide tert-butyl (4,5-difluoro-2-(hydroxymethyl)benzyl)carbamate, which was used without further purification. $^1$H NMR (400 MHz, $CDCl_3$) δ 7.17 (m, 2H), 5.10 (s, 1H), 4.67 (d, J=4.8 Hz, 2H), 4.30 (d, J=6.0 Hz, 2H), 1.46 (s, 10H).

Synthesis of tert-butyl
(2-(chloromethyl)-4,5-difluorobenzyl)carbamate
(191g)

To a suspension of tert-butyl (4,5-difluoro-2-(hydroxymethyl)benzyl)carbamate (35.2 g, 128 mmol) in $CH_2Cl_2$ (350 mL) was added $Et_3N$ (39.1 g, 386 mmol) and methanesulfonyl chloride (17.7 g, 154 mmol). After stirring for 1 h, the reaction mixture was poured into water and extracted with $CH_2Cl_2$ (3×). The combined organic phase was washed with brine, dried over $Na_2SO_4$, filtered, and concentrated to afford tert-butyl (2-(chloromethyl)-4,5-difluorobenzyl)carbamate, which was used without further purification. $^1$H NMR (400 MHz, $CDCl_3$) δ 7.18 (m, 2H), 4.98 (s, 1H), 4.58 (s, 2H), 4.37 (d, J=6.0 Hz, 2H), 1.47 (s, 9H).

Synthesis of dimethyl 2-(2-(((tert-butoxycarbonyl)amino)methyl)-4,5-difluorobenzyl)malonate (191h)

To a suspension of 60% sodium hydride (6.20 g, 155 mmol) in THF (750 mL) was added dimethyl malonate (20.5 g, 155 mmol). At 0° C., a solution of tert-butyl (2-(chloromethyl)-4,5-difluorobenzyl)carbamate (37.7 g, 129 mmol) in THF (260 mL) was added and left to stir for 16 h. Acetic acid was added to acidify to pH 5 and water was added. The mixture was extracted with EtOAc (3×) and the combined organic phase was washed with saturated aqueous $NaHCO_3$. The organic phase was dried over $Na_2SO_4$, filtered, and concentrated to afford dimethyl 2-(2-(((tert-butoxycarbonyl)amino)methyl)-4,5-difluorobenzyl)malonate, which was used without further purification. MS (m/z) 288.0 [M−Boc+H]$^+$.

Synthesis of dimethyl
2-(2-(aminomethyl)-4,5-difluorobenzyl)malonate
hydrochloride (191i)

To a solution of dimethyl 2-(2-(((tert-butoxycarbonyl)amino)methyl)-4,5-difluorobenzyl)malonate (31.8 g, 82.0 mmol) in EtOAc (320 mL) was added 4 M HCl in EtOAc (160 mL) dropwise. After 3 h, the reaction mixture was concentrated to afford dimethyl 2-(2-(aminomethyl)-4,5-difluorobenzyl)malonate hydrochloride, which was used without further purification. $^1$H NMR (400 MHz, $CD_3OD$) δ 7.17 (dd, J=11.0, 8.0 Hz, 1H), 7.06 (dd, J=11.0, 8.0 Hz, 1H), 4.00 (s, 2H), 3.67 (t, J=8.0 Hz, 1H), 3.45 (s, 7H), 3.04 (m, 3H).

Synthesis of methyl 7,8-difluoro-3-oxo-2,3,4,5-tetrahydro-1H-benzo[c]azepine-4-carboxylate (191j)

To a solution of dimethyl 2-(2-(aminomethyl)-4,5-difluorobenzyl)malonate hydrochloride (23.9 g, 73.8 mmol) in MeOH (168 mL) was added triethylamine (11.2 g, 111 mmol). The reaction mixture was stirred at 50° C. for 5 h and concentrated to afford methyl 7,8-difluoro-3-oxo-2,3,4,5-tetrahydro-1H-benzo[c]azepine-4-carboxylate, which was used without further purification. MS (m/z) 256.0 [M+H]$^+$. $^1$H NMR (400 MHz, $CDCl_3$) δ 7.03 (q, J=10.8, 8.0 Hz, 1H), 6.95 (dd, J=10.4, 7.6 Hz, 1H), 6.82 (s, 1H), 4.72 (dd, J=4.8 Hz, 1H), 4.17 (dd, J=16.0, 6.0 Hz, 1H), 3.99 (dd, J=11.6, 4.4 Hz, 1H), 3.79 (s, 3H), 3.40 (m, 1H), 3.18 (dd, J=5.2 Hz, 1H).

Synthesis of methyl 7,8-difluoro-4-methyl-3-oxo-2, 3,4,5-tetrahydro-1H-benzo[c]azepine-4-carboxylate (191k)

To a solution of methyl 7,8-difluoro-3-oxo-2,3,4,5-tetrahydro-1H-benzo[c]azepine-4-carboxylate (3.0 g, 11.8 mmol) in THF (36 mL) at −78° C. was added 2.5 M n-BuLi in hexanes (4.7 mL, 11.8 mmol). The reaction mixture was warmed to rt for 10 min then cooled to −78° C. Iodomethane (0.73 mL, 11.8 mmol) was added and the reaction was allowed to warm to rt overnight. Saturated aqueous NH$_4$Cl was added and the mixture was extracted with EtOAc (2×). The combined organic phase was dried over Na$_2$SO$_4$, filtered, concentrated, and purified by column chromatography (0-100% EtOAc/heptane) to afford methyl 7,8-difluoro-4-methyl-3-oxo-2,3,4,5-tetrahydro-1H-benzo[c]azepine-4-carboxylate. MS (m/z) 270.09 [M+H]$^+$.

Synthesis of 7,8-difluoro-4-methyl-3-oxo-2,3,4,5-tetrahydro-1H-benzo[c]azepine-4-carboxylic acid (191l)

To a flask containing methyl 7,8-difluoro-4-methyl-3-oxo-2,3,4,5-tetrahydro-1H-benzo[c]azepine-4-carboxylate (1.19 g, 4.41 mmol) was added 1:1 THF/water (30 mL) and LiOH.H$_2$O (0.56 g, 13.2 mmol). The reaction mixture was stirred at rt for 6 h, acidified with 1 M HCl, and extracted with EtOAc (2×). The combined organic phase was dried over Na$_2$SO$_4$, filtered, and concentrated to afford 7,8-difluoro-4-methyl-3-oxo-2,3,4,5-tetrahydro-1H-benzo[c]azepine-4-carboxylic acid, which was used without further purification. MS (m/z) 256.02 [M+H]$^+$.

Synthesis of tert-butyl (7,8-difluoro-4-methyl-3-oxo-2,3,4,5-tetrahydro-1H-benzo[c]azepin-4-yl)carbamate (191m)

To a solution of 7,8-difluoro-4-methyl-3-oxo-2,3,4,5-tetrahydro-1H-benzo[c]azepine-4-carboxylic acid (1.06 g, 4.15 mmol) in t-BuOH (25 mL) was added triethylamine (1.04 mL, 7.48 mmol) and DPPA (1.35 mL, 6.23 mmol). The reaction mixture was stirred at rt for 1 h then heated to 90° C. for 16 h. After cooling to rt, EtOAc was added and the solution was washed with water, 1 N HCl, and saturated aqueous NaHCO$_3$. The organic phase was dried over Na$_2$SO$_4$, filtered, concentrated, and purified by column chromatography (0-100% EtOAc/heptane) to provide tert-butyl (7,8-difluoro-4-methyl-3-oxo-2,3,4,5-tetrahydro-1H-benzo[c]azepin-4-yl)carbamate. MS (m/z) 326.88 [M+H]$^+$.

Synthesis of tert-butyl (7,8-difluoro-4-methyl-2,3,4,5-tetrahydro-1H-benzo[c]azepin-4-yl)carbamate (191n)

To a solution of tert-butyl (7,8-difluoro-4-methyl-3-oxo-2,3,4,5-tetrahydro-1H-benzo[c]azepin-4-yl)carbamate (0.286 g, 0.875 mmol) in THF (22 mL) at 0° C. was added 1 M borane-THF solution (3.50 mL, 3.50 mmol). The reaction mixture was allowed to warm to rt and stir for 2 h. The reaction mixture was cooled to 0° C. and quenched with MeOH. After 5 min, the mixture was concentrated, diluted with EtOAc, and washed with 1 M NaOH. The aqueous phase was extracted with EtOAc and the combined organic phase was dried over Na$_2$SO$_4$, filtered, and concentrated to afford tert-butyl (7,8-difluoro-4-methyl-2,3,4,5-tetrahydro-1H-benzo[c]azepin-4-yl)carbamate, which was used in the next step without further purification. MS (m/z) 312.97 [M+H]$^+$.

Synthesis of 7,8-difluoro-4-methyl-2,3,4,5-tetrahydro-1H-benzo[c]azepin-4-amine (191o)

To a solution of tert-butyl (7,8-difluoro-4-methyl-2,3,4,5-tetrahydro-1H-benzo[c]azepin-4-yl)carbamate (0.096 g, 0.306 mmol) in CH$_2$Cl$_2$ (2 mL) was added TFA (0.70 mL, 9.18 mmol) at rt. The reaction mixture was stirred for 3 h and concentrated to afford 7,8-difluoro-4-methyl-2,3,4,5-tetrahydro-1H-benzo[c]azepin-4-amine, which was used in the next step without further purification. MS (m/z) 213.02 [M+H]$^+$.

Synthesis of 1-(benzyloxy)-9,10-difluoro-6-methyl-2,14-dioxo-N-(2,4,6-trifluorobenzyl)-2,7,12,14-tetrahydro-6H-6,13-methanobenzo[f]pyrido[1,2-a][1,4]diazonine-3-carboxamide (191p)

To a solution of 7,8-difluoro-4-methyl-2,3,4,5-tetrahydro-1H-benzo[c]azepin-4-amine (0.065 g, 0.306 mmol) and methyl 3-(benzyloxy)-4-oxo-5-((2,4,6-trifluorobenzyl)carbamoyl)-4H-pyran-2-carboxylate (0.137 g, 0.306 mmol) in 6:1 THF/EtOH (3.5 mL) was added triethylamine (3.17 mL, 22.8 mmol). The reaction mixture was stirred at rt for 16 h and concentrated. The residue was purified by column chromatography (20-100% EtOAc/heptane) to afford 1-(benzyloxy)-9,10-difluoro-6-methyl-2,14-dioxo-N-(2,4,6-trifluorobenzyl)-2,7,12,14-tetrahydro-6H-6,13-methanobenzo[f]pyrido[1,2-a][1,4]diazonine-3-carboxamide. MS (m/z) 610.07 [M+H]$^+$.

Synthesis of (6R)-9,10-difluoro-1-hydroxy-6-methyl-2,14-dioxo-N-(2,4,6-trifluorobenzyl)-2,7,12,14-tetrahydro-6H-6,13-methanobenzo[f]pyrido[1,2-a][1,4]diazonine-3-carboxamide (191-1) and (6S)-9,10-difluoro-1-hydroxy-6-methyl-2,14-dioxo-N-(2,4,6-trifluorobenzyl)-2,7,12,14-tetrahydro-6H-6,13-methanobenzo[f]pyrido[1,2-a][1,4]diazonine-3-carboxamide (191-2)

1-(Benzyloxy)-9,10-difluoro-6-methyl-2,14-dioxo-N-(2,4,6-trifluorobenzyl)-2,7,12,14-tetrahydro-6H-6,13-methanobenzo[f]pyrido[1,2-a][1,4]diazonine-3-carboxamide was separated into its individual enantiomers by preparative SFC on an OJ-H column using 25% EtOH co-solvent to provide (6R)-1-(benzyloxy)-9,10-difluoro-6-methyl-2,14-dioxo-N-(2,4,6-trifluorobenzyl)-2,7,12,14-tetrahydro-6H-6,13-methanobenzo[f]pyrido[1,2-a][1,4]diazonine-3-carboxamide as the first eluting peak and (6S)-1-(benzyloxy)-9,10-difluoro-6-methyl-2,14-dioxo-N-(2,4,6-trifluorobenzyl)-2,7,12,14-tetrahydro-6H-6,13-methanobenzo[f]pyrido[1,2-a][1,4]diazonine-3-carboxamide as the second eluting peak. The separated enantiomers were dissolved in 1:1 toluene/TFA (2 mL). The reaction mixture was stirred at rt for 2 h and concentrated. The residue was dissolved in MeCN and purified by preparative HPLC (column, Gemini 10μ C18 110A, AXI/; 250×21.2 mm) eluting 5-100% acetonitrile (0.1% TFA) in water (0.1% TFA) over 30 minutes. The combined fractions were lyophilized to afford (6R)-9,10-difluoro-1-hydroxy-6-methyl-2,14-dioxo-N-(2,4,6-trifluorobenzyl)-2,7,12,14-tetrahydro-6H-6,13-methanobenzo[f]pyrido[1,2-a][1,4]diazonine-3-carboxamide and (6S)-9,10- difluoro-1-hydroxy-6-methyl-2,14-dioxo-N-(2,4,6-trifluorobenzyl)-2,7,12,14-tetrahydro-6H-6,13-methanobenzo[f]pyrido[1,2-a][1,4]diazonine-3-carboxamide. Peak 1: MS (m/z) 520.16 [M+H]+. 1H NMR (400 MHz, DMSO-d6) δ 10.37 (t, J=5.8 Hz, 1H), 8.36 (s, 1H), 7.42 (dd, J=11.6, 8.1 Hz, 1H), 7.31 (dd, J=11.4, 8.1 Hz, 1H), 7.21 (t, J=8.6 Hz, 2H), 5.52 (d, J=16.7 Hz, 1H), 4.65-4.51 (m, 2H), 4.43 (d, J=16.7 Hz, 1H), 3.68 (d, J=14.7 Hz, 1H), 3.40 (d, J=14.7 Hz, 1H), 3.03 (s, 2H), 1.60 (s, 3H). 19F NMR (376 MHz, DMSO-d6) δ −109.34 (ddd, J=15.5, 9.3, 6.2 Hz), −112.57 (t, J=7.3 Hz), −140.74 (ddd, J=23.0, 11.5, 8.2 Hz), −141.75 (dt, J=20.8, 9.9 Hz). Peak 2: MS (m/z) 520.18 [M+H]+. 1H NMR (400 MHz, DMSO-d6) δ 10.37 (t, J=5.8 Hz, 1H), 8.36 (s, 1H), 7.42 (dd, J=11.7, 8.1 Hz, 1H), 7.31 (dd, J=11.4, 8.1 Hz, 1H), 7.21 (t, J=8.6 Hz, 2H), 5.52 (d, J=16.8 Hz, 1H), 4.67-4.49 (m, 2H), 4.43 (d, J=16.8 Hz, 1H), 3.68 (d, J=14.7 Hz, 1H), 3.40 (d, J=14.7 Hz, 1H), 3.03 (s, 2H), 1.60 (s, 3H). 19F NMR (376 MHz, DMSO-d6) δ −109.34 (tt, J=9.2, 6.3 Hz), −112.57 (t, J=7.2 Hz), −140.74 (dt, J=21.3, 9.9 Hz), −141.75 (dt, J=20.6, 9.9 Hz).

Example 189: Synthesis of (3R,6R,7S)—N-(2,4-difluorobenzyl)-3-(fluoromethyl)-12-hydroxy-6-methyl-1,11-dioxo-1,6,7,11-tetrahydro-3H-2,7-methanopyrido[1,2-a][1,4]diazonine-10-carboxamide (192)

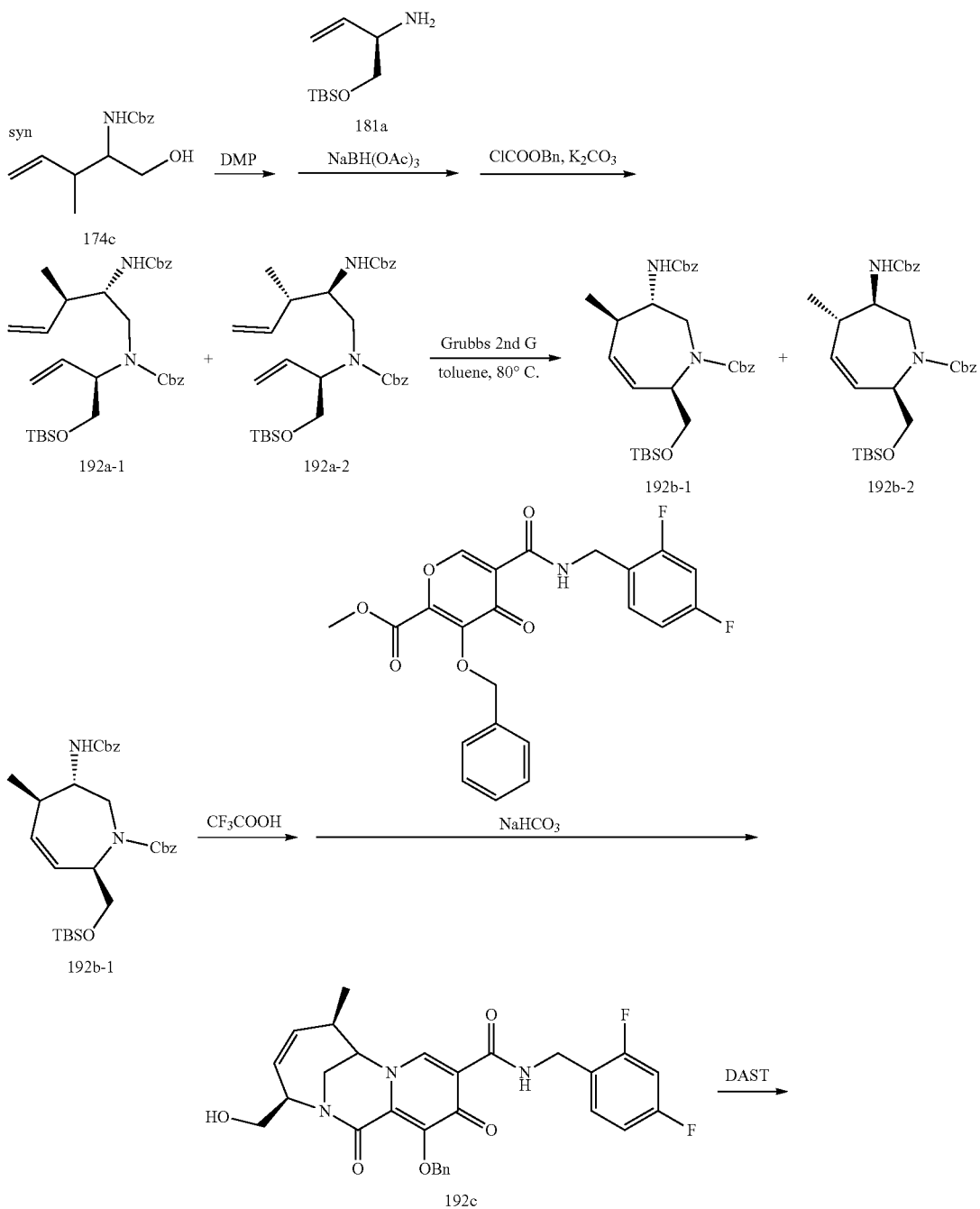

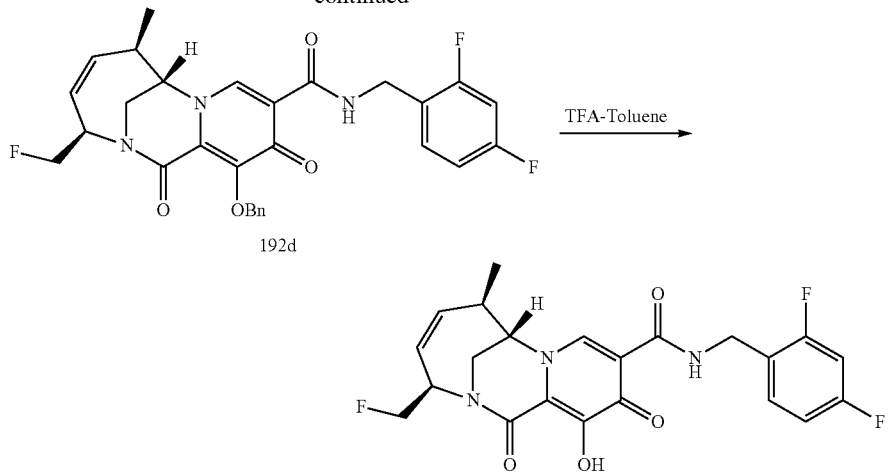

Synthesis of benzyl ((2S,3R)-2-(((benzyloxy)carbonyl)amino)-3-methylpent-4-en-1-yl)((R)-1-((tert-butyldimethylsilyl)oxy)but-3-en-2-yl)carbamate (192a-1) and benzyl ((2R,3S)-2-(((benzyloxy)carbonyl)amino)-3-methylpent-4-en-1-yl)((R)-1-((tert-butyldimethylsilyl)oxy)but-3-en-2-yl)carbamate (192a-2)

The title compounds were synthesized in a manner similar to a mixture of benzyl ((2S,3R)-2-(((benzyloxy)carbonyl)amino)-3-methylpent-4-en-1-yl)((S)-but-3-en-2-yl)carbamate (173d-1) and benzyl ((2R,3S)-2-(((benzyloxy)carbonyl)amino)-3-methylpent-4-en-1-yl)((S)-but-3-en-2-yl)carbamate (173d-2) except using (R)-1-((tert-butyldimethylsilyl)oxy)but-3-en-2-amine (181a) instead of (2S)-but-3-en-2-amine hydrochloride. MS (m/z) 567.30 [M+H]+.

Synthesis of benzyl (3S,4R,7R)-3-(((benzyloxy)carbonyl)amino)-7-(((tert-butyldimethylsilyl)oxy)methyl)-4-methyl-2,3,4,7-tetrahydro-1H-azepine-1-carboxylate (192b-1) and benzyl (3R,4S,7R)-3-(((benzyloxy)carbonyl)amino)-7-(((tert-butyldimethylsilyl)oxy)methyl)-4-methyl-2,3,4,7-tetrahydro-1H-azepine-1-carboxylate (192b-2)

The title compounds were synthesized and separated in a manner similar to (3S,4R,7S) and (3R,4S,7S)-3-(((benzyloxy)carbonyl)amino)-4,7-dimethyl-2,3,4,7-tetrahydro-1H-azepine-1-carboxylate (174e-1 and 174e-2) except using benzyl ((2S,3R)-2-(((benzyloxy)carbonyl)amino)-3-methylpent-4-en-1-yl)((R)-1-((tert-butyldimethylsilyl)oxy)but-3-en-2-yl)carbamate (192a-1) and benzyl ((2R,3S)-2-(((benzyloxy)carbonyl)amino)-3-methylpent-4-en-1-yl)((R)-1-((tert-butyldimethylsilyl)oxy)but-3-en-2-yl)carbamate (192a-2) instead of benzyl ((2S,3R)-2-(((benzyloxy)carbonyl)amino)-3-methylpent-4-en-1-yl)((S)-but-3-en-2-yl)carbamate (174d-1) and benzyl ((2R,3S)-2-(((benzyloxy)carbonyl)amino)-3-methylpent-4-en-1-yl)((S)-but-3-en-2-yl) carbamate (174d-2). MS (m/z) 539.30 [M+H]+.

Synthesis of (3R,6R,7S)-12-(benzyloxy)-N-(2,4-difluorobenzyl)-3-(hydroxymethyl)-6-methyl-1,11-dioxo-1,6,7,11-tetrahydro-3H-2,7-methanopyrido[1,2-a][1,4]diazonine-10-carboxamide (192c)

Benzyl (3S,4R,7R)-3-(((benzyloxy)carbonyl)amino)-7-(((tert-butyldimethylsilyl) oxy)methyl)-4-methyl-2,3,4,7-tetrahydro-1H-azepine-1-carboxylate (192b-1) (285.3 mg, 0.530 mmol) was dissolved in TFA (5 mL) and heated to 100° C. in a sealed vial for 2 h. The reaction mixture was concentrated to get black viscous syrup, which was co-evaporated with toluene once. A mixture of the residue, methyl 3-(benzyloxy)-5-((2,4-difluorobenzyl)carbamoyl)-4-oxo-4H-pyran-2-carboxylate, and sodium bicarbonate (267.8 mg, 3.19 mmol) in water (3 mL) and methanol (6 mL) was stirred at rt for 30 min, at 50° C. for 19 h, and at 60° C. for 10 h. The reaction mixture was concentrated to remove most of methanol and the resulting mixture was dissolved with dichloromethane (20 mL) and water (~20 mL). After the separated two fractions, the aq fraction was extracted with dichloromethane (×1). The organic fractions were combined, dried (MgSO4), and concentrated. The residue was purified with column chromatography on silica gel eluting 0-20% methanol in dichloromethane to get 201.1 mg of the title compound: MS (m/z) 536.11 [M+H]+.

Synthesis of (3R,6R,7S)-12-(benzyloxy)-N-(2,4-difluorobenzyl)-3-(fluoromethyl)-6-methyl-1,11-dioxo-1,6,7,11-tetrahydro-3H-2,7-methanopyrido[1,2-a][1,4]diazonine-10-carboxamide (192d)

A solution of (3R,6R,7S)-12-(benzyloxy)-N-(2,4-difluorobenzyl)-3-(hydroxymethyl)-6-methyl-1,11-dioxo-1,6,7,11-tetrahydro-3H-2,7-methanopyrido[1,2-a][1,4]diazonine-10-carboxamide (192c) (201.1 mg, 376 umol) in dichloromethane (6 mL) was stirred at 0° C. as DAST (0.15 mL, 1.14 mmol) was added. After 30 min, the reaction mixture was stirred at rt for 18 h. While the reaction mixture was stirred at 0° C., saturated sodium bicarbonate (~30 mL) was added, and the product was extracted with dichloromethane (20 mL×2). The two organic extracts were combined, dried (MgSO4) and concentrated. Purification with silica gel chromatography with 0-100% EtOAc/Heptane afford the product. MS (m/z) 538.20 [M+H]+.

Synthesis of (3R,6R,7S)-12-(benzyloxy)-N-(2,4-difluorobenzyl)-3-(fluoromethyl)-6-methyl-1,11-dioxo-1,6,7,11-tetrahydro-3H-2,7-methanopyrido[1,2-a][1,4]diazonine-10-carboxamide (192)

(3R,6R,7S)-12-(benzyloxy)-N-(2,4-difluorobenzyl)-3-(fluoromethyl)-6-methyl-1,11-dioxo-1,6,7,11-tetrahydro-3H-2,7-methanopyrido[1,2-a][1,4]diazonine-10-carboxamide (192d) (101 mg, 0.19 mmol) was dissolved in toluene (1 mL) and TFA (2 mL) and stirred at rt for 2 h. After the reaction mixture was concentrated, the residue was dissolved in DMF before filtered. The filtrate was purified by preparative HPLC (2 injections: column, Gemini 5 um C18 110A, LC column 100×30 mm) eluting 20-45% acetonitrile (0.1% TFA) in water (0.1% TFA) over 60 min.) The product containing fraction was freeze-dried to get 12.8 mg (15.2%) of the title compound: MS (m/z) 448.13 [M+H]+. 1H NMR (400 MHz, Acetonitrile-$d_3$) δ 10.26 (s, 1H), 8.38 (s, 1H), 7.41 (td, J=9.2, 8.8, 6.5 Hz, 1H), 7.04-6.84 (m, 2H), 5.62-5.53 (m, 1H), 5.50 (ddd, J=11.5, 2.4, 1.6 Hz, 1H), 5.40 (d, J=23.2 Hz, 1H), 4.74-4.65 (m, 1H), 4.65-4.50 (m, 3H), 4.22 (ddd, J=6.6, 3.1, 1.3 Hz, 1H), 4.00 (dd, J=14.5, 3.0 Hz, 1H), 3.73-3.62 (m, 1H), 2.73 (td, J=6.8, 3.4 Hz, 1H), 1.21 (d, J=7.1 Hz, 3H).

Example 190: Preparation of (3R,6R,7S)—N-(2,4-difluorobenzyl)-3-(fluoromethyl)-12-hydroxy-6-methyl-1,11-dioxo-1,4,5,6,7,11-hexahydro-3H-2,7-methanopyrido[1,2-a][1,4]diazonine-10-carboxamide (193)

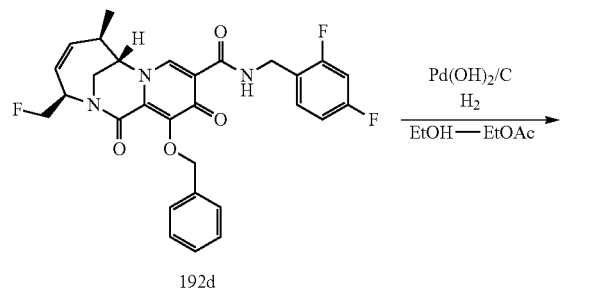

(3R,6R,7S)-12-(Benzyloxy)-N-(2,4-difluorobenzyl)-3-(fluoromethyl)-6-methyl-1,11-dioxo-1,6,7,11-tetrahydro-3H-2,7-methanopyrido[1,2-a][1,4]diazonine-10-carboxamide (192d) (101 mg, 0.188 mmol) was dissolved in EtOH (3 mL) and Ethyl Acetate (2 mL) and 20% Pd(OH)$_2$/C (71 mg) was added before stirred under H$_2$ atmosphere for 4 h. The reaction mixture was filtered through celite pad and the celite pad was washed with ethyl acetate. The reaction mixture was concentrated to dryness. The residue was dissolved in DMF and was purified by preparative HPLC (column, Gemini 5 um C18 110A, LC column 100×30 mm) eluting 15-65% acetonitrile (0.1% TFA) in water (0.1% TFA) over 20 min.) to afford lyophilized form of product. MS (m/z) 436.10 [M+H]+.

Example 191: Preparation of 6-(fluoromethyl)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide, 6-(fluoromethyl)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide, 6-(fluoromethyl)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide, and 6-(fluoromethyl)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (194-1, 194-2, 194-3, and 194-4)

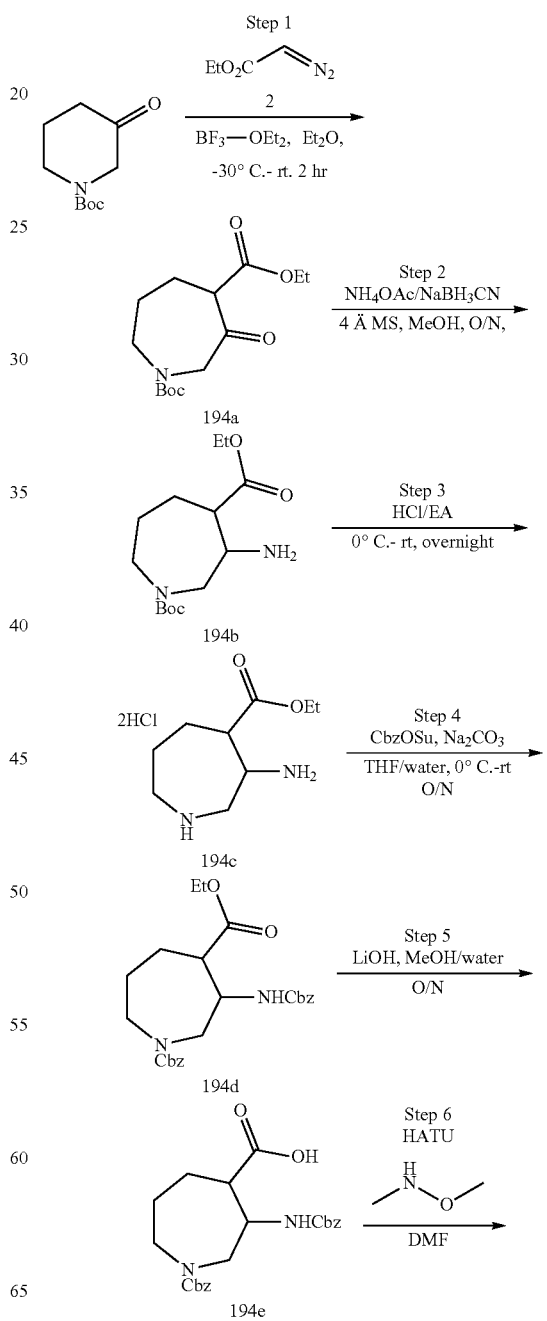

437
-continued
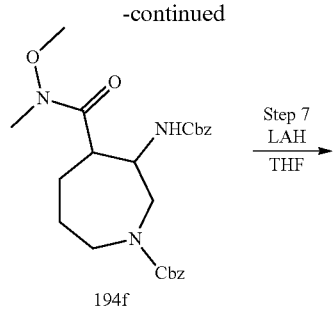
194f
Step 7
LAH
THF
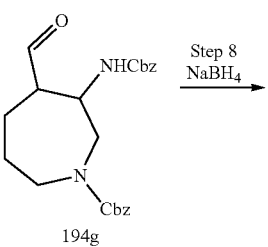
194g
Step 8
NaBH₄
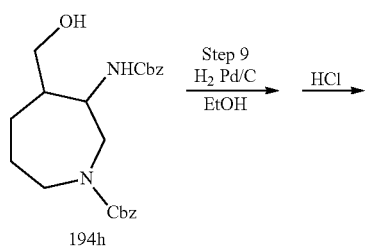
194h
Step 9
H₂ Pd/C
EtOH
HCl
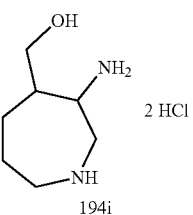
194i
2 HCl
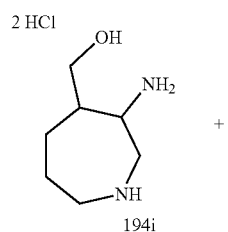
194i
+
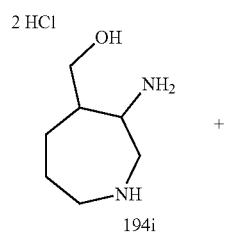
Step 10
NaHCO₃
MeOH / water
438
-continued
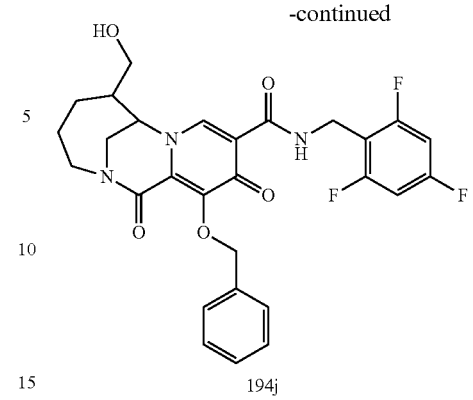
194j
Step 11
DeoxoFluor
DCM
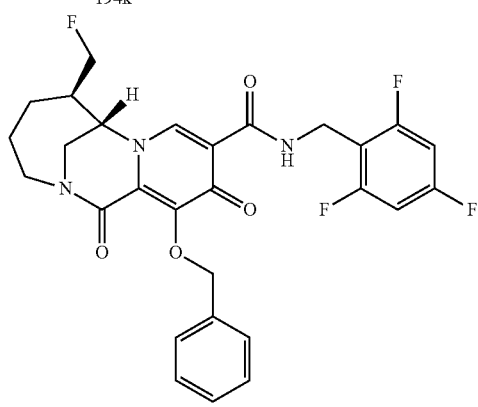
194k
Step 12
Chiral SFC
seapration
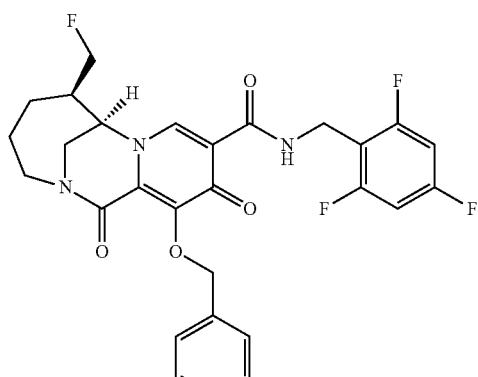
194-I-P1
194-I-P2

439
-continued
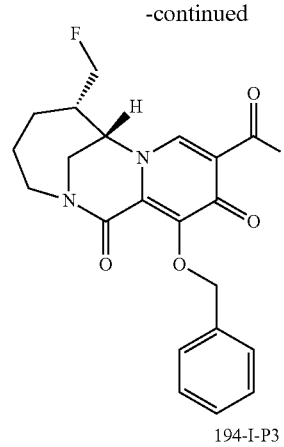
194-I-P3
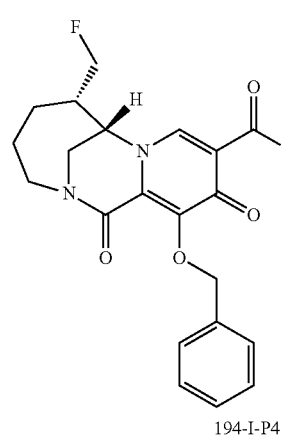
194-I-P4
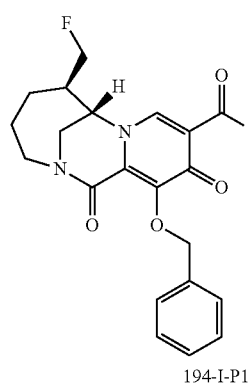
194-I-P1
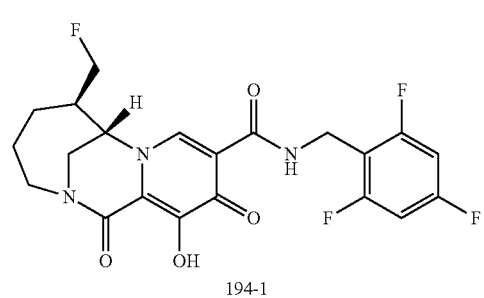
194-1
440
-continued
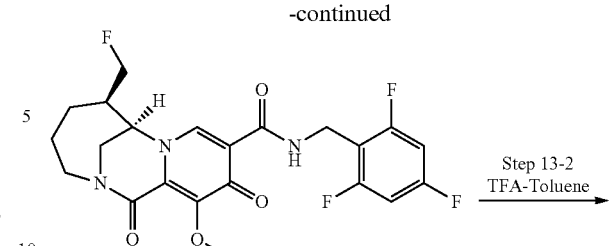
194-I-P2 → Step 13-2 TFA-Toluene
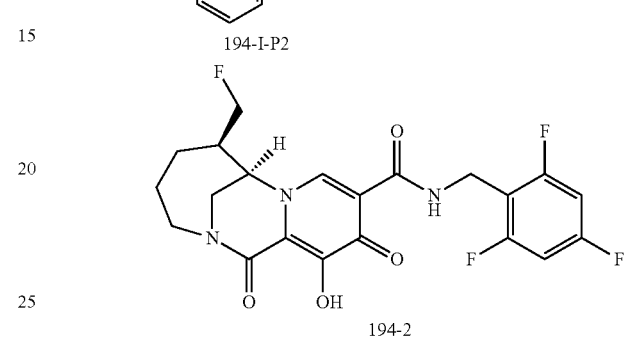
194-2
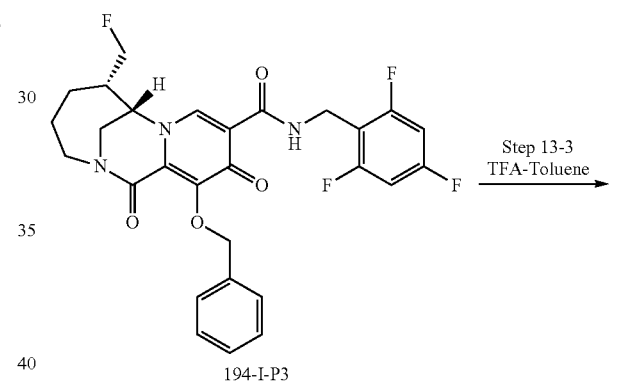
194-I-P3 → Step 13-3 TFA-Toluene
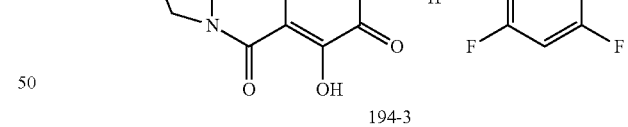
194-3
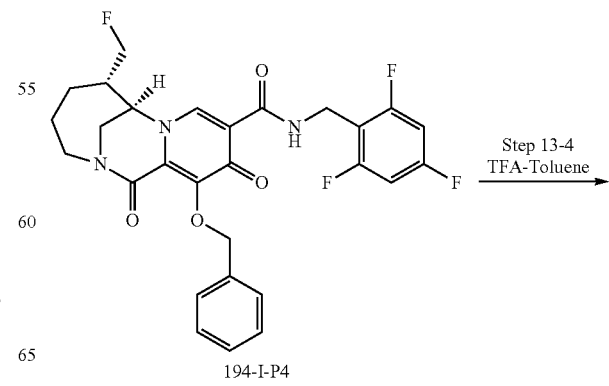
194-I-P4 → Step 13-4 TFA-Toluene

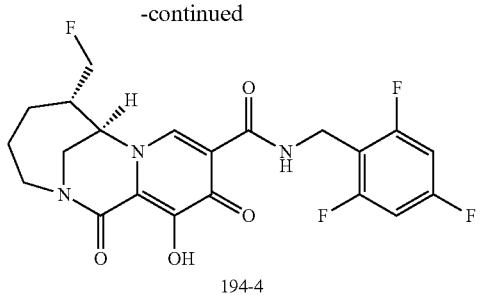

194-4

Step 1. Synthesis of 1-(tert-butyl) 4-ethyl 3-oxoazepane-1,4-dicarboxylate (194a)

To a solution of tert-butyl 3-oxopiperidine-1-carboxylate (50.0 g, 251.0 mmol, 1.0 eq) in diethyl ether (250 mL) at −30° C. was added a solution of boron trifluoride etherate (32.0 g, 326 mmol, 1.3 eq) in diethyl ether (100 mL) dropwise. The mixture was stirred at the same temperature for 10-15 min. A solution of compound 2 (37.3 g, 326.0 mmol, 1.3 eq) in diethyl ether (130 mL) was added dropwise at −30° C. The mixture was stirred at the same temperature for additional 1.5 hr. After the reaction mixture was warmed-up to room temperature, ethyl acetate (250 mL) was added, and the organic phase was washed with 30% aqueous potassium carbonate (1 L) and brine (300 mL). The organic phase was dried over anhydrous sodium sulfate and evaporated under reduced pressure to afford crude product (70 g). The crude product was purified by column chromatography on a silica gel (petroleum ether:ethyl acetate, 100:1 to 3:1) to afford compound (194a). MS (m/z): 286.16 [M+H]$^+$.

Step 2. Synthesis of 1-(tert-butyl) 4-ethyl 3-aminoazepane-1,4-dicarboxylate (194b)

A reaction mixture of 1-(tert-butyl) 4-ethyl 3-oxoazepane-1,4-dicarboxylate (194a) (18.2 g, 64.0 mmol, 1.0 eq), ammonium acetate (25.0 g, 319.0 mmol, 5.0 eq) and 4 Å MS (27.3 g) in methanol (180 mL) was stirred at ambient temperature under nitrogen for 1 hr. Sodium cyanoborohydride (12.0 g, 191.4 mmol, 3.0 eq) was added and the mixture was stirred overnight. Once the compound (194a) was consumed completely, the reaction mixture was filtered through a pad of celite. The filtration was concentrated under reduce pressure. The residue was poured into saturated aqueous sodium carbonate solution. The mixture was extracted with ethyl acetate and the combined organic phases were concentrated. The residue was adjusted to pH 2 with 1 M HCl (100 mL). The mixture was extracted twice diethyl ether. The aqueous phase was adjusted to pH 9 with 1N NaOH, and extracted with ethyl acetate. The organic phase was dried over sodium sulfate and concentrated to afford product (194b), which was used in next step without further purification. MS (m/z): 287.19 [M+H]$^+$.

Step 3. Synthesis of ethyl 3-aminoazepane-4-carboxylate (194c)

To a solution of 1-(tert-butyl) 4-ethyl 3-aminoazepane-1,4-dicarboxylate (194b) (11.5 g, 40.2 mmol, 1.0 eq) in ethyl acetate (30 mL) was added HCl/EA (3.0 M, 80 mL, 6.0 eq) at 0° C. The reaction mixture was stirred overnight. The reaction mixture was monitored by LC-MS. Then mixture was concentrated under reduce pressure to afford crude product (194c), which was used in next step without further purification. MS (m/z): 187.14 [M+H]$^+$.

Step 4. Synthesis of 1-benzyl 4-ethyl 3-(((benzyloxy)carbonyl)amino)azepane-1,4-dicarboxylate (200d)

To a solution of crude intermediate ethyl 3-aminoazepane-4-carboxylate (194c) (11.8 g, 46.0 mmol, 1.0 eq) and sodium carbonate (24.1 g, 228.0 mmol, 5.0 eq) in THF/water (2:1, 300 mL) at 0° C. was added N-(benzyloxycarbonyloxy)succinimide (34.0 g, 137.0 mmol, 3.0 eq). The reaction mixture was stirred at ambient temperature overnight. The reaction was monitored by LC-MS. The mixture was added ethyl acetate and the organic layer was separated, washed with brine, dried with sodium sulfate, filtered and concentrated under reduced pressure to afford compound (194d). MS (m/z): 455.21 [M+H]$^+$.

Step 5. Synthesis of 1-((benzyloxy)carbonyl)-3-(((benzyloxy)carbonyl)amino)azepane-4-carboxylic acid (194e)

To a solution of intermediate 1-benzyl 4-ethyl 3-(((benzyloxy)carbonyl)amino) azepane-1,4-dicarboxylate (194d) (19.5 g, 42.9 mmol, 1.0 eq) in methanol/water (3:2, 500 mL) was added lithium hydroxide hydrate (5.4 g, 129.0 mmol, 3.0 eq). Once the reaction completed, the reaction mixture was concentrated under reduce pressure. The residue was added 6 N HCl till the solution reached pH 1-2. The mixture was extracted with ethyl acetate and the combined organic was dried over sodium sulfate, filtered and concentrated to afford crude product (20 g). The crude product was purified by prep-HPLC (C18, 0.1% TFA in MeCN—H$_2$O) to afford product (194e). MS (m/z): 427.35 [M+H]$^+$. $^1$H NMR (400 MHz, DMSO-d6) δ 12.19 (m, 1H), 7.38-7.20 (m, 10H), 5.10-4.86 (m, 4H), 4.34-4.31 (m, 1H), 4.05 (m, 1H), 3.61-3.57 (m, 2H), 3.11-3.05 (m, 2H), 2.50 (m, 1H), 2.41 (m, 1H) and 1.88-1.46 (m, 4H).

Step 6. Synthesis of benzyl 3-(((benzyloxy)carbonyl)amino)-4-(methoxy(methyl)carbamoyl) azepane-1-carboxylate (194f)

1-((benzyloxy)carbonyl)-3-(((benzyloxy)carbonyl) amino)azepane-4-carboxylic acid (194e) (1.1 g, 2.58 mmol) and HATU (1.18 g, 3.10 mmol) were dissolved in DMF (2 mL) and cooled to 0° C. Then DIEA (1.0 g, 7.70 mmol) was added. The resulting reaction mixture was stirred for 30 min. N,O-dimethylhydroxylamine hydrochloride (0.252 g, 2.58 mmol) was added. The reaction mixture was allowed to warm to rt and was stirred for 3 h. The final reaction mixture was then partitioned with ethyl acetate and water. The organic layer was separated, washed with 5% LiCl and saturated brine. It was then dried with MgSO$_4$ and filtered. The filtrate was concentrated to dryness. The residue was purified with silica gel chromatography eluted with EtOAc and Heptane to afford product (194f). MS (m/z): 470.20 [M+H]$^+$.

Step 7. Synthesis of benzyl 3-(((benzyloxy)carbonyl)amino)-4-formylazepane-1-carboxylate (194g)

Benzyl 3-(((benzyloxy)carbonyl)amino)-4-(methoxy (methyl)carbamoyl) azepane-1-carboxylate (194f) (0.69 g, 1.47 mmol) was dissolved in THF (2 mL). The solution was cooled to 0° C. LAH (2M in THF) (0.808 mL, 1.62 mmol)

was added dropwise and the solution was kept at 0° C. for 1 hour. Reaction was then quenched slowly with NaHCO$_3$ (sat) (25 mL) at 0° C. Salts was precipitated out after 10 min. The resulting mixture was gradually warmed up to rt over 2 hours. The crude product was then extracted with ether (2×10 mL), then EtOAc (3×10 mL). Organic phase was washed with brine, dried over MgSO$_4$ and was filtered. The filtrate was concentrated to afford the crude product (194g) which was used in the next step. MS (m/z): 411.11 [M+H]$^+$.

Step 8. Synthesis of benzyl 3-(((benzyloxy)carbonyl)amino)-4-(hydroxymethyl)azepane-1-carboxylate (194h)

Benzyl 3-(((benzyloxy)carbonyl)amino)-4-formylazepane-1-carboxylate (194g) (0.367 g, 0.089 mmol) was dissolved in MeOH (5 mL). NaBH$_4$ (17 mg, 0.067 mmol). The reaction mixture was stirred at rt overnight. Reaction mixture was then quenched with NaHCO$_3$ (sat) (10 mL) and the crude product was extracted with EtoAc (3×10 mL). Organic phase was then washed with brine, dried with MgSO$_4$ and filtered. The filtrate was concentrated to afford the alcohol product (194h) which was used for next step. MS (m/z): 413.08 [M+H]$^+$.

Step 9. Synthesis of (3-aminoazepan-4-yl)methanol (194i)

Benzyl 3-(((benzyloxy)carbonyl)amino)-4-(hydroxymethyl)azepane-1-carboxylate (194h) (0.30 g, 0.073 mmol) was dissolved in EtOH (5 mL) and Pd/C (10%) (30 mg) was added. The mixture was charged with hydrogenolysis system with stirring at rt overnight. HCl (4 M in dioxane) (5 mL) was added to the reaction mixture. Reaction mixture was then filtered through celite plug. The filtrate was concentrated to dryness to afford the diamine HCl salt (194i) which was used for next step. MS (m/z): 145.00 [M+H]$^+$.

Step 10. Synthesis of 12-(benzyloxy)-6-(hydroxymethyl)-1,11-dioxo-N-(2,4,6-trifluorobenzyl)-1,4,5,6,7,11-hexahydro-3H-2,7-methanopyrido[1,2-a][1,4]diazonine-10-carboxamide (194j)

The title compound was prepared in a manner similar to 12-(benzyloxy)-7-methyl-1,11-dioxo-N-(2,4,6-trifluorobenzyl)-1,4,5,6,7,11 hexahydro-3H-2,7-methanopyrido[1,2-a][1,4]diazonine-10-carboxamide (18d) using (3-aminoazepan-4-yl)methanol (194i) instead of 3-methylazepan-3-amine (18c). MS (m/z): 542.20 [M+H]$^+$.

Step 11. Synthesis of 12-(benzyloxy)-6-(fluoromethyl)-1,11-dioxo-N-(2,4,6-trifluorobenzyl)-1,4,5,6,7,11-hexahydro-3H-2,7-methanopyrido[1,2-a][1,4]diazonine-10-carboxamide (194k)

12-(benzyloxy)-6-(hydroxymethyl)-1,11-dioxo-N-(2,4,6-trifluorobenzyl)-1,4,5,6,7,11-hexahydro-3H-2,7-methanopyrido[1,2-a][1,4]diazonine-10-carboxamide (194j) (50 mg, 0.092 mmol) was dissolved in DCM (1 mL). The solution was cooled down to 0° C. under argon. To this solution was added DeoxoFluor (0.245g, 1.11 mmol) under argon. The resulting mixture was stirred at room temperature for 40 hours. Reaction mixture was then quenched with NaHCO$_3$ (sat.) (10 mL). The crude product was subject to extraction with DCM (10 mL). Organic phase was then separated and concentrated. The residue was purified on silica gel column with 0-100% EtOAc/Heptane to afford product (194k). MS (m/z): 544.18 [M+H]$^+$.

Step 12. Preparation of 12-(benzyloxy)-6-(fluoromethyl)-1,11-dioxo-N-(2,4,6-trifluorobenzyl)-1,4,5,6,7,11-hexahydro-3H-2,7-methanopyrido[1,2-a][1,4]diazonine-10-carboxamide (194-1-P1), 12-(benzyloxy)-6-(fluoromethyl)-1,11-dioxo-N-(2,4,6-trifluorobenzyl)-1,4,5,6,7,11-hexahydro-3H-2,7-methanopyrido[1,2-a][1,4]diazonine-10-carboxamide (194-1-P2), 12-(benzyloxy)-6-(fluoromethyl)-1,11-dioxo-N-(2,4,6-trifluorobenzyl)-1,4,5,6,7,11-hexahydro-3H-2,7-methanopyrido[1,2-a][1,4]diazonine-10-carboxamide (194-1-P3) and 12-(benzyloxy)-6-(fluoromethyl)-1,11-dioxo-N-(2,4,6-trifluorobenzyl)-1,4,5,6,7,11-hexahydro-3H-2,7-methanopyrido[1,2-a][1,4]diazonine-10-carboxamide (194-1-P4)

Title compounds were separated from chiral SFC-IA system eluted with 30% IPA-NH$_3$ to afford 194-1-P1, 194-1-P2, 194-1-P3 and 194-1-P4 in the order of ascending retention time of each peak. MS (m/z): 544.18 [M+H]$^+$.

Step 13-1. Synthesis of 6-(fluoromethyl)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (194-1)

The title compound was prepared in a manner similar to 6,12-dihydroxy-1,11-dioxo-N-(2,4,6-trifluorobenzyl)-1,4,5,6,7,11-hexahydro-3H-2,7-methanopyrido [1,2-a][1,4]diazonine-10-carboxamide (11) except using 12-(benzyloxy)-6-(fluoromethyl)-1,11-dioxo-N-(2,4,6-trifluorobenzyl)-1,4,5,6,7,11-hexahydro-3H-2,7-methanopyrido[1,2-a][1,4]diazonine-10-carboxamide (194-1-P1) instead of 12-(Benzyloxy)-6-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (10a). MS (m/z): 454.21 [M+H]$^+$. $^1$H NMR (400 MHz, Chloroform-d) δ 10.45 (s, 1H), 8.54 (s, 1H), 6.89-6.38 (m, 2H), 4.82-4.54 (m, 3H), 4.54-4.24 (m, 2H), 4.19-3.85 (m, 2H), 3.56 (dd, J=14.7, 1.7 Hz, 1H), 3.24 (dd, J=13.7, 8.0 Hz, 1H), 2.41-2.22 (m, 2H), 2.02-1.77 (m, 1H), 1.63 (dd, J=15.4, 7.0 Hz, 1H), 1.23-0.90 (m, 1H).

Step 13-2. Synthesis of 6-(fluoromethyl)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (194-2)

The title compound was prepared in a manner similar to 6,12-dihydroxy-1,11-dioxo-N-(2,4,6-trifluorobenzyl)1,4,5,6,7,11-hexahydro-3H-2,7-methanopyrido [1,2-a][1,4]diazonine-10-carboxamide (11) except using 12-(benzyloxy)-6-(fluoromethyl)-1,11-dioxo-N-(2,4,6-trifluorobenzyl)-1,4,5,6,7,11-hexahydro-3H-2,7-methanopyrido[1,2-a][1,4]diazonine-10-carboxamide (194-1-P2) instead of 12-(benzyloxy)-6-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (10a). MS (m/z): 454.26 [M+H]$^+$. 1H NMR (400 MHz, Chloroform-d) δ 10.37 (s, 1H), 8.50 (d, J=4.4 Hz, 1H), 6.69 (t, J=8.1 Hz, 2H), 4.71-4.33 (m, 6H), 4.05-3.84 (m, 1H), 3.77-3.50 (m, 1H), 3.03 (ddd, J=13.9, 8.9, 5.5 Hz, 1H), 2.31-1.36 (m, 5H).

Step 13-3. Synthesis of 6-(fluoromethyl)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (194-3)

The title compound was prepared in a manner similar to 6,12-dihydroxy-1,11-dioxo-N-(2,4,6-trifluorobenzyl)1,4,5,6,7,11-hexahydro-3H-2,7-methanopyrido [1,2-a][1,4]diazonine-10-carboxamide (11) except using 12-(benzyloxy)-6-(fluoromethyl)-1,11-dioxo-N-(2,4,6-trifluorobenzyl)-1,4,5,6,7,11-hexahydro-3H-2,7-methanopyrido[1,2-a][1,4]diazonine-10-carboxamide (194-1-P3) instead of 12-(benzyloxy)-6-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (10a). MS (m/z): 454.24 [M+H]+. ¹H NMR (400 MHz, Chloroform-d) δ 10.37 (s, 1H), 8.50 (d, J=4.4 Hz, 1H), 6.69 (t, J=8.1 Hz, 2H), 4.71-4.33 (m, 6H), 4.05-3.84 (m, 1H), 3.77-3.50 (m, 1H), 3.03 (ddd, J=13.9, 8.9, 5.5 Hz, 1H), 2.31-1.36 (m, 5H).

Step 13-4. Synthesis of 6-(fluoromethyl)-12-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (194-4)

The title compound was prepared in a manner similar to 6,12-dihydroxy-1,11-dioxo-N-(2,4,6-trifluorobenzyl)1,4,5,6,7,11-hexahydro-3H-2,7-methanopyrido [1,2-a][1,4]diazonine-10-carboxamide (11) except using 12-(benzyloxy)-6-(fluoromethyl)-1,11-dioxo-N-(2,4,6-trifluorobenzyl)-1,4,5,6,7,11-hexahydro-3H-2,7-methanopyrido[1,2-a][1,4]diazonine-10-carboxamide (194-1-P4) instead of 12-(benzyloxy)-6-hydroxy-1,11-dioxo-N-(2,4,6-trifluorobenzyl)-1,4,5,6,7,11-hexahydro-3H-2,7-methanopyrido[1,2-a][1,4]diazonine-10-carboxamide (10a). MS (m/z): ¹H NMR (400 MHz, Chloroform-d) δ 10.45 (s, 1H), 8.54 (s, 1H), 6.89-6.38 (m, 2H), 4.82-4.54 (m, 3H), 4.54-4.24 (m, 2H), 4.19-3.85 (m, 2H), 3.56 (dd, J=14.7, 1.7 Hz, 1H), 3.24 (dd, J=13.7, 8.0 Hz, 1H), 2.41-2.22 (m, 2H), 2.02-1.77 (m, 1H), 1.63 (dd, J=15.4, 7.0 Hz, 1H), 1.23-0.90 (m, 1H).

Example 192: (3S,6R,7R)-12-hydroxy-3,6-dimethyl-1,11-dioxo-N-(2,4,6-trifluorobenzyl)-1,3,4,6,7,11-hexahydro-2,7-methanopyrido[1,2-d][1,4,7]oxadiazonine-10-carboxamide (195)

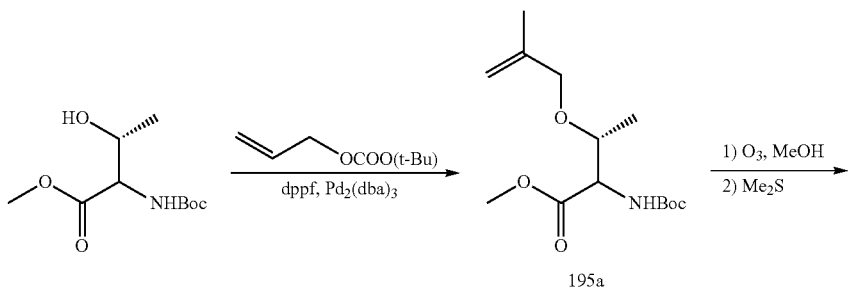

195a

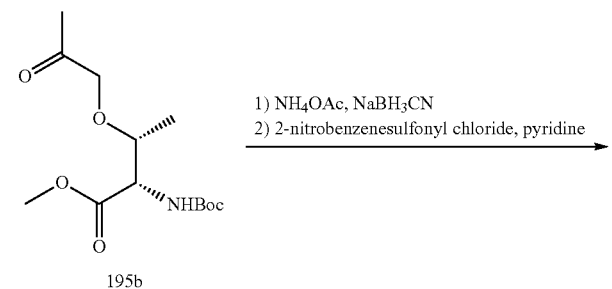

195b

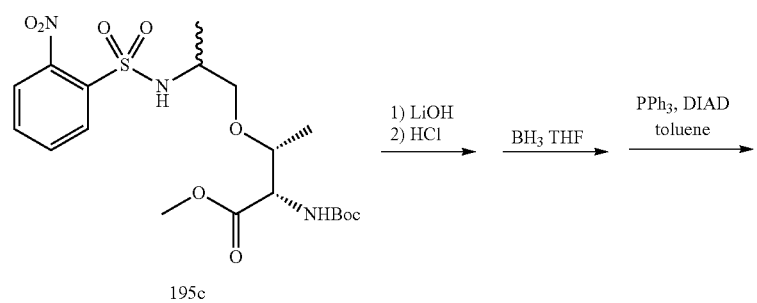

195c

-continued
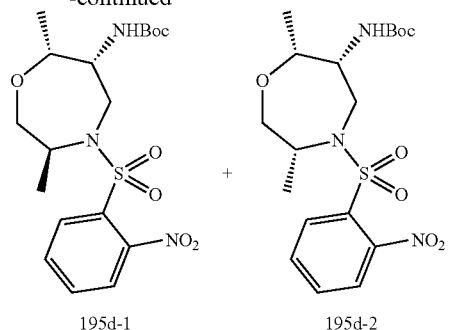
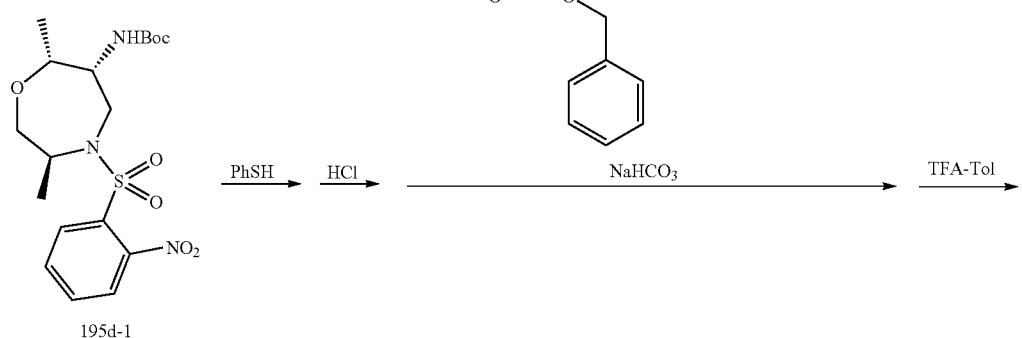
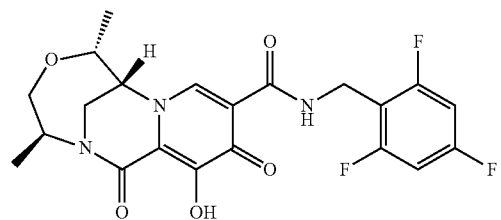
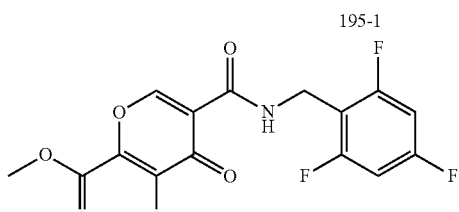
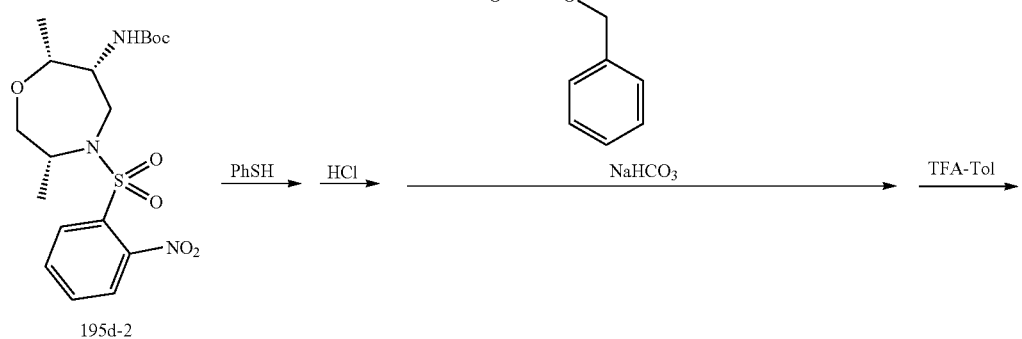

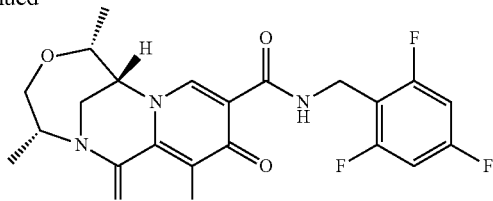

196

Synthesis of methyl N-(tert-butoxycarbonyl)-O-(2-methylallyl)-L-threoninate (195a)

A solution of L-Boc-Thr-OMe (703.2 mg, 3.01 mmol) and tert-butyl 2-methylallyl carbonate (1039 mg, 6.03 mmol) in tetrahydrofuran (30 mL) was degassed by placing under vacuum and backfilling with $N_2$ (3×). To this solution were added 1,1'-bis(diphenylphosphino) ferrocene (335.3 mg, 0.605 mmol) and tris(dibenzylideneacetone)dipalladium(0) (278.3 mg, 0.304 mmol) and degassed again before heating at 55° C. After 1.5 h, the reaction mixture was cooled to rt, and filtered to remove any insoluble material. The filtrate was concentrated, and the residue was purified by column chromatography on silica gel eluting 0-25% ethyl acetate in hexane to get the product. MS (m/z) 188.15 $[M+H-C_4H_8]^+$.

Synthesis of methyl N-(tert-butoxycarbonyl)-O-(2-oxopropyl)-L-threoninate (195b)

A solution of methyl N-(tert-butoxycarbonyl)-O-(2-methylallyl)-L-threoninate (195a) (672.9 mg, 2.34 mmol) in methanol (30 mL) was stirred at −78° C. as ozone was bubbled until blue color appeared. After the blue color appeared, $Me_2S$ (10 mL) was added and the reaction mixture warmed to rt and stirred for 3 h. The resulting solution was concentrated and the residue was purified by column chromatography on silica gel eluting 20-80% ethyl acetate in hexane to the product. MS (m/z) 312.11 $[M+Na]^+$.

Synthesis of methyl N-(tert-butoxycarbonyl)-O-(2-((2-nitrophenyl)sulfonamido)propyl)-L-threoninate (195c)

A solution of methyl N-(tert-butoxycarbonyl)-O-(2-oxopropyl)-L-threoninate (195b) (638.6 mg, 2.21 mmol) and ammonium acetate (1033.5 mg, 13.4 mmol) in methanol (3.3 mL) was stirred at rt as sodium cyanoborohydride (134.3 mg, 2.14 mmol) was added. The reaction was stirred at rt for 2 h. After the reaction mixture was concentrated, the residue was dissolved in some water (20 mL), acidified with 1 N HCl (~1 mL), and then diluted with 5% $Na_2CO_3$ (20 mL) before the product was extracted with dichloromethane (3×40 mL). The extracts were combined, dried ($MgSO_4$), and concentrated.

The residue was dissolved in pyridine (6.5 mL) and stirred at rt as 2-nitrobenzenesulfonyl chloride (514.7 mg, 2.32 mmol) was added. After 30 min at rt, the reaction mixture was concentrated to remove most of excess pyridine. After the residue was dissolved in ethyl acetate (~50 mL) and washed with 10% aq. citric acid solution, the aqueous fraction was extracted with ethyl acetate (50 mL×1). The organic fractions were combined, dried ($MgSO_4$), and concentrated. The residue was purified by column chromatography on silica gel eluting 30-70% ethyl acetate in hexane to get methyl N-(tert-butoxycarbonyl)-O-(2-((2-nitrophenyl)sulfonamido)propyl)-L-threoninate (195c): MS (m/z) 498.06 $[M+Na]^+$.

Synthesis of tert-Butyl ((3S,4S,7S)-4,7-dimethyl-1-((2-nitrophenyl)sulfonyl)azepan-3-yl)carbamate (195d-1) and tert-butyl ((3S,4S,7R)-4,7-dimethyl-1-((2-nitrophenyl)sulfonyl)azepan-3-yl)carbamate (195d-2)

A solution of methyl N-(tert-butoxycarbonyl)-O-(2-((2-nitrophenyl)sulfonamido)propyl)-L-threoninate (195c) (407.9 mg, 0.858 mmol) in methanol (4.3 mL) and tetrahydrofuran (4.3 mL) was stirred at rt as 1 N lithium hydroxide (4.3 mL) was added. After 18 h at rt, the reaction mixture was concentrated to remove most of organic solvent and acidified by addition of 1 N HCl (4.3 mL), before the product was extracted with ethyl acetate (~25 mL×2). After the extracts were washed with brine (~25 mL×1), the organic fractions were combined, dried ($MgSO_4$), and concentrated to get a crude acid.

The crude acid in tetrahydrofuran (2 mL) was stirred at 0° C. as 1 M borane tetrahydrofuran complex (1.1 mL) was added. After 5 min, the reaction mixture was stirred at rt for 1 h and additional 1 M borane tetrahydrofuran complex (1 mL) was added. After 1 h at rt, another 1 M borane tetrahydrofuran complex (1 mL) was added and the resulting mixture was stirred at rt overnight. To the reaction mixture was added water (10 mL) to remove any excess borane, before potassium carbonate (1 g, 7.25 mmol) and di-tert-butyl dicarbonate (~323 mg, 1.48 mmol) were added at rt. The resulting mixture was stirred for 4 h. The reaction mixture was diluted with 10% citric acid and the product was extracted with ethyl acetate (25 mL×2). After the extracts were washed with brine (25 mL×1), the two fractions were combined, dried ($MgSO_4$), and concentrated. The residue was purified by column chromatography on silica gel eluting 40%-100% ethyl acetate to get 207.1 mg (53.9%) of the diastereomeric mixture: MS (m/z) 470.07 $[M+Na]^+$.

A solution of the diastereomeric alcohol mixture (207.1 mg, 0.463 mmol) and triphenylphosphine (213.2 mg, 0.813 mmol) in toluene (93 mL, 5 mM) was stirred at rt as a solution of diisopropyl azodicarboxylate (0.14 mL, 0.711 mmol) in toluene (0.9 mL) was added over 45 min. After addition, the resulting solution was stirred 1 h at rt. The reaction mixture was concentrated, and the residue was purified by column chromatography on silica gel eluting 10-100% ethyl acetate in hexanes to get two diastereomers separately.

195d-1: 68.5 mg (34.5%): MS (m/z) 452.10 [M+Na]$^+$
195d-2: 82.0 mg (41.3%): MS (m/z) 452.05 [M+Na]$^+$

Synthesis of (3S,6R,7R)-12-hydroxy-3,6-dimethyl-1,11-dioxo-N-(2,4,6-trifluorobenzyl)-1,3,4,6,7,11-hexahydro-2,7-methanopyrido[1,2-d][1,4,7]oxadiazonine-10-carboxamide (195-1)

A solution of tert-butyl ((3S,4S,7S)-4,7-dimethyl-1-((2-nitrophenyl)sulfonyl)azepan-3-yl)carbamate (195d-1) (68.5 mg, 0.15 mmol), cesium carbonate (104.5 mg, 0.321 mmol), and benzenethiol (43.1 mg, 0.391 mmol) in acetonitrile (1 mL) was stirred at rt for 1.5 h. The resulting solution was concentrated, and the residue was dissolved in 4 N HCl in 1,4-dioxane (5 mL). After 1 h at rt, the solution was concentrated and co-evaporated with toluene once.

A mixture of the above residue, methyl 3-(benzyloxy)-4-oxo-5-((2,4,6-trifluorobenzyl)carbamoyl)-4H-pyran-2-carboxylate, 72.3 mg, 0.162 mmol), and sodium bicarbonate (69.6 mg, 0.829 mmol) in methanol (8 mL) and water (2 mL) was stirred at rt over the weekend, and at 50° C. for 24 h. The reaction mixture was diluted with water (25 mL) and the product was extracted with ethyl acetate (~20 mL×2). The extracts were washed with brine (20 mL×1), combined, dried (MgSO$_4$), and concentrated. The residue was purified by column chromatography on silica gel eluting 0-15% methanol in dichloromethane to get the product: MS (m/z) 542.10 [M+H]$^+$ To a solution of this product in toluene (0.5 mL) was added trifluoroacetic acid (4 mL) at rt. After stirring 2 h at rt, the reaction mixture was concentrated, and the residue was dissolved in DMF and filtered before purified by preparative HPLC (column, Gemini 5 um C18 110A, LC column 100×30 mm) eluting 15-70% acetonitrile (0.1% TFA) in water (0.1% TFA) over 20 min.) The product containing fraction was freeze-dried to get the title compound: MS (m/z) 452.13 [M+H]$^+$. $^1$H NMR (400 MHz, Acetonitrile-d$_3$) δ 10.30 (s, 1H), 8.30 (s, 1H), 6.92-6.75 (m, 2H), 4.60 (d, J=5.5 Hz, 2H), 4.27 (q, J=1.9 Hz, 1H), 4.03-3.94 (m, 2H), 3.85 (dd, J=11.3, 7.2 Hz, 1H), 3.75 (h, J=6.8 Hz, 1H), 3.64 (dd, J=11.3, 7.2 Hz, 1H), 3.48 (dd, J=15.0, 2.3 Hz, 1H), 1.64 (d, J=6.9 Hz, 3H), 1.11 (d, J=6.5 Hz, 3H). $^{19}$F NMR (376 MHz, Acetonitrile-d$_3$) δ −77.37, −111.15 (tt, J=9.0, 6.1 Hz), −113.86 (t, J=7.2 Hz).

Example 193: Synthesis of (3R,6R,7R)-12-hydroxy-3,6-dimethyl-1,11-dioxo-N-(2,4,6-trifluorobenzyl)-1,3,4,6,7,11-hexahydro-2,7-methanopyrido[1,2-d][1,4,7]oxadiazonine-10-carboxamide (196)

The title compound was synthesized in a manner similar to (3S,6R,7R)-12-hydroxy-3,6-dimethyl-1,11-dioxo-N-(2,4,6-trifluorobenzyl)-1,3,4,6,7,11-hexahydro-2,7-methanopyrido[1,2-d][1,4,7]oxadiazonine-10-carboxamide (195) except using tert-butyl ((3S,4S,7R)-4,7-dimethyl-1-((2-nitrophenyl)sulfonyl)azepan-3-yl)carbamate (195d-2) instead of tert-Butyl ((3S,4S,7S)-4,7-dimethyl-1-((2-nitrophenyl)sulfonyl)azepan-3-yl)carbamate (195d-1): MS (m/z) 452.12 [M+H]$^+$. $^1$H NMR (400 MHz, Acetonitrile-d$_3$) δ 10.37 (s, 1H), 8.28 (s, 1H), 6.92-6.76 (m, 2H), 4.74 (dp, J=10.6, 6.8 Hz, 1H), 4.59 (d, J=5.6 Hz, 2H), 4.30 (q, J=2.6 Hz, 1H), 4.08 (dd, J=12.9, 6.8 Hz, 1H), 3.89 (qd, J=6.5, 2.7 Hz, 1H), 3.80 (dd, J=15.3, 2.0 Hz, 1H), 3.74 (dd, J=15.3, 2.8 Hz, 1H), 3.18 (dd, J=12.9, 10.5 Hz, 1H), 1.15 (d, J=6.8 Hz, 3H), 1.01 (d, J=6.5 Hz, 3H). $^{19}$F NMR (376 MHz, Acetonitrile-d$_3$) δ −77.36, −111.20 (ddd, J=15.2, 9.1, 6.1 Hz), −113.88 (p, J=7.6 Hz).

Example 194: Preparation of (3R,6R,7R)-N-(2,4-difluorobenzyl)-12-hydroxy-3,6-dimethyl-1,11-dioxo-1,3,4,6,7,11-hexahydro-2,7-methanopyrido[1,2-d][1,4,7]oxadiazonine-10-carboxamide (197)

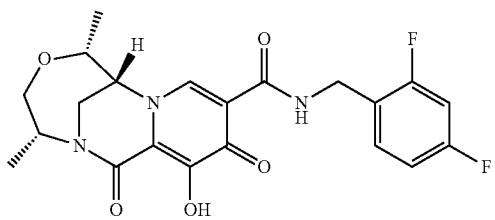 [SMILES: C[C@@H]1CO[C@H](C)[C@H]2CN1C(=O)c1c(O)c(=O)c(C(=O)NCc3ccc(F)cc3F)cn12]

The title compound was synthesized in a manner similar to (3R,6R,7R)-12-hydroxy-3,6-dimethyl-1,11-dioxo-N-(2,4,6-trifluorobenzyl)-1,3,4,6,7,11-hexahydro-2,7-methanopyrido[1,2-d][1,4,7]oxadiazonine-10-carboxamide (196) using methyl 3-(benzyloxy)-5-((2,4-difluorobenzyl)carbamoyl)-4-oxo-4H-pyran-2-carboxylate: MS (m/z) 434.16 [M+H]$^+$. $^1$H NMR (400 MHz, Acetonitrile-d$_3$) δ 10.37 (s, 1H), 8.33 (s, 1H), 7.41 (td, J=9.2, 8.8, 6.4 Hz, 1H), 7.01-6.85 (m, 2H), 4.75 (dp, J=10.5, 6.8 Hz, 1H), 4.58 (d, J=5.6 Hz, 2H), 4.34 (q, J=2.6 Hz, 1H), 4.09 (dd, J=12.9, 6.8 Hz, 1H), 3.90 (qd, J=6.4, 2.7 Hz, 1H), 3.86-3.65 (m, 2H), 3.19 (dd, J=12.9, 10.6 Hz, 1H), 1.16 (d, J=6.8 Hz, 3H), 1.02 (d, J=6.5 Hz, 3H). $^{19}$F NMR (376 MHz, Acetonitrile-d$_3$) δ −77.34, −114.05 (ddd, J=15.6, 8.8, 6.9 Hz), −116.43—116.70 (m).

Example 195: HIV MT-4 Antiviral and Cytotoxicity Assay

Antiviral Assay in MT-4 Cells

Compounds were tested in a high-throughput 384-well assay format for their ability to inhibit the replication of HIV-1 (IIIB) in MT-4 cells. Compounds were serially diluted (1:3) in DMSO on 384-well polypropylene plates and further diluted 200-fold into complete RPMI media (10% FBS, 1% P/S) using the Biotek Micro Flow and Labcyte ECHO acoustic dispenser. Each plate contained up to 8 test compounds, with negative (No Drug Control) and 5 μM AZT positive controls. MT-4 cells were pre-infected with 10 μL of either RPMI (mock-infected) or a fresh 1:250 dilution of HIV-1 IIIB concentrated virus stock. Infected and uninfected MT-4 cells were further diluted in complete RPMI media and added to each plate using a Micro Flow dispenser. After 5 days incubation in a humidified and temperature controlled incubator (37° C.), Cell Titer Glo (Promega) was added to the assay plates and chemiluminescence read using an Envision plate-reader. EC$_{50}$ values were defined as the compound concentration that causes a 50% decrease in luminescence signal, and were calculated using a sigmoidal dose-response model to generate curve fits.

Cytotoxicity Assay in MT-4 Cells

Assays were performed as above except uninfected MT-4 cells were added to each well containing test compound. In addition, 10 μM puromycin was added to the last column of each assay plate to assess a base level of cytotoxicity.

Example 196: HIV MT-4 Serum Shift Antiviral Reporter Assay

To quantify the amount of protein binding to human serum, compounds were serially diluted (1:3) in DMSO and acoustically transferred onto 384-well assay plates via a Labcyte ECHO robot. Each plate contained up to 8 test compounds, including negative and positive controls, (DMSO, 5 μM AZT respectively). Assay plates were prepared in duplicate, and tested in either CCM (cell culture media) or HS/CCM (human serum/cell culture media). MT-4 cells were first pre-infected with pLai RLuc reporter virus for 2 h at 37° C., then further diluted in either CCM (RPMI media, 10% FBS, 1% P/S) or HS/CCM (RPMI media, 10% FBS, 50% HS, 1% P/S), and subsequently added to each plate using a Biotek Micro Flow dispenser. After a 72-h incubation in a humidified and temperature controlled incubator (37° C.), *Renilla* Glo (Promega) was added to all assay plates and chemiluminescence read using an Envision plate-reader. $EC_{50}$ values were defined as the compound concentration that causes a 50% decrease in luminescence signal, and were calculated using a sigmoidal dose-response model to generate curve fits. To determine the amount of protein binding, $EC_{50}$ fold shifts (or $EC_{50}$ shifts) were calculated by dividing $EC_{50}$ (HS/CCM)/$EC_{50}$ (CCM).

Compounds of the present disclosure demonstrate antiviral activity in this assay as depicted in Table 1 below. Accordingly, the compounds of the embodiments disclosed herein may be useful for treating the proliferation of the HIV virus, treating AIDS, or delaying the onset of AIDS or ARC symptoms.

TABLE 1

| Compound No. | $EC_{50}$ (nM) | $CC_{50}$ (nM) | Antiviral Serum Shift RLuc | | |
|---|---|---|---|---|---|
| | | | CCM | 50% HS | $EC_{50}$ shift |
| 1-1 | 16.5 | >50000 | 3.64 | 4.85 | 1.3 |
| 1-2 | 5.7 | 20721 | 1.37 | 13.91 | 10.2 |
| rac-1 | 3.9 | >47853 | NA | NA | |
| 2 | 3.4 | >47845 | NA | NA | |
| 3-1 | 4.2 | >40240 | 0.85 | 71.52 | 84.4 |
| 3-2 | 5.4 | >43345 | 1.60 | 3.86 | 2.4 |
| 4-1 | 6.4 | 23325 | NA | NA | |
| 4-2 | 4.8 | 10679 | 1.11 | 4.36 | 3.9 |
| 5-1 | 2 | 11077 | 0.235 | 1.24 | 5.3 |
| 5-2 | 2.9 | 19470 | 0.72 | 142.04 | 196.5 |
| 6 | 19.9 | 25381 | NA | NA | |
| 7 | 1.4 | 8807 | 0.28 | 1.47 | 5.2 |
| 8 | 1.5 | 20756 | 0.41 | 1.41 | 3.4 |
| 9 | 1.8 | 6606 | 0.33 | 1.684 | 5.1 |
| 10-1 | 3.2 | 37062 | 1.02 | 1141.8 | 1116.1 |
| 10-2 | 1 | 16065 | 0.27 | 5.04 | 18.7 |
| 11 | 7.2 | >50000 | NA | NA | |
| 12 | 4.1 | >50000 | NA | NA | |
| 13 | 1.3 | 17176 | NA | NA | |
| 14-1 | 3 | 22209 | 0.79 | 1.88 | 2.4 |
| 14-2 | 2.7 | 19928 | 0.5665 | 0.4138 | 0.7 |
| 15-1 | 1.7 | 18338 | 0.32 | 11.59 | 35.9 |
| 15-2 | 1.4 | 15304 | 0.29 | 4.32 | 15.1 |
| 16-1 | 2.1 | 14374 | 0.25 | 3.22 | 13.1 |
| 16-2 | 5.3 | 36178 | 0.85 | 82.5 | 97.1 |
| 17-1a | 1.5 | 12903 | NA | NA | |
| 17-1b | 1.2 | 10866 | 0.26 | 3.10 | 11.9 |
| 17-2b | 1.2 | 10985 | 0.31 | 101.43 | 326.4 |
| 18 | 1.4 | 29387 | NA | NA | |
| 19 | 4 | >50000 | 1.21 | 4.35 | 3.6 |
| 20 | 5.6 | 37193 | 1.83 | 33.44 | 18.3 |
| 21 | 21.4 | 10516 | NA | NA | |
| 22 | 16.2 | 11026 | 2.6393 | 359.8344 | 136.3 |
| 23 | 59.9 | 11980 | NA | NA | |
| 24 | 27.3 | 13791 | NA | NA | |
| 24-1 | 10.3 | 13564 | NA | NA | |
| 25 | 1.7 | 12551 | 0.1908 | 1.9216 | 10.1 |
| 25-1 | 1.3 | 11509 | 0.42 | 36.56 | 87.8 |
| 25-2 | 1.463 | 10839 | 0.285 | 1.142 | 4.007 |
| 26-1 | 1.4 | 15922 | 0.354 | 33.447 | 94.483 |
| 26-2 | 1.315 | 14384 | 0.353 | 2.29 | 6.484 |
| 27 | >100 | 10928 | NA | NA | |
| 28 | 13.5 | >50000 | NA | NA | |
| 29 | 7 | >50000 | NA | NA | |
| 30 | 6.9 | 1655 | NA | NA | |
| 31 | >100 | >50000 | NA | NA | |
| 32 | >100 | >50000 | NA | NA | |
| 33 | 7 | >50000 | NA | NA | |
| 34 | 3.3 | 16352 | 2.06 | 9.56 | 4.6 |
| 35 | 1.5 | 4964 | 0.4235 | 44.379 | 104.8 |
| 36 | 2 | 17682 | 0.9168 | 7.16 | 7.8 |
| 37-1 | 21.4 | 10516 | NA | NA | |
| 37-2 | 1.2 | 12932 | NA | NA | |
| 38-1 | 16.3 | 11026 | 2.64 | 359.83 | 136.3 |
| 38-2 | 0.93 | 12819 | NA | NA | |
| 40-1 | 4.2 | 10966 | 0.784 | 15.2 | 19.4 |
| 40-2 | 1.3 | 10429 | 0.2565 | 1.104 | 4.3 |
| 41-1 | 1.6 | 15600 | 0.335 | 6.642 | 19.8 |
| 41-2 | 1.4 | 14327 | 0.26 | 0.968 | 3.7 |
| 42-1 | 1.6 | 7491 | 0.28 | 1.343 | 4.8 |
| 43-1 | 41.5029 | 8095.09 | 4.3509 | 146.894 | 33.762 |
| 43-2 | 1.5656 | 9153.77 | 0.2888 | 0.6471 | 2.241 |
| 44-1 | 1.7143 | 10675.1 | 0.6771 | 2.3294 | 3.440 |
| 44-2 | 2.3584 | 15093.6 | 0.2639 | 36.7682 | 139.326 |
| 45-1 | 1.66 | 6896.98 | 0.3592 | 2.5622 | 7.133 |
| 45-2 | 30.2907 | 8893.66 | NA | NA | |
| 46-1 | 90.1808 | 9243.32 | NA | NA | |
| 46-2 | 1.4061 | 12461.7 | 0.2038 | 2.9056 | 14.257 |
| 47-1 | 4.9335 | 11069 | 0.6818 | 25.7126 | 37.713 |
| 47-2 | 1.1557 | 8719.43 | 0.2475 | 1.0146 | 4.099 |
| 48-1 | >33.9968 | >13825.5 | NA | NA | |
| 48-2 | 2.3814 | 17623.5 | 0.3576 | 1.5217 | 4.255 |
| 49-1 | 36.4791 | >15749.7 | NA | NA | |
| 49-2 | 2.3763 | 7198.79 | 0.2017 | 1.1149 | 5.528 |
| 50-1 | 1.3936 | >13523.5 | 0.265 | 0.9483 | 3.578 |
| 50-2 | 32.4997 | 32295.8 | NA | NA | |
| 51 | 1.1661 | 4394.79 | 0.2148 | 2.1426 | 9.975 |
| 52-1 | 2.1501 | 13106.8 | 0.2451 | 6.1848 | 25.234 |
| 52-2 | 1.6848 | 5840.28 | 0.3836 | 2.1863 | 5.699 |
| 52-3 | 3.0542 | 15511.9 | 0.5886 | 114.386 | 194.336 |
| 52-4 | 1.3294 | 10251.2 | 0.2185 | 7.5383 | 34.500 |
| 53-1 | 2.1319 | 13201.3 | 0.5412 | 6.1285 | 11.324 |
| 53-2 | 6.1991 | 28411.9 | 1.5767 | 2.2704 | 1.440 |
| 53-3 | 1.9369 | 11225.7 | 0.2232 | 75.2215 | 337.014 |
| 53-4 | 4.7227 | >44439.9 | 0.6964 | 18.2792 | 26.248 |
| 54 | 35.9773 | 1461.26 | NA | NA | |
| 55-1 | >89.3998 | 13022.9 | NA | NA | |
| 55-2 | 1.7959 | 7325.14 | 0.3124 | 1.318 | 4.219 |
| 56-1 | 3.9932 | >39448 | 0.9668 | 1.9124 | 1.978 |
| 56-2 | 1.8588 | 17796.6 | 0.4008 | 1.0814 | 2.698 |
| 56-3 | 5.2398 | 16142.8 | 0.3121 | 13.2839 | 42.563 |
| 56-4 | 8.0928 | 30483.9 | 2.1575 | 15.3982 | 7.137 |
| 57-1 | 1.2217 | 6903.94 | 0.2281 | 2.357 | 10.333 |
| 57-2 | 1.7716 | 8911.35 | 0.3958 | 133.192 | 336.513 |
| 58 | 0.9864 | 4150.27 | 0.25 | 1.674 | 6.696 |
| 59-1 | 1.5296 | 14950.9 | 0.3614 | 26.4155 | 73.092 |
| 59-2 | 2.1544 | 18793.7 | 0.5467 | 55.2076 | 100.983 |
| 60-1 | 1.7688 | 13875.4 | 0.4567 | 1.5982 | 3.499 |
| 60-2 | 1.9709 | 14014.7 | 0.3278 | 102.119 | 311.528 |
| 60-3 | 2.2327 | 14779.9 | 0.3762 | 14.7718 | 39.266 |
| 61-1 | 1.8541 | 10269.7 | 0.2057 | 72.0046 | 350.047 |
| 61-2 | 2.511 | 16921.8 | 0.1425 | 13.8153 | 96.949 |
| 62 | 1.271 | 3460.16 | 0.2923 | 4.2163 | 14.425 |
| 63-1 | 1.697 | 13831 | 0.4605 | 2.1551 | 4.680 |
| 63-2 | 8.1449 | 14345 | NA | NA | |
| 64-1 | 17.511 | 14798.4 | NA | NA | |
| 64-1 | 1.8112 | 12304.8 | 0.3187 | 3.3134 | 10.397 |
| 65-1 | 1.729 | 8803.93 | 0.2974 | 28.5257 | 95.917 |
| 65-2 | 1.662 | 8818.84 | 0.3408 | 3.4706 | 10.184 |
| 66-1 | 1.759 | 11138.1 | 0.2257 | 20.3357 | 90.101 |
| 66-2 | 1.6776 | 10415.4 | 0.2939 | 4.5498 | 15.481 |
| 67 | 2.435 | 23927 | 0.4373 | 1.49 | 3.407 |
| 68 | 1.2016 | 3582.46 | 0.2786 | 1.173 | 4.210 |
| 69 | 1.9526 | 36668.6 | 0.1991 | 1.0555 | 5.301 |
| 70 | 1.4143 | 13305.3 | 0.3216 | 1.3223 | 4.112 |
| 71 | 2.1381 | 15023.4 | 0.3019 | 1.6648 | 5.514 |
| 72-1 | 1.5745 | 9990.49 | 0.2812 | 5.3609 | 19.064 |
| 72-2 | 4.272 | 12071 | 0.267 | 33.9942 | 127.319 |

TABLE 1-continued

| Compound No. | EC$_{50}$ (nM) | CC$_{50}$ (nM) | Antiviral Serum Shift RLuc CCM | 50% HS | EC$_{50}$ shift |
|---|---|---|---|---|---|
| 73-1 | 5.1985 | >50000 | 0.7154 | 0.897 | 1.254 |
| 73-2 | 1.8176 | 23088.5 | 0.2834 | 0.9188 | 3.242 |
| 74 | 1.5209 | 7282.09 | 0.4924 | 13.7527 | 27.930 |
| 75-1 | 3.7581 | 15064 | 0.5954 | 297.933 | 500.391 |
| 75-2 | 2.0852 | 26015.7 | 0.4731 | 2.1855 | 4.620 |
| 76 | 7.9887 | 23714.2 | NA | NA | |
| 77 | 2.1699 | 15139 | 0.7625 | 2.1291 | 2.792 |
| 78 | 9.5602 | >50000 | 1.9344 | 3.7613 | 1.944 |
| 79-1 | 58.5033 | >50000 | 19.4934 | 23.5172 | 1.206 |
| 79-2 | 17.6754 | >50000 | 5.3345 | 6.6114 | 1.239 |
| 80-1 | 2.2408 | 10418 | 0.3479 | 0.6513 | 1.872 |
| 80-2 | 5.3482 | 13431.2 | 0.6178 | 7.5443 | 12.212 |
| 81-1 | 1.9611 | 23908.4 | 0.4657 | 0.6486 | 1.393 |
| 81-2 | 1.3471 | 11217.3 | 0.3037 | 0.7366 | 2.425 |
| 82-1 | 20.4772 | >50000 | 4.4991 | 5.1564 | 1.146 |
| 82-2 | 9.5667 | >50000 | 2.0893 | 3.0001 | 1.436 |
| 83-1 | 39.0323 | >50000 | 8.1859 | 7.0836 | 0.865 |
| 83-2 | 12.7625 | >50000 | 2.1459 | 2.0813 | 0.970 |
| 84 | 2.0148 | 37242.9 | 0.4269 | 1.3577 | 3.180 |
| 85-1 | 5.6415 | >49893.8 | 1.0561 | 1.5656 | 1.482 |
| 85-2 | 5.8471 | >49303.7 | NA | NA | |
| 86-1 | 27.0189 | >30284.7 | NA | NA | |
| 86-2 | 1.1029 | 13670.1 | 0.2624 | 0.4997 | 1.904 |
| 87-1 | 6.087 | >50000 | NA | NA | |
| 87-2 | 1.7405 | >50000 | NA | NA | |
| 88 | 1.6118 | >23363.4 | 0.2689 | 1.6221 | 6.032 |
| 89 | 2.3821 | >47882.8 | 0.6695 | 4.3871 | 6.553 |
| 90-1 | 24.1091 | >32641.1 | NA | NA | |
| 90-2 | 2.4192 | >20829 | 0.361 | 1.2158 | 3.368 |
| 91 | 23.2445 | >50000 | NA | NA | |
| 92-1 | 535.14 | >50000 | NA | NA | |
| 92-2 | 2.0073 | >39254.4 | 0.309 | 0.7718 | 2.498 |
| 93 | 2.2394 | >40448 | 0.462 | 1.5453 | 3.345 |
| 94 | 1.1501 | 13696.6 | 0.4106 | 1.7331 | 4.221 |
| 95 | 31.5104 | >50000 | 5.1827 | 4.8359 | 0.933 |
| 96 | 18.1014 | >50000 | 3.0937 | 3.3317 | 1.077 |
| 97-1 | 2.8464 | 6060.22 | NA | NA | |
| 97-2 | 6.0509 | 16260 | NA | NA | |
| 98 | 1.2675 | 14265.2 | 0.2843 | 19.248 | 67.703 |
| 99-1 | 1.5281 | >22228.6 | NA | NA | |
| 99-2 | 3.021 | >23444.8 | NA | NA | |
| 100 | 1.5795 | 9442.24 | 0.6311 | 1.775 | 2.813 |
| 101 | 1.5175 | 19491 | 0.2198 | 1.617 | 7.357 |
| 102 | 37.5089 | >50000 | NA | NA | |
| 103-1 | 8.9698 | >50000 | NA | NA | |
| 103-2 | 9.2042 | >50000 | NA | NA | |
| 104-1 | 1.479 | 11939.9 | 0.3228 | 1.9889 | 6.161 |
| 104-2 | 35.3472 | 13969.1 | NA | NA | |
| 105 | 1.899 | 22298.7 | NA | NA | |
| 106 | 2.3221 | 6844.95 | NA | NA | |
| 107-1 | 15.1187 | >50000 | NA | NA | |
| 107-2 | 12.1483 | >50000 | NA | NA | |
| 108-1 | 0.9969 | 16138.7 | 0.1998 | 1.3121 | 6.567 |
| 108-2 | 0.9175 | 11845.4 | 0.3349 | 1.5468 | 4.619 |
| 109-1 | 1.8113 | 11327.4 | 0.5269 | 50.7701 | 96.356 |
| 109-2 | 1.4698 | 11818.7 | 0.2359 | 4.3422 | 18.407 |
| 110-1 | 1.9954 | 9868.68 | 0.3228 | 2.747 | 8.510 |
| 110-2 | 30.4848 | 6332.17 | 4.8116 | 53.7139 | 11.163 |
| 111-1 | 2.0089 | 5912.44 | 0.447 | 7.1154 | 15.918 |
| 111-2 | 56.851 | 9940.86 | NA | NA | |
| 112 | 0.7118 | 8028.02 | 0.182 | 27.8338 | 152.933 |
| 113 | 1.4222 | 16935.5 | 0.514 | 0.6202 | 1.207 |
| 114 | 2.2672 | 30489 | 0.7168 | 1.0436 | 1.456 |
| 115-1 | 1.4845 | 12153.2 | 0.2714 | 0.7128 | 2.626 |
| 115-2 | 2.5788 | 28067.8 | NA | NA | |
| 116-1 | 1.2026 | 16262.2 | 0.2683 | 1.3691 | 5.103 |
| 116-2 | 1.6357 | 9680.88 | NA | NA | |
| 117-1 | 1.9335 | 13268.3 | 0.3301 | 7.166 | 21.709 |
| 117-2 | 3.5287 | 15724.1 | 0.6029 | 1267.17 | 2101.791 |
| 118-1 | 0.7901 | 11522.9 | 0.2961 | 0.8808 | 2.975 |
| 118-2 | 1.1698 | 11582.2 | 0.2494 | 0.5069 | 2.032 |
| 119-1 | 1.4988 | 15186 | 0.4315 | 62.3024 | 144.386 |
| 119-2 | 1.983 | 8483.29 | 0.5243 | 86.2519 | 164.509 |
| 120-1 | 3.5357 | 8986.12 | 0.3707 | 4.9645 | 13.392 |
| 120-2 | >59.3595 | 11062.5 | 14.0291 | 238.69 | 17.014 |
| 121 | 1.7604 | 24771 | 0.235 | 0.505 | 2.149 |
| 122-1 | 2.5734 | 4735.96 | 0.5341 | 4.7769 | 8.944 |
| 122-2 | 14.4383 | 4770.25 | 3.7701 | 298.119 | 79.075 |
| 123-1 | 2.0494 | 13672.6 | 0.3156 | 3.674 | 11.641 |
| 123-2 | 1.9315 | 14557 | 0.2446 | 440.282 | 1800.008 |
| 124 | 2.7895 | 15437.2 | NA | NA | |
| 125 | 2.948 | 10204.6 | 0.3284 | 1.9723 | 6.006 |
| 126 | 4.7536 | 15442 | NA | NA | |
| 127-1 | 1.378 | 5634.36 | 0.3244 | 2.9319 | 9.038 |
| 127-2 | 3.9334 | 13694.7 | NA | NA | |
| 128-1 | 2.1461 | >47213 | 0.763 | 7.6094 | 9.973 |
| 128-2 | 7.3666 | >50000 | NA | NA | |
| 129 | 1.5298 | 7439.4 | 0.3086 | 4.2136 | 13.654 |
| 130-1 | 1.5289 | 12157 | 0.2134 | 4.1657 | 19.521 |
| 130-2 | | | NA | NA | |
| 131 | 1.6815 | 10195.9 | 0.2502 | 10.9846 | 43.903 |
| 132-1 | 8.8316 | >50000 | NA | NA | |
| 132-2 | 2.783 | 25724.3 | NA | NA | |
| 132-3 | 2.1399 | 24111.3 | NA | NA | |
| 133 | | | 0.5333 | 1.6556 | 3.104 |
| 134-1 | 3.2852 | 16241.4 | NA | NA | |
| 134-2 | 5.7021 | 10640.8 | NA | NA | |
| 135-1 | 3.3583 | >50000 | NA | NA | |
| 135-2 | 4.7742 | >50000 | NA | NA | |
| 136-1 | 39.8746 | 12419 | NA | NA | |
| 136-2 | 1.552 | 6545.11 | 0.3924 | 5.7141 | 14.562 |
| 137-1 | 2.6342 | 14729.8 | 0.1842 | 0.7073 | 3.840 |
| 137-2 | 2.0207 | 20664 | 0.1819 | 0.8205 | 4.511 |
| 138 | 3.1738 | 5018.92 | 0.7077 | 8.7019 | 12.296 |
| 139-1 | 14.8201 | >50000 | 3.9339 | 84.3485 | 21.441 |
| 139-2 | 9.1146 | >50000 | NA | NA | |
| 140-1 | 24.0951 | 14626.6 | NA | NA | |
| 140-2 | 1.9245 | 5230.63 | 0.3472 | 22.3881 | 64.482 |
| 141 | >100 | >50000 | 29.6111 | 198.922 | 6.718 |
| 142-1 | 1.9701 | 8415.1 | 0.3544 | 1.18 | 3.330 |
| 142-2 | 1.8664 | 13574.7 | 0.3627 | 2.8081 | 7.742 |
| 143-1 | 22.6592 | >50000 | 4.749 | 132.466 | 27.893 |
| 143-2 | 12.7969 | >50000 | NA | NA | |
| 144-1 | 1.6536 | 9179.34 | 0.2851 | 2.6289 | 9.221 |
| 144-2 | 1.9794 | 13916.8 | 0.4688 | 4.4642 | 9.523 |
| 145 | 0.8221 | 8849.89 | 0.2177 | 0.9196 | 4.224 |
| 146 | 1.757 | >50000 | 0.2265 | 1.1178 | 4.935 |
| 147 | 2.1391 | 6909.44 | 0.3752 | 3.64 | 9.701 |
| 148 | 1.6707 | 13841.3 | 0.1822 | 6.3387 | 34.790 |
| 149 | 1.5901 | 10021.4 | 0.2549 | 2.973 | 11.663 |
| 150 | 1.9813 | 8487.89 | 0.1711 | 4.4132 | 25.793 |
| 151-1 | 4.2684 | 12462.7 | 0.729 | 1143.52 | 1568.615 |
| 151-2 | 1.7492 | 7203.1 | 0.4402 | 77.2201 | 16.402 |
| 152 | 4.0469 | 12031.9 | NA | NA | |
| 153 | 29.7938 | 5614.41 | NA | NA | |
| 154-1 | 1.6409 | 8849.89 | 0.2969 | 4.291 | 14.453 |
| 154-2 | 1.9412 | 15228.9 | 0.3057 | 7.1366 | 23.345 |
| 155-1 | 3.0511 | 39480.7 | NA | NA | |
| 155-2 | 4.4293 | >41262.5 | NA | NA | |
| 156 | 1.7471 | 13691.4 | 0.1867 | 41.3025 | 221.224 |
| 157 | 5.3621 | 23691.5 | 1.6105 | 5.7498 | 3.570 |
| 158 | 1.6658 | 8825.72 | 0.3062 | 49.749 | 162.472 |
| 159 | 3.5226 | >43568.6 | 0.9759 | 2.5602 | 2.623 |
| 160 | 1.5183 | 11378.3 | 0.3682 | 1.1935 | 3.241 |
| 161 | 2.1023 | 4631.34 | 0.3001 | 1.015 | 3.382 |
| 162-1 | 1.1448 | 16215.6 | 0.067 | 11.919 | 177.9 |
| 162-2 | 2.5844 | 14355.2 | 0.118 | 15.329 | 129.91 |
| 163-1 | 1.259 | 20186.2 | 0.0674 | 11.9187 | 176.835 |
| 163-2 | 2.2876 | 13770.6 | 0.1183 | 15.3293 | 129.580 |
| 164 | 1.208 | 10399.5 | 0.3329 | 13.3338 | 40.053 |
| 165 | 1.0993 | 9610.76 | 0.3511 | 7.3266 | 20.868 |
| 166 | 2.499 | 15575 | 0.5830 | 1.625 | 2.787 |
| 167 | 3.231 | 18651 | NA | NA | |
| 168 | 1.747 | 13692 | 0.1870 | 41.303 | 220.87 |
| 169 | 1.398 | 11767 | 0.3220 | 2.887 | 8.966 |
| 170 | 1.21 | 9862.3 | NA | NA | |
| 171 | 0.962 | 4193.6 | 0.387 | 8.497 | 21.956 |
| 172-1 | 2.4 | 15614 | 0.6890 | 42.748 | 62.044 |
| 172-2 | 1.471 | 12813 | 0.4170 | 2.615 | 6.271 |
| 173 | 1.235 | 12478 | 0.3630 | 13.888 | 38.259 |
| 174 | 1.26 | 11385 | 0.3460 | 58.433 | 168.88 |
| 175 | 1.287 | 7743 | 0.4120 | 20.934 | 50.811 |

TABLE 1-continued

| Compound No. | EC50 (nM) | CC50 (nM) | Antiviral Serum Shift RLuc | | |
|---|---|---|---|---|---|
| | | | CCM | 50% HS | EC50 shift |
| 176 | 0.8290 | 7770.8 | 0.263 | 16.736 | 63.635 |
| 177 | 0.9150 | 8544.5 | 0.294 | 11.072 | 37.66 |
| 178 | 2.136 | 16697 | 0.43 | 6.559 | 15.253 |
| 179 | 1.492 | 13137 | 0.335 | 0.803 | 2.397 |
| 180 | 1.208 | 10400 | 0.32 | 13.537 | 42.303 |
| 181 | 1.085 | 9709.9 | 0.385 | 7.65 | 19.87 |
| 182 | 4.256 | 20352 | NA | NA | |
| 183 | 0.869 | 10477 | 0.262 | 5.715 | 21.813 |
| 184 | 1.038 | 9432.7 | 0.311 | 4.059 | 13.051 |
| 185 | 3.293 | 3548.1 | 0.984 | 4.876 | 4.955 |
| 186 | 0.612 | 11420 | 0.306 | 60.179 | 196.66 |
| 187 | 1.184 | 10752 | 0.383 | 44.043 | 115 |
| 188 | 1.185 | 12164 | 0.421 | 3.481 | 8.268 |
| 189 | 1.56 | 12319 | 0.411 | 6.061 | 14.747 |
| 190 | 1.808 | 22825 | 0.434 | 14.176 | 32.664 |
| 191-1 | 2.61 | 11603 | 0.611 | 2.693 | 4.408 |
| 191-2 | 1.44 | 11828 | 0.361 | 1.932 | 5.352 |
| 192 | 0.913 | 5572.5 | 0.252 | 6.57 | 26.071 |
| 193 | NA | NA | NA | NA | |
| 194-1 | 1.393 | 10769 | 0.683 | 222.37 | 325.57 |
| 194-2 | 1.503 | 10513 | 0.378 | 2.992 | 7.915 |
| 194-3 | 1.276 | 11481 | 0.554 | 139.14 | 251.16 |
| 194-4 | 1.746 | 11264 | 0.397 | 3.477 | 8.758 |
| 195 | 1.729 | 16700 | 0.441 | 10.448 | 23.692 |
| 196 | 2.08 | 25856 | 0.469 | 14.315 | 30.522 |
| 197 | 1.49 | 22379 | 0.589 | 8.35 | 14.177 |

NA: not tested

The data in Table 1 represents an average over time of each assay for each compound. For certain compounds, multiple assays have been conducted.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments have been described herein for purposes of illustration, various modifications may be made without deviating from the spirit and scope of the disclosure. Accordingly, the disclosure is not limited except as by the appended claims.

We claim:

1. A compound of formula (I):

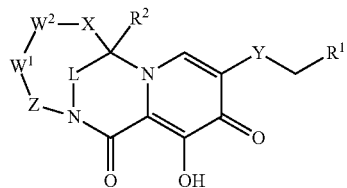

or a pharmaceutically acceptable salt thereof, wherein $R^1$ is H or $C_{6-10}$aryl, wherein $C_{6-10}$aryl is optionally substituted with one to four $R^{41}$, wherein each $R^{41}$ is independently halo, $C_{1-6}$alkyl, $C_{1-4}$haloalkyl, cyano, —O—$C_{1-4}$alkyl, or $C_{1-4}$alkyl-O—$C_{1-4}$alkyl;

$R^2$ is H, $C_{1-6}$alkyl, or $C_{1-4}$haloalkyl;

L is —$CR^{3a}R^{3b}$—, —C(O)—, —$SO_2$—, —$CH_2$—$CH_2$—, or —N($R^a$)—;

$W^1$ is a bond or —$CR^{4a}R^{4b}$—;

$W^2$ is —$CR^{5a}R^{5b}$—, —$CR^{5a}R^{5b}CR^{5c}R^{5d}$—, —$CR^{6a}$=$CR^{6b}$—, —N($R^7$)—, —O—, —S(O)$_n$—, —C(O)—, —C(O)O—, —C(O)NH—, —$CR^{5a}R^{5b}$—N($R^7$)—, —$CR^{5a}R^{5b}$—O—, —$CR^{5a}R^{5b}$—S(O)$_n$—, —$CR^{5a}R^{5b}$—C(O)—, —$CR^{5a}R^{5b}$—C(O)O—, —$CR^{5a}R^{5b}$—OC(O)—, —$CR^{5a}R^{5b}$—C(O)NH—, or —$CR^{5a}R^{5b}$—NHC(O)—;

X is a bond or —$CR^{8a}R^{8b}$—;

Y is —C(O)NH— or Q, wherein Q is

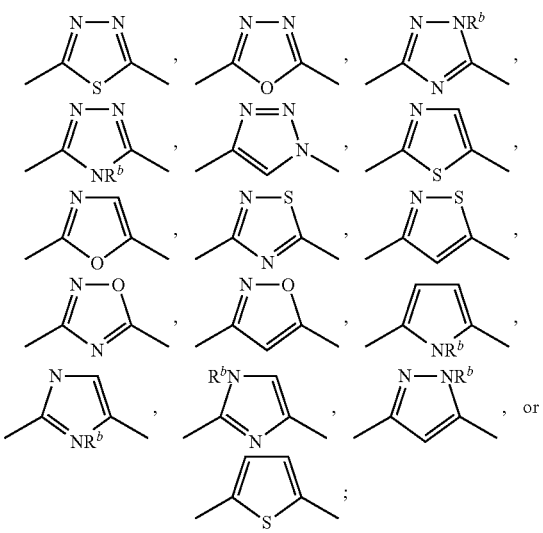

Z is —$CR^{9a}R^{9b}$—, —$CR^{9a}R^{9b}CR^{9c}R^{9d}$—, or —$CR^{10a}$=$CR^{10b}$—;

$R^{3a}$ and $R^{3b}$ are independently H, $C_{1-6}$alkyl, $C_{1-4}$haloalkyl, or —O—$C_{1-4}$alkyl; or optionally:

$R^{3a}$ and $R^{3b}$ together with the carbon atom to which they are attached form a 3- to 7-membered saturated or partially unsaturated spiro ring containing 0 to 2 heteroatoms selected from N, O, and S, wherein the spiro ring is optionally substituted with one to three $R^{42}$, wherein each $R^{42}$ is independently halo, $C_{1-4}$alkyl or $C_{1-4}$haloalkyl;

$R^{4a}$ and $R^{4b}$ are independently H, $C_{1-6}$alkyl, $C_{1-4}$haloalkyl, or halo;

$R^{5a}$, $R^{5b}$, $R^{5c}$, and $R^{5d}$ are independently H, $C_{1-6}$alkyl, $C_{1-4}$haloalkyl, halo, hydroxyl, cyano, —O—$C_{1-4}$alkyl, or $C_{1-4}$alkylene-O—$C_{1-4}$alkyl; or optionally:

$R^{5a}$ and $R^{5b}$ or $R^{5c}$ and $R^{5d}$ together with the carbon atom to which they are attached form a 3- to 7-membered saturated or partially unsaturated spiro ring containing 0 to 2 heteroatoms selected from N, O, and S, wherein the spiro ring is optionally substituted with one to three $R^{43}$, wherein each $R^{43}$ is independently halo, $C_{1-4}$alkyl or $C_{1-4}$haloalkyl; or $R^{5a}$ and $R^{5c}$ or $R^{5b}$ and $R^{5d}$ together with the carbon atoms to which each is attached form a 3- to 7-membered saturated or partially unsaturated fused ring containing 0 heteroatoms or 1 heteroatom selected from N, O, and S, wherein the fused ring is optionally substituted with one to three $R^{43}$, wherein each $R^{43}$ is independently halo, $C_{1-4}$alkyl or $C_{1-4}$haloalkyl;

each $R^{6a}$ and $R^{6b}$ is independently H, halo, $C_{1-4}$haloalkyl, or $C_{1-6}$alkyl; optionally:
- $R^{6a}$ and $R^{6b}$ together with the carbon atoms to which each is attached form a 5- to 10-membered partially unsaturated fused ring containing 0 heteroatoms or 1 heteroatom selected from N, O, and S, or a 5- to 10-membered fused aromatic ring, or a 5- to 10-membered fused heteroaromatic ring containing 1 to 2 heteroatoms selected from N, O and S, wherein the partially unsaturated fused ring, fused aromatic ring, or fused heteroaromatic ring is optionally substituted with one to four $R^{44}$, wherein each $R^{44}$ is independently halo or $C_{1-4}$ alkyl;

$R^7$ is H, $C_{1-6}$alkyl, $C_{1-4}$haloalkyl, $C(O)R^c$, or $SO_2R^c$;

$R^{8a}$ and $R^{8b}$ are each independently H, hydroxyl, —O—$C_{1-4}$alkyl, $C_{1-4}$alkylene-O—$C_{1-4}$alkyl, $C_{1-6}$alkyl, $C_{1-4}$haloalkyl, cyano, or halo; or optionally:
- $R^{8a}$ and $R^{8b}$ together with the carbon atom to which they are attached form a 3- to 7-membered saturated or partially unsaturated spiro ring containing 0 to 2 heteroatoms selected from N, O, and S, wherein the spiro ring is optionally substituted with one to four $R^{45}$, wherein each $R^{45}$ is independently halo, $C_{1-4}$alkyl or $C_{1-4}$haloalkyl; or optionally:
- $R^{8a}$ is H, hydroxyl, —O—$C_{1-4}$alkyl, $C_{1-4}$alkylene-O—$C_{1-4}$alkyl, $C_{1-6}$alkyl, $C_{1-4}$haloalkyl, cyano, or halo; and
- $R^{8b}$ and one of $R^{5a}$, $R^{5b}$, $R^{5c}$, $R^{5d}$, and $R^7$ together with the atoms to which each is attached form a 3- to 7-membered saturated or partially unsaturated fused ring containing 0 to 2 heteroatoms selected from N, O and S, wherein the fused ring is optionally substituted with one to four $R^{45}$, wherein each $R^{45}$ is independently halo or $C_{1-4}$alkyl; or
- $R^{8b}$ and $R^2$ together with the carbon atoms to which each is attached form a 3- to 7-membered saturated or partially unsaturated fused ring containing 0 to 2 heteroatoms selected from N, O and S, wherein the fused ring is optionally substituted with one to four $R^{45}$, wherein each $R^{45}$ is independently halo or $C_{1-4}$ alkyl;

$R^{9a}$, $R^{9b}$, $R^{9c}$, and $R^{9d}$ are independently H, $C_{1-6}$alkyl, $C_{1-4}$haloalkyl, or halo; or optionally:
- $R^{9a}$ and $R^{9b}$ or $R^{9c}$ and $R^{9d}$ together with the carbon atom to which they are attached form a 3- to 7-membered saturated or partially unsaturated spiro ring containing 0 to 2 heteroatoms selected from N, O, and S, wherein the spiro ring is optionally substituted with one to three $R^{46}$, wherein each $R^{46}$ is independently halo, $C_{1-4}$alkyl or $C_{1-4}$haloalkyl; or
- $R^{9a}$ and $R^{9c}$ or $R^{9b}$ and $R^{9d}$ together with the carbon atoms to which each is attached form a 3- to 7-membered saturated or partially unsaturated fused ring containing 0 heteroatoms or 1 heteroatom selected from N, O, and S, wherein the fused ring is optionally substituted with one to three $R^{46}$, wherein each $R^{46}$ is independently halo, $C_{1-4}$alkyl, or $C_{1-4}$haloalkyl; or
- one of $R^{9a}$, $R^{9b}$, $R^{9c}$, and $R^{9d}$ and one of $R^{4a}$, $R^{4b}$, $R^{5a}$, $R^{5b}$, and $R^7$ together with the atoms to which each is attached form a 3- to 7-membered saturated or partially unsaturated fused ring containing 0 to 2 heteroatoms selected from N, O and S, wherein the fused ring is optionally substituted with one to four $R^{46}$, wherein each $R^{46}$ is independently halo or $C_{1-4}$alkyl;

$R^{10a}$ and $R^{10b}$ are independently H, halo, $C_{1-4}$haloalkyl, or $C_{1-6}$alkyl; or optionally:
- $R^{10a}$ and $R^{10b}$ together with the carbon atoms to which each is attached form a 5- to 10-membered partially unsaturated fused ring containing 0 heteroatoms or 1 heteroatom selected from N, O, and S, or a 5- to 10-membered fused aromatic ring, or a 5- to 10-membered fused heteroaromatic ring containing 1 to 2 heteroatoms selected from N, O and S, wherein the partially unsaturated fused ring, fused aromatic ring, or fused heteroaromatic ring is optionally substituted with one to four $R^{47}$, wherein each $R^{47}$ is independently halo or $C_{1-4}$ alkyl;

$R^a$ is independently H, $C_{1-6}$alkyl, $C_{1-6}$haloalkyl, $C(O)R^c$, or $SO_2R^c$;

$R^b$ is H or $C_{1-4}$alkyl;

$R^c$ is $C_{1-4}$alkyl or —O—$C_{1-4}$alkyl; and each n is 0, 1, or 2.

2. The compound of claim 1, or a pharmaceutically acceptable salt thereof, wherein $R^2$ is selected from the group consisting of H, —$CH_3$, —$CH_2CH_3$, and —$CH_2F$, or $R^2$ and $R^{8b}$ together with the carbon to which they are attached form a 3-membered fused carbocyclic ring.

3. The compound of claim 1, or a pharmaceutically acceptable salt thereof, wherein $R^2$ is selected from the group consisting of H, —$CH_3$, —$CH_2CH_3$, and —$CH_2F$.

4. The compound of claim 1, or a pharmaceutically acceptable salt thereof, wherein Y is —C(O)NH—.

5. The compound of claim 1, or a pharmaceutically acceptable salt thereof, having a the formula (II):

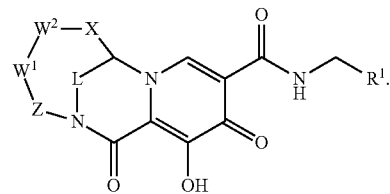

6. The compound of claim 1, or a pharmaceutically acceptable salt thereof, wherein $R^1$ is phenyl, optionally substituted with one to four $R^{41}$, wherein each $R^{41}$ is independently halo, $C_{1-4}$alkyl, $C_{1-4}$haloalkyl, cyano, —O—$C_{1-4}$alkyl, or $C_{1-4}$alkyl-O—$C_{1-4}$alkyl.

7. The compound of claim 1, or a pharmaceutically acceptable salt thereof, wherein $R^1$ is phenyl substituted with one, two, three, or four halogens.

8. The compound of claim 1, or a pharmaceutically acceptable salt thereof, having a the formula (IV):

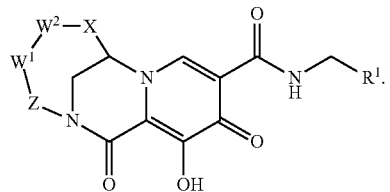

9. The compound of claim 1, or a pharmaceutically acceptable salt thereof, having a the formula:

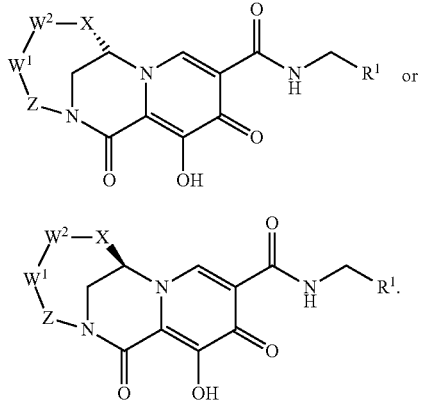

Va

Vb

10. The compound of claim 1, or a pharmaceutically acceptable salt thereof, wherein $W^1$ is a bond or —$CR^{4a}R^{4b}$—; wherein $R^{4a}$ and $R^{4b}$ are independently H, $C_{1-6}$alkyl, or halo.

11. The compound of claim 1, or a pharmaceutically acceptable salt thereof, wherein $W^1$ is bond, —$CH_2$—, —$CF_2$—, —$CH(F)$—, —$CH(CH_3)$—, or —$CF(CH_3)$—.

12. The compound of claim 1, or a pharmaceutically acceptable salt thereof, wherein $W^2$ is selected from the group consisting of —$CR^{5a}R^{5b}$—, —$CR^{5a}R^{5b}CR^{5c}R^{5d}$—, —$CR^{6a}=CR^{6b}$—, —$N(R^7)$—, —O—, —$S(O)_n$—, —C(O)—, —$CR^{5a}R^{5b}$—C(O)—, and —$CR^{5a}R^{5b}$—O—; wherein
  each $R^{5a}$, $R^{5b}$, $R^{5c}$, and $R^{5d}$ are independently H, $C_{1-4}$alkyl, $C_{1-4}$haloalkyl, halo, hydroxyl, cyano, —O—$C_{1-4}$alkyl, or $C_{1-4}$alkylene-O—$C_{1-4}$alkyl; or
  $R^{5a}$ and $R^{5b}$, $R^{5c}$ and $R^{5d}$, $R^{5a}$ and $R^{5c}$, or $R^{5b}$ and $R^{5d}$ together with the carbon atoms to which each is attached form a 3 to 7 membered saturated or partially unsaturated carbocyclic ring, optionally substituted with one to three $R^{43}$, wherein each $R^{43}$ is independently halo, $C_{1-4}$alkyl or $C_{1-4}$haloalkyl;
  each $R^{6a}$ and $R^{6b}$ are independently H, halo, $C_{1-4}$haloalkyl, or $C_{1-4}$alkyl; or
  $R^{6a}$ and $R^{6b}$ together with the atoms to which each is attached form (i) a 5 to 10 membered fused aromatic ring or (ii) a 5 to 10 membered fused heteroaromatic ring containing 1 to 2 heteroatoms selected from N, O and S, wherein the 5-10 membered fused aromatic ring or the 5-10-membered fused heteroaromatic ring is optionally substituted with one to four $R^{44}$, wherein each $R^{44}$ is independently halo or $C_{1-4}$alkyl;
  $R^7$ is H, $C_{1-4}$alkyl, $C_{1-4}$haloalkyl, C(O)$R^c$, or SO$_2R^c$;
  $R^c$ is a $C_{1-4}$alkyl; and
  n is 0, 1, or 2.

13. The compound of claim 1, or a pharmaceutically acceptable salt thereof, wherein $W^2$ is selected from the group consisting of —$CR^{5a}R^{5b}$—, —$CR^{5a}R^{5b}CR^{5c}R^{5d}$—, —$CR^{6a}=CR^{6b}$—, —$N(R^7)$—, —O—, —$S(O)_n$—, —C(O)—, —$CR^{5a}R^{5b}$—C(O)—, and —$CR^{5a}R^{5b}$—O—; wherein
  each $R^{5a}$, $R^{5b}$, $R^{5c}$, and $R^{5d}$ are independently H, $C_{1-4}$alkyl, halo, hydroxyl, or —O—$C_{1-4}$alkyl; or
  $R^{5a}$ and $R^{5b}$, $R^{5c}$ and $R^{5d}$, $R^{5a}$ and $R^{5c}$, or $R^{5b}$ and $R^{5d}$ together with the carbon atoms to which each is attached form a 3-membered carbocyclic ring;

each $R^{6a}$ and $R^{6b}$ are independently H, halo, or $C_{1-4}$alkyl; or
$R^{6a}$ and $R^{6b}$ together with the atoms to which each is attached form (i) a fused phenyl ring or (ii) a 5-6 membered fused heteroaromatic ring containing 1 to 2 heteroatoms selected from N and O, wherein the fused phenyl ring or the 5-6 membered fused heteroaromatic ring is optionally substituted with one or two $R^{44}$, wherein each $R^{44}$ is independently halo or $C_{1-4}$alkyl;
$R^7$ is H, $C_{1-4}$alkyl, $C_{1-4}$haloalkyl, C(O)$R^c$, or SO$_2R^c$;
$R^c$ is a $C_{1-4}$alkyl; and
n is 0 or 1.

14. The compound of claim 1, or a pharmaceutically acceptable salt thereof, wherein $W^2$ is selected from the group consisting of —$CR^{5a}R^{5b}$—, —$CR^{5a}R^{5b}CR^{5c}R^{5d}$—, —$CR^{6a}=CR^{6b}$—, —$N(R^7)$—, —O—, —$S(O)_n$—, —C(O)—, —$CR^{5a}R^{5b}$—C(O)—, and —$CR^{5a}R^{5b}$—O—; wherein
  each $R^{5a}$, $R^{5b}$, $R^{5c}$, and $R^{5d}$ are independently H, —CH$_3$, halo, hydroxyl, or —OCH$_3$; or
  $R^{5a}$ and $R^{5b}$, $R^{5c}$ and $R^{5d}$, $R^{5a}$ and $R^{5c}$, or $R^{5b}$ and $R^{5d}$ together with the carbon atoms to which each is attached form a 3-membered carbocyclic ring;
  each $R^{6a}$ and $R^{6b}$ are independently H, halo, or CH$_3$; or
  $R^{6a}$ and $R^{6b}$ together with the atoms to which each is attached form (i) a fused phenyl ring or (ii) a 5 membered fused heteroaromatic ring containing 1 to 2 heteroatoms selected from N and O, wherein the fused phenyl ring or the 5 membered fused heteroaromatic ring is optionally substituted with one or two $R^{44}$, wherein each $R^{44}$ is independently halo or CH$_3$;
  $R^7$ is H, —CH$_3$, —CH(CH$_3$)$_2$, —CF$_3$, —C(O)$R^c$, or —SO$_2R^c$;
  $R^c$ is —CH$_3$; and
  n is 0 or 1.

15. The compound of claim 1, or a pharmaceutically acceptable salt thereof, wherein $W^2$ is selected from the group consisting of —$CR^{5a}R^{5b}$—, —$CR^{5a}R^{5b}CR^{5c}R^{5d}$—, —$CR^{6a}=CR^{6b}$—, —$N(R^7)$—, —O—, —$S(O)_n$—, —C(O)—, —$CR^{5a}R^{5b}$—C(O)—, and —$CR^{5a}R^{5b}$—O—; wherein
  each $R^{5a}$, $R^{5b}$, $R^{5c}$, and $R^{5d}$ are independently H, —CH$_3$, halo, hydroxyl, or —OCH$_3$;
  each $R^{6a}$ and $R^{6b}$ are independently H, halo, or —CH$_3$;
  $R^7$ is H, —CH$_3$, —CH(CH$_3$)$_2$, —CF$_3$, —C(O)$R^c$, or —SO$_2R^c$;
  $R^c$ is —CH$_3$; and
  n is 0 or 1.

16. The compound of claim 1, or a pharmaceutically acceptable salt thereof, wherein $W^2$ is —CH$_2$—, —CH$_2$CH$_2$—, —CH=CH—,

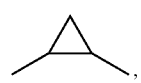,

—NH—, —N(CH$_3$)—, —N(CH(CH$_3$)$_2$)—, —N(C(O)CH$_3$)—, —N(SO$_2$CH$_3$)—, —O—, or —CH$_2$—O—.

17. The compound of claim 1, or a pharmaceutically acceptable salt thereof, wherein X is a bond or —$CR^{8a}R^{8b}$—, wherein $R^{8a}$ and $R^{8b}$ are independently H, hydroxyl, —O—$C_{1-4}$alkyl, $C_{1-4}$alkyl, $C_{1-4}$haloalkyl, or halo; or
$R^{8a}$ and $R^{8b}$ together with the carbon to which they are attached form a 3 to 5-membered saturated spiro ring containing 0 to 2 heteroatoms selected from N, O, and S, wherein the spiro ring is optionally substituted with one to four $R^{45}$, wherein each $R^{45}$ is independently halo, $C_{1-4}$alkyl or $C_{1-4}$haloalkyl.

18. The compound of claim 1, or a pharmaceutically acceptable salt thereof, wherein X is a bond or —$CR^{8a}R^{8b}$—, wherein $R^{8a}$ and $R^{8b}$ are independently H, hydroxyl, —O—$C_{1-4}$alkyl, $C_{1-4}$alkyl, $C_{1-4}$haloalkyl, or halo, or
$R^{8a}$ and $R^{8b}$ together with the carbon to which they are attached form a 3-membered saturated spiro carbocyclic ring.

19. The compound of claim 1, or a pharmaceutically acceptable salt thereof, wherein X is a bond, —$CH_2$—, —$CF_2$—, —CH(F)—, —CH(Cl)—, —CH(OH)—, —C($CH_2F$)(H)—, —C($CH_2F$)(OH)—, —C($CH_3$)(OH)—, —CH($OCH_3$)—, —C($CH_2CH_3$)($OCH_3$)—, —C($CH_2CH_3$)(OH)—, —CH($CH_3$)—, —CH($CH_2CH_3$)—, —CF($CH_3$)—, —CF($CH_2CH_3$)—, or —$CR^{8a}R^{8b}$—, wherein $R^{8a}$ and $R^{8b}$ together with the carbon to which they are attached form a spiro cyclopropane ring.

20. The compound of claim 1, or a pharmaceutically acceptable salt thereof, wherein X is a bond, —$CH_2$—, —$CF_2$—, —CH(F)—, —CH(Cl)—, —CH(OH)—, —C($CH_2F$)(H)—, —C($CH_2F$)(OH)—, —C($CH_3$)(OH)—, —CH($OCH_3$)—, —C($CH_2CH_3$)($OCH_3$)—, —C($CH_2CH_3$)(OH)—, —CH($CH_3$)—, —CH($CH_2CH_3$)—, —CF($CH_3$)—, or —CF($CH_2CH_3$)—.

21. The compound of claim 1, or a pharmaceutically acceptable salt thereof, wherein X is —$CR^{8a}R^{8b}$—, wherein $R^{8a}$ and $R^{8b}$ together with the carbon to which they are attached form a 3 to 5-membered saturated spiro ring containing 0 to 2 heteroatoms selected from N, O, and S, wherein the spiro ring is optionally substituted with one to four $R^{45}$, wherein each $R^{45}$ is independently halo, $C_{1-4}$alkyl or $C_{1-4}$haloalky.

22. The compound of claim 1, or the pharmaceutically acceptable salt thereof, wherein X is —$CR^{8a}R^{8b}$—, wherein $R^{8a}$ and $R^{8b}$ together with the carbon to which they are attached form a 3-membered spiro carbocyclic ring.

23. The compound of claim 1, or a pharmaceutically acceptable salt thereof, having a the formula (VIII):

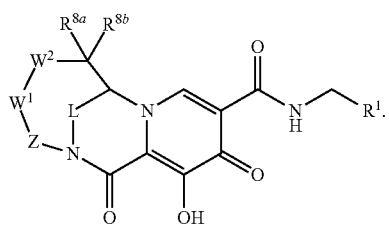

VIII

24. The compound of claim 1, or a pharmaceutically acceptable salt thereof, wherein Z is —$CR^{9a}R^{9b}$—, —$CR^{9a}R^{9b}CR^{9c}R^{9d}$—, or —$CR^{10a}$=$CR^{10b}$—; wherein
$R^{9a}$, $R^{9b}$, $R^{9c}$, and $R^{9d}$ are each independently H, $C_{1-4}$alkyl, $C_{1-4}$haloalkyl, or halo; or
$R^{9a}$ and $R^{9b}$ or $R^{9c}$ and $R^{9d}$ together with the carbon atom to which they are attached form a 3 to 7 membered saturated or partially unsaturated spiro ring containing 0 to 2 heteroatoms selected from N, O, and S, wherein the spiro ring is optionally substituted with one to three $R^{46}$, wherein each $R^{46}$ is independently halo, $C_{1-4}$alkyl or $C_{1-4}$haloalkyl;

$R^{10a}$ and $R^{10b}$ are independently H, halo, $C_{1-4}$haloalkyl, or $C_{1-6}$alkyl; or
$R^{10a}$ and $R^{10b}$ together with the carbon atoms to which each is attached form (i) a 5-10 membered partially unsaturated fused ring containing 0 heteroatoms or 1 heteroatom selected from N, O, and S, (ii) a 5-10 membered fused aromatic ring, or (iii) a 5-10 membered fused heteroaromatic ring containing 1 to 2 heteroatoms selected from N, O and S, wherein the 5-10 membered partially unsaturated fused ring, 5-10 membered fused aromatic ring, or 5-10 membered fused heteroaromatic ring is optionally substituted with one to four $R^{47}$, wherein each $R^{47}$ is independently halo or $C_{1-4}$alkyl.

25. The compound of claim 1, or a pharmaceutically acceptable salt thereof, wherein Z is —$CR^{9a}R^{9b}$—, —$CR^{9a}R^{9b}CR^{9c}R^{9d}$—, or —$CR^{10a}$=$CR^{10b}$—; wherein
$R^{9a}$, $R^{9b}$, $R^{9c}$, and $R^{9d}$ are each independently H, $CH_3$, $CH_2CH_3$, $CHF_2$, or halo; or
$R^{9a}$ and $R^{9b}$ or $R^{9c}$ and $R^{9d}$ together with the carbon atom to which they are attached form a 3-membered carbocyclic ring;
$R^{10a}$ and $R^{10b}$ are independently H, halo, or $CH_3$; or
$R^{10a}$ and $R^{10b}$ together with the carbon atoms to which each is attached form (i) a fused phenyl ring or (ii) a 5-6 membered fused heteroaromatic ring containing 1 to 2 heteroatoms selected from N, O and S, wherein the fused phenyl ring or the fused heteroaromatic ring is optionally substituted with one to two $R^{47}$, wherein each $R^{47}$ is independently halo or $CH_3$.

26. The compound of claim 1, or a pharmaceutically acceptable salt thereof, wherein Z is —$CH_2$—, —CH($CH_3$)—, —$CH_2$—$CH_2$—,

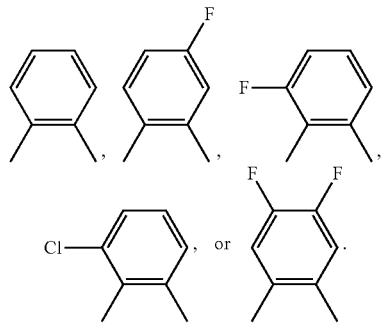

27. The compound of claim 1, or a pharmaceutically acceptable salt thereof, wherein the compound has a formula (IX):

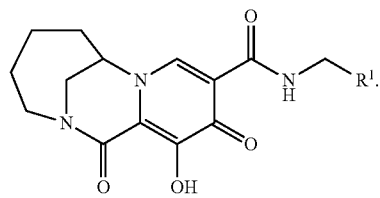

IX

28. The compound of claim 1, or a pharmaceutically acceptable salt thereof, wherein the compound has a formula (IXa):

29. The compound of claim 1, or a pharmaceutically acceptable salt thereof, wherein the compound has a formula (IXb):

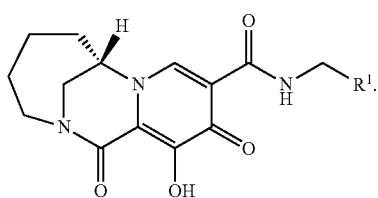
Formula (IXa)

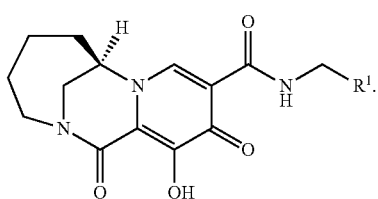
IXb

30. The compound of claim 1, or a pharmaceutically acceptable salt thereof, wherein the compound has a Formula (X):

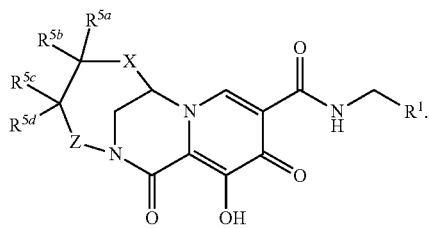
Formula (X)

31. The compound of claim 1, or a pharmaceutically acceptable salt thereof, wherein the compound has a Formula (Xa):

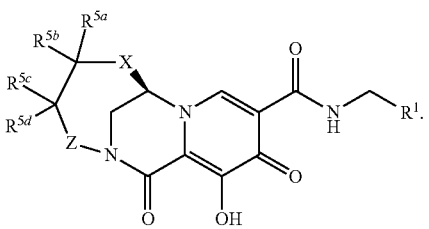
Formula (Xa)

32. The compound of claim 1, or a pharmaceutically acceptable salt thereof, wherein the compound has a Formula (Xb):

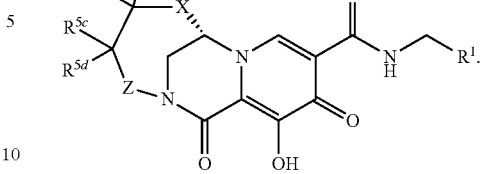
Formula (Xb)

33. The compound of claim 30, or a pharmaceutically acceptable salt thereof, wherein X is bond or —$CR^{8a}R^{8b}$—; wherein $R^{8a}$ and $R^{8b}$ are each independently H, hydroxyl, —O—$C_{1-4}$alkyl, $C_{1-4}$alkylene-O—$C_{1-4}$alkyl, $C_{1-6}$alkyl, $C_{1-4}$haloalkyl, cyano, or halo.

34. The compound of claim 30, or a pharmaceutically acceptable salt thereof, wherein X is -$CR^{8a}R^{8b}$—; wherein $R^{8a}$ and $R^{8b}$ are each independently H, $C_{1-6}$alkyl, $C_{1-4}$haloalkyl, or halo.

35. The compound of claim 30, or a pharmaceutically acceptable salt thereof, wherein Z is —$CR^{9a}R^{9b}$— or —$CR^{9a}R^{9b}CR^{9c}R^{9d}$; wherein $R^{9a}$, $R^{9b}$, $R^{9c}$, and $R^{9d}$ are each independently H, $C_{1-6}$alkyl, or $C_{1-4}$haloalkyl.

36. The compound of claim 30, or a pharmaceutically acceptable salt thereof, wherein Z is —$CR^{9a}R^{9b}$—.

37. The compound of claim 30, or a pharmaceutically acceptable salt thereof, wherein $R^{9a}$, $R^{9b}$, $R^{9c}$, and $R^{9d}$ are each independently H, —$CH_3$, —$CHF_2$, or —$CH_2F$.

38. The compound of claim 30, or a pharmaceutically acceptable salt thereof, wherein each $R^{5a}$, $R^{5b}$, $R^{5c}$, and $R^{5d}$ is independently H, halo, $C_{1-4}$haloalkyl, or $C_{1-6}$alkyl.

39. The compound of claim 1, or a pharmaceutically acceptable salt thereof, wherein the compound has a Formula (XI):

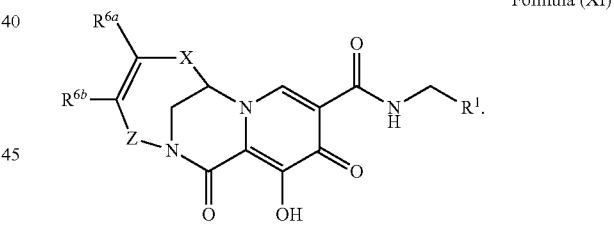
Formula (XI)

40. The compound of claim 1, or a pharmaceutically acceptable salt thereof, wherein the compound has a Formula (XIa):

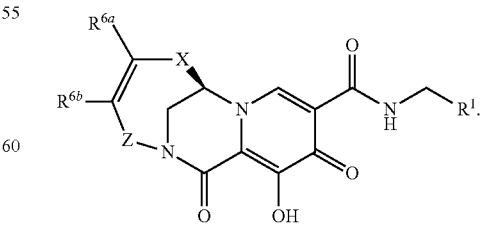
Formula (XIa)

41. The compound of claim 1, or a pharmaceutically acceptable salt thereof, wherein the compound has a Formula (XIb):

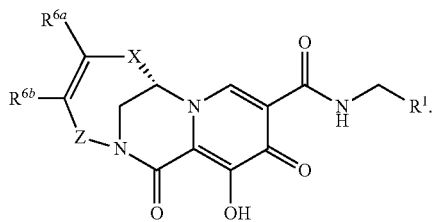

Formula (XIb)

42. The compound of claim 39, or a pharmaceutically acceptable salt thereof, wherein X is bond or —$CR^{8a}R^{8b}$—; wherein $R^{8a}$ and $R^{8b}$ are each independently H, hydroxyl, —O—$C_{1-4}$alkyl, $C_{1-4}$alkylene-O—$C_{1-4}$alkyl, $C_{1-6}$alkyl, $C_{1-4}$haloalkyl, cyano, or halo.

43. The compound of claim 39, or a pharmaceutically acceptable salt thereof, wherein $R^{8a}$ and $R^{8b}$ are each independently H, —$CH_3$, —$CHF_2$, —$CH_2F$, or halo.

44. The compound of claim 39, or a pharmaceutically acceptable salt thereof, wherein Z is —$CR^{9a}R^{9b}$— or —$CR^{9a}R^{9b}CR^{9c}R^{9d}$; wherein $R^{9a}$, $R^{9b}$, $R^{9c}$, and $R^{9d}$ are each independently H, $C_{1-6}$alkyl, or $C_{1-4}$haloalkyl.

45. The compound of claim 39, or a pharmaceutically acceptable salt thereof, wherein $R^{9a}$, $R^{9b}$, $R^{9c}$, and $R^{9d}$ are each independently H, —$CH_3$, —$CHF_2$, or —$CH_2F$.

46. The compound of claim 39, or a pharmaceutically acceptable salt thereof, wherein each $R^{6a}$ and $R^{6b}$ is independently H, halo, $C_{1-4}$haloalkyl, or $C_{1-6}$alkyl.

47. A pharmaceutical composition comprising a therapeutically effective amount of a compound of claim 1, or a pharmaceutically acceptable salt thereof, and a pharmaceutically acceptable excipient.

* * * * *